(12) United States Patent
Schwartz et al.

(10) Patent No.: US 12,291,738 B2
(45) Date of Patent: May 6, 2025

(54) METHODS AND/OR USE OF OLIGONUCLEOTIDE CONJUGATES FOR ASSAYS AND FLOW CYTOMETRY DETECTIONS

(71) Applicants: The University of Chicago, Chicago, IL (US); EMD Millipore Corporation, Burlington, MA (US)

(72) Inventors: David A. Schwartz, Encinitas, CA (US); Jimmy Williams, Santee, CA (US); Xinfang Zhao, San Diego, CA (US); Chunfang Zhao, San Diego, CA (US); William B. Busa, Bahama, NC (US); Stephen J. Kron, Oak Park, IL (US); Amy Catherine Flor, Chicago, IL (US)

(73) Assignees: The University of Chicago, Chicago, IL (US); EMD Millipore Corporation, Burlington, MA (US)

( * ) Notice: Subject to any disclaimer, the term of this patent is extended or adjusted under 35 U.S.C. 154(b) by 0 days.

(21) Appl. No.: 17/369,771

(22) Filed: Jul. 7, 2021

(65) Prior Publication Data
US 2022/0170073 A1    Jun. 2, 2022

Related U.S. Application Data

(63) Continuation of application No. 13/302,877, filed on Nov. 22, 2011, now abandoned.

(60) Provisional application No. 61/483,186, filed on May 6, 2011, provisional application No. 61/344,931, filed on Nov. 22, 2010.

(51) Int. Cl.
*C12Q 1/6804* (2018.01)
*C07H 21/00* (2006.01)
*C12Q 1/6834* (2018.01)

(52) U.S. Cl.
CPC .......... *C12Q 1/6804* (2013.01); *C07H 21/00* (2013.01); *C12Q 1/6834* (2013.01)

(58) Field of Classification Search
CPC ............... C12Q 1/6804; C12Q 1/6834; C12Q 2525/313; C07H 21/00
See application file for complete search history.

(56) References Cited

U.S. PATENT DOCUMENTS

| | | |
|---|---|---|
| 4,650,675 A | 3/1987 | Borel et al. |
| 4,975,532 A | 12/1990 | Rowley et al. |
| 5,124,246 A | 6/1992 | Urdea et al. |
| 5,175,270 A | 12/1992 | Nilsen et al. |
| 5,206,370 A | 4/1993 | Schwartz et al. |
| 5,391,723 A | 2/1995 | Priest |
| 5,420,285 A | 5/1995 | Schwartz et al. |
| 5,427,932 A | 6/1995 | Weier et al. |
| 5,624,802 A | 4/1997 | Urdea et al. |
| 5,648,213 A | 7/1997 | Reddy et al. |
| 5,665,539 A | 9/1997 | Sano et al. |
| 5,679,778 A | 10/1997 | Abrams et al. |
| 5,695,936 A | 12/1997 | Mandrand et al. |
| 5,753,520 A | 5/1998 | Schwartz et al. |
| 5,902,724 A | 5/1999 | Lane et al. |
| 6,072,043 A | 6/2000 | Nilsen |
| 6,077,668 A | 6/2000 | Kool |
| 6,110,687 A | 8/2000 | Nilsen |
| 6,117,631 A | 9/2000 | Nilsen |
| 6,217,845 B1 | 4/2001 | Schwartz et al. |
| 6,242,184 B1 | 6/2001 | Singer et al. |
| 6,245,513 B1 | 6/2001 | Lane et al. |
| 6,274,723 B1 | 8/2001 | Nilsen |
| 6,451,588 B1 | 9/2002 | Egholm et al. |
| 6,600,026 B1 | 7/2003 | Yu |
| 6,686,461 B1 | 2/2004 | Schwartz et al. |
| 6,800,728 B2 | 10/2004 | Schwartz |
| 6,911,535 B2 | 6/2005 | Schwartz |
| 6,942,972 B2 | 9/2005 | Farooqui et al. |

(Continued)

FOREIGN PATENT DOCUMENTS

| | | |
|---|---|---|
| WO | 1994/001448 A1 | 1/1994 |
| WO | 1998/02580 A2 | 1/1998 |

(Continued)

OTHER PUBLICATIONS

Adler et al., "Sensitivity by Combination: Immuno-PCR and Related Technologies", Analyst, 2008, 133:702-18.
Bailey et al., "DNA-Encoded Antibody Libraries: A Unified Platform for Multiplexed Cell Sorting and Detection of Genes and Proteins", J Am Chem Soc, 2007, 129:959-67.
Bradford, Zenon® Labeling Technology, Invitrogen, "Imperial College Flow Cytometry Course", Oct. 17, 2007. 1-41.

(Continued)

*Primary Examiner* — Narayan K Bhat
(74) *Attorney, Agent, or Firm* — Norton Rose Fulbright US LLP

(57) ABSTRACT

The present disclosure is directed to methods and/or uses of oligonucleotide conjugates for assays and flow cytometry detections and related systems and/or kits. Certain methods are directed to a method for detecting one or more biological targets of a sample in a detection assay, comprising: providing a molecular probe, comprising a binding moiety and an oligonucleotide sequence, to a sample comprising one or more biological targets; binding the one or more biological targets with the binding moiety; providing a detectable component to the sample, wherein the detectable component comprises a signal generating moiety conjugated to an oligonucleotide sequence complementary to the oligonucleotide sequence of the molecular probe; hydridizing the oligonucleotide sequence of the target-bound molecular probe to the detectable component; and detecting a signal generated from the hydridized detectable component. Various other embodiments, applications etc. are disclosed herein.

25 Claims, 83 Drawing Sheets
Specification includes a Sequence Listing.

(56) References Cited

U.S. PATENT DOCUMENTS

| | | | |
|---|---|---|---|
| 7,041,453 | B2 | 5/2006 | Yang |
| 7,102,024 | B1 | 9/2006 | Schwartz et al. |
| 7,122,310 | B2 | 10/2006 | Usui et al. |
| 7,173,125 | B2 | 2/2007 | Schwartz et al. |
| 7,183,052 | B2 | 2/2007 | Sorge |
| 7,306,904 | B2 | 12/2007 | Landegren et al. |
| 7,462,689 | B2 | 12/2008 | Schwartz |
| 7,476,502 | B2 | 1/2009 | Willey |
| 7,732,628 | B2 | 6/2010 | Schwartz et al. |
| 8,846,875 | B2 | 9/2014 | Schwartz et al. |
| 9,222,936 | B2 | 12/2015 | Schwartz et al. |
| 2002/0028455 | A1 | 3/2002 | Laibinis et al. |
| 2003/0013857 | A1 | 1/2003 | Schwartz |
| 2003/0022163 | A1 | 1/2003 | Mandrekar et al. |
| 2003/0124521 | A1 | 7/2003 | Coull et al. |
| 2003/0148335 | A1 | 8/2003 | Shen et al. |
| 2003/0198977 | A1 | 10/2003 | Nolan et al. |
| 2004/0002095 | A1 | 1/2004 | Liu et al. |
| 2004/0023248 | A1 | 2/2004 | O'Malley |
| 2004/0038217 | A1 | 2/2004 | Yang |
| 2004/0071664 | A1 | 4/2004 | McHale et al. |
| 2004/0248144 | A1 | 12/2004 | Mir |
| 2005/0095627 | A1 | 5/2005 | Kolman et al. |
| 2005/0164292 | A1 | 7/2005 | Farooqui et al. |
| 2007/0111222 | A1 | 5/2007 | Chasin et al. |
| 2007/0243551 | A1 | 10/2007 | Reddy et al. |
| 2008/0221343 | A1 | 9/2008 | Schwartz et al. |
| 2009/0035823 | A1 | 2/2009 | Soldatov et al. |
| 2009/0051912 | A1 | 2/2009 | Salazar et al. |
| 2009/0142755 | A1 | 6/2009 | Albitar |
| 2010/0059446 | A1 | 3/2010 | Rascalou et al. |
| 2010/0105145 | A1 | 4/2010 | Winther |
| 2010/0151472 | A1 | 6/2010 | Nolan et al. |
| 2010/0159446 | A1 | 6/2010 | Haff et al. |
| 2011/0160076 | A1 | 6/2011 | Alexander et al. |
| 2011/0177500 | A1 | 7/2011 | Winther et al. |
| 2015/0218209 | A1 | 8/2015 | Schwartz et al. |

FOREIGN PATENT DOCUMENTS

| | | | |
|---|---|---|---|
| WO | 2001/070685 | A2 | 9/2001 |
| WO | 2002/010432 | A2 | 2/2002 |
| WO | 2002/057422 | A2 | 7/2002 |
| WO | 2003/081202 | A2 | 10/2003 |
| WO | 2006/128138 | A2 | 11/2006 |
| WO | 2007/023390 | A2 | 3/2007 |
| WO | 2007/026252 | A2 | 3/2007 |
| WO | 2007/031874 | A2 | 3/2007 |
| WO | 2008/016680 | A1 | 2/2008 |
| WO | 2008/140452 | A1 | 11/2008 |
| WO | 2009/012343 | A2 | 1/2009 |
| WO | 2011/100493 | A1 | 8/2011 |

OTHER PUBLICATIONS

Conlon et al., Pyrene Excimer Signaling Molecular Beacons for Probing Nucleic Acids, J Am Chem Soc, 2008, 130(1):336-342.

Cuppoletti et al., "Oligomeric Fluorescent Labels for DNA", Bioconjugate Chemical, 2005, 16(3):528-534.

Feldkamp et al., "Microarray-Based in vitro Evaluation of DNA Oligomer Libraries Designed in silico", Chem Phys. Chem, 2004, 5:367-72.

Forget et al., "Efficient Preparation of Carbohydrate-Oligonucleotide Conjugates (COCs) Using Oxime Bond Formation," Tetrahedron Letters, 2001, 42:7829-7832.

Ljungquist et al., "Immobilization and Recovery of Fusion Protiens and B-Lymphocyte Cells Using Magnetic Separation", DNA and Cell Biology, 1993, 12(2):191-97.

Mora et al., "Protein Detection Enhanced by 3DNA Dendrimer Signal Amplification," BioTechniques, May 2008, 44:815-818.

Niemeyer, C.M., "Semisynthetic DNA-Protein Conjugates for Biosensing and Nanofabrication", Angew Chem Int, 2010, 49:1200-16.

Niemeyer, C.M., "Bioorganic Applications of Semisynthetic DNA-Protein Conjugates", Chem Eur J, 2001, 7/15:3188-95.

Ollivier et al., "Synthesis of Oligonucleotide-Peptide Conjugates Using Hydrazone Chemical Ligation," Tetrahedron Letters, 2002, 43:997-999.

Ornatsky et al., Journal of Immunological Methods, Jul. 2010, 361:1-20.

Sano et al., "Immuno-PCR: Very Sensitive Antigen Detection by Means of Specific Antibody-DNA Conjugates", Science, Oct. 2, 1992, 258:120-22.

Schroeder et al., "User Configurable Microfluidic Device for Multiplexed Immunoassays Based on DNA-Directed Assembly", Anal Chem, 2009, 81:1275-79.

Schwartz, Methods and/or Use of Oligonucleotide Conjugates for Assays and Detections, U.S. Appl. No. 61/483,186, filed May 6, 2011.

Schwartz, Methods and/or Use of Oligonucleotide Conjugates for Assays and Detections, U.S. Appl. No. 61/344,931, filed Nov. 22, 2010.

Schwartz, Preparation and/or Purification of Oligonucleotide Conjugates, U.S. Appl. No. 61/282,434, filed Feb. 12, 2010.

Scouten, et al., "Reversible Immobilization of Antibodies on Magnetic Beads", Anal Biochem, 1992, 205:313-18.

Tyagi and Kramer, Nature Biotechnology, Mar. 1996, 14:303-308.

Antibody-Oligonucleotide All-in-One Conjugation Kit User Manual, Catalog No. A-9202-001, V.06.18.10, Solulink (2009).

Final Office Action received for U.S. Appl. No. 13/302,877 dated Jul. 8, 2020, 32 pages.

Final Office Action received for U.S. Appl. No. 13/302,877 dated Feb. 21, 2020, 33 pages.

Non-Final Office Action received for U.S. Appl. No. 13/302,877 dated Feb. 11, 2019, 30 pages.

Non-Final Office Action received for U.S. Appl. No. 13/302,877 dated Jun. 8, 2018, 27 pages.

Final Office Action received for U.S. Appl. No. 13/302,877 dated Nov. 21, 2017, 29 pages.

Non-Final Office Action received for U.S. Appl. No. 13/302,877 dated May 22, 2017, 27 pages.

Non-Final Office Action received for U.S. Appl. No. 13/302,877 dated Jan. 30, 2015, 17 pages.

Non-Final Office Action received for U.S. Appl. No. 13/302,877 dated Jun. 18, 2014, 18 pages.

Final Office Action received for U.S. Appl. No. 13/302,877 dated Oct. 30, 2013, 17 pages.

Final Office Action received for U.S. Appl. No. 13/302,877 dated Jan. 3, 2013, 43 pages.

EPO Communication and Communication Annex in corresponding European Appl. 11842603.0, dated Dec. 19, 2014.

Extended European Supplementary Search Report, dated Apr. 11, 2014, in corresponding European Application No. 11842603.0-1404.

International Preliminary Report on Patentability dated May 22, 2013 for PCT/US2011/061874.

International Search Report dated May 25, 2012 for PCT/US2011/061874.

International Search Report dated May 20, 2011 for PCT/US2011/024439.

```
                          SEQUENCE LISTING

<160> NUMBER OF SEQ ID NOS: 27

<210> SEQ ID NO 1
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 1

His His His His His His
1               5

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 2
gactgacgaa ccgctttgcc tgactgatcg ctaaatcgtg                           40

<210> SEQ ID NO 3
<211> LENGTH: 60
<212> TYPE: DNA
<213> ORGANISM: Artificial Sequence
<220> FEATURE:
```

<223> OTHER INFORMATION: Synthetic oligonucleotide

<400> SEQUENCE: 3
ttgcatcgcc cttggactac gactgacgaa ccgctttgcc tgactgatcg ctaaatcgtg    60

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
cctgcgtcgt ttaaggaagt ac    22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
gtacttcctt aaacgacgca gg    22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
ggtccggtca taaagcgata ag    22

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
cttatcgctt tatgaccgga cc    22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
gtggaaagtg gcaatcgtga ag    22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
cttcacgatt gccactttcc ac    22

```
<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gctgacatag agtgcgatac                                                      20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gtatcgcact ctatgtcagc                                                      20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
tgtgctcgtc tctgcatact                                                      20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
agtatgcaga gacgagcaca                                                      20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
atgtacgtga gatgcagcag                                                      20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ctgctgcatc tcacgtacat                                                      20

<210> SEQ ID NO 16
<211> LENGTH: 51
<212> TYPE: DNA
<213> ORGANISM: Artificial Sequence
<220> FEATURE:
<223> OTHER INFORMATION: Synthetic oligonucleotide
```

```
<400> SEQUENCE: 16
ggtccggtca taaagcgata atgttaattg tacttcctta aacgacgcag g          51

<210> SEQ ID NO 17
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 17
gtggaaagtg gcaatcgtga agttaattgt acttccttaa acgacgcagg            50

<210> SEQ ID NO 18
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 18
gctgacatag agtgcgatac ttaattgtac ttccttaaac gacgcagg              48

<210> SEQ ID NO 19
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 19
tgtgctcgtc tctgcatact ttaattgtac ttccttaaac gacgcagg              48

<210> SEQ ID NO 20
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 20
atgtacgtga tgcagcagtt aattgtactt ccttaaacga cgcagg                46

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ggaagcggtg ctatccatct                                             20

<210> SEQ ID NO 22
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 22
cacccagccg atgacctctt agtttcacgc                                  30

<210> SEQ ID NO 23
<211> LENGTH: 40
```

```
<212> TYPE: DNA
<213> ORGANISM: Artificial Sequence
<220> FEATURE:
<223> OTHER INFORMATION: Synthetic oligonucleotide

<400> SEQUENCE: 23
cacccagccg atgacctctt agtttcacgc aaagcacacg                        40

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
agatggatag caccgcttcc                                              20

<210> SEQ ID NO 25
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 25
gcgtgaaact aagaggtcat cggctgggtg                                   30

<210> SEQ ID NO 26
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 26
cgtgtgcttt gcgtgaaact aagaggtcat cggctgggtg                        40

<210> SEQ ID NO 27
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 27
ttaattaatt aattaattaa ttttaattaa ttaattaatt aattgtactt ccttaaacga  60
cgcagg                                                             66
```

METHODS AND/OR USE OF OLIGONUCLEOTIDE CONJUGATES FOR ASSAYS AND FLOW CYTOMETRY DETECTIONS

CROSS-REFERENCE

Each of the following documents are incorporated herein by reference in its entirety: U.S. Pat. Nos. 7,462,689; 6,800,728; 7,173,125; 6,686,461; 7,102,024; 6,911,535; 6,217,845; 5,753,520; 5,420,285; 5,679,778; and 5,206,370. U.S. patent application Ser. No. 11/787,932, filed on Apr. 18, 2007, now U.S. Patent Publication No. 2008/0221343, published Sep. 11, 2008. U.S. Patent Application No. 61/282,434, filed on Feb. 12, 2010. International Application No. PCT/US2001/09252, filed on Mar. 22, 2001, now World Publication No. WO 2001/70685; International Application No. PCT/US2001/023775, filed on Jul. 27, 2001, now World Publication No. WO 2002/010432; International Application No. PCT/US2002/001161, filed on Jan. 16, 2002, now World Publication No. WO 2002/057422. SoluLink manual, entitled "Antibody-Oligonucleotide All-in-One Conjugation Kit User Manual", Catalog No. A-9201-001, January 2010. This application is a continuation of U.S. patent application Ser. No. 13/302,877, filed on Nov. 22, 2011, now U.S. Patent Publication No. 2012/0258880, which claims the benefit of U.S. Patent Application No. 61/344,931, filed Nov. 22, 2010, and U.S. Patent Application No. 61/483,186, filed May 6, 2011, the entire contents of which are incorporated herein by reference.

STATEMENT REGARDING FEDERALLY SPONSORED RESEARCH OR DEVELOPMENT

This invention was made with Government support under Grant number 5R43AI091340-02 awarded by National Institutes of Health. The government has certain rights in the invention.

INCORPORATION OF SEQUENCE LISTING

A paper copy of the Sequence Listing and a computer readable form of the Sequence Listing containing the file named "EMDM0002_II_ST25.txt", created on Feb. 14, 2022 which is 5,907 bytes in size (as measured in MICROSOFT WINDOWS® EXPLORER), are provided herein and are herein incorporated by reference. This Sequence Listing consists of SEQ ID NOs:1-27.

FIELD

The present disclosure relates to and may be applied to the methods and/or uses of oligonucleotide conjugates for assays and flow cytometry detections and related systems and/or kits.

BACKGROUND

Current diagnostic tools fail to satisfy certain desired requirements for diagnostic assays. For example, current diagnostic tools do not readily diagnose diseases at earlier stages, yield the information required to direct clinicians to treat patients safely with advanced therapeutics, quantify the effectiveness of the new multi-pathogen/component vaccines, correlate information from gene sequencing with the protein expression in cells, aid drug developers to better understand the activities and toxicities of drugs in development from pre-clinical to Phase III, allow scientists to study and understand intra- and inter-cellular interactions, and a wide range of other research-based biological and clinical assays.

One of the bottlenecks of current tools is their limit in the number of assays that can be performed simultaneously or substantially simultaneously. For example, in most cases, current protein diagnostic assays only detect 1-10 protein biomarkers simultaneously, or substantially simultaneously. In the clinic, for example, the prostate cancer PSA assay measures only a single protein, the prostate-specific antigen protein, and the breast cancer Hercept Test measures only a single receptor, the Her2 receptor. However, a multitude of interactions and pathways occur continuously in the cell and many of these interactions and pathways are altered in diseased cells. Therefore, in order to more fully understand the functioning of a cell, including the multi-variant processes conducted within and between normal healthy-cells, as well as the alterations of these cellular processes in various disease states, new technologies are needed to track and correlate a greater number of genetic, protein, and other cellular component changes. Access to this greater amount of information will allow the development of higher content assays, thereby resulting in more informed clinical decisions and improved patient outcomes.

Bioconjugates have been employed in a wide variety of molecular biology applications. For example, bioconjugates are used in biochemical assays and diagnostic assays to improve assay sensitivity. Bioconjugates, such as oligonucleotides conjugated to antibodies or enzymes, have been used as hybridization probes in immunoassays or as probes in the development of sensitive nucleic acid-based diagnostic assays. Such conjugates may be prepared by a variety of methods, such as glutaraldehyde crosslinking, maleimide-thiol coupling, isothiocyanate-amine coupling, hydrazone coupling, oxime coupling, and Schiff base formation/reduction.

Despite the promise that bioconjugates hold in the area of biomedical research, such as improving assay sensitivity, simplifying nucleic acid detection schemes, clinical studies, development of both in vitro and in vivo diagnostic assays as well as in vivo therapies, and the like, bioconjugates have not yet achieved their desired potential in these molecular biology, biomedical and diagnostic applications. This deficiency is due, in part, to the inefficient and less than quantitative preparation of bioconjugates, which may involve multiple steps and may require, for example, the protein, the oligonucleotide, or both, to be modified with the appropriate linking moiety and then purified before being combined and reacted with each other. Often the modification reaction may have a lengthy reaction time and may result in forming an unstable protein or oligomer intermediate that must be purified and used immediately. For these and other reasons, the yields to prepare these bioconjugates are highly variable, and are greatly dependent on what techniques are used. In addition, another issue is that conventional conjugation chemistries lack the flexibility to cost effectively supply the large number of various conjugates users need.

Another reason that has hindered the widespread use of bioconjugates is the methods used to purify and isolate bioconjugates. Because of the inefficiencies in the conjugation chemistries used to prepare bioconjugates, often the resulting bioconjugate product may require several purification steps to obtain a purified bioconjugate, which can have a detrimental effect on the stability or activity of the final bioconjugate, its yield as well as be time consuming and expensive to prepare and/or purify.

Up to this point, the purification of bioconjugates has been accomplished using, for example, size exclusion chromatography, or occasionally, ion exchange chromatography. The requirement for chromatography for purification of bioconjugates has been a significant barrier for the routine use of bioconjugates, such as antibody-oligonucleotide bioconjugates in diagnostic assays. For these and other reasons, the costs of preparing and purifying bioconjugates have been expensive and have been difficult to make with reproducible results.

Developments in conjugation chemistry have improved the efficiency of preparing bioconjugates. For example, SoluLink™ has developed conjugation chemistry that can be used to prepare a biomolecule-oligonucleotide conjugate, such as antibody-oligonucleotide bioconjugate, with at least 80% efficiency. Accordingly, the preparation of bioconjugates using efficient conjugation chemistries has allowed for the ability to explore efficient, mild, robust, simple, high yielding purification or combinations thereof methods to provide bioconjugates, for example, biomolecule-oligonucleotide conjugates, such as antibody-oligonucleotide bioconjugates, in high yield having high purity to facilitate their use in molecular biology, biomedical, and diagnostic research and application.

There still remains a need for methods, systems and or kits that provide a more efficient, robust, mild, simple, high-yielding purification or combinations thereof of such bioconjugates to provide high purity bioconjugates for use in biomedical research and diagnostic assays. There is also a need for methods, systems and/or kits that increase the number of assays that can be performed simultaneously or substantially simultaneously. The present disclosure is directed to address one or more of these problems as well as other problems not addressed in this background.

SUMMARY

Certain embodiments provide for methods of detecting one or more molecular targets in a sample using biomolecule-oligonucleotide conjugates, comprising: i) forming biomolecule-oligonucleotide conjugates at greater than 80% efficiency from at least one or more modified biomolecules and at least one or more modified oligonucleotides, wherein the formed biomolecule-oligonucleotide conjugates comprise one or more detectable components; ii) combining the formed biomolecule-oligonucleotide conjugates with the sample comprising the one or more molecular targets; iii) contacting the one or more molecular targets in the sample with the formed biomolecule-oligonucleotide conjugates; and iv) detecting the contacted one or more molecular targets.

Certain embodiments provide methods for isolating biomolecule-oligonucleotide conjugates, for example, antibody-oligonucleotide conjugates, protein-oligonucleotide conjugates, or peptide-oligonucleotide conjugates, comprising: i) introducing a modified biomolecule into a buffered solution; ii) conjugating the modified biomolecules with at least one modified oligonucleotide at greater than 80% efficiency to form biomolecule-oligonucleotide conjugates and iii) isolating the biomolecule-oligonucleotide conjugates from the conjugation solution by binding the conjugates to an immobilized binder. As an alternative to using an immobilized binder other isolation techniques may also be used, for example, chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

In certain embodiments, detecting a contacted one or more molecular targets, for example, a biomolecule-oligonucleotide conjugate contacted one or more molecular targets, may comprise using one or more of the following, comprising: flow cytometry; immunomagnetic cellular depletion; immunomagnetic cell capture; multiplex bead arrays; microarrays, including antibody arrays, bead arrays, and cellular arrays; solution phase capture; chemiluminescence detection; infrared detection; microscopy, imaging; high content screening (HCS); immunohistochemistry (IHC); immunocytochemistry (ICC); in situ hybridization (ISH); enzyme immuno-assays (EIA); enzyme linked immuno-assays (ELISA); ELISpot; blotting methods, such as a Western blot, Southern blot, and/or Southwestern blot; labeling inside electrophoresis systems, labeling on surfaces, and/or labeling on arrays; PCR amplification; elongation followed by PCR amplification; immunoprecipitation, such as co-immunoprecipitation or chromatin immunoprecipitation; pretargeting imaging or therapeutic agents and/or combinations thereof. In certain embodiments, a kit and/or system for detecting one or more molecular targets in a sample, may comprise one or more prepared, purified and/or isolated molecular probes, such as one or more biomolecule-oligonucleotide conjugates, for example, antibody-oligonucleotide conjugates, protein-oligonucleotide conjugates, or peptide-oligonucleotide conjugates, one or more prepared, purified and/or isolated universal adapters, and/or one or more prepared, purified and/or isolated detectable components, wherein each of the molecular probes, universal adapters, and/or detectable components may comprise one or more spacer groups. In certain embodiments, the kit and/or system for detecting one or more molecular targets in a sample may be used in a method of detecting one or more molecular targets in a sample.

In certain aspects, the immobilized binder may comprise a metal ion wherein the metal ion is a divalent metal ion, a transition metal ion, a divalent transition metal ion, or combinations thereof. In certain aspects, the transition metal ion is selected from the group comprising: nickel ion, zinc ion, copper ion, iron ion and cobalt ion. In certain aspects, the modified antibody may include a histidine-rich region. In certain aspects, the immobilized binder may further comprise an organic chelator selected from the group comprising: iminodiacetic acid, nitrilotriacetic acid and bicinchoninic acid. In certain aspects, the immobilized binder may comprise an immobilized antibody.

In certain aspects, the modified biomolecule, for example, a modified antibody, modified protein, or modified peptide, may comprise a molecular tag incorporated using protein engineering techniques. In certain aspects, the molecular tag may be selected from the group comprising: poly-histidine tag; Flag Tag; Myc-Tag; S-tag; a peptide tag; and/or combinations or derivatives thereof. In certain aspects, the immobilized antibody may be complementary to the molecular tag that is bound to the modified biomolecule. In certain aspects, the immobilized antibody may be raised against the molecular tag that is bound to the modified biomolecule. The molecular tag may be a peptide tag. In certain aspects, the immobilized binder may be an antibody raised against the conjugative linker joining the modified biomolecule to the at least one modified oligonucleotide.

In certain embodiments, the conjugating efficiency of forming a molecular probe, such as a biomolecule-oligonucleotide conjugate, is greater than about 80%, 85%, 90%, 92%, 95%, 96%, 97%, 98%, 98.5%, or 99%. In certain embodiments, the conjugating efficiency of forming a molecular probe, such as a biomolecule-oligonucleotide conjugate, is at least about 85%, 90%, 92%, 95%, 96%, 97%, 98%, 98.5%, or 99%.

In certain embodiments, the conjugating efficiency of forming a detectable component, comprising one or more signal generating moieties conjugated directly to an oligonucleotide sequence complementary to the oligonucleotide sequence of a molecular probe or an oligonucleotide sequence complementary to the oligonucleotide sequence of a universal adapter, is greater than about 80%, 85%, 90%, 92%, 95%, 96%, 97%, 98%, 98.5%, 99%. In certain embodiments, the conjugating efficiency of forming a detectable component, comprising one or more signal generating moieties and an oligonucleotide sequence complementary to the oligonucleotide sequence of a molecular probe or an oligonucleotide sequence complementary to the oligonucleotide sequence of a universal adapter, is at least about 85%, 90%, 92%, 95%, 96%, 97%, 98%, 98.5%, or 99%. In certain embodiments, the conjugating efficiency of forming a detectable component, comprising one or more signal generating moieties conjugated indirectly, via a scaffold, to an oligonucleotide sequence complementary to the oligonucleotide sequence of a molecular probe or an oligonucleotide sequence complementary to the oligonucleotide sequence of a universal adapter, is greater than about 80%, 85%, 90%, 92%, 95%, 96%, 97%, 98%, 98.5%, or 99%. In certain embodiments, the conjugating efficiency of forming a detectable component, comprising a scaffold, comprising one or more signal generating moieties, conjugated directly to an oligonucleotide sequence complementary to the oligonucleotide sequence of a molecular probe or an oligonucleotide sequence complementary to the oligonucleotide sequence of a universal adapter, is greater than about 80%, 85%, 90%, 92%, 95%, 96%, 97%, 98%, 98.5%, or 99%.

in certain embodiments, the biomolecule-oligonucleotide conjugates, such as antibody-oligonucleotide conjugates or protein-oligonucleotide conjugates, comprises on average at least 0.5 modified oligonucleotides per biomolecule. For example, the modified antibody (e.g. biomolecule-oligonucleotide conjugate) is prepared from an IgG, IgA, IgE, or IgM type antibody. In certain aspects, the modified antibody comprises an antibody that has been prepared by attaching at least one moiety comprising a reactive linker capable of conjugating to a modified oligonucleotide. This at least one moiety may be attached by a covalent bond. Furthermore, the at least one moiety may comprise a spacer group, for example, a polymerized ethylene oxide, such as PEG or PEO.

In certain aspects, the modified biomolecules, for example, the modified antibodies, modified proteins, or modified peptides may be prepared by attaching at least one moiety comprising a reactive linker capable of conjugating to a modified oligonucleotide. This at least one moiety may be attached by a covalent bond. The modified biomolecules may further comprise a molecular tag. Furthermore, the at least one moiety may comprise a spacer group, for example, a polymerized ethylene oxide, such as PEG or PEO.

In certain embodiments, the at least one moiety comprising a reactive linker may be HyNic (6-HydrazinoNicotinamide). In certain aspects, the modified biomolecule, for example, modified antibody, modified protein, or modified peptide may comprise a HyNic-modified biomolecule (i.e., covalently modified to display a hydrazinonicotinate reactive moiety). The modified oligonucleotide may also comprise a 4-FB-modified oligonucleotide (i.e., covalently modified to display a 4-formylbenzamide moiety). In certain aspects, the modified biomolecule may be a biomolecule that has been modified by attaching at least one moiety that is a reactive linker capable of conjugating to a modified oligonucleotide. The modified biomolecule may further comprise a molecular tag. In certain aspects, the modified biomolecule may comprise an antibody that has been further modified by attaching a biotin that may bind to an avidin or a hapten or peptide that may bind to an antibody or a histidine fusion peptide capable of chelating a metal ion.

In certain embodiments, the conjugate may be formed with a covalent linkage. The covalent linkage may be selected from the group comprising: an amide, an oxime, a hydrazone, a sulfide, an ether, an enol ether, a thiolether, an ester, a triazole and/or a disulfide. The covalent linkage may comprise a hydrazone. The hydrazone may be a bis-arylhydrazone. Furthermore, the covalent linkage may be UV-traceable.

In certain embodiments, the methods of preparing conjugates and the methods of detecting molecular targets disclosed herein may be mild, robust, more efficient, cost effective, simple, and/or combinations thereof as compared to conventional methods. In addition, such methods may provide high purity bioconjugates for use in biomedical applications and/or diagnostic assays.

In certain embodiments, the biomolecule-oligonucleotide conjugates, for example, antibody-oligonucleotide conjugates, protein-oligonucleotide conjugates, or peptide-oligonucleotide conjugates may comprise at least one modified oligonucleotide. In certain embodiments, the biomolecule-oligonucleotide conjugates may comprise a composition of biomolecule-oligonucleotide conjugates having on average between 1.0 and 5, or between 1 and 2.5 modified oligonucleotides conjugated to the biomolecule. In certain embodiments, the methods disclosed yield at least between about 30-80%, 40-80%, 40-70%, 60-80% or 70-80% of an isolated biomolecule-oligonucleotide conjugates, with respect to starting modified biomolecule.

In certain embodiments, the biomolecule-oligonucleotide conjugates, for example, antibody-oligonucleotide conjugates, protein-oligonucleotide conjugates, or peptide-oligonucleotide conjugates may comprise at least one or more detectable fluorophores. For example, at least one or at least two detectable fluorophores. The biomolecule-oligonucleotide conjugates may also comprise at least one or more detectable poly-fluorophores.

In certain embodiments, the least a portion of the biomolecule-oligonucleotide conjugates may comprise at least one or more different modified oligonucleotides, such as two different modified oligonucleotides.

Certain embodiments provide methods for isolating biomolecule-oligonucleotide conjugates comprising: i) conjugating a modified biomolecule with at least one modified oligonucleotide to form biomolecule-oligonucleotide conjugates, wherein greater than 80% of the modified biomolecules are conjugated; ii) adding the conjugation reaction mixture to a column having a stationary phase comprising a binder that has been immobilized to the stationary phase; iii) binding the biomolecule-oligonucleotide conjugates selectively to the immobilized binder; iv) eluting reaction components away from the bound biomolecule-oligonucleotide conjugates and v) isolating the biomolecule-oligonucleotide conjugates by releasing the bound, biomolecule-oligonucleotide conjugates with a displacing agent selective for the binder. As an alternative to using an immobilized binder other isolation techniques may also be used, for example, chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

The preparation methods may be used as part of a kit and/or system of preparing, purifying and/or isolating biomolecule-oligonucleotide conjugates, for example, antibody-oligonucleotide conjugates, protein-oligonucleotide conjugates, or peptide-oligonucleotide conjugates. In certain embodiments, the conjugating efficiency is greater than about 80%, 85%, 90%, 92%, 95%, 96%, 97%, 98%, 98.5%, or 99%. In certain embodiments, the methods disclosed yield at least between about 30-80%, 40-80%, 40-70%, 60-80% or 70-80% of an isolated biomolecule-oligonucleotide conjugates, with respect to starting modified biomolecule.

In certain embodiments, the isolation methods may be used as part of a kit and/or system of preparing, purifying and/or isolating biomolecule-oligonucleotide conjugates, for example, antibody-oligonucleotide conjugates, protein-oligonucleotide conjugates, or peptide-oligonucleotide conjugates. In certain embodiments, the conjugating efficiency is greater than about 80%, 85%, 90%, 92%, 95%, 96%, 97%, 98%, 98.5%, or 99%. In certain embodiments, the methods disclosed yields of at least between about 30-80%, 40-80%, 40-70%, 60-80% or at least between about 70-80% of an isolated biomolecule-oligonucleotide conjugates, with respect to starting modified biomolecule.

In certain embodiments, the detection methods may be used as part of a kit and/or system of preparing, purifying and/or isolating biomolecule-oligonucleotide conjugates, for example, antibody-oligonucleotide conjugates, protein-oligonucleotide conjugates, or peptide-oligonucleotide conjugates, followed by further utilizing the prepared, purified and/or isolated, biomolecule-oligonucleotide conjugates in an assay, for example, in a detection assay, such as in a singleplex or multiplex assay, for example, a singleplex or multiplex immunodetection assay, for detecting one or more biological targets in a sample. In certain embodiments, the conjugating efficiency is greater than about 80%, 85%, 90%, 92%, 95%, 96%, 97%, 98%, 98.5%, or 99%. In certain embodiments, the methods disclosed yield at least between about 30-80%, 40-80%, 40-70%, 60-80% or at least between about 70-80% of an isolated biomolecule-oligonucleotide conjugates, with respect to starting modified biomolecule.

In certain embodiments, the modified biomolecule, for example, a modified antibody, modified protein, or modified peptide, may include a histidine-rich region.

In certain embodiments, the stationary phase used may comprise a water insoluble support. For example, the stationary phase may be agarose, other inert natural, synthetic polymeric materials and/or magnetic.

In certain aspects, the immobilized binder may comprise an immobilized antibody. In certain aspects, the modified biomolecule may further comprise a molecular tag. Furthermore, the immobilized antibody may be selective for the molecular tag that is bound to the modified biomolecule.

In certain embodiments, modified biomolecules are provided. These compounds are prepared, for example, by reaction of a biomolecule of interest with one of the functionalities of a bifunctional reagent. The modified biomolecules are available for conjugation or immobilization using the remaining functional group. Biomolecules for use herein include, but are not limited to, proteins including antibodies, glycoproteins, peptides, oligonucleotides, RNA and/or DNA.

In certain embodiments, modified solid supports, or substantially solid supports, are also provided, including, but not limited to, synthetic polymers, beads, glass, slides, metals and/or particles that have been modified by reaction with a bifunctional reagent to afford modified synthetic polymers, beads, latex, glass, slides, metals, including colloidal metals and/or particles that possess a hydrazino or oxyamino group. Combinations of modified solid supports, or substantially solid supports, are also contemplated. For example, these modified solid, or substantially solid, supports are useful in immobilization of biomolecules that possess or are modified to possess a carbonyl group. The immobilized biomolecules may also be used indiagnostic and/or therapeutic applications.

In certain embodiments, methods for purifying conjugates of biomolecules (for example, biomolecule-oligonucleotide conjugates) may involve metal chelation chromatography that utilizes the interaction of a metal ion, for example, $Ni^{2+}$ ion, $Zn^{2+}$ ion, $Cu^{2+}$ ion, $Fe^{2+}$ ion, or $Co^{2+}$ ion and the antibody. For example, an aqueous mixture of biomolecule-oligonucleotide conjugates and free, or substantially free, modified-oligonucleotide, may be contacted with a water insoluble stationary phase which has the metal ion chelated to the phase. In certain embodiments, the conjugate chelates with the metal ion whereas neither of the specified free modified-oligonucleotide chelate. In certain embodiments, subsequent washing of the phase with a mild buffer may remove, or substantially remove, the unbound modified-oligonucleotide. In certain embodiments, the biomolecule-oligonucleotide conjugates may then be eluted from the phase and recovered in a form free, sufficiently free, or substantially free, of unconjugated modified-oligonucleotide.

In certain embodiments, the biomolecule-oligonucleotide conjugates, for example, antibody-oligonucleotide conjugates, protein-oligonucleotide conjugates, or peptide-oligonucleotide conjugates, may be used in diagnostic and/or therapeutic applications.

Other embodiments, aspects, features, and/or advantages of this technology will become apparent from the following detailed description when taken in conjunction with the accompanying drawings, which are a part of this disclosure and which illustrate, by way of example, certain principles of the disclosed technology.

BRIEF DESCRIPTION OF THE FIGURES

In order to facilitate a more detailed understanding of the nature of certain embodiments disclosed herein, exemplary embodiments of processes, systems, kits, preparations, methods, purifications, or combinations thereof, will now be described in further detail, by way of example only, with reference to the accompanying figures in which.

DETAILED DESCRIPTION

Figure 1:
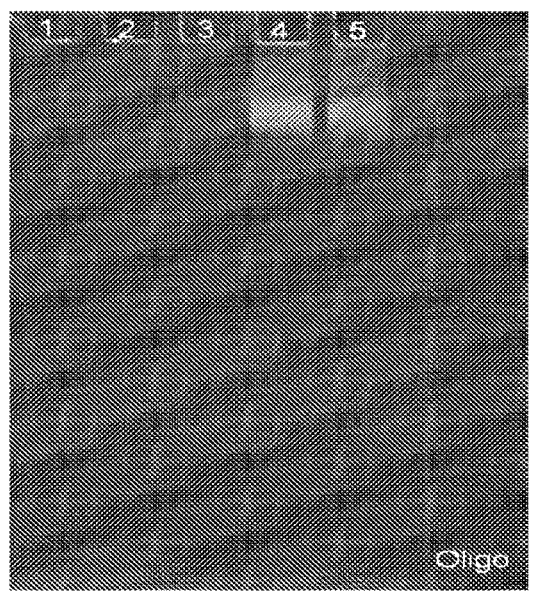
FIG. 1 is a gel electrophoresis loading 400 ng of antibody with SYBR stain, containing the following lanes: Marker (lane 1); SFB-H1A (lane 2); HyNic-Bovine IgG (lane 3); Bovine IgG/H1A crude (lane 4) and Bovine IgG/H1A purified (lane 5), in accordance with certain embodiments.

The following description is provided in relation to several embodiments which may share common characteristics and features. It is to be understood that one or more features of one embodiment may be combinable with one or more features of the other embodiments. In addition, a single feature or combination of features in certain embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The subject headings used in the detailed description are included only for the ease of reference of the reader and should not be used to limit the subject matter found throughout the disclosure or the claims. The subject headings should not be used in construing the scope of the claims or the claim limitations.

Certain Terms and Definitions

The term "molecular probe" may refer to a conjugate, for example, a bioconjugate, comprising a binding moiety and an oligonucleotide, for example a binding moiety conjugated to an oligonucleotide. The molecular probe may comprise a biomolecule conjugated to an oligonucleotide, for example, a biomolecule-oligonucleotide conjugate, such as an antibody-oligonucleotide conjugate, an (antibody fragment)-oligonucleotide conjugate, a protein-oligonucleotide conjugate, or a peptide-oligonucleotide conjugate. The molecular probe may comprise a binding moiety, such as a biomolecule, conjugated to one or more oligonucleotides, for example, conjugated to two oligonucleotides, three oligonucleotides, or four oligonucleotides.

The term "binding moiety" may refer to a moiety, molecule, or substance that binds at least one target in a sample. For example, a binding moiety may comprise a biomolecule, a synthetic molecule, a biopolymer, or a portion of the biomolecule, synthetic molecule, or biopolymer. Suitable binding moiety may include, but is not limited to, an antibody, antibody-fragment, such as a single chain variable fragment ("scFv"), genetically-modified antibody, genetically-modified antibody-fragment, antigen, a protein, a peptide, a carbohydrate, a nuclear receptor, a small molecule, a drug or drug-like molecule, or combinations or derivatives thereof. The binding moiety may be capable of recognizing and binding a target. The binding moiety may also comprise a specific binding affinity for a target. The binding moiety may comprise one or more oligonucleotides, for example, may be conjugated to one or more oligonucleotides. The binding moiety may comprise a spacer group. The binding moiety may also comprise a universal adapter.

The term "biomolecule" may refer to a compound found in nature, a derivative of a compound found in nature, a synthetically modified analog of a compound found in nature, a genetically engineered analog of a compound found in nature, a genetically engineered modified analog of a compound found in nature. For example, biomolecules may be and/or include, but are not limited to, proteins; antibodies; antibody-fragments; haptens; glycoproteins; cell-membrane proteins; enzymes, such as alkaline phosphatase, β-galactosidase, horseradish peroxidase, or urease; peptides; peptide nucleic acids (PNAs); locked nucleic acids (LNAs); genetically engineered peptides; genetically engineered proteins; genetically engineered antibodies; genetically engineered antibody-fragments; oligonucleotides; RNA; DNA; saccharide-containing molecules; monosaccharides; disaccharides; trisaccharides; oligosaccharides; polysaccharides, such as dextran; small molecules, including drug-like molecules; drugs; antigens, such as tumor antigens; pathogens; toxins; polymers, including biopolymers and/or dendrimers; nuclear receptors; nuclear receptor substrates and/or ligands; cytokines; epitopes, including peptide epitopes, antigen epitopes, and/or pathogen epitopes; enzyme substrates; and/or combinations or derivatives thereof.

The term "biopolymer" may refer to a compound found in nature, a derivative of a compound found in nature, a synthetically modified analog of a compound found in nature, a genetically engineered analog of a compound found in nature, a genetically engineered modified analog of a compound found in nature, wherein the biopolymer may be made up of monomeric units. For example, biopolymers may be and/or include, but are not limited to, oligonucleotides, RNA, DNA, peptides, peptide nucleic acids (PNAs), locked nucleic acids (LNAs), derivatized forms of nucleic acids, proteins including antibodies, glycoproteins, enzymes, oligosaccharides, and/or derivatives thereof. Examples of monomeric units include, but are not limited to, nucleotides, nucleosides, amino acids, PNA monomers, monosaccharides, and derivatives thereof.

The term "molecular tag" may refer to a peptide sequence that is attached to a molecule. For example, the molecular tag may be a peptide sequence that is recognized as an antigen by an antibody. The molecular tag may include, but is not limited to, a poly-histidine tag, for example, a Flag Tag, a Myc-Tag, an S-tag, a StrepTag, a calmodulin tag, or a peptide tag that an antibody has been raised against. The molecular tag may be attached to a molecule by synthetic means, by utilization of recombinant methodologies, genetic engineering, or combinations thereof. The molecular tag may be a cloned short stretch of polyhistidines that is attached either onto the amino or carboxy terminus of a protein. The molecular tag may be recognized by an antibody. The molecular tag may form a chelate with a metal ion. For example, the molecular tag may be a poly-histidine tag or a tetra-cysteine tag that may form a chelate with a metal ion. Alternatively, the molecular tag may be a protein domain or other folded peptide domain or domains. For example, the molecular tag may be a glutathione-S-transferase tag, a HaloTag®, a maltose binding protein-tag, a monomeric avidin domain, a protein A immunoglobulin-binding Z domain, a green fluorescent protein-tag, or a thioredoxin-tag. The protein domain may bind to another protein, a peptide or a ligand, by non-covalent or by covalent means.

The term "modified" may refer to a modification of a molecule, such as a biomolecule or a biopolymer, either by chemical synthesis, bio-engineering, or the like. The molecule may be modified by the attachment of a moiety, for example by a covalent bond, onto the molecule, such that once attached, the now modified molecule is capable of reacting with another molecule to form a conjugate. The moiety may attach to the molecule to form the modified molecule includes a reactive group, or a linkable group available to link, i.e., conjugate, to another complementary reactive group attached to another molecule. The modified molecule may comprise a reactive group that is protected, and requires deprotection before being available to link, i.e., conjugate, to another reactive group attached to another molecule. The modification of a molecule may further comprise attaching a spacer group, a molecular tag, a fusion protein comprising a histidine rich region, or combinations thereof.

The term "bioconjugate" may refer to a conjugate of at least two biomolecules, of at least two biopolymers, or at least one biomolecule and at least one biopolymer. The bioconjugate may also include one or more linkages between the individual components that have been conjugated. The bioconjugate may also include one or more spacer groups between the one or more linkages joining the one or more individual components, or the spacer group may be between the individual component and the linkage. For example, the spacer group may include, but is not limited to an ethyleneoxide moiety, a polymer formed from repeating—(—$CH_2$—$CH_2O$—)— moieties, PEG, or PEO.

The term "conjugate" may represent a compound containing at least two components linked together. The individual components may be linked directly through one or more covalent bonds, or one or more ionic bonds, or by chelation, or mixtures thereof. The linkage, or conjugation, may include one or more spacer groups between the one or more linkages joining the one or more individual components, or may be between the individual component and the linkage. The individual components that may be linked together may include, but is not limited to biologically derived biopolymers, modified biopolymers, biologically derived biomolecules, and synthetically derived molecules. For example, the conjugate may comprise a first component, such as a protein, that may be linked, i.e., conjugated, directly through one or more covalent bonds to a second component, such as an oligonucleotide, to form a conjugate. The conjugate and/or the linkage of the conjugate may be stable to thermolysis, stable to hydrolysis, may be biocompatible, or combinations thereof.

The term "hybrid" may refer to a multicomponent composition formed by bringing together at least two conjugates, formed as disclosed herein and comprised of at least one probe conjugate and at least one detector conjugate. A probe conjugate, for example, may be comprised of an antibody, binding protein, nucleic acid aptamer, ligand, chemical compound and/or other molecule specific to a target. In certain embodiments, a hybrid would typically be comprised of a single probe and a single detector wherein the oligonucleotide component of the probe is complementary to the oligonucleotide component of the detector. Certain embodiments are directed to when the probe conjugate is an antibody conjugated to two or three oligonucleotides. Alternatively, the probe conjugate may be an antibody conjugated to one, one to two, two to three, two to four, three to five, four to seven, or five or more oligonucleotides. Alternatively, the probe conjugate may be an antibody conjugated to one oligonucleotide sequence, two sequences, three sequences or three or more sequences. In certain embodiments, a detector is comprised of a detectable component, inclusive of a scaffold, a nucleic acid, and/or other chemical compounds, to which is appended fluorescent or other optically active chemical groups, or binding moieties such as biotin or digoxigenin, or peptides such as epitopes, or proteins such as avidin or phycoerythrin or enzymes, or particles such as quantum dots, or colloidal gold, or latex beads, or surfaces such as glass or polymers or plastics. In certain embodiments, the detector is a dextran or other scaffold covalently modified with multiple fluorophores and a single oligonucleotide. In other embodiments, the detector is an enzyme, fluorescent protein, or other protein conjugated to a single oligonucleotide. Further, a hybrid is formed when complementary oligonucleotides on a probe conjugate and a detector conjugate are allowed to anneal or hybridize, based on complementary and base pairing, to form a double-stranded nucleic acid linkage between the probe component and the detector component. In certain embodiments a small volume, around 10, 20, 25, 30, 40, 45, 50, 55, 60, 65, 70, 80, 90 microliters or less, of a solution of an antibody-oligonucleotide probe conjugate, wherein the antibody molecule bears two or three oligonucleotides, and then to add a specific volume, around 50, 75, 100, 125, 150, 200, 225, 250, 300, or 400 microliters or less, of a solution of a fluorescent dextran bearing a single complementary oligonucleotide. In certain embodiments, the concentrations of the first oligonucleotide and the second complementary oligonucleotide in the final solution would be approximately equal based on moles of bases that are available to base pair, allowing nearly complete formation of double stranded hybridization products. The resulting hybrid would thus comprise a single antibody linked to one, two or three dextran scaffolds, where the linker is comprised of a double stranded nucleic acid. Alternatively, in certain embodiments, a hybrid might contain a greater number of detectors linked to each probe, thereby achieving greater sensitivity. In certain embodiments, an antibody linked to one or more oligonucleotides would be combined with a detector comprised of a particle or bead or surface coated with a complementary oligonucleotide. Here, the hybrid would comprise the particle or bead or surface coated with the probe, linked by double-stranded nucleic acids. In certain embodiments, an antibody is joined to a fluorescent dextran in solution, the resulting hybrid is functionally equivalent, or substantially equivalent, to an antibody which has been covalently labeled with a fluorophore and may be used for biological tests in the same manner as a labeled or tagged antibody, as for direct labeling. In certain embodiments, the probe is allowed to bind to its target prior to formation of the hybrid. Here, in certain embodiments, an antigen is exposed to an antibody-oligonucleotide conjugate as a probe. Then, a detector, such as the complementary oligonucleotide covalently linked to a fluorescent dextran or a fluorescent protein or an enzyme would be introduced. Herein, the annealing or hybridization of the complementary sequences would then bring the detector into proximity with the target via its interaction with the probe. In these embodiments, the hybrid is formed in situ, to perform indirect labeling. In certain embodiments, where the probe is an antibody conjugated to one or more than one oligonucleotide, and the probe is allowed to contact the target, and then, where the detector is a particle or bead or surface coated with the complementary oligonucleotide, and the detector is combined with the target and probe, a hybrid can be formed to capture the target and probe onto the solid material, by hybridization and formation of double stranded nucleic acid linkers between the probe and detector components.

The term "preassembly" or "preassembly hybridization" or preassembled hybrids" may refer to assembly via hybridization of oligonucleotide sequence containing components prior to contacting a sample or binding a target. For example, a molecular probe and a detectable component may be preassembled via hybridization prior to either the molecular probe, the detectable component, or both, contacting the sample, or prior to the molecular probe recognizing or binding a target. In certain embodiments, a molecular probe and a universal adapter may be preassembled via hybridization prior to either the molecular probe, the universal adapter, or both, contacting the sample, or prior to the molecular probe recognizing or binding a target. In certain embodiments, a detectable component and a universal adapter may be preassembled via hybridization prior to either the detectable component, the universal adapter, or both, contacting the sample, or prior to the molecular probe recognizing or binding a target. In certain embodiments, a molecular probe and a detectable component and a universal adapter may be preassembled via hybridization prior to either the molecular probe, the detectable component, the universal adapter, or combinations thereof, contacting the sample, or prior to the molecular probe recognizing or binding a target.

The term "linkage" may refer to the connection between two molecules, for example, the connection between two modified molecules. The linkage may be formed by the formation of a covalent bond. Suitable covalent linkage may include, but is not limited to the formation of an amide bond, an oxime bond, a hydrazone bond, a triazole bond, a sulfide bond, an ether bond, an enol ether bond, an ester bond, or a disulfide bond. The hydrazone bond may be, for example, a bis-arylhydrazone bond. The linkage may provide a UV-traceable characteristic that may be used to detect or quantify the amount of conjugate formed.

The term "spacer group" may refer to a molecular moiety or molecular segment that may join atoms, molecules, or functional groups together through chemical bonds. Suitable spacer groups may be of sufficient length or size such that the steric hindrance or steric clashes between the joined components may be minimized. In certain embodiments, a molecular probe, such as a biomolecule-oligonucleotide conjugate may comprise a spacer group located between the biomolecule and the oligonucleotide. The spacer group may, for example, minimize steric hindrance between two or more oligonucleotides on a single biomolecule, such as an antibody; may minimize steric hindrance between a signal generating moiety conjugated to an oligonucleotide; and/or may minimize steric hindrances between multiple signal generating moieties on a single detectable component and the oligonucleotide on said detectable component. The spacer group may increase the solubility of the detectable component or the molecular probe; may reduce steric hindrance and thereby improve detection efficiency; may prevent unwanted interactions by shielding the joined components; may provide a general and significant lower non-specific background for the detection method and/or system; may reduce steric hindrance and thereby increase the binding affinity of the molecular probe and/or the binding moiety for a particular target; may reduce steric hindrance and thereby decrease the level of the background and risk of false positive detection signals; may reduce steric hindrance and thereby increase the hybridization of the molecular probe with the detectable component and/or universal adapter; may prevent or minimize the reduction of signal that is generated from a detectable component when the detectable component is in close proximity to another detectable component, such as when one signal generating moiety in close proximity to another signal generating moiety; or combinations thereof. The spacer may be stable to thermolysis, stable to hydrolysis, may be biocompatible, or combinations thereof. Suitable spacer groups may include, but are not limited to an ethyleneoxide moiety, a polymer formed from repeating—($-CH_2-CH_2O-$)—moieties, such as polymerized ethylene oxide, for example, polyethylene glycol (PEG); polyethylene oxide (PEO); 6-amino-hexanoic acid; succinimyl 4-(N-maleimidomethyl) cyclohexan-1-carboxylate (SMCC). The spacer group may also be a homobifunctional spacer group, such as divinyl sulfone (DVS), glutaric dialdehyde, hexane di-isocyanate, dimethylapimidate, 1,5-difluoro-2,4-dinitrobenzene. In certain embodiments, the spacer group may be a heterobifunctional spacer group, such as N-gamma-maleimidobutyryloxy succinimide ester (GMBS). The spacer group may be a zero length spacer groups, such as 1-ethyl-3-(3-dimethylaminopropyl)carbodiimide.

The term "complementary reactive groups" may represent those groups that, when reacted together, form a covalent linkage. For example, a hydrazino group may be complementary to a carbonyl derivative. For example, an oxyamino group may also be complementary to a carbonyl derivative. For example, an amino reactive group may refer to moieties that may react directly with amine moieties forming amide bonds. For example, a thiol reactive group may refer to moieties that may react directly with sulfhydryl groups forming stable sulfide bonds.

The term "derivative of a compound" may include, for example, a salt, ester, enol ether, enol ester, solvate or hydrate thereof that may be prepared. Salts may include, but are not limited to, pharmaceutically acceptable salts; amine salts; alkali metal salts, such as but not limited to lithium, potassium and sodium; alkali earth metal salts, such as but not limited to barium, calcium and magnesium; transition metal salts, such as but not limited to nickel, zinc, copper, cobalt, and iron; and other metal salts, such as but not limited to sodium hydrogen phosphate and disodium phosphate; and also may include, but is not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. For example, esters may include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Enol ethers may include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Enol esters may include, but are not limited to, derivatives of formula C═C(OC(O)R) where R is hydrogen, alkyl, alkenyl, alkynyl, aryl, heteroaryl, aralkyl, heteroaralkyl, cycloalkyl or heterocyclyl. Solvates and hydrates are complexes of a compound with one or more solvent or water molecule, for example, 1 to about 100, 1 to about 10, 1 to about 2, 3 or 4, solvent or water molecules.

The term "amino acid" may refer to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

The term "synthetic molecule" may refer to a small molecule or polymer that is not naturally derived.

In certain embodiments, the compounds provided herein may contain chiral centers. Such chiral centers may be of either the (R) or (S) configuration, or may be mixtures thereof. For example, the compounds provided herein may be enantiomerically pure, diastereomerically pure, or stereoisomerically pure. The compounds provided herein may also be stereoisomeric mixtures or diastereomeric mixtures. For example, in the case of amino acid residues, each residue may be of either the L or D form. The preferred configuration for naturally occurring amino acid residues is L.

The term "oligonucleotide" or "oligonucleotide sequence" or "oligo" or "oligonucleotide-barcode tag" or "oligo-barcode tag" may refer to a nucleic acid, including, but not limited to, a ribonucleic acid (RNA); a deoxyribonucleic acid (DNA); a mixed ribonucleotide-deoxyribonucleotide, i.e., the oligonucleotide may include ribose or deoxyribose sugars or a mixture of both; and analogs thereof; of various lengths; including chromosomes and genomic material, such as PCR products or sequencing reaction products, for example, DNA including double and single stranded forms. Single stranded forms of the oligonucleotides are also provided. Alternatively, the oligonucleotide may include other 5-carbon or 6-carbon sugars, such as, for example, arabinose, xylose, glucose, galactose, or deoxy derivatives thereof or other mixtures of sugars. In certain embodiments, the oligonucleotide may refer to nucleic acid molecules of 2-2000 nucleosides in length. In certain embodiments, the oligonucleotide sequence and/or an oligonucleotide sequence complementary to the oligonucleotide sequence, may comprise a 3'-oligonucleotide, a 5'-oligonucleotide, a phosphorothioate, an LNA, a PNA, a morpholino, other alternative backbones, or combinations or derivatives thereof. Suitable oligonucleotide may be composed of naturally occurring nucleosides adenosine, guanosine, cytidine, thymidine and uridine, modified nucleosides, substituted nucleosides or unsubstituted nucleosides, purine or pyrimidine base, or combinations thereof. Such purine and pyrimidine bases include, but are not limited to, natural purines and pyrimidines such as adenine, cytosine, thymine, guanine, uracil, or other purines and pyrimidines, such as isocytosine, 6-methyluracil, 4,6-di-hydroxypyrimidine, hypoxanthine, xanthine, 2,6-diaminopurine, 5-azacytosine, 5-methyl cytosine, and the like. The nucleosides may also be unnatural nucleosides. The nucleosides may be joined by naturally occurring phosphodiester linkages or modified linkages. The nucleosides may also be joined by phosphorothioate linkages or methylphosphonate linkages.

The term "nucleobase" may refer to a heterocyclic moiety that is found in naturally occurring oligonucleotides, including ribonucleic acids (RNA) and deoxyribonucleic acids (DNA), and analogs thereof, including deaza analogs. The nucleobase may include, but is not limited to, cytosines, uracils, adenines, guanines and thymines, and analogs thereof including deaza analogs.

The term "nucleotide analog" may refer to a peptide nucleic acid (PNA) and/or locked nucleic acid (LNA).

The term "universal adapter" may refer to a substance that may be capable of linking, for example, by hybridization, a molecular probe to a detectable component. For example, a universal adapter may comprise at least two oligonucleotide sequence segments. The universal adapter may further comprise at least one polymer and/or at least one spacer group. A universal adapter comprising the at least two oligonucleotide sequence segments, may, for example, specifically hybridize a first oligonucleotide sequence segment of the at least two oligonucleotide sequence segments to a molecular probe, and specifically hybridize a second oligonucleotide sequence segment of the at least two oligonucleotide sequence segments to a detectable component. A universal adapter may comprise more than two oligonucleotide sequence segments, for example, multiple segments of the same oligonucleotide sequence or multiple different oligonucleotide sequences. The universal adapter may further be used to link one type of molecular probe to one or more than one different detectable components, or vice versa. The universal adapter may also function as "master template" to link a molecular probe to several different detectable components. A universal adapter may link detectable component to one or more different kinds of molecular probes. A universal adapter may enhance and/or increase the signal generated, and subsequently detected, from a hybridized molecular probe comprising a bound target and one or more detectable components, one or more signal generating moieties, and/or combinations thereof. In certain embodiments, the universal adapter comprising one or more of the same oligonucleotide sequence segments may specifically hybridize to one or more detectable components, which may increase the number of signal generating moieties linked to a given molecular probe bound to a target in a sample, wherein the molecular probe is hybridized to said universal adapter.

The term "detectable component" may refer to a molecule comprising one or more signal generating moieties and at least one oligonucleotide sequence that allow for the detection of the presence of a target, such as a biological target, in a sample, in certain embodiments. The at least one oligonucleotide sequence may be capable of linking or binding, such as by hybridization, directly to a molecular probe or indirectly to a molecular probe through an optional universal adaptor. The detectable component may comprise a signal generating moiety conjugated directly to an oligonucleotide sequence. The detectable component may comprise one or more signal generating moieties and an oligonucleotide sequence, for example, one or more signal generating moieties conjugated directly to an oligonucleotide sequence. The detectable component may comprise one or more signal generating moieties and an oligonucleotide sequence, for example, one or more signal generating moieties conjugated indirectly to an oligonucleotide sequence. The detectable component may comprise one or more signal generating moieties, an oligonucleotide sequence, and a scaffold, for example, one or more signal generating moieties conjugated directly scaffold comprising an oligonucleotide sequence, for example, a scaffold conjugated to an oligonucleotide sequence. For example, the oligonucleotide sequence may be conjugated directly to a scaffold, for example a dextran or another hydrophilic polymer or a dendrimer, comprising one or more signal generating moieties. The oligonucleotide sequence of the detectable component may be a complementary oligonucleotide sequence, for example, the oligonucleotide sequence of the detectable component may be complementary to an oligonucleotide sequence of a molecular probe.

The term "signal generating moiety" may refer to a molecule which may be detected directly or indirectly so as to reveal the presence of a target in the sample. In certain embodiments, a signal generating moiety may be "directly detectable" such that it may be detected without the need of an additional molecule; for example, a directly detectable signal generating moiety may be a fluorescent dye, a luminescent species, a phosphorescent species, a radioactive substance, a nanoparticle, a diffracting particle, a raman particle, a metal particle, a magnetic particle, a bead, an RFID tag, or a microbarcode particle or other combinations thereof. In certain embodiments, a signal generating moiety may be "indirectly detectable" such that it may require the employment of one or more additional molecules to be detected; for example, an indirectly detectable signal generating moiety may be an enzyme that effects a color change in a suitable substrate, as well as other molecules that may be specifically recognized by another substance carrying a label or react with a substance carrying a label, an antibody, an antigen, a nucleic acid or nucleic acid analog, a ligand, a substrate, or a hapten. In certain embodiments, a signal generating moiety may be a fluorophore, sometimes called a fluorochrome (a fluorescent compound); chromophores; biofluorescent proteins, such as phycoerythrin (R-PE), allophycocyanin (APC) and Peridinin Chlorophyll Protein Complex (PerCP); fluorophore labeled DNA dendrimers; Quantum Dots or other fluorescent crystalline nanoparticles; tandem dyes, such as a FRET dye; a chemiluminescent compound, a electrochemiluminescent label, a bioluminescent label, a polymer; a polymer particle; a bead or other solid surface; a Raman particle; a heavy metal chelate; gold or other metal particles or heavy atoms; a spin label; a radioactive isotope; a secondary reporter; a hapten; aminohexyl; pyrene; a nucleic acid or nucleic acid analog; a protein; a peptide ligand or substrate; a receptor; an enzyme; an enzyme that catalyzes a color change in a substrate; an enzyme substrate; an antibody; an antibody fragment; an antigen; or combinations or derivatives thereof.

The term "scaffold" may comprise a polymer, such as a hydrophilic polymer, a biopolymer or a biologically inspired polymer, for example, an acrylate polymer; a substituted polyether; a substituted polystyrene; a polyethylene oxide; a nucleic acid; a polysaccharide molecule, such as a dextran; a linear polymer; a branched polymer; a dendrimer; or combinations or derivatives thereof. The scaffold, such as a dendrimer, may be labeled by standard techniques, for example, by the use of fluorochromes (or fluorescent compounds), enzymes (e.g., alkaline phosphatase and horseradish peroxidase), heavy metal chelates, secondary reporters or radioactive isotopes.

The term "sample" may refer to a composition potentially containing a target, such as a biological target.

The term "complex sample" may refer to a sample of material to be analyzed that has multiple targets. For example, the sample may contain at least 2, 5, 10, 15, 20, 30, 50, 75, 100, 500, 1000, 5000, 10,000, 50,000, or 100,000 targets. In certain embodiments, the range of targets may be between 5 to 50, 10 to 100, 25 to 100, 50 to 250, 50 to 5000, 500 to 10,000, 250 to 50,000, 50 to 100,000, 15 to 500, 15 to 1000, 15 to 10,000, or 20 to 10,000. This sample could be heterogeneous or homogeneous mixture. The complex sample may also include those described in the term "sample" provided herein.

The terms "targets" or "biological targets" may refer to one or more substances potentially present in a sample that are capable of detection.

The term "detection assay" or "detection method" or "method of detection" or "method for detection" may refer to a singleplex detection assay or multiplex detection assay.

Molecular Probes, Antibodies and/or Biomolecule-Oligonucleotide Conjugates

A suitable molecular probe may comprise, for example, a monoclonal antibody, polyclonal antibody, antibody fragment, or a protein fragment, may be conjugated to an oligonucleotide, which may be detected by a detectable component, comprising a complementary oligonucleotide sequence and one or more signal generating moieties, by hybridizing the oligonucleotide of the molecular probe to the complementary oligonucleotide sequence of the detectable component. in certain embodiments, the complementary oligonucleotide may be conjugated to one or more signal generating moieties. The complementary oligonucleotide may be conjugated to a scaffold, such as a dendrimer or a dextran, comprising the one or more signal generating moieties, such as fluorophors, secondary reporters, for example, a biotin, an enzyme, a heavy metal chelate, or a radioactive isotope, wherein the one or more signal generating moieties may be detected. The one or more signal generating moieties may comprise combinations of different signal generating moieties. In certain embodiments, the molecular probe may comprise a binding moiety conjugated to a hapten, wherein the hapten is further bound to a receptor-oligonucleotide conjugate, for example, antibody-biotin conjugate, wherein the biotin is further bound to a Streptavidin-oligonucleotide conjugate, or for example, an antibody-peptide conjugate, wherein the peptide is further bound to an anti-peptide-antibody-oligonucleotide conjugate.

A suitable molecular probe may comprise a binding moiety and an oligonucleotide, for example, a biomolecule-oligonucleotide conjugate, such as an antibody-oligonucleotide conjugate, an (antibody fragment)-oligonucleotide conjugate, a protein-oligonucleotide conjugate, a (protein fragment)-oligonucleotide conjugate, a peptide-oligonucleotide conjugate, may have a molecular weight of between about 15,000 Daltons and about 450,000 Daltons. For example, the molecular probe, may have a molecular weight of between about 25,000 and about 400,000 Daltons, about 30,000 and about 350,000 Daltons; about 15,000 and about 300,000 Daltons; 50,000 and about 250,000 Daltons; about 50,000 and about 200,000 Daltons; about 15,000 and about 75,000 Daltons; or about 15,000 and about 50,000 Daltons. The molecular probe, may have a molecular weight of less than or about 450,000 Daltons, 400,000 Daltons, 350,000 Daltons, 300,000 Daltons, 275,000 Daltons, 225,000 Daltons, 200,000 Daltons, 175,000 Daltons, 150,000 Daltons, 120,000 Daltons, 100,000 Daltons, 80,000 Daltons, 60,000 Daltons, 50,000 Dalton, 40,000 Daltons, 30,000 Daltons; or 20,000 Daltons. The molecular weight of the molecular probe may affect the specific binding affinity to a target.

As used herein "specific binding" or "specifically binding" or "binding affinity" in certain embodiments may mean having a binding affinity as measured by dissociation constant for a specific target at less than $10^{-4}$ molar (M), $10^{-5}$M, $10^{-6}$ M, $10^{-7}$ M, $10^{-8}$M, $10^{-9}$M, $10^{-12}$ M, or $10^{-15}$M.

As used herein the amount of false positives generated by the detection methods may mean, in certain embodiments, events wherein the binding moiety binds to an unintended target in addition to binding to the desired target. Similarly, as used herein the amount of false negatives generated by the detection methods may mean, in certain embodiments, events wherein the binding moiety binds to an unintended target at the expense of binding to the desired target. For example, unintended binding of aggregates, debris, contaminants, plastic, glass or metal contact surfaces, particles, containers, tubes, filters, and/or pipette tips. Another example would be an antibody binding to an antigen for which it has no binding affinity or substantially no binding affinity. In certain embodiments, the amount of false positives may be less than 10%, 7%, 5%, 3% or 1% of the true positives. In certain embodiments, the amount of false positives generated by the detection methods may be less than those of secondary antibody detection methods. In certain embodiments, the amount of false negatives may be less than 10%, 7%, 5%, 3% or 1% of the true positives. In certain embodiments, the amount of false negatives generated by the detection methods may be less than those of secondary antibody detection methods.

As used herein the solubility of a molecular probe, comprising a binding moiety conjugated to one or more oligonucleotides, in certain embodiments may mean a molecular probe having solubility greater than, the same solubility, substantially the same solubility, or at least 98%, 95%, 93%, 90%, 85%, 75%, 65%, or 50% of the solubility of the unconjugated binding moiety. In certain embodiments, the solubility of the molecular probe may be sufficient to minimize the non-specific binding to a target. The solubility of the molecular probe may affect the specific binding affinity to a target. For example, to one or more biological targets.

As used herein neutral charge in certain embodiments may mean wherein the solubility of a molecular probe does not need to be enhanced by the addition of a polycharged species. For example, neutral charge may mean wherein the molecular probe is sufficiently soluble such that further modification of the molecular probe to enhance its solubility is unnecessary. In certain embodiments, neutral charge may mean wherein the molecular probe is sufficiently soluble to be utilized to be provided to the sample such that further modification of the molecular probe to enhance its solubility is unnecessary.

A suitable antibody or immunoglobulin may comprise, for example, natural antibodies, artificial antibodies, genetically engineered antibodies, monovalent antibodies, polyvalent antibodies, monoclonal antibodies, polyclonal antibodies, camelids, monobodies, scFvs and/or fragments or derivatives thereof. In certain applications, the antibody or immunoglobulin molecules may be monoclonal, polyclonal, monospecific, polyspecific, humanized, single-chain, chimeric, camelid single domain, shark single domain, synthetic, recombinant, hybrid, mutated, CDR-grafted antibodies, and/or fragments or derivatives thereof. In certain embodiments, antibodies may be derived from mammal species, for example, rat, mouse, goat, guinea pig, donkey, rabbit, horse, lama, camel, or avian species, such as chicken or duck. The origin of the antibody is defined by the genomic sequence irrespective of the method of production. The antibodies may be of various isotypes, e.g., IgG, IgM, IgA, IgD, IgE or subclasses, e.g., IgG1, IgG2, IgG3, IgG4. The antibodies may be produced recombinantly, or by other means, which may include antibody fragments which can still bind antigen, for example, a Fab, a F(ab)$_2$, Fv, scFv, VhH, and/or V-NAR. The antibody, including an antibody fragment, may be recombinantly engineered to include an epitope, for example, a peptide. In certain embodiments, the epitope may be a Myc tag, a FLAG tag, an HA tag, an S tag, a Streptag, a His tag, a V5 tag. In certain embodiments, the peptide tag may serve as a F1Ash tag, a biotinylation tag, Sfp tag, or other peptide subject to covalent modification. The antibody may be chemically modified to include a hapten, for example a small molecule or a peptide. The hapten may be a nitrophenyl group, a dinitrophenyl group, a digoxygenin, a biotin, a Myc tag, a FLAG tag, an HA tag, an S tag, a Streptag, a His tag, a V5 tag, a ReAsh tag, a F1Ash tag, a biotinylation tag, Sfp tag, or other chemical or peptide tag subject to covalent modification. Inclusion of an epitope or hapten in an antibody or antibody fragment may facilitate subsequent binding of a molecular probe, detectable component, binding moiety, or signal generating moiety. In certain embodiments, peptide tag haptens chemically conjugated to protein binders can be used in conjunction with anti-peptide tag antibody-signal detector conjugates in singleplex and multiplex immunodetection assays, such as immunohistochemistry (IHC), flow cytometry, microscopy, imaging, high content screening (HCS), immunocytochemistry (ICC), immunomagnetic cellular depletion, immunomagnetic cell capture, in situ hybridization (ISH), enzyme immuno-assay (EIA), enzyme linked immuno-assay (ELISA), ELISpot, arrays including bead arrays, multiplex bead array, microarray, antibody array, cellular array, solution phase capture, chemiluminescence detection, infrared detection, blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof. The antibody may include, for example, hybrid antibodies having at least two antigen or epitope binding sites, single polypeptide chain antibodies, bispecific recombinant antibodies (e.g. quadromas, triomes), interspecies hybrid antibodies, and molecules that have been chemically modified and may be regarded as derivatives of such molecules and which may be prepared either by methods of antibody production or by DNA recombination, using hybridoma techniques or antibody engineering or synthetically or semisynthetically.

A suitable polyclonal antibody may be produced through a variety of methods. For example, various animals may be immunized for this purpose by injecting them with an antigen, for example the target biological molecule, or another molecule sharing an epitope of the target biological molecule. Such antigen molecules may be of natural origin or obtained by DNA recombination or synthetic methods, or fragments thereof and the desired polyclonal antibodies are obtained from the resulting sera and may be purified. Alternatively, intact cells that array the target biological molecule may be used. Various adjuvants may also be used for increasing the immune response to the administration of antigen, depending on the animal selected for immunization. Examples of these adjuvants include Freund's adjuvant, mineral gels such as aluminum hydroxide, surfactant substances such as polyanions, peptides, oil emulsions, haemocyanins, dinitrophenol or lysolecithin.

A suitable primary antibody may contain an antigen binding region which can specifically bind to an antigen target in a sample, such as an immunohistochemistry sample, may be employed. For example, a primary antibody may be comprised within a primary binding moiety or a primary molecular probe. A suitable secondary antibody may contain an antigen binding region which can specifically bind to the primary antibody, for example, the constant region of the primary antibody. The secondary antibody may be conjugated to a polymer. The polymer may be conjugated with between about 2-20 secondary antibodies, or may be conjugated with between about 1-5 tertiary antibodies, such as 1, 2, 3, 4, or 5 tertiary antibodies. The secondary antibody may act as a secondary binding moiety, while in other embodiments, the secondary antibody may act as molecular probe, recognizing the target, such as an antigen, indirectly through a primary antibody. A suitable tertiary antibody may contain an antigen binding region which can specifically bind to the secondary antibody, for example, a constant region of the secondary antibody, or a hapten linked to the secondary antibody or a polymer conjugated to the secondary antibody. For example, the tertiary antibody may be conjugated to a polymer, such as between about 1-20 tertiary antibodies. The polymer may be conjugated with between about 1-5 tertiary antibodies, such as 1, 2, 3, 4, or 5 tertiary antibodies. The tertiary antibody may act as a tertiary binding moiety. In other embodiments, the tertiary antibody may act as molecular probe, recognizing the target, such as an antigen, indirectly through a primary antibody and a secondary antibody.

The stoichiometry of the conjugation reaction to form the biomolecule-oligonucleotide conjugates, for example, the antibody-oligonucleotide conjugates, protein-oligonucleotide conjugates, (protein fragment)-oligonucleotide conjugates, or peptide-oligonucleotide conjugates, may comprise one equivalent of modified biomolecule and at least 0.5 equivalents of modified oligonucleotide. Other examples are at least 1.0 equivalent, at least 1.5 equivalents, at least 2.0 equivalents, at least 2.5 equivalents, at least 3.0 equivalents, at least 3.5 equivalents, or at least 4.0 equivalents of modified oligonucleotide. The stoichiometry of the conjugation reaction to form the biomolecule-oligonucleotide conjugates, may comprise one equivalent of modified biomolecule and between about 0.5 and about 2.0 of modified oligonucleotide, for example, between about 1.5 and about 2.5 equivalents, between about 2.0 and about 2.5 equivalents, between about 2.0 and about 3.0 equivalents, between about 2.5 and about 3.5 equivalents, between about 3.0 and about 3.5 equivalents, between about 3.0 and about 4.0 equivalents, or between about 3.5 and about 4.5 equivalents modified oligonucleotide. In certain embodiments, the stoichiometry of the conjugation reaction may be adjusted to form biomolecule-oligonucleotide conjugates, for example, antibody-oligonucleotide conjugates, protein-oligonucleotide conjugates, or peptide-oligonucleotide conjugates, that retain sufficient immunoreactivity of the biomolecule, such as an antibody, that has been conjugated.

Suitable molecular probes, such as biomolecule-oligonucleotide conjugates, for example, antibody-oligonucleotide conjugates, protein-oligonucleotide conjugates, (protein fragment)-oligonucleotide conjugates, or peptide-oligonucleotide conjugates, may be the conjugation product of one modified biomolecule and on average between 1.0 and 2.0 modified oligonucleotides that have conjugated to the modified biomolecule. For example, the biomolecule-oligonucleotide conjugates may be the conjugation product of one modified biomolecule and on average between 1.0 and 2.0, between 1.5 and 2.5, between 2.0 and 2.5, between 2.0 and 3.0, between 2.5 and 3.5, between 2.5 and 3.0, between 3.0 and 4.0, between 3.0 and 3.5, or between 3.5 and 4.5 modified oligonucleotides that have conjugated to the modified biomolecule.

Suitable molecular probes, such as biomolecule-oligonucleotide conjugates, for example, antibody-oligonucleotide conjugates, protein-oligonucleotide conjugates, (protein fragment)-oligonucleotide conjugates, or peptide-oligonucleotide conjugates, may comprise on average a molar ratio of about 1:1 to about 1:4.5, about 1:1 to about 1:4, about 1:1 to about 1:3.5, about 1:1 to about 1:3, about 1:1 to about 1:2.5, about 1:1 to about 1:2 or about 1:1 to about 1:1.5 biomolecule to oligonucleotides. In certain embodiments, the molecular probes may comprise on average a molar ratio of about 1:1, 1:2, 1:3, or 1:4 biomolecule to oligonucleotides.

A suitable molecular probe may comprise a binding specificity for an analyte, such as a target and/or biological target, for example, a binding specificity of about $10^{-4}$ M to about $10^{-15}$ M, about $10^{-5}$ M to about $10^{-15}$ M, about $10^{-6}$ M to about $10^{-15}$ M, about $10^{-7}$ M to about $10^{-15}$ M, about $10^{-9}$ M to about $10^{-15}$ M, or about $10^{-12}$ M to about $10^{-15}$ M for an analyte.

The biomolecule-oligonucleotide conjugates may be a mixture of biomolecule-oligonucleotide conjugates having modified oligonucleotides that have been conjugated to the modified biomolecule, but wherein the linkage points of the oligonucleotides to the biomolecule are not uniformly identical across the entire sample. For example, a prepared, purified and isolated biomolecule-oligonucleotide conjugates sample may have one biomolecule-oligonucleotide conjugate that has one set of linkage points for each of the oligonucleotides conjugated to the biomolecule, and the same sample may have a different biomolecule-oligonucleotide conjugate that has a similar number of oligonucleotides conjugated to that biomolecule, but having a different set of linkage points for each of those oligonucleotides conjugated.

Suitable molecular probes may specifically bind to a molecule expressed by diseased cells and another molecular probe may specifically bind to another molecule expressed by disease cells. For example, such embodiments may be useful for diagnosing a disease in a subject where the disease may be better diagnosed by detecting a combination of two or more markers in a sample. In these embodiments, one or more molecular probes that specifically bind to a cell type specific marker also can be utilized. The sample may be from various sources, and may be a particular set of cells or group of cells from a subject or patient.

Suitable molecular probes may specifically bind to a molecule expressed by a particular organism and another molecular probe may specifically bind to another molecule expressed by the organism. These embodiments may be useful for detecting an organism in a sample where the organism may be better detected by identifying two or more markers in a sample. In certain embodiments, the one or more molecular probes may specifically bind to a cell type specific marker. Such embodiments may be useful for detecting a particular strain of organism in a sample (e.g., a biological sample, a sample from animal meat for human consumption, or an environmental sample), where the strain is specifically detected by a combination of a genus-associated molecule and a species-associated molecule, for example. Such embodiments may be useful for detecting a pathogenic organism in a biological sample for diagnosing a disease caused by the organism (e.g., hepatitis C infection in a human blood sample), and for detecting a particular organism in an environmental sample for agricultural and anti-bioterrorism applications. For example, a molecular probe may be used to detect the presence, absence or levels of beneficial bacteria in soil to determine suitability for growing crops, and for detecting a pathogenic organism such as anthrax in soil or water samples for combating bioterrorism.

Suitable modified biomolecules may be prepared by reaction of a biomolecule of interest with one of the functionalities of a bifunctional reagent. The modified biomolecules are then available for conjugation or immobilization using the remaining functional group. In certain embodiments, the modified biomolecule may comprise one or more of the following, comprising a modified protein; a modified peptide; a modified antibody; a modified glycoprotein; a modified monosaccharide; a modified disaccharide; a modified trisaccharide; a modified polysaccharide; a modified dextran; a modified drug-like molecule; a modified drug; a modified small molecule; a modified pathogen; a modified toxin; a modified polymer; a modified biopolymer; a modified dendrimer; a modified nuclear receptor; a modified nuclear receptor ligand; a modified cytokine; a modified epitope; a modified peptide epitope; a modified antigen epitope; a modified pathogen epitope; a modified enzyme; a modified enzyme substrate; a modified cell-membrane protein; and/or combinations or derivatives thereof.

As used herein the efficiency of the hybridization of a conjugated oligonucleotide sequence to a conjugated complementary oligonucleotide sequence in certain embodiments may mean a conjugated oligonucleotide sequence and conjugated complementary oligonucleotide sequence having a hybridization efficiency of at least 98%, 95%, 93%, 90%, 85%, 75%, 65%, or 50% of the hybridization efficiency of the unconjugated oligonucleotide. In certain embodiments, hybridization of at least 98% of a conjugated oligonucleotide sequence to a conjugated complementary oligonucleotide sequence may be obtained by equimolar concentration of the conjugated complementary oligonucleotide sequence. In some embodiments, hybridization of at least 98% of a conjugated oligonucleotide sequence to a conjugated complementary oligonucleotide sequence may be obtained by providing an excess of the conjugated complementary oligonucleotide sequence, one and one tenth fold, one and one half fold, two fold, five fold, ten fold, one hundred fold, or one thousand fold.

Detection—Multiplex, Signal Generating Moiety

The oligonucleotide sequence on the detectable component may be a unique, distinguishable, and/or specifically designed oligonucleotide sequence complementary to the oligonucleotide sequence of the selected molecular probe. The oligonucleotide sequence on the molecular probe may be a unique, distinguishable, and/or specifically designed oligonucleotide sequence complementary to the oligonucleotide sequence of the selected detectable component. For example, a sample having a first and a second target may be detected by a first molecular probe binding to a first target that is specifically hybridized with a first detectable component having a specifically designed complementary oligonucleotide sequence to the first molecular probe, and a second molecular probe binding to a second target is specifically hybridized with a second detectable component having a specifically designed complementary oligonucleotide sequence to the second molecular probe. This flexibility to design the oligonucleotide sequences of the molecular probes and the detectable components permits the detection of multiple targets in a sample. For example, this permits the specific design of a multi-plex detection system wherein the target-bound molecular probe may be detected with a choice of a great number of signal generating moieties, as compared to a directly labeled binding moiety, such as a labeled secondary antibody. This flexibility permits the specific design of a multi-plex detection system wherein the binding affinity of the molecular probe for the particular target is maintained and unperturbed, as compared to a directly labeled binding moiety, such as a labeled secondary antibody, which may be altered by the presence of one or more signal generating moieties.

Enhanced signal, in certain embodiments, may mean wherein the enhancement of the signal may be related to the structure and nature of the detectable component, such as the structure and nature of the scaffold conjugated to the oligonucleotide. For example, the enhancement of the signal may be related to the number of signal generating moieties. The one or more detectable components may provide an enhanced signal that minimizes detection errors from background noise. The one or more signal generating moieties may provide an enhanced signal that minimizes detection errors from background noise. In certain embodiments, the enhanced signal may be at least twice the signal of a detectable component comprising a single signal generating moiety conjugated to an oligonucleotide, such as at least 3×, 4×, 5×, 7×, 9×, or 10×. In certain embodiments, the amount of enhanced signal may be higher, for example, at least 20×, 30×, 50×, 100×, 500×, 1000×, 10,000×, and 100,000× the signal of a detectable component comprising a single signal generating moiety conjugated to an oligonucleotide. By enhancing the signal this may have the advantage of reducing or further minimizing detection errors from background noise. For example, in certain embodiments, the detections errors may be reduced or further minimized by at least 5%, 7%, 9%, 10%, or 15%.

A suitable detectable component may comprise one or more universal adapters; may comprise at least one polymer and/or at least one spacer groups; or combinations thereof. In certain embodiments, the detectable component may be used to detect one or more targets, at least two targets, at least 3 targets; at least 4; at least 5; at least 10; at least 15; at least 20; at least 25; at least 30; at least 35; at least 40; at least 45; at least 50; at least 75; at least 100; at least 125; at least 150; at least 200; at least 400; at least 1,000; at least 4,000; at least 10,000; or detect at least 50,000 targets within a sample. In certain embodiments, multiple targets in a sample may not be expressed in equal amounts, which may require differential amplification.

A suitable detectable component may comprise one or more signal generating moieties, for example, a detectable component may comprise an average of between about 1 to about 100,000, about 1 to about 10,000, about 1 to about 1,000, about 1 to about 500, about 1 to about 100, about 1 to about 50, about 1 to about 20, about 1 to about 10, about 1 to about 5, about 5 to about 50,000, about 5 to about 5,000, about 5 to about 1,000, about 5 to about 100, about 5 to about 50, about 5 to about 20; or about 5 to about 10 signal generating moieties.

The stoichiometry of the conjugation reaction to form the detectable components, for example, a complementary oligonucleotide-signal generating moiety conjugate, or a complementary of igonucleotide-scaffold conjugate, wherein the scaffold comprises one or more signal generating moieties, may comprise one equivalent of modified signal generating moiety and at least 0.5 equivalents of modified complementary oligonucleotide or may comprise one equivalent of modified scaffold, comprising one or more signal generating moieties, and at least 0.5 equivalents of modified complementary oligonucleotide. For example, the stoichiometry of the conjugation reaction to form the detectable components, comprising a complementary oligonucleotide-signal generating moiety conjugate, may comprise one equivalent of modified signal generating moiety and at least 1.0 equivalents, 1.5 equivalents, 2.0 equivalents, 2.5 equivalents, 3.0 equivalents, 3.5 equivalents, or 4.0 equivalents of modified complementary oligonucleotide. For example, the stoichiometry of the conjugation reaction to form the detectable components, comprising a complementary oligonucleotide-scaffold conjugate, wherein the scaffold comprises one or more signal generating moieties, may comprise one equivalent of modified scaffold and at least 1.0 equivalents, 1.5 equivalents, 2.0 equivalents, 2.5 equivalents, 3.0 equivalents, 3.5 equivalents, or 4.0 equivalents of modified complementary oligonucleotide.

Suitable detectable components, may comprise a molar ratio of about 1:1 complementary oligonucleotide to signal generating moiety. For example, the detectable component, may comprise a molar ratio of about 1:1 complementary oligonucleotide to scaffold, wherein the scaffold, such as dextran, comprises one or more signal generating moieties, such as one or more fluorophors. in certain embodiments, the number of signal generating moieties may be adjusted depending on the length of the scaffold, such as dextran or dendrimer that is utilized. For example, longer scaffolds, such as longer dextrans, may be utilized to increase the number of signal generating moieties on a detectable component. In certain embodiments, adjusting the number of signal generating moieties, for example, increasing the number, may adjust the sensitivity of detection, such increase the sensitivity of detection.

Figure 77:
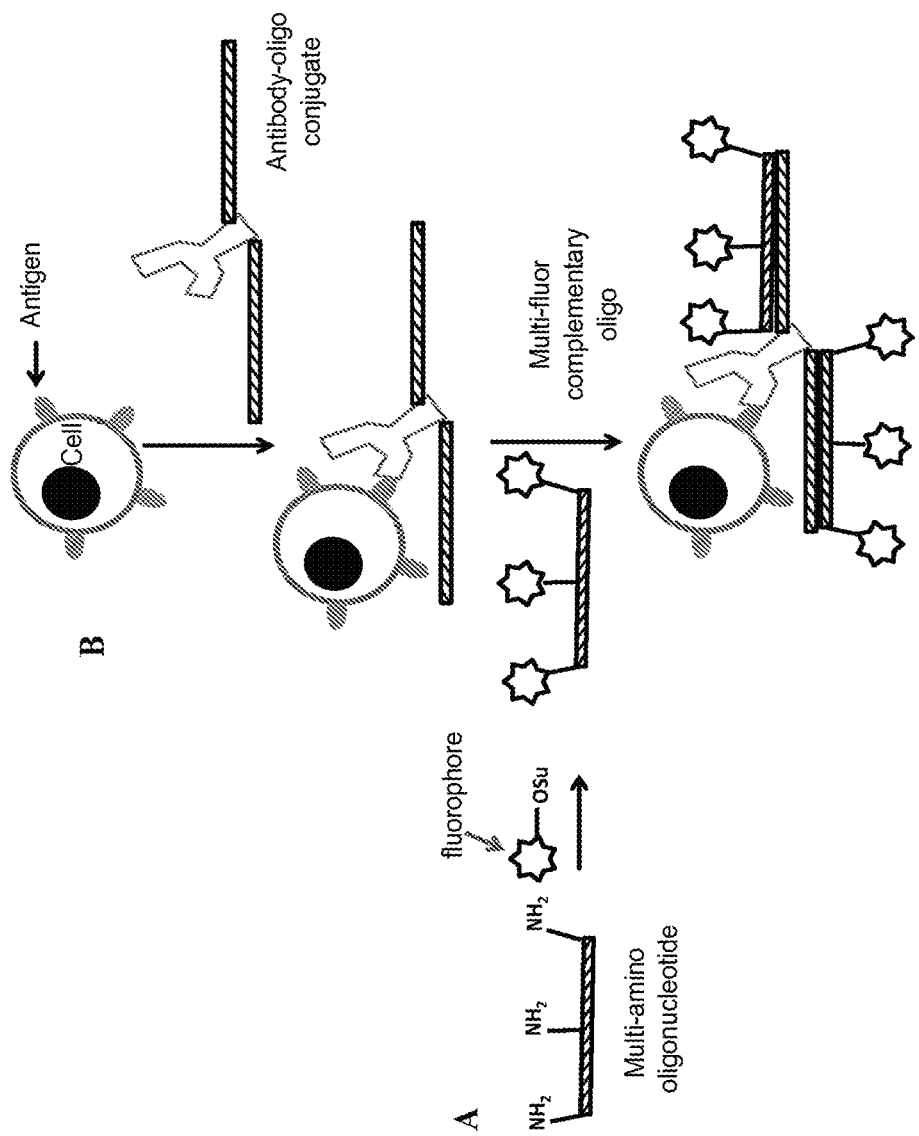
FIG. 77 illustrates an exemplary schematic representation of self assembly, according to certain embodiments.
Figure 78:
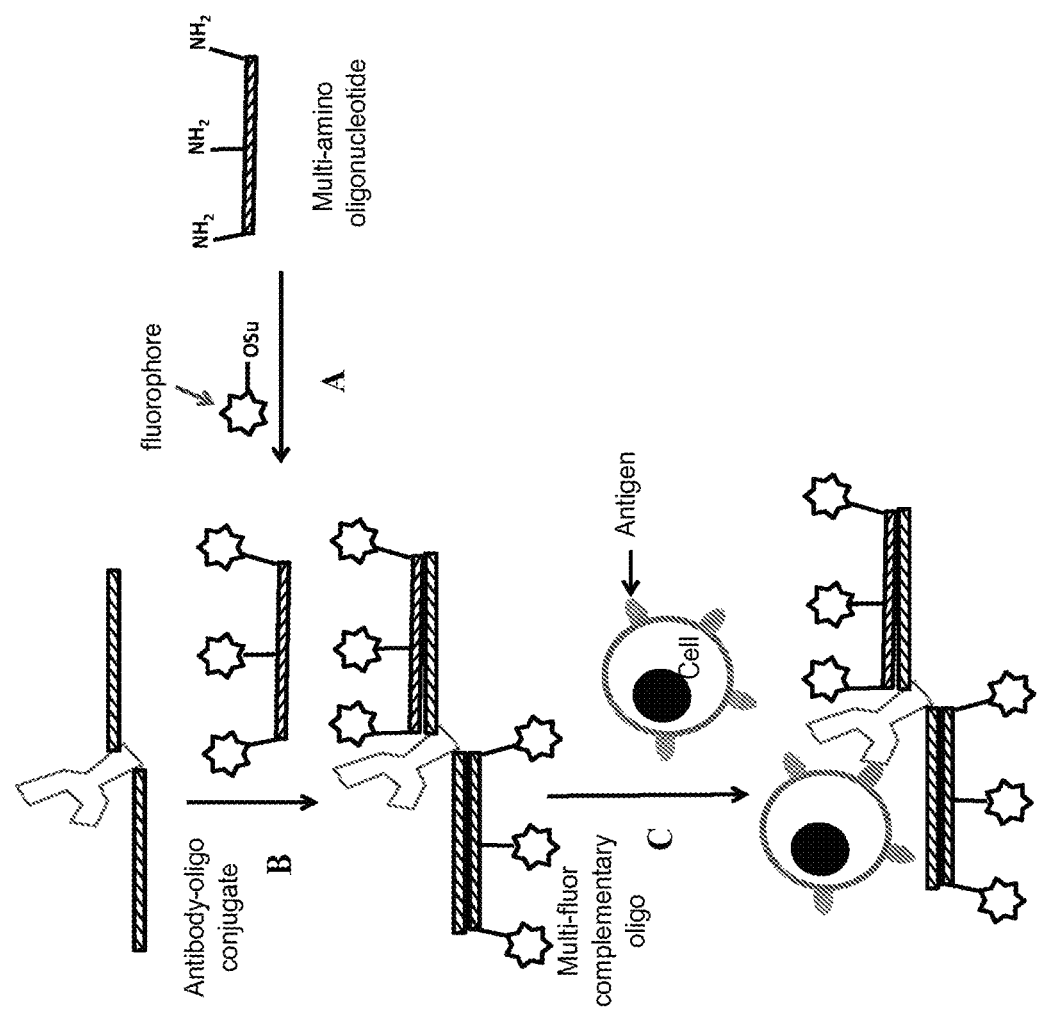
FIG. 78 illustrates an exemplary schematic representation of preassembly, according to certain embodiments.

In certain embodiments, one or more complementary detectors wherein the fluorophores are directly conjugated to the oligonucleotide. These multi-fluor detectors may be prepared from an oligonucleotide of 15-70 bases wherein 2-10 fluorophores are directly conjugated to 2-10 bases modified with reactive linker groups, e.g., amino groups, attached to the base wherein the hydrogen bonding of the base is substantial not affected (or not affected), i.e., on its minor groove side, and the fluorophores are spaced apart such that FRET does not occur or is minimized. In certain embodiments, the number of bases may vary, for example, 10 to 30, 15 to 20, 15 to 30, 20 to 60, 40 to 70, etc. In certain embodiments, the number of fluorophores may vary, for example, 2 to 5, 3 to 8, 2 to 8, 4 to 10, 5 to 9, etc. FIG. 78 schematically presents the (A) preparation of the multi-fluor oligonucleotide, (B) its hybridization to an antibody-complementary oligonucleotide conjugate and (C) it binding to an antigen on a cell membrane, according to certain embodiments. it is recognized that the order of assembly may be changed wherein the antibody-oligonucleotide conjugate is added to the cell, allowed to bind, washed and then the multi-fluor hybrid is added and allowed to hybridized. FIG. 77 is a schematic presentation, according to certain embodiments, of the use of antibody-oligonucleotide conjugates and complementary oligonucleotides to which fluorophores are directly conjugated wherein the antibody-oligonucleotide conjugate is added to the biological sample and allowed to bind and subsequently detected by the addition of the complementary oligonucleotide to which fluorophores are directly conjugated.

A suitable signal generating moiety may be detected by the presence of a color, or a change in color in the sample. In certain embodiments, more than one type of signal generating moiety may be used, for example, by attaching distinguishable signal generating moiety to a single detectable component or by using more than one detectable component, each carrying a different and distinguishable signal generating moiety.

A suitable signal generating moiety may be a protein, such as an enzyme, for example, alkaline phosphatase (AP); Horseradish Peroxidase (HRP); beta-galactosidase (βGAL); glucose-6-phosphate dehydrogenase; beta-N-acetylglucosaminidase; beta-glucuronidase; invertase; Xanthine Oxidase; firefly luciferase; or glucose oxidase (GO). Substrates that may be used for horse radish peroxidase (HRP) may include 3,3'-diaminobenzidine (DAB); diaminobenzidine with nickel enhancement; 3-amino-9-ethylcarbazole (AEC); benzidine dihydrochloride (BDHC); Hanker-Yates reagent (HYR); Indophane blue (IB); tetramethylbenzidine (TMB); 4-chloro-1-naphtol (CN); α-naphtol pyronin (α-NP); o-dianisidine (OD); 5-bromo-4-chloro-3-indolylphosphate (BCIP); Nitro blue tetrazolium (NBT); 2-(p-iodophenyl)-3-p-nitrophenyl-5-phenyl tetrazolium chloride (INT); tetranitro blue tetrazolium (TNBT); or δ-bromo-chloro-S-indoxyl-beta-D-galactoside/ferro-ferricyanide (BCIG/FF). Substrates that may be used for Alkaline Phosphatase may include Naphthol-AS-B 1-phosphate/fast red TR (NABP/FR); Naphthol-AS-MX-phosphate/fast red TR (NAMP/FR); Naphthol-AS-B 1-phosphate/fast red TR (NABP/FR); Naphthol-AS-MX-phosphate/fast red TR (NAMP/FR); Naphthol-AS-B1-phosphate/new fiischin (NABP/NF); bromochloroindolyl phosphate/nitroblue tetrazolium (BCIP/NBT); or 5-Bromo-4-chloro-3-indolyl-β-δ-galactopyranoside (BCIG).

Other suitable signal generating moieties may be a heavy metal chelate, for example, europium, lanthanum, yttrium, gold; a dendrimer of heavy metal chelates; gold particles; or coated gold particles, which may be converted by silver stains. Other suitable signal generating moieties may be a stable isotope bound to a chelator, for example, a polymer-based heavy metal chelates conjugated to antibodies and/or other binders may be used to multiplex protein analysis using a technique named CyTOF (CYtometry Time Of Flight). Heavy metal isotopes of Ru, Rh, Pd, Ag, In, La, Hf, Re, Ir, Pt, Au, Ce, Pr, Nd, Sm, Eu, Gd, Tb, Dy, Ho, Er, Tm, Yb and/or Lu may be used. In certain embodiments, a signal generating moiety may be a radioactive isotope, for example, $^{125}I$, $^{131}I$, $^{3}H$, $^{14}C$, $^{35}S$; a radioactive isotope of cobalt; a radioactive isotope of selenium; or a radioactive isotope of phosphorous. In certain embodiments, a signal generating moiety may be a secondary reporter, for example, biotin, streptavidin, avidin, digoxigenin, dinitrophenyl. In certain embodiments, the signal generating moiety, such as a hapten, may be conjugated to a fluorophore, peptide, nitrotyrosine, biotin, avidin, strepavidin, 2,4-dinitrophenyl, digoxigenin, bromodcoxy uridine, sulfonate, acetylaminofluorene, mercury trinitrophenol, or estradiol. In certain embodiments, a signal generating moiety may be a polymer particle; micro particle; a bead; a latex particle of polystyrene, PMMA or silica. In certain embodiments, a signal generating moiety may be a particle embedded with specific isotopes of heavy metals in defined relative abundance as a barcode. In certain embodiments, a signal generating moiety may be a particle embedded with fluorescent dyes, or polymer micelles or capsules which may contain dyes, enzymes or substrates. In certain embodiments, a signal generating moiety may be luminol, isoluminol, acridinium esters, 1,2-dioxetanes, pyridopyridazines, and/or ruthenium derivatives.

For example, a signal generating moiety may be a fluorophore. Fluorescence generally refers to the physical process in which light is emitted from the compound after a short interval following absorption of radiation. Generally, the emitted light is of lower energy and longer wavelength than that absorbed. In certain embodiments, the energy may be transferred from one fluorophore to another prior to emission of light. In certain embodiments, the fluorescence of the fluorophores used herein can be detected using standard techniques to measure fluorescence. The fluorophore may be, for example, fluorescein, or its derivatives, such as fluorescein-5-isothiocyanate (FITC), 5-(and 6)-carboxyfluorescein, 5- or 6-carboxyfluorescein, 6-(fluorescein)-5-(and 6)-carboxamido hexanoic acid, fluorescein isothiocyanate; rhodamine, or its derivatives, such as tetramethylrhodamine and tetramethylrhodamine-5-(and-6)-isothiocyanate (TR1TC). In certain embodiments, the fluorophore may comprise coumarin dyes, such as (diethylamino)coumarin or 7-amino-4-methylcoumarin-3-acetic acid, succinimidyl ester (AMCA); sulforhodamine 101 sulfonyl chloride, TexasRed™, TexasRed™ sulfonyl chloride; 5-(and-6)-carboxyrhodamine 101, succinimidyl ester, also known as 5-(and-6)-carboxy-X-rhodamine, succinimidyl ester (CXR); lissamine or lissamine derivatives such as lissamine rhodamine B sulfonyl Chloride (LisR); 5-(and-6)-carboxyfluorescein, succinimidyl ester (CFI); fluorescein-5-isothiocyanate (FITC); 7-diethylaminocoumarin-3-carboxylic acid, succinimidyl ester (DECCA); 5-(and-6)-carboxytetramethylrhodamine, succinimidyl ester (CTMR); 7-hydroxycoumarin-3-carboxylic acid, succinimidyl ester (HCCA); 6-fluorescein-5-(and-6)-carboxamidolhexanoic acid (FCHA); N-(4,4-difluoro-5,7-dimethyl-4-bora-3a,4a-diaza-3-indacenepropionic acid, succinimidyl ester; also known as 5,7-dimethyl BODIPY™ propionic acid, succinimidyl ester (DMBP); "activated fluorescein derivative" (FAP), available from Molecular Probes, Inc.; eosin-5-isothiocyanate (EITC); erythrosin-5-isothiocyanate (ErITC); and Cascade™ Blue acetylazide (CBAA) (the 0-acetylazide derivative of 1-hydroxy-3,6,8-pyrenetrisulfonic acid). In certain embodiments, the fluorophore may comprise fluorescent proteins such as phycoerythrin, allophycocyanin, green fluorescent protein and its analogs or derivatives, fluorescent amino acids such as tyrosine and tryptophan and their analogs, fluorescent nucleosides, and other fluorescent molecules such as organic dyes, including Cy2, Cy3, Cy 3.5, Cy5, Cy5.5, Cy 7, IR dyes, Dyomics dyes, Oregon green 488, pacific blue, rhodamine green, and Alexa dyes. In certain embodiments, the fluorophore may take advantage of fluorescence energy transfer and comprise conjugates of R-phycoerythrin or allophycocyanin to organic dyes, such as Cy2, Cy3, Cy 3.5, Cy5, Cy5.5, Cy 7, Dyomics dyes, or Alexa dyes. In certain embodiments, the fluorophore may comprise an inorganic fluorescent colloidal particle such as a quantum dot or other fluorescent nanoparticle, such as particles based on semiconductor material like CdS-coated CdSe nanocrystallites.

In certain embodiments, the signal generating moiety may be linked to the oligonucleotide sequence by a covalent attachment or a non-covalent attachment. The signal generating moiety may also be linked to the oligonucleotide sequence before, during, or after the hybridization event.

In certain embodiments, a molecular probe, universal adaptor, and/or detectable component may be pre-hybridized prior to bringing the composition into contact with a sample, comprising one or more molecular targets. For example, three or more, four or more, five or more molecular probes, universal adapters, and/or detectable components, may be pre-hybridized prior to bringing the composition into contact with a sample comprising one or more molecular targets. In certain embodiments, two or more molecular probes, universal adapters, and/or detectable components, each of which may comprise one or more spacer groups, may be pre-hybridized prior to bringing the composition into contact with a sample, comprising one or more molecular targets.

Samples and/or Targets

A suitable sample may comprise one or more targets, such as one or more of a protein; a peptide; a carbohydrate; a nucleic acid; a lipid; a small molecule; a toxin; a drug or drug-like molecule, or derivatives thereof; or may comprise a combination of targets that may be proteins; peptides; carbohydrates; nucleic acids; lipids; small molecules; toxins; drugs or drug-like molecules, or derivatives thereof. For example, a sample may comprise a defined combination of natural and/or chemically synthesized species. In certain embodiments, the composition of a sample may not be fully known. The sample may include a cell, a group of cells, may be prepared from a cell or group of cells, may be a purified fraction from a cell preparation, may be a purified molecule. For example, the sample may comprise cells, such as mammalian cells (e.g., human cells); insect cells; yeast cells; fungal cells; and/or bacterial cells. The cells, for example, may be from multicellular organism (e.g., insects and mammals) derived from specific portions of the organism (e.g., specific tissues, organs, or fluids). Cells may be contacted by hybrids in vitro or in vivo, and may be contacted by hybrids when in suspension or when attached to a solid surface. Cells may not be significantly modified during the process, may be fixed to a solid support, and/or may be made permeable using standard methods. The sample may include cells, products produced by cells, cellular components, and/or mixtures thereof. The sample may include cellular components, such as a nucleus, cytoplasm, plasma cell membrane, nucleolus, mitochondria, vacuoles, subcellular organelles, endoplasmic reticulum and/or Golgi apparatus. The sample may include cells, tissue samples, and/or organs, such as molecular antigens produced from groups of cells, tissue samples, and/or organs. In certain embodiments, the sample may comprise or be derived from, but not limited to, clinical, industrial, agricultural and environmental samples. For example, sample material often may be of medical, veterinary, environmental, nutritional or industrial significance, and include body fluids, such as blood, serum, plasma, cerebrospinal fluid, synovial fluid, saliva, milk, sputum, lung aspirates, mucus, teardrops, exudates, secretions, urine, and fecal matter; microbial culture fluids; aerosols; crop materials; animal meat (e.g., for human consumption or animal feed); and soils and ground waters. In certain embodiments, the sample may comprise, but is not limited to, molecules in pathogens, viruses, bacteria, yeast, fungi, amoebae and insects; molecules in diseased or non-diseased pest animals such as mice and rats; molecules in diseased and non-diseased domestic animals, such as domestic equines, bovines, porcines, caprines, canines, felines, avians and fish; and molecules in diseased and non-diseased humans. In certain embodiments, the sample may comprise, but is not limited to, biological samples derived from a human or other animal source (such as, for example, body fluids, such as blood, serum, plasma, cerebrospinal fluid, synovial fluid, saliva, milk, sputum, lung aspirates, mucus, teardrops, exudates, secretions, urine, a biopsy sample, a histology tissue sample, a PAP smear, a mole, a wart, etc.) including samples derived from a bacterial or viral preparation, as well as other samples (such as, for example, agricultural products, waste or drinking water, milk or other processed foodstuff, air, etc.). In certain embodiments, the sample may comprise one or more of the following: tissue cells, cells cultured in vitro, recombinant cells, infected cells, cells from laboratory animals, cells from mammal patients, cells from human patients, mesenchemal stem cells, stem cells, immuno-competent cells, adipose cells, fibroblasts, natural-killer cells (NK-cells), monocytes, lymphocytes, lymph node cells, T-cells, B-cells, exudate cells, effusion cells, cancer cells, blood cells, red blood cells, leukocytes, white blood cells, organ cells, skin cells, liver cells, splenocytes, kidney cells, intestinal cells, lung cells, heart cells, or neuronal cells.

Suitable samples may comprise a range of analytes, such as targets and/or biological targets, having a wide range of binding specificities, for example, about $10^{-4}$ M to about $10^{-15}$ M, about $10^{-5}$M to about $10^{-15}$ M, about $10^{-6}$ M to about $10^{15}$M, about $10^{-7}$ M to about $10^{15}$M, about $10^{-9}$M to about $10^{15}$M, or about $10^{12}$M to about $10^{15}$M.

As used herein homogeneous in certain embodiments may mean a sample having substantially the same class of targets, or the same class of targets, for example, at least 60% 70%, 80%, 90%, 95%, or 98% of the same class of targets. For example, classes of targets may include, but are not limited to the class of proteins, the class of sugar-containing compounds, the class of antibodies, the class of peptides, the class of toxins, the class of pathogens, or the class of antigens.

A suitable target or biological target may include, but is not limited to, an antigen; an antibody; an enzyme; an enzyme substrate; a nuclear receptor; a nuclear receptor ligand; a co-factor; a pathogen; a toxin; a protein, such as a glycoprotein, a lipoprotein, a phosphoprotein, an acetylated protein, an hydroxylated protein, a sulfonated protein, a nitrosylated protein, or a methylated protein; a protein fragment, such as a peptide, a polypeptide or a modified polypeptide; a nucleic acid, such as a nucleic acid molecule, a nucleic acid segment, a nucleic acid molecule of a pathogen or tumor cell, a mutated nucleic acid, a variant nucleic acid, a modified nucleic acid, a methylated nucleic acid, or an oxidatively damaged nucleic acid; an epitope; a lipid; a glyco-lipid; a sugar; a carbohydrate-containing molecule, such as disaccharide, oligosaccharide, or a polysaccharide; a starch; a drug or drug-like molecule; a small molecule; a salt; an ion; or one of a variety of other organic and inorganic substances; which may be free in solution or bound to another substance; or combinations or derivatives thereof. The target may be recognized by, for example, a suitable molecular probe, comprising a binding moiety. The recognition may be direct, while in other embodiments, the recognition may be indirect, via another binding moiety, such as by at least one primary, secondary, or higher order binding moiety. The target may be expressed on the surface of the sample, such as on a membrane, cell-membrane, or interface. The target may be contained in the interior of the sample. In the case of a cell sample, for example, an interior target may comprise a target located within the cell membrane, periplasmic space, cytoplasm, or nucleus, or within an intracellular compartment or organelle. The target may include viral particles, or portions thereof, for example, a nucleic acid segment or a protein. The viral particle may be a free viral particle, i.e., not associated with another molecule, or it may be associated with a sample described above. The target may include products derived from DNA damage, an infective agent (e.g., a virus, bacterium, or fungus), a nucleotide analog or derivative (e.g., bromodeoxyuridine (BrdU)) or a modified nucleotide (e.g., a biotinylated nucleotide)); a small organic or inorganic compound; an antisense nucleic acid (e.g., a PNA); a catalytic nucleic acid (e.g., a ribozyme); an inhibitory nucleic acid (e.g., a short inhibitory RNA (siRNA)); a polypeptide (e.g a cytokine or growth factor); an antibody or a peptide mimetic. For example, small organic or inorganic compounds may have a molecular weight of 10,000 g/mol or less, 5,000 g/mol or less, 1,000 g/mol or less, or 500 g/mol or less. Compounds may be obtained using combinatorial library methods, such as spatially addressable parallel solid phase or solution phase libraries; synthetic library methods requiring deconvolution; "one-bead one-compound" library methods; and synthetic library methods using affinity chromatography selection. The libraries may include siRNA molecule libraries or peptide mimetic libraries.

Other suitable targets may include a molecular antigen, which may be a peptide or protein or may comprise a portion of a peptide or protein. For example, the target may be an antigen, such as a subregion of a protein, such as in the N-terminus, C-terminus, extracellular region, intracellular region, transmembrane region, active site (e.g., nucleotide binding region or a substrate binding region), a domain (e.g., an SH2 or SH3 domain) or a post-translationally modified region (e.g., phosphorylated, glycosylated, methylated, acetylated, nitrosylated, sulfated, farnesylated, myrisloylaled, paliloylaled, sumoylaled or ubiquinylaled region). The target may be an antigen, comprising a modification moiety or a portion thereof (e.g., the glycosyl group or a portion thereof) or may be a modification moiety in conjunction with amino acids of the protein or peptide to which it is linked (e.g., a phosphoryl group in combination with one or more amino acids of the protein or peptide). The protein may be a signal transduction factor, cell proliferation factor, apoptosis factor, angiogenesis factor, senescence factor, or cell interaction factor. Suitable examples of cell interaction factors may include, but are not limited to, cadherins (e.g., cadherins E, N, BR, P, R, and M; desmocollins; desmogleins; and protocadherins); connexins; integrins; proteoglycans; immunoglobulins, cell adhesion molecules (e.g., ALCAM, NCAM-1 (CD56), ICAM-1 and ICAM-2, CD44, LFA-1, LFA-2, LFA-3, LECAM-1, VLA-4, ELAM and N-CAM); selectins (e.g., L-selectin (CD62L), E-selectin (CD62e), and P-selectin (CD62P)); agrin; CD34; and a cell surface protein that is cyclically internalized or internalized in response to ligand binding. Examples of signal transduction factors may include, but are not limited to, protein kinases (e.g., mitogen activated protein (MAP) kinase and protein kinases that directly or indirectly phosphorylate it, Janus kinase (JAKI), cyclin dependent kinases, epidermal growth factor (EGF) receptor, platelet-derived growth factor (PDGF) receptor, fibroblast-derived growth factor receptor (FGF), insulin receptor and insulin-like growth factor (IGF) receptor); protein phosphatases (e.g., PTPIB, PP2A and PP2C); GDP/GTP binding proteins (e.g., Ras, Raf, ARF, Ran and Rho); GTPase activating proteins (GAFs); guanine nucleotide exchange factors (GEFs); proteases (e.g., caspase 3, 8 and 9), ubiquitin ligases (e.g., MDM2, an E3 ubiquitin ligase), acetylation and methylation proteins (e.g., p300/CBP, a histone acetyl transferase) and tumor suppressors (e.g., p53, which is activated by factors such as oxygen tension, oncogene signaling, DNA damage and metabolite depletion). The protein may be a nucleic acid-associated protein (e.g., histone, transcription factor, activator, repressor, co-regulator, polymerase or origin recognition complex (ORC) protein), which directly binds to a nucleic acid or binds to another protein bound to a nucleic acid.

Detection Assay

A suitable detection assay may comprise or may be used in connection with singleplex and multiplex assays, such as immunoassays, protein detection assays, immunodetection, enzyme linked immuno-assays (ELISA), immunomagnetic cellular depletion, immunomagnetic cell capture, flow cytometry, immunohistochemistry (IHC), immunocytochemistry (ICC), in situ hybridization (ISH), ELISpot, enzyme immuno-assays (EIA), blotting methods (e.g. Western, Southern, Southwestern, and Northern), arrays, bead arrays, multiplex bead array, microarray, antibody array, cellular array, solution phase capture, chemiluminescence detection, infrared detection, labeling inside electrophoresis systems or on surfaces or arrays, PCR amplification, elongation followed by PCR amplification, precipitation, immunoprecipitation, co-immunoprecipitation, chromatin immunoprecipitation, pretargeting imaging, therapeutic agent, nucleic acid hybridization assays, microscopy, imaging, high content screening (HCS), other assay or detection formats, for example, that are useful in research as well as in diagnosing diseases or conditions, or combinations or derivatives thereof. In certain embodiments, the assay may analyze expression patterns of genes or levels of proteins within a sample. In certain embodiments, the IHC, ISH and cytological techniques may be performed in a matrix of tissue, cell and proteins which may be partly cross-linked and very inhomogeneous in nature. In certain embodiments, the assay may be an IHC method of detecting targets using either direct labeling or secondary antibody-based or hapten-based labeling, such as EnVision™ (DakoCytomation), Powervision® (Immunovision, Springdale, AZ), the NBA' kit (Zymed Laboratories Inc., South San Francisco, CA), HistoFine® (Nichirei Corp, Tokyo, Japan). In certain embodiments, the methods disclosed herein may provide an enhanced signal or an increased flexibility in IHC detection platforms.

Isolating Biomolecule-Oligonucleotide Conjugates and/or Modified Oligonucleotide In certain embodiments, methods for isolating biomolecule-oligonucleotide conjugates may comprise: i) introducing a modified biomolecule into a buffered solution; ii) conjugating the modified biomolecules with at least one modified oligonucleotide at greater than about 80% efficiency to form biomolecule-oligonucleotide conjugates; and iii) isolating the biomolecule-oligonucleotide conjugates from the conjugation solution by binding the conjugates to an immobilized binder. The methods may comprise conjugation at greater than about 85%, greater than 90%, greater than 95%, or greater than about 98% efficiency to form biomolecule-oligonucleotide conjugates. In certain embodiments, other isolation techniques may be used, for example, size exclusion chromatography. In certain embodiments, the isolation technique may be selected from one or more of the following: chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, or hydrophobic interaction chromatography.

For example, the modified oligonucleotide may be prepared by reacting with a bifunctional molecular reagent containing a first reactive component that forms a covalent bond with the oligonucleotide, and a second reactive component that may form a linkage with a complementary reactive component on a modified biomolecule or a tagged biomolecule. In certain embodiments, the second reactive component may be protected such that it will not react until removed following incorporation onto the oligonucleotide.

A suitable modified oligonucleotide may be prepared by incorporating amino groups either 3',5' or internally using other methods and reagents. For example, the modified oligonucleotide may be prepared by reacting with a moiety that is a bifunctional molecular reagent, such as an aromatic aldehyde or ketone, aromatic hydrazino or oxyamino modification reagent, to incorporate a hydrazino or oxyamino function respectively.

A suitable modified oligonucleotide may be prepared by post-synthetically modification of oligonucleotides prepared via polymerases or reverse transcriptases with nucleoside triphosphates possessing an aromatic aldehyde, aromatic hydrazine, oxyamino, or an amino group. For example, the modified oligonucleotide may be prepared by post-synthetically modification of oligonucleotides by incorporation of an aromatic aldehyde or ketone, aromatic hydrazino or oxyamino group, using a moiety that is a bifunctional molecular reagent, such as an aromatic aldehyde or ketone, aromatic hydrazino or oxyamino reagent.

The modified biomolecules, such as, modified antibodies, modified proteins, or modified peptides, may be prepared from biomolecules that are derived from eukaryotic cells. The modified biomolecules may also be prepared from biomolecules that are derived from prokaryotic cells. The modified biomolecule may include a molecular tag. The modified biomolecule may be modified antibody, wherein the modified antibody may be prepared from an antibody that contains a histidine rich sequence near the hinge region. In certain embodiments, the modified biomolecule may be modified antibody, wherein the modified antibody may be exclusive of, i.e., do not contain, a histidine rich sequence near the hinge region.

In certain embodiments, the phosphorus-containing moieties of the modified oligonucleotides may contain, for example, a phosphate, phosphonate, alkylphosphonate, aminoalkyl phosphonate, thiophosphonate, phosphoramidate, phosphorodiamidate, phosphorothioate, phosphorothionate, phosphorothiolate, phosphoramidothiolate, and phosphorimidate. The phosphorus-containing moieties of the modified oligonucleotides may be modified with a cationic, anionic, or zwitterionic moiety. The modified oligonucleotides may also contain backbone linkages which do not contain phosphorus, such as carbonates, carboxymethyl esters, acetamidates, carbamates, acetals, and the like or derivatives thereof.

A suitable modified biomolecule may be a modified antibody, comprising an antibody that includes a histidine-rich region, for example, an antibody having a histidine-rich region near the hinge region of the antibody. The modified antibody may comprise an antibody that is exclusive of having a histidine-rich region. The modified antibody may comprise an antibody that is of the IgG type antibody or the IgM type antibody. The modified antibody may comprise one or more molecular tags, for example, but not limited to, a poly-histidine tag, a Flag Tag, a Myc tag, or a peptide tag that an antibody has been raised against. The modified antibody may comprise a poly-histidine fusion protein. The modified antibody may comprise one or more spacer groups, for example, such as a polyethylene glycol (PEG) or a polyethylene oxide group (PEO). The modified antibody may comprise one or moieties that include a reactive group, for example, a reactive group that may form a covalent bond when reacted with a complementary reactive group that may be part of a modified oligonucleotide. The modified antibody may be, for example, a HyNic or 4FB-modified antibody.

A suitable modified biomolecule may be a modified protein or a modified peptide, comprising a protein that includes a histidine-rich region, for example, a protein having a histidine-rich region incorporated during solid phase synthesis. For example, the modified protein may comprise a protein that is exclusive of having a histidine-rich region. In certain embodiments, the modified protein may comprise one or more molecular tags, for example, but not limited to, a poly-histidine tag, a Flag Tag, a Myc tag, or a peptide tag that an antibody has been raised against. The modified protein may comprise a poly-histidine fusion protein. The modified protein may comprise one or more spacer groups, for example, such as a polyethylene glycol (PEG) or a polyethylene oxide group (PEO). The modified protein may comprise one or moieties that include a reactive group, for example, a reactive group that may form a covalent bond when reacted with a complementary reactive group that may be part of a modified oligonucleotide. The modified protein may be, for example, a HyNic or 4FB-modified protein.

in certain embodiments, at least one modified oligonucleotide may comprise one or more oligonucleotides that have been modified, for example, at least two modified oligonucleotides, at least three, at least four modified oligonucleotides. The at least one modified oligonucleotide may comprise two different modified oligonucleotides, for example, three different modified nucleotides or four different modified oligonucleotides. The at least one modified oligonucleotide may comprise one or more spacer groups, for example, a PEG or PEO group. The modified oligonucleotide may comprise one or moieties that include a reactive group, for example, a reactive group that may form a covalent bond when reacted with a complementary reactive group that may be part of a modified antibody. The modified oligonucleotide may be, for example, a 4-FB-modified oligonucleotide.

In certain embodiments, the biomolecule-oligonucleotide conjugates, for example, antibody-oligonucleotide conjugates, protein-oligonucleotide conjugates, (protein fragment)-oligonucleotide conjugates, or peptide-oligonucleotide conjugates, may be purified and/or isolated by binding to an immobilized binder. A suitable immobilized binder may comprise a metal ion, for example, a divalent metal ion, such as a transition metal ion. The metal ion may include, but is not limited to, a nickel ion, a zinc ion, a copper ion, an iron ion, or a cobalt ion. The metal ion may be immobilized by chelation to a stationary phase in a column. A suitable stationary phase may comprise an organic chelator that immobilizes and/or binds the metal ion. For example, the organic chelator may be selected from the group that includes, but is not limited to, iminodiacetic acid, nitrilotriacetic acid, and/or bicinchoninic acid. The stationary phase may be a water insoluble support, for example, the stationary phase may be agarose.

A suitable immobilized binder may comprise an immobilized antibody. The immobilized antibody may recognize and bind a portion of the modified biomolecule, such as a modified antibody, and/or a portion of the biomolecule-oligonucleotide conjugates, such as an antibody-oligonucleotide conjugate. The immobilized antibody may recognize and bind a modified biomolecule comprising a molecular tag, wherein the immobilized antibody is an antibody that has been raised to include that particular molecular tag. The immobilized antibody may recognize and bind the linkage formed during the conjugation reaction of the modified biomolecules, such as modified antibodies, modified proteins, or modified peptides, and the modified oligonucleotide, wherein the immobilized antibody is an antibody that has been raised to include that particular conjugation linkage.

Other suitable biomolecule-oligonucleotide conjugates, for example, antibody-oligonucleotide conjugates, protein-oligonucleotide conjugates, (protein fragment)-oligonucleotide conjugates, or peptide-oligonucleotide conjugates, may be purified and/or isolated by adding the conjugation reaction mixture to a column having a stationary phase comprising a binder that has been immobilized, or substantially immobilized, to the stationary phase. The immobilized binder may comprise an immobilized antibody bound to the stationary phase. The immobilized binder may comprise a metal ion, for example, a divalent metal ion, such as a transition metal ion. The metal ion may be immobilized by chelation to a stationary phase in a column. The metal ion may include, but is not limited to, a nickel ion, a zinc ion, a copper ion, an iron ion, or a cobalt ion.

Preparing, Purifying, and/or Isolating the Biomolecule-Oligonucleotide Conjugates A suitable method of preparing, purifying, and/or isolating the biomolecule-oligonucleotide conjugates may be by selectively binding the conjugates to a binder that is immobilized, or substantially immobilized, on a stationary phase, eluting the reaction components away from the bound conjugate, and then releasing the biomolecule-oligonucleotide conjugates by adding a displacing agent that is selective for the immobilized binder. The method for isolating biomolecule-oligonucleotide conjugates, may comprise: i) conjugating a modified biomolecule with at least one modified oligonucleotide to form biomolecule-oligonucleotide conjugates, wherein greater than 80% of the modified biomolecules are conjugated; ii) adding the conjugation reaction mixture to a column having a stationary phase comprising a binder that has been immobilized to the stationary phase; iii) binding the biomolecule-oligonucleotide conjugates selectively to the immobilized binder; iv) eluting reaction components away from the bound biomolecule-oligonucleotide conjugates; and v) isolating the biomolecule-oligonucleotide conjugates by releasing the bound biomolecule-oligonucleotide conjugates with a displacing agent selective for the binder. The immobilized binder may be a metal ion and the displacing agent may be a solution comprising a chelator for the metal, for example, EDTA. The immobilized binder may be an immobilized antibody and the displacing agent may be a solution comprising a molecular tag that is recognized by the immobilized antibody.

In certain embodiments, the method of preparing, purifying, and/or isolating the molecular probes, such as biomolecule-oligonucleotide conjugates, for example, antibody-oligonucleotide conjugates, protein-oligonucleotide conjugates, (protein fragment)-oligonucleotide conjugates, or peptide-oligonucleotide conjugates, may be mild, robust, simple, high yielding or combinations thereof. For example, the method may yield at least about 30% isolated molecular probes, for example, biomolecule-oligonucleotide conjugates, with respect to starting modified biomolecule. In other methods, the yield may be at least 40%, 50%, 65%, 70%, 75%, 80%, 85%, 90%, or at least 95% isolated molecular probe, such as, biomolecule-oligonucleotide conjugates, with respect to starting modified biomolecule. In other methods, the purity of the prepared, purified, and/or isolated molecular probe may be at least 40%, 50%, 65%, 70%, 75%, 80%, 85%, 90%, 95%, 97%, 98%, or 99%.

In certain embodiments, the method of preparing, purifying, and/or isolating the biomolecule-oligonucleotide conjugates may provide more than one process by which to bind and release the biomolecule-oligonucleotide conjugates. For example, the formed biomolecule-oligonucleotide conjugates may be antibody-oligonucleotide conjugates, that may comprise a histidine-rich region included in the hinge region of the biomolecule, for example, antibody, which may be bound by chelating to a metal ion immobilized on a column, and the formed biomolecule-oligonucleotide conjugates, such as antibody-oligonucleotide conjugates, may further comprise a molecular tag that is recognized and may be bound by an antibody, for example, an antibody immobilized on a stationary phase. For example, the formed biomolecule-oligonucleotide conjugates may be antibody-oligonucleotide conjugates, that may comprise a biomolecule, for example, an antibody, that is exclusive of, i.e., does not include a histidine-rich region, and the formed biomolecule-oligonucleotide conjugates, such as antibody-oligonucleotide conjugates, may further comprise a molecular tag that is recognized and may be bound by an antibody, for example, an antibody immobilized on a stationary phase, and wherein the molecular tag may also be bound by chelating to a metal ion. For example, the molecular tag may be a histidine-rich His-6 tag.

In certain embodiments, the biomolecule-oligonucleotide conjugates, for example, antibody-oligonucleotide conjugates, protein-oligonucleotide conjugates, (protein fragment)-oligonucleotide conjugates, or peptide-oligonucleotide conjugates, may comprise one or more detectable fluorophores, two or more detectable fluorophores, or three or more detectable fluorophores. In certain embodiments, the biomolecule-oligonucleotide conjugates may comprise two or more different modified oligonucleotides, for example, three or more different modified oligonucleotides, that have conjugated to the biomolecule, where in each modified oligonucleotide comprises a different fluorophore. The formation of the biomolecule-oligonucleotide conjugates may form an additional fluorophore and/or chromophore during the conjugation reaction.

In certain embodiments, the method of preparing, purifying, and/or isolating a detectable component may be simple, high yielding or combinations thereof. For example, the method may yield at least 30% 40%, 50%, 65%, 70%, 75%, 80%, 85%, 90%, or 95% isolated detectable component. In other methods, the purity of the prepared, purified, and/or isolated detectable component may be at least 40%, 50%, 65%, 70%, 75%, 80%, 85%, 90%, 95%, 97%, 98%, or 99%.

Detection

Suitable methods of detection may also include direct and/or indirect detection of the oligonucleotide or oligonucleotides of the molecular probe. For example by the use of DNA hybridization or DNA sequence analysis or DNA sequence amplification. In certain embodiments, the oligonucleotide or oligonucleotides may be detected by hybridization to an array of complementary oligonucleotides. In certain embodiments, the oligonucleotide or oligonucleotides may be detected by polymerization of complementary DNA sequence. In certain embodiments, detection may be by the use of immuno-PCR, a hybrid of PCR and immunoassay systems, which combines the versatile molecular recognition of antibodies with the amplification potential of DNA replication. The technique of immuno-PCR involves the in-situ assembly of the labeled DNA-antibody complex during the assay, creating variable stoichiometry in both the attachment of the DNA label, and the assembly of the components. For example, the purified, labeled DNA may be added to a hybridization solution containing denatured nucleic acids (RNA or DNA) from a sample to be tested. The aqueous conditions of the hybridization solution may be adjusted to allow nucleic acid hybridization or reannealing, thereby allowing the labeled molecules to hybridize with unlabeled, complementary sequence counterparts. Duplex formation can be monitored by digestion with single strand-specific nucleases (such as S1 nuclease). Recovery and quantitation of the resistant, i.e., double-stranded, reannealed material provides a measure of the nucleic acid sequence tested for. The amount of hybridization may be a function of the initial concentration of DNA and the time allowed for reannealing. Therefore, increased initial DNA concentrations can lead to substantially reduced hybridization times. This technique may be an additional means to monitor the presence of a target in a sample, such as an antigen, of interest in a detection method, such as a Western blot assay.

A suitable method of detection may comprise a multiplex assay, utilizing one or more molecular probes, one or more detectable components, and one or more universal adapters, wherein the one or more molecular probes may comprise identical oligonucleotide sequences that are complementary to a first oligonucleotide sequence segment of the one or more universal adapters. In certain embodiments, the method of detecting may comprise a multiplex assay, utilizing one or more molecular probes, one or more universal adapters, and one or more detectable components, wherein the one or more molecular probes comprise one or more biomolecules conjugated to identical oligonucleotide sequences, wherein the one or more universal adapters comprise identical first oligonucleotide sequence segments complementary to the oligonucleotide sequences of the one or more molecular probes and a second, unique oligonucleotide sequence segment complementary to the oligonucleotide sequence of the one or more detectable components, and wherein the one or more detectable components comprise unique oligonucleotide sequences complementary to the second, unique oligonucleotide sequence segment of the one or more universal adapters.

A suitable method of detection of one or more molecular targets in a sample may provide using one or more detectable components comprising one or more signal generating moieties. For example, the method of detecting one or more molecular targets in a sample may provide using one or more molecular probes, one or more detectable components, one or more universal adapters, and/or one or more spacer groups, or combinations thereof. In certain embodiments, the method of detecting one or more molecular targets in a sample, comprising using one or more molecular probes, one or more detectable components, one or more universal adapters, and/or one or more spacer groups, may be provided in multiple layers to increase the flexibility of a detection system, to enhance and/or increase the signal from the one or more molecular targets, such as to enhance and/or increase the signal generated from the one or more molecular probe bound targets, to enhance and/or increase the efficiency of the signal generated from the one or more molecular probe bound targets, to enhance and/or increase the efficiency of the molecular probe binding the one or more molecular targets. The method of detecting may be compatible with one or more detection systems, such as, for example, singleplex and multiplex assays, such as immunoassays, protein detection assays, immunodetection, enzyme linked immuno-assays (ELISA), immunomagnetic cellular depletion, immunomagnetic cell capture, flow cytometry, immunohistochemistry (IHC), immunocytochemistry (ICC), in situ hybridization (ISH), ELISpot, enzyme immuno-assays (EIA), blotting methods (e.g. Western, Southern, Southwestern, and Northern), arrays, bead arrays, multiplex bead array, microarray, antibody array, cellular array, solution phase capture, chemiluminescence detection, infrared detection, labeling inside electrophoresis systems or on surfaces or arrays, PCR amplification, elongation followed by PCR amplification, precipitation, immunoprecipitation, co-immunoprecipitation, chromatin immunoprecipitation, pretargeting imaging, therapeutic agent, nucleic acid hybridization assays, microspeopy, imaging, high content screening (HCS), other assay or detection formats, for example, that are useful in research as well as in diagnosing diseases or conditions, or combinations or derivatives thereof. In certain embodiments, the method of detecting may be compatible with one or more different types of molecular targets, molecular probes, detectable components, universal adapters, and/or spacer groups. The method of detecting one or more molecular targets in a sample may be provided by an increased and/or enhanced signal generated from the one or more molecular probe bound targets, by, for example, increasing the number of detectable components utilized to detect each molecular target, and/or by amplification of the signal by the instrumentation utilized. The method of detecting one or more molecular targets in a sample, may be provided by an increased and/or enhanced signal generated from the one or more molecular probe bound targets, for example, molecular probes comprising antibodies, for example, molecular targets comprising antigens, wherein the signal generated and detected may be amplified by the antibody-antigen complex.

In certain embodiments, a method of detection of one or more molecular targets in a complex sample using one or more detectable components and one or more molecular probes, may comprise a multiplex assay, such as a multiplex immunodetection assay. The time of conducting the method of detection from the start of preparation of the hybrids to the end of detection may be about 0.5-10, 1-9, 1-8, 1-7, 1-6, 1-5, 1-4, 1-3, 1-2, 2-5, 2-4 or 2-3 hours.

In certain embodiments, a method of detection of one or more molecular targets in a sample may utilize one or more detectable components and one or more molecular probes, comprising biomolecule-oligonucleotide conjugates, comprising: i) forming the molecular probes at greater than 80% efficiency from at least one or more modified biomolecules and at least one or more modified oligonucleotides; ii) forming the detectable components at greater than 80% efficiency from a modified oligonucleotide and least one or more signal generating moieties, wherein the modified oligonucleotide is complementary to the modified oligonucleotide of the formed molecular probe; iii) providing the formed biomolecular probes to the sample comprising the one or more molecular targets; iv) contacting the one or more molecular targets in the sample with the formed molecular probes; iv) providing the detectable component to the sample comprising the contacted molecular probes; v) hybridizing the complementary oligonucleotide of the detectable component with the oligonucleotide of the contacted molecular probe; vi) detecting the one or more signal generating moieties of the hybridized molecular probes contacted to the one or more molecular targets.

A suitable method for detection of one or more target molecules may comprise extending the oligonucleotide by PCR methods prior to detection. For example, the method of detection may comprise determining the amount of hybridization product or extension product, for example, determining a quantified amount of hybridization product or extension product. The one or more molecular probes may comprise a nucleic acid binding protein identical to, or substantially identical to, a lac repressor protein or fragment thereof, which binds to a functional lacO subsequence in a hybrid nucleic acid, hybridization product or extension product. The nucleic acid binding agent may comprise one or more signal generating moities.

A suitable method for detection of one or more target molecules may comprise detecting disease-specific molecules, identifying whether a certain cell type in a sample carries a disease-specific marker, and/or determining progression of a disease or condition. For example, disease specific markers may be molecules expressed by diseased cells, such as cancer cells, but not by non-diseased cells. A disease specific marker may be a molecule expressed by a pathogenic organism but not the host organism invades, and sometimes is a molecule expressed by a cell invaded by a pathogenic organism and not by host cells not invaded by the organism. A molecular probe may specifically bind to a cancer-specific molecule, such as a marker specific for hepatocarcinoma cells. A molecular probe may specifically bind to molecules expressed specifically by liver, colon, uterus, and kidney cells. Certain embodiments may be useful for determining cell types and organs that are diseased, and are useful for determining the extent to which a disease has spread. A molecular probe may specifically bind to a molecule specific for a progressive stage of a disease and may be included in the diagnostic, such as a molecular probe that specifically binds to a molecule specific for metastatic cells but not non-metastatic cells. A molecular probe may specifically bind to a molecular marker specific to a cell type, diseased cell, or organism, and various markers specific to a cell type, diseased cell, or organism may be selected as a target for these diagnostic applications. For examples, specific markers may include, but are not limited to, EBNAI a viral nuclear antigen found in EBV infected B-cells; S1OOP, S100A4, prostate stem cell antigen, lipocalin 2, claudins 3 and 4, and trefoil factors I and 2 in pancreatic adenocarcinoma; CD antigens, microphthalmia transcription factor (MITF), and members of the Bc1-2 family in neoplastic mast cells; a cell surface marker, such as CDs, HLAs; or intracellular markers such as actins and tubulins as a healthy cell marker. In certain embodiments, hybridization products or extension products may be detected using various methods described herein.

Suitable methods of detection of one or more molecular targets, including the utilization of kits and/or systems, may be useful for therapeutic applications. in certain therapeutic embodiments, one or more molecular probes, one or more detectable components, may be provided to an in vitro or ex vivo sample from a patient or administered to a patient in vivo. In certain therapeutic embodiments, the provided, or administered one or more molecular probes and one or more detectable components, may further comprise a universal adapter. One or molecular targets may be bound by the one or more molecular probes, and detected upon hybridization with the one or more detectable components and/or universal adapters and one or more detectable components. The detectable components may comprise one or more signal generating moieties. The hybridized product may be extended by endogenous enzymes present in the sample or subject, and sometimes is extended by exogenous components delivered to the sample or subject (e.g., a polymerase and/or nucleotides, such as a PCR method).

A suitable method for identifying a disease or condition in a subject may comprise delivering a first molecular probe and a second molecular probe to a subject, wherein the first molecular probe comprises a first binding moiety partner and a first oligonucleotide and the second molecular probe comprises a second binding moiety partner and a second oligonucleotide. The method may further comprise a universal adapter. The first binding moiety partner and second binding moiety partner specifically bind to a first binding region or second binding region in a target molecule, or a first target molecule and a second target molecule, where each target molecule may be independently selected from a target molecule specifically expressed by a diseased cell, a target molecule specifically expressed by a pathogenic organism, and a target molecule specifically expressed by a certain cell type. The first oligonucleotide may comprise a first oligonucleotide sequence complementary to a second oligonucleotide sequence in the second oligonucleotide and may be capable of forming a hybridized product with the second oligonucleotide when the first hybrid is bound to the first target molecule or first target molecular region and the second hybrid is bound to the second target molecule or second target molecular region, and the first target molecule and the second target molecule are in proximity or the first target molecular region and second target molecular region are in proximity. The hybridized product may be extended by delivering exogenous components that extend the hybridized product (e.g., a polymerase and/or nucleotides, such as a PCR method), and a targeting component that may specifically bind to an oligonucleotide sequence in the hybridized product or extension product may be delivered. The targeting component may comprise one or more signal generating moieties, and the targeting component may be detected by delivering a secondary agent, such as a secondary antibody, that specifically binds to the targeting component and comprises one or more signal generating moieties. The hybrids, targeting component, and other diagnostic components may be delivered in an amount effective to identify the disease or condition in the subject and/or patient.

A suitable kit for detection of one or more molecular targets in a sample may comprise preparing, purifying, and/or isolating, one or more molecular probes, one or more universal adapters, and/or one or more detectable components, each of which may comprise one or more spacer groups, and providing to the sample the prepared, purified, and/or isolated one or more molecular probes, one or more universal adapters, and/or one or more detectable components, each of which may comprise one or more spacer groups. For example, the kit for detecting one or more molecular targets in a sample may be utilized in a method of detection. A suitable kit and/or system for detecting one or more molecular targets in a sample, may comprise one or more prepared, purified and/or isolated molecular probes, such as one or more biomolecule-oligonucleotide conjugates, for example, antibody-oligonucleotide conjugates, protein-oligonucleotide conjugates, or peptide-oligonucleotide conjugates, one or more prepared, purified and/or isolated universal adapters, and/or one or more prepared, purified and/or isolated detectable components, wherein each of the molecular probes, universal adapters, and/or detectable components may comprise one or more spacer groups. The kit and/or system for detecting one or more molecular targets in a sample may be used in a method of detecting one or more molecular targets in a sample. For example, the method of detecting the one or more molecular targets may comprise utilizing one or more of the following detection techniques and/or methods, including, but is not limited to: singleplex and multiplex assays, such as immunoassays, protein detection assays, immunodetection, enzyme linked immuno-assays (ELISA), immunomagnetic cellular depletion, immunomagnetic cell capture, flow cytometry, immunohistochemistry (IHC), immunocytochemistry (ICC), in situ hybridization (ISH), ELISpot, enzyme immuno-assays (EIA), blotting methods (e.g. Western, Southern, Southwestern, and Northern), arrays, bead arrays, multiplex bead array, microarray, antibody array, cellular array, solution phase capture, chemiluminescence detection, infrared detection, labeling inside electrophoresis systems or on surfaces or arrays, PCR amplification, elongation followed by PCR amplification, precipitation, immunoprecipitation, co-immunoprecipitation, chromatin immunoprecipitation, pretargeting imaging, therapeutic agent, nucleic acid hybridization assays, microspeopy, imaging, high content screening (HCS), other assay or detection formats, for example, that are useful in research as well as in diagnosing diseases or conditions, or combinations or derivatives thereof and/or combinations thereof. The kit for detecting one or more molecular targets in a sample may further comprise one or more binding moieties. The kit for detecting one or more molecular targets in a sample may further comprise one or more signal generating moieties. The kit for detecting one or more molecular targets in a sample may further comprise one or more scaffolds, wherein the one or more scaffolds may comprise one or more signal generating moieties.

In certain embodiments, a plurality of molecular probes, comprising binding moieties conjugated to oligonucleotides, and a plurality of detectable components, comprising signal generating moieties conjugated to complementary oligonucleotides, may be preassembled, i.e., combined and allowed to hybridize to form a composition comprising a plurality of hybridized molecular probe-detectable components, that may then be followed by contacting the preassembled composition with a sample, comprising one or more molecular targets. In certain embodiments, the preassembled composition, comprising a plurality of hybridized molecular probe-detectable components, may then be used in an assay to perform both recognition and detection functions. In certain embodiments, the plurality of molecular probes may comprise one or more antibodies. In certain embodiments, the plurality of detectable components may comprise one or more signal generating moieties. The plurality of molecular probes and/or the plurality of detectable components may comprise one or more spacer groups. The plurality of molecular probes may comprise, for example, 2 or more molecular probes, such as 3 or more, 4 or more, 5 or more, 10 or more, 2.5 or more, 100 or more molecular probes. Similarly, the plurality of detectable components may comprise, for example, 2 or more detectable components, such as 3 or more, 4 or more, 5 or more, 10 or more, 25 or more, 100 or more detectable components.

In certain embodiments, the oligonucleotides of the plurality of molecular probes and the plurality of detectable components may not be complementary, for example, the plurality of detectable components may comprise signal generating moieties conjugated to oligonucleotides that are not complementary to the oligonucleotides of the plurality of molecular probes. When the plurality of molecular probes and the plurality of detectable components comprise oligonucleotides that are non-complementary, these may be combined together along with a plurality of adaptor oligonucleotides. The plurality of adaptor oligonucleotides may comprise oligonucleotides sequence segments that may be complementary to the plurality of molecular probes and oligonucleotides sequence segments that may be complementary to the plurality of detectable components. The plurality of molecular probes, the plurality of detectable components, and the plurality of adaptor oligonucleotides, may then be allowed to preassemble, i.e., hybridize to form a composition comprising a plurality of molecular probe-adapter-detectable components, that may then be followed by contacting the composition with a sample, comprising one or more molecular targets.

In certain embodiments, a molecular probe may be combined with a plurality of detectable components, for example, 2 or more detectable components, such as 3 or more, 4 or more, 5 or more, 10 or more, 25 or more, 100 or more detectable components, to allow for detection in a plurality of assays, such as in a plurality of fluorescent channels, or alternatively, in a plurality of assay formats, such a fluorescent assay and an enzymatic activity assay. Similarly, a plurality of molecular probes, for example, 2 or more molecular probes, such as 3 or more, 4 or more, 5 or more, 10 or more, 25 or more, 100 or more molecular probes, may be combined with a detectable component, to allow for detection in a fluorescent channel for samples containing a plurality of targets.

Preassembly Hybridization

In certain embodiments, the process of conducting the preassembly hybridization prior to contacting a sample, may be advantageous for certain applications, assays, and/or methods, and may lend itself to creating novel formats, tests, assays, and/or classes of products. Preassembly may allow the formation of the molecular probe-detectable components, and their purification and/or validation, in a different time or place from their actual use or application in an assay, which may be of significant value. The process of preassembly may be performed, for example, by the end-user immediately prior to its use in an assay, or separately for example, by a commercial supplier which may then be provided to the end user.

Advantageously, the process of preassembly may allow for the use of a strategy for multiplexed detection, wherein one or more molecular probes may be combined with one or more detectable components on an as-needed basis. For example, with a selection of one or more detectable components available, such as 2 or more detectable components, such as 3 or more, 4 or more, 5 or more, 10 or more, 25 or more, 100 or more detectable components available, it may be possible to select a specific detectable component to be associated with one or more molecular probes, such as in an assay comprised of a plurality of molecular probes to be contacted with a complex sample comprising one or more molecular targets. In certain embodiments, a plurality of detectable components may be prepared by conjugating a unique oligonucleotide to a plurality of signal generating moieties, for example a plurality of scaffolds comprising unique organic fluorophores, such that the plurality of detectable components corresponds to a plurality of channels of a commercial flow cytometer. Then, to match a specific binding moiety, such as an antibody, to a particular channel, a molecular probe and the detectable component bearing the appropriate fluorophore would be preassembled. By conducting the process of preassembly, appropriately matching particular binding moieties to particular detectable components, a panel of unique tests may be prepared in advance to allow for a multiplexed assay, for example a multiplexed assay of a pattern of immunoreactivities on a population of cells, such as would be used in immunophenotyping by flow cytometry. In addition, in certain embodiments, based on the results of a first multiplexed assay, a second panel of hybrids may be preassembled to further characterize the sample. In certain embodiments, one or more panels of preassembled hybrids may be used to characterize a sample comprising one or more molecular targets, such as 2 or more panels, for example, 3 or more, 4 or more, 5 or more, 10 or more, 25 or more, 100 or more panels.

In certain embodiments, the process of preassembly may be readily adaptable to automation. For example, a plurality of molecular probes, such as 2 or more, 3 or more, 4 or more, 5 or more, 10 or more, 25 or more, 100 or more, 1,000 or more, or 10,000 or more molecular probes, may be placed into individual containers or wells that may then be addressed individually by a robotic tool. Similarly, a plurality of detectable components, such as 2 or more, 3 or more, 4 or more, 5 or more, 10 or more, 25 or more, 100 or more, 1,000 or more, or 10,000 or more detectable components may be placed into individual containers or wells that may then be addressed individually by a robotic tool. From these pluralities of individual molecular probes and individual detectable components, a plurality of predetermined combinations, for example predetermined by a table or a computation, may be preassembled. For example, a plurality of unique combinations or sets of molecular probes and detectable components may be brought together by combining an aliquot of a specific molecular probe and an aliquot of a specific detectable component, in another container or well to allow their hybridization to form a complex, wherein the amounts employed provide the appropriate ratios of oligonucleotides to allow proper stoichiometry. In certain embodiments, the automated system may perform the steps of mixing to match the specific binding moiety, such as an antibody, to a particular fluorescence channel, to form a panel or set under the control of a user. Alternatively, the automated system might select the specific binding moiety, such as an antibody, and match it to a particular fluorescence channel, to form a panel or set according to an algorithm. In certain embodiments, the automated system may perform the steps of mixing to match each specific binding moiety, such as an antibody, to a particular fluorescence channel, to form a panel or set under the control of a user. Alternatively, the automated system might select each specific binding moiety, such as an antibody, and match it to a particular channel, to form a panel or set according to an algorithm. Using a preassembly format, a plurality of these sets, such as two or more sets, three or more, four or more, five or more, ten or more, twenty or more, fifty or more, one hundred or more, one thousand or more, or ten thousand or more sets may be preassembled on an as-needed basis to then be used, for example used in an assay. Advantageously, use of unique preassembled sets of molecular probes and detectable components, automated multiplexed immunodetection assays, such as in flow cytometry, imaging, microscopy, high content screening (HCS), ELISA, ELISpot, or immunohistochemistry, to examine populations and subpopulations of circulating lymphocytes, may be accomplished rapidly, cost-effectively and/or with a minimal selection of reagents. Such an automated system may be able to perform a series of preassembly steps, to create a panel of multiplexed sets that perform a defined or adaptive sequence of tests to characterize a sample. In certain embodiments, the automated system may perform, for example, immunophenotyping by subjecting the sample to analysis by multiple sets, formed in order by the process of preassembly, that are defined by a defined protocol. Alternatively, an automated system may select at least in part the constituents of one or more sets to be used for immunophenotyping based at least in part on the results of one or more previous sets, by applying an algorithm that incorporates at least in part the one or more prior results to determine at least in part one or more subsequent set, and then using the principles of preassembly, to form one or more additional sets as needed, thereby achieving speed and specificity that exceed what can be obtained by other techniques.

Preparation, Purification and/or Isolation

Figure 10:
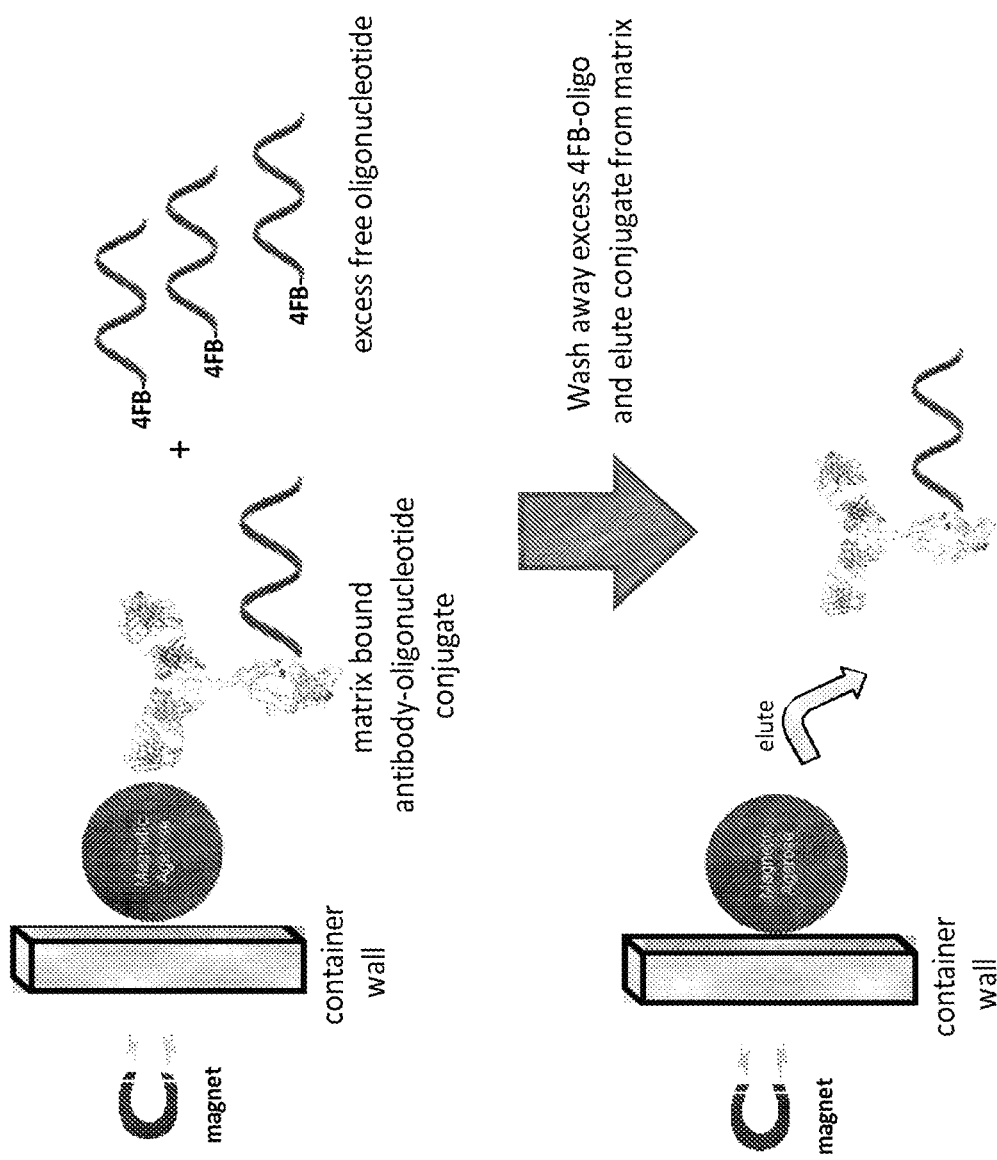
FIG. 10: Magnetic affinity purification of antibody-oligonucleotide conjugate, in accordance with certain embodiments.

In certain embodiments, the antibody-oligonucleotide conjugates may be purified as depicted in FIG. 10. For example, the conjugation reaction mixture, comprising antibody-oligonucleotide conjugates and excess modified oligonucleotide may be purified by binding the antibody-oligonucleotide conjugates to a column comprising agarose and metal ions immobilized within the stationary phase of the column (which may be called "magnetic agarose" or "magnetic affinity beads"). The prepared antibody-oligonucleotide conjugates may include moieties, such as a histidine rich region, that may bind to metal ions that are immobilized on the stationary phase of the column—which may now be separated from the excess modified oligonucleotide, which do not have functionality that may bind to the metal ions in a similar chelating fashion. Once the excess modified oligonucleotide has been washed by a series of elutions, the bound antibody-oligonucleotide conjugates may be released by eluting with a displacing agent, such as another chelating moiety, for example, EDTA.

Figure 11:
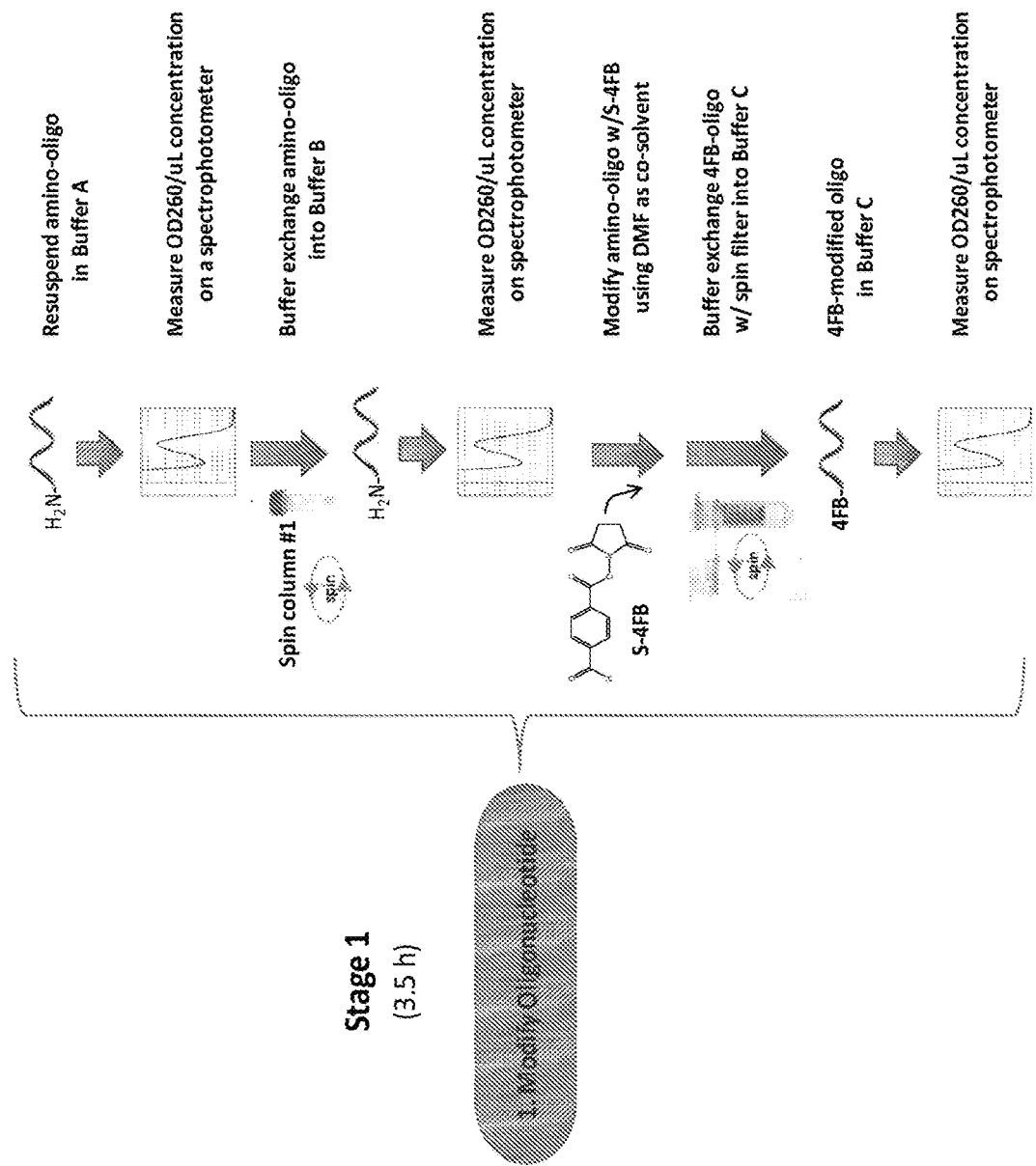
FIG. 11: Stage 1: Modification of the oligonucleotide to form a modified oligonucleotide, in accordance with certain embodiments.

In certain embodiments, the modified oligonucleotides may be prepared as depicted in FIG. 11. For example, in Stage 1, the modified oligonucleotides may be prepared by resuspending an amino-oligonucleotide in a buffer (Buffer A). The oligonucleotide concentration (OD260/µL) may be determined by spectrophotometer measurement. Once the concentration has been determined, the buffer solution may be exchanged by sequential centrifuge spin down and resuspension of the resulting pellet in Buffer B to prepare for reacting with the modifying reagent, followed by measuring the oligonucleotide concentration (OD260/µL) in Buffer B by spectrophotometer measurement. Modification of the oligonucleotide may be conducted, for example, with S-4FB, using dimethylformamide (DMF) as a cosolvent. Once the reaction has completed, the reaction mixture may be spun down and the Buffer C exchanged into the system. Finally, the modified-oligonucleotide (4FB-modified oligonucleotide) concentration can be measured (OD260/µL) by spectrophotometer measurement, now in Buffer C.

In certain embodiments, the modified oligonucleotide may be prepared by solid phase synthesis. The solid phase synthesis may also include the direct incorporation of a linker during the solid phase oligonucleotide synthesis. The solid phase synthesis may also include the direct incorporation of a linker during the solid phase modified oligonucleotide synthesis.

Figure 12:
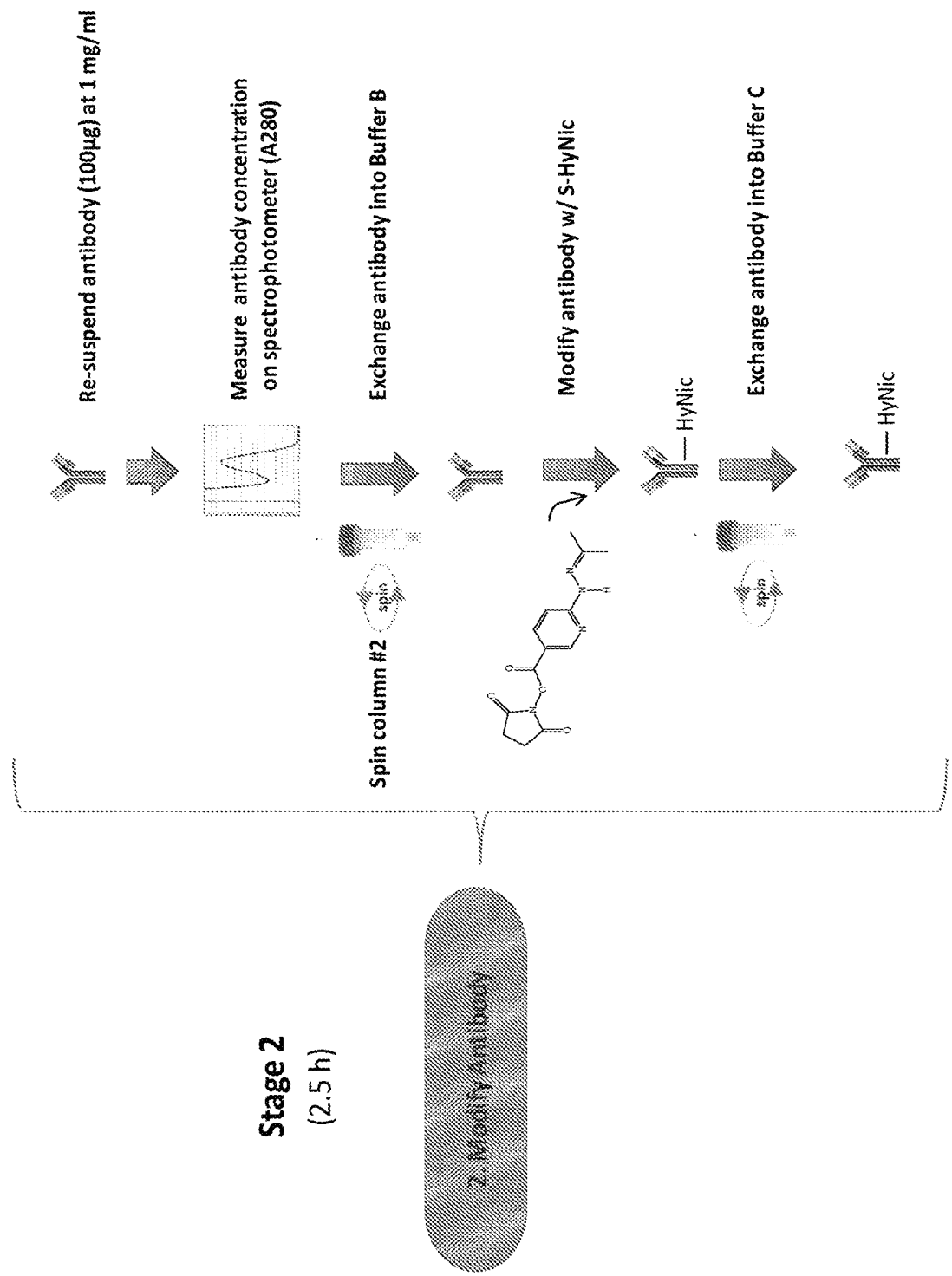
FIG. 12: Stage 2: Modification of the antibody to form a modified antibody, in accordance with certain embodiments.

In certain embodiments, the modified antibody may be prepared as depicted in FIG. 12. For example, in Stage 2, the modified antibodies may be prepared by resuspending the antibody in a buffer (for example 100 µg antibody at 1 mg/mL concentration). The antibody concentration (A280) may be determined by spectrophotometer measurement. Once the concentration has been determined, the buffer solution may be exchanged by sequential centrifuge spin down and resuspension of the resulting pellet in Buffer B to prepare for reacting with the modifying reagent, for example, with S-HyNic. Once the reaction to modify the antibody has been completed, the reaction mixture may be spun down and the modified antibody, for example a S-HyNic-modified antibody, may be exchanged into Buffer C. Finally, the modified-antibody concentration, for example, the S-HyNic-modified antibody concentration, may be measured by a spectrophotometer measurement, now in Buffer C.

Figure 13:
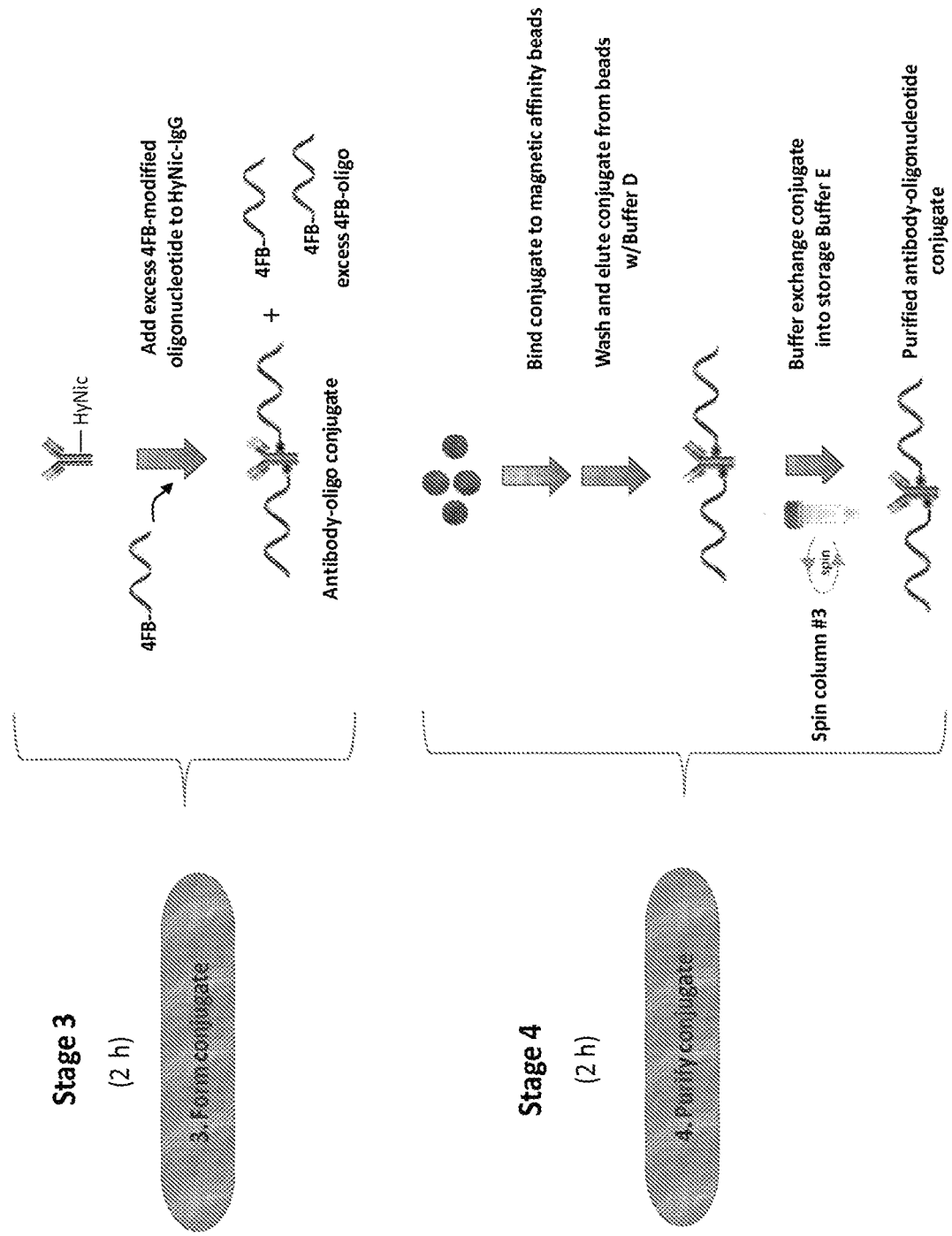
FIG. 13: Stage 3: Formation of the antibody-oligonucleotide conjugate. Stage 4: Purification of the antibody-oligonucleotide conjugate, in accordance with certain embodiments.

In certain embodiments, the conjugation of a modified antibody with a modified oligonucleotide may be conducted as depicted in Stage 3 in FIG. 13. For example, in Stage 3, the modified-antibody, a 5-HyNic-modified antibody, may be reacted with an excess of the modified-oligonucleotide (4FB-modified oligonucleotide), to form antibody-oligonucleotide conjugates having at least one oligonucleotide conjugated to each modified-antibody The reaction mixture will also have unreacted modified-oligonucleotide (4FB-modified oligonucleotide).

In certain embodiments, the purification and isolation of antibody-oligonucleotide conjugates may be conducted as depicted in Stage 4 in FIG. 13. For example, in Stage 4, the conjugation reaction mixture, comprising antibody-oligonucleotide conjugates and excess unreacted modified-oligonucleotides (4FB-modified oligonucleotide), may be placed in contact with "magnetic affinity beads," for example, beads having metal ions immobilized that are available to be bound selectively, by chelation, with the product antibody-oligonucleotide conjugates but not with the unreacted modified-oligonucleotides. Once the antibody-oligonucleotide conjugates have been bound to the magnetic affinity beads, the beads are washed to remove the remaining reaction components other than the bound antibody-oligonucleotide conjugates. The antibody-oligonucleotide conjugates are then released with a displacing agent, such as Buffer D, which then is buffered exchanged with Buffer E via sequential spin down and resuspension series, to provide purified antibody-oligonucleotide conjugates.

in certain embodiments, the protein-oligonucleotide conjugates may be prepared or purified, or both, as depicted in FIGS. 9, 10, 12 and 13, where a protein is modified rather than an antibody, and utilizing modified oligonucleotides as depicted in FIGS. 9, 10, 11 and 13.

Figure 14:
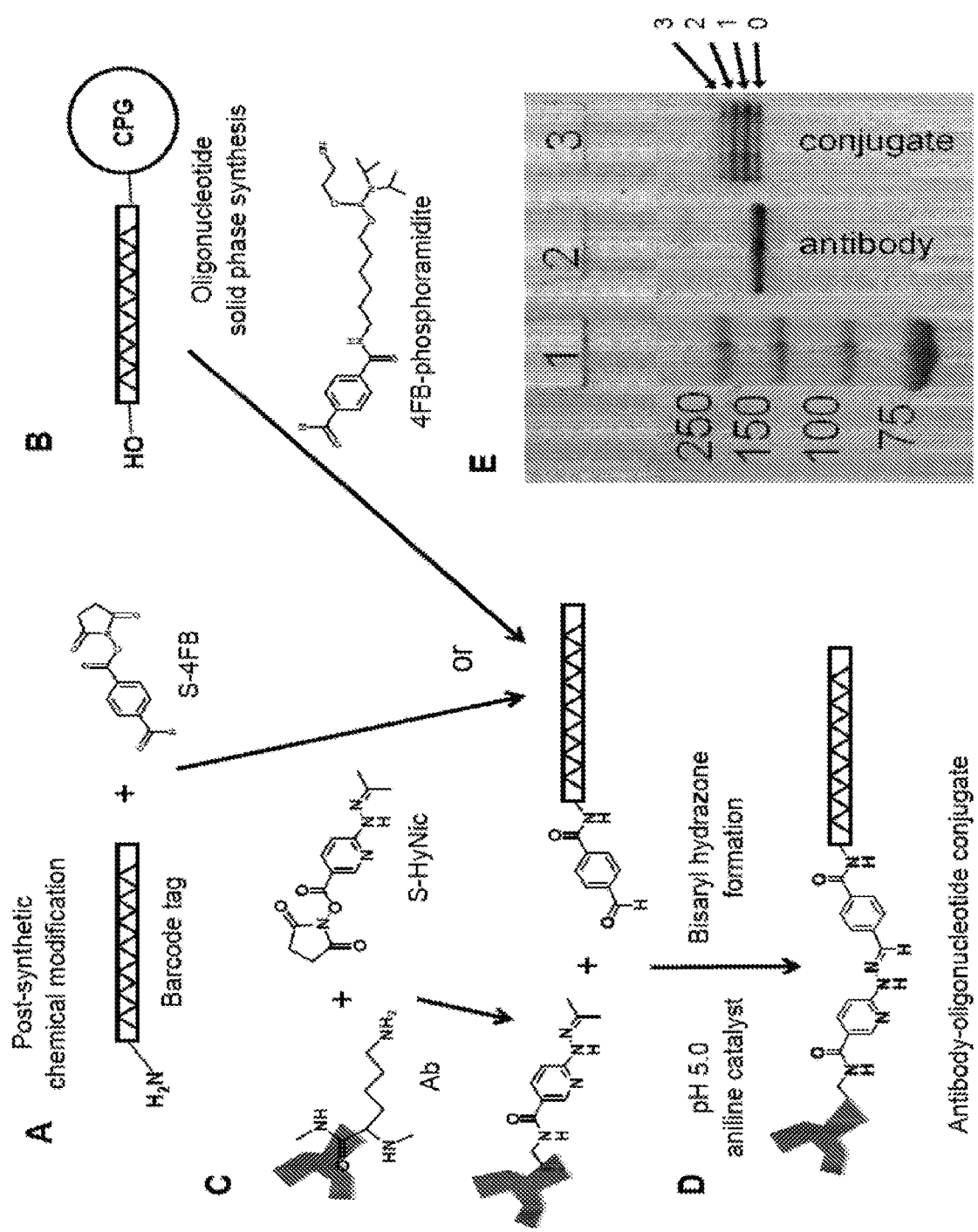
FIG. 14: is a scheme presenting the HyNic/4FB chemistry used to conjugate oligonucleotides (oligonucleotide barcode tags) to antibodies and results, in accordance with certain embodiments.

In certain embodiments, an antibody such as a monoclonal antibody directed against a specific antigen of interest may be conjugated to an oligonucleotide to form a conjugate. In FIG. 14, the process for forming an antibody-oligonucleotide conjugate is presented diagrammatically. Here, the conjugation takes advantage of the chemical reaction between the HyNic and 4FB moieties to promote full conversion of the antibody to conjugate. (A) represents a post-synthetic chemical modification method to prepare a 4FB modified oligonucleotide. Here, an amino-oligonucleotide, for example, a $C_6$-amino-oligonucleotide, that encodes a specific barcode tag sequence is prepared by solid phase phosphoramidite chemistry. Then, using the N-hydroxysuccinimide reactivity of sulfo-succinimidyl activated 4-formyl benzoate (S-4FB), the oligonucleotide is modified and activated. Alternatively, in (B), the oligonucleotide is synthesized by solid phase phosphoramidite chemistry with a terminal 4FB phosphoramidite monomer. The oligonucleotide may be of a number of different lengths to incorporate one or more barcodes, chemistries to incorporate alternative backbones, bases, or inert linkers, or geometries, such as tandem repeats or branched dendrimers to allow incorporation of multiple copies of the barcode sequence, as can readily be formed by standard means. Further, the 4FB moiety might be incorporated by a number of alternative chemistries or by biochemical means using enzymes. Further, a 4FB moiety might be placed at either the 3' or 5' end, or in the middle or close to either end of an oligonucleotide. In parallel, in (C), the antibody or other protein, biomolecule, or other probe would be reacted to incorporate one or more HyNic moieties as via reaction of the N-hydroxysuccinimide reactivity of sulfo-succinimidyl activated 6-hydrazinopyridine-3-carboxylate (S-HyNic) with a primary amine, such as a Lysine amino acid epsilon amino group which are prevalent on the surface of proteins. Five mole equivalents of S-HyNic to each mole equivalent of antibody might be used. Other chemical or biochemical means could be used to modify the antibody or other probe molecule to display one or more HyNic moieties. Then, after purifying the 4FB-modified oligonucleotide and HyNic-modified antibody, they can be brought together, typically with a molar excess of the oligonucleotide to the antibody. Via the formation of the bisarylhydrazone bond, the antibody-oligonucleotide conjugate (D) is formed. As shown in (E), non-denaturing polyacrylamide gel electrophoresis of the HyNic modified antibody formed in (C) in Lane 2 reveals a single prominent band at approximately 200 kD apparent mass. In Lane 3, the antibody-oligonucleotide conjugate formed in (D) demonstrates multiple bands indicating multiple molecular forms. Here the one mole equivalent of HyNic-antibody was combined with approximately three mole equivalents of 4FB-oligonucleotide. As indicated by the numbering, the bands are consistent with the conjugation of 0, 1, 2, or 3 oligonucleotides to the antibody. Thus, this process yields a mixture of HyNic-modified antibody, 4FB-oligonucleotide and antibody-oligonucleotide conjugates with one or more oligonucleotides coupled to each antibody. By varying the mole ratio of S-HyNic to antibody and of 4FB-modified oligonucleotide to HyNic-modified antibody, essentially all, or nearly all, of the antibody can be converted to oligonucleotide conjugate.

Figure 15:
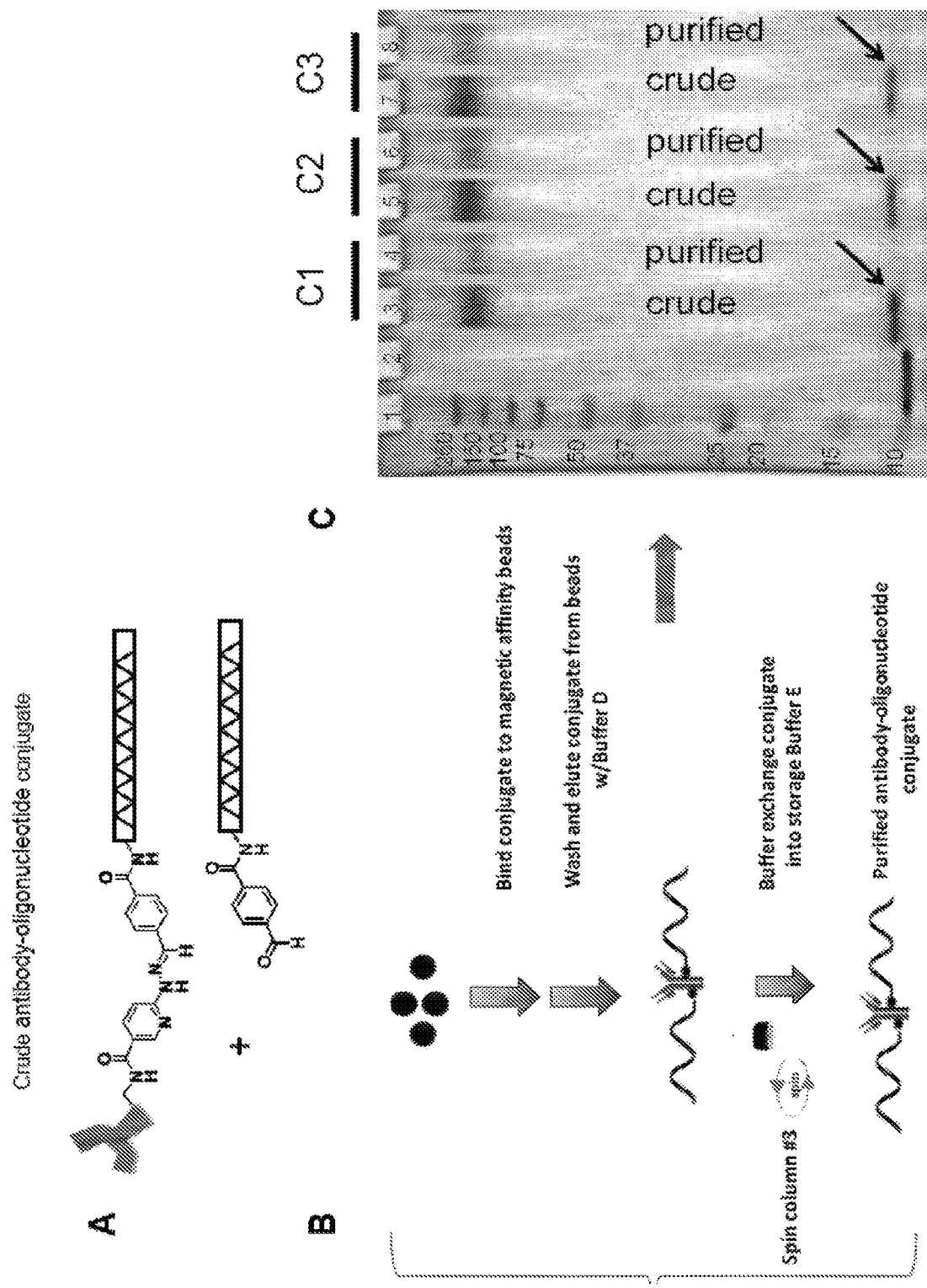
FIG. 15: is a scheme presenting steps used to prepare purified bis-arlyhydrazone based antibody-oligonucleotide conjugates and results, in accordance with certain embodiments.

In certain embodiments, the purification and isolation of antibody-oligonucleotide conjugates obtained by the reaction of HyNic-modified antibody with a mole excess of 4FB-modified oligonucleotide may be desirable, as shown in FIG. 15. A chemical separation may be conducted in order to isolate the antibody-oligonucleotide conjugate away from unincorporated oligonucleotide. For example, the conjugation reaction mixture (A), comprising antibody-oligonucleotide conjugates and excess unreacted 4FB-modified-oligonucleotides, may be placed in contact with "magnetic affinity beads," for example, beads having metal ions immobilized by chelation that are available to be bound selectively with a binding site on the antibody. Thus, the product antibody-oligonucleotide conjugates will be substantially captured onto the beads and the unreacted 4FB modified-oligonucleotides will not. Once the antibody-oligonucleotide conjugates have been bound to the magnetic affinity beads, the beads are washed to remove the remaining reaction components other than the bound antibody-oligonucleotide conjugates. The antibody-oligonucleotide conjugates are then released with a displacing agent, such as Buffer D, which then is buffer-exchanged with storage Buffer E by applying the solution to a centrifugal desalting column pre-equilibrated with Buffer E. The eluent after centrifugation yields the purified antibody-oligonucleotide conjugate.

Immunodetection Assays and/or Detection

Figure 16:
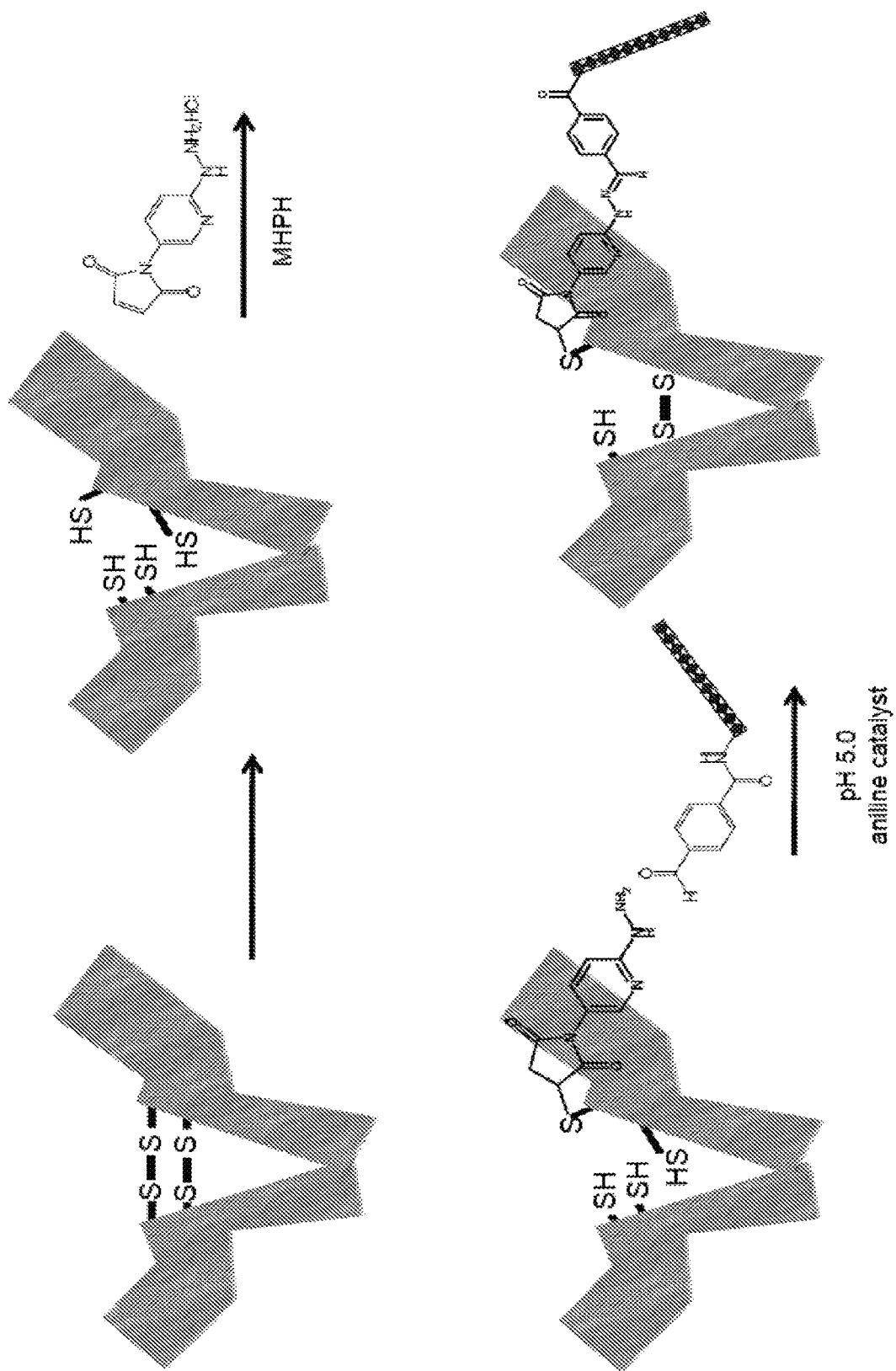
FIG. 16: is a scheme presenting preparation of 1:1 antibody-oligonucleotide conjugate via a controlled reduction of disulfide bonds in the hinge region of an antibody, followed by reaction of a resultant thiol with a thiol-reactive aromatic hydrazine, MHPH, to form a hydrazine containing adduct, and then conjugated with a 4FB-oligonucleotide in the presence of aniline catalyst to form the 1:1 antibody-oligonucleotide conjugate, in accordance with certain embodiments.

In certain embodiments, 1/1 antibody-oligonucleotide conjugates may be required for immunodetection assays. Site specific 1/1 antibody-oligonucleotides conjugates can be prepared as schematically presented in FIG. 16 wherein antibodies are reduced under controlled conditions to reduce two exposed disulfide bonds in the hinge region, followed by quenching of the reduced protein with MHPH, a thiol reactive aromatic hydrazine bifunctional modification reagent, followed by desalting and conjugation to a 4FB-modified oligonucleotide in the presence of aniline catalysis. In a non-site selective procedure, the antibody is controllably modified with S-HyNic to incorporate <3 HyNic moieties followed by conjugation to 0.75 or less mole equivalents of a 4FB-oligonucleotide in the presence or absence of aniline catalyst, the unconjugated oligonucleotide is removed by size exclusion chromatography, the unconjugated antibody is removed by ion exchange chromatography and the conjugate released from the cationic support to isolate the pure antibody-oligonucleotide conjugate.

Figure 17:
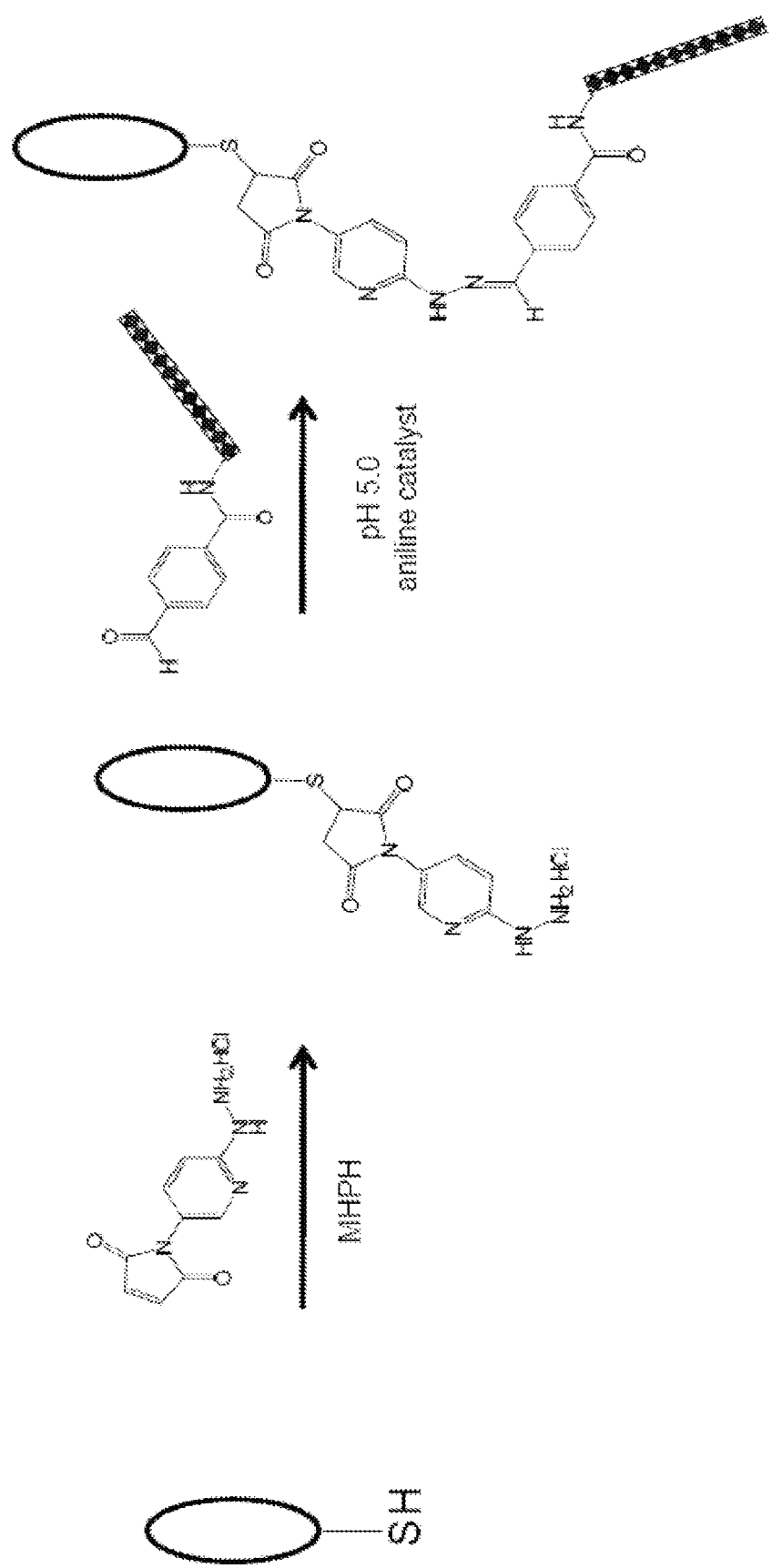
FIG. 17: is a scheme presenting the preparation of a conjugate between an oligonucleotide and a cysteine-containing engineered protein, formed by reacting a cysteine-containing engineered protein with a thiol-reactive aromatic hydrazine, MHPH, to form a hydrazine-containing adduct, and then conjugated with a 4FB-oligonucleotide in the presence of aniline catalyst to form the engineered protein-oligonucleotide conjugate, in accordance with certain embodiments.

In certain embodiments, protein binders other than full antibodies including Fab', Fab'-2 that possess free cysteine moities, protein binders such as scFvs, monobodies, nanobodies, diabodies and camelids engineered to incorporate a single cysteine, or proteins engineered to incorporate unnatural amino acids such as acetyl-phenylalanine incorporated using engineered tRNAs, and aptamers can be barcoded with oligonucleotides and employed in immunodetection assays. FIG. 17 presents schematically a procedure to incorporate a single oligonucleotide barcode on a protein containing a single cysteine using the HyNic/4FB couple to produce an 1/1 protein-oligonucleotide conjugate mediated by an bis-arylhydrazone bond.

Figure 18:
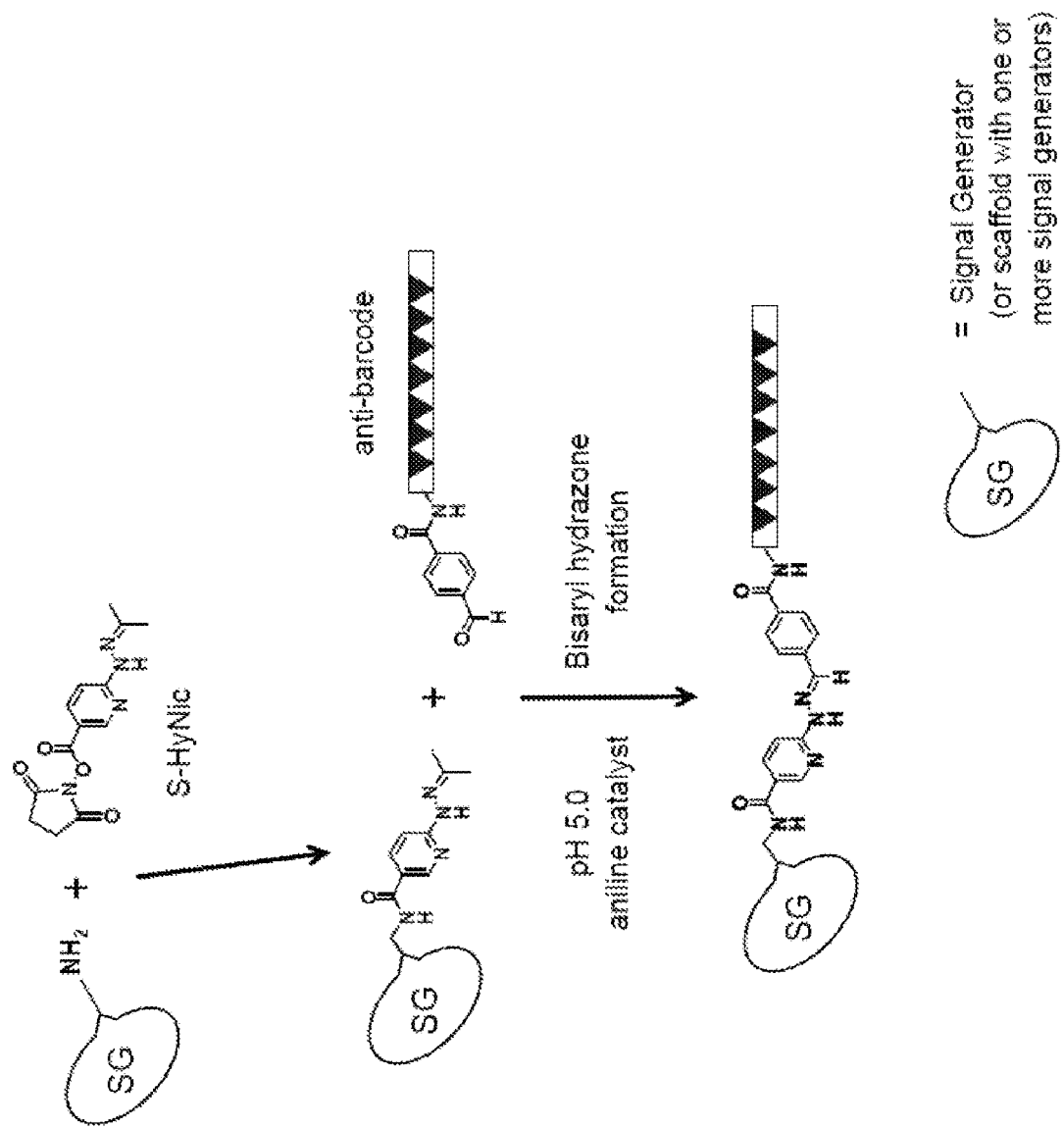
FIG. 18: is a general scheme presenting the preparation of oligonucleotide-signal generators using a HyNic-4FB coupling, in accordance with certain embodiments.

In certain embodiments, a variety of signal generators can be conjugated to the complementary oligonucleotide. Oligonucleotide-signal generator conjugates can also be prepared using the HyNic-4FB couple. FIG. 18 presents schematically a method wherein an amino-substituted signal generator is modified to incorporate a HyNic moiety and is conjugated to a 4FB-oligonucleotide in the presence or absence of aniline catalyst. Other methods may also be employed. Signal generators that may be incorporated into complementary oligonucleotides, such as those of FIG. 18, include but are not limited to, fluorescent protein; fluorophore; fluorosphere; quantum dot; enzyme; nucleic acid; scaffold; dendrimer; hydrogel; buckyballs; nanoparticles; nanogold; colloidal gold; microparticle; magnetic particle; bead; microarray; microfluidic device; wetted surface; biological cells; or derivatives or combinations thereof.

Figure 19:
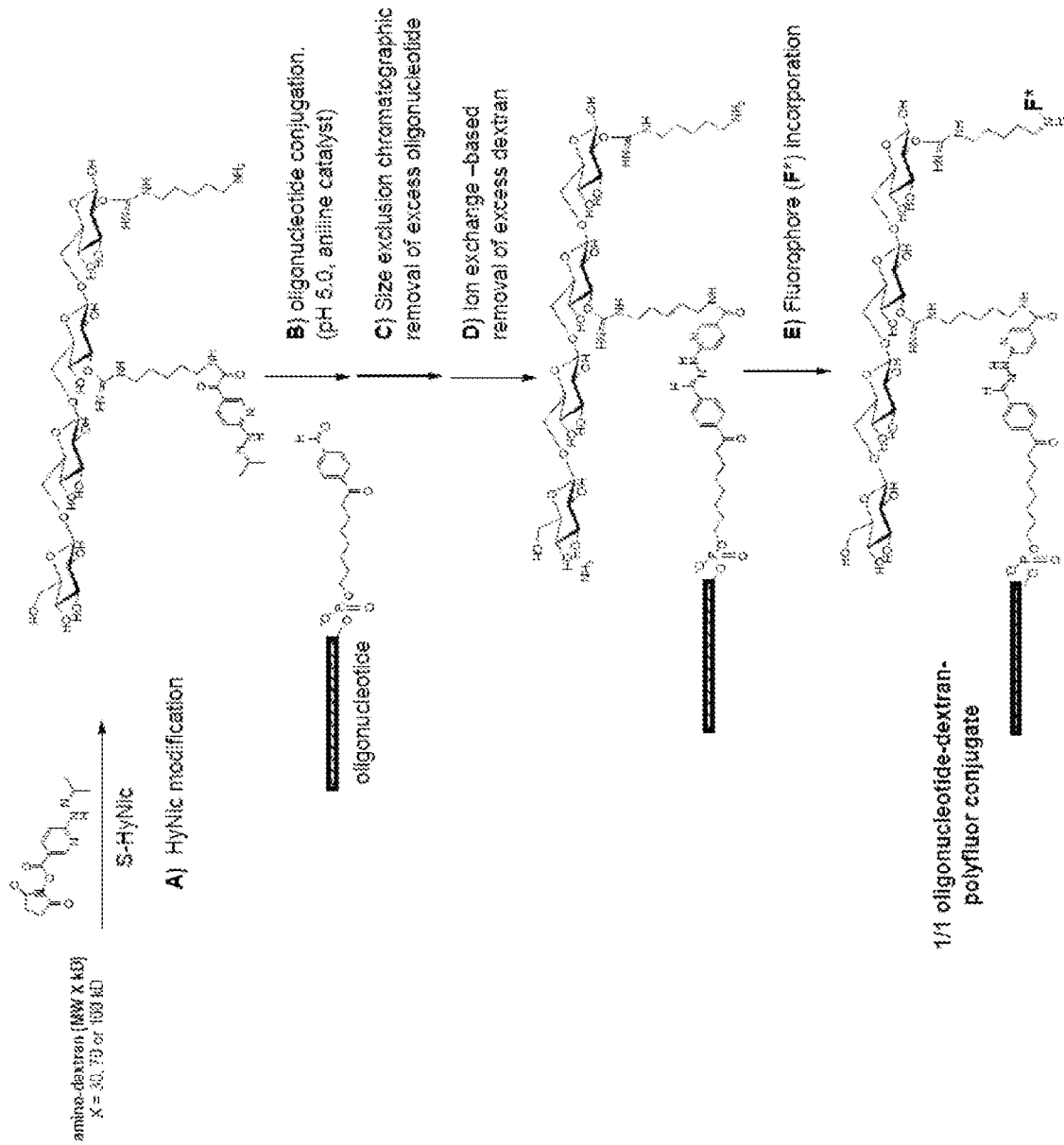
FIG. 19: is a scheme presenting the preparation of a complementary oligonucleotide-dextran-polyfluor conjugate with 1:1 oligonucleotide to dextran stoichiometry, in accordance with certain embodiments.

In certain embodiments, complementary detectors can be prepared wherein the detector construct is prepared such that the stoichiometry of the construct is 1 oligonucleotide conjugated to a single scaffold to which multiple signal generators are covalently bound. FIG. 19 presents the scheme described in the examples that was used. The complementary detector was prepared in the following multi-step protocol: (A) amino-dextran, a 50,000 mean molecular weight polysaccharide bearing 40 to 50 amine groups per molecule, was modified by reaction with sulfo-succinimidyl activated 6-hydrazinopyridine-3-carboxylate (S-HyNic) to incorporate 2-3 HyNic groups per molecule; (B) to each mole equivalent of HyNic-amino-dextran was added 0.5 mole equivalents of complementary 4FB-modified oligonucleotide; (C) unconjugated 4FB-oligonucleotide was removed by size exclusion column chromatography; (D) unconjugated dextran was removed by ion exchange column chromatography in which the oligonucleotide-amino-dextran conjugate was adsorbed on the cationic support, the unconjugated dextran was washed away and the oligonucleotide-amino dextran conjugate was eluted from the support; (E) the oligonucleotide-amino dextran conjugate was exchanged into pH 7.4 phosphate buffer and remaining amino groups on the dextran component of the oligonucleotide-amino dextran conjugate were then modified by combining for each mole equivalent of oligonucleotide-dextran conjugate, 5 mole equivalents of an N-hydroxysuccinimide-modified fluorescent organic dye; and the resulting oligonucleotide-dextran-fluorophore conjugate was purified by dialysis.

Figure 20:
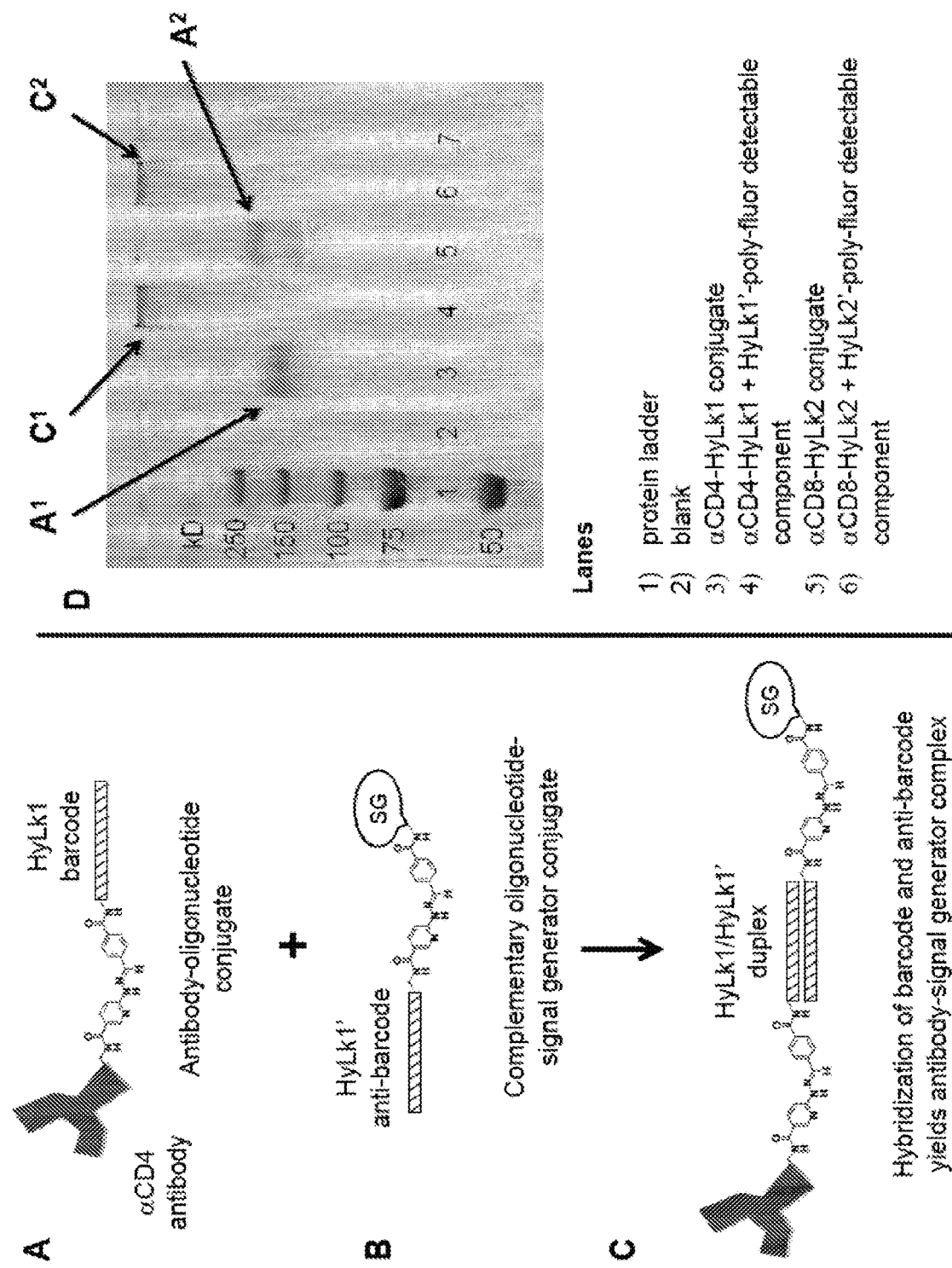
FIG. 20: (Left) is a schematic representation of the hybridization of an antibody-oligonucleotide conjugate (A), with a complementary oligonucleotide-fluorescently labeled scaffold (B), to form the hybridization product (C). (Right) Polyacrylamide gel results demonstrating the hybridization of two oligonucleotide conjugates (lanes 3 and 5) as compared to their respective complementary oligonucleotide-dextran scaffold conjugates (lanes 4 and 6), in accordance with certain embodiments.

In certain embodiments, the antibody-oligonucleotide conjugates or other oligonucleotide modified materials bearing a specific oligonucleotide sequence that serves as a specific barcode, may be combined with detector conjugate composed of a complementary oligonucleotide sequence that serves as the anti-barcode, chemically linked to a signal generator, such as an oligonucleotide-dextran-fluorophore conjugate. Given the principles of hybridization of complementary sequences, this interaction will result in DNA-directed self assembly, leading to formation of a complex where the antibody is stably associated with the signal generator via a double stranded oligonucleotide linker. FIG. 20 presents a schematic presentation of the process of mixing (A), an antibody-oligonucleotide conjugate formed by the reaction of HyNic-modified antibody to a 4FB-modified oligonucleotide barcode, with (B), a complementary anti-barcode oligonucleotide similarly conjugated to a signal generator. The interaction of the two oligonucleotides forms (C), a complex comprising an antibody now labeled with a signal generator, linked by the hybridized oligonucleotides. This interaction is documented by a native polyacrylamide gel electrophoresis analysis, (D). In Lanes 3 and 5, two distinct antibody-oligonucleotide conjugates each demonstrate a range of species of characteristic mobility, e.g. $A^1$ and $A^2$. As shown in Lanes 4 and 6, upon the addition of a complementary oligonucleotide-dextran-fluorophore conjugate, the two antibodies appear in a new form with greatly decreased mobility, e.g. $C^1$ and $C^2$. Here greater than 95% of each antibody-oligonucleotide conjugate has hybridized to the detector as indicated by the nearly quantitative shift of the product to the slower mobility form.

Self-Assembly

Figure 21:
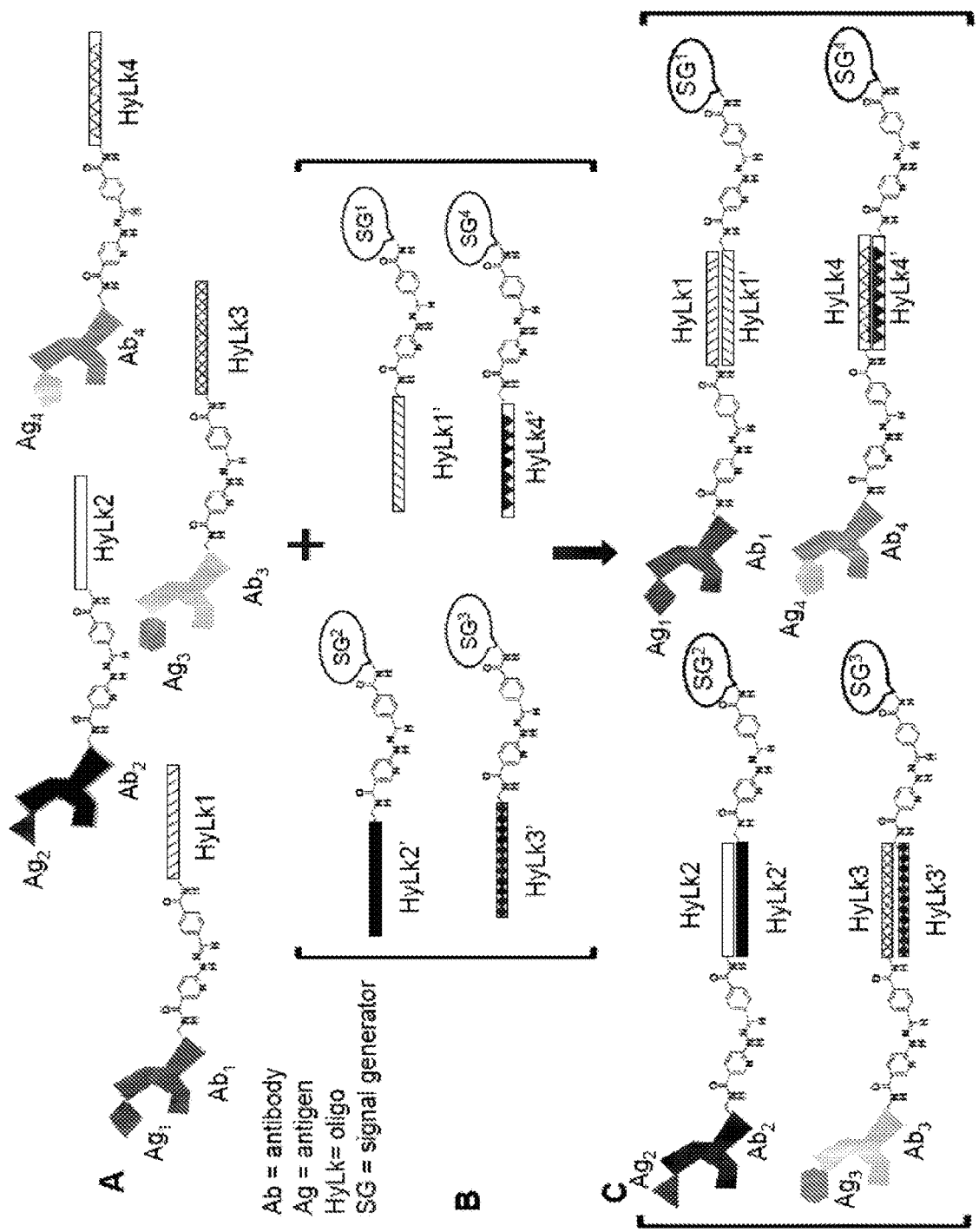
FIG. 21: is a schematic representation of conjugate self assembly, wherein a series of antibody-oligonucleotides (A), and a series of complementary oligonucleotide-signal generators (B), self-assemble via hybridization to form hybridization products (C), in accordance with certain embodiments.

In certain embodiments, the principle of self-assembly directed by hybridization between pairs of complementary oligonucleotides can be used to facilitate the independent formation of multiple complexes where each species represents a specific signal generator linked by a double stranded oligonucleotide to a specific antibody. As diagrammed in FIG. 21, in (A), multiple antibodies denoted $Ab_1$, $Ab_2$, $Ab_3$, $Ab_4$, etc., each conjugated to a different barcode oligonucleotide denoted HyLk1, HyLk2, HyLk3, HyLk4, etc., might be applied as probes to interrogate a complex biological sample. By the principle of binding of antibodies to their cognate antigen epitopes, the different antibody-oligonucleotide conjugates might interact with the sample to form distinct immune complexes that might distribute to distinct locations or be associated with distinct features, for example. Then, in (B), a set of anti-barcode oligonucleotides comprising the complementary sequences, denoted as HyLk1', HyLk2', HyLk3', HyLk4', etc., and conjugated to different signal generators, denoted as $SG_1$, $SG_2$, $SG_3$, $SG_4$ etc., can be added. Then, in (C), by the principle of DNA directed self-assembly, each barcode antibody would hybridize to its anti-barcode signal generator to form complexes. This would bring each signal generator into the distribution of each antibody, so that e.g. the distribution of Abi could be determined by the distribution of $SG_1$, distribution of Abe could be determined by the distribution of $SG_2$, etc.

Figure 22:
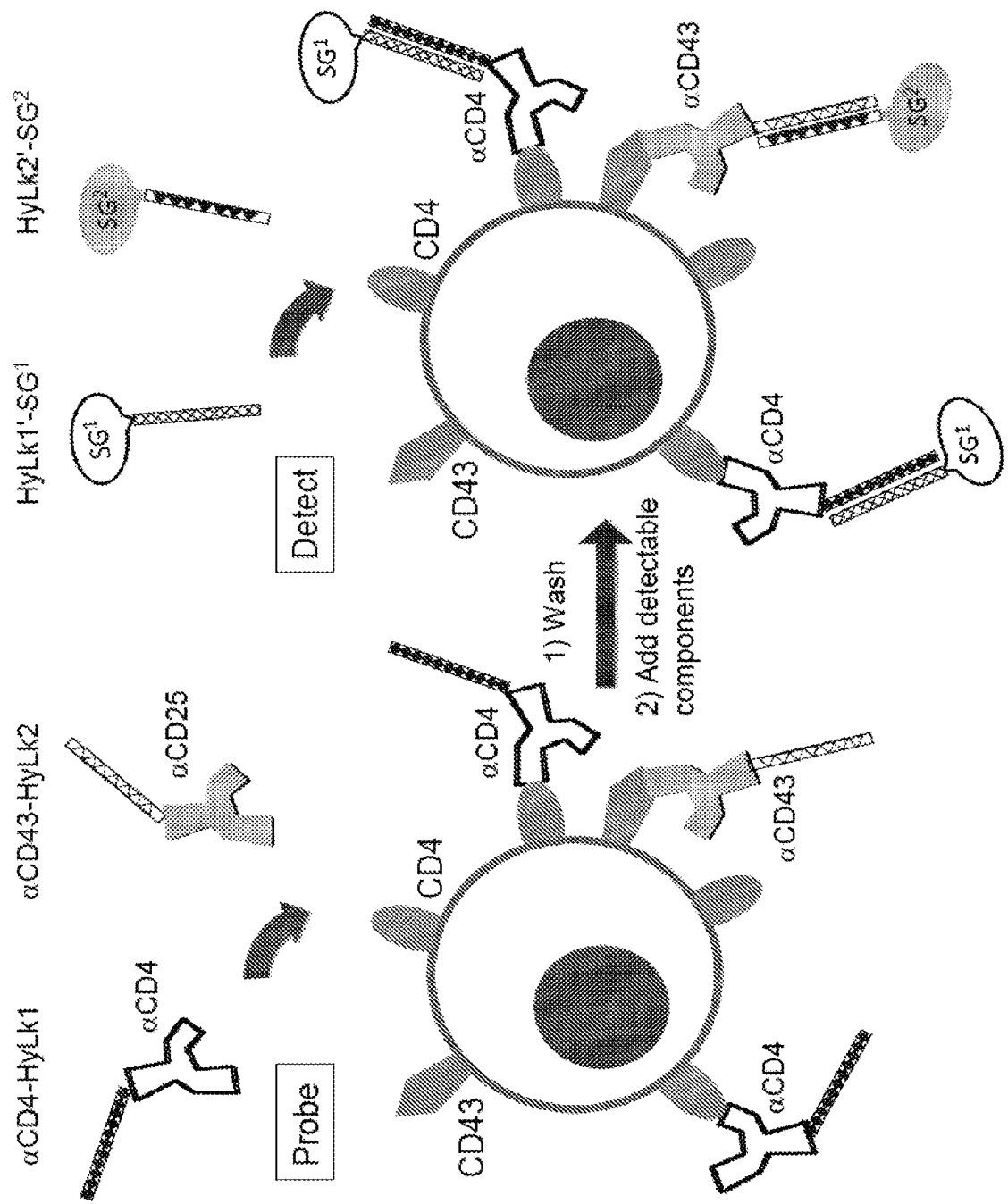
FIG. 22: is a schematic representation of a two-plex flow cytometry experiment mediated by self assembly by hybridization of antibody-oligonucleotide conjugates bound to their respective antigens (Probe) followed by hybridization to their complementary oligonucleotide-signal generator conjugates (Detect), in accordance with certain embodiments.

In certain embodiments, the principle of self-assembly directed by hybridization between pairs of complementary oligonucleotides can be used to facilitate the independent formation of multiple complexes where each species represents a specific signal generator linked by a double stranded oligonucleotide to a specific antibody. Thus, mixtures of antibody-oligonucleotide conjugates can be used to detect one or more antigens present on the surface of a living cell and then mixtures of detectors comprising the complementary oligonucleotide conjugated to readily distinguished signal generators, in this case each a dextran scaffold modified with fluorophores of specific spectral properties, can be applied to allow detection of the binding of each antibody independently in a single experiment, using the methodologies of flow cytometry. As diagrammed in FIG. 22, a sample of cells to be characterized, such as mouse splenocytes, are treated with a mixture of antibody-oligonucleotide probes, such as a mouse monoclonal antibody directed against the mouse T helper cell surface glycoprotein CD4 (αCD4) conjugated to deoxyribose oligonucleotide HyLk1 and a mouse monoclonal antibody against the CD43 sialophorin characteristic of T cells (αCD43) conjugated to deoxyribose oligonucleotide HyLk2. After allowing time for binding, the cells are washed so that the solution is free of unbound antibody-oligonucleotide conjugates. Then a mixture of complementary oligonucleotide detectors which are conjugated to fluorescent proteins or fluorescent dextrans, here a HyLk1' conjugated to signal generator 1 (SG) and HyLk2' conjugated to signal generator 2 ($SG^2$), are added to detect the bound antibodies. The resulting hybridization of HyLk1 to HyLk1' and HyLk2 to HyLk2' then links SG' to cells presenting CD4 and $SG^2$ to cells presenting CD43. As shown here, the cell indicated would be identified by flow cytometry as displaying fluorescence from both signal generators $SG^1$ and $SG^2$, which would then lead to the conclusion that this cell is potentially a $CD4^+$ $CD43^+$ T cell.

Detectors Comprising the Complementary Oligonucleotide

Figure 23:
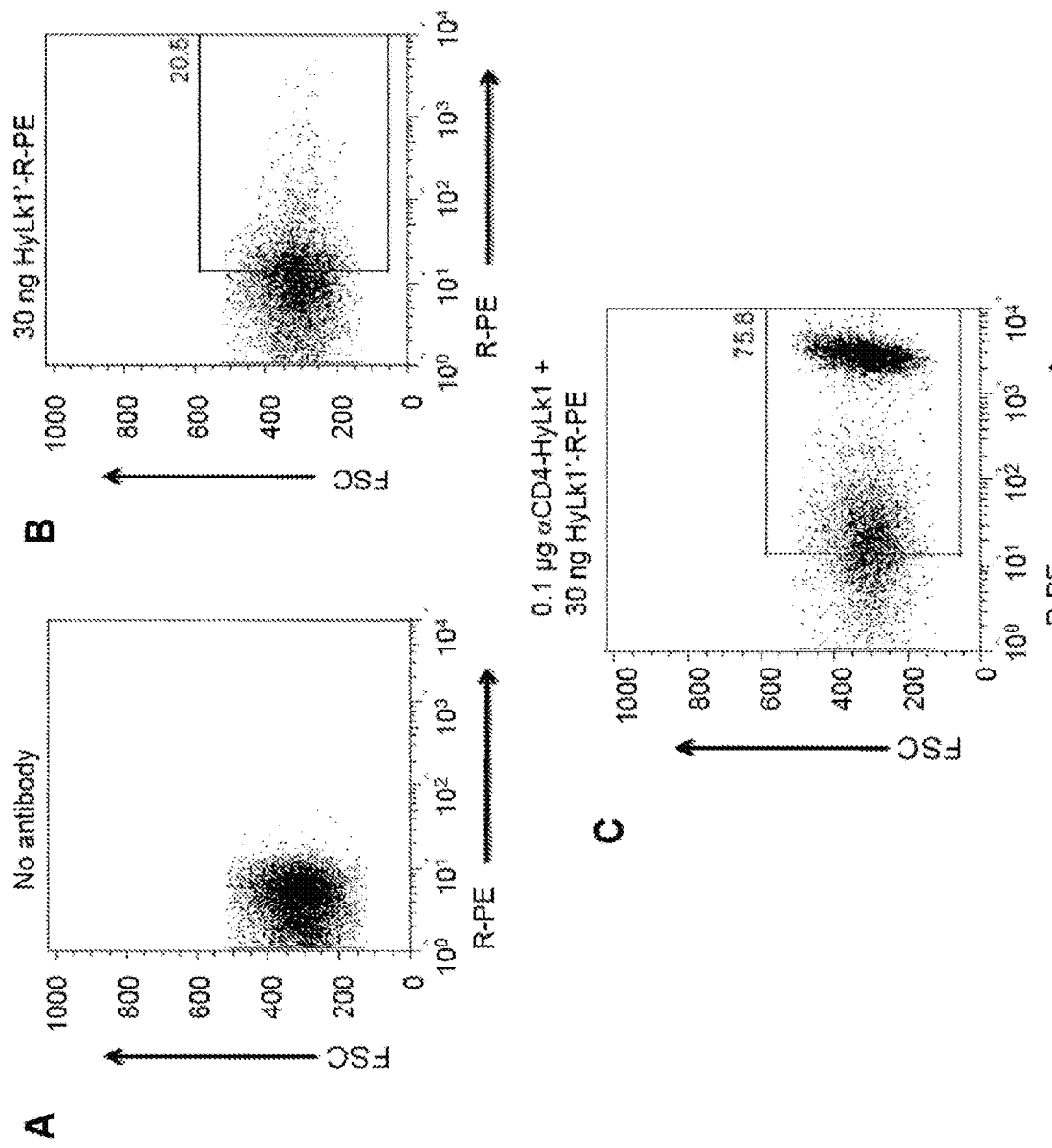
FIG. 23: is flow cytometry results demonstrating detection of CD4 on living cells using α-CD4 antibody-HyLk1 conjugate+HyLk1'-R-phycoerythrin conjugate, in accordance with certain embodiments.

In certain embodiments, antibody-oligonucleotide conjugates and detectors comprising the complementary oligonucleotide conjugated to a signal generator, in this case a complementary oligonucleotide HyLk 1' conjugated by bisarylhydrazone linkage to R-phycoerythrin (R-PE), a biofluorescent protein, can be used to detect the CD4 cell surface protein on splenocytes in flow cytometry. FIG. 23 compares a set of two dimensional flow cytometry plots, where each cell that is detected is indicated by a dot representing its specific forward scatter. FSC denoted on the Y-axis, and its specific fluorescence in the R-PE channel, denoted by R-PE on the X axis. The dots represent approximately 10,000 individual cells examined in a single experiment. As shown in plot (A) in the upper left, when splenocytes are gated to select for lymphocytes, they demonstrate a characteristic forward scatter of approximately 300 FSC Units, and display approximately a fluorescence intensity in the R-PE fluorescence channel of 5 R-PE Units. Here, the value of 5 R-PE Units represents the background due to endogenous fluorescence, limitations of the instrumentation and other features. In the flow cytometry plot (B) on the upper right, addition of 30 ng of HyLk conjugated to R-PE detector to the splenocytes causes the lymphocytes to display increased fluorescence in the R-PE channel, with a median intensity of approximately 10 R-PE Units. This control experiment reveals the detector background signal, which may be ascribed to non-specific binding of the detectors to the lymphocytes. For the experiment, in plot (C) in the lower panel, 0.1 ug of αCD4 conjugated by bisarylhydrazone chemistry to HyLk1 was first added to the splenocytes and allowed to bind. Then the cells were washed and treated with 30 ng of HyLk1'-R-PE. The cells were then analyzed by flow cytometry as before. Note that two populations of cells are detected, one with a median intensity of 20 R-PE Units and a second with a median intensity of 3000 R-PE Units. The 3000 R-PE Unit population represents the subset of splenocytes that would be considered as CD4 positive ($CD4^+$) by this assay, which normally identifies presumptive T helper cells. The 20 R-PE Unit population represents the cells that bound low levels of the antibody and/or the detector and are considered CD4 negative ($CD4^-$), and represents the non-specific background in the experiment. A proxy for the signal to background (S/B) of this experiment can be estimated as the ratio of the median intensity of the CD4⁺ and CD4⁻ populations, $CD4+_i/CD4-_i$, which here would be calculated as greater than (>) 100. It is common to consider that a S/B>100 is a characteristic of a high quality biochemical assay.

Figure 24:
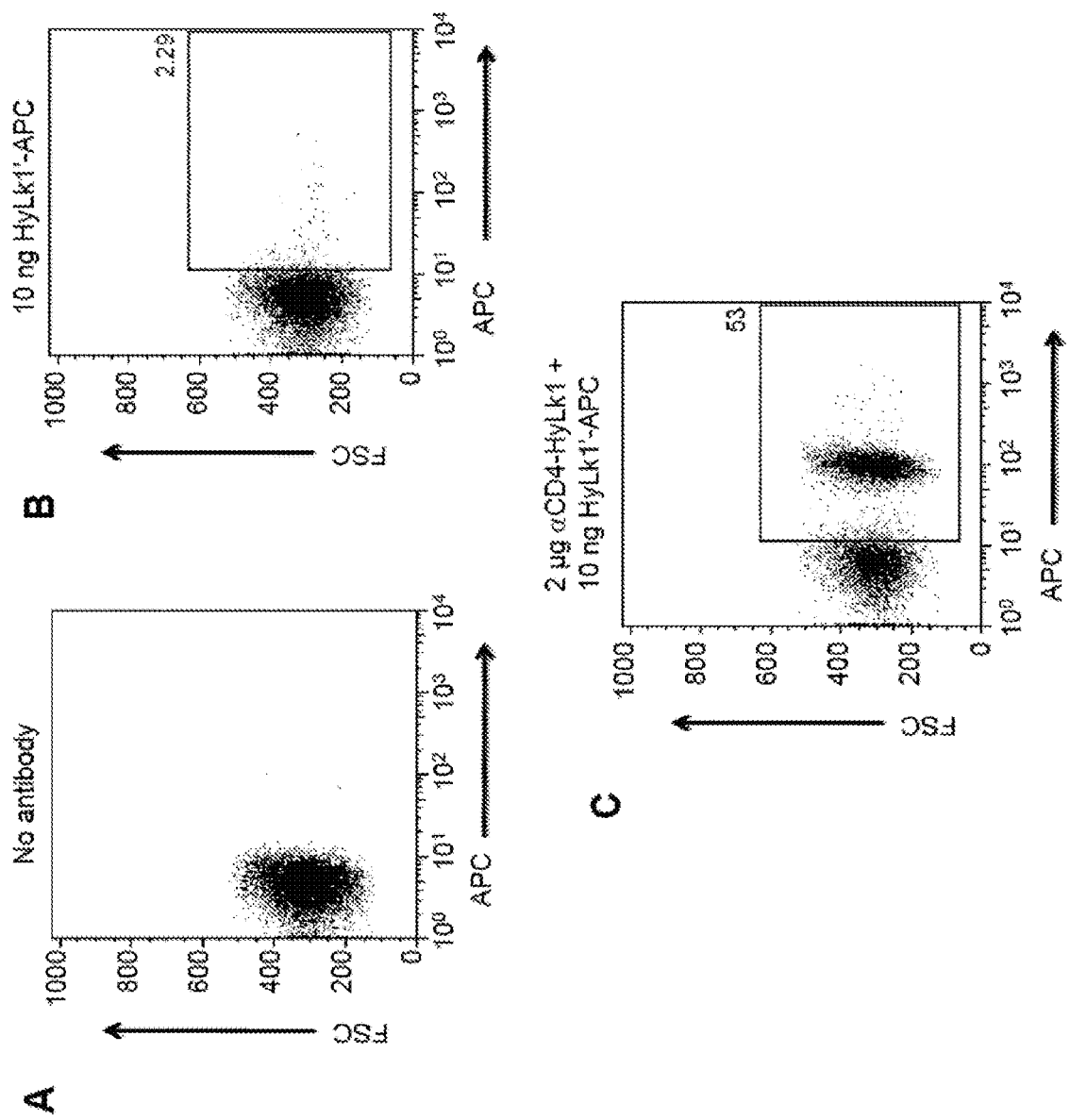
FIG. 24: is flow cytometry results demonstrating detection of CD4 on living cells using α-CD4 antibody-HyLk1 conjugate+HyLk1'-allophycocyanin conjugate, in accordance with certain embodiments.

In certain embodiments, antibody-oligonucleotide conjugates and detectors comprising the complementary oligonucleotide conjugated to a signal generator, in this case a complementary oligonucleotide conjugated to the biofluorescent protein allophycocyanin (APC), can be used to detect biomarker in flow cytometry. As shown in FIG. 24, the plot (A) in the upper left indicates the background fluorescence for lymphocytes, which has a median value of approximately 5 APC Units. The plot (B) in the upper right indicates that after addition of 10 ng of HyLk1' conjugated by bisarylhydrazone chemistry to APC (HyLk1'-APC), the median fluorescence does not increase appreciably and remains at 5 APC Units, indicating that the non-specific binding of the detector is negligible. The lower plot (C) indicates the results when splenocytes were treated with 2 µg of αCD4 conjugated to HyLk1, washed, treated with 10 ng of HyLk1'-APC and analyzed by flow cytometry. Here, the two populations indicate a CD4⁻ population of cells at approximately 10 APC Units and a CD4⁺ population at 100 APC Units. The S/B here is estimated at approximately 20.

Figure 25:
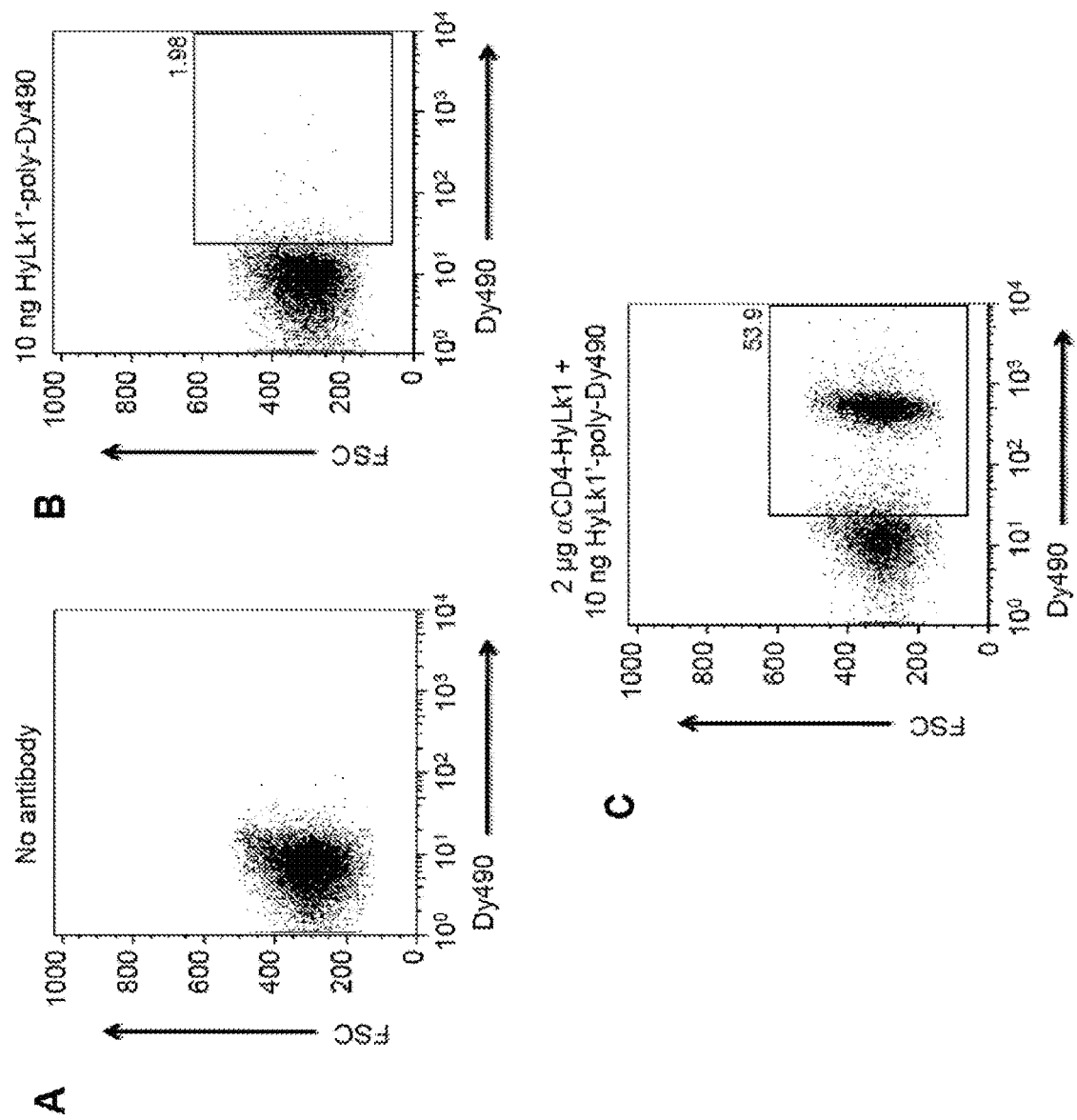
FIG. 25: is flow cytometry results demonstrating detection of CD4 on living cells using α-CD4 antibody-HyLk1 conjugate+HyLk1'-poly-Dy490 conjugate, in accordance with certain embodiments.

In certain embodiments, antibody-oligonucleotide conjugates and detectors comprising the complementary oligonucleotide conjugated to a signal generator, in this case a complementary oligonucleotide conjugated to a dextran scaffold to which multiple DyLite 490 fluorophores have been coupled, can be used to detect biomarker in flow cytometry. As shown in FIG. 25, the plot (A) in the upper left indicates the background fluorescence for lymphocytes, which has a median value of approximately 5 Dy490 Units. The plot (B) in the upper right indicates that after addition of 10 ng of HyLk1' conjugated by bisarylhydrazone chemistry to dextran which was then labeled with DyLite 490 (HyLk1'-poly-Dy490), the median fluorescence increases to 10 Dy490 Units, indicating measurable non-specific binding of the detector. The lower plot (C) indicates the results when splenocytes were treated with 2 µg of αCD4 conjugated to HyLk1, washed, treated with 10 ng of HyLk1'-poly-Dy490 and analyzed by flow cytometry. Here, the two populations indicate a CD4⁻ population of cells at approximately 10 Dy490 Units and a CD4⁺ population at 500 Dy490 Units. The SB here is estimated at approximately 50.

Flow Cytometry, Western Blot, Library of Monoclonal Antibodies, Beads, ELISA

Figure 26:
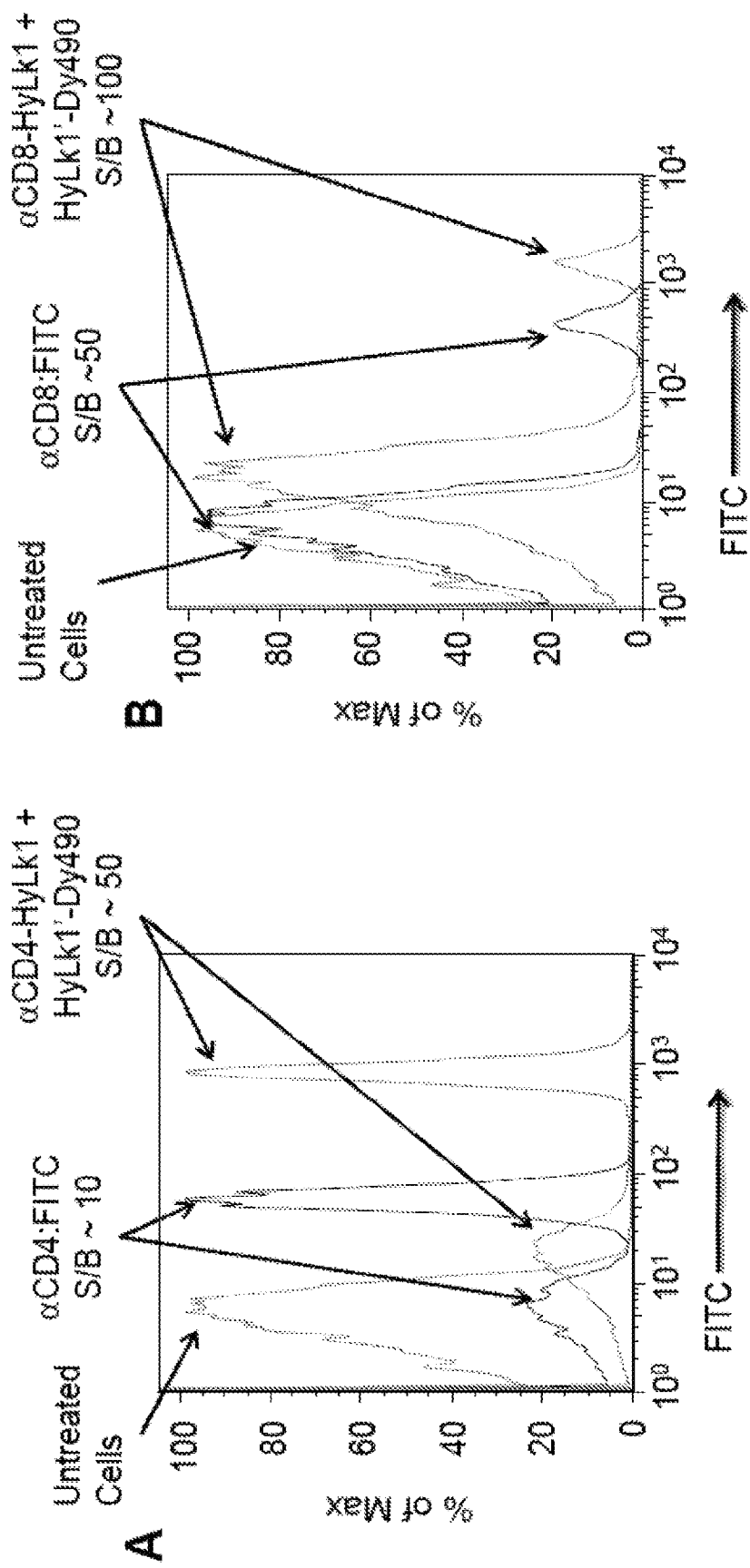
FIG. 26: is comparing flow cytometry detection results of either an α-CD4 antibody (A) or an α-CD8 antibody (B) on living cells, wherein the α-CD4 or α-CD8 antibodies are directly labeled with FITC or are labeled via antibody-HyLk1 conjugate and HyLk1'-poly-Dy490 conjugates, in accordance with certain embodiments.
Figure 27:
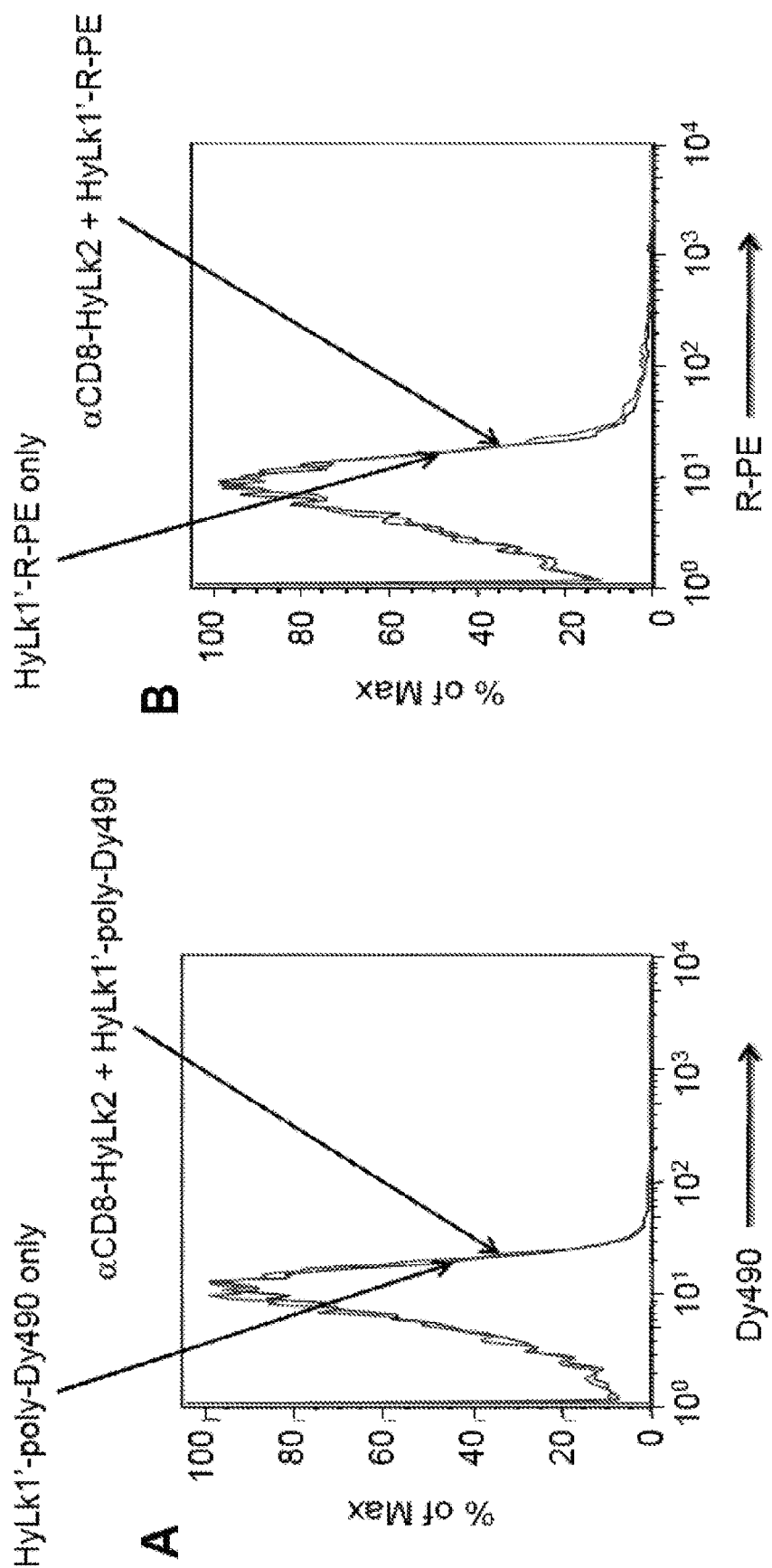
FIG. 27: in both (A) and (B) are results demonstrating absence of crosstalk between antibody-oligonucleotide conjugates and non-complementary oligonucleotide fluorophore conjugates, in accordance with certain embodiments.

A limiting feature for success of flow cytometry analysis to detect antigens present in or on individual cells is the sensitivity and specificity of detection of that antigen. In general, antibodies are commonly used as probes, given their properties as sensitive and specific detection reagents. When the antibodies are rendered fluorescent, they may be detected by flow cytometry. Direct fluorescent labeling of antibodies to form stable, covalent antibody-fluorophore conjugates such as F1TC conjugates, R-PE conjugates, APC conjugates or others allows their facile use in flow cytometry, but may alter the favorable properties of the antibody as a detection reagent. In particular, conjugation to multiple small organic fluorophores may inactivate a significant fraction of antibodies or alter solubility. Conjugation to fluorescent proteins R-PE or APC may impair accessibility of the antibody combining site to antigen epitopes. An antibody-oligonucleotide conjugate may be used for flow cytometry as an alternative to an antibody-fluorophore conjugate. The detectors may comprise the complementary oligonucleotide conjugated to a signal generator. These may comprise a scaffold molecule conjugated to multiple small organic fluorophores, such as HyLk1' conjugated by bisarylhydrazone chemistry to dextran which was then labeled with DyLite 490 (HyLk1'-poly-Dy490). As shown in FIG. 26, a comparison of commercially available antibody-fluorophore conjugates to antibody-oligonucleotide conjugates recognizing surface antigens CD4, a T helper cell surface antigen, and CD8, a cytotoxic T cell surface antigen, was performed. Alternatively, αCD4:FITC or αCD8:FITC were applied under standard conditions to splenocytes and the sample subjected to flow cytometry. Then, a αCD4-HyLk1 conjugate or a αCD8-HyLk1 conjugate were applied to the splenocytes and the sample subjected to flow cytometry. The graphs represent histograms summarizing the flow cytometry data, gated to detect lymphocytes, obtained from (A), unstained splenocytes or stained using the αCD4:FITC or stained using the αCD4-HyLk1/HyLk1'-poly-Dy490 couple, and (B), unstained splenocytes or stained using αCD8:FITC or stained using the αCD8-HyLk1/HyLk 1'-poly-Dy490 couple. The Y-axis represents the relative abundance of cells that displayed a specific intensity of fluorescence in the FITC channel, as distributed on the X-axis. As shown in A and B, the αCD4:FITC and αCD8:FITC reagents displayed the favorable property of a small fluorescence background with respect to cells that would be considered CD4⁺ or CD8⁺, respectively. By comparison, as shown in A and B, applying either the αCD4-HyLk1/HyLk1'-poly-Dy490 couple or the αCD8-HyLk1/HyLk1'-poly-Dy490 couple caused a shift of the cells to increased signal in the FITC channel, including those that would be considered CD4⁺ or CD8⁺, respectively. This would be interpreted as non-specific background, a potentially unfavorable feature. As shown in A, a similar fraction of cells in each population demonstrated a high staining level when treated with αCD4:FITC or αCD4-HyLk1/HyLk1'-poly-Dy490, representing CD4⁺ cells. Similarly, as shown in B, a similar fraction of cells in each population demonstrated a high staining level when treated with αCD8:FITC or αCDS-HyLk1/HyLk1'-poly-Dy490, representing CD8⁺ cells. The median intensity of CD4⁺ cells as detected by αCD4:FITC is significantly less than those detected by αCD4-HyLk1/HyLk1'-poly-Dy490. Similarly, the median intensity of CD8⁺ cells as detected by αCD8:FITC is significantly less than those detected by αCD8-HyLk1/HyLk1'-poly-Dy490. The higher intensity of cells that display positive staining would be interpreted as signal, a favorable feature. As a measure of sensitivity and specificity and the quality of the assay, examining the ratio of median intensity of the CD4⁺ to CD4⁻ cells or the CD8⁺ to CD8⁻ cells offers a measurement of signal to background (S/B). Here, the commercial reagents display a S/B of ~10 for αCD4:FITC and ~50 for αCD8:FITC. Here, the oligonucleotide conjugates display a S/B of ~50 for αCD4-HyLk1/HyLk1'-poly-Dy490 and ~100 for αCD8-HyLk1/HyLk1'-poly-Dy490. These data suggest that the prototype olignucleotide conjugates and complementary oligonucleotide detectors compare well to existing commercialized reagents as detection reagents.

in certain embodiments, more than one antibody-oligonucleotide conjugates will be brought into contact with detectors comprising one complementary oligonucleotide conjugated to a signal generator as well as one or more non-complementary oligonucleotides conjugated to signal generators, as an alternative to multiple conventional antibody-fluorophore conjugates used together to analyze multiple antigens in a single experiment. An advantage of the direct conjugation of the fluorescence signal generator to the antibody is the high potential for correct identification of an antibody based on a fluorescence signal alone. Under conditions where multiple antibody-oligonucleotide conjugates are used along with multiple oligonucleotide-signal generator conjugates, it may be desirable to have no appreciable interaction between non-complementary pairs. As such, a consideration in evaluating the antibody-oligonucleotide conjugates and oligonucleotide-signal generators is to investigate the potential for interactions between pairs of non-complementary oligonucleotides leading to false positive signals, commonly described as crosstalk. Toward testing crosstalk between noncomplementary pairs, splenocytes were stained and analyzed by flow cytometry to compare the fluorescence of lymphocytes that were treated with no antibody, or with αCD8-HyLk2, and then treated with the non-complementary probe HyLk1'-poly-Dy490 or HyLk1'-R-PE. In FIG. 27, the results of flow cytometry are displayed as plots of the relative incidence of cells on the Y-axis that display a fluorescence intensity as indicated on the X-axis for the indicated fluorescence channel, FITC or R-PE. In graph (A), the presence or absence of αCD8-HyLk2 has no appreciable effect on the median fluorescence after treatment with HyLk1'-poly-Dy490. Similarly, in (B), the presence or absence of αCD8-HyLk2 has no appreciable effect on the median fluorescence after treatment with HyLk1'-R-PE. These results suggest that cross-talk is not a significant feature of non-specific background in experiments using antibody-oligonucleotide conjugates.

Figure 28:
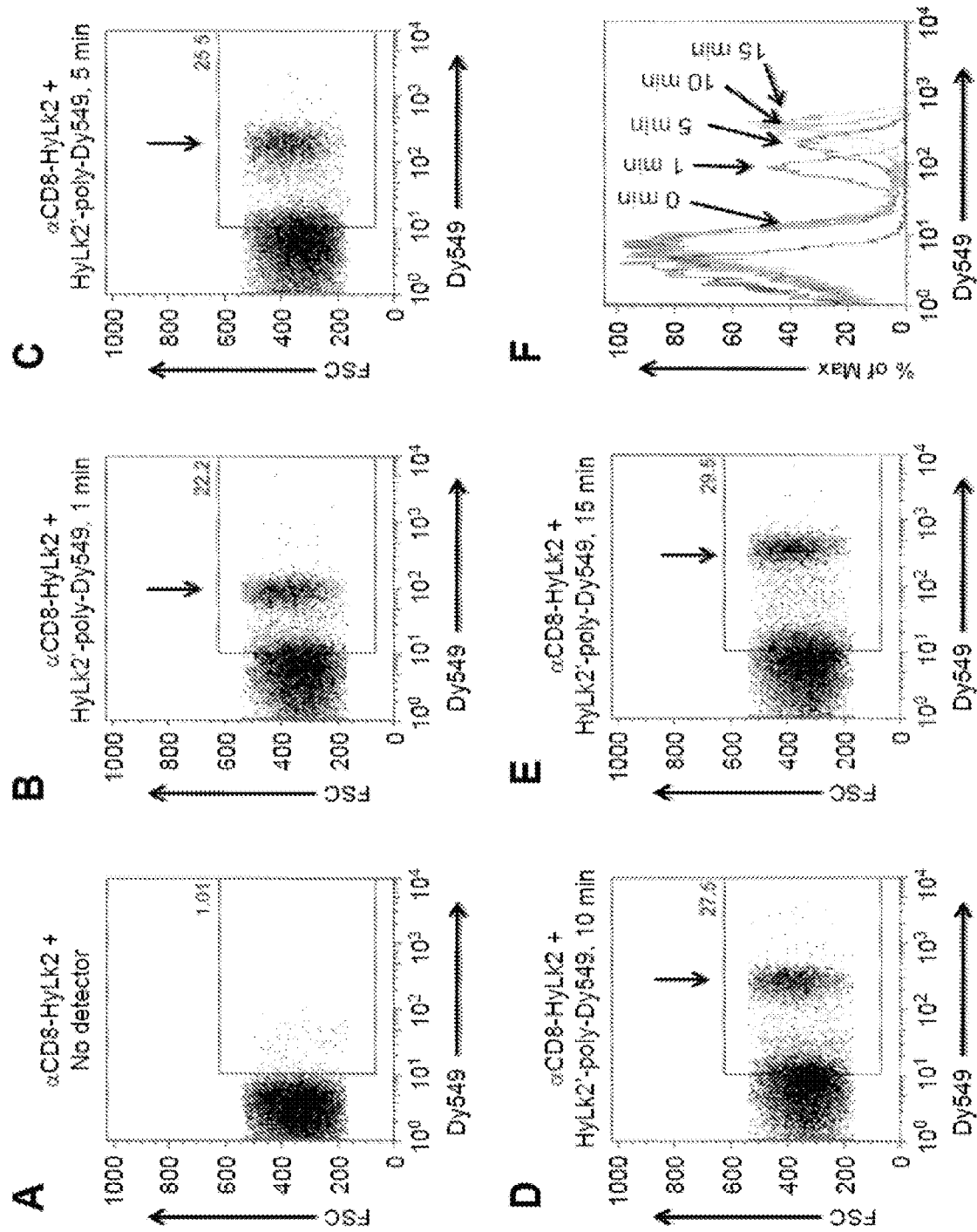
FIG. 28: is results demonstrating a time course experiment (A)-(E) of labeling by hybridization between an antibody-oligonucleotide conjugate and complementary oligonucleotide-polyfluor conjugate, with graph (F) showing the results of (A)-(E) superimposed, in accordance with certain embodiments.

In certain embodiments, antibody-oligonucleotide conjugates and detectors comprising the complementary oligonucleotide conjugated to a signal generator, in this case a scaffold modified with multiple fluorophores, can be used to detect cell surface antigens by flow cytometry as an alternative to conventional antibody-fluorophore conjugates. Another perceived advantage of direct conjugation of antibodies to fluorophores is that the binding of antibody to the antigen simultaneously, or substantially simultaneously, achieves the fluorescent labeling step, potentially saving time. Toward examining the speed of interaction of antibody-oligonucleotide conjugates and complementary oligonucleotides conjugated to dextran scaffolds modified by fluorophores, an experiment was conducted where splenocytes stained with αCD8-HyLk2 were washed and then contacted with HyLk2'-poly-Dy549 for specific times and then immediately introduced into the flow cytometer. The graphs (A) through (E) in FIG. 28 represent two-dimensional flow cytometry plots of the experiment where (A) demonstrates the background signal prior to addition of the HyLk2'-poly-Dy549 detector and then (B), (C), (D) and (E) represent the staining and detection of CD8⁺ cells at 1 minute, 5 minutes, 10 minutes and 15 minutes after addition of the HyLk2'-poly-Dy549 detector. The data from (A) to (E) are superimposed in (F) plotted as a histogram of relative abundance of cells at each fluorescence intensity, allowing direct comparison. As can be seen, the addition of HyLk2'-poly-Dy549 causes a shift of the CD8⁻ cells within one minute from a median value of ~3 Units to ~7 Units. These cells do not become appreciably more fluorescent over the subsequent incubation. At 1 minute, the CD8⁺ cells form a distinct population, indicated by the arrow in (B), that displays a median intensity of 100 Units. At 5 minutes in (C), the CD8⁺ population displays increased fluorescence to ~200 Units. At 10 minutes in (D), the CD8⁺ population displays increased fluorescence to ~300 Units and at 15 minutes in (E), the fluorescence is ~400 Units. These results indicate, in certain embodiments, that incubation times as short as 1 to 15 minutes are sufficient for hybridization of the oligonucleotides conjugated to dextran scaffolds modified by fluorophores to the antibody-oligonucleotide conjugates to permit detection of antigens with high signal to background.

Depending on the particular application incubation times to permit sufficient detection may vary. In certain embodiments, incubation times to permit sufficient detection may include overnight, 1 minute to 1 hour, 5 minutes to 20 minutes, 30 minutes to 1 hour, 20 minutes to 2 hours, 1 to 4 hours, 3 to 8 hours, or 6 to 12 hours.

Figure 29:
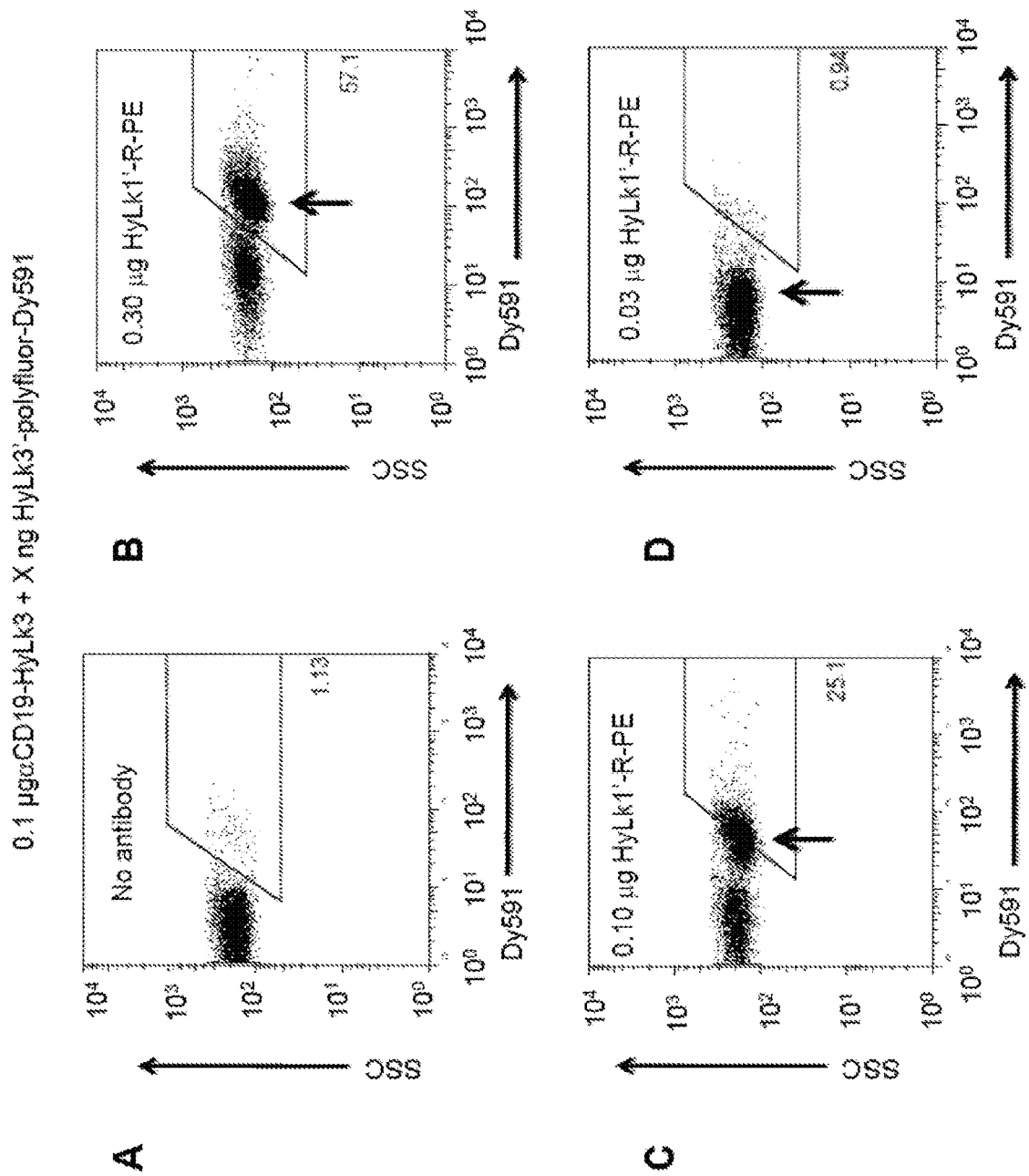
FIG. 29: is results of an experiment (A)-(D) titrating the amount of complementary oligonucleotide-R-phycoerythrin conjugate sufficient to produce a desired signal, in accordance with certain embodiments.

In certain embodiments, antibody-oligonucleotide conjugates and detectors comprising the complementary oligonucleotide conjugated to a signal generator, in this case a scaffold modified with multiple fluorophores, can be used to detect cell surface markers in flow cytometry to further characterize a cellular sample by exploiting alternative fluorophores that can be detected independently from another reference fluorophore. Here, each pair of antibody-oligonucleotide conjugates and complementary oligonucleotide conjugated to a signal generator may need to be examined to obtain the optimal signal to background, in a process of optimization. As shown in FIG. 29 an anti-CD19 antibody recognizing the CD19 B lymphocyte surface antigen, conjugated to HyLk3 was added to splenocytes, allowed to bind, washed and subsequently the complementary HyLk3'oligonucleotide coupled to a dextran scaffold modified with Dy591 was added and the cells analyzed by flow cytometry. Shown are a set of four two-dimensional flow cytometry plots, where each cell that is detected is indicated by a dot representing its specific side scatter, SSC denoted on the Y-axis, and its specific fluorescence in the channel detecting Dy591 on the X-axis. In A), the splenocytes were left unstained and gated for lymphocytes, demonstrating a single distribution of cells that display a median intensity of 3 Dy591 intensity units. In B), C) and D), the splenocytes were treated with 0.1 μg of αCD19-HyLk3 before washing and treating with 0.3 0.1 μg or 0.03 μg of HyLk3'-poly-Dy591, respectively. Two subpopulations stained cells can be distinguished in B) and C), that represent CD19⁺ and CD19⁻ cells. In B), the CD19⁺ cells display a median intensity of ~100 units, while the CD19⁻ cells are shifted due to non-specific background to a median intensity of ~20 units, yielding a S/B or ~5. Here, the detector reagent would be considered to be present in excess to an optimal amount. In C) the CD19⁺ cells display a median intensity of ~50 units, while the CD19⁻ cells are not appreciably shifted due to non-specific background, yielding a S/B or ~10. Here, the detector would be considered to be close to an optimal amount. In D), the presumptive CD19⁺ cells cannot be reliably distinguished from the CD19⁻ cells. Here, the detector would be considered to be below the optimal amount.

Figure 30:
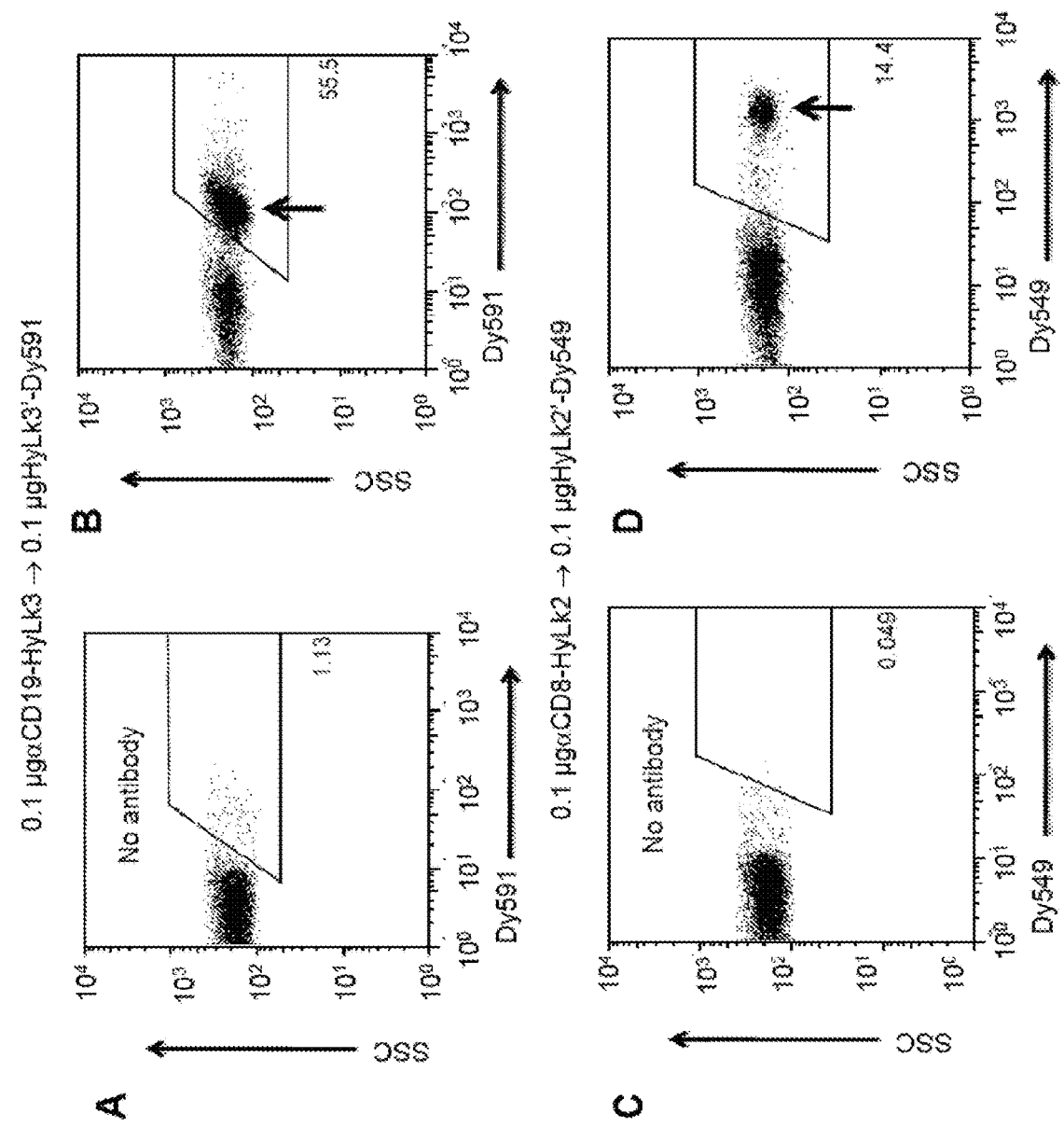
FIG. 30: (Top; A-B) is flow cytometry results demonstrating detection of CD19 on living cells using α-CD19 antibody-HyLk3 conjugate+HyLk3'-poly-DY591 and (Bottom; C-D) results demonstrating detection of CD8 on living cells using α-CD8 antibody-HyLk2 conjugate+HyLk2'-poly-DY549, in accordance with certain embodiments.

In certain embodiments, antibody-oligonucleotide conjugates and detectors comprising the complementary oligonucleotide conjugated to a signal generator, in this case a scaffold modified with multiple fluorophores, can be used to detect detect cell surface markers in flow cytometry to characterize a cellular sample. As shown in FIG. 30, a splenocyte preparation was examined to independently determine the proportion of cells that might be CD19⁺ or CD8⁺, based on binding of antibody-oligonucleotide conjugates. In plots A and B, the optimal conditions determined above of 0.1 μg of αCD19-HyLk3 and then 0.1 μg of HyLk3'-poly-Dy591 were applied, yielding plot B. Note that the median fluorescence intensity of the CD19⁻ fraction is only slightly greater than the unstained control in plot A. In plots C and D, 0.1 μg of an anti-CD8 antibody conjugated to HyLk2, αCD8-HyLk2, was added to splenocytes, allowed to bind, washed and subsequently 0.1 µg of the complementary HyLk2'oligonucleotide conjugated to the dextran scaffold and modified with Dy549, HyLk2'-poly-Dy549, was added and the cells analyzed by flow cytometry, yielding plot D. Note that the median fluorescence intensity of the CD19⁻ fraction is only slightly greater than the unstained control in plot C.

Figure 31:
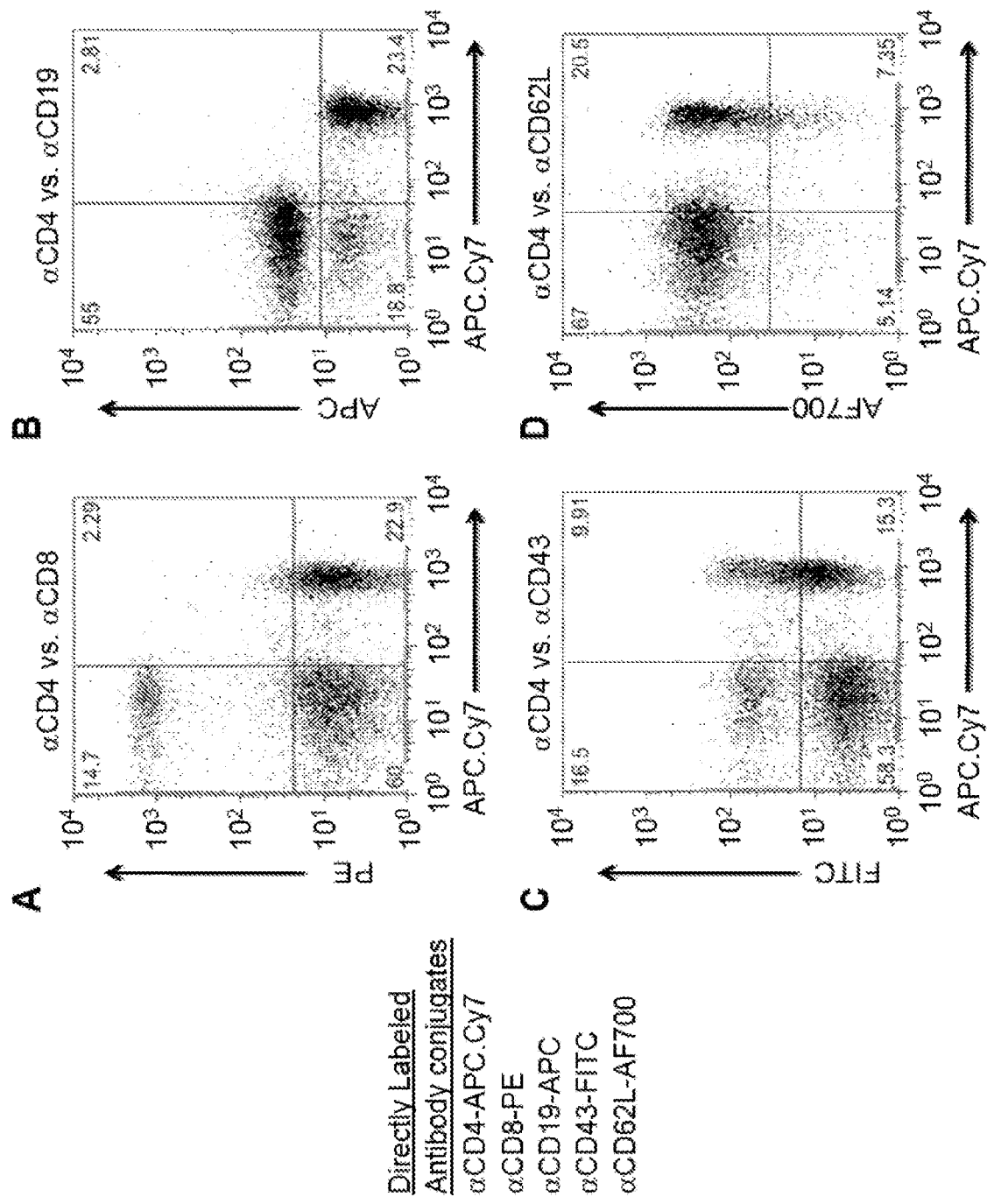
FIG. 31: is a 5-Plex flow cytometry experiment (A)-(D) using 5 commercially available antibody-fluorophore conjugates (Directly Labeled Antibody conjugates). In this experiment, the same panel of antibodies was used as in FIG. 32 as a reference example to compare the performance of each panel, in accordance with certain embodiments.

It is common in flow cytometry of complex cellular samples to detect two or more surface antigens in a multiplex experiment, as a method to distinguish between cells with overlapping patterns of surface antigen expression. FIG. 31 demonstrates an experiment wherein 5 commercially sourced antibody-fluorophore are used to perform a multiplex flow cytometry experiment on mouse splenocytes. The antibodies recognize CD4 (T cell receptor co-receptor MEW class 11 restricted, HIV receptor, T helper cell antigen), CD8 (T cell receptor co-receptor, cytotoxic T cell antigen), CD19 (B lymphocyte surface antigen), CD43 (sialophorin, characteristic of both T and B lymphocytes), and CD62L (L-selectin, characteristic of T and B lymphocytes). In each of the two-dimensional flow cytometry plots shown, cells gated to display only lymphocytes are represented by dots and their position with respect to the X-axis represents the intensity of the staining of each cell by the αCD4-APC.Cy7 tandem conjugate. In plot (A), the Y-axis displays the staining with αCD8-PE. As shown, many lymphocytes are unstained by either probe (lower left quadrant) and score as $CD4^-$ $CD8^-$, likely representing primarily B lymphocytes. Some lymphocytes can be identified as $CD4^+$ (lower right quadrant) and some $CD8^+$ (upper left quadrant) but few, if any, are identified as $CD4^+$ $CD8^+$ (upper right quadrant). These surface antigens are often restricted to different classes of T cells. In turn, a similar analysis applies to (B), where the Y-axis represents staining with αCD19-APC. These results show an apparent lack of $CD4^+$ $CD19^+$ cells, recognizing that CD4 is a T cell antigen and CD19 is a B cell antigen. The cells in the lower loft quadrant are likely to represent primarily $CD8^+$ T cells. In (C), where the Y-axis represents staining with αCD43-FITC, some cells are scored as $CD4^+$ $CD43^+$, insofar as CD43 is a characteristic antigen of T cells, including $CD4^+$ T cells. In (D), where the Y-axis represents staining with αCD62L-AF700, most $CD4^+$ cells are also $CD62L^+$, as are most of the $CD4^-$ cells including the $CD8^+$ T cells and the B cells.

Figure 32:
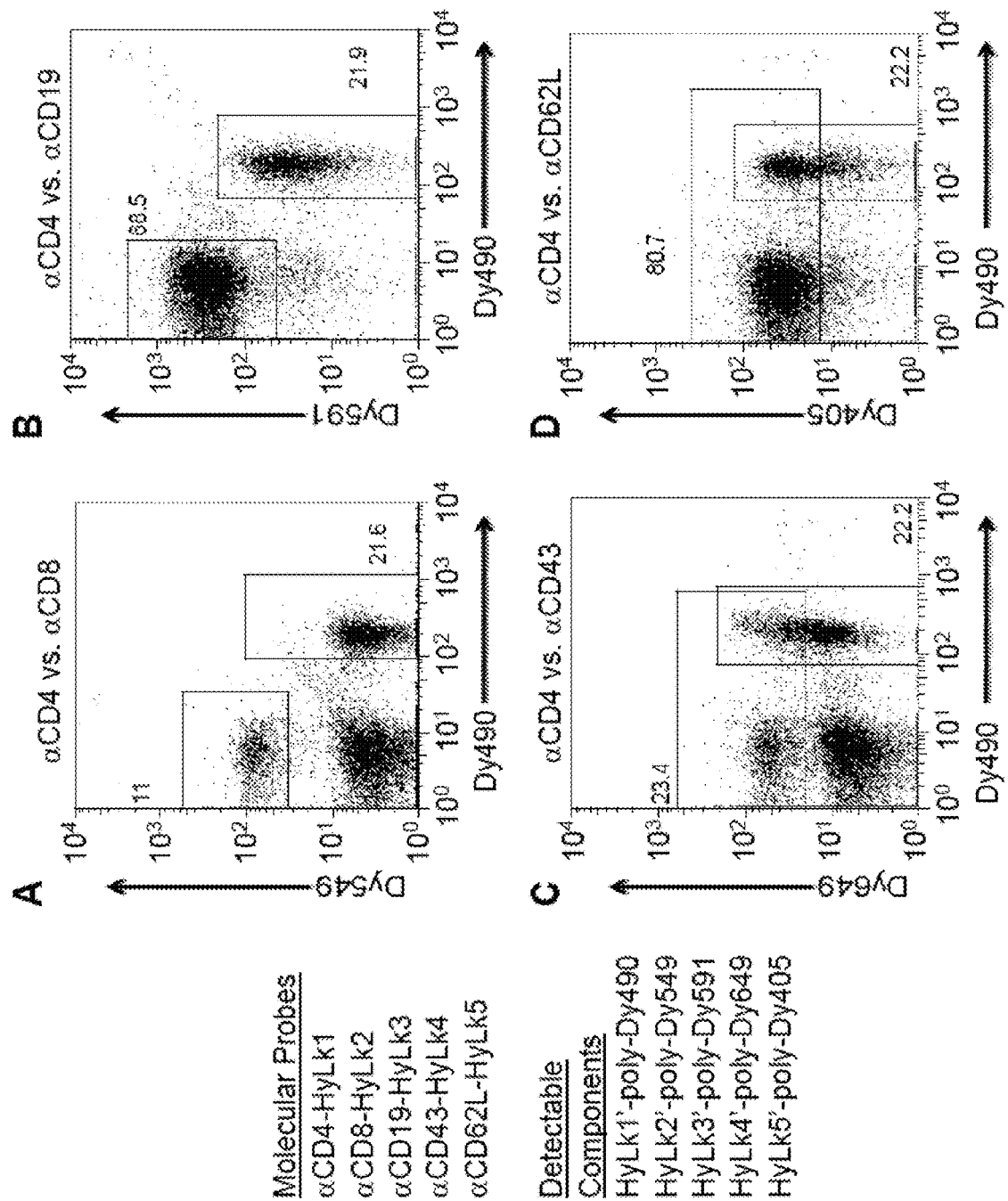
FIG. 32: is a 5-Plex flow cytometry experiment (A)-(D) using 5 different oligonucleotide-antibody conjugates (Molecular Probes) followed by addition of the complementary oligonucleotide-poly-fluor conjugates (Detectable Components), in accordance with certain embodiments. The pattern of immune reactivity is to be compared with the panel in FIG. 31 for the same antibodies but using direct fluorescent conjugates.

In certain embodiments, multiple antibody-oligonucleotide conjugates and their complementary detectors can be used simultaneously, or substantially simultaneously, to detect two or more protein biomarkers in a multiplex experiment, as a method to distinguish between cells with overlapping patterns of surface antigen expression. Here, the potential of antibody-oligonucleotide conjugates and complementary oligonucleotide detectors in such an assay is evaluated. As shown in FIG. 32, αCD4-HyLk1, αCD8-HyLk2, αCD19-HyLk3, αCD43-HyLk4 and αCD62L-HyLk5 conjugates were added simultaneously to lymphocytes, allowed to bind and washed. Subsequently, the five complementary oligo-dextran-fluorophore conjugates, HyLk1'-poly-Dy490, HyLk2'-poly-Dy549, HyLk3'-poly-Dy591, HyLk4'-poly-Dy649 and HyLk5'-poly-Dy405 were added simultaneously, allowed to hybridize and the fluorescent signals were detected by flow cytometry. Here, the flow cytometry data are represented by a series of two dimensional plots, where each cell is represented by a dot at the position of its intensity in the Dy490 (FITC) fluorescence channel as indicated on the X-axis and by intensity of the indicated fluorescence channel on the Y-axis. In (A), the Y-axis represents αCD8 binding by Dy549 fluorescence intensity. Both CD4-' and $CD8^+$ cells are detected, but not $CD4^+$ $CD8^+$ cells. In (B), the Y-axis represents αCD19 binding by Dy591 fluorescence intensity, demonstrating the capability to distinguish CD19-' B cells from $CD4^+$ T cells. In (C), αCD43 binding is represented by Dy649 fluorescence on the Y-axis, demonstrating the result that some $CD43^+$ cells are CDLL and that some $CD4^+$ cells are $CD43^+$. Finally, in (D), the binding of αCD62L is represented by Dy405 fluorescence on the Y-axis, demonstrating the result that most CDLL cells are also $CD62L^+$. Comparison of the distributions of the ability to distinguish markers and relative numbers of cells between the results using commercial conjugates shown in FIG. 31 to using DNA directed assembly to form complexes between antibody-oligonucleotide conjugates and complementary oligonucleotide detectors shown in FIG. 32 reveals similar results.

Figure 33:
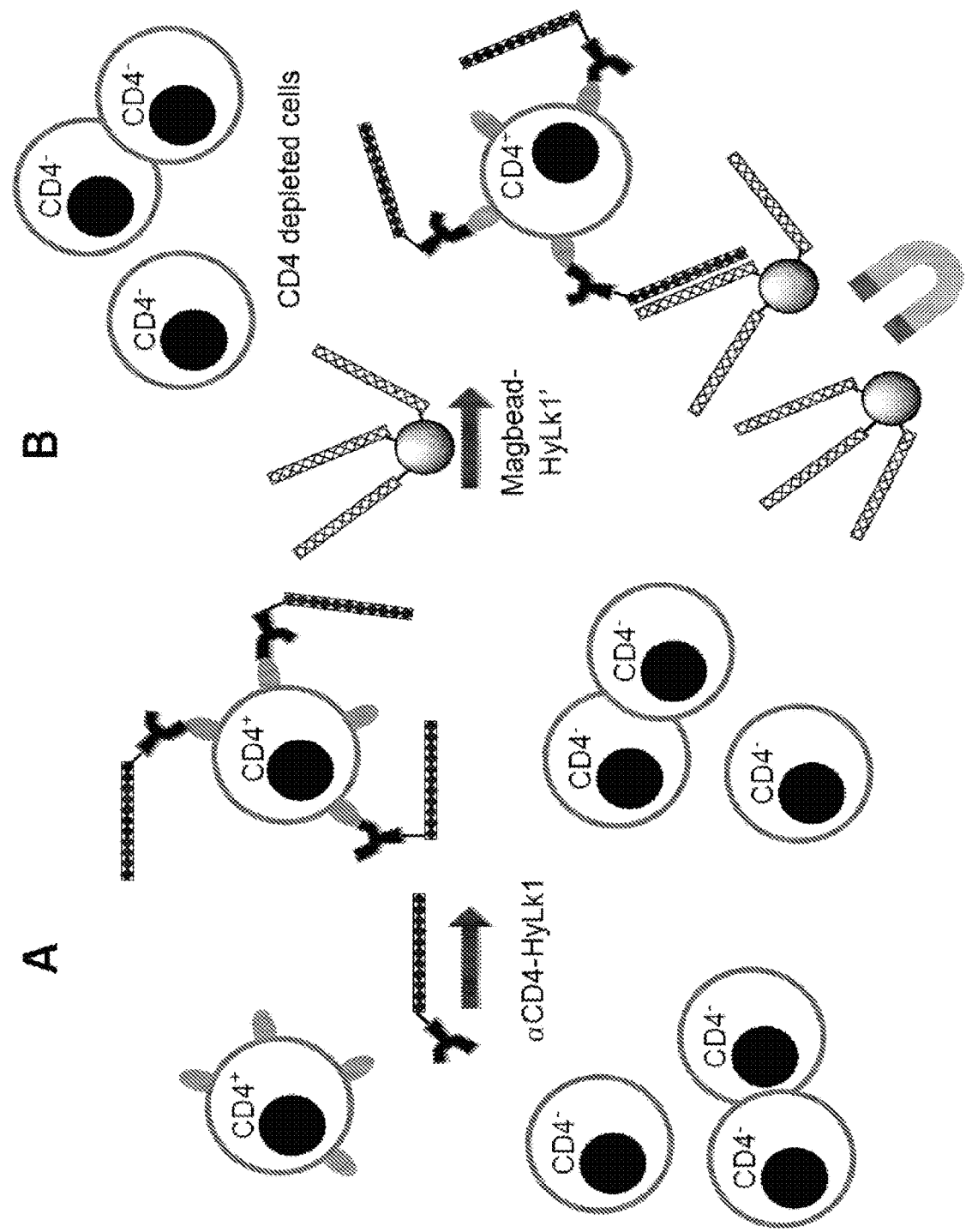
FIG. 33: is a scheme presenting hybridization-mediated immunomagnetic separation of CD4⁺ cells, with (A) a binding of α-CD4-oligonucleotide conjugate and (B) a hybridization to a complementary oligonucleotide-immobilized paramagnetic bead and attraction by a magnet, in accordance with certain embodiments.

In certain embodiments, antibody-oligonucleotide conjugates can be used to bind to a cell surface antigen on a specific cell or type of cell that may or may not be present in a mixture of cells and other biological components such as blood or another in a biological fluid, and these cells can be captured by hybridization to the complementary oligonucleotide immobilized on a magnetic bead or other solid surface. Then, using a magnetic field, these cells can be removed from the rest of the sample such as other cells, plasma, or other sample components. In some embodiments, the sample such as blood, depleted of the captured cells, can then be used for a purpose such as transfusion. Here, the method would be used for negative selection. In other embodiments, the isolated cells can then be used for some purpose such as transplantation, culture or subjected to analysis. Here, the method would be used for positive selection or cell enrichment. FIG. 33 illustrates this concept. Here an α-CD4-HyLk1 conjugate is added to the sample and the conjugates selectively binds to the $CD4^+$ T helper cell shown but not to other lymphocytes or other blood cells such as monocytes, granulocytes, platelets or other blood cells. Subsequently HyLk1'-magnetic beads are added to the sample and the CD4-' cells bound to the magnetic bead are isolated away from the other cells by application of a magnet.

Figure 80:
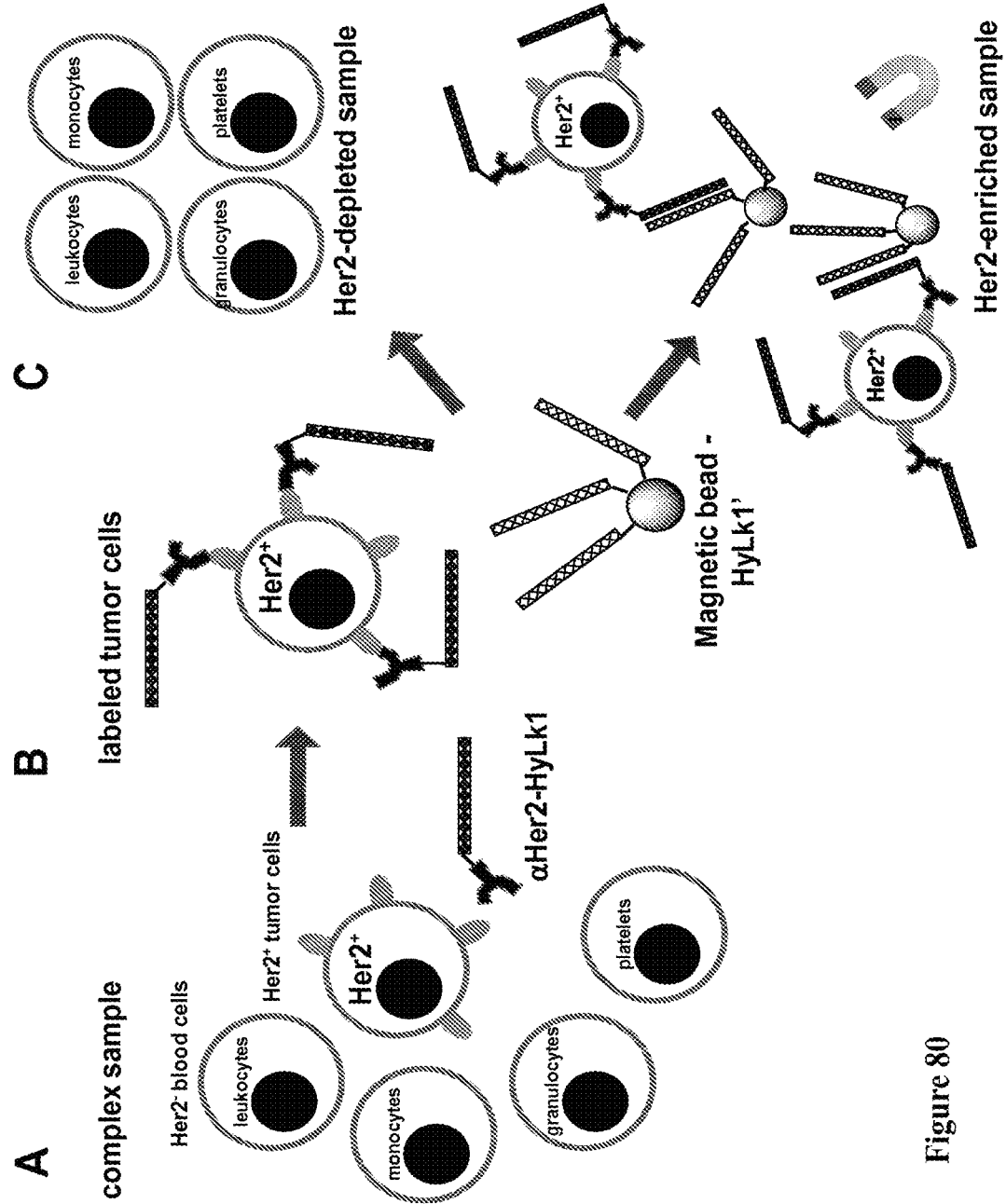
FIG. 80 is an exemplary scheme presenting hybridization-mediated immunomagnetic separation of Her2+ cells from a complex mixture of cell, by (A) a binding of a herceptin-oligonucleotide conjugate and (B) a hybridization to a complementary oligonucleotide-immobilized paramagnetic bead and attraction by a magnet, in accordance with certain embodiments.
Figure 82:
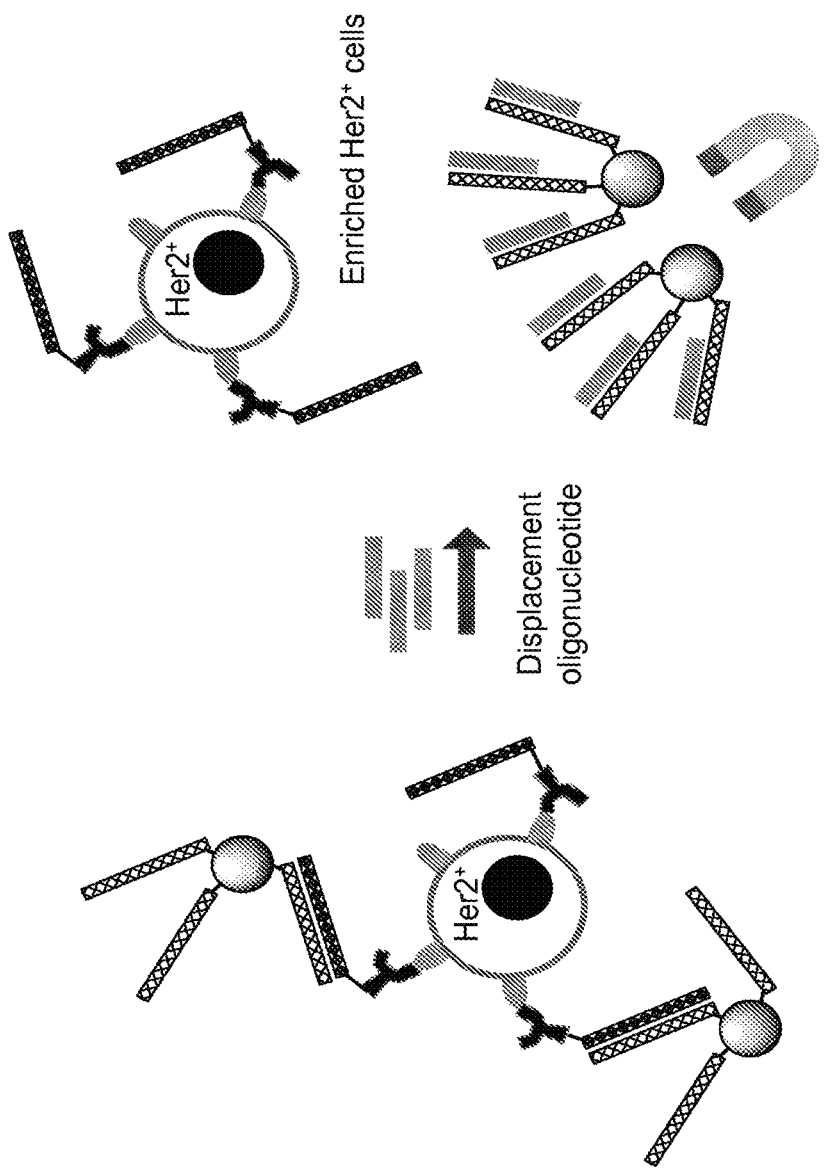
FIG. 82 is an exemplary scheme presenting hybridization-mediated immunomagnetic separation of CD4' cells and their release by strand displacement of the hybridization by a displacement oligonucleotide such as a peptide nucleic acid (PNA) or a locked nucleic acid (LNA), in accordance with certain embodiments.

In certain embodiments, the sample, depleted of the captured cells, may then be used for a purpose such as transfusion. Here, the method would be used for negative selection. In other embodiments, the method would be used for positive selection or cell enrichment, with the enriched population being used for downstream analysis. FIG. 80 illustrates the depletion/enrichment concept, in which (A) Her2 antibody (Herceptin®, Genentech, California) conjugated to oligo HyLk1 is added to a complex blood sample. The Herceptin-HyLk1 conjugate selectively binds to $Her2^+$ tumor cells, but not to $Her2^-$ blood cells, including leukocytes, monocytes, granulocytes, and platelets. HyLk1'-magnetic particles are added to the sample (B), and HyLk1-antibody labeled $Her2^+$ cells bound by hybridization to the magnetic particles are isolated from $Her2^-$ cells by application of a magnet (C), resulting in a Her2-depleted sample and a Her2-enriched sample. In FIG. 82, depletion of human $Her2^+$ tumor cells from a sample of cultured leukocytes is illustrated using certain methods described herein. 10% Her2-overexpressing human breast adenocarcinoma cells were spiked into a culture of human leukocyte cells. The sample was (A) undepleted, (B, C) subjected to 'mock' depletion methods without one or more necessary components, (D) Her2-depleted using conventional methods, (E) Her2-depleted using conventional methods, modified with the 2-step approach included in the HybriLink strategy disclosed herein but without the use of oligos; or (F) Her2-depleted using HybriLink strategy disclosed herein. Following treatment, the samples were stained with fluorescent antibodies against tumor cell markers Her2 (PE conjugate) and EpCAM (APC conjugate) to distinguish leukocytes (Her2$^-$ EpCAM$^-$) from tumor cells (Her2$^+$ EpCAM$^+$). EpCAM was used as a secondary tumor cell marker to confirm depletion of tumor cells, given that binding of Herceptin during cellular labeling prior to magnetic depletion potentially interferes with downstream Her2 staining, should the Her2 antibodies target the same protein epitope, thereby giving a false positive indication of successful depletion. Double-staining with αEpCAM provides a control against false depletion staining. Following αHer2: PE/αEpCAM:APC staining, cells were analyzed using a BD LSRII cytometer equipped with 561 nm and 633 nm lasers and appropriate optical fluorochrome filters. Raw data files were visualized using FlowJo software (TreeStar, Inc., Ashland, Oregon). Positive staining gates were established based on fluorescent intensity of cells stained with host IgG isotype-fluorochrome controls (Data not shown). In undepleted cell population (A), 9.95% of cells are Her2$^+$ EpCAM$^+$ tumor cells, and 68.5% are Her2$^-$ EpCAM$^-$, for a tumor cell:leukocyte ratio of 1:6.9. Samples subjected to "mock" depletion, in either the absence of complementary oligo HyLk 1' on magnetic beads (panel B) or in the absence of both oligo:IgG and complementary HyLk1' oligo on beads (panel C) did not exhibit successful depletion, indicating that beads unlabeled by complementary oligo have no nonspecific affinity for tumor cells, HyLk1 oligonucleotide, or Herceptin antibody conjugates, any of which would interfere with successful depletion. Samples depleted using current state-of-the-art methods (panel C), in which biotinylated Herceptin was immobilized on to streptavidin-surfaced magnetic nanospheres and applied to cells, showed a 56% depletion of tumor cells, a 1:18.3 tumor cell/leukocyte ratio, and a depletion ratio of 2.7×. A modified state-of-the-art method, in which cells were labeled by Herceptin-biotin, and then isolated using streptavidin surfaced nanospheres, was less successful than conventional methods, resulting in 32.2% (1.8×) Her2 depletion. However, samples depleted using the HybriLink depletion method described herein exhibited a tumor cell depletion of 77.9%, with a tumor cell/leukocyte ratio of 1:39.0, or 5.7× depletion ratio. The remaining tumor cell population was just 2.2%. Panel G summarizes statistical data contained herein. Example 31 describes experimental methodology.

Figure 34:
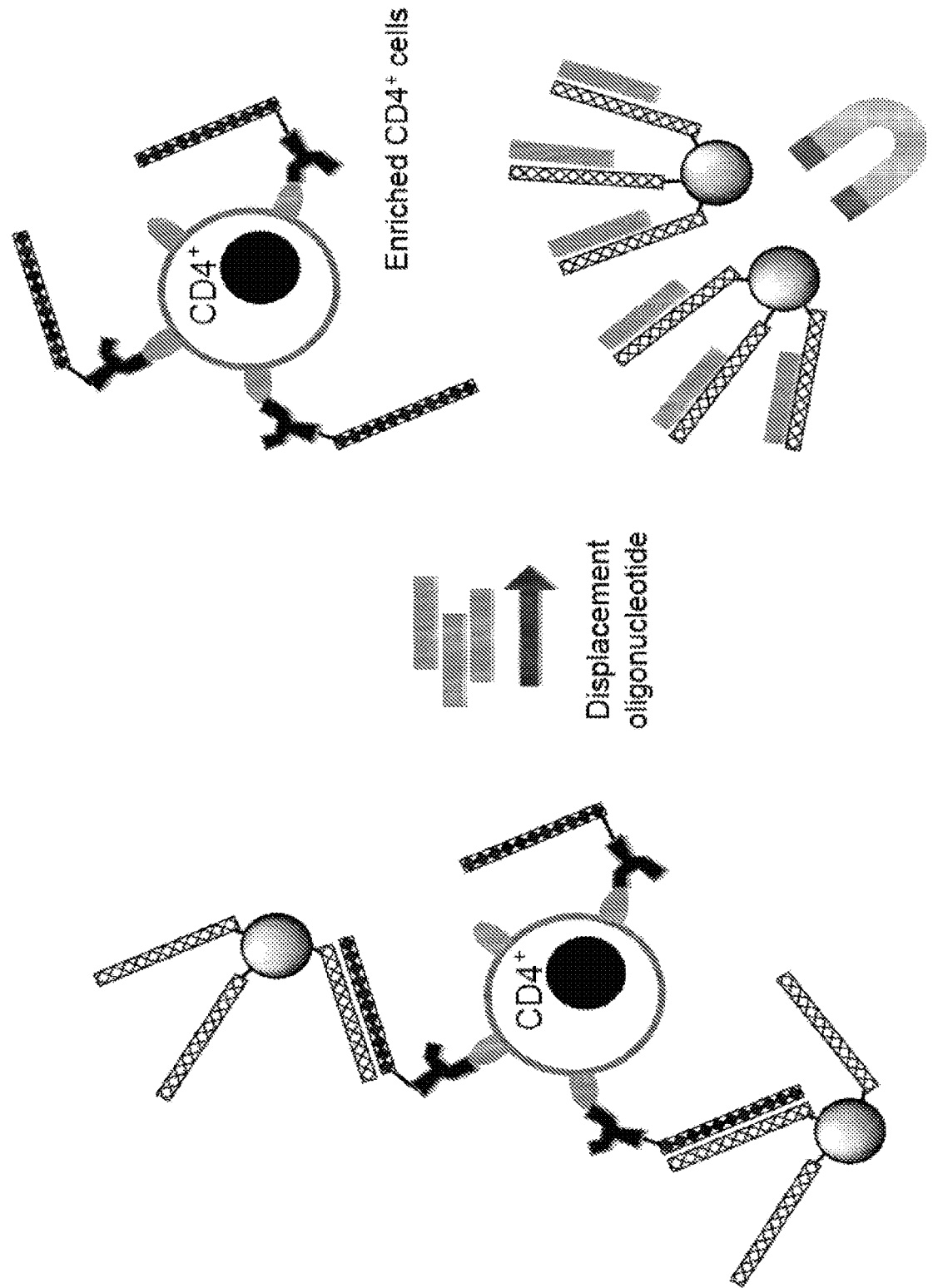
FIG. 34: is a scheme presenting hybridization-mediated immunomagnetic separation of CD4⁺ cells and their release by strand displacement of the hybridization by a displacement oligonucleotide such as a peptide nucleic acid (PNA) or a locked nucleic acid (LNA), in accordance with certain embodiments.
Figure 35:
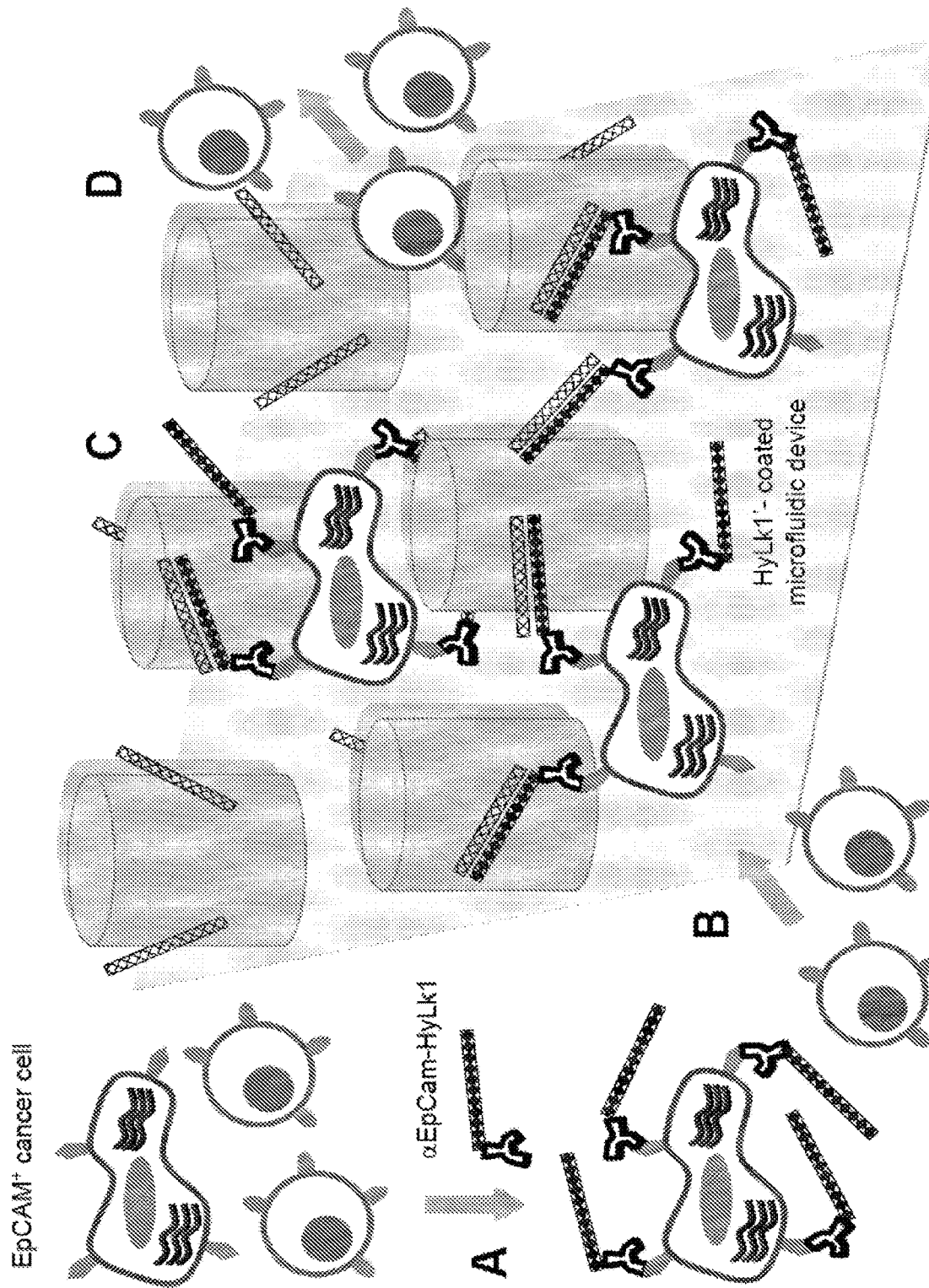
FIG. 35: is a schematic representation of isolation of an epithelial cell, such as a circulating cancer cell, in a microfluidic device using α-Epithelial Cell adhesion molecule antibody-oligonucleotide conjugates and their complementary oligonucleotides immobilized in a microfluidic channel while allowing lymphocytes to escape, in accordance with certain embodiments.

In certain embodiments, it may be necessary to both capture a specific cell type by immunomagnetic protocols and subsequently release the cell for further analyses. Cells isolated by hybridization using oligonucleotides prepared from natural nucleic acids as presented in FIG. 34, can be released from the magnetic beads by strand displacement of the hybrid formed between the antibody-oligonucleotide conjugate bound to the cell surface and the complementary oligonucleotide on the bead. Here, oligonucleotides based on peptide nucleic acid (PNAs), locked nucleic acid (LNAs), morpholino or other oligonucleotide analogs that are capable of strand invasion of DNA duplexes will be designed to hybridize to the strand coupled to the magnetic bead releasing the cell from the bead. The isolated cells would subsequently be available for transplantation, culture, or analysis by flow cytometry, imaging, microscopy, high content screening (HCS), ELISA, ELISpot, or immunohistochemistry, or other assays. In certain embodiments, one or multiple antibody-oligonucleotide conjugates and their complementary detector-signal generator conjugates can be used to capture cells in a microfluidic device in which complementary oligonucleotides are immobilized in specific spots or on specific posts. Here, as presented diagrammatically in FIG. 35, using the example of the capture of circulating EpCam$^+$ cancer cells, (A) anti-EpCam antibody-HyLk1conjugate is added to a blood sample, allowed to bind and (B) the sample is allowed to flow through a microfluidic channel containing posts to which HyLk1' is immobilized and the anti-EpCam antibody-HyLk1 conjugate/EpCam$^+$ cell complex are captured by hybridization. Other cells, such as lymphocytes may flow through the microfluidic device.

Figure 83:
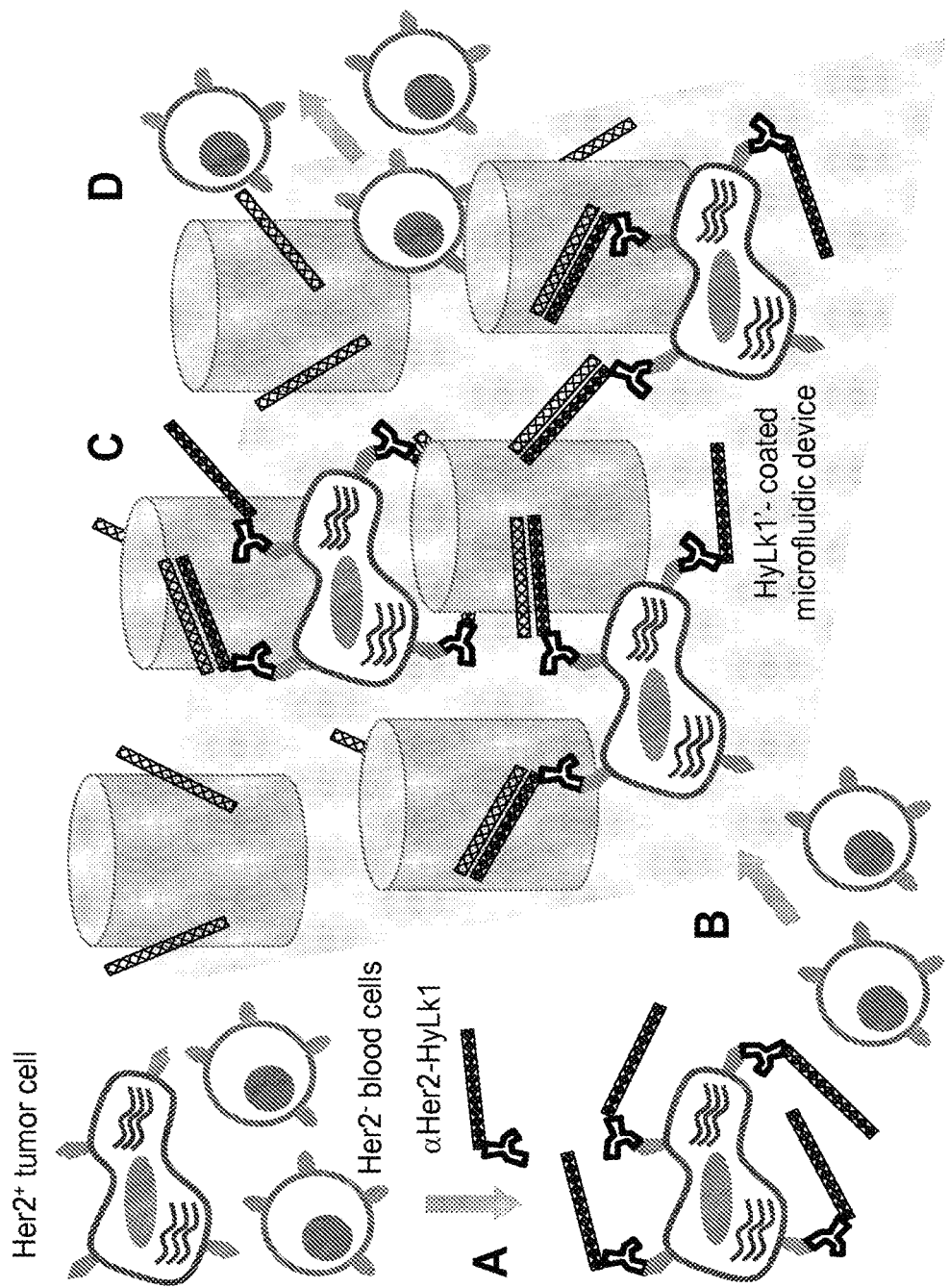
FIG. 83: is a schematic representation of isolation of an epithelial cell, such as a circulating cancer cell, in a microfluidic device using a Herceptin antibody-oligonucleotide conjugate and its complementary oligonucleotide immobilized in a microfluidic channel while allowing lymphocytes to escape, in accordance with certain embodiments.

In certain embodiments, cells may be released from the magnetic particles by strand displacement of the hybrid formed between the antibody-oligonucleotide conjugate bound to the cell surface and the complementary oligonucleotide on the bead. Here, oligonucleotides based on peptide nucleic acid (PNAs), locked nucleic acid (LNAs), morpholino or other oligonucleotide analogs that are capable of strand invasion of DNA duplexes may designed to hybridize to the strand coupled to the magnetic bead releasing the cell from the bead. The isolated cells would subsequently be available for transplantation, culture, or analysis by flow cytometry, imaging, microscopy, high content screening (HCS), ELISA, ELISpot, immunohistochemistry (IHC), or other assays. In certain embodiments, one or multiple antibody-oligonucleotide conjugates and their complementary detector-signal generator conjugates may be used to capture cells in a microfluidic device in which complementary oligonucleotides are immobilized in specific spots or on specific posts. Here, as presented diagrammatically in FIG. 83, using the example of the capture of Her2$^+$ cancer cells circulating in a complex whole blood sample, (A) Her2 antibody-HyLk1 conjugate is added to the sample, allowed to bind, and (B) the sample is allowed to flow through a microfluidic channel containing posts to which HyLk1' is immobilized; thereby, HyLk1-Her2 antibody-Her2-' cell complexes are captured by hybridization, while Her2-blood cells, such as leukocytes, monocytes, granulocytes, and platelets, may flow through the microfluidic device.

Figure 36:
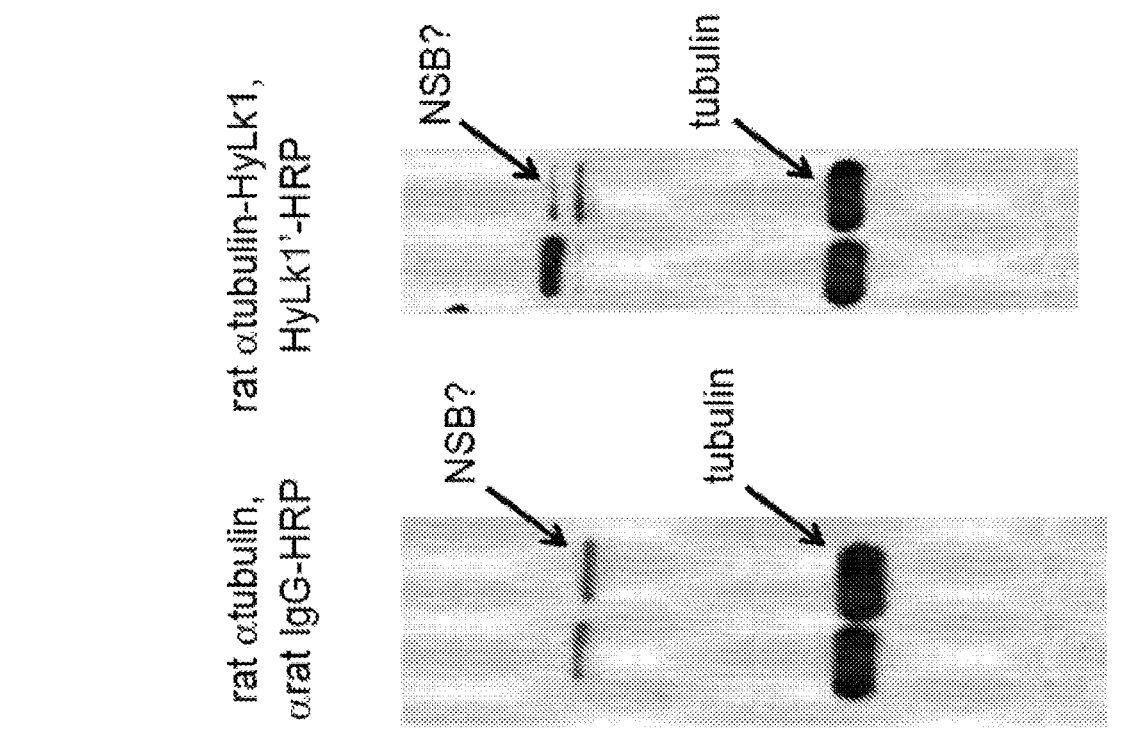
FIG. 36: (Left) is a schematic representation of detection of an antigen in a Western Blot experiment using an antibody-oligonucleotide conjugate/complementary oligonucleotide-signal generator pair. (Right) Results comparing a classical Western Blot experiment detecting tubulin and a likely non-specific band using a primary α-tubulin antibody/secondary antibody-HRP conjugate to a Western Blot prepared using an α-tubulin antibody-oligonucleotide conjugate and complementary oligonucleotide-HRP conjugate, in accordance with certain embodiments.
Figure 36:
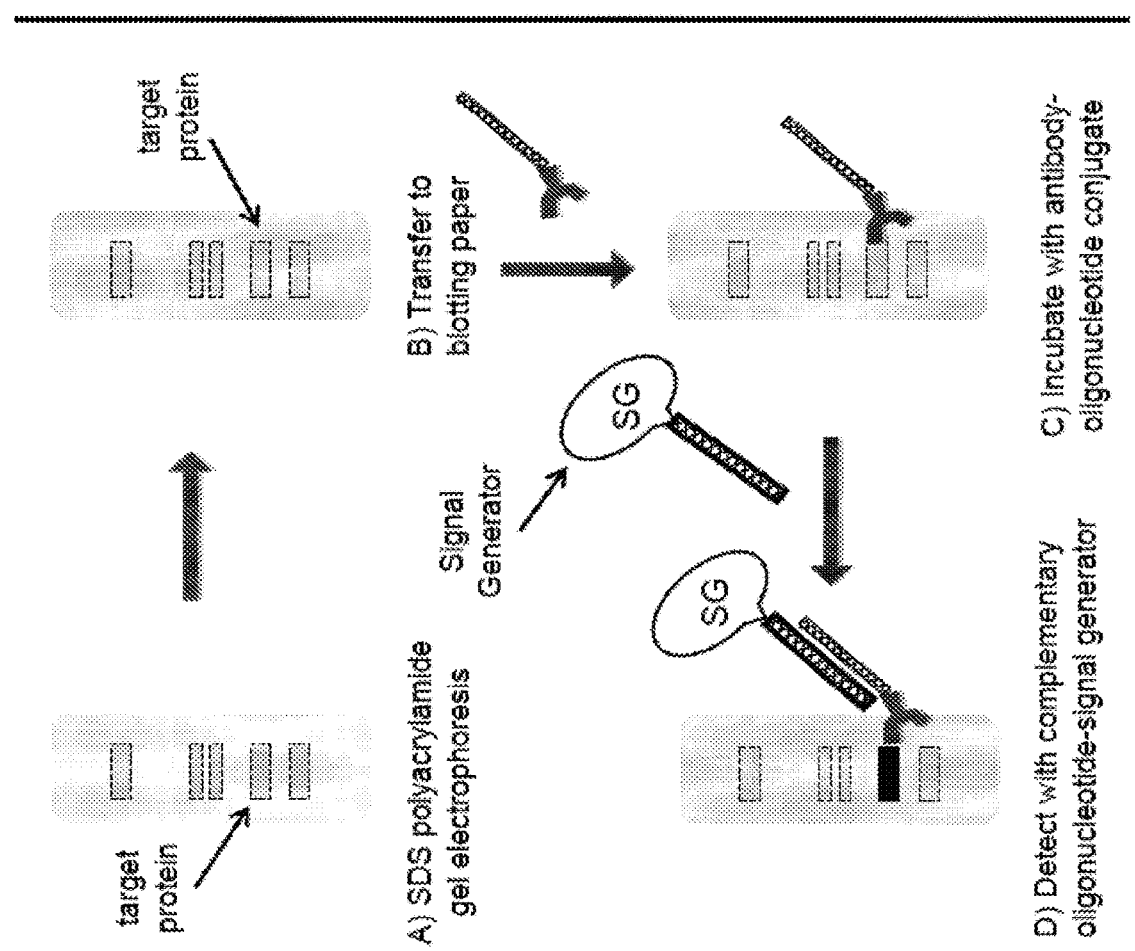

In certain embodiments, one or multiple antibody-oligonucleotide conjugates and their complementary detector-signal generator conjugates can be used individually or simultaneously to detect one or more protein biomarkers in a single or multiplex Western blot experiment. The potential of antibody-oligonucleotide conjugates and complementary oligonucleotide detectors in such an assay is evaluated. The protocol as shown schematically in FIG. 36 (left) wherein total protein from a cell lysate is electrophoresed, transferred to a nitrocellulose membrane, and detected in two steps by initially incubating the membrane with an antibody-oligonucleotide conjugate followed by incubation with a complementary oligonucleotide-signal generator conjugate. As an example, the signal generator might be a horseradish peroxidase conjugate which can be localized on the blot by standard chemi-luminescent detection. This method was exemplified in a Western Blot assay using a human cancer cell line, A431, that was untreated or treated with epidermal growth factor (EGF). The cells were lysed and the protein fraction was electrophoresed, transferred to a nitrocellulose membrane. As a control experiment, the cytoskeletal protein tubulin was detected either by standard Western Blot conditions using a rat monoclonal anti-tubulin antibody followed by incubation with an anti-rat immunoglobulin secondary antibody-HRP conjugate and developed using standard chemiluminescent methods. A separate blot was incubated successively with the same rat monoclonal anti-tubulin conjugated to HyLk1, washed, incubated with a HyLk1'-HRP conjugate and developed using standard chemiluminescent methods. The results documented in FIG. 36 (right) show that both methods detect tubulin and a non-specific band to a similar degree with respect to sensitivity and specificity.

Figure 37:
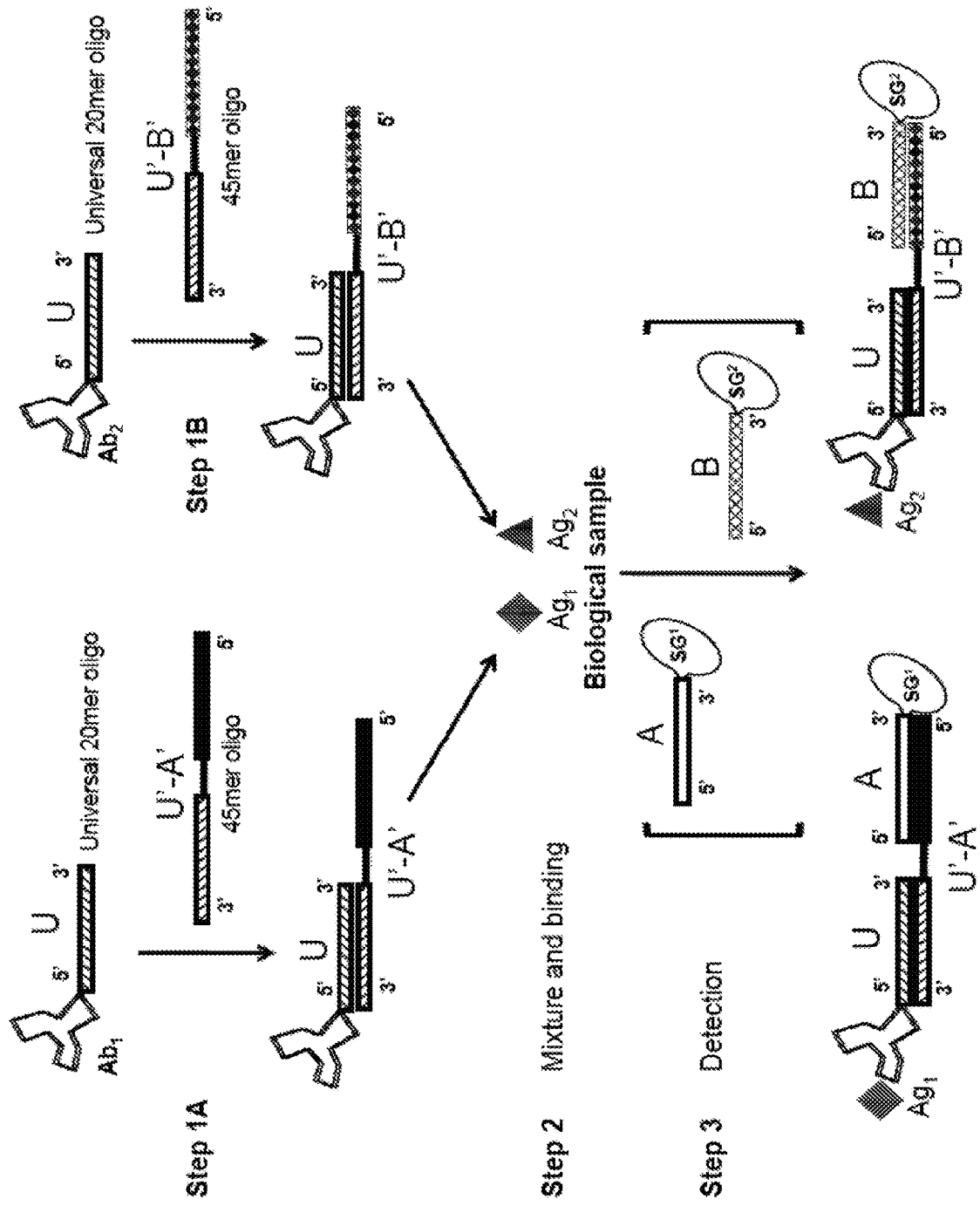
FIG. 37: is a schematic representation of an Universal Adapter protocol, wherein each antibody is conjugated to oligonucleotides of the same Universal sequence, but each is then hybridized to a distinct Universal Adaptor prior to their use in a multiplexed experiment, to allow them to be differentiated, and then performing a detection experiment, wherein the signal generator is linked to the 5'-end of the oligonucleotide-signal generator conjugate, in accordance with certain embodiments.

In certain embodiments, it will be advantageous to have a method whereby various single antibody-oligonucleotide conjugates can be linked by hybridization to a choice of oligonucleotide-signal generator conjugates. Such an application may allow a large catalog of antibodies, such as a library of monoclonal antibodies with different specificities to antigens, to be used together in multiplexed experiments. Here, assigning a single barcode to each antibody would be impractical. Instead, conjugating a single common oligonucleotide to each antibody would be preferable. To accomplish this, as schematically represented in FIG. 37, a Universal Sequence (U) that can be conjugated to an antibody was specified. Thereafter, a set of adapter oligonucleotides that incorporate two sequences, one that hybridizes to the Universal Sequence (U') and the second that is complementary to the sequence on an oligonucleotide-signal generator conjugate (A', B', etc.) may be designed. The complement to the Universal Sequence may be linked to the sequence that hybridizes to the signal generator via several non-hybridized bases or a polyethylene glycol chain or other non-nucleic acid hydrophilic linker such as a dendrimer to form individual adapters, e.g. U'-A', U'-B', and so on. Then, each antibody-Universal Sequence conjugate would be mixed individually to an adapter and allowed to hybridize as in Step 1. Then, in Step 2, the antibody-Universal Sequence conjugate/adapter complexes can be used individually or mixed together in an experiment to probe a biological sample. When the cognate oligonucleotide-signal generator conjugates are applied, as in Step 3, each hybridizes to the specific antibody carrying its complementary adapter. As can be recognized, a panel of such adapter oligonucleotides each comprising one sequence complementary to the Universal Sequence and a second sequence complementary to an oligonucleotide-signal generator conjugate would allow a mix and match method to readily incorporate by hybridization a panel of different signal generators onto a panel of antibody-Universal Sequence oligonucleotide conjugates.

Figure 38:
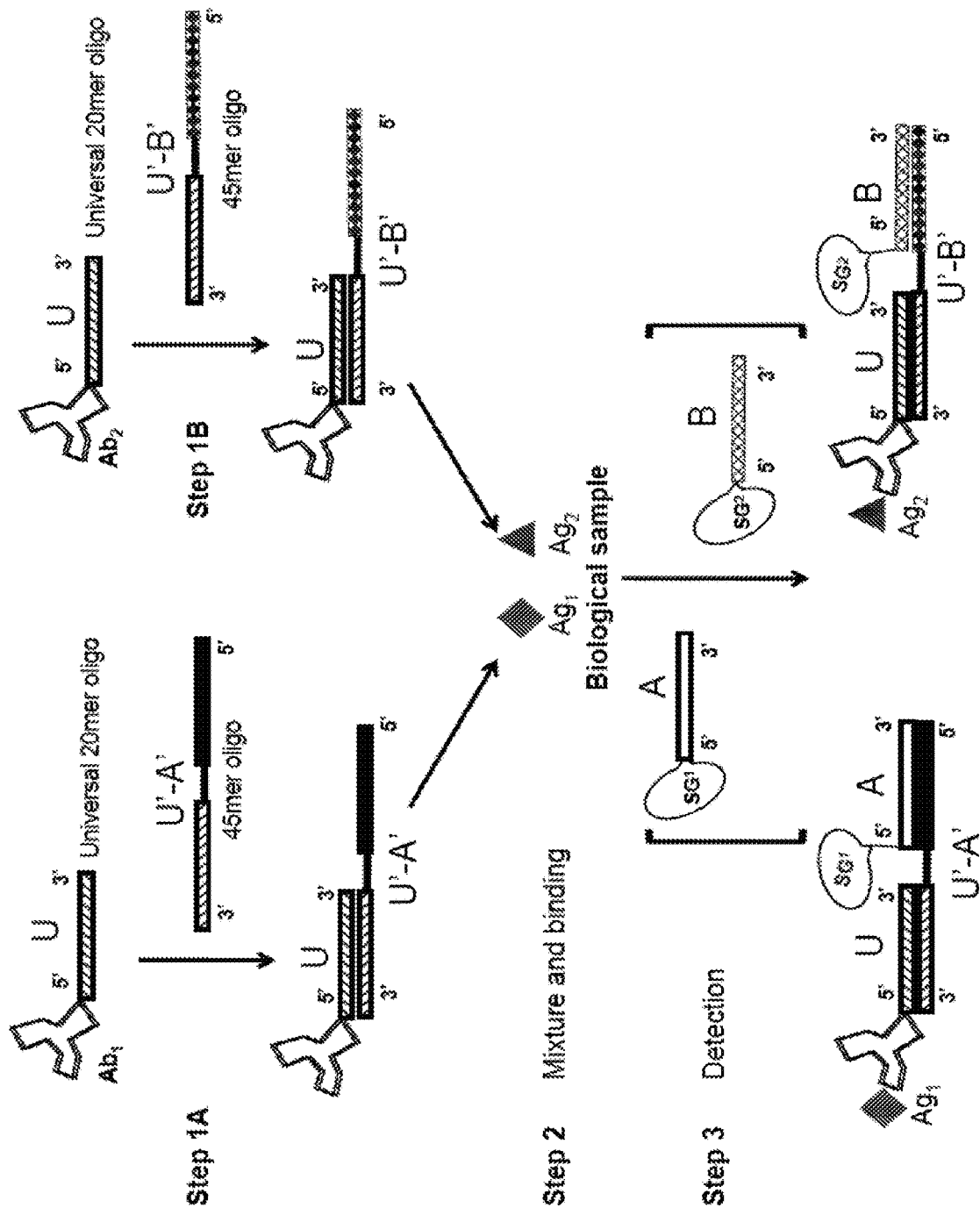
FIG. 38: is a schematic representation of a Universal Adapter protocol, wherein each antibodies is conjugated to oligonucleotides of the same Universal sequence, but each is then hybridized to a distinct Universal Adaptor prior to their use in a multiplexed experiment, to allow them to be differentiated, and then performing a detection experiment, wherein the signal generator is linked to the 3'-end of the oligonucleotide-signal generator conjugate, in accordance with certain embodiments.

In certain embodiments, a signal generator may be incorporated on the 5'-end of the oligonucleotide-signal generator conjugate as shown in FIG. 38 or internally in the sequence.

Figure 39:
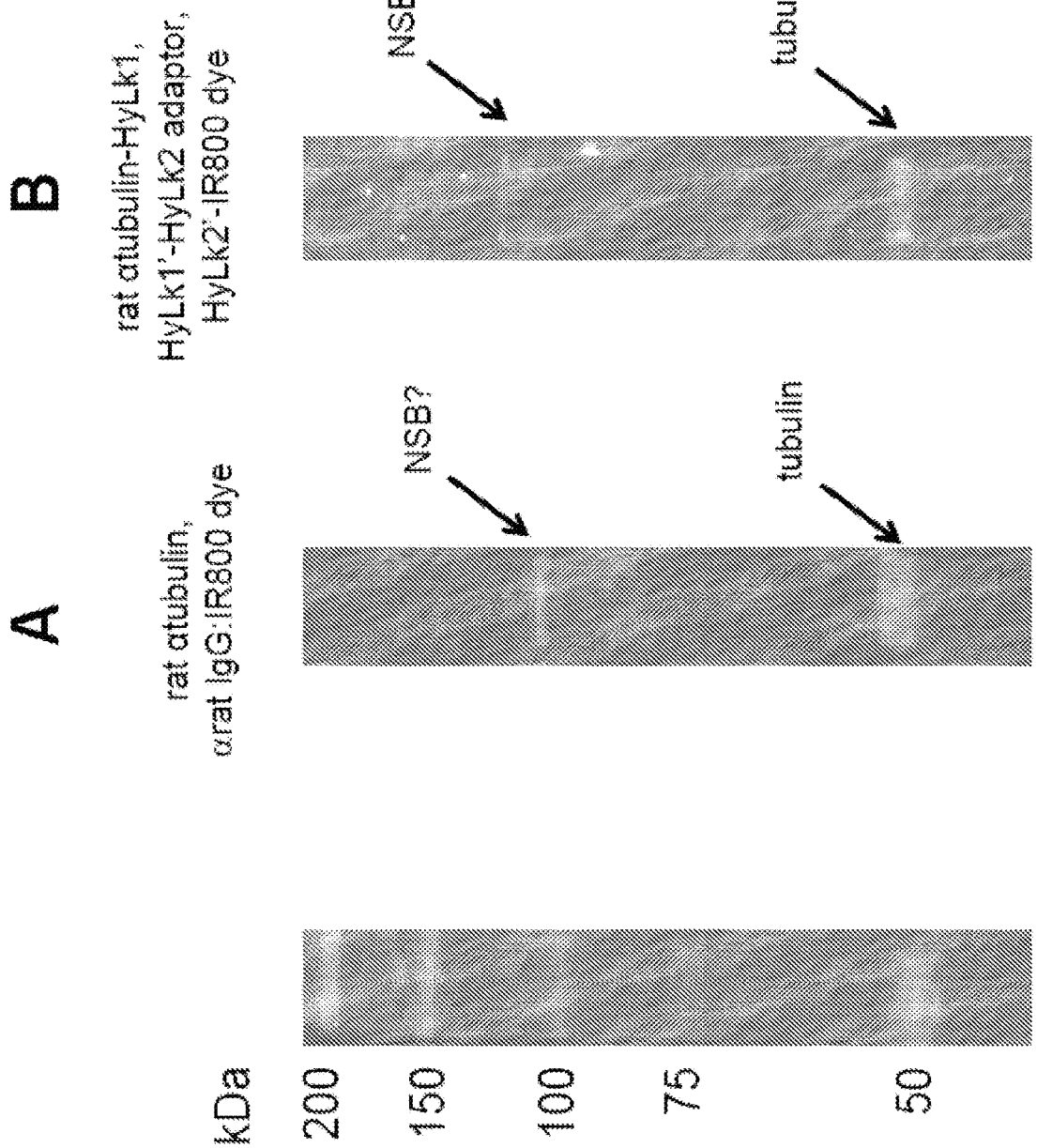
FIG. 39: is infrared fluorescent Western Blot detection results performed using an α-tubulin antibody then detected by an IR800-dyc labeled secondary anti-immunoglobulin antibody compared to using an α-tubulin antibody-HyLk1 oligonucleotide conjugate an HyLk2' oligonucleotide-dextran-poly-IR800 dye conjugate mediated by hybridization to an HyLkr-HyLk2 adaptor oligonucleotide as presented in FIG. 32, in accordance with certain embodiments.

In certain embodiments, an adapter can be used in an immunodetection assay to allow a series of alternative signal generators to be used with a single antibody-oligonucleotide conjugate. Here, two Western blots identical to those shown in FIG. 36 were probed for analysis by infrared imaging by a LI-COR instrument. In FIG. 39, the conventional approach of using an anti-rat immunoglobulin antibody conjugated to LI-COR IR800 dye is shown in A. In B, the rat anti-tubulin-oligonucleotide conjugate was initially hybridized to an oligonucleotide designed to incorporate HyLk 1' and HyLk2' in tandem. This complex was then incubated with the nitrocellulose membrane and washed. Then, a HyLk2'-poly-IR800 dye signal generator conjugate was applied. LI-COR imaging reveals similar fluorescent detection of the tubulin band and the non-specific background band documents the results showing that the standard primary antibody/secondary antibody-IR800 conjugate method and the Universal Adapter method both detect tubulin.

Figure 40:
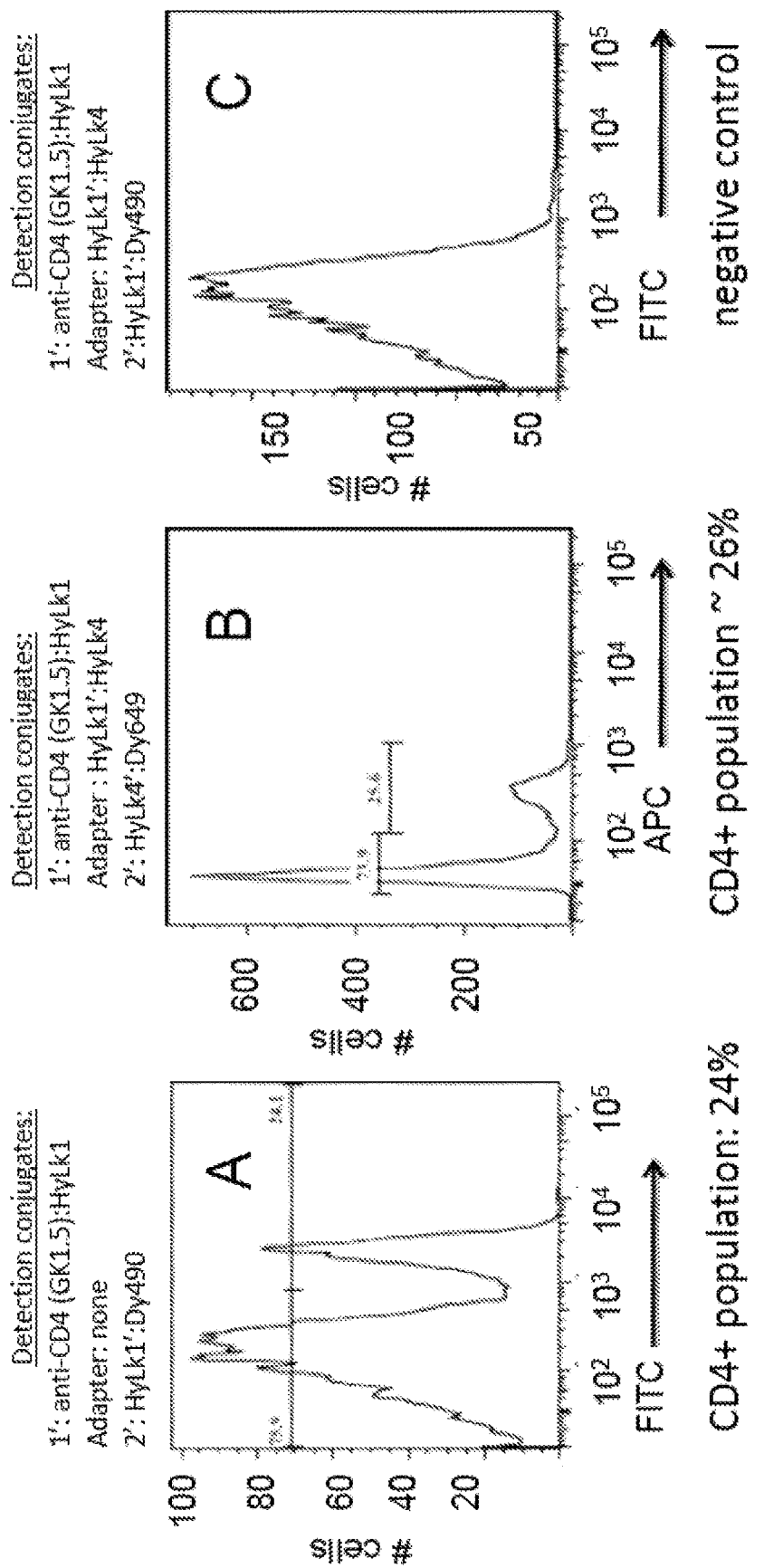
FIG. 40: is flow cytometry results demonstrating the use of an adapter method, showing (A) a positive control: Binding of a molecular probe and then hybridization with its complement detectable component, in the absence of an adapter; (B) use of an adapter: Binding of a molecular probe, hybridization with a complementary sequence on an adapter, and then hybridization of a second sequence on the adapter with complementary sequence on a detectable component; and (C) a negative control: Binding of a molecular probe and addition of an adapter having a non-complementary sequence to the detectable component, showing no signal when analyzed by flow cytometry; in accordance with certain embodiments.

The adapter method can also be used in flow cytometry as shown in FIG. 40. Here as a positive control α-CD4 antibody-HyLk1 conjugate was added to splenocytes, allowed to bind and washed. Subsequently, complementary HyLk1'-poly-Dy490 was added, allowed to hybridize and detected by flow cytometry, which showed that 24% of the cells were CD4$^+$ (A). in the adapter method, α-CD4 antibody-HyLk1 conjugate was added to lymphocytes, allowed to bind and washed. In (B), this was followed by addition of an adapter oligonucleotide designed to incorporate HyLk1' and HyLk4 in tandem. The adapter was allowed to hybridize to the HyLk1 conjugated to α-CD4 antibody and then washed. Subsequently, complementary HyLk4'-poly-Dy649 was added allowed to hybridize and was detected by flow cytometry, which showed that 26% of the cells were CD4$^+$ (B). In a negative control experiment (C), the α-CD4-HyLk1 probe was added to lymphocytes, then the HyLk1':HyLk4 adapter and then the HyLk1'-poly-Dy490 detector. If the adapter hybridizes, and thereby occludes access of the detector to the α-CD4-HyLk1 probe, flow cytometry may reveal no CD4I cells.

In certain embodiments, multiple antibody-oligonucleotide conjugates may be used simultaneously, or substantially simultaneously, to detect two or more protein biomarkers in a multiplex bead array experiment. Here, the detection uses solid-phase sandwich immunoassays with matched pairs of antibodies, wherein a capture antibody tethers an antigen to a surface and the subsequent binding of a detector antibody that recognizes a distinct epitope on the antigen confirms detection. The method is schematically presented in FIG. 41 wherein (A) an antibody-oligonucleotide conjugate formed from a capture antibody is added to a sample containing the antigen and allowed to bind, then (B) coded non-magnetic or magnetic beads conjugated to the complementary oligonucleotide are added to the sample wherein the antigen/antibody-oligonucleotide complex hybridizes to the bead. Then, in (C), a biotinylated detector antibody is added and allowed to bind and in (D) streptavidin/R-phycoerythrin (SAPE) is added. The resulting labeling of the bead by SAPE as in (E) allows the presence of antigen to be detected by, for example, flow cytometry. In general, the relative intensity of R-PE fluorescence will correspond to the relative abundance of the antigen when multiple samples are compared by this assay.

Figure 41:
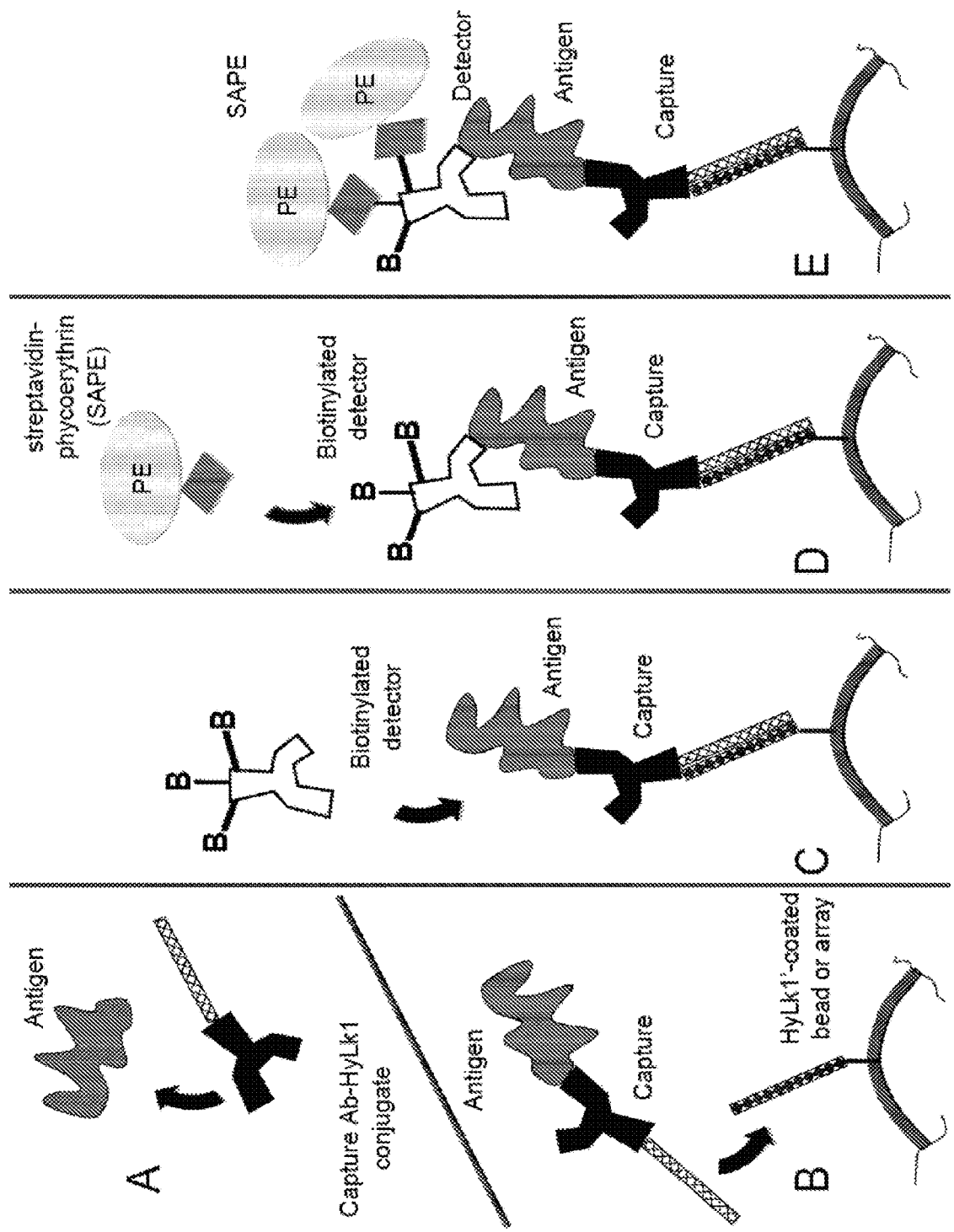
FIG. 41: is a schematic representing steps in an antibody-oligonucleotide directed multiplex bead array protocol, wherein (A) the antigen is captured by an antibody-oligonucleotide conjugate, (B) complementary oligonucleotide-beads are added and the antigen/antibody-oligonucleotide complex is captured by hybridization, (C) a biotinylated detector antibody conjugate is added followed by (D) addition of Streptavidin-R-PE conjugate signal detector, to form the resulting capture adduct (E), in accordance with certain embodiments.
Figure 42:
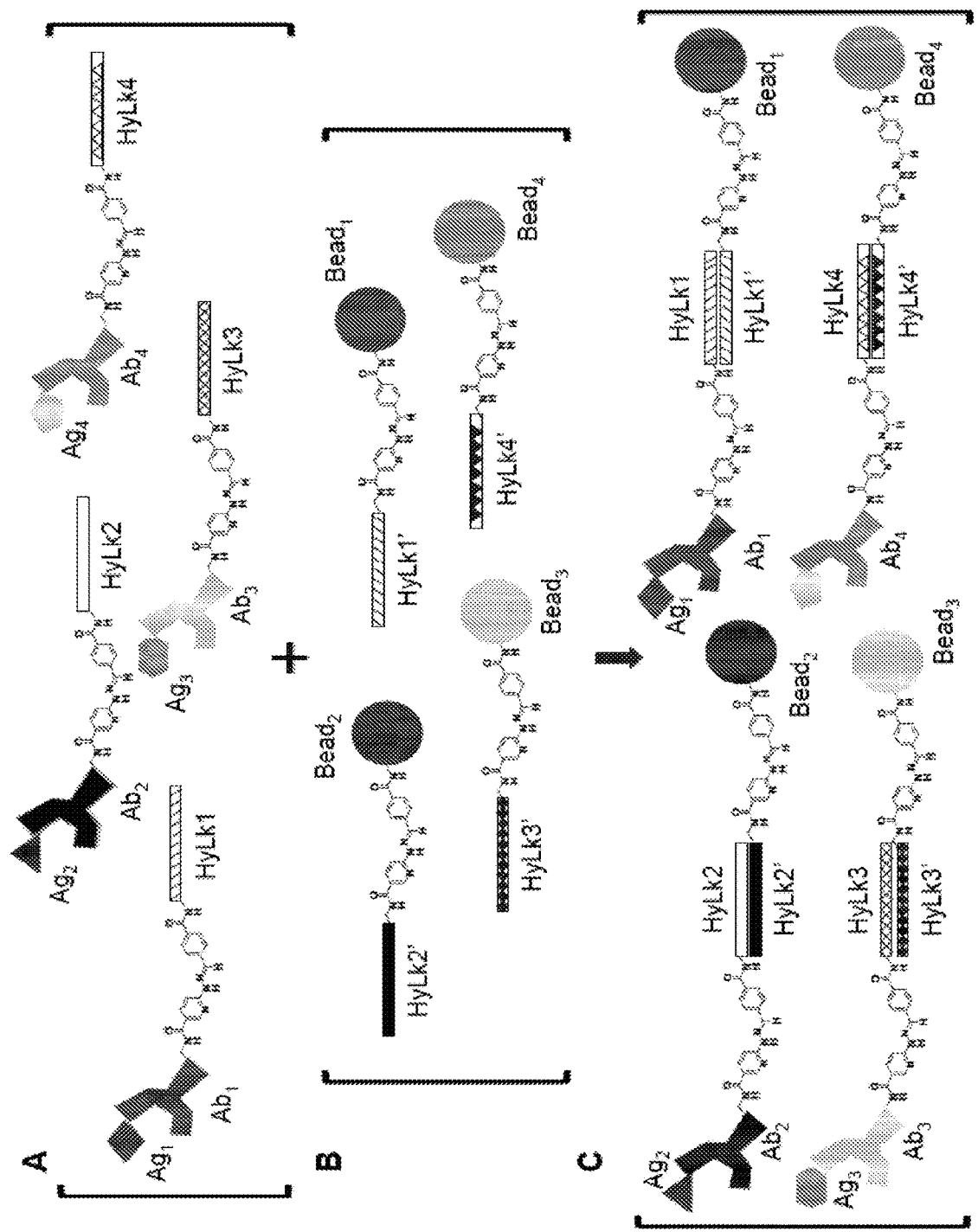
FIG. 42: is a schematic representation of a multiplex antibody-oligonucleotide/complementary oligonucleotide-bead conjugate self-assembly, in accordance with certain embodiments, such as in FIG. 41.

FIG. 42 presents schematically the self assembly of multiplex bead arrays for analysis of multiple antigens in a single sample, as an extension of the principle described in FIG. 41. As an illustrative example, the diagram shows four antibody-oligonucleotide conjugates assembling with four bead sets, such as non-magnetic or magnetic fluorescently coded beads, conjugated to their respective complementary oligonucleotides. Here, multiple antibody-oligonucleotide conjugates ($Ab_x$-HyLkX) might be added to a biological sample and each could bind its target antigen ($Ag_x$), as shown in (A). Thus, $Ab_1$-HyLk1 might bind $Ag_1$, $Ab_2$-HyLk2 might bind $Ag_2$, and so on. Then, as in (B), a mixture of multiple sets of fluorescently coded beads, each bearing a different oligonucleotide (HyLkX-$Bead_x$), would be added. Using DNA directed assembly this allows self assembly of each antibody-oligonucleotide conjugate onto the cognate fluorescently coded bead as in (C). Then, not shown, addition of a mixture of biotinylated detector antibodies specific to each antigen, or biotinylated detector antibodies that might detect a common feature such as phosphorylation of tyrosine, to form a sandwich complex, followed by washing, and then detection by SAPE and washing, followed by analysis by, for example, flow cytometry. As such, the abundance of $Ag_1$ in the sample could be determined by the SAPE signal associated with Beach, abundance of $Ag_2$ could be determined by the SAPE signal associated with $Bead_2$), etc. Repeating this process with greater numbers of matched pairs of antibodies and beads sets, and then performing the analysis on multiple samples may provide for substantially straightforward multiplexed quantitation of the relative abundance of multiple antigens, or relative phosphorylation, or other features, in multiple samples.

Figure 43:
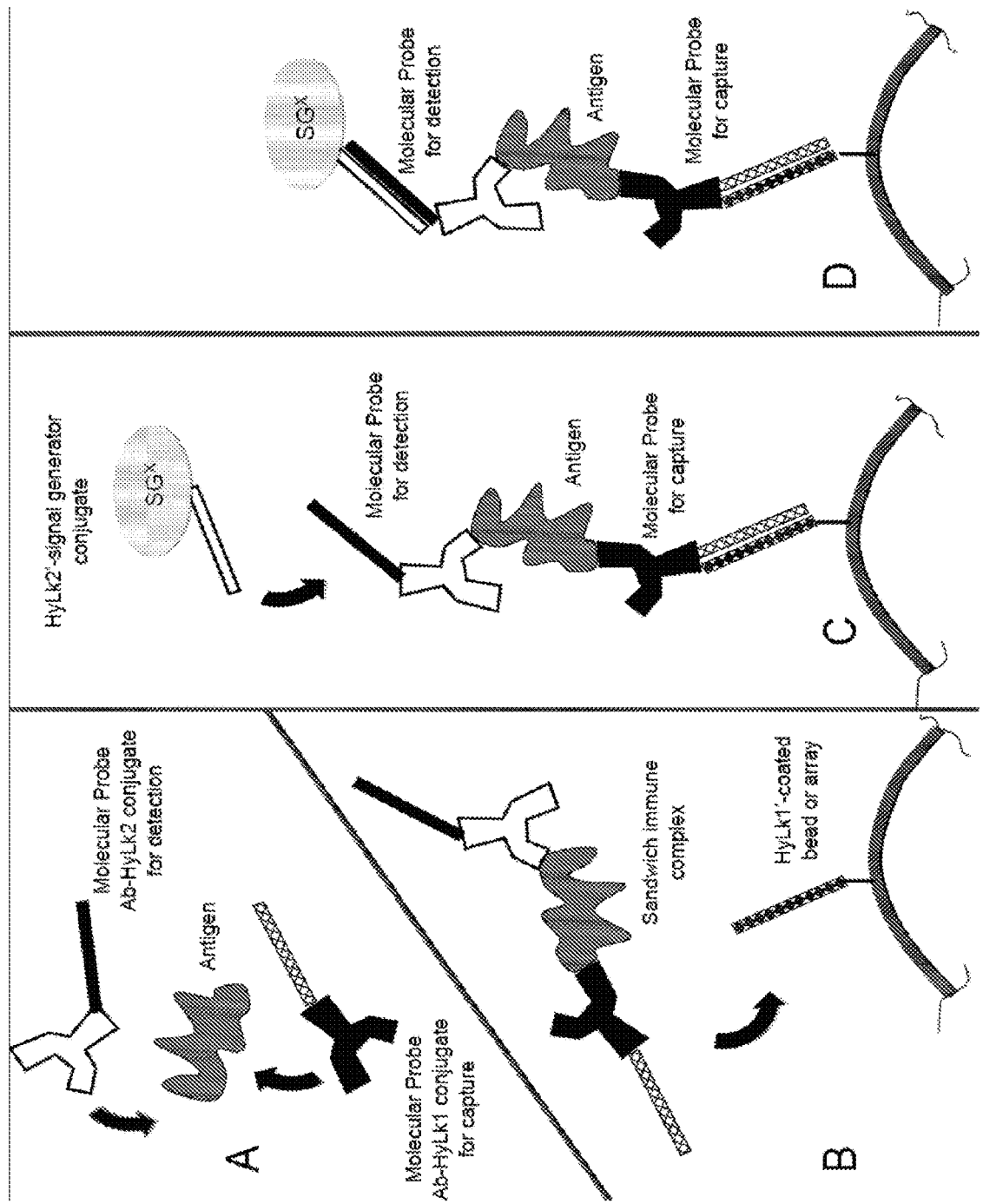
FIG. 43: is a scheme representing steps in an antibody-oligonucleotide directed bead array protocol, wherein (A) the antigen is captured by two molecular probes, comprising an antibody-oligonucleotide conjugate for detection and an antibody-oligonucleotide conjugate for capture to form a "sandwich immune complex," (B) a complementary oligonucleotide-bead is added and the sandwich immune complex is captured by hybridization with the oligonucleotide barcode sequence from the antibody-oligonucleotide conjugate for capture, (C) addition of a detectable component comprising an oligonucleotide sequence complementary to the antibody-conjugate for detection, resulting in (D) the hybridized formation of a fully captured and detectable complex, in accordance with certain embodiments.

In certain embodiments, antibody-oligonucleotide conjugates and detectors comprising the complementary oligonucleotide conjugated to a signal generator, in this case a scaffold modified with multiple fluorophores, can be used in a multiplex bead array assay to simultaneously, or substantially simultaneously, detect multiple analytes from a sample. FIG. 43 schematically presents the method wherein two antibody-oligonucleotide conjugates, Ab-HyLk1 and Ab-HyLk2, against a single protein target prepared from either two monoclonal antibodies to different epitopes on the target analyte that have been conjugated to the two different oligonucleotides or from a polyclonal antibody that has been split into two parts and conjugated to the two different oligonucleotides, then (A) the antibody-oligonucleotide pairs (comprising an antibody-oligonucleotide conjugate for detection and an antibody-oligonucleotide conjugate for capture) are added to a sample wherein the analyte is captured to form a sandwich immune complex, (B) fluorescently coded beads conjugated to the HyLk oligonucleotide complementary to the capture antibody-HyLk1 oligonucleotide conjugate are added to the sample wherein the sandwich immune complex hybridizes to the bead, then (C) a HyLk2' complementary oligonucleotide-signal generator conjugate where the SGX represents one or more signal generators, such as a biofluorescent protein such as R-PE or a polyfluor conjugate, is added and allowed to hybridize to the detector antibody-HyLk2 oligonucleotide conjugate, tethering the fluorescent signal generator to the bead as in (D), allowing steps of washing and detection as, for example, by flow cytometry. As described, this scheme presents the method of a single-plex assay. However, by using the scheme as provided in FIG. 42, the design of the assay allows facile use of multiplexing with multiple sets of matched pairs for sandwich immunoassay, via capture antibody-oligonucleotide conjugates hybridizing to their complementary fluorescently coded bead sets, and detection of the detector antibody-oligonucleotide complexes by hybridization to complementary oligonucleotides conjugated to fluorescence signal generators such as R-PE. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Figure 44:
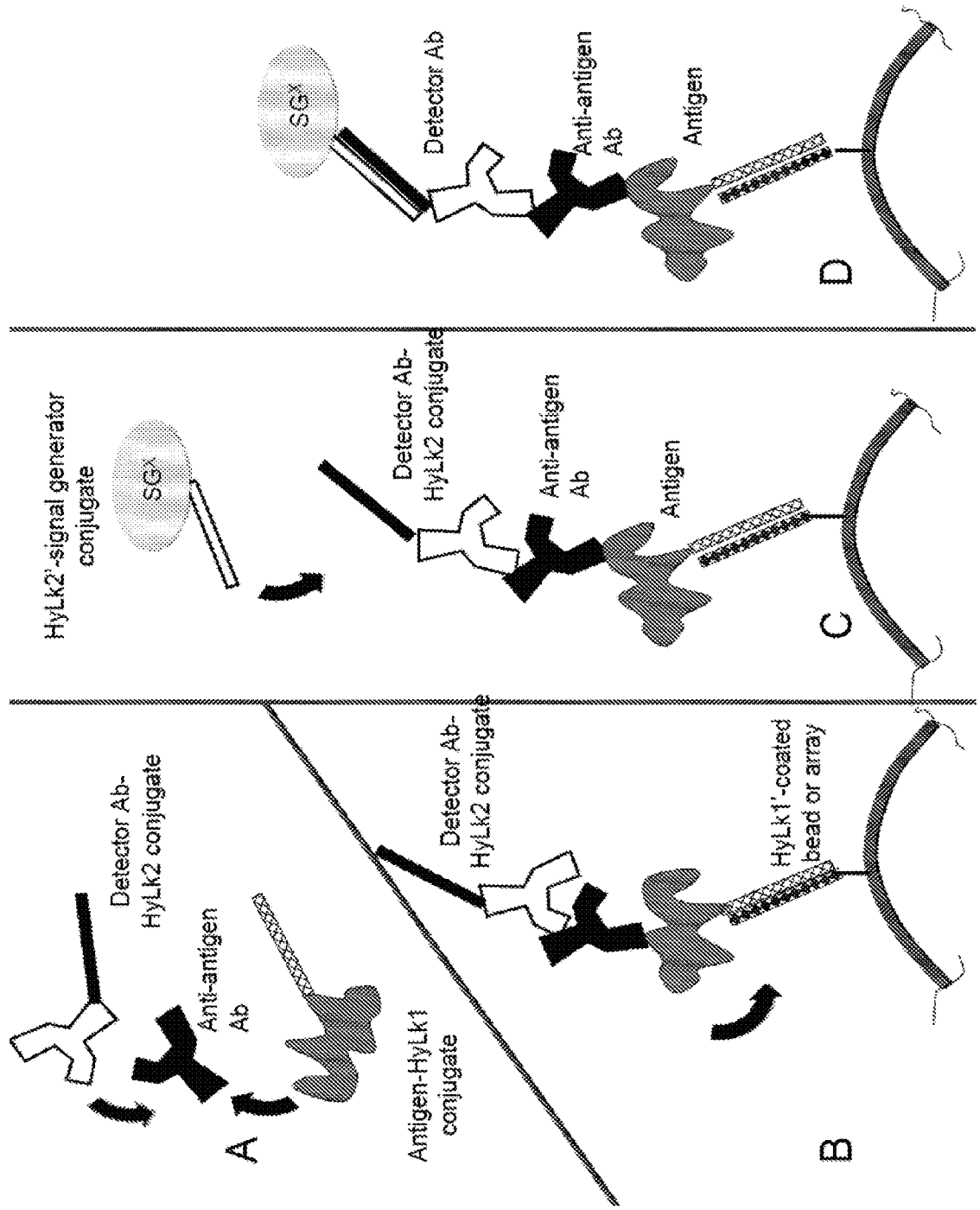
FIG. 44: is a scheme representing steps in an antibody-oligonucleotide directed bead array protocol, to simultaneously, or substantially simultaneously, detect and quantify auto-antibodies from a sample and detect and quantify the isotype response in a serology assay, wherein (A) an antigen conjugate and an anti-isotype specific antibody conjugate are added to a sample wherein the anti-antigen antibody is captured by both oligonucleotide conjugates and (B) added to mixture are complementary detectable components (distinct bead conjugates) resulting in the capture of the complex by hybridization to the captured antigen, (C) the complex is detected by the addition of complementary detectable components, in accordance with certain embodiments.

In certain embodiments, antigen-oligonucleotide conjugates and anti-isotype specific antibody-oligonucleotide conjugates and their complementary oligonucleotide conjugated to a signal generator, in this case a scaffold modified with multiple fluorophores, can be used in a multiplex bead array assay to simultaneously, or substantially simultaneously, detect and quantify antigen-specific antibodies such as auto-antibodies, antibodies generated from a vaccination or other isotype specific antibodies such as TgE from a sample and detect and quantify the isotype response in a serology assay. FIG. 44 schematically presents a self-assembly-based method wherein (A) an antigen-HyLk1 conjugate and an anti-isotype specific antibody-HyLk2 conjugate are added to the blood sample wherein the anti-antigen antibody is captured by both oligonucleotide conjugates and (B) added to mixture are HyLk1'-fluorescently distinct bead conjugates resulting in the capture of the complex by hybridization to HyLk1 conjugated to the antigen, (C) the complex is detected by the addition of a HyLk2'-signal generator conjugate. As described, this scheme presents the method of a single plex assay. However, the design of the assay allows facile use of multiplexing with multiple antigen-oligonucleotide conjugates and their complementary bead sets along with multiple anti-isotype antibody-oligonucleotide complexes and complementary oligonucleotide signal generators each conjugated to a different signal generator. However, in certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Figure 45:
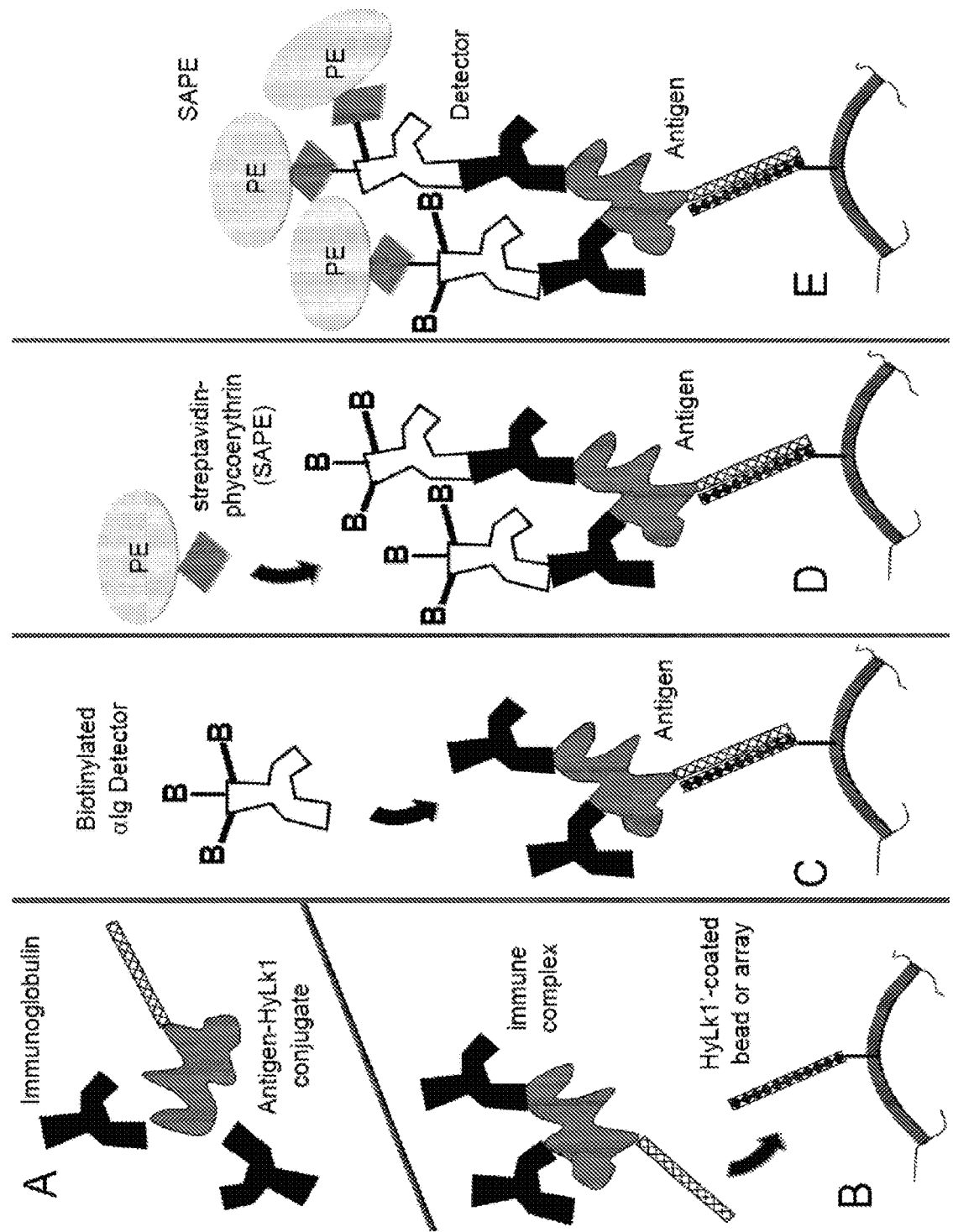
FIG. 45: is a scheme representing the steps in an antigen-oligonucleotide directed bead array protocol wherein (A) the anti-antigen antibody is captured by its cognate antigen-oligonucleotide conjugate, (B) complementary oligonucleotide-beads are added and the anti-antigen antibody/antigen-oligonucleotide complex ("immune complex") is captured by hybridization, (C) a biotinylated detector antibody conjugate is added followed by (D) addition of Streptavidin-R-PE conjugate signal detector, resulting in (E) the formation of a captured and detectable complex, in accordance with certain embodiments.
Figure 75:
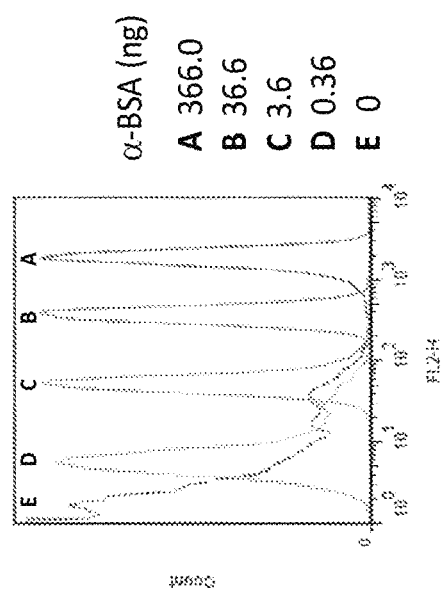
FIG. 75 shows the flow cytometry results of the capture and detection of α-BSA antibody using BSA-HyLk1 conjugate immobilized on Compel-HyLk1' beads from 366 to 0.36 ng.
Figure 76:
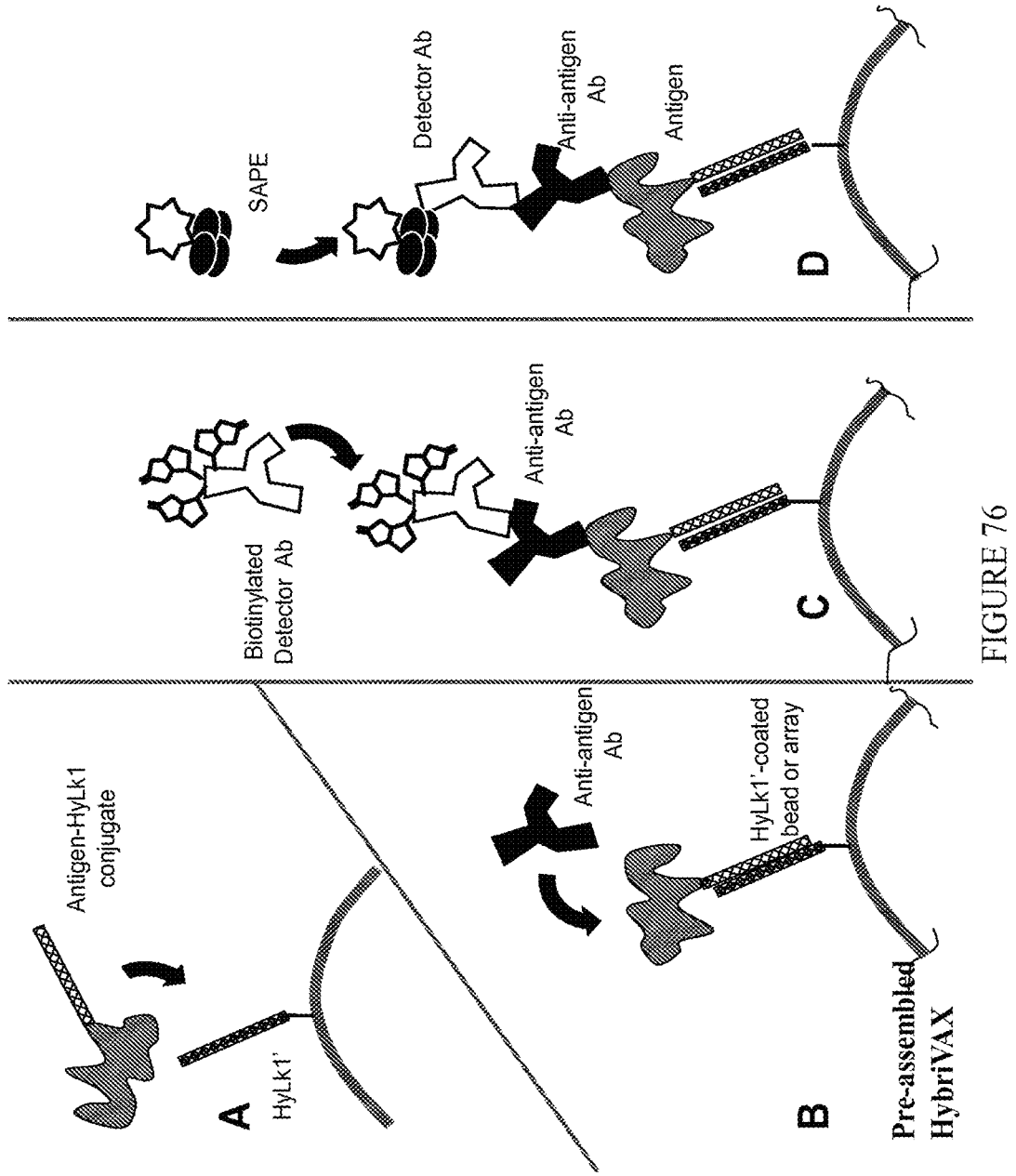
FIG. 76 illustrates an exemplary step wise protocol that may be used to capture and detect an antigen from a biological sample, according to certain embodiments.

In certain embodiments, in a pre-assembly-based assay antigen-oligonucleotide conjugates may be hybridized to their complementary oligonucleotide immobilized on a bead or a bead encoded with for example a fluorophore to be distinct from other beads, added to the biological sample to bind the cognate antigen, washed and detected with an -antibody antibody (see exemplary FIG. 76). Example 24 exemplifies the detection of a rabbit-BSA antibody that was captured by a BSA-HyLk1 conjugate pre-hybridized to a bead immobilized to complementary HyLk1', followed by detection with a biotinylated goat-rabbit antibody subsequently labeled with a streptavidin-phycoerythrin conjugate (SAPE) and analyzed by flow cytometry. The flow cytometry results (FIG. 75) presents the results of the capture and detection of -BSA antibody using BSA-HyLk1 conjugate immobilized on Compel-HyLk1' beads from 366 to 0.36 ng. However, in certain embodiments, the order of assembly and addition to a sample might be varied, so that the capture antibodies might be combined with sample prior to addition of the beads, and the detector antibodies might be added to the sample prior to or along with the capture antibodies, or might be added after forming the antigen-capture antibody complex on the beads and washing, or in other sequences as might be possible.

in certain embodiments, it will be useful to determine the level and/or type of immune response to antigens such as viruses, bacterial carbohydrates, viral proteins, protein therapeutics. Antigen-oligonucleotide conjugates and their complementary detectors may be used to simultaneously, or substantially simultaneously, detect for example their cognate antibodies in a multiplex experiment to detect and titer the amount of antibody present in a biological sample. This would allow for example multiplex detection and quantification of the level of antibodies produced following immunization with a multiple antigen (e.g., combination) vaccine. FIG. 45 schematically presents the procedure wherein (A) an antigen-HyLk1 oligonucleotide conjugate added to a biological sample is bound by immunoglobulins present in the sample, (B) complementary HyLk1' oligonucleotide conjugated onto a fluorescently coded bead is added and the antigen-oligonucleotide/antibody complex hybridizes to the bead, (C) the antibody analyte is detected by addition of a biotinylated anti-immunoglobulin detector antibody, (D) addition of a streptavidin/R-PE (SAPE) conjugate tethers the fluorescent detector to the bead (E) to permit detection using, for example, a flow cytometer. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Figure 46:
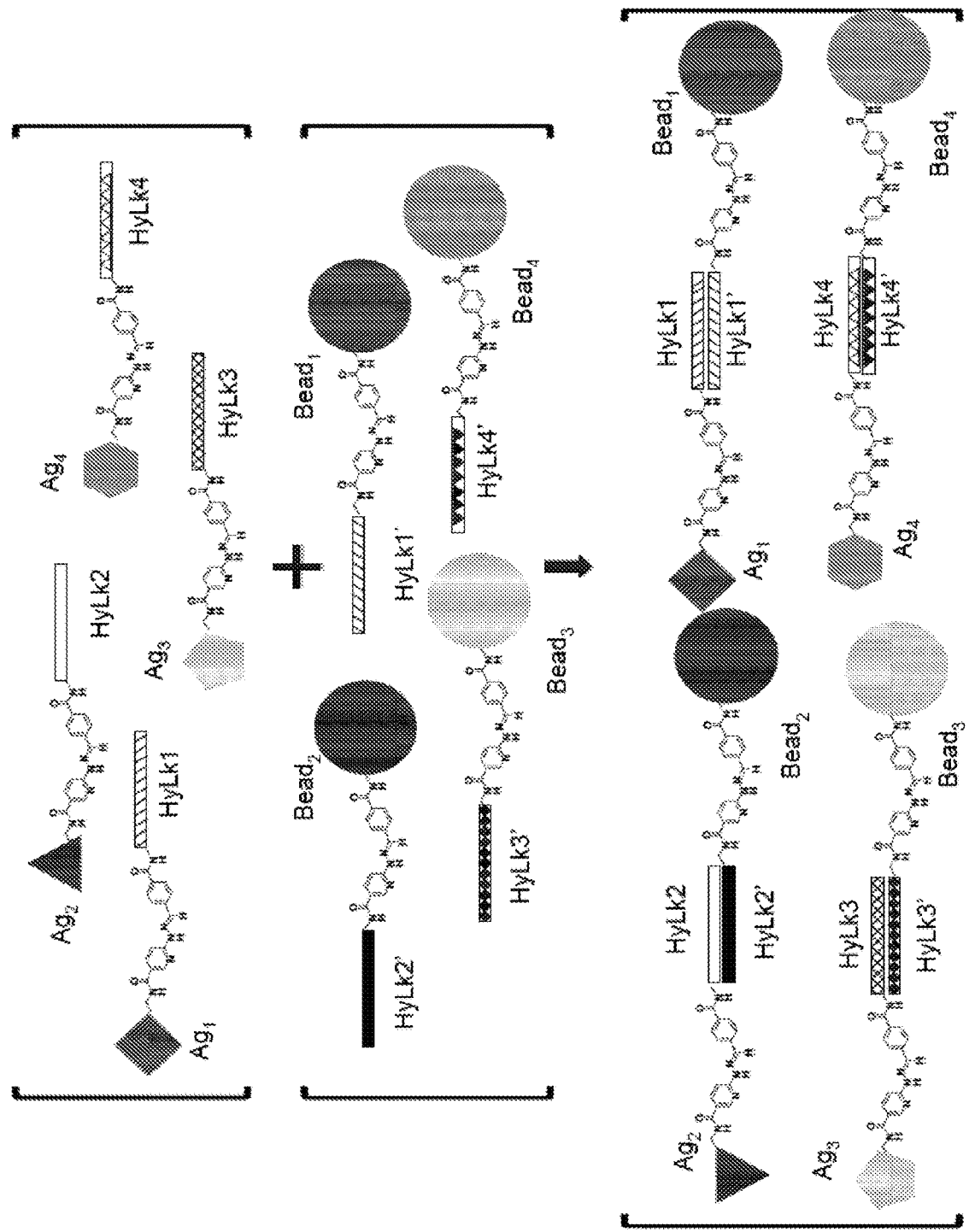
FIG. 46: is a schematic representation of a multiplex antigen-oligonucleotide/complementary oligonucleotide-bead conjugate self-assembly, in accordance with certain embodiments, such as in FIGS. 43, 44 and 45.

In certain embodiments, antigen-oligonucleotide conjugates and detectors comprising the complementary oligonucleotide conjugated to a signal generator can be used in a multiplex bead array assay to simultaneously, or substantially simultaneously, detect multiple immunoglobulin specificities from a single sample. FIG. 46 presents schematically the self assembly of multiplex bead arrays for analysis of multiple antibody specificities in a single sample, as an extension of the principle described in FIG. 45. As an illustrative example, the diagram shows four antigen-oligonucleotide conjugates assembling with four bead sets, such as non-magnetic or magnetic fluorescently coded beads, conjugated to their respective complementary oligonucleotides. Here, multiple antigen-oligonucleotide conjugates ($Ag_x$-HyLkX) might be prepared so that each could be bound by a different immunoglobulin as in (A). Then, as in (B), a mixture of multiple sets of fluorescently coded beads, each bearing a different oligonucleotide (HyLkX-$Bead_x$), would be added. Using DNA directed assembly this allows self assembly of each antigen-oligonucleotide conjugate onto the cognate fluorescently coded bead as in (C). Then, not shown, these complexes could be added to a serum sample to allow binding of immunoglobulins. After washing, addition of biotinylated detector anti-immunoglobulin antibodies to form a sandwich complex, followed by washing, and then detection by SAPE and washing, followed by analysis by, for example, flow cytometry. As such, the abundance of immunoglobulin reactive to $Ag_1$ in the sample could be determined by the SAPE signal associated with $Bead_1$, reactivity to Age could be determined by the SAPE signal associated with $Bead_2$, etc. Repeating this process with greater numbers of antigens and beads sets, and then performing the analysis on multiple samples may provide for substantially straightforward serology for multiple antigens in multiple serum samples. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

In certain embodiments, the principle of self-assembly directed by hybridization between pairs of complementary oligonucleotides can be used to facilitate the independent formation of multiple complexes. Thus in a bead array format, mixtures of antigen-oligonucleotide conjugates can be used to detect and quantify one or more anti-antigen antibodies in a serology assay and using pairs of anti-isotypic antibody-oligonucleotide conjugates with complementary oligonucleotide-signal generators will be able to specifically detect and quantify the isotype response. However, in certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Figure 47:
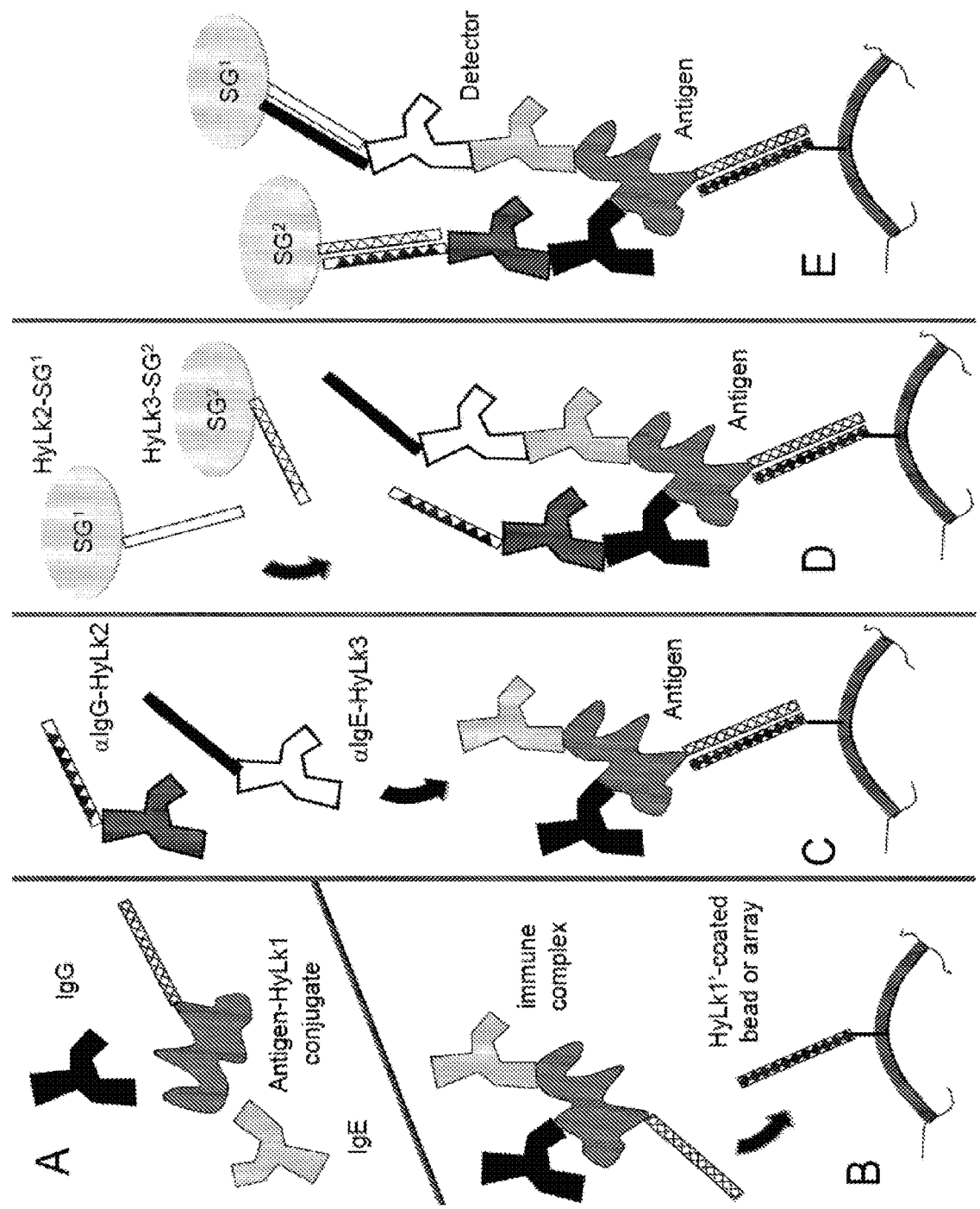
FIG. 47: is a schematic representing the steps in an antigen-oligonucleotide directed bead array protocol wherein (A) the anti-antigen antibody or antibodies, i.e., IgG, IgM, IgA, or IgE, is captured by its cognate antigen-oligonucleotide conjugate, (B) complementary oligonucleotide-beads are added and the anti-antigen antibody/antigen-oligonucleotide complex ("immune complex") is captured by hybridization, (C) antibody-oligonucleotide conjugates specific for the anti-antigen antibodies ("anti-antigen antibody detectors") are added followed by (D) the addition of complementary oligonucleotide-signal detector conjugates that recognize their respective oligonucleotide sequences on the anti-antigen antibody detectors allowing identification of the antibody isotype response, in accordance with certain embodiments.

The steps of self-assembly are illustrated in FIG. 47. Here (A) antigen-HyLk1 conjugate is added to the serum sample binding to its cognate antibodies, (B) coded beads immobilized with HyLk1' is added to the sample wherein the antibody/antigen-HyLk1 complex hybridizes to the HyLk1' bead, (C) here for example an anti-IgG antibody conjugated to HyLk2 and an anti-IgE antibody conjugated to HyLk3 are added and allowed to bind to its their targets, (D) HyLk2'-SG' and HyLk3'-$SG^2$ fluorescent detectors are added, allowed to hybridize and (E) detected by, for example, a flow cytometer.

Figure 48:
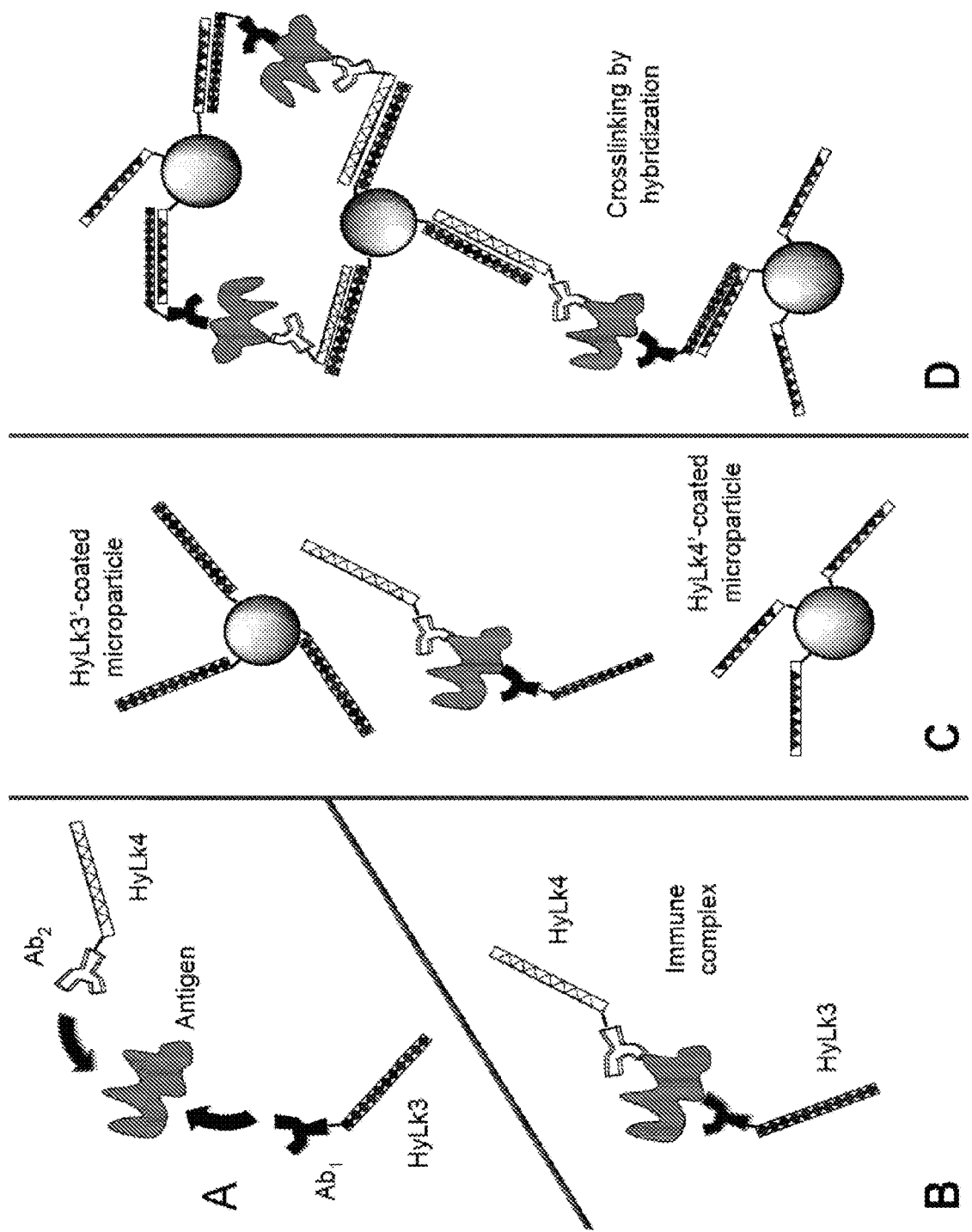
FIG. 48: is a schematic representation of the use of antibody-oligonucleotide conjugate/complementary oligo bead conjugates in an immunoturbidity assay, wherein (A) a pair of antibody-oligonucleotide conjugates ("capture antibody-conjugates") directed to independent epitopes of an antigen are added to a sample, (B) allowed to bind to form an "immune complex," (C) the mixture is added to beads conjugated to oligonucleotides complementary to the oligonucleotides on the capture antibody-conjugates, and (4) allowed to hybridize leading to crosslinking by hybridization, in accordance with certain embodiments.

In certain embodiments, antibody-oligonucleotide conjugates and beads conjugated to their respective complementary oligonucleotide can be used in an immunoturbidity assay, which may be automated. FIG. 48 schematically presents one iteration, according to certain embodiments, of this assay wherein two antibody-oligonucleotide conjugates against a single protein target prepared from two monoclonal antibodies to different epitopes on the target analyte are conjugated to two different oligonucleotides, Hylk3 and HyLk4, are added (A) to a sample containing the cognate antigen, (B) allowed to bind, (C) combined with a mixture of two sets of the latex beads or gold particles immobilized to their respective, HyLk3' or HyLk4' complementary oligonucleotides, of a size that they are in suspension in hybridization buffer. As shown in (D) in FIG. 46, contact with the immune complex formed by the two antibodies binding as a sandwich to the antigen permits crosslinking between beads by hybridization, leading to agglutination of the beads in the tube. In general, the degree of agglutination will be in proportion to the abundance of antigen, and is detected, for example, visually or using a standard immunoturbidity reader. In an alternate iteration a polyclonal antibody against a biomarker target is conjugated to an oligonucleotide. Also prepared is its complementary oligonucleotide immobilized on latex beads or gold particles of a size that they are in suspension in hybridization buffer. These conjugates are processed as described herein and the amount of agglutination may be determined on, for example, an immunotubidity reader to measure the abundance of the biomarker target in the sample. The order of assembly and/or addition to a sample may be varied, for example, so that the antibody-oligonucleotide conjugate(s) may be combined with the beads prior to contact with the sample or after, or may be added after forming the antigen-capture antibody complex. FIG. 48 schematically presents the method wherein two antibody-oligonucleotide conjugates against a single protein target prepared from either two monoclonal antibodies to different epitopes on the target analyte are conjugated to two different oligonucleotides, Hylk3 and HyLk4, or from a polyclonal antibody that has been split into two parts and conjugated to the two different oligonucleotides are added (A) to a sample containing the cognate antigen, (B) allowed to bind, (C) added to a tube containing two sets of latex beads, of a size that they are in suspension in hybridization buffer, each conjugated to one of the two complementary oligonucleotides HyLk3' or HyLk4'. As shown in (D), contact with the immune complex formed by the two antibodies binding as a sandwich to the antigen permits crosslinking among beads by hybridization, leading to agglutination of the beads in the tube. In general, the degree of agglutination will be in proportion to the abundance of antigen, and is detected, for example, using a standard immunoturbidity reader. Here, for example, a polyclonalantibody that has been raised against a biomarker target is divided and one half is conjugated to HyLk3 and one half is conjugated to HyLk4. Also prepared are two sets of beads conjugated to HyLk3' and HyLk4' respectively. These conjugates are processed as described herein and the amount of agglutination may be determined on an immunotubidity reader to measure the abundance of the biomarker target in the sample. However, in certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

In certain embodiments, antibody-oligonucleotide conjugates and detectors comprising the complementary oligonucleotide conjugated to a signal generator can be used in an ELISA-based assay using either fluorescent or enzyme-based detection. As presented in FIG. 49, (A) HyLk1' oligonucleotides are immobilized by covalent attachment on a solid surface such as a plastic 96 well plate, and in the sample to be analyzed, (B) a capture antibody-HyLk1 oligonucleotide conjugate binds to its cognate antigen where present, (C) the sample is then added to the oligonucleotide-coated surface and the antibody-oligonucleotide/antigen complex hybridizes to the HyLk 1', tethering the immune complex, (D) a biotinylated detector antibody specific to that antigen is added and (E) detected using a streptavidin-signal generator conjugate such as an enzyme or biofluorescent protein. However, in certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Figure 49:
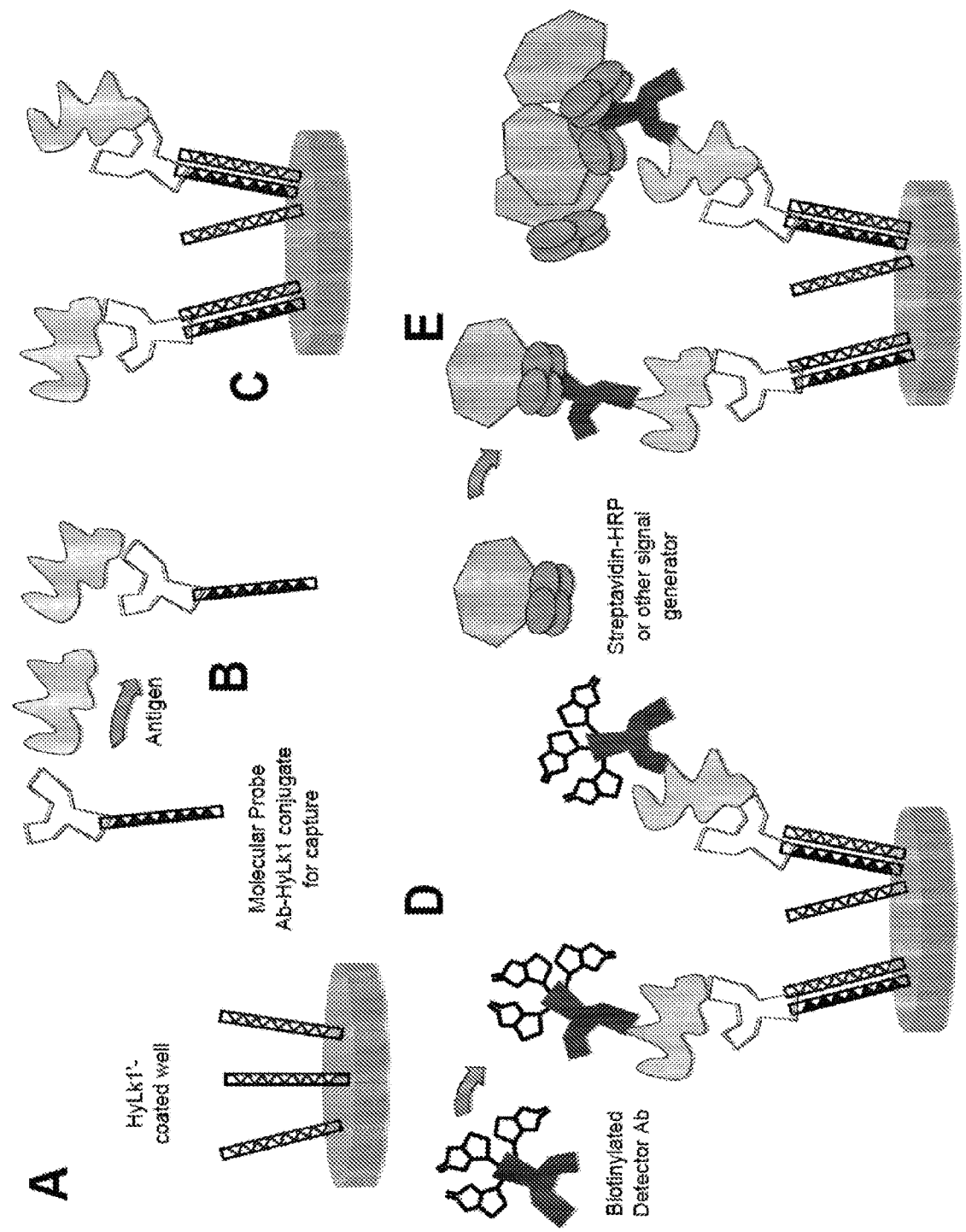
FIG. 49: is a schematic representing steps in an antibody-oligonucleotide directed ELISA or planar array protocol wherein (A) an oligonucleotide is immobilized (e.g., on a 96-well plate or planar array surface), (B) the antigen is captured by an antibody-oligonucleotide conjugate, (C) the sample containing the antigen/antibody-oligonucleotide complex is incubated with the surface and captured by hybridization, (D) a biotinylated detector antibody conjugate is added to bind the captured antigen, followed by (E) addition of Streptavidin-HRP conjugate signal detector, in accordance with certain embodiments.
Figure 50:
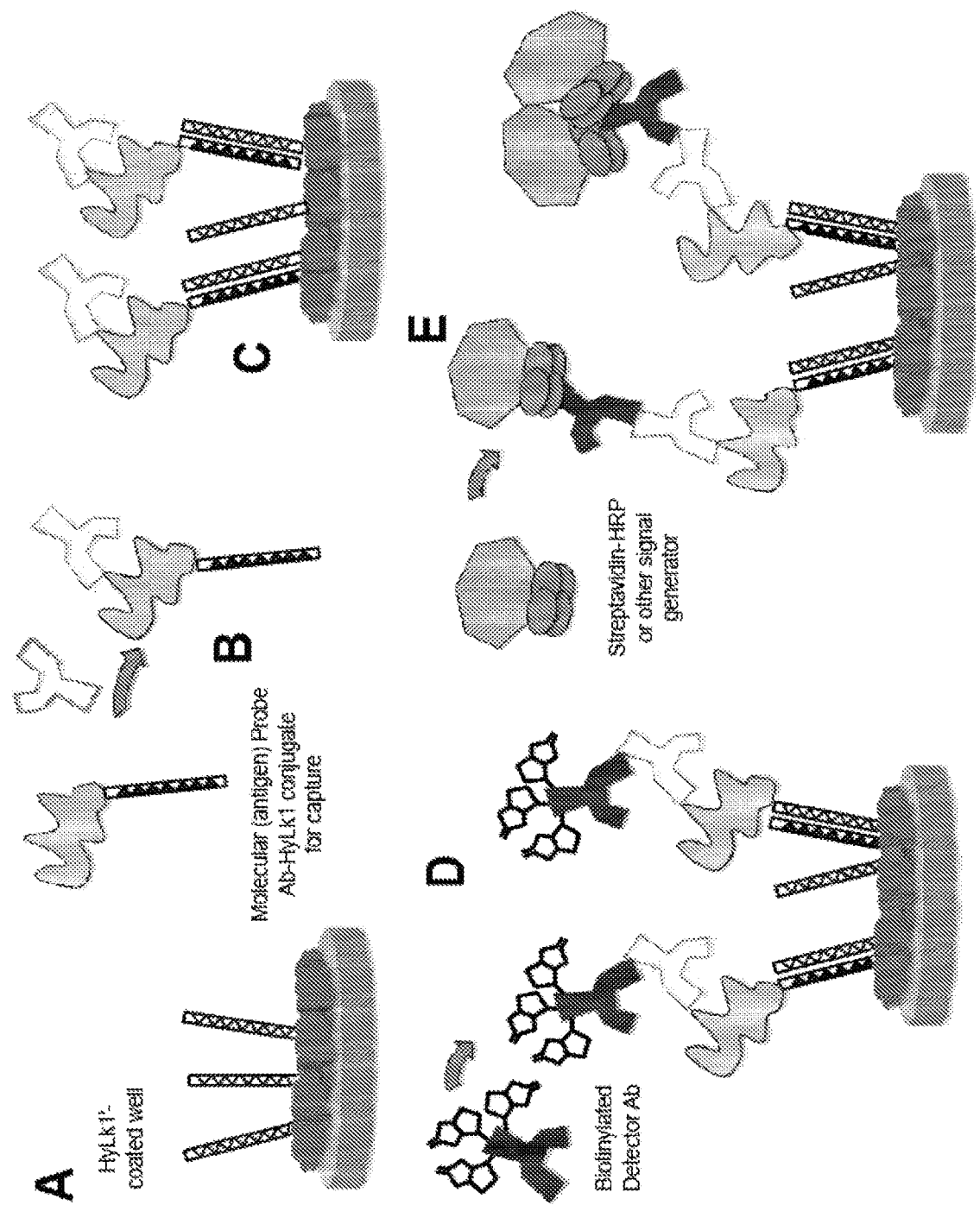
FIG. 50: is a schematic representing steps in an antigen-oligonucleotide directed ELISA or planar array protocol wherein (A) an oligonucleotide is conjugated to BSA and the oligonucleotide-BSA conjugate is immobilized (e.g., on a 96-well plate or planar array surface), (B) the antibody is captured by an antigen-oligonucleotide conjugate, (C) the sample containing the antibody/antigen-oligonucleotide complex is incubated with the surface and captured by hybridization, (D) a biotinylated detector antibody conjugate is added to bind the captured antibody, followed by (E) addition of Streptavidin-HRP conjugate signal detector, in accordance with certain embodiments.

The method of FIG. 50 is similar to FIG. 49 except that the oligonucleotide is initially conjugated to a carrier protein such as bovine serum albumin (BSA) and thereby immobilized to the surface. Here, (A) oligonucleotides are immobilized on a solid surface such as a plastic 96 well plate but via covalent attachment or non-covalent adsorption of BSA-HyLk conjugate, and in the sample to be analyzed, (B) a capture antibody-HyLk1 oligonucleotide conjugate binds to its cognate antigen where present, (C) the sample is then added to the BSA-HyLk1-coated surface and the antibody-oligonucleotide/antigen complex hybridizes to HyLk tethering the immune complex, (D) a biotinylated detector antibody specific to that antigen is added and (E) detected using a streptavidin-signal generator conjugate such as an enzyme or biofluorescent protein. Use of this indirect immobilization method may be advantageous as: (i) the BSA may prevent non-specific binding to the plastic surface, (ii) the attachment to a protein linker may better present the oligonucleotide for hybridization (iii), less oligonucleotide would be required as conjugation to protein is more efficient than immobilization on plastic, and (iv) BSA will better anchor the oligonucleotide to the plate by multi-point contact. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Figure 51:
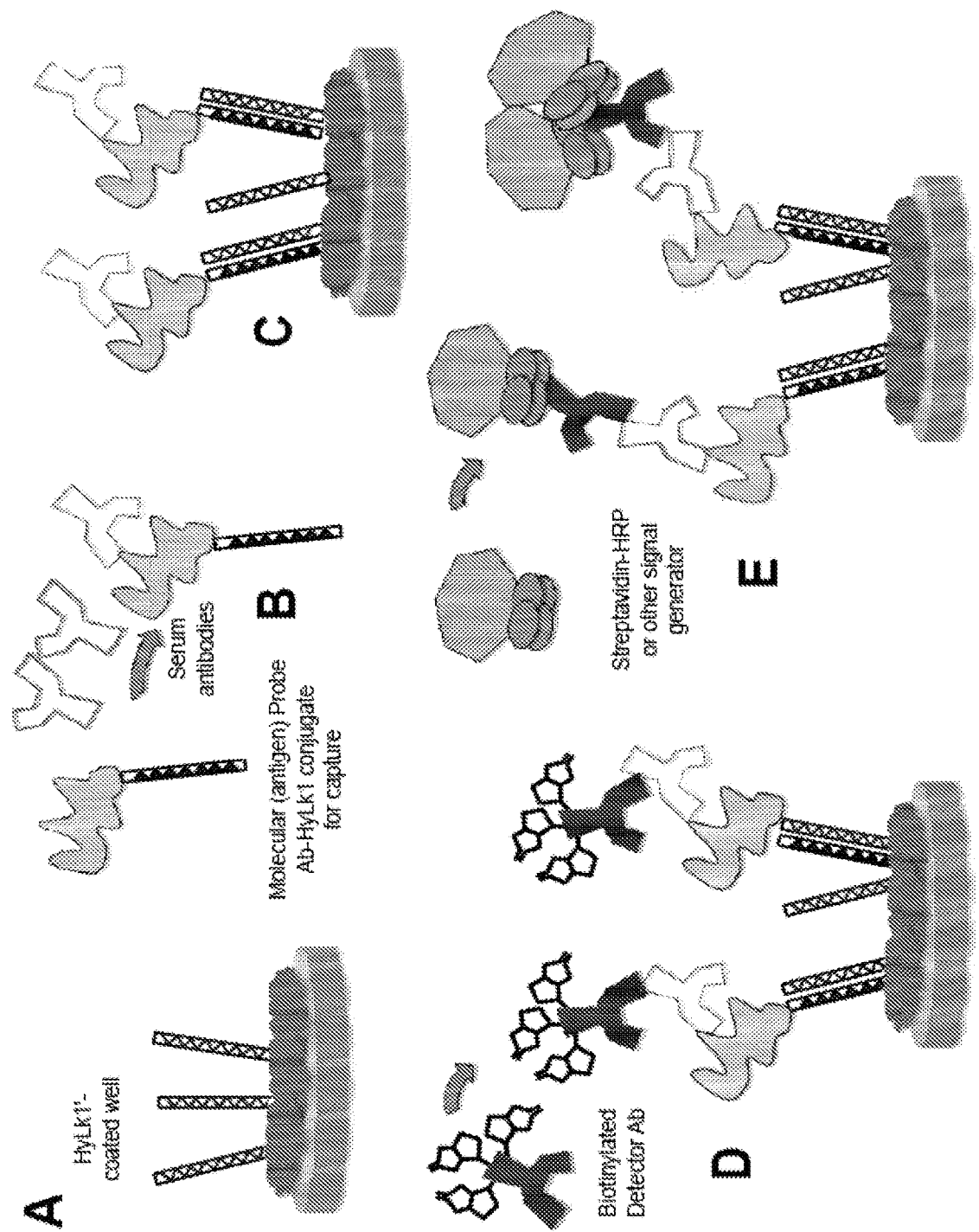
FIG. 51: is a schematic representing similar steps as those in FIG. 50, but wherein the steps are directed to an ELISA or planar array protocol in a serology-based assay to detect anti-antigen antibodies, in accordance with certain embodiments.

In certain embodiments, antigen-oligonucleotide conjugates and detectors comprising the complementary oligonucleotide conjugated to a signal generator can be used in an ELISA format in a serology-based assay to detect anti-antigen antibodies. FIG. 51 schematically presents a protocol to accomplish this wherein an (A) a HyLkr complementary oligonucleotide has been immobilized by attachment or adsorption of a BSA-HyLk1' conjugate, (B) an antigen-oligonucleotide conjugate is mixed with the biological sample capturing the anti-antigen immunoglobulin, (C) the resulting immune complex is captured by hybridization, (D) a biotinylated anti-antibody is added and (E) detected using a streptavidin-signal generator conjugated to an enzyme or biofluorescent protein. Similar schemes may be used with complementary oligonucleotides directly conjugated to the surface of the ELTSA plate.

The bead-based examples illustrated herein may be applicable to both self-assembly, i.e. wherein the capture-oligonucleotide conjugates are added to the biological sample and then captured on beads, as well as pre-assembly, wherein the capture-oligonucleotide conjugate is pre-hybridized to its bead then mixtures of beads are combined and added to the biological sample. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Immunocytochemistry

Figure 52:
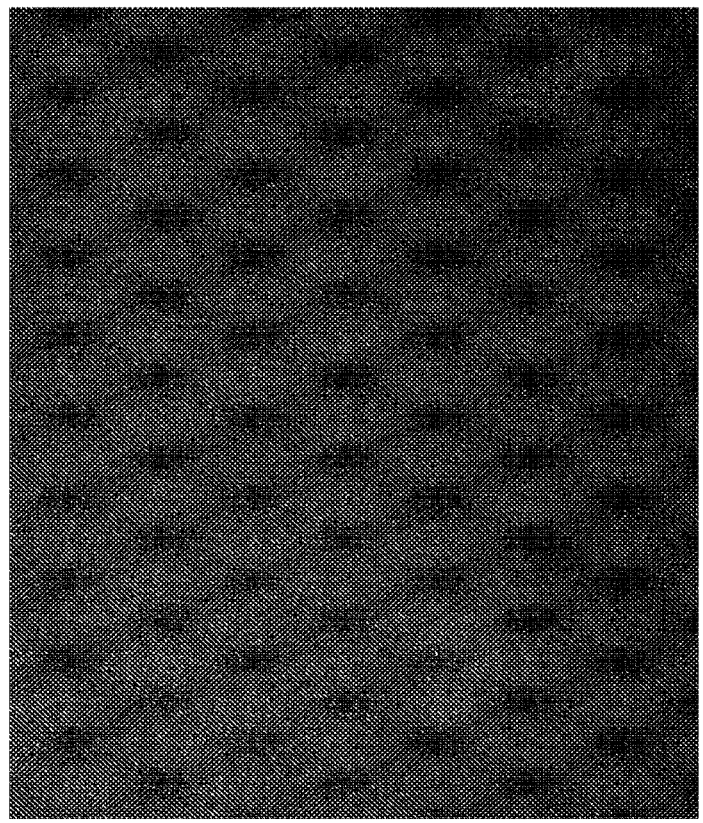
FIG. 52: is showing results of an immunocytochemistry experiment to examine tubulin distribution in cells, wherein an α-tubulin HyLk1 oligonucleotide conjugate molecular probe is imaged using an HyLk1' complementary oligonucleotide-poly-Dy490 fluorophore detector and the fluorescein channel of an epifluorescence microscope as in (A) while the HyLk1'-poly-Dy490 probe alone yields no similar image, according to certain embodiments.
Figure 52:
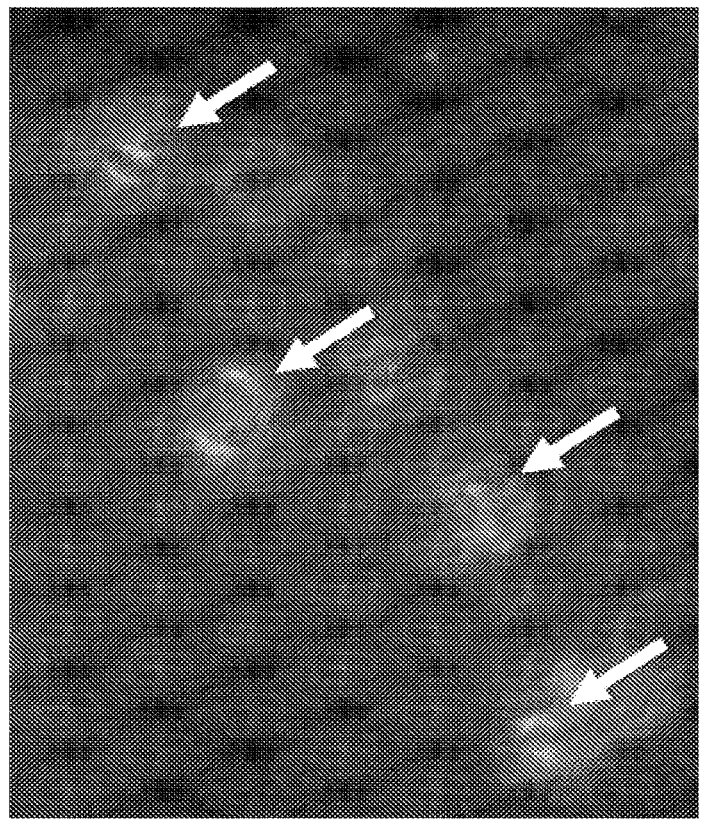
Figure 53:
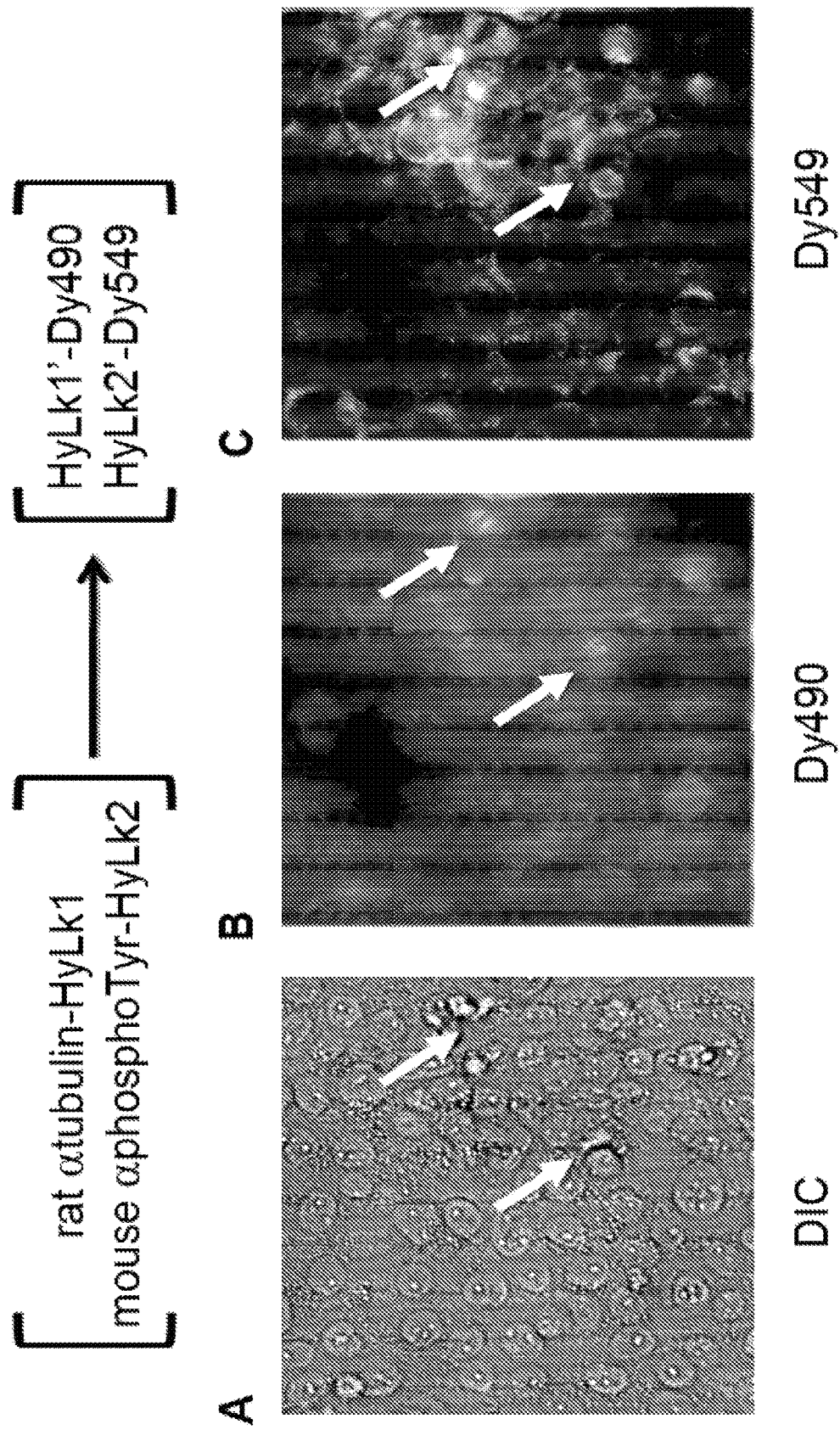
FIG. 53: is showing imaging results of the distribution of tubulin and the distribution of phosphotyrosine-containing proteins using antibody-oligonucleotide conjugates and their respective complementary detectors applied in mixtures, wherein a mixture of an α-tubulin-HyLk1 probe and α-phosphotyrosine-HyLk2 probe are applied and then detected by a mixture of HyLk1'-poly-Dy490 and HyLk2'-poly-Dy549, allowing their distribution in (A) cells imaged in brightfield to be distinguished as in (B) using a fluorescein filter set and (C) using a rhodamine filter set, according to certain embodiments.

In certain embodiments, antigen-oligonucleotide conjugates and detectors comprising the complementary oligonucleotide conjugated to a signal generator may be used in immunocytochemistry and related methods to determine the abundance and localization of one or more specific antigens within cells. Where the signal generators can be distinguished, as is readily achieved by using fluorophores with distinct fluorescence properties, it would be straightforward to independently determine and then compare the localizations of multiple antigens within a single cell. After applying the probes and detectors, the sample would be subjected to microscopic imaging using optical means to illuminate the sample at each of the different fluorescence excitation bands and record the image at the corresponding emission bands, using sets of optical filters or other means. To determine the relative distributions, the images could then be compared to registration images such as a phase contrast or other brightfield image and then compared to each other to evaluate the distributions of intensity of fluorescence. Determination of cellular abundance and distribution of antigens might commonly be pursued to examine cells grown in the laboratory to pursue an experiment, or toward diagnosis, to examine cells obtained from a biological sample such as blood or other cell-containing fluid or extracted from a solid tissue as via a fine-needle biopsy, tissue print or other common method. As an example, as shown in FIG. 52 and FIG. 53, growing human cancer cells adhering to a glass surface were permeabilized with a detergent, and fixed and dehydrated with methanol. The cells were rehydrated and incubated with BSA to block nonspecific binding of probes and detectors. Then, a mixture of two probes, a rat anti-tubulin monoclonal antibody-HyLk1 conjugate and a mouse anti-phosphotyrosine monoclonal antibody-HyLk2 conjugate were applied. Then, the free probes were washed away and a mixture of HyLkr-poly-Dy490 and HyLk2'-poly-Dy549, both oligonucleotide conjugates to fluorescently labeled amino dextrans, were applied. Then excess detector conjugates were washed away and the cells were imaged by epifluorescence microscopy. As shown in FIG. 52, the characteristic distribution of tubulin in cells can be appreciated, particularly in those cells indicated by the white arrows that may be performing mitosis, a step in cell division where the microtubules align in the cell to mediate separation of chromosomes. In (A), both the anti-tubulin-oligonucleotide conjugate probe and complementary oligonucleotide-fluorescence scaffold detector were applied. Here, one infers that the distribution of fluorescence in the image corresponds to the distribution of tubulin in the cells insofar as the control experiment shown in (B), where only the fluorescent detector was applied, demonstrates a lower fluorescent signal and displays no subcellular distribution.

Differential Interference Contrast Brightfield

In FIG. 53, in (A), a single field of cells is shown imaged by Differential Interference Contrast brightfield, and in (B) and (C), respectively, the same field imaged using two fluorescent filter sets, the FITC filters to detect Dy490 distribution and the rhodamine filters to detect Dy549 distribution. The three images allow independent evaluation and comparison of the shape of the cells, the distribution of tubulin and the distribution of phosphotyrosine-containing proteins. The independent nature of the detection can be appreciated at the position indicated by the white arrows in each image. The arrows indicate two cells apparently performing mitosis, based on the pattern of distribution of tubulin. However, in the region of concentrated tubulin staining, staining for phosphotyrosine appears to be absent.

Preassembly

Figure 54:
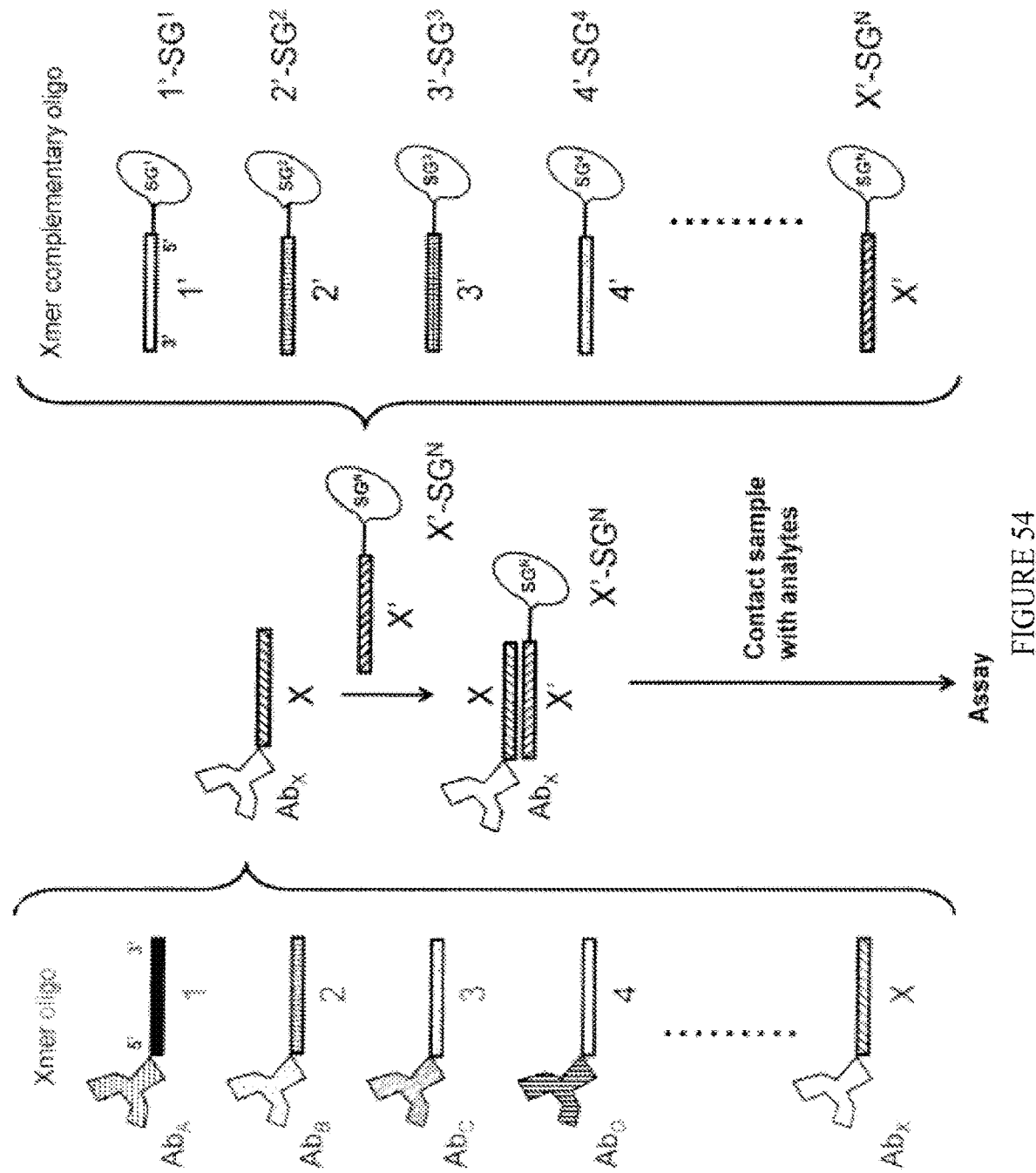
FIG. 54: is a schematic representation of the process of preassembly using pairs of complementary oligonucleotides in which a plurality of molecular probes and a plurality of detectable components are hybridized, i.e., preassembled, to form a plurality of preassembled molecular probe-detectable component hybrids, prior to contacting with a sample comprising one or more molecular targets. The preassembly process may be completed by individual preassembly, followed by pooling, then contacting with the sample, or alternatively, may be completed by pooling the plurality of molecular probes and plurality of detectable components, preassembling by hybridization, and then contacting the pooled preassembled hybrids with the sample.

FIG. 54 diagrammatically presents the process of preassembly using pairs of complementary oligonucleotides in which a plurality of molecular probes, here a series of antibody-oligonucleotide conjugates, and a plurality of detectable components, here a series of signal generating moieties-complementary oligonucleotide conjugates, are hybridized, i.e., preassembled, to form a plurality of preassembled molecular probe-detectable component hybrids. The unique pairing of the molecular probes and the detectable components, may be predefined, as in this scheme, based on the complementarities of the oligonucleotides conjugated to the binding moiety and signal generating moieties, respectively. In one embodiment, the preassembly process may be completed by first mixing a plurality of antibody-oligonucleotide conjugates together to form a pool of the antibody-oligonucleotide conjugates, and then second, and separately, mixing a plurality of signal generating moiety-complementary oligonucleotide conjugates together to form a pool of the signal generating moiety-complementary oligonucleotide conjugates. Subsequently, the pool of the antibody-oligonucleotide conjugates and the pool of the signal generating moiety-complementary oligonucleotide conjugates are then mixed together, allowing for the hybridization of the complementary oligonucleotide sequences to form the plurality of preassembled antibody-signal generating moiety hybrids. In certain embodiments, an individual molecular probe, such as an individual antibody-oligonucleotide, may be combined and preassembled with its complementary detectable component comprising a complementary oligonucleotide sequence, one at a time, each combination allowed to preassemble (i.e., hybridize). in certain embodiments, the individually preassembled molecular probe-detectable component hybrids may be mixed and pooled together. In certain embodiments, the preassembled molecular probe-detectable component hybrids, either individual sets or a plurality of sets may then be brought into contact with a sample comprising one or more molecular targets.

Figure 55:
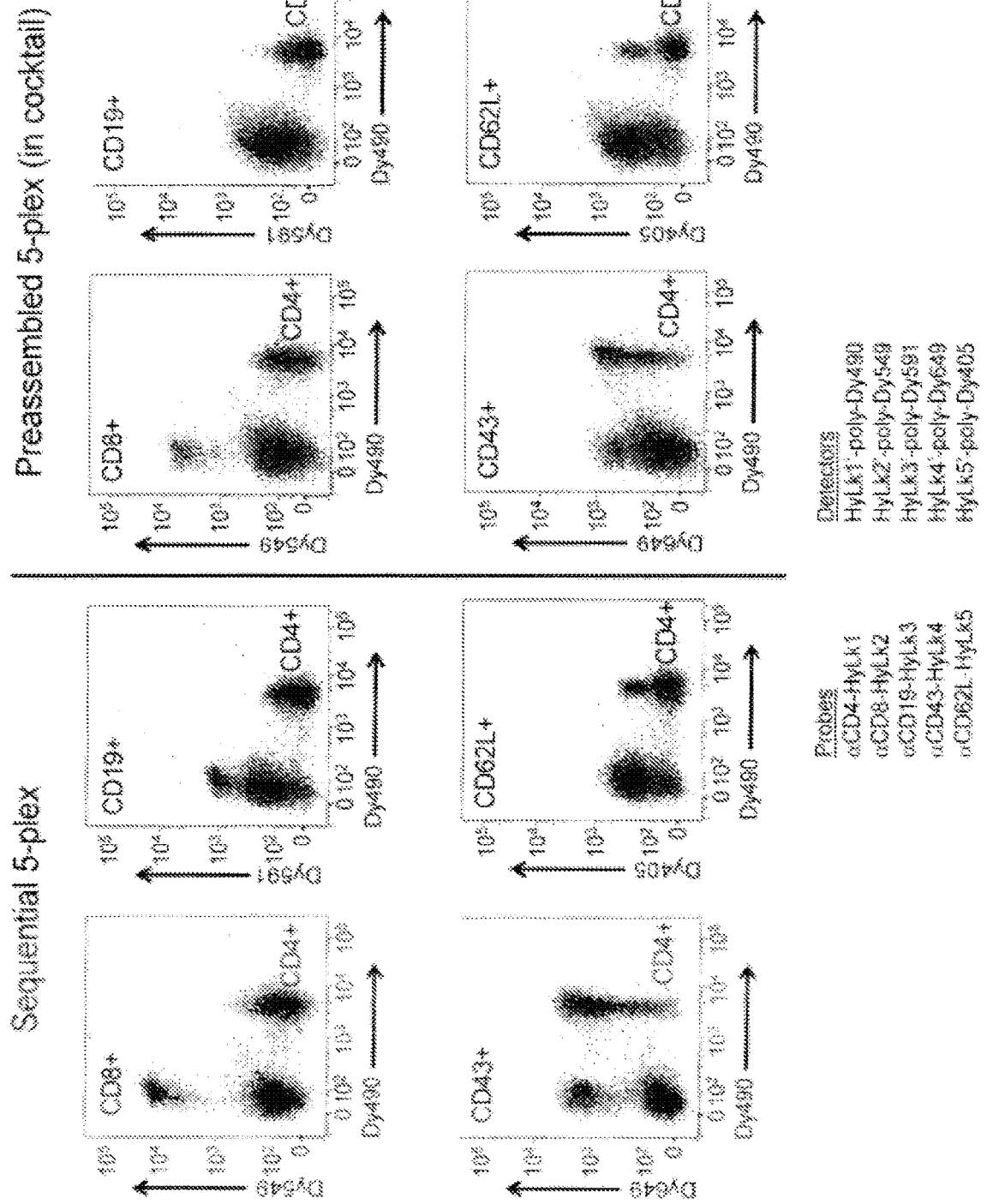
FIG. 55: Are flow cytometry results demonstrating the process of preassembly on mouse splenocytes, as compared to sequential assembly in which the probes are applied in a first step and then the detectors in a second step. The flow cytometry dot plots on the left (labeled "sequential 5-plex"), illustrate the sequence of using the αCD4-HyLk1, αCD8-HyLk2, αCD19-HyLk3, αCD43-HyLk4 and αCD62L-HyLk5 antibody-oligonucleotide conjugates as applied to the mouse splenocytes, followed by washing, then hybridizing with the HyLk1'-Dy490, HyLk2'-Dy549, HyLk3'-Dy591, HyLk4'-Dy649 and HyLk5'-Dy405 detectors, and then analyzed by flow cytometry. The flow cytometry dot plots on the right (labeled "Preassembled 5-plex (in pool)"), illustrate the combining the single pool of antibody-oligonucleotide conjugates comprising αCD4-HyLk1, αCD8-HyLk2, αCD19-HyLk3, αCD43-HyLk4 and αCD62L-HyLk5, preassembling via hybridization with the complementary polyfluor signal generating moiety conjugates HyLk1'-Dy490, HyLk2'-Dy549, HyLk3'-Dy591, HyLk4'-Dy649 and HyLk5'-Dy405, then contacting the preassembled hybrids with mouse splenocytes as a pooled mixture, followed by binding, washing, and then analyzed by flow cytometry.

FIG. 55 presents results from an experiment demonstrating the process of preassembly as applied to a flow cytometry experiment on mouse splenocytes, and compares these results to sequential assembly in which the probes are applied in a first step and then the detectors in a second step. In the four flow cytometry dot plots on the left (labeled "sequential 5-plex"), the experiment was performed according to Example 10-B, wherein the CD4-HyLk1, CD8-HyLk2, CD19-HyLk3, CD43-HyLk4 and CD62L-HyLk5 antibody-oligonucleotide conjugates were applied to the mouse splenocytes for 30 minutes at 4° C., followed by washing, and then the HyLk1'-Dy490, HyLk2'-Dy549, HyLk3'-Dy591, HyLk4'-Dy649 and HyLk5'-Dy405 detectors were applied 15 minutes at room temperature, followed by washing and flow cytometry. In the example on the right (labeled "Preassembled 5-plex (in pool)"), the CD4-HyLk1, CD8-HyLk2, CD19-HyLk3, CD43-HyLk4 and CD62L-HyLk5 were combined in equal amounts in a single tube to form a pool of antibody-oligonucleotide conjugates. Then, the complementary polyfluor signal generating moiety conjugates HyLk1'-Dy490, HyLk2'-Dy549, HyLk3'-Dy591, HyLk4'-Dy649 and HyLk5'-Dy405 were added in molar excess and allowed to hybridize for 15 minutes at room temperature. The preassembled antibody-signal generating moiety hybrids were then added to mouse splenocytes as a pooled mixture, allowed to bind 30 minutes at 4° C., washed, and then analyzed by flow cytometry. Qualitatively similar results were obtained by each method, indicating that the order of assembly is not critical to the use of nucleic acid hybridization to form hybrids between molecular probes and detectable components to enable detection of multiple analytes, for example multiple biological targets in a sample.

Figure 56:
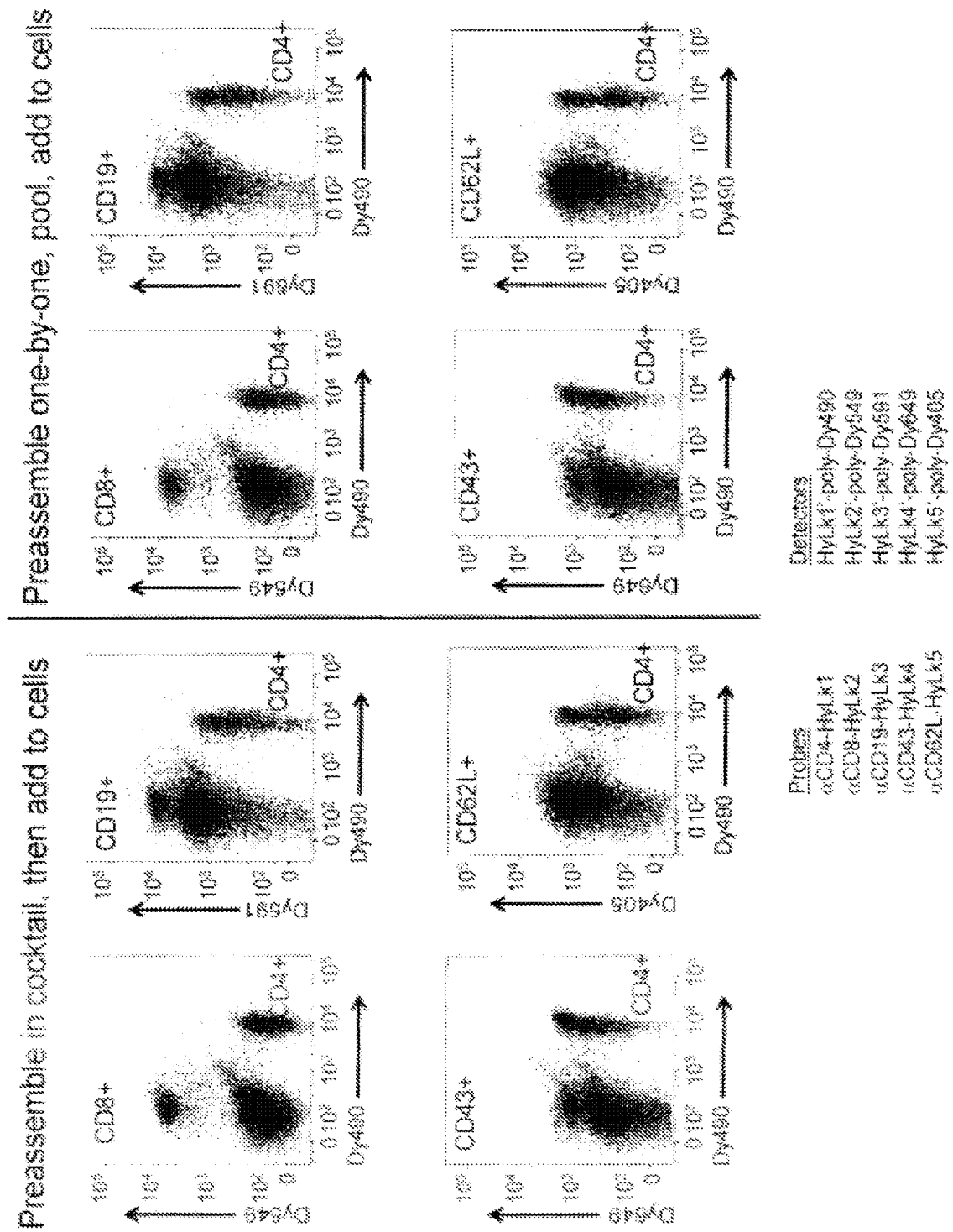
FIG. 56: is results comparing the use of two alternative methods of preassembly, the left (labeled "Preassemble in pool, then add to cells"), and the right (labeled "Preassemble one-by-one, pool, add to cells"). The comparable results of the two alternative methods of preassembly suggest that either these alternatives, or other preassembly protocols, may be followed with similar success.

FIG. 56 presents results comparing the use of two alternative methods of preassembly. In the example on the left (labeled "Preassemble in pool, then add to cells"), the CD4-HyLk1, CD8-HyLk2, CD19-HyLk3, CD43-HyLk4 and CD62L-HyLk5 were combined to form a pool, the complementary polyfluor signal generating moiety conjugates HyLk1'-Dy490, HyLk2'-Dy549, HyLk3'-Dy591, HyLk4'-Dy649 and HyLk5'-Dy40.5 were added in molar excess, incubated, and the mixture was then added to mouse splenocytes before analysis by flow cytometry as in FIG. 55. On the right (labeled "Preassemble one-by-one, pool, add to cells"), the CD4-HyLk1, CD8-HyLk2, CD19-HyLk3, CD43-HyLk4 and CD62L-HyLk5 were each individually combined with their complementary polyfluor signal generating moiety conjugates HyLk1'-Dy490, HyLk2'-Dy549, HyLk3'-Dy591, HyLk4'-Dy649 and HyLk5'-Dy405 in separate tubes, incubated to permit preassembly hybridization, added individually to the splenocytes, allowed to bind 30 minutes at 4° C., washed, and then analyzed by flow cytometry. The comparable results of the two alternative methods of preassembly suggest that either these alternatives, or other preassembly protocols, may be followed with similar success.

The examples illustrated herein may be applicable to both self-assembly, i.e., wherein the capture-oligonucleotide conjugates are added to the biological sample and then captured on beads, as well as pre-assembly, wherein the capture-oligonucleotide conjugate is pre-hybridized to its bead then mixtures of beads are combined and added to the biological sample. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Cross-Talk

Figure 57:
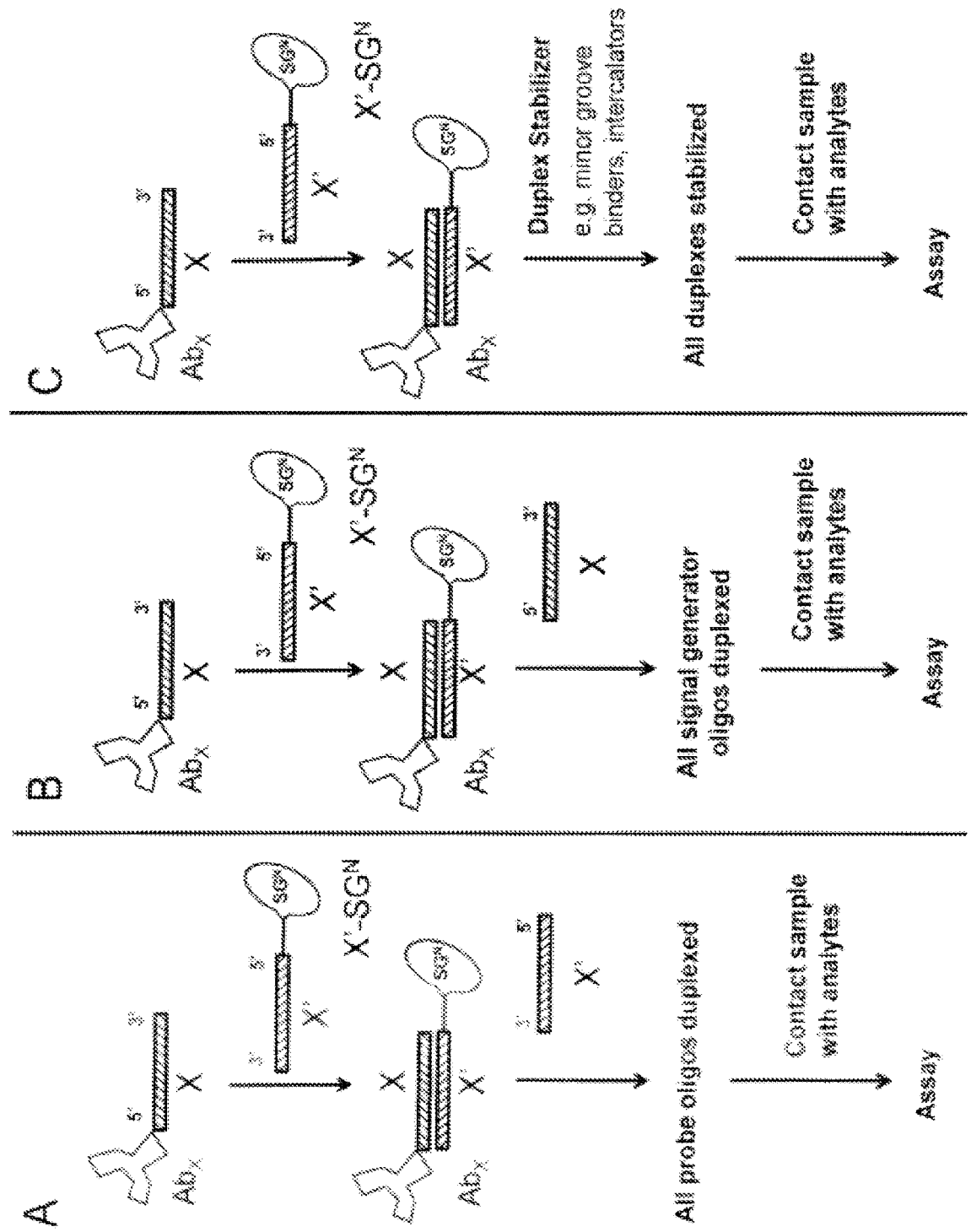
FIG. 57: illustrates several schemes that may be considered to address and/or decrease the potential for cross-talk, such as in panel A, by hybridizing the oligonucleotide sequence of a non-hybridized molecular probe with an unconjugated complementary oligonucleotide, or as illustrated in panel B, by hybridizing the complementary oligonucleotide sequence of a non-hybridized detectable component with an unconjugated oligonucleotide, or as illustrated in panel C, stabilizing the duplexes formed by the preassembly hybridization of the molecular probe(s) and the detectable component(s) with natural or synthetic minor groove binding agents or with natural or synthetic intercalating agents.

Several schemes, such as those exemplified in FIG. 57 may be considered to address and/or decrease the potential for cross-talk, e.g., non-specific labeling or background, such that a molecular probe may be falsely detected or obscured, due to a natural process of oligonucleotide dissociation and hybridization. Some processes that may be used to address the concern regarding cross-talk include, for example, as illustrated in panel A, wherein the oligonucleotide sequence of a non-hybridized molecular probe (i.e., not hybridized to a complementary detectable component, may be hybridized with an unconjugated complementary oligonucleotide. Similarly, in the process illustrated in panel B, the complementary oligonucleotide sequence of a non-hybridized detectable component may be hybridized to an unconjugated oligonucleotide. In other embodiments, such as those shown in panel C, the duplexes that are formed by preassembly hybridization of the molecular probe(s) and the detectable component(s) may be stabilized to prevent dissociation, for example, by the addition of natural or synthetic minor groove binding agents, such as distamycin or Hoechst 33258, or of natural or synthetic intercalating agents, such as daunomycin or ethidium bromide.

Universal Oligonucleotide Sequence

In certain embodiments, one or more binding moieties, such as one or more antibodies, may be conjugated to a universal oligonucleotide sequence, i.e., a single, common oligonucleotide that serves as a universal tag, to provide one or more molecular probes differing in the identity of the binding moiety conjugated to the universal oligonucleotide sequence. Similarly, one or more signal generating moieties, such as one or more scaffolds comprising one or more organic fluorophores, may be conjugated to a universal complementary oligonucleotide sequence (i.e., an oligonucleotide sequence complementary that serves as a universal tag) to provide one or more detectable components to facilitate detection in one or more channels and/or formats, such as one or more fluorescent channels, detection via one or more enzymes through enzymatic reactivity, or one or more particles. Using the process of preassembly, forming preassembled molecular probe-detectable component hybrids by selecting the molecular probes to be used and individually hybridizing these to selected detectable components in their own tubes, thereby forming the selected pairings individually, provides a method that avoids or substantially avoids indiscriminate hybridization events between molecular probes and detectable components that are all combined at once so that the specificity would be lost via cross-talk. The individually preassembled hybrids of the process disclosed herein, may then be stabilized. In certain embodiments, the stabilized preassembled hybrids may then be pooled together, and may then be subsequently contacted with a sample comprising one or more molecular targets, to perform a multiplexed assay.

Figure 58:
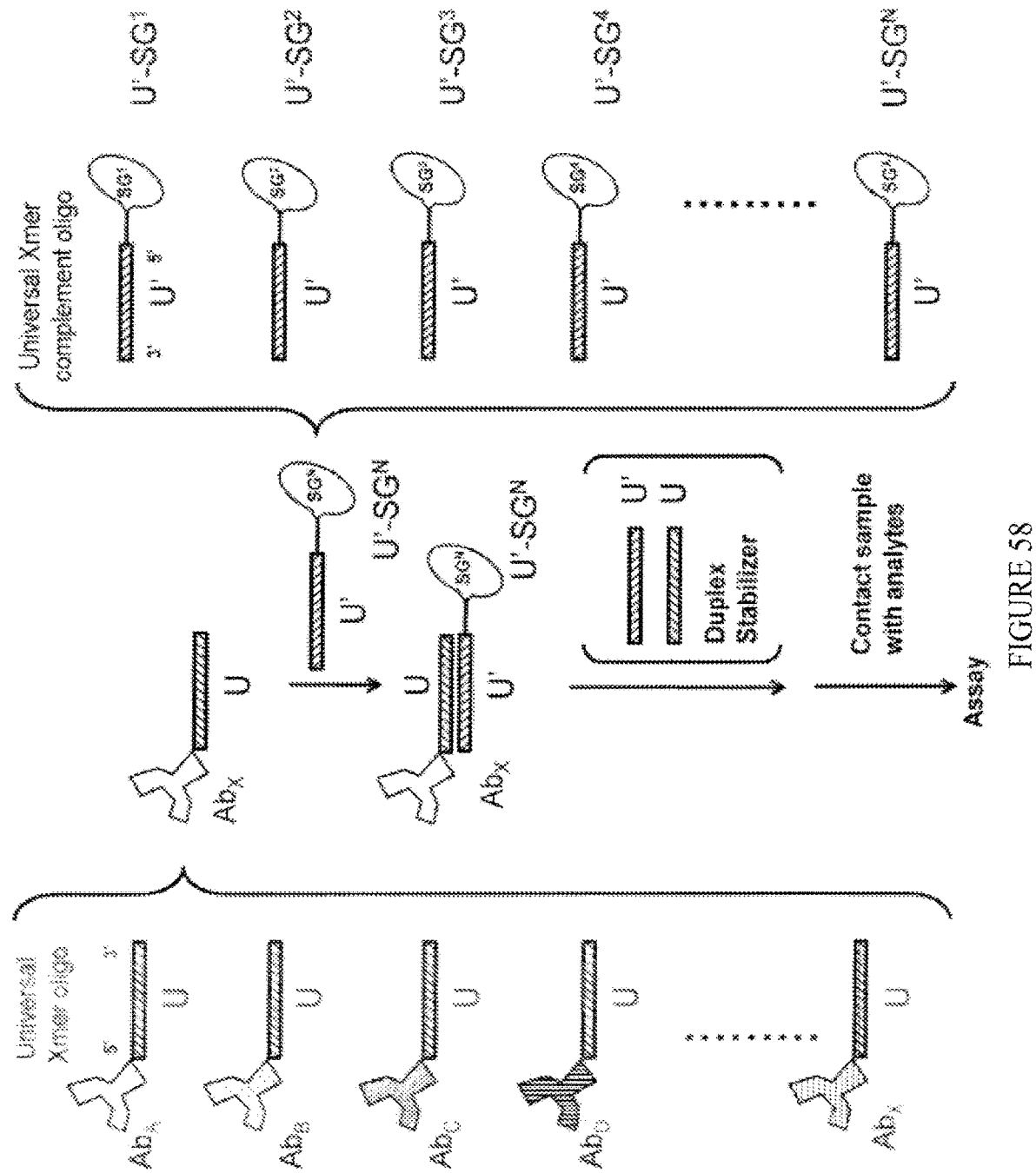
FIG. 58: illustrates a preassembly process utilizing a universal oligonucleotide conjugated to a panel of molecular probes that are individually combined with a universal oligonucleotide complement conjugated to a panel of signal generating moieties. The preassembled molecular probe-signal generating moiety hybrids may then be stabilized with unconjugated oligonucleotides or duplex stabilizers, followed by contacting with a sample comprising one or more molecular targets or analytes to perform one or more assays.
Figure 59:
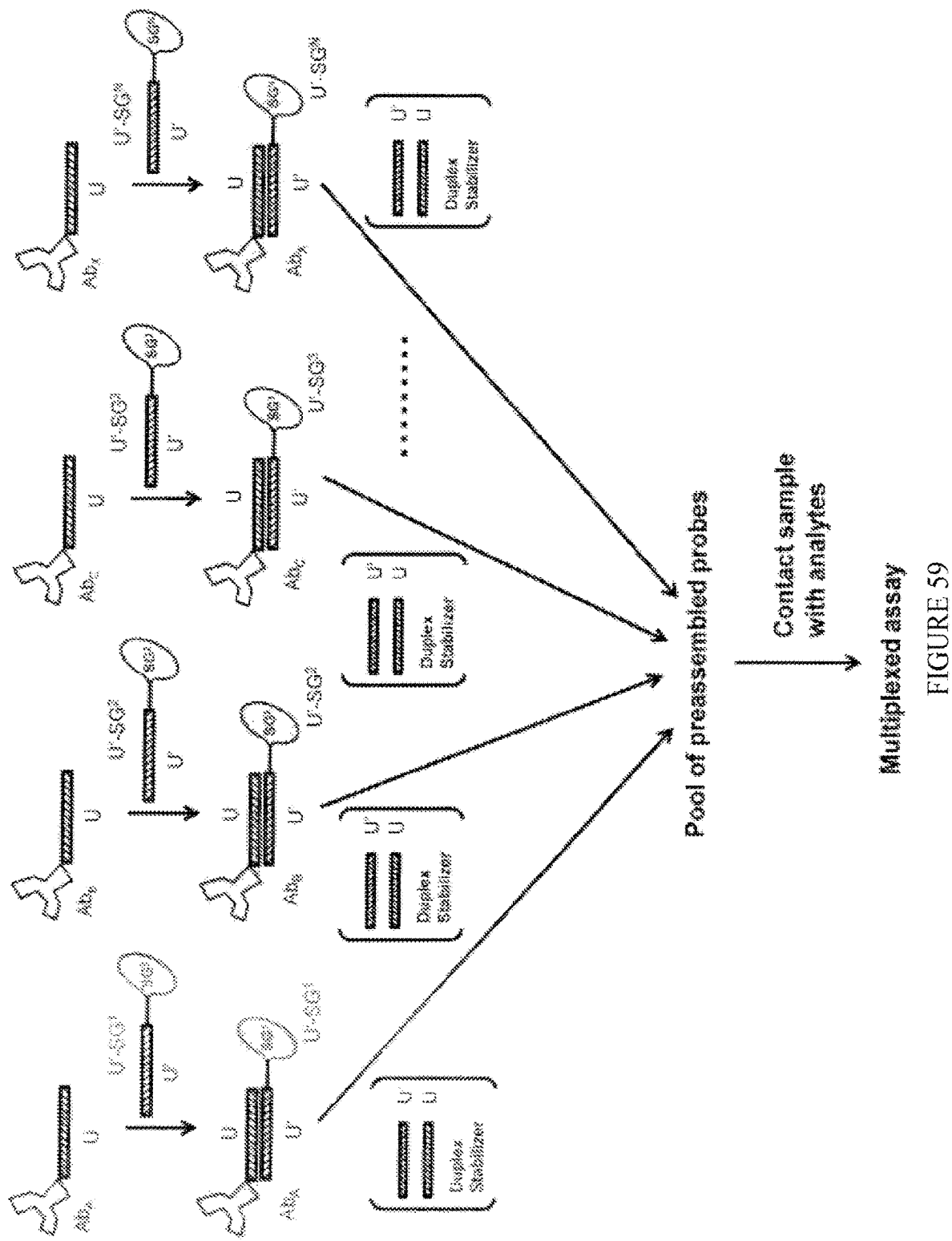
FIG. 59: illustrates the stabilizing and then pooling of a panel of individually preassembled antibody-signal generating moiety hybrids, followed by contacting with a sample comprising one or more molecular targets or analytes to perform an assay.

In FIG. 58 is diagrammed an example wherein a universal oligonucleotide is conjugated to a panel of molecular probes and a universal oligonucleotide complement is conjugated to a panel of signal generating moieties. For example, a panel of antibody-universal oligonucleotide conjugates are individually combined (i.e., preassembled) with a panel complementary universal oligonucleotide-signal generating moieties in separate tubes to form preassembled antibody-signal generating moiety hybrids prior to stabilization. The preassembled hybrids may be stabilized and then may be contacted with a sample comprising one or more molecular targets or analytes to perform an assay. In certain embodiments, as illustrated in FIG. 59, the stabilized preassembled hybrids may first be combined or mixed together to form a pool of stabilized preassembled hybrids, and then the pool of stabilized preassembled hybrids may then be contacted with a sample comprising one or more molecular targets or analytes to perform an assay.

Figure 60:
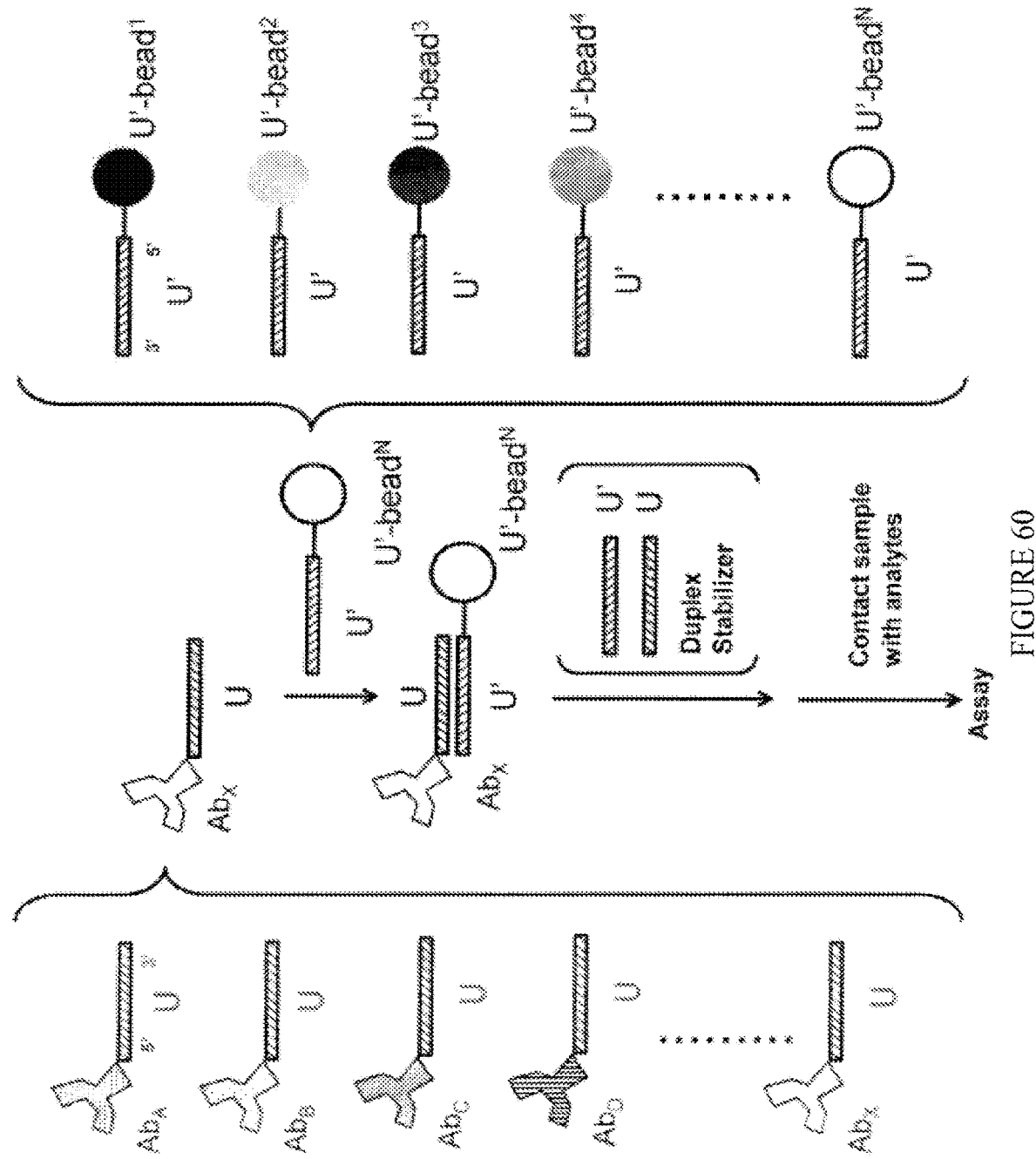
FIG. 60: illustrates a preassembly process utilizing a universal oligonucleotide conjugated to a panel of molecular probes, such as a panel of monoclonal antibodies that are individually combined with a universal oligonucleotide complement conjugated to a panel of barcoded particles, that may be used in a flow cytometry-based multiplexed immunodetection assays. The preassembled antibody-bead hybrids may then be stabilized with unconjugated oligonucleotides or duplex stabilizers. The individual stabilized preassembled antibody-bead hybrids may then be contacted with a sample comprising one or more molecular targets or analytes to perform one or more assays.
Figure 61:
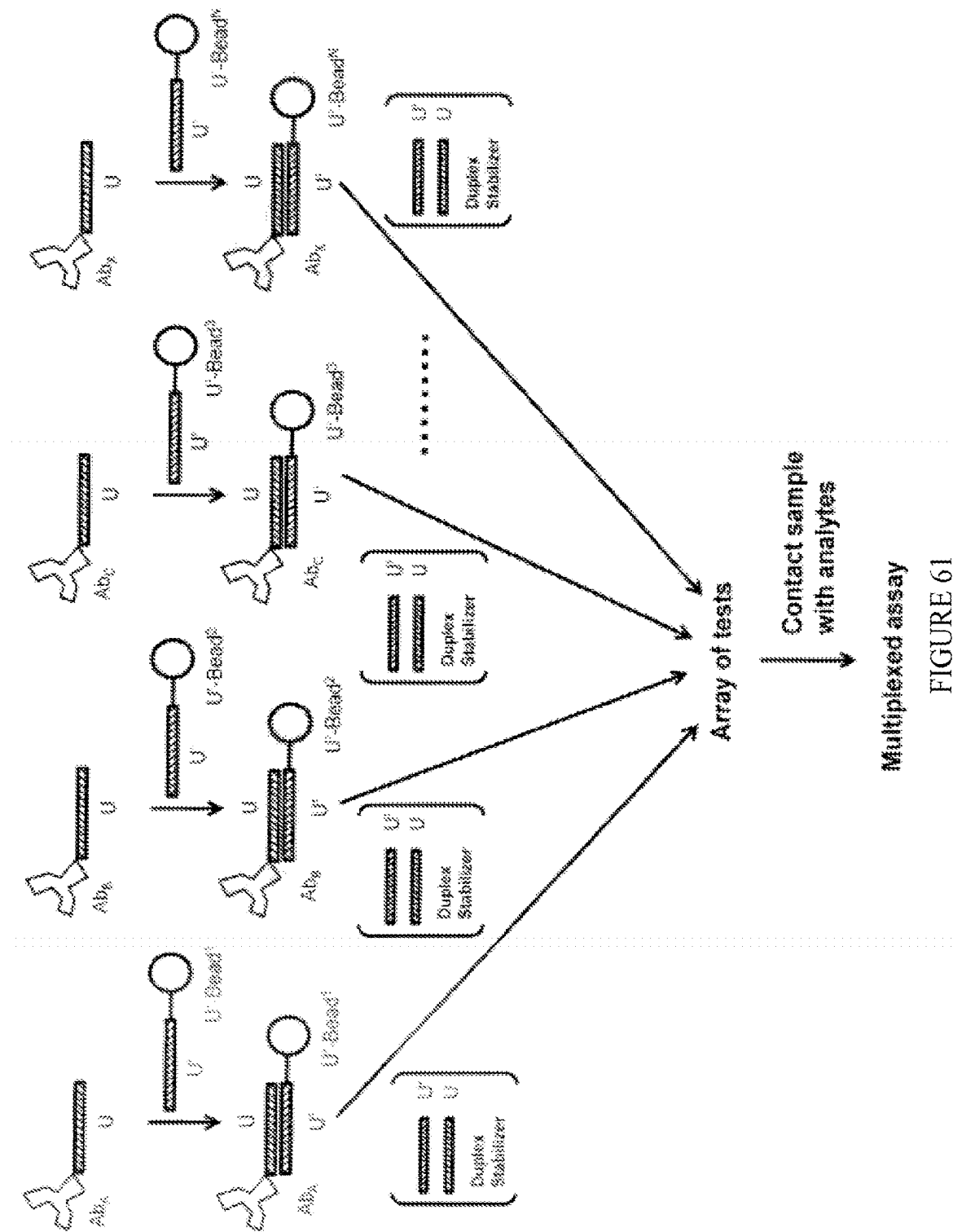
FIG. 61: illustrates the stabilizing and then pooling of a panel of individually preassembled antibody-bead hybrids, followed by contacting with a sample comprising one or more molecular targets or analytes to perform an assay.

The process of preassembly using a universal oligonucleotide and its complement has particular value in assembling assays on barcoded particles, for example with flow cytometry-based multiplexed immunodetection assays. As shown in FIG. 60, a panel of monoclonal antibodies (or other affinity agents that form the capture reagents for sandwich immunoassays) may be conjugated to a universal oligonucleotide. Similarly, a panel of barcoded particles may be conjugated to the complementary universal oligonucleotide. A multiplexed immunoassay array may be assembled by individually preassembling (combining) an antibody-universal conjugate, such as a monoclonal antibody-universal conjugate, with a barcoded particle, such as a bead-complementary universal oligonucleotide conjugate, to allow for hybridization to form a preassembled antibody-bead hybrid. The preassembled antibody-bead hybrids may then be stabilized with unconjugated oligonucleotides or duplex stabilizers. The individual stabilized preassembled antibody-bead hybrids may then be contacted with a sample comprising one or more molecular targets or analytes to perform one or more assays. Alternatively, as illustrated in FIG. 61, the individual stabilized preassembled antibody-bead hybrids may be combined with other preassembled sets of stabilized preassembled antibody-bead hybrids to form a pool, that may then be contacted with a sample comprising one or more molecular targets or analytes to perform one or more assays. Once the one or more molecular targets or analytes are bound, the remaining unbound sample may be washed away and the one or more bound targets or analytes may be detected, for example, by the addition of detector reagents, such as polyclonal antibodies, or polyclonal antibodies in a biotinylated form. After washing away unbound detectors, binding of the barcoded particles may be detected, for example by a streptavidin-based probe or other means.

Barcode

Figure 62:
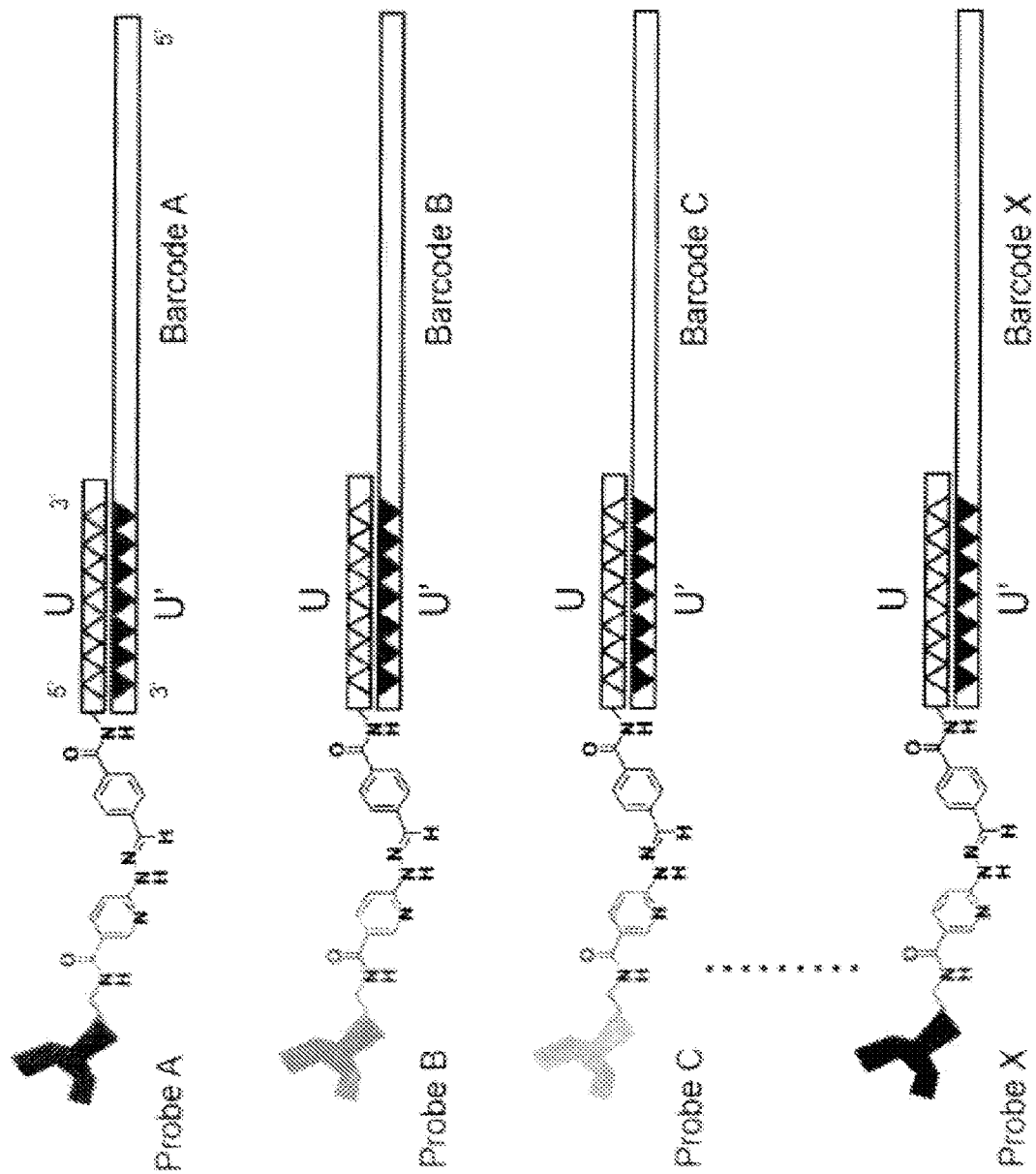
FIG. 62: illustrates the preassembly of barcoded oligonucleotide detectable components, comprising a first oligonucleotide sequence, such as a 20-oligonucleotide universal sequence, comprising an oligonucleotide sequence complementary to a universal oligonucleotide conjugated to a molecular probe, and a second oligonucleotide sequence, such as a 20-oligonucleotide unique sequence, comprising a sequence that is unique to that detectable component.
Figure 63:
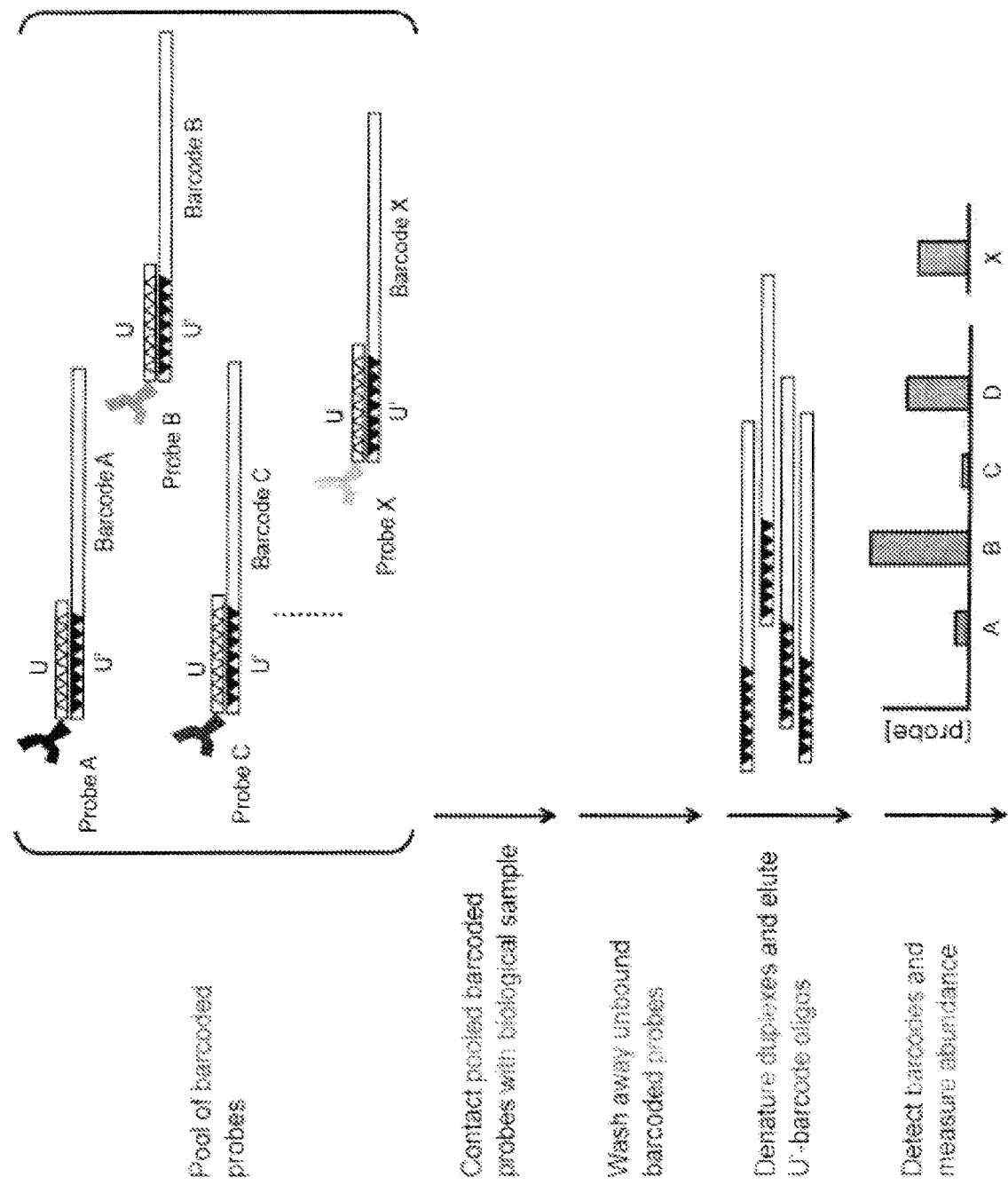
FIG. 63: illustrates the pooling of the individually preassembled molecular probe-barcoded oligonucleotide detectable component hybrids, contacting with a sample comprising one or more molecular targets or analytes, followed by washing, disassociation of the hybrids, elution, and analysis.

In certain embodiments, the detectable component may be a nucleic acid, such as an oligonucleotide, or a sequence thereof. Oligonucleotides may be readily applied as detectable components if they include a sequence barcode, called herein as "barcoded oligonucleotide detectable components," that may be recognized by either the binding of other detectable components, for example, a complementary oligonucleotide sequence conjugated to one or more fluorescent signal generating moieties or other signal generating moiety tags, or by hybridization to an array, or by sequence analysis, or by combinations or derivatives thereof. In certain embodiments, the barcoded oligonucleotide detectable component may comprise a first oligonucleotide sequence, such as a 20-oligonucleotide universal sequence, comprising a complementary oligonucleotide sequence that permits hybridization to a universal oligonucleotide conjugated to a molecular probe, and a second oligonucleotide sequence, such as a 20-oligonucleotide unique sequence, comprising a sequence that is unique to that detectable component, and optionally other sequences that may be used to enable detection. The barcoded oligonucleotide detectable components may then be readily adapted to the process of preassembly by assigning the individual sequences of the barcoded oligonucleotide detectable components to particular molecular probes, as shown in FIG. 62. The hybrids may be individually formed by selecting a molecular probe, combining it with a barcoded oligonucleotide detectable component, allowing for hybridization to occur, followed by stabilization of the preassembled molecular probe-barcoded oligonucleotide detectable component hybrid. In certain embodiments, the stabilized preassembled molecular probe-barcoded oligonucleotide detectable component hybrids may be pooled, as shown in FIG. 63, and then contacted with a sample comprising ono or more molecular targets or analytes. After washing to remove unbound sample, the barcoded oligonucleotide detectable components that have been retained and/or bound to the sample may then be assayed, for example, by dissociating the hybridized barcoded oligonucleotide detectable components away from their respective molecular probes, such as by denaturing the duplexes. The de-hybridized barcoded oligonucleotide detectable components may then be eluted and analyzed, either qualitatively for the presence of, or quantitatively for the abundance of, each barcoded oligonucleotide detectable component. In certain embodiments, the process may be combined with a DNA sequencing technology, wherein such a combination may enable very high levels of multiplexing, such as tens, hundreds, or thousands, and may offer accurate quantitation, broad dynamic range, low background and/or high specificity.

Preassembly

Figure 64:
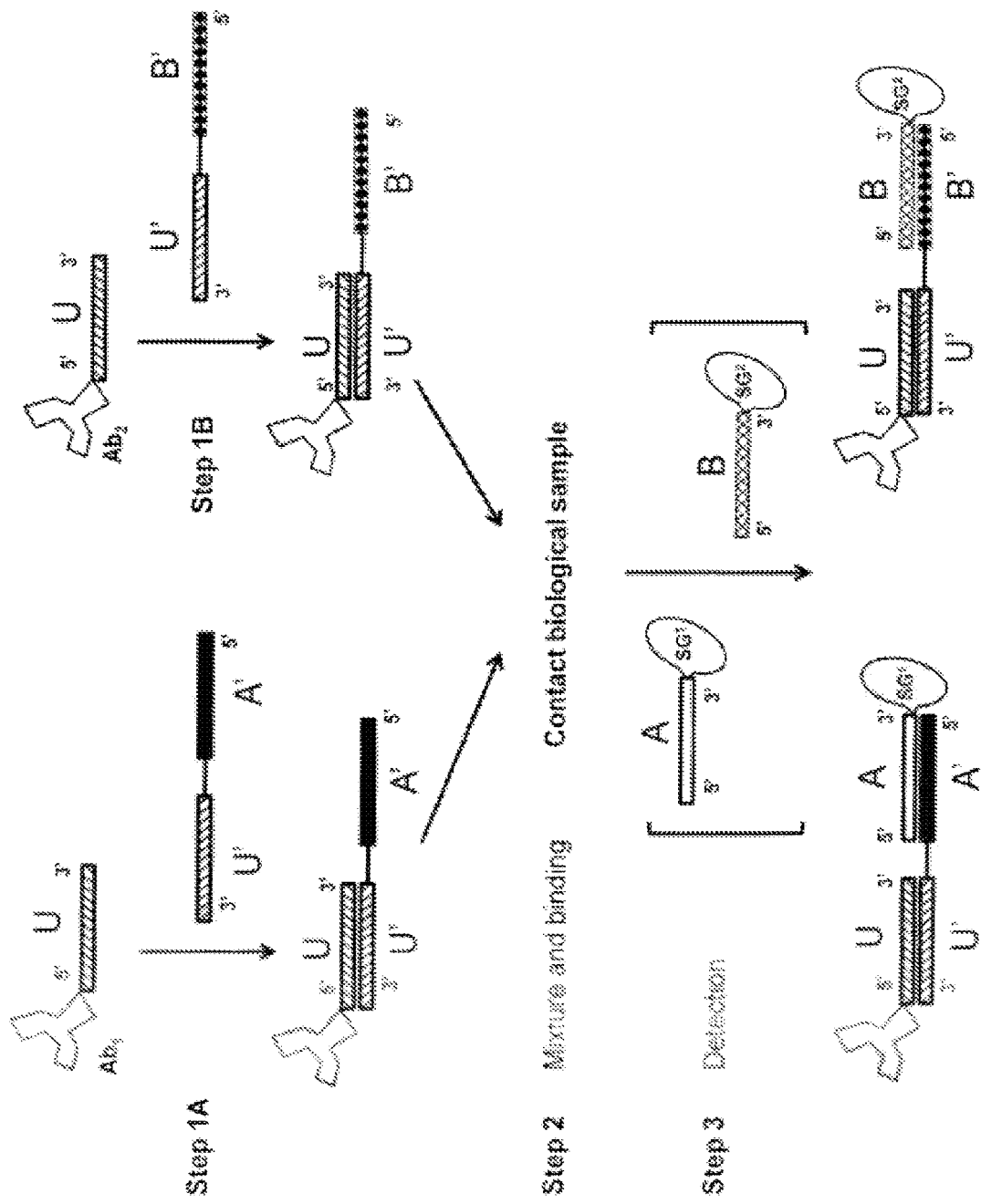
FIG. 64: illustrates the process of preassembly with the use of one or more universal adapters.

As shown in FIG. 64, the process of preassembly is compatible with the use of one or more universal adapters, comprising a common, universal oligonucleotide sequence that is complementary to a universal oligonucleotide sequence conjugated to a molecular probe and a unique oligonucleotide sequence that is complementary to a unique detectable component, wherein the unique detectable component comprises a unique oligonucleotide sequence conjugated to a particular signal generating moiety. The one or more universal adapters may comprise 45-mer sequences, wherein the universal sequence may be a 20-mer oligonucleotide sequence, and the unique oligonucleotide sequence may be a 20-mer oligonucleotide sequence. In certain embodiments, one or more molecular probes conjugated to universal oligonucleotides may be preassembled with one or more universal adapters, comprising a complementary universal oligonucleotide sequence and a unique oligonucleotide sequence, by individually mixing a particular molecular probe with a particular universal adapter, thereby allowing hybridization to occur to form a preassembled molecular probe-universal adapter hybrid. In certain embodiments, the preassembled molecular probe-universal adapter hybrid may be stabilized, may then be pooled with the other the stabilized preassembled molecular probe-universal adapter hybrids. The pooled stabilized preassembled hybrids may then be contacted with a sample, comprising one or more molecular targets or analytes, followed by binding of the one or more molecular targets with the one or more pooled stabilized preassembled molecular probes. In certain embodiments, one or more detectable components, comprising one or more signal generating moieties conjugated to unique oligonucleotide sequences complementary to particular unique sequences of the one or more universal adapters may be added to label the one or more bound targets in the sample, thereby facilitating detection of the one or more targets. In certain embodiments, this process may be used to combine the processes of preassembly and ordered assembly in cases where there might be advantages to both.

Figure 65:
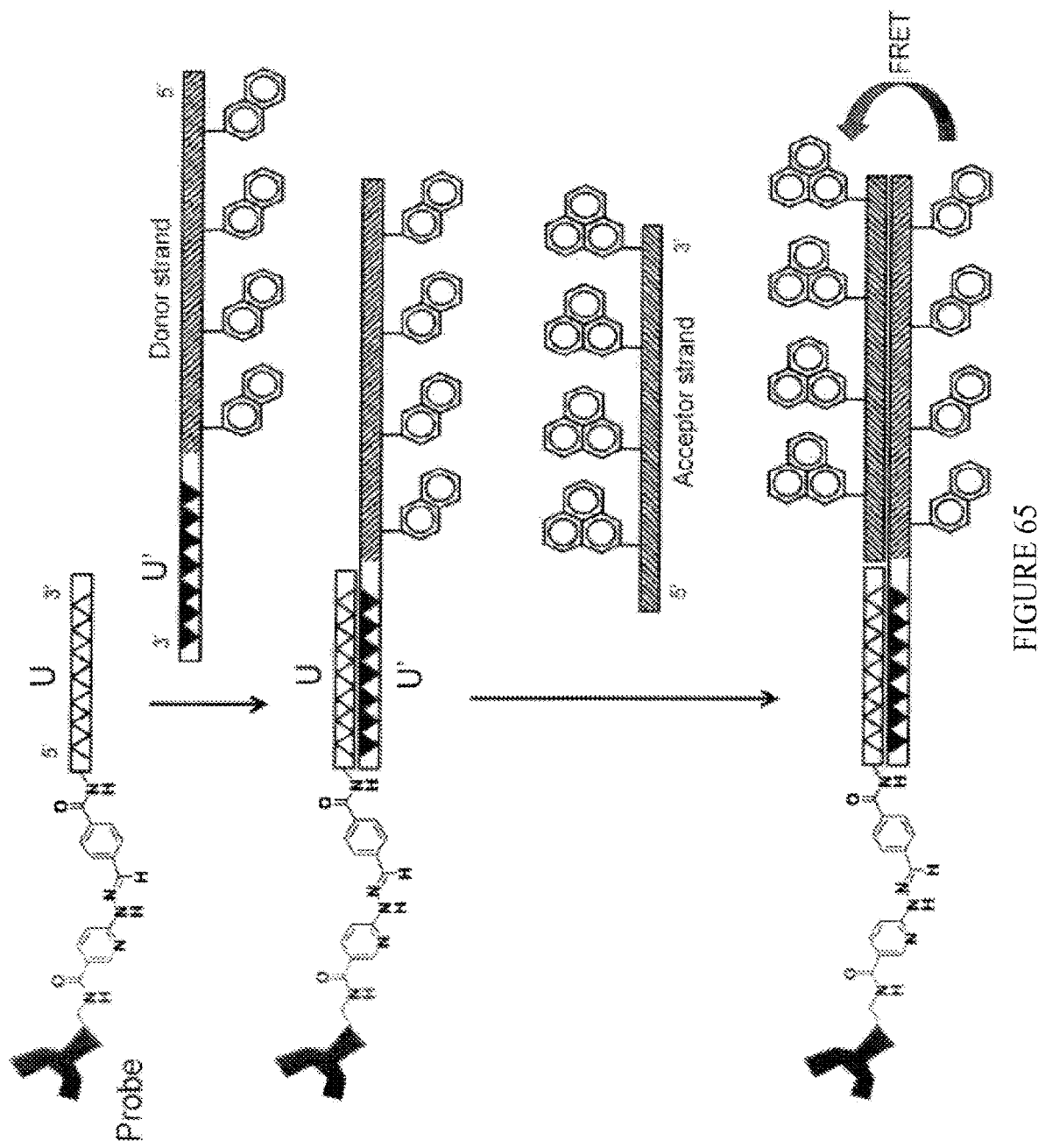
FIG. 65: illustrates the use of detectable components that comprise an oligonucleotide sequence that has been chemically modified with fluorescent moieties to enable detection by fluorescence resonance energy transfer (FRET).

As diagrammed in FIG. 65, the detectable components may be designed to comprise a first oligonucleotide sequence that is complementary to an oligonucleotide sequence of a molecular probe and a second oligonucleotide sequence that comprises a sequence that has been chemically modified with fluorescent moieties. In certain embodiments, the complementary oligonucleotide sequence of a molecular probe is hybridized, i.e., preassembled, with the first oligonucleotide sequence of a detectable component to form a preassembled hybrid comprising a non-hybridized second oligonucleotide sequence that comprises a sequence that has been chemically modified with fluorescent moieties. The preassembled hybrid may then be combined with an oligonucleotide sequence complementary to the second oligonucleotide sequence, comprising an oligonucleotide sequence modified with other fluorescent moieties, thereby forming a hybridized ternary complex. In certain embodiments, the second oligonucleotide sequence may be labeled with fluorescent groups that can perform fluorescence resonance energy transfer (FRET) with fluorescent groups on the oligonucleotide sequence complementary to the second oligonucleotide sequence. FRET may result in a shift in fluorescent emission wavelength and/or to quenching of fluorescence. In certain embodiments, the hybridization of the second oligonucleotide sequence may be detected by a FRET signal, thereby allowing for a means of qualitatively, or possible quantitatively, detecting the presence of a specific molecular probe and/or the formation of a particular molecular probe-target complex.

Figure 66:
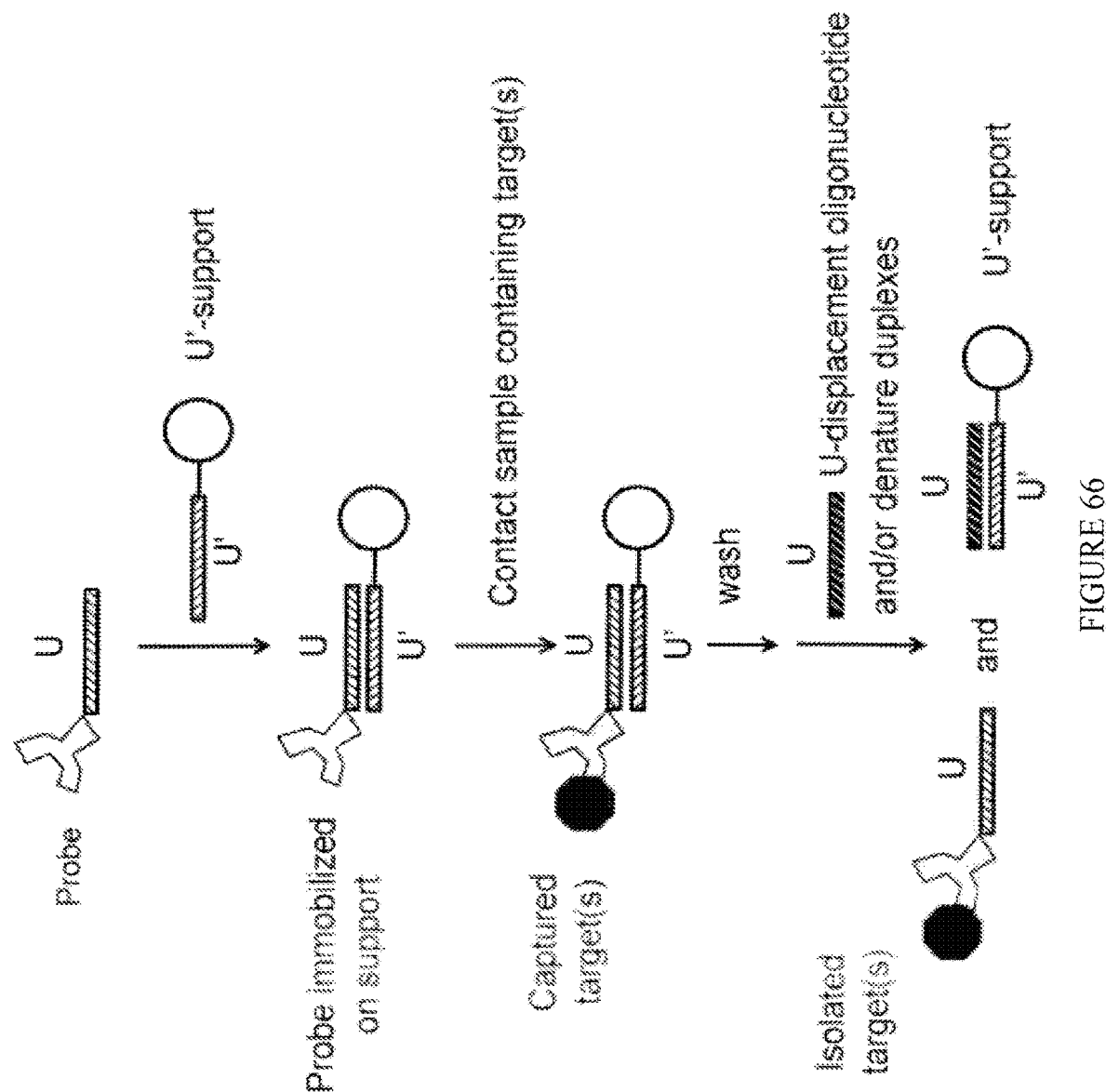
FIG. 66: illustrates the preassembly of one or more molecular probes with one or more supports to form a preassembled affinity matrix or material. The preassembled affinity matrix or material may then be used, for example, to affinity capture, purify, and then release one or more molecular targets, such as one or more biomolecular targets, each as a complex bound to the particular molecular probe.

In certain embodiments, one or more molecular probes may be preassembled with one or more supports, such as a solid support, particle, or gel support, conjugated to oligonucleotide sequences complementary to the molecular probe oligonucleotide sequence. The supports may be but are not limited to, for example, agarose or magnetic beads. In certain embodiments, the one or more molecular probes may be combined, as a plurality or individually with the one or more supports conjugated to complementary oligonucleotide sequences, followed by hybridization, to form a preassembled affinity matrix or material. The preassembled affinity matrix or material may then be used, for example, to affinity capture, purify, and then release one or more molecular targets, such as one or more biomolecular targets, each as a complex bound to the particular molecular probe. For example, as diagrammed in FIG. 66, a molecular probe conjugated to a universal oligonucleotide sequence may be combined with the complementary oligonucleotide conjugated to a support to allow for preassembly hybridization and thereby form an affinity matrix. In certain embodiments, the affinity matrix may then be washed to remove free molecular probe. The affinity matrix may be, for example, combined with a sample comprising one or more molecular targets to enable binding and capture of the one or more targets. In certain embodiments, the unbound components of the sample may then be washed away. In certain embodiments, it may be useful to use a displacement oligonucleotide or to denature the hybridization complex to release the bound target-molecular probe complex from the support for further analysis. The displacement oligonucleotide may be, for example, another oligonucleotide sequence, an LNA, or a PNA, or combinations or derivatives thereof.

Figure 67:
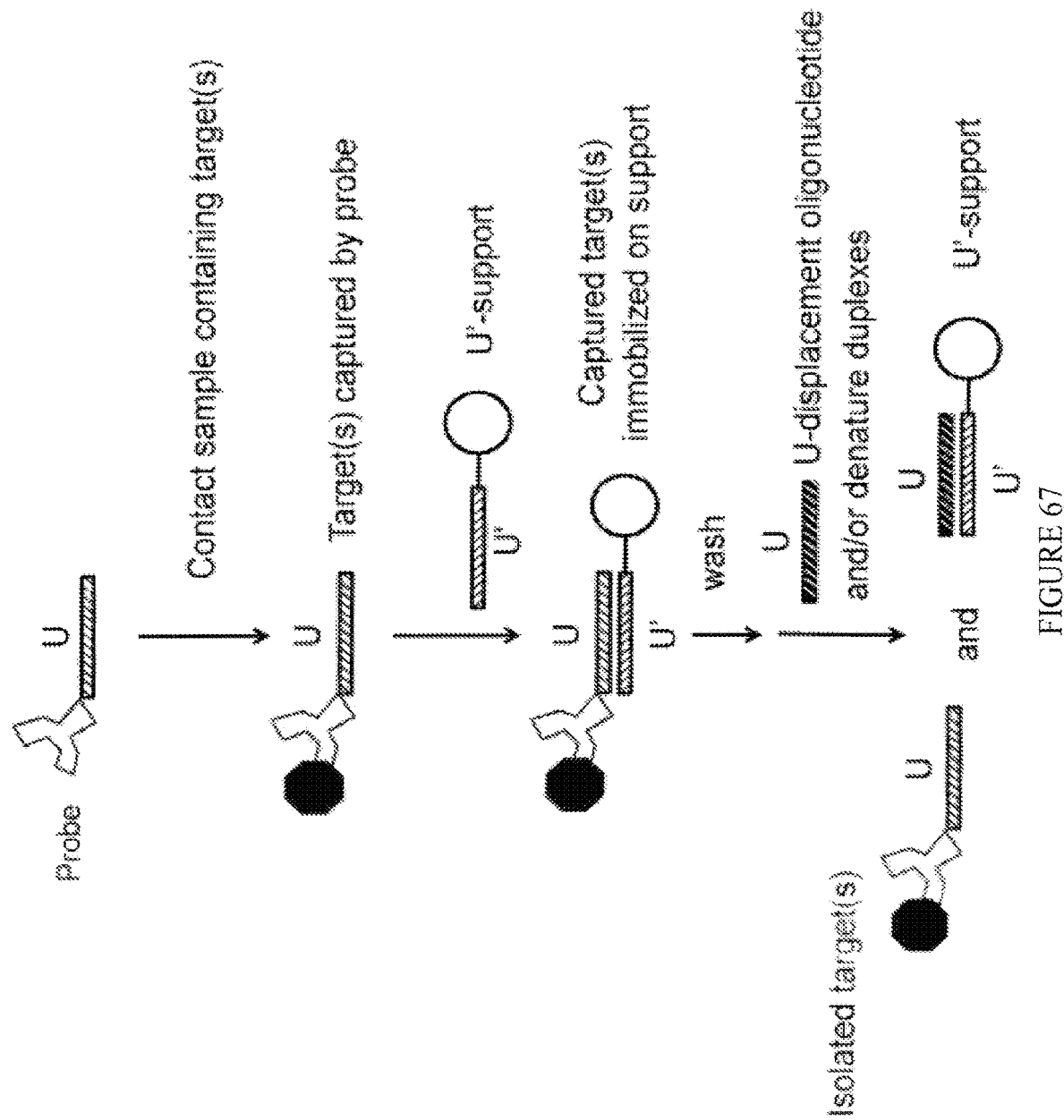
FIG. 67: illustrates a molecular probe conjugated to a universal oligonucleotide may be combined with a sample comprising one or more molecular targets to bind the one or more targets, which may then be captured by a complementary oligonucleotide conjugated to a support via hybridization.

Alternatively, as diagrammed in FIG. 67, a molecular probe conjugated to a universal oligonucleotide may be combined with a sample comprising one or more molecular targets to bind the one or more targets. The bound target-molecular probe complex may then be captured by a complementary oligonucleotide conjugated to a support via hybridization. In certain embodiments, the other components of the sample may be washed away. In certain embodiments, it may be useful to use a displacement oligonucleotide or to denature the hybridization complex to release the bound target-molecular probe complex from the support for further analysis. The displacement oligonucleotide may be, for example, another oligonucleotide sequence, an LNA, or a PNA, or combinations or derivatives thereof. The examples illustrated herein may be applicable to both self-assembly, i.e. wherein the capture-oligonucleotide conjugates are added to the biological sample and then captured on beads, as well as pre-assembly, wherein the capture-oligonucleotide conjugate is pre-hybridized to its bead then mixtures of beads are combined and added to the biological sample. In certain embodiments, the order of assembly and addition to a sample might be varied, so that the capture antibodies might be combined with the beads prior to contact with the sample or after, and the detector antibodies might be added to the sample prior to or along with the capture antibodies, or might be added after forming the antigen-capture antibody complex on the beads and washing, or in other sequences as might be possible.

Minimizing Complexity For Antibody Labeling Choice

Certain embodiments are directed to methods and/or systems for reducing to a manageable proportions the number of catalog products a vendor of labeled antibodies (or other bio-molecules used as binding detectors) must manufacture, stock, market, and/or distribute in order to fully satisfy customers' needs for a substantially complete choice of label alternatives for a substantial portion of the antibodies in the catalog. In certain aspects, a complete choice of label alternatives for any given antibody in the catalog.

Antibodies—biological proteins exhibiting high-affinity binding of single target molecules—are widely employed throughout biological research, clinical diagnostics, pharmaceutical drug discovery, and other disciplines to enable immunoassays to detect and quantify molecules of interest ('analytes'). Commonly, an antibody employed in immunoassays must be labeled with another molecule to render them detectable; frequently, the labels employed are fluorescent molecules (or 'fluors'), which emit light over characteristic wavelength ranges (or 'colors'). Approximately 36 different fluors are commercially available today as antibody labels, covering the color gamut from deep red to violet. In 'multiplexed' assays, which aim to detect two or more different analytes in the same sample, two or more different antibodies are typically employed together (for example, one for each analyte, although other variations are possible), and typically the antibodies are labeled with a different colored fluor to enable them to be detected individually. Multiplexed assays are increasingly common in flow cytometry, where as many as sixteen different analytes may be detected simultaneously or substantially simultaneously. This creates a need for antibodies labeled in a wide range of colors (i.e., at least 4, 5, 6, 7, 8, 9, 10, 11, 12, 13, 14, 15, 16, or more).

As it is conventionally practiced, labeling an antibody with a fluor is a highly skilled task beyond the means of most users, so antibody vendors market antibodies pre-labeled with fluors. This presents the vendor with a 'combinatorial explosion' problem: offering X different antibodies each labeled in Y different colors requires the vendor to manufacture, stock, market, and distribute a total of X*Y individual products. For example, one leading vendor offers approximately 529 different anti-human antibodies suitable for flow cytometry, labeled with any of 16 different fluors, thus requiring 16*529=8,464 different products in order to offer customers a complete selection (not counting products available in multiple unit sizes). Large numbers such as these prove impractical in practice, so vendors commonly offer only a very few of their most popular antibodies in a wide range of label colors, and offer the rest of their antibodies labeled with typically no more than two or three colors (and frequently only one). This trade-off reduces the complexity (in the case of one leading vendor reducing the product offerings to approximately 1,511) at the expense of reducing the likelihood of being able to satisfy a users' need for a particular antibody labeled with a particular color (in the present example, 82% of all possible antibody/color combinations are not available from one leading vendor). Antibody vendors compete among themselves, in part, by offering antibody/color combinations different from those of their competitors, so users frequently rely upon a combination of several vendors to meet their full range of needs. Thus, a company which does not offer a full range of antibody/color combinations loses business to its competitors.

Certain disclosed embodiments make antibody labeling simple enough for users to perform at point of use (see Example 22). In certain embodiments one or more antibodies are conjugated with one or more short oligonucleotides A, and one or more fluors are conjugated with one or more short complementary oligonucleotide A'. When such one or more antibodies and such one or more fluors are mixed in solution, the complementary oligonucleotides bind one another, yielding one or more fluorescently-labeled antibody via formation of the A:A' hybrid. In certain embodiments, each antibody is conjugated with a short oligonucleotide A, and each fluor is conjugated with a short complementary oligonucleotide A'. When such an antibody and such a fluor are mixed in solution, the complementary oligonucleotides bind one another, yielding a fluorescently-labeled antibody via formation of the A:A' hybrid.

Certain embodiments are directed to methods and/or systems that simply and effectively reduce the complexity of vendors offering a complete collection of antibody/color combinations to their customers. A substantial portion or each of the X antibodies in the vendor's catalog is offered conjugated to oligonucleotide A, and a substantial portion or each of the Y fluors in the vendor's catalog is offered conjugated to oligonucleotide A'. A customer or user requiring a given antibody labeled with a given fluor then need only purchase the two oligonucleotide-conjugated products (one fluor and one antibody), and mix them at point of use. Thus, the vendor offers customers or users a complete choice, or a substantially more complete choice, of the possible antibody/color combinations while significantly reducing the complexity by offering X+Y products, as opposed to X*Y products. In the example of the leading vendor's catalog discussed herein a total of 16+529=545 products would offer customers a substantially complete or complete range of antibody/color choices while reducing the number of products required by (8,464−545)/8,464=94%.

Currently, some vendors attempt to at least partially accommodate customers' needs for a wide choice of labels by offering antibodies conjugated with biotin, a small molecule vitamin, and fluors conjugated with streptavidin, a bacterial protein which binds biotin with high affinity. In principle, a customer can purchase a biotin-conjugated antibody, a streptavidin-conjugated fluor, and mix these together to label any antibody with any fluor. Some of the disadvantages of this conventional approach include one or more of the following:

Streptavidin is a relatively large protein (66 kDa in its active tetrameric form), potentially presenting steric hindrance problems in labeling analytes.

Streptavidin is a somewhat 'sticky' protein which may bind non-specifically to sample components, producing high backgrounds.

Because biotin is a common biological molecule, endogenous biotin can cause background and specificity issues when performing assays with certain biotin-rich tissues such as brain and liver.

Samples containing endogenous biotin-binding proteins, such as eggs or bacteria, pose specificity and background problems.

Harsh conditions are required to break the streptavidin-biotin bonds in order to strip and re-probe samples.

Streptavidin-conjugated fluors are subject to proteolysis, thermal denaturation, and other causes of product degradation Because streptavidin is tetrameric (has four biotin binding sites) it can crosslink multiple biotinylated antibodies These disadvantages render the biotin/streptavidin technology an unfavored choice for most users. Another technology which is known in the art involves a technology, in which IgG antibody can be labeled by the user with a fluorophore-labeled Fab fragment directed against the Fc portion of that IgG. In practice, this technology has proven problematic. The antibody/Fab complex is stable for only minutes. Additionally, this technology is applicable only to the labeling of IgG antibodies. Finally, fluorophore-conjugated Fab fragments are expensive, complicated, and time-consuming to produce.

in contrast, certain disclosed embodiments have one or more of the following advantages. In certain aspects, the oligonucleotide hybrid is stable for an extended period of time. In certain aspects, the technology disclosed herein can be used to label a large range of antibody isotypes. In certain aspects, the technology disclosed herein is simple to use and/or more economical to manufacture. The oligonucleotides employed, in certain aspects, are small (about 6 kDa) compared to streptavidin, and thus present less steric hindrance. In certain aspects, smaller oligonucleotides demonstrate substantially less stickiness and substantially little non-specific binding. In certain aspects, a properly chosen oligonucleotide sequence will not find endogenous complementary sequences in biological samples, or at least reduce endogenous complementary sequences in biological samples, thus avoiding, or substantially reducing, higher background staining. In certain aspects, relatively mild conditions can be employed to disassemble the oligonucleotide hybrids for strip and re-probe techniques. Generally, oligonucleotide-conjugated fluors are not subject to significant proteolysis and/or significant thermal denaturation as potential sources of product degradation. In certain aspects, complementary oligonucleotides hybridize in a strict 1:1 ratio; accordingly, they are least likely to or cannot crosslink multiple antibodies.

Certain embodiments are directed to methods and/or systems comprising: i) a first series of molecular probes prepared by independently conjugating a first oligonucleotide sequence to at least 10 binding moieties; and ii) a second series of detectable components prepared by independently conjugating a second oligonucleotide sequence to at least 3 signal generating moieties, wherein the second oligonucleotide sequence is complementary to the first oligonucleotide sequence; wherein: a) an appropriate amount of a molecular probe from the first series may be mixed with an appropriate amount of a detectable component from the second series to produce a hybridized molecular probe-detectable component; and b) at least 90% of possible combinations of said first and second series may be produced. In certain aspects, a substantial portion, at least a majority, at least 60%, 70%, 75%, 80%, 85%, 92%, 96%, 98%, 99% or 100% of possible combinations of said first and second series may be produced. In certain aspects, the first series of molecular probes may be prepared by independently conjugating the first oligonucleotide sequence to at least 3 binding moieties, for example, at least 5, 8, 15, 20, 25, 30, 50, 100, 150, 200, 250, 300, 350, 400, 450, 500, 750, or at least 1000 binding moieties, or between 3-10, 4-9, 5-12, 6-14, 7-16, 8-19, 9-20, 10-25, 12-30, 25-50, 40-70, 50-80, 75-100, 80-125, 115-150, 130-200, 150-250, 175-300, 200-400, 300-500, 350-750, 400-800, or 500-1000 binding moieties. In certain aspects, the second series of detectable components may be prepared by independently conjugating the second oligonucleotide sequence to at least 3 signal generating moieties, for example at least 2 signal generating moieties, at least 4, 5, 6, 7, 8, 9, 10, 11, 12, 13, 14, 15, 17, 20, 25, or 30 signal generating moieties, or between 2-5, 3-5, 3-6, 4-7, 4-9, 5-8, 5-10, 5-12, 6-14, 7-15, 8-13, 9-16, 10-17, 11-18, 12-19, 15-20, 10-25, 12-30, or 25-50 signal generating moieties. Certain embodiments are directed to methods and/or systems for reducing to manageable proportions the number of catalog products a vendor of labeled molecular probes must manufacture, stock, market, and distribute, comprising: i) a first series of customizable molecular probes prepared by conjugating a first oligonucleotide sequence to at least 10 binding moieties; and ii) a second series of customizable detectable components prepared by conjugating a second oligonucleotide sequence to at least 3 signal generating moieties, wherein the second oligonucleotide sequence is complementary to the first oligonucleotide sequence; wherein: a) an appropriate amount of a customized molecular probe from the first series may be mixed with an appropriate amount of a customized detectable component from the second series to produce a hybridized molecular probe-detectable component; and b) at least 90% of possible combinations of said first and second series may be produced. In certain aspects, a substantial portion, at least a majority, at least 60%, 70%, 75%, 80%, 85%, 92%, 96%, 98%, 99% or 100% of possible combinations of said first and second series may be produced. In certain aspects, the first series of customizable molecular probes may be prepared by independently conjugating the first oligonucleotide sequence to at least 3 binding moieties, for example, at least 5, 8, 15, 20, 25, 30, 50, 100, 150, 200, 250, 300, 350, 400, 450, 500, 750, or at least 1000 binding moieties, or between 3-10, 4-9, 5-12, 6-14, 7-16, 8-19, 9-20, 10-25, 12-30, 25-50, 40-70, 50-80, 75-100, 80-125, 115-150, 130-200, 150-250, 175-300, 200-400, 300-500, 350-750, 400-800, or 500-1000 binding moieties. In certain aspects, the second series of customizable detectable components may be prepared by independently conjugating the second oligonucleotide sequence to at least 3 signal generating moieties, for example at least 2 signal generating moieties, at least 4, 5, 6, 7, 8, 9, 10, 11, 12, 13, 14, 15, 17, 20, 25, or 30 signal generating moieties, or between 2-5, 3-5, 3-6, 4-7, 4-9, 5-8, 5-10, 5-12, 6-14, 7-15, 8-13, 9-16, 10-17, 11-18, 12-19, 15-20, 10-25, 12-30, or 25-50 signal generating moieties.

Certain embodiments are directed to methods and/or systems comprising: i) a first series of molecular probes prepared by independently conjugating a first oligonucleotide sequence to at least 10 binding moieties; and ii) a second series of detectable components prepared by conjugating a second oligonucleotide sequence to at least 3 scaffolds having one or more signal generating moieties, wherein the second oligonucleotide sequence is complementary to the first oligonucleotide sequence; wherein: a) an appropriate amount of a molecular probe from the first series may be mixed with an appropriate amount of a detectable component from the second series to produce a hybridized molecular probe-detectable component; and b) at least 90% of possible combinations of said first and second series may be produced. In certain aspects, a substantial portion, at least a majority, at least 60%, 70%, 75%, 80%, 85%, 92%, 96%, 98%, 99% or 100% of possible combinations of said first and second series may be produced. In certain aspects, the first series of molecular probes may be prepared by independently conjugating the first oligonucleotide sequence to at least 3 binding moieties, for example, at least 5, 8, 15, 20, 25, 30, 50, 100, 150, 200, 250, 300, 350, 400, 450, 500, 750, or at least 1000 binding moieties, or between 3-10, 4-9, 5-12, 6-14, 7-16, 8-19, 9-20, 10-25, 12-30, 25-50, 40-70, 50-80, 75-100, 80-125, 115-150, 130-200, 150-250, 175-300, 200-400, 300-500, 350-750, 400-800, or 500-1000 binding moieties. In certain aspects, the second series of detectable components may be prepared by independently conjugating the second oligonucleotide sequence to the one or more scaffolds, for example, at least 2, 3, 4, 5, 6, 7, 8, 9, or 10 scaffolds, or between 2-5, 3-6, 4-7, 5-8, 6-9, 7-10, or 8-15 scaffolds, wherein the one or more scaffolds comprises at least 3 signal generating moieties, for example at least 2 signal generating moieties, at least 4, 5, 6, 7, 8, 9, 10, 11, 12, 13, 14, 15, 17, 20, 25, or 30 signal generating moieties, or between 2-5, 3-5, 3-6, 4-7, 4-9, 5-8, 5-10, 5-12, 6-14, 7-15, 8-13, 9-16, 10-17, 11-18, 12-19, 15-20, 10-25, 12-30, or 25-50 signal generating moieties. In certain aspects, the scaffolds may be selected from a bead, a dendrimer, a polysaccharide molecule, a dextran, a protein, a peptide, a second oligonucleotide sequence, a portion of the oligonucleotide sequence that is not complementary to the oligonucleotide sequence of the molecular probe, a polymer, a hydrophilic polymer, a nanoparticle, or combinations or derivatives thereof.

Certain embodiments are directed to methods comprising: i) preparing a first series of molecular probes by independently conjugating a first oligonucleotide sequence to at least 10 binding moieties; and ii) preparing a second series of detectable components by independently conjugating a second oligonucleotide sequence to at least 3 signal generating moieties, wherein the second oligonucleotide sequence is complementary to the first oligonucleotide sequence; and iii) mixing, independently and in a matrix or semi-matrix fashion, an appropriate amount of a molecular probe from the first series with an appropriate amount of a detectable component from the second series to produce a plurality of hybridized molecular probe-detectable components; wherein at least 90% of possible combinations of said first and second series may be produced. In certain aspects, a substantial portion, at least a majority, at least 60%, 70%, 75%, 80%, 85%, 92%, 96%, 98%, 99% or 100% of possible combinations of said first and second series may be produced. In certain aspects, the first series of molecular probes may be prepared by independently conjugating the first oligonucleotide sequence to at least 3 binding moieties, for example, at least 5, 8, 15, 20, 25, 30, 50, 100, 150, 200, 250, 300, 350, 400, 450, 500, 750, or at least 1000 binding moieties, or between 3-10, 4-9, 5-12, 6-14, 7-16, 8-19, 9-20, 10-25, 12-30, 25-50, 40-70, 50-80, 75-100, 80-125, 115-150, 130-200, 150-250, 175-300, 200-400, 300-500, 350-750, 400-800, or 500-1000 binding moieties. In certain aspects, the second series of detectable components may be prepared by independently conjugating the second oligonucleotide sequence to at least 3 signal generating moieties, for example at least 2 signal generating moieties, at least 4, 5, 6, 7, 8, 9, 10, 11, 12, 13, 14, 15, 17, 20, 25, or 30 signal generating moieties, or between 2-5, 3-5, 3-6, 4-7, 4-9, 5-8, 5-10, 5-12, 6-14, 7-15, 8-13, 9-16, 10-17, 11-18, 12-19, 15-20, 10-25, 12-30, or 25-50 signal generating moieties.

Certain embodiments are to a catalog, comprising: i) a first series of at least 10 customizable antibodies, comprising at least one first oligonucleotide sequence conjugated to the antibodies; and ii) a second series of at least 3 customizable detectable components, comprising at least one second oligonucleotide sequence conjugated to the detectable components, wherein the second oligonucleotide sequence is complementary to the first oligonucleotide sequence; wherein: a) an appropriate amount of a antibody from the first series may be mixed with an appropriate amount of a detectable component from the second series to produce a hybridized antibody-detectable component; and b) at least 90% of possible combinations of said first and second series may be produced. In certain aspects, a substantial portion, at least a majority, at least 60%, 70%, 75%, 80%, 85%, 92%, 96%, 98%, 99% or 100% of possible combinations of said first and second series may be in the catalog. In certain aspects, the first series of customizable antibodies may be prepared by independently conjugating the first oligonucleotide sequence to at least 3 antibodies, for example, at least 5, 8, 15, 20, 25, 30, 50, 100, 150, 200, 250, 300, 350, 400, 450, 500, 750, or at least 1000 antibodies, or between 3-10, 4-9, 5-12, 6-14, 7-16, 8-19, 9-20, 10-25, 12-30, 25-50, 40-70, 50-80, 75-100, 80-125, 115-150, 130-200, 150-250, 175-300, 200-400, 300-500, 350-750, 400-800, or 500-1000 antibodies. In certain aspects, the second series of customizable detectable components may be prepared by independently conjugating the second oligonucleotide sequence to at least 3 signal generating moieties, for example at least 2 signal generating moieties, at least 4, 5, 6, 7, 8, 9, 10, 11, 12, 13, 14, 15, 17, 20, 25, or 30 signal generating moieties, or between 2-5, 3-5, 3-6, 4-7, 4-9, 5-8, 5-10, 5-12, 6-14, 7-15, 8-13, 9-16, 10-17, 11-18, 12-19, 15-20, 10-25, 12-30, or 25-50 signal generating moieties Certain embodiments are directed to methods and/or systems further comprising a third series of universal adapters prepared by independently selecting and pairing a complementary first oligonucleotide sequence segment to the first oligonucleotide sequence of the first series with a complementary second oligonucleotide sequence segment to the second oligonucleotide sequence of the second series. Certain embodiments are to a catalog, further comprising a third series of universal adapters prepared by independently selecting and pairing a complementary first oligonucleotide sequence segment to the first oligonucleotide sequence of the first series with a complementary second oligonucleotide sequence segment to the second oligonucleotide sequence of the second series. In certain aspects, at least 90% of possible combinations of said complementary first oligonucleotide sequence segment and said complementary second oligonucleotide sequence segment may be produced. In certain aspects, a substantial portion, at least a majority, at least 60%, 70%, 75%, 80%, 85%, 92%, 96%, 98%, 99% or 100% of possible combinations of said complementary first oligonucleotide sequence segment and said complementary second oligonucleotide sequence segment may be produced. In certain aspects, the third series of universal adapters may be prepared by independently selecting and pairing at least 3 of the complementary first oligonucleotide sequence segments with at least 3 said complementary second oligonucleotide sequence segments, for example, at least 5, 8, 15, 20, 25, 30, 50, 100, 150, 200, 250, 300, 350, 400, 450, 500, 750, or at least 1000, or between 3-10, 4-9, 5-12, 6-14, 7-16, 8-19, 9-20, 10-2.5, 12-30, 2.5-50, 40-70, 50-80, 7.5-100, 80-125, 11.5-1.50, 130-200, 1.50-250, 175-300, 200-400, 300-500, 350-750, 400-800, or 500-1000, of the complementary first oligonucleotide sequence segments may be prepared by independently selected and paired with at least 5, 8, 15, 20, 25, 30, 50, 100, 150, 200, 250, 300, 350, 400, 450, 500, 750, or at least 1000, or between 3-10, 4-9, 5-12, 6-14, 7-16, 8-19, 9-20, 10-25, 12-30, 25-50, 40-70, 50-80, 75-100, 80-125, 115-150, 130-200, 150-250, 175-300, 200-400, 300-500, 350-750, 400-800, or 500-1000, of the complementary second oligonucleotide sequence segments.

Optimization of Antibody Degree of Labeling

Certain embodiments are directed to systems and/or methods for optimization of antibody degree of labeling. Certain embodiments provide systems and/or methods that allow users to choose one or more optimal degrees of labeling for one or more antibodies, thereby avoiding spillover errors in multiplexed immunoassays. For example, for use in multiplexed flow cytometry.

Antibodies—biological proteins exhibiting high-affinity binding of single target molecules—are widely employed throughout biological research, clinical diagnostics, pharmaceutical drug discovery, and other disciplines to enable immunoassays to detect and quantify molecules of interest ('antigens'). Typically, an antibody employed in immunoassays must be labeled with another molecule to render them detectable; frequently, the labels employed are fluorescent molecules (or 'fluors'), which emit light over characteristic wavelength ranges (or 'colors'). Approximately 36 different fluors are commercially available today as antibody labels, covering the color gamut from deep red to violet. In 'multiplexed' assays, which aim to detect two or more different analytes in the same sample, two or more different antibodies are typically employed together, the two more different antibodies are labeled with different colored fluors to allow them to be detected individually. Multiplexed assays are increasingly common in flow cytometry, where multiply different analytes may be detected in the assay.

A substantially number of the fluors used to label antibodies have relatively broad emission spectra (the range of wavelengths over which they emit fluorescent light), so that in multiplexed studies employing antibodies labeled with, for example, two fluors (1 and 2) the flow cytometer detection channel dedicated to detection of fluor 1's emission may also "see" a relatively small amount of the light emitted by fluor 2. This is often referred to as spillover. Some flow cytometers provide so-called 'compensation' mechanisms to correct for this spillover either electronically or via software, but compensation often lacks sufficient accuracy and, in the case of a very bright signal from fluor 1 spilling over into a channel observing a comparatively dim signal from fluor 2 the unavoidable consequence of compensation is often an increase in the coefficient of variation of the fluor 2 signal, which presents as a broadening of the apparent intensity distribution of fluor 2's signal. This broadening of fluor 2's intensity distribution constitutes an artifact which it is desirable to avoid in many instances, as the artifact makes it difficult and sometime impossible, to determine the percentage of cells in the sample which express the antigen reported by the fluor 2-labeled antibody with sufficient accuracy. Certain embodiments of the present disclosure are directed to allowing flow cytometrists to optimize, or substantial optimize, improve or fine tune the brightness of a first labeled antibody fluor 1's fluorescence to minimize, substantially minimize or reduce its spillover into the detection channel for a second labeled antibody fluor2. This may also be accomplished in assays that have 3, 4, 5, 6, 7, 8, 9, or more fluors that may be affected by the spillover of one or more other fluors.

Certain disclosed embodiments provide methods and/or systems that allow the user to adjust the brightness of a primary-labeled antibody. In certain embodiments one or more antibodies are conjugated with one or more short oligonucleotides A, and one or more Certain disclosed embodiments provide methods and/or systems that allow the user to adjust the brightness of a primary-labeled antibody. In certain embodiments one or more antibodies are conjugated with one or more short oligonucleotides A, and one or more fluors are conjugated with one or more short complementary oligonucleotide A'. When such one or more antibodies and such one or more fluors are mixed in solution, the complementary oligonucleotides bind one another, yielding one or more fluorescently-labeled antibody via formation of the A:A' hybrid. In certain embodiments fluors are conjugated with one or more short complementary oligonucleotide A'. When such one or more antibodies and such one or more fluors are mixed in solution, the complementary oligonucleotides bind one another, yielding one or more fluorescently-labeled antibody via formation of the A:A' hybrid. In certain embodiments, each antibody is conjugated with a short oligonucleotide A, and each fluor is conjugated with a short complementary oligonucleotide A'. When such an antibody and such a fluor are mixed in solution, the complementary oligonucleotides bind one another, yielding a fluorescently-labeled antibody via formation of the A:A' hybrid.

Certain embodiments are directed to kits that can be used for adjusting the brightness a fluorescently-labeled antibody. These kits make this adjustment substantially easier for the user. For example, certain embodiments are directed to a kit comprising one or more oligonucleotide-conjugated antibodies and two or more vials of complementary oligonucleotide-conjugated fluors, wherein the two or more oligonucleotide-conjugated fluors bear the same fluorescent reporter molecule, substantially the same fluorescent reporter molecule or a similar fluorescent reporter molecule, but at two or more different degrees of labeling, or 'brightness' (for example without limitation, four fluors per conjugate in a first vial, and 8 fluors per conjugate in a second vial), thus providing 'dimmer and 'brighter' labels for the end-user to choose from. In the example of the previous section, the user might choose to minimize or even eliminate the c.v. broadening artifact by labeling antibody fluor 1 with a dimmer label (lower degree of labeling) and antibody fluor 2 with a brighter label (higher degree of labeling). Due to the physics of fluorescence, spillover is rarely reciprocal between two fluors, because many fluorophores' emission spectra are asymmetrical.

Due, in part, to the 'combinatorial explosion' problem faced by labeled antibody vendors as discussed herein, vendors have encountered difficulties in readily providing an antibody labeled in a variety of degrees of labeling. Consequently, rather than making all permutations available or customizing particular antibodies with specified degrees of labeling, the vendors must pre-determine what antibodies are to be made available, and typically only with the highest feasible degree of labeling. Thus, end-users are unable to systematically adjust degree of labeling in order to minimize compensation artifacts. Instead, users sometimes may choose different labels where spillover is a problem, using an inherently dim fluor to minimize spillover. However, many antibodies are not commercially available labeled with a large variety of possible fluors, so an appropriate dim fluor may not be available, in which case the user is forced to accept the compensation artifact.

In the prior art, the only practical means to optimize labeling brightness (for example, to achieve dimmer labeling) is for the user to perform his own antibody labeling in-house (or to contract with a vendor for custom labeling), adjusting the labeling protocol to yield a lower degree of labeling. This is a time-consuming and highly skilled task which is beyond the ability of most users, and custom labeling contracts are expensive and have long lead times. Additionally, conventional covalent labeling protocols are difficult or impossible to control sufficiently to achieve a pre-determined precise degree of labeling. In contrast, certain kits, methods, and or systems of the present disclosure make it simple and quick for the user to achieve precisely the degree of labeling required (as illustrated in Example 21).

Certain embodiments are directed to a tunable detection method, kit and/or system, comprising: i) a molecular probe prepared by conjugating a first oligonucleotide sequence to a binding moiety; ii) a series of detectable components, comprising different amounts of a signal generating moiety conjugated to a second oligonucleotide sequence, wherein the different amounts of the signal generating moiety provides a range of intensities of the signal generated, and wherein the second oligonucleotide sequence is complementary to the first oligonucleotide sequence; wherein: a) the intensity of the signal generated can be tuned over a range 1.25 to 2×, 1.5 to 3×, 2 to 4×, 1.25 to 1.75×, 2 to 6×, 3 to 5×, 3 to 6×, or 2 to 10× by selecting the detectable component having a greater or lesser intensity. In certain embodiments, the intensity of the signal generated can be tuned over a range extending from the limit of self-quenching to the intensity of a single signal generating moiety.

Certain embodiments are directed to a tunable detection method, kit and/or system, comprising: i) a molecular probe prepared by conjugating a first oligonucleotide sequence to a binding moiety; ii) a series of detectable components, comprising different amounts of a signal generating moiety conjugated to a second oligonucleotide sequence, wherein the different amounts of the signal generating moiety provides a range of intensities of the signal generated, and wherein the second oligonucleotide sequence is complementary to the first oligonucleotide sequence; wherein: a) the intensity of the signal generated from a target-bound molecular probe that is hybridized to a detectable component can be tuned over a range greater than an order of magnitude by selecting the detectable component having a greater or lesser intensity.

Simplifying Development of Multiplexed Flow Cytometry Assays

Certain embodiments are directed to systems and/or methods for simplifying development of multiplexed flow cytometry assays. These methods and/or systems may also be used for simplifying other multiplexed assays as well, for example immunohistochemistry, microarray-based assays, bead-based assays, immunosorbant assays, etc. Multiplexed flow cytometry assays employ cocktails of two or more antibodies, wherein the two or more antibodies are typically labeled with a different-colored fluorophore, to analyze, for example, the sub-populations of cells in a cell sample where one or more of those sub-populations are distinguished from other sub-population(s) within the sample by the co-occurrence (or lack of co-occurrence) of two or more protein markers on or in the cells of the sub-population of interest. In certain embodiments multiplexed flow cytometry assays employ cocktails of two or more antibodies, wherein the two or more antibodies are each labeled with a different-colored fluorophore, to analyze, for example, the sub-populations of cells in a cell sample where one or more of those sub-populations are distinguished from other sub-population(s) within the sample by the co-occurrence (or lack of co-occurrence) of two or more protein markers on or in the cells of the sub-population of interest. As an example without limitation, consider the following hypothetical cell sample comprised of (at least) three different cell types, wherein the cell types are defined by the specified collection of protein markers indicated in Table 10-A.

TABLE 10-A

|             | Marker X | Marker Y | Marker Z |
|-------------|----------|----------|----------|
| Cell Type 1 | +        | +        | −        |
| Cell Type 2 | +        | −        | +        |
| Cell Type 3 | +        | +        | +        |
| Cell Type 4 | −        | +        | +        |

Table 10-A shows a collection of protein markers identifying 4 distinct cell types in a hypothetical sample. "+" indicates the presence of the indicated marker on the indicated cell type, whereas "−" indicates its absence.

In the example, no single marker can enable the unambiguous identification of the four cell types. Similarly, no combination of just two markers can identify the three cell types (because cell types 1 and 3 are both X+/Y+, cell types 2 and 3 are both X+/Z+, and cell types 3 and 4 are both Y+/Z+). Only the combination of the markers X, Y, and Z permits a unique immunophenotype to be assigned to each of the four cell types. It is therefore necessary to employ a cocktail of three distinct antibodies (Abs)—Ab-X, Ab-Y, and Ab-Z (which bind exclusively to markers X, Y, and Z, respectively)—in order to separately enumerate the number of cells of each of these four cell types occurring in this sample.

Examples of such multiplexed flow cytometry assays are common in blood analysis (where a single blood sample may contain 5, 10, 15, 20 or more different cell types), immunology (where 4, 5, 6, 7 or more distinguishable cell types may be present in a sample), and stem cell research (where the total number of distinguishable cell types in a sample still frequently remains undefined at present)

The example of Table 10-A assumes that the distinct immunophenotypes of the four cell types of interest has already been defined. In early stages of research, the effort to define such distinguishing immunophenotypes may require multiplexing a much larger number of antibodies in order to identify distinguishing combinations. It has been estimated that the human genome encodes approximately 1,000 different cell surface proteins.

In order for the 3 antibodies in this example to be separately distinguished by a flow cytometer it is necessary to separately label them with 3 distinct fluors, (F1-1, F1-2, and F1-3, respectively) whose fluorescence emission spectra do not substantially overlap.

Further to the present example, if Ab-X, Ab-Y, and Ab-Z are commercially available labeled with F1-1, F1-2, and F1-3, respectively, then the cytometrist may conduct the assay by purchasing the three labeled reagents Ab-X:F1-1, Ab-Y:F1-2, and Ab-Z:F1-3. In contrast, if (for example) Ab-Y and Ab-Z are both commercially available only labeled with F1-2, then the assay cannot be performed using commercial reagents. This situation is not infrequent. A review of the labeled antibody offerings of numerous commercial vendors indicates that the median number of fluor colors in which a commercial primary-labeled antibody is available is around 2.

There therefore exists a need for systems and/or methods for antibodies to be quickly and easily labeled by cytometrists with the desired fluor (approximately 3 or more distinct fluors are used in flow cytometry), in order to facilitate the development and conduct of multiplexed assays. Using certain disclosed embodiments this may be accomplished as discussed herein. One exemplary approached is discussed in Example 29. The advantages of using the disclosed embodiments include one or more of the following: time savings (as users avoid complicated planning tasks to determine which antibodies can be accommodated in which detector channels); flexibility (when a new antibody is added to an existing multiplex panel it may be added in the available detector channel without further modification of the existing panel, since the colors are made available by certain embodiments of the present disclosure); and the ability to optimize panels by minimizing spectral spill-over from a channel measuring a high-abundance marker into a channel measuring a low-abundance marker.

Automation

Many assays employing antibodies or other probes to detect multiple targets or analytes within samples or complex samples are often performed by skilled personnel who select the targets to be investigated, perform extensive manipulation of the sample and of the assay reagents, or combinations thereof to obtain useful data. When multiple targets or analytes are examined in a single sample by performing multiple assays in parallel without substantially reducing reliability and/or reproducibility, this has the potential to offer one or more advantages such as in speed and/or confidence in results. Speed is obtained by increasing the number of targets examined in substantially the same time. Confidence is increased by permitting the experiment or to embed positive and/or negative controls that validate the experiment. Nonetheless, while such multiplexed assays are desirable, they are difficult to perform by comparison to simple assays of single targets or analytes. One or more limitations of the current methods serve as barriers to development of multiplexed assays. For example, one or more of the following: the ability to label individual probes with readily distinguishable detectors is particularly poorly matched to this task; the common methods and chemistries for labeling probes such as antibodies with detectors such as fluorescent groups may require optimization of each reaction for each pair; a similar situation is also found to attach a probe such as an antibody to a particle. As a result, except for assays that will be performed multiple times and/or will be utilized by multiple experimenters, the effort to develop and validate a multiplexed assay is generally considered impractical. Alternatively, once a multiplexed assay panel is developed, it is not readily amenable to adaptation. For example, adding and/or exchanging one antibody probe for another may lead to loss of reliability and/or reproducibility for the whole panel. Certain of the disclosed embodiments are directed to increase the number of assays that can be performed simultaneously or substantially simultaneously and to address one or more of these problems in the art and other problems addressed herein.

For example, panels of antibodies are often used in flow cytometry such as in the use of flow cytometry to examine the relative abundance of cells in a sample that bear distinct patterns of surface antigens, as may be performed in immunophenotyping, by employing panels of antibodies that are labeled with fluorophores. These fluorophores are often selected so that one or more antibodies may be detected in a different fluorescence channel and the one or more antibodies may need to be compared to different controls. Current methods for labeling antibodies with fluorescent groups are poorly matched to facile development of panels. The modification of each antibody with each fluorescent group is relatively inefficient and must be optimized. Further, the resulting fluorescent conjugate must typically be purified before use. Further, extensive prior experience is required to obtain reliable and/or reproducible results. Even then, the difficulty of designing and validating each panel creates a high barrier. Certain embodiments are directed to creating such a panel of fluorescently labeled antibodies to detect multiple targets on cells with high reliability and/or reproducibility. This reduces the high barrier to development of new panels and/or modification of existing panels.

Another example, as disclosed herein, is the use of bead arrays or microarrays as panels of immunoassays to examine multiple targets in a soluble sample. Also disclosed herein is the use of multiple antibodies, often called capture antibodies that will bind a particular soluble target or analyte that may or may not be in a sample. Then, a second antibody, the detector, may bind to another site on the target to form a sandwich. Alternatively, a competitor target or analyte might bind to the capture antibody left unbound. This second binding can then be detected by fluorescent or other tags. A scanning device is then used to record the results by matching. To multiplex this sandwich immunoassay, the one or more capture antibodies would be bound to a different particle type, distinguishable by one or more fluorescent or other barcode, or tethered to a distinct position on a surface. A scanning device may then be used to record the results by examining the bead type or microarray position. Alternatively, multiple antigens might be selected as probes to determine the presence of antibodies, as in the detection of humoral immune responses. Again, to perform a multiplexed experiment, the one or more antigens may be bound to one or more different particle types or positions in a surface array. Similarly, current methods are poorly matched to simple and straightforward coating of particles or surfaces with antibodies or antigens. The attachment of antibodies or antigens is unpredictable, typically requiring optimization and then careful washing to remove unbound probe and/or blocking to passivate or otherwise decrease nonspecific binding of uncoated surfaces of beads or arrays. Certain embodiments are directed to creating such a bead array or microarray bearing multiple different antibody or antigen probes to detect multiple targets or analytes with high reliability and/or reproducibility. Similarly, this reduces the high barrier to development of new panels and/or modification of existing panels.

It is well appreciated that automated systems can be of great advantage in performing immunoassays, particularly if they are able to rapidly and reliably perform multiplexed assays based on panels of tests. Further, an automated system might be of particular advantage if it could assemble panels in many combinations, allowing use of a wide range of antibodies or antigens, matched to a broad collection of fluorescent groups or fluorescent particles, and providing the panels on an as-needed basis. However, current methods, as described herein, are poorly matched to automation where assembly of a multiplexed assay would require new combinations of one or more antibodies with different fluorescent groups or of one or more antibodies and/or antigens with different fluorescent particles. The inefficient chemistry currently used is incompatible with simple and rapid assembly of such pairs on an as-needed basis. As disclosed herein, certain embodiments are directed to applying automation to combine antibodies with fluorescent groups or to bind antibodies to beads and thereby obtain reliable and/or reproducible panels on demand. This results in great advantages of multiplexing for increased speed and/or greater confidence. Certain embodiments disclosed herein are directed to automated systems and take into account the design and/or operational features of such devices. For example, devices and/or systems that analyze flow cytometry samples and/or bead arrays gain advantages from application of the methods and/or systems described herein. Certain embodiments make the selection of optimal combinations of antibody probes and/or fluorescent detectors or fluorescent beads much easier. Thus, the operator need only define the panel of targets to be assayed and the automated system may design and/or form the multiplexed panel. Furthermore, certain embodiments are directed to automated systems that incorporate algorithms to allow the results of a prior assay for one panel of targets to help choose the targets to be tested in a subsequent panel of assays, thereby allowing the system to perform a series of tests with or without direct supervision or input of the operator. The systems and/or methods disclosed herein permit an increase in the number of different targets that may be examined within one or more panels, and thereby perform multiple assays with high reliability and/or reproducibility. This provides significant advantages. Certain embodiments are directed to increasing the ability of an automated system able to match a much larger number of antibodies, antigens, other probes or combinations thereof with individual or multiple members of a larger set of fluorescent groups or set of fluorescent beads to create a much larger range of multiplexed panels that may be performed with greater speed and higher confidence.

The following examples are provided by way of illustration, and are not intended to be limiting of the present disclosure. While certain embodiments have been disclosed, it will be understood that each is capable of further modification and that this application is intended to cover variations, uses, or adaptations of the disclosure embodiments.

EXAMPLES

The following examples and protocols are given as particular embodiments of the disclosure and to demonstrate the advantages thereof. It is understood that the examples and protocols are given by way of illustration and are not intended to limit the specification or the claims that follow. Additional information is also found in the attached Solu-Link manual, entitled Antibody-Oligonucleotide All-in-One Conjugation Kit User Manual, Catalog No. A-9201-001.

The conjugation examples below include a (1) HyNic antibody modification step, (2) conversion of an amino-oligonucleotide to a 4FB-oligonucleotide and (3) and conjugation step. Following are common procedures used in the Examples that follow.

Antibody-HyNic Modification: The antibody is exchanged into Modification Buffer (100 mM phosphate, 150 mM NaCl, pH 7.4) and a solution of S-HyNic in anhydrous DMF (X equivalents as described below) are mixed and incubated at room temperature for 1.5 h. The HyNic-antibody is purified to remove excess modification reagent and simultaneously buffer exchanged into Conjugation Buffer (100 mM phosphate, 150 mM NaCl, pH 6.0) using a Zeba desalting column (ThermoPierce, Rockford, IL).

4FB-oligonucleotide preparation: 3'- or 5'-amino-modified oligonucleotide is exchanged into Modification Buffer and the concentration is adjusted between 0.2 and 0.5 OD/µL. To the volume of amino-oligonucleotide is added a ½ volume of DMF followed by addition of S-4FB (20 equivalents in DMF). The reaction is incubated at room temperature for 1.5 hours, diluted to 400 µL with Conjugation Buffer (100 mM phosphate, 150 mM NaCl, pH 6.0) and desalted using a 5K MWCO Vivaspin diafiltration apparatus. The 4FB-modified oligonucleotide is washed with Conjugation Buffer (3×400 the OD/µL of the purified oligonucleotide is determined and used directly in the following conjugation reaction.

HyNic-antibody/4FB-oligonucleotide conjugation: To the HyNic-antibody (1 mol equiv) in conjugation buffer is added 4FB-oligonucleotide (3-5 equiv as described in the experiments). To the reaction mixture is added ¹/₁₀th volume TurboLink Buffer (100 mM aniline, 100 mM phosphate and 150 mM NaCl, pH 6.0. The reactions are incubated for 2 hours and purified as described below.

The gel data in the Figures were run on 4-12% Novex Bis-tris gels (Tnvitrogen, Carlsbad, CA) using MOPS Running Buffer (Invitrogen). Samples were loaded using NuPage LDS Sample Buffer (Invitrogen) without DTT or heating prior to loading.

Gels were developed as indicated with Coomassie blue for visual protein detection, Lumetein protein stain (Biotium, Hayward, CA) or DNA DNA Silver Stain (GE Healthcare, Piscataway, NJ).

Example 1

Figure 2:
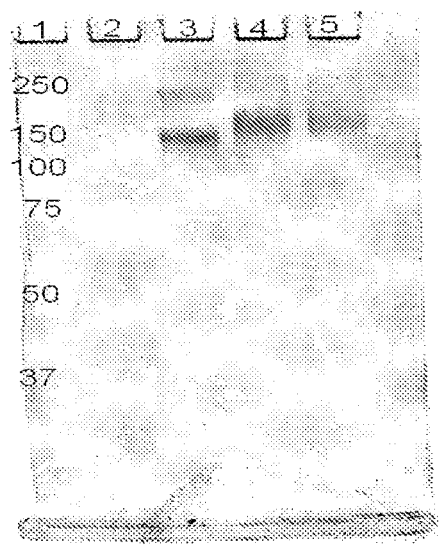
FIG. 2 is a gel electrophoresis loading 400 ng of antibody with Lumitein stain, containing the following lanes: Marker (lane 1); SFB-H1A (lane 2); HyNic-Bovine IgG (lane 3); Bovine igG/H1A crude (lane 4) and Bovine IgG/H1A purified (lane 5), in accordance with certain embodiments.
Figure 3:
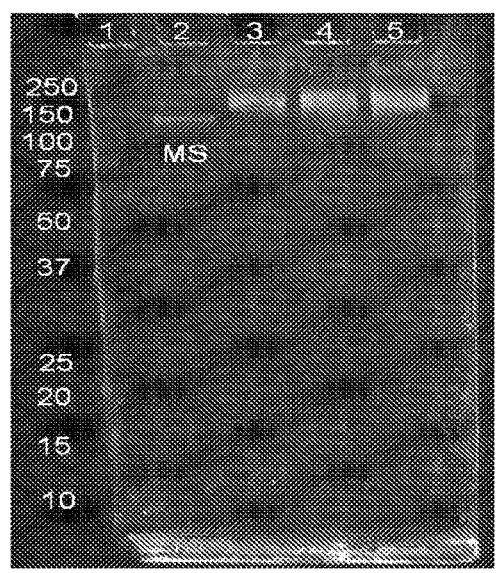
FIG. 3 is a gel electrophoresis loading 500 ng of antibody with Commassie stain, containing the following lanes: Marker (lane 1); SFB-H1A (lane 2); HyNic-Bovine IgG (lane 3); Bovine IgG/H1A crude (lane 4) and Bovine IgG/H1A purified (lane 5), in accordance with certain embodiments.
Figure 4:
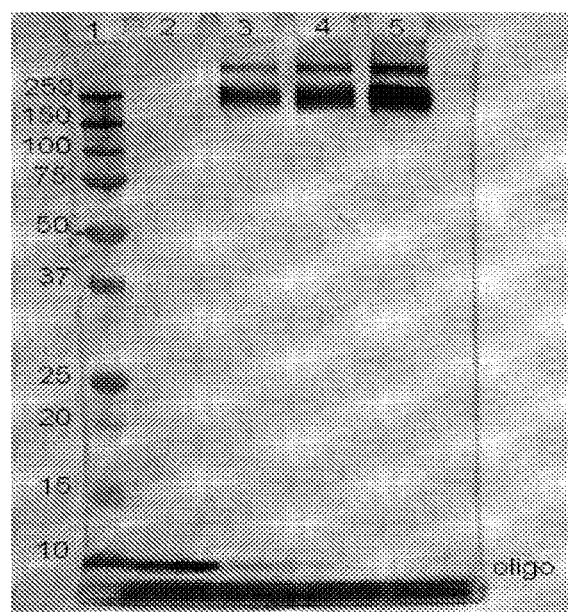
FIG. 4 is a gel electrophoresis with Lumitein stain, containing the following lanes: Marker (lane 1); HyNic-MS anti-FITC 150 ng (lane 2); MS anti-FITC/HIA crude 300 ng (lane 3); MS anti-FITC/HIA purified 300 ng (lane 4) and MS anti-FITC/H1A purified 450 ng (lane 5), in accordance with certain embodiments.

In this Example a polyclonal antibody (bovine IgG (bIgG)) and a mouse monoclonal antibody (anti-FITC monoclonal antibody; Jackson ImmunoResearch (Chadds Ford, PA)) were modified at 4 mg/mL with S-HyNic (20 equivalents). Following desalting into Conjugation Buffer the HyNic-antibodies were treated with a 35mer 5'-4FB oligonucleotide (5 equivalents). The conjugates were purified using USY-20 size exclusion Ultrafiltration Units (Advantec MFS, Inc., Dublin, CA). The DNA Silver stained PAGE results for conjugation to bIgG are presented in FIG. 1. The loading, stain and samples in each lane are:
Loading: 400 ng antibody
Visualization/stain: Sybr Gold stain
Lane 1. Marker
Lane 2. 4FB-35mer oligonucleotide
Lane 3. HyNic-Bovine TgG
Lane 4. Bovine igG/4FB-35mer oligonucleotide crude
Lane 5. Bovine IgG/4FB-35mer oligonucleotide purified The Lumetein stained PAGE results for conjugation to b-IgG are presented in FIG. 2. As shown in the gel in FIG. 2, there is significant conversion of antibody to conjugate. Lane 4 presents the shift of the product band to higher molecular weight and minor amounts of starting antibody as compared to Lane 3. In that the sensitivity of Lumetein fluorescent protein stain is 1 ng this result would indicate greater than 90% conversion of antibody to conjugate as 400 ng of antibody were loaded in each lane. The loading, stain and samples in each lane are:
Loading: 400 ng antibody
Visualization/stain: Lumetein stain (Biotium; Hayward, CA)
Lane 1. Marker
Lane 2. 4FB-35mer oligonucleotide
Lane 3. HyNic-Bovine IgG
Lane 4. Bovine IgG/4FB-35mer oligonucleotide crude
Lane 5. Bovine IgG/4FB-35mer oligonucleotide purified The Lumetein stained PAGE results for conjugation to anti-FITC monoclonal antibody are presented in FIG. 3. No unconjugated antibody is seen in lanes 3, 4 and 5 therefore based on the efficiency of conversion of antibody to conjugate is greater than 95% based on the sensitivity of the Lumetein stain. The loading, stain and samples in each lane are:

Loading: 150 ng antibody
Visualization/stain: Lumetein stain
Lane 1. Marker
Lane 2. HyNic-MS anti-FITC 150 ng
Lane 3. MS anti-FITC/4FB-35mer oligonucleotide crude 300 ng
Lane 4. MS anti-FITC/4FB-35mer oligonucleotide purified 300 ng
Lane 5. MS anti-FITC/4FB-35mer oligonucleotide purified 450 ng The DNA Silver stained PAGE results for conjugation to anti-FITC monoclonal antibody are presented in FIG. 4. Unconjugated oligo can be seen in both lanes 4 and 5 demonstrating the inefficiency in removing excess oligonucleotide using the USY 20 diafiltration filter. The sensitivity of DNA Silver Stain is ~50 pg oligo.

The loading, stain and samples in each lane are:
Loading: 150 ng antibody
Visualization/stain: Lumetein stain
Lane 1. Marker
Lane 2. HyNic-MS anti-FITC 150 ng
Lane 3. MS anti-FITC/4FB-35mer oligonucleotide crude 300 ng
Lane 4. MS anti-FITC/4FB-35mer oligonucleotide purified 300 ng
Lane 5. MS anti-FITC/4FB-35mer oligonucleotide purified 450 ng Example 2

This experiment compares purification of antibody-oligonucleotide conjugates by diafiltration and adsorbing the conjugate on a Zinc-chelate modified magnetic bead, washing the beads with buffer to remove excess 4FB-oligonucleotide and eluting the conjugate from the bead with imidazole-based eluting buffer.

Crude conjugate mixture prepared in Example 1 was purified by either a 100 kD MWCO Vivaspin diafiltration spin column or Zinc-magnetic-bead to remove free oligo:
(A) Diafiltration purification: Conjugate was diluted into PBS (400 ptL) placed in the diafiltration apparatus and concentrated. The retentate was diluted with PBS and concentrated 3 more times.
(B) Zinc-chelate-magnetic-bead purification: Added crude conjugated antibody/oligo mixture to Zn SepFast Mag (Biotoolmics, UK) and bind for 30-40 mM. The beads were washed (0.4 mL) with 25 mM sodium phosphate, 300 mM sodium chloride, 0.05% Tween-20, pH 7.5 4 times. The conjugate was eluted from the beads with 2 5 mM EDTA, 300 mM NaCl, 250 mM Imidazole, 75 ug/mL HIS-6 peptide, pH 6.0, 4 times. The purified conjugate was exchanged into 10 mM sodium phosphate, 149 mM sodium chloride, 1 mM EDTA, 0.05% sodium azide, pH 7.2.

Figure 5:
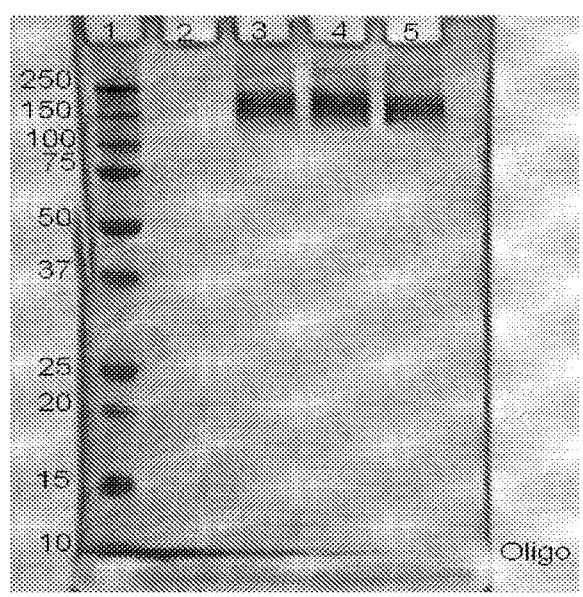
FIG. 5 is a gel electrophoresis loading 300 ng of antibody with DNA Silver stain containing the following lanes: Marker (lane 1); 4FB-H1A (lane 2); Bovine IgG/H1A crude (lane 3); Bovine IgG/H1A purified with Diafiltration spin column 100K (lane 4) and Bovine IgG/H1A purified Zinc-His-tag-magnetic-bead (lane 5), in accordance with certain embodiments.

As shown in FIG. 5, loading 300 ng of antibody and developing with DNA Silver stain demonstrated near quantitative removal of excess oligonucleotide by adsorbing Ab-oligonucleotide conjugate on Zinc magnetic beads followed by release as no excess oligo is present in Lane 5 while oligo can be seen in Lane 4. The loading, stain and samples in each lane are:
Loading 300 ng of antibody
Stain: DNA Silver stain
Lane 1. Marker
Lane 2. 4FB-34FB-35mer oligonucleotide
Lane 3. Bovine IgG/34FB-35mer oligonucleotide crude
Lane 4. Bovine IgG/4FB-35mer oligonucleotide purified with Diafiltration spin column 100K
Lane 5. Bovine IgG/4FB-35mer oligonucleotide purified Zinc-magnetic-bead Based on the sensitivity of DNA Silver Stain greater than 98% of the excess is removed using this method.

Example 3

Figure 6:
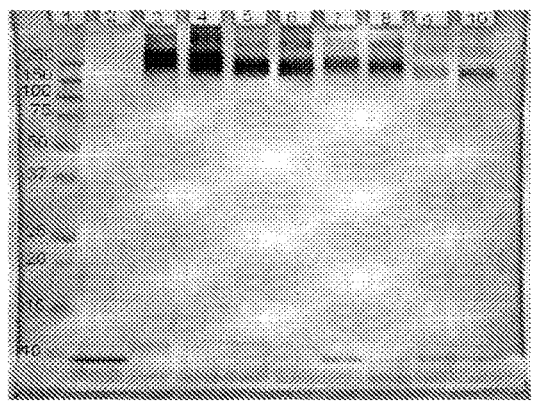
FIG. 6 is a gel electrophoresis loading Loading 300 ng of antibody with Silver stain containing the following lanes: Marker (lane 1); 4FB-46mer 4FB-oligonucleotide (lane 2); 1:5 MS anti-FTTC/46mer 4FB-oligonucleotide crude (lane 3); 1:5 MS anti-FITC/46mer 4FB-oligonucleotide purified (lane 4); 1:3 MS anti-FITC/46mer 4FB-oligonucleotide crude (lane 5); 1:3 MS anti-FITC/46mer 4FB-oligonucleotide purified (lane 6); 1:5 MS anti-FITC/36mer 4FB-oligonucleotide crude (lane 7); 1:5 MS anti-FITC/36mer 4FB-oligonucleotide purified (lane 8); 1:3 MS anti-FITC/36mer 4FB-oligonucleotide crude (lane 9) and 1:3 MS anti-FITC/36mer 4FB-oligonucleotide purified (lane 10), in accordance with certain embodiments.

This experiment was designed to determine the optimal number of equivalents of 4FB-oligonucleotide to be reacted with 1 mol equivalent HyNic-antibody to yield greater than 90% conjugate. To that end a 46mer and a 35mer 4FB oligonucleotide were added to HyNic-anti-FITC antibody at both 3 and 5 mol equiv/mol antibody. The conjugates were purified by adsorption/desorption on Zn-magnetic beads as described in Example 2. The loading, stain and samples in each lane are:
Loading: 300 ng of antibody
Stain: DNA Silver stain
Lane 1. Marker
Lane 2. 4FB-46mer 4FB-oligonucleotide
Lane 3. 1:5 MS anti-FITC/4FB-46mer oligonucleotide crude
Lane 4. 1:5 MS anti-FITC/4FB-46mer oligonucleotide purified
Lane 5. 1:3 MS anti-FITC/4FB-46mer oligonucleotide crude
Lane 6. 1:3 MS anti-FITC/4FB-46mer oligonucleotide purified
Lane 7. 1:5 MS anti-FITC/4FB-35mer oligonucleotide crude
Lane 8. 1:5 MS anti-FITC/4FB-35mer oligonucleotide purified
Lane 9. 1:3 MS anti-FITC/4FB-35mer oligonucleotide crude
Lane 10. 1:3 MS anti-FITC/4FB-35mer oligonucleotide purified The DNA Silver stained PAGE results are presented in FIG. 6, include crude reaction and purified product samples demonstrating that 5 equivalents yielded a conjugate with more oligonucleotides/antibody as deduced by the darker bands in the samples where 5 equivalents of oligonucleotide were added.

Example 4

Figure 7:
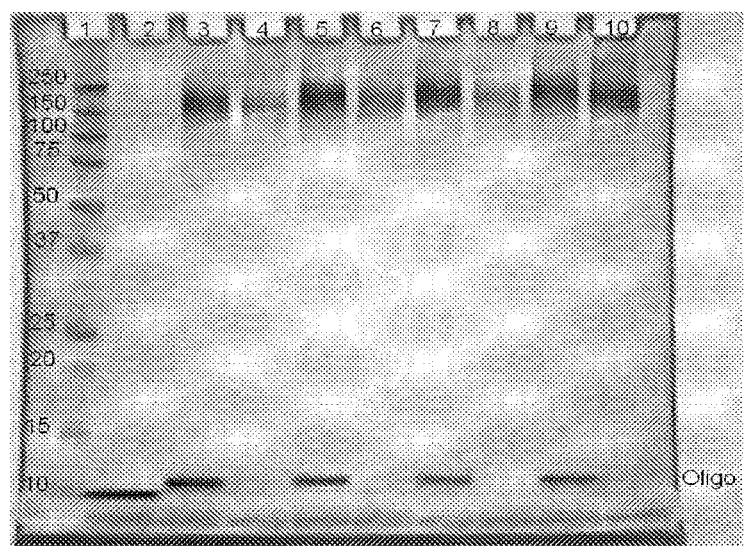
FIG. 7 is a gel electrophoresis loading 300 ng of antibody with Silver stain, containing the following lanes: Marker (lane 1); SFB-H1A (lane 2); 20×Bovine IgG/DG2A crude (lane 3); 20×Bovine IgG/DG2A purified (lane 4); 30×Bovine IgG/DG2A crude (lane 5); 30×Bovine IgG/DG2A purified (lane 6); 40×Bovine IgG/DG2A crude (lane 7); 40×Bovine IgG/DG2A purified (lane 8); 50×Bovine IgG/DG2A crude (lane 9) and 50×Bovine IgG/DG2A purified (lane 10), in accordance with certain embodiments.

This experiment was designed to determine the optimal number of equivalents of S-HyNic to be added to the antibody at 1 mg/mL to yield greater than 90% conversion to conjugate. In one experiment bIgG was reacted with 20×, 30×, 40× and 50× equivalents of S-HyNic and reacted with 5 equivalents of a 46mer 4FB-oligonucleotide. The DNA Silver stained PAGE results are presented in FIG. 7, showing excellent conversion to conjugate in the reactions as evidenced by the dark bands in each lane and as the number of equivalents of S-HyNic are increased the number of oligonucleotides/antibody increases as the conjugate bands penetrate the gel less as the number of equivalents of S-HyNic increases resulting in the conjugation of more oligonucleotides/antibody. The loading, stain and samples in each lane are:
Loading 300 ng of antibody
Stain: DNA Silver stain
Lane 1. Marker
Lane 2. 4FB-35mer oligonucleotide
Lane 3. 20×Bovine IgG/4FB-46mer oligonucleotide crude Lane 4. 20×Bovine IgG/4FB-46mer oligonucleotide purified
Lane 5. 30×Bovine IgG/4FB-46mer oligonucleotide crude
Lane 6. 30×Bovine IgG/4FB-46mer oligonucleotide purified
Lane 7. 40×Bovine IgG/4FB-46mer oligonucleotide crude
Lane 8. 40×Bovine IgG/4FB-46mer oligonucleotide purified
Lane 9. 50×Bovine IgG/4FB-46mer oligonucleotide crude
Lane 10. 50×Bovine IgG/4FB-46mer oligonucleotide purified Example 5

Figure 8:
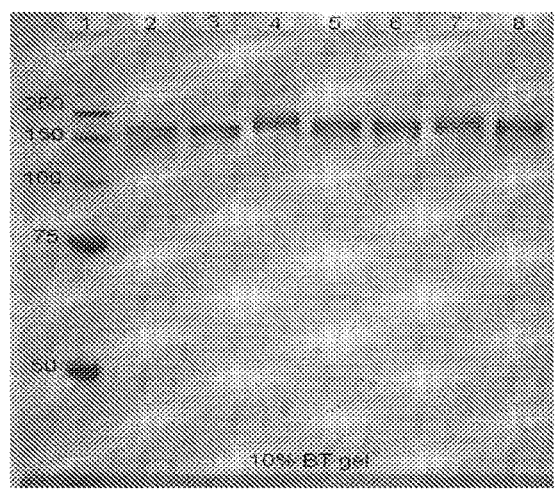
FIG. 8 is a gel electrophoresis of 1.0 itg of antibody with Commassie stain, containing the following lanes: Marker (lane 1); HyNic-MS anti-FITC (lane 2); Purified MS anti-FITC/V3B 19 bp (lane 3); Purified MS anti-FITC/H1A 35 bp (Ab 4 mg/ml) (lane 4); Purified MS anti-FITC/Amino-40 40 bp (lane 5); Purified MS anti-FITC/Amino-40 40 bp (lane 6); Purified MS anti-FITC/DG2A 46 bp (lane 7) and Purified MS anti-FITC/Amino-60 60 bp (lane 8), in accordance with certain embodiments.
Figure 9:
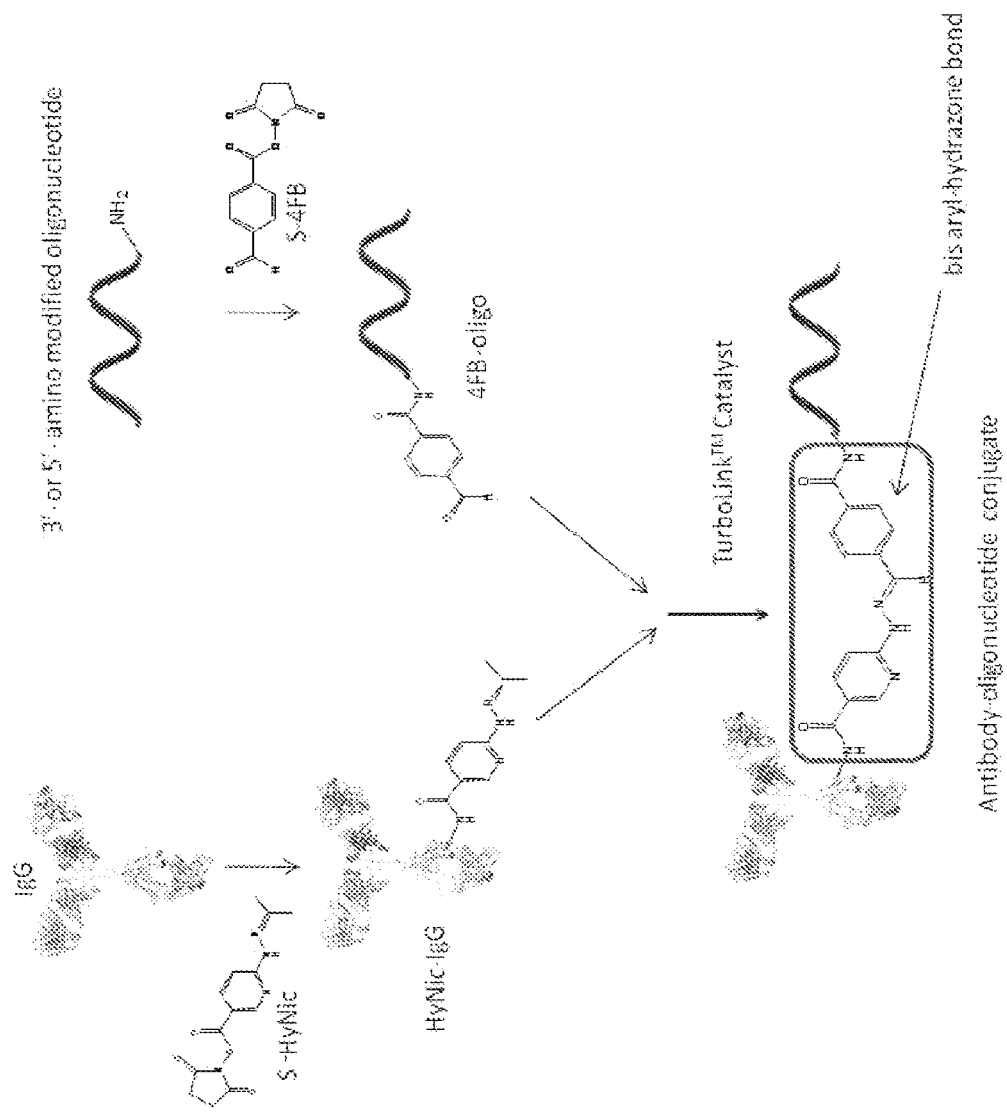
FIG. 9: Conjugation of HyNic-modified antibody with 4FB-oligonucleotide, in accordance with certain embodiments.

To determine the effect of length of oligonucleotide on conjugation efficiency 5 mol equivalents of 19mer, 39mer, 40mer, 46mer and 60mer 4FB-modified oligonucleotides were reacted with a anti-Fitc monoclonal antibody that had been modified with 30 equivalents S-HyNic at 1 mg/mL antibody concentration. The DNA Silver stained PAGE results of the purified conjugates are presented in FIG. 8, showing equivalent band density in each lane indicating that 4FB-oligonucleotides for length 19mer to 60mer conjugate with equal efficiency. The loading, stain and samples in each lane are:
Loading 1.0 ug of antibody
Stain: Commassie blue
Lane 1. Marker
Lane 2. HyNic-MS anti-FITC
Lane 3. Purified MS anti-FITC/4FB 19mer 4FB oligonucleotide
Lane 4. Purified MS anti-FITC/4FB-35mer oligonucleotide
Lane 5. Purified MS anti-FITC/4FB-40mer oligonucleotide
Lane 6. Purified MS anti-FITC/4FB-40mer oligonucleotide
Lane 7. Purified MS anti-FITC/4FB-46mer oligonucleotide
Lane 8. Purified MS anti-FITC/4FB-60mer oligonucleotide The yields of the reactions based on BCA Protein Assay (ThertnoPierce, Rockford, IL) were 55%, 52%, 50%, 50%, 47% and 50% for the 19mer, 39mer, 40mer, 46mer and 60mer 4FB-modified oligonucleotides conjugations respectively.

Example 6 this Example a polyclonal antibody (bovine IgG (bIgG)) and a mouse monoclonal antibody (anti-FITC monoclonal antibody; Jackson ImmunoResearch (Chadds Ford, PA)) were modified at 4 mg/mL with S-HyNic (20 equivalents). Following desalting into Conjugation Buffer the HyNic-antibodies were treated with a 35mer 5'-4FB oligonucleotide (5 equivalents). The conjugates were purified using USY-20 size exclusion Ultrafiltration Units (Advantec MFS, Inc., Dublin, CA). The DNA Silver stained PAGE results for conjugation to bIgG are presented in FIG. 1. The loading, stain and samples in each lane are: This example presents the preparation and purification of an oligonucleotide/antibody conjugate using the optimized conditions as determined in the Examples above. In this experiment 40mer and 60 mer 5'-amino-oligonucleotides as shown in TABLE I were 4FB-modified and conjugated to an antibody that was reacted with 30 equivalents of S-HyNic at 1 mg/mL then purified using the Zn-magnetic bead adsorption/desorption method.

TABLE 1

| # | # Base Pairs | MW | Ext Coeff | Oligonucleotide Sequence |
|---|---|---|---|---|
| Oligo-1 | 40 | 12451.2 | 374000 | 5'-G ACT GAC GAA CCG CTT TGC CTG ACT GAT CGC TAA ATC GTG-NH$_2$ |
| Oligo-2 | 60 | 18557.1 | 550200 | 5'-TTG CAT CGC CCT TGG ACT ACG ACT GAC GAA CCG CTT TGC CTG ACT GAT CGC TAA ATC GTG-NH$_2$ |

First, a stock solution of bovine IgG (bIgG) 5 mg/mL in modification buffer (100 mM phosphate, 150 'TIM NaCl, pH 7.4; Sigma (St. Louis, MO)) was prepared. bIgG stock solution (20 µL; 100 ug bIgG) was diluted with modification buffer (80 µL) to prepare a 1 mg/mL solution and was exchanged into modification buffer (using a 0.5 mL Zeba 7K Desalting columns (ThertnoPierce, Rockville, IL)) pre-equilibrated with modification buffer. A stock solution of S-HyNic (1.0 mg dissolved in anhydrous DMF (200 µL); SoluLink Biosciences (San Diego, CA)) was prepared. To the bTgG in modification buffer was added S-HyNic/DMF solution (1.12 µL; 30 mol equivalents). The mixture was mixed thoroughly by pipette and incubated at room temperature for 2.0 h. Using a 0.5 mL Zeba column the reaction mixture was desalted and buffer exchanged into conjugation buffer (100 mM phosphate, 150 mM NaCl, pH 6.0). This HyNic-antibody was used directly in the conjugation reaction.

A 3'-Amino-modified 40mer Oligo-1 (11.1 ODs; Eurogentec (San Diego, CA)) was dissolved in 50 mM NaOH (30 µL) and was buffer exchanged into modification buffer using a 0.5 mL Zeba desalting column pre-equilibrated in modification buffer. The OD/µL of the final oligo solution was determined to be 0.33 OD/µL. A stock solution of S-4FB (1.0 mg; SoluLink Biosciences) in anhydrous DMF (25 µL) was prepared. To the desalted oligo was added DMF (15 µL) followed by S-4FB/DMF solution (3.7 µL; 20 mol equivalents). The reaction mixture was thoroughly mixed and allowed to incubate at room temperature for 2 h. The reaction mixture was exchanged into conjugation buffer (100 mM phosphate, 150 mM NaCl, pH 6.0) using a 0.5 mL Zeba desalting column pre-equilibrated with conjugation buffer and the OD/µL was determined. This prepared a 4FB modified 5'-amino-modified oligonucleotide that was used directly in the conjugation step.

3'-4FB-40mer Oligo-1 (30.8 µL; 5 mol equivalents) was added followed by addition of TurboLink™ Catalyst (14 µL (¹⁄₁₀ volume); 100 mM aniline, 100 mM phosphate, 150 mM NaCl, pH 6.0). The reaction mixture was incubated at room temperature for 2 hours.

The IMAC Zn SepFast MAG Media (120 µL of a 50% slurry, Biotoohnics, UK) was prepped by addition of the beads 1.5 mL microcentrifuge tube, magnetizing the beads on a magnetic stand and the supernatant was removed. The beads were washed three times with binding buffer (200 µL; 100 mM phosphate, 150 mM NaCl; pH 6.0). Following removal of the final wash the entire volume (~110 µL) of the completed antibody-oligonucleotide conjugation reaction was added directly onto the bead pellet. The reaction/bead mixture was carefully mixed by swirling with a pipette tip for 30 seconds. The beads were allowed to settle for 15 min at room temperature (18-25° C.). The slurry was mixed again by swirling and allowed to settle for an additional 15 min. The tube was placed on a magnetic stand for 1 min to pellet the beads and the supernatant was gently removed and discarded. The bead pellet was washed three more times with 400 AL wash buffer discarding the supernatant each time.

The conjugate was then eluted and removed from the beads by adding 50 μL bead elution buffer (300 mM imidazole, 300 mM NaCl, 50 mM EDTA, 70 μg/mL (83.3 μM) (His)$_6$ peptide to the bead pellet. The slurry was gently mixed by swirling with a pipette tip for 30 sec and incubate the settled slurry for 15 minutes mixing gently at 5 minute intervals. The tube was placed into the magnetic stand to allow the beads to pellet for 1 min. The supernatant containing the affinity purified antibody-oligonucleotide conjugate was transferred into a new 1.5 mL tube. The beads were eluted three more times with 50 μL elution buffer to obtain the maximum conjugate recovery. The combined eluants were buffer exchanged into storage buffer (PBS, 1 in M EDTA). Oligonucleotide concentration was determined spectrophotometrically by determining the conjugate's absorbance at 260 nm. Antibody concentration was determined using the BCA assay (ThermoPierce, Rockville, IL). Typical yields are 30-50% based on protein BCA assay. The molar substitution ratio is 2.0-2.5 oligonucleotides/antibody. The conjugates were further analyzed by gel electrophoresis using 12% Bis-Tris Gel (Invitrogen (Carlsbad, CA)) and visualized by UV-backshadowing followed by Coomassie Blue or DNA Silver Stain (GE HealthCare (Piscataway, NJ)).

Example 7

Protocol for Preparation of an Antibody/Oligonucleotide Conjugate on a Solid Phase Support (Prospective).

MAC Zn SepFast MAG Media (120 μLot-a 50% slurry, Biotoolmics, UK) can be prepped by addition of the beads 1.5 mL microcentrifuge tube, magnetizing the beads on a magnetic stand and the supernatant can be removed. The beads can be washed three times with Binding Buffer (200 μL; 100 mM phosphate, 150 mM NaCl; pH 6.0). Antibody (100 ug) in 100 in Binding Buffer is added to the beads. The antibody/bead mixture can be carefully mixed by swirling with a pipette tip for 30 seconds. The beads can be allowed to settle for 15 min at room temperature (18-25° C.). The slurry can be mixed again by swirling and allowed to settle for an additional 15 min. The tube can be placed on a magnetic stand for 1 min to pellet the beads and the supernatant can be gently removed and discarded. The bead pellet can be washed three more times with 400 μL Modification Buffer discarding the supernatant each time. To the bead slurry can be added a 20 mg/mL solution sulfo-S-HyNic (20-50 mol equivalents) in Modification Buffer. The beads can be swirled and allowed to incubate at room temperature for 2 h. The bead reaction mixture can be diluted to 400 μL with Conjugation Buffer swirled and allowed to stand for 15 min. The tube can be placed on a magnetic stand for 1 min to pellet the beads and the supernatant can be gently removed and discarded. The bead pellet can be washed three more times with 400 μL, Conjugation Buffer discarding the supernatant each time. To the beads can be added 4FB-oligonucleotide (3-5 equivalents) and a ¹⁄₁₀ volume of TurboLink buffer. The reaction mixture can be swirled and allowed to incubate at room temperature for 1-16 h. The tube can be placed on a magnetic stand for 1 min to pellet the beads and the supernatant can be gently removed and discarded. The beads can be washed with 25 mM sodium phosphate, 300 mM sodium chloride, 0.05% Tween-20, pH 7.5 for 4 times. The conjugate can be eluted from the beads with 2 5 mM EDTA, 300 mM NaCl, 250 mM Imidazole, 75 μg/mL HIS-6 peptide, pH 6.0, 4 times. The purified conjugate can be exchanged into 10 mM sodium phosphate, 149 mM sodium chloride, 1 mM EDTA, 0.05% sodium azide, pH 7.2.

Example 8

Protocol for Preparation and Purification of Protein/Oligonucleotide Conjugate (Prospective):

For example, a Streptavidin/oligonucleotide conjugate can be prepared and purified using the following protocol.

Step 1: To a solution of streptavidin (1000 μL of a 5 mg/mL solution; Roche Biosciences) in modification buffer can be added a solution of S-4FB (9.7 μL of a 10 mg/mL solution in anhydrous DMF; 10 mol equiv.). The reaction mixture can be gently vortexed and allowed to stand at room temperature for 1.5 h. The reaction mixture can be desalted into conjugation buffer using a 2 mL Zeba column pre-equilibrated with conjugation buffer.

Step 2: His-tag conjugation: To 4FB-streptavidin prepared in step 1 can be added HyNic-Peg2-His6-NH$_2$ (SoluLink Biosciences; 4.2 μL of a 20 mg/mL solution in conjugation buffer; 0.75 mol equivalent). The His6-StAv conjugate can be purified by adsorption of the conjugate using His-Tag Purification Chelating Agarose Beads (Agarose Bead Technologies (Tampa, FL) followed by washing to remove unconjugated streptavidin. The conjugate can be eluted off the beads using imidazole/EDTA buffer. The isolated HyNic-Peg2-streptavidin conjugate can be desalted into conjugation buffer using a 5 MWCO diafiltration apparatus to both desalt and remove unconjugated HyNic-Peg2-His6-NH$_2$.

Step 3: Preparation of HyNic-oligonucleotide: A 5'-amino-modified 38mer oligonucleotide can be exchanged and concentrated into modification buffer (100 mM phosphate, 150 mM NaCl, pH 7.4) using a 5K MWCO Vivaspin column (Sartorius Stedim, Purchase, NY). The final concentration can be adjusted to 0.3 OD/. To the oligo in modification buffer (33.4 μL; 30 nmol) is added DMF (16.7 μL) and S-HyNic (11 μL of a 10 mg/mL solution in DMF; 15 equivalents; SoluLink Biosciences). The reaction mixture can be vortexed and allowed to stand at room temperature for 1.5 hours). The reaction mixture can be desalted into conjugation buffer (100 mM phosphate, 150 mM NaCl, pH 6.0) using a 5 KDa MWCO VivaSpin column. Resuspension into conjugation buffer and concentration can be repeated 3 times. The oligo concentration can be adjusted to 0.25 OD/μL.

Step 4: Oligo conjugation and conjugate purification: To the 4FB-StAv-His-tag conjugate in Conjugation Buffer prepared in Step 2 (1 mol equivalent) can be added HyNic-38mer oligonucleotide (2.0 mol equiv) in conjugation and ¹⁄₁₀ volume TurboLink catalyst. The reaction mixture can be incubated at room temperature for 2 hours and the 38mer oligonucleotide-StAv-His-tag conjugate can be purified by addition of the reaction mixture to Zinc-His-tag magnetic beads and incubated for 30 min to allow the conjugate to bind to the beads. The supernatant can be removed and the buffer (0.4 mL) can be added to the beads and the mixture can be gently mixed using a pipette, incubated for 5 min and supernatant can be removed. This washing procedure can be repeated 3 more times. The conjugate can be eluted from the beads by adding elution buffer (100 mM imidazole; EDTA;

buffer) incubating for 15 minutes. The supernatant can be removed and collected in a separate tube. The elution procedure can be repeated three more times. The combined eluants can be exchanged into 5 mM EDTA, PBS using a 0.5 mL pre-equilibrated Zeba column.

Example 9

General reagents and buffers: Modification Buffer (MB)-100 mM phosphate, 150 mM NaCl, pH 7.4: Conjugation Buffer (CB)-100 mM phosphate, 150 mM NaCl, pH 6.0.

General procedure to prepare 5'-4FB-oligonucleotides from 5'-amino-HyLk oligonucleotides (see Table 2): 5'-amino-HyLk oligonucleotides (synthesized at Eurogentec, San Diego, CA) were dissolved in Modification Buffer (500 µL) and desalted using 5K MWCO VivaSpin diafiltration devices (SartoriusStedim, Purchase, NY). The oligonucleotides were diluted to 190-250 µmol/µL. A solution of S-4FB (38.11 mg) in anhydrous DMF (500 µL) was prepared. In a specific example- to amino-HyLk2' (50-150 ODs) in Modification Buffer was added DMF (½ vol) followed by S-4FB/DMF solution containing 20 mol equiv. S-4FB. The reaction mixture was incubated at room temperature for 2 h diluted to 500 µL with nuclease free water and concentrated and washed three times with nuclease free water using 5K MWCO VivaSpin diafiltration devices. The concentration of the recovered oligonucleotide was determined. The degree of 4FB incorporation was determined by a colorimetric assay wherein the 4FB-oligonucleotides were incubated with 2-hydrazinopyridine to form a chromophoric bis-arylhydrazone that absorbs at A345 with molar extinction coefficient of 24500. This was performed by adding 4FB-oligonucleotide (2 µL) to a 50 µM solution of 2-hydrazinopyridine dihydrochloride in 100 mM MES, pH 5.0 (18 µL; SigmaAldrich; St. Louis, MO) and incubated at 37° C. for 30 min followed by determination of the A345 absorbance using a NanoDrop spectrophotometer (ThermoFisher). The degree of modification was calculated using the following formula (measured A350/measured A280)/(hydrazone molar extinction coefficient (24500)/theoretical oligonucleotide molar extinction coefficient). Here, the degree of labeling was 0.67-0.96.

TABLE 2

| HyLk Sequences | |
|---|---|
| HyLk-1 | 5'-amino-cctgcgtcgtttaaggaagtac |
| HyLk-1' | 5'-amino-gtacttccttaaacgacgcagg |
| HyLk-2 | 5'-amino-ggtccggtcataaagcgataag |
| HyLk-2' | 5'-amino-cttatcgctttatgaccggacc |
| HyLk-3 | 5'-amino-gtggaaagtggcaatcgtgaag |
| HyLk-3' | 5'-amino-cttcacgattgccactttccac |
| HyLk-4 | 5'-amino-gctgacatagagtgcgatac |
| HyLk-4' | 5'-amino-gtatcgcactctatgtcagc |
| HyLk-5 | 5'-amino-tgtgctcgtctctgcatact |
| HyLk-5' | 5'-amino-agtatgcagagacgagcaca |
| HyLk-6 | 5'-amino-atgtacgtgagatgcagcag |
| HyLk-6' | 5'-amino-ctgctgcatctcacgtacat |

Example 10

General procedure to conjugate 4FB-HyLk oligonucleotides to HyNic-modified antibodies: The following example is representative of the protocol used to prepare the antibody/oligonucleotide conjugates used.

Step 1) S-HyNic/antibody modification: anti-GK1.5 was concentrated to ~5 mg/mL using a 30 kD MWCO VivaSpin diafiltration apparatus followed by desalting into Modification Buffer using a 0.5 mL Zeba desalting device. Anti GK1.5 concentration was determined using the BCA protein assay (ThermoPierce). A solution of S-HyNic (8.4 mg/mL) in anhydrous DMF was prepared. To anti-GK1.5 (0.5 mg; 167 µL of a 3 mg/mL solution) was added S-HyNic/DMF solution (2.3 µL; 20 mol equiv). The reaction mixture was incubated at room temperature for 2.5 hours then desalted into Conjugation Buffer using Zeba desalting columns. The concentration of the HyNic-modified protein was determined to be 2.45 mg/mL.

Step 2) 4FB-oligonucleotide/HyNic antibody conjugation: To the solution of HyNic-anti-GK1.5 prepared in step 1 (0.5 mg; 3.27 nmol) was added 4FB-HyLk-1 (3 mol equiv) and incubated at room temperature overnight. The conjugate was purified by size exclusion chromatography using a SuperDex 200 column (GE HealthCare) eluting with 100 mM phosphate, 150 mM NaCl, pH 7.2 at 0.5 mL/min. The protein concentration of the conjugate was determined to be 0.122 mg/mL using the BCA assay.

TABLE 3 below lists the conjugates prepared and their respective data:

| Conjugate | Antibody | Clone | Isotype |
|---|---|---|---|
| GK1.5 (α-CD4)-HyLk1 | α-CD4 (rat anti-mouse) | GK1.5 | IgG2a |
| 145-2C11 (α-CD3)-HyLk2 | α-CD3e (hamster anti-mouse) | 145-2C11 | IgG |
| 145-2C11 (α-CD3)-HyLk3 | α-CD3e (hamster anti-mouse) | 145-2C11 | IgG |
| 2.43.1 (α-CD8)-HyLk1 | α-CD8 (rat anti-mouse) | 2.43.1 | IgG2b |
| 2.43.1 (α-CD8)-HyLk2 | α-CD8 (rat anti-mouse) | 2.43.1 | IgG2b |
| 1D3 (α-CD19)-HyLk3 | α-CD19 (rat anti-mouse) | 1D3 | 1 gG1 |

Example 10-B

Pre-Assembly of Antibody-Oligonucleotide Conjugates to Complementary Oligonucleotide-Dextran-Polyfluorophore Conjugates.

Oligonucleotide sequences are detailed in Example 9, Table 2.

Antibody clone and isotype information is detailed in Example 10, Table 3.

Antibody:oligonucleotide labeling conjugates were prepared as described in Example 10.

Complementary oligonucleotide-dextran-polyfluorochrome detector conjugates were prepared as described in Example 10.

Antibody: oligonucleotide conjugates and complementary oligonucleotide:dextran:polyfluorochrome conjugates matched to create preassembled labeling constructs are shown in Table 3B.

TABLE 3B

Conjugated used to prepare preassembled labeling constructs:

| Antibody-Oligonucleotide Labeling Conjugate | Oligonucleotide:Dextran: Polyfluorochrome Detector Conjugate |
|---|---|
| α-CD4:HyLk1 | HyLk1':Dextran:Dy490 |
| α-CD8:HyLk2 | HyLk2':Dextran:Dy549 |
| α-CD19:HyLk3 | HyLk3':Dextran:Dy591 |
| α-CD43:HyLk4 | HyLk4':Dextran:Dy649 |
| α-CD62L:HyLk5 | HyLk5':Dextran:Dy405 |

Preassembly procedure: Antibody-oligonucleotide labeling conjugates were aliquoted at 0.1 µg (=6.67 pmol) IgG/sample. Each conjugate was determined by A260 assay to have a molar substitution ratio of oligonucleotide/antibody of approximately 2.0, as described in Example 6. Therefore, each sample of antibody conjugate contains 2.0× 6.67=13.3 pmol of conjugated oligonucleotide. Complementary oligonucleotide-dextran-polyfluorochrome detector conjugates were added at a 1:1 oligonucleotide ratio. Each detector conjugate was determined to have a component ratio of 1 mol complementary oligonucleotide: 1 mol dextran: 5 mol fluorochrome, as described in Example 6. Therefore, one sample of preassembled labeling construct contains the following components: 6.67 pmol IgG, 13.3 pmol oligonucleotide; 13.3 pmol complementary oligonucleotide, 13.3 pmol dextran, 66.5 pmol fluorochrome. For constructs prepared singly—one labeling conjugate combined with one detector conjugate—elements were mixed in 404, final volume of 1% BSA-DPBS buffer and incubated with rotation for 15 minutes at 24° C. For constructs prepared "in cocktail", as a mixture of five labeling conjugates and five detector conjugates, elements were combined in 2004, final volume of 1% BSA-DPBS buffer and incubated with rotation for 15 minutes at 24° C.

Cell staining by preassembled labeling constructs: Spleen from a C57BL/6 normal mouse was processed into a single cell suspension, and red blood cells were lysed by hypotonic solution. Splenic leukocytes were aliquoted at a concentration of $1.2 \times 10^6$ cells/sample, washed once in a buffer of 1% BSA in 1× Ca- and Mg-free DPBS, and resuspended for 20 minutes in 504, of αFcR hybridoma culture supernatant to block non-specific binding of antibody IgG to cells. Preassembled labeling constructs were then added to blocked leukocytes. Singly preassembled constructs were pooled and then added to cells; constructs assembled in "cocktail" were directly added to cells. For either method, final IgG concentration was 0.5 µg/250 µL or 2 µg/mL. Cells were stained for 30 minutes at 4° C., followed by one wash in 5004, 1% BSA-DPBS to remove excess labeling construct.

Flow cytometric analysis: Samples were analyzed using a BD LSRII flow cytometer equipped with lasers and optical detectors suitable for excitation of Dyomics fluorochromes and capture of emission spectra. 10,000 events were taken per sample. Cell debris and macrophage/granulocyte populations were excluded by gating lymphocytes based on cell size on FSC vs. SSC dot plots. Analysis of lymphocyte population subsets $CD4^+$, $CD8^+$, $CD19^+$, $CD43^+$ and $CD62L^+$ was performed using FlowJo software (Tree Star, Inc). Results are presented in FIG. 56.

Example 11

Biofluor-oligonucleotide conjugate synthesis: Biofluor-oligonucleotide conjugates were prepared using the following 3-step general procedure (1) biofluor modification with S-HyNic, (2) preparation of 4FB-oligonucleotide by modification of an amino-oligonucleotide with S-4FB (see above general procedure) and (3) conjugation of the HyNic-biofluor to 4FB-oligonucleotide.

Step 1) Biofluor modification procedure: R-Phycoerythrin (Febico, Taiwan) was exchanged into Modification Buffer (100 mM phosphate, 150 mM NaCl, pH 7.4) by dialysis. To a solution of R-PE (0.20 mg; 35 µL of 5.6 mg/mL solution) in Conjugation Buffer was added S-HyNic (0.77 µL of a 6.0 mg/mL solution in anhydrous DMF; 20 mol equiv). The reaction mixture was gently vortexed and allowed to react for 2.5 h at room temperature. HyNic-R-PE was purified by desalting on a 0.5 mL Zeba desalting column (ThermoPierce, Rockford IL) pre-equilibrated with Conjugation Buffer (100 mM phosphate, 150 in M NaCl, pH 6.0).

Step 3) Conjugate formation: To a solution of HyNic-R-PE (175 ug of a 2.0 mg/mL solution in Conjugation Buffer) was added 4FB-HyLk2' (15 ug of a 0.32 OD/µL solution in Conjugation Buffer: 3 mol equiv) and TurboLink buffer (1.8 µL; 100 mM aniline, 100 mM phosphate, 150 mM NaCl, pH 6.0; Solulink Biosciences, San Diego, CA) The reaction mixture was incubated at room temperature for 4 h at room temperature and at 4° C. for 16 h. The conjugate was purified by size exclusion chromatography on a SuperDex 200 column (GE HealthCare, Piscataway, NJ) to remove excess oligonucleotide. The conjugate was characterized by gel electrophoresis.

TABLE 4

Biofluor-oligonucleotide conjugates made by above protocol:

| Biofluor | Oligonucleotide |
|---|---|
| R-PE | HyLk-2' |
| APC | HyLk-1' |
| PerCP | HyLk-3' |

Example 11-B

Following the protocol of Example 11, the following is a standard procedure to prepare an oligonucleotide-tandem dye conjugate: An oligonucleotide-biofluor protein, e.g. R-PE, crosslinked APC or PerCP, as prepared above is concentrated using a diafiltration apparatus to 1-2 mg/mL biofluor concentration and buffer exchanged into Modification Buffer. A 20 mg/mL solution of second dye, e.g. Cy2, Cy3, Cy 3.5, Cy5, Cy5.5, Cy 7, Dyomics dyes, or Alexa dyes, in anhydrous DMF is prepared. To a solution of the oligonucleotide-biofluor conjugate is added 10-30 equivalents of dye to incorporate sufficient dye to quench the donor fluorescence nearly completely, i.e. degree of modification 4-8. The resulting phycobiliproteins conjugate is excited at 488 nm and the fluorescence emission is compared to that of unmodified R-PE excited at the same wavelength. Highly efficient energy transfer (>99%) occurs from the protein to the fluorescent dye.

Example 12-A

Complementary Oligonucleotide-dextran-polyfluorophore Preparation: The procedure reported below was designed to prepare 1/1 oligonucleotide/amino-dextran conjugates by conjugating <0.5 oligonucleotide/dextran and isolating the heterodimer by (1) removal of excess oligonucleotide by size exclusion chromatography followed by (2) removal of excess amino-dextran by ion exchange chromatography. Subsequently the 1/1 oligonucleotide/dextran conjugate was modified with dye-N-hydroxysuccinimide esters to incorporate the desired dyes/dextran. This method can be used with amino-dextrans of various molecular weights and the level of dye incorporation can be increased with increasing amino-dextran molecular weight. Furthermore, this method could be used with other polymeric or dendrimeric scaffolds such as PANAM dendrimers (SigmaAldrich).

Step 1) Amino-dextran desalting: 70 kD amino-dextran (14.3 mg; Invitrogen; Carlsbad, CA) was dissolved in modification buffer (1.0 mL), vortexed and heated at 55° C. to complete dissolution of the amino-dextran. The solution was desalted into Modification Buffer using a 5 mL Zeba desalting column (Thermo Pierce; Rockford, IL). Volume after desalting was 1.27 mL and theoretical recovery was 11.26 mg/mL.

Step 2A) HyNic incorporation on amino-dextran: To a solution of amino-dextran in Modification Buffer (0.24 umol; 14.3 mg; 1.27 mL of a 11.26 mg/mL solution) was treated with a solution of S-HyNic (11.32 µL of a 26.2 mg/mL solution in anhydrous DMF; 5 mol equiv) and the solution was incubated at room temperature for 2.5 h and desalted into Conjugation Buffer using a 5 mL Zeba desalting column using a 250 µL buffer stacker. The volume after desalting was 1.65 mL and a theoretical concentration based on 100% recovery of 8.67 mg/mL.

Step 2B) HyNic incorporation quantification: A 100 mM solution of 2-sulfo-benzaldehyde (2-SB) SigmaAldrich; St. Louis, MO) in 100 mM IVIES, pH 6.0 was prepared. HyNic-dextran as prepared above (2 µL) was added to the 2-SB solution (18 µL). A blank reaction wherein water (2 µL) was added to 2-SB (18 µL) was also prepared. The solutions were incubated at 40° C. for 30 min followed by determination of the absorbance of the solution at A345. The concentration of the chromophoric hydrazone product was determined using its extinction coefficient of 28000. The HyNic substitution ratio, i.e. the average number of HyNic groups/dextran, was determined by dividing the hydrazone concentration by the dextran concentration. In this reaction the MSR was 3.36.

Step 3A) To a solution of HyNic-dextran as prepared in 2A (3.0 mg; 43 nmol) was added 4FB-HyLkX'-oligonucleotide (0.5 equiv) and the reaction was incubated at room temperature for 15 h. To remove excess oligonucleotide from the conjugate the solutions were purified by size exclusion chromatography on a SuperDex 200 column (GE HealthCare) using Loading Buffer (20 mM HEPES, 25 mM NaCl; pH 7.00) as eluant at 1 mg/mL flow rate. The initial % of the first peak was collected and concentrated to <800 µL using 5K MWCO VivaSpin columns and the conjugates were diluted to 800 µL with Loading Buffer. UV spectra of the conjugates were nearly identical with respect to A350/A280 ratios. The A350 absorbance measures the bis-arylhydrazone conjugate bond. To isolate oligonucleotide/dextran conjugate the solutions were passed through Vivapure Q Mini H devices using Loading Buffer in two 400 aliquots. The filter devices were washed with Loading Buffer (2×400 µL) to remove free dextran. The HyLkX'-oligonucleotide/dextran conjugates were eluted from the support with 90 mM, 450 mM, and 750 mM NaCl in Loading Buffer. Most of the conjugate eluted in the 450 and 750 mM fractions. These two, along with the 90 mM elution, were pooled to afford conjugate in 1200 µL total volume. The pools were concentrated down to approximately 150 split, and desalted into Modification Buffer over two 0.5 mL Zebas with 30 µL stacker.

Step 3B) General example of fluorophore incorporation on oligonucleotide-amino-dextran heterodimer conjugates: A solution of Dy490 (1.0 mg; Dyomics, Germany) was dissolved in anhydrous DMF (100 To a solution of oligonucleotide-dextran heterodimer (1.06 mg; 14.1 umol) in Modification Buffer was added Dy490/DMF solution (12 µL; 10.7 mol equiv) and the reaction mixture was allowed to incubate for 2 h at room temperature than overnight at 4° C. The reaction mixture was diluted with Modification Buffer (1 mL) and loaded into a 10 kD dialysis cassette (ThermoPierce) and dialyzed against PBS (700 mL) overnight and a further 700 mL for 6 h. TABLE 5: The following oligonucleotide/dextran/dye conjugates were prepared by the above method:

TABLE 5

| Oligo | Dye |
| --- | --- |
| HyLk-1' | Dy-490 |
| HyLk-1' | LT-COR 680LT |
| HyLk-2' | LI-COR 800CW |
| HyLk-5' | Dy-405 |
| HyLk-6' | Dy-681 |
| HyLk-1' | Dy490 |
| HyLk-2' | Dy549 |
| HyLk-3' | Dy591 |
| HyLk-4' | Dy649 |
| HyLk-5' | Dy405 |
| HyLk-6' | Dy681 |

Example 12-B

Preparation of Oligonucleotide-Dextran-Polyfluors with Increasing Numbers of Fluors/Dextran:

The following procedure was used to prepare oligonucleotide-dextran-polyfluors of increasing numbers of fluors/dextran: Solutions of Dy490, Dy591 and Dy649 in anhydrous DMF (20 mg/mL) were prepared. To solutions of 20mer HyLk1'/amino-dextran heterodimer (1.0 mg at 1.0 mg/mL based on dextran as determined using the resorcinol assay) in Modification Buffer as prepared in Example 12-A (Step 3A) were added aliquots of dyes as listed in Table 5-B. The reactions were incubated at room temperature for 3 h and transferred to Pierce Slide-A-Lyzer MINT Dialysis Units, 20K MWCO and dialyzed against 0.1M sodium phosphate, 0.15M NaCl, pH 7.2 for 8 h and the buffer was changed and dialysis was continued for 4 h. The final conjugates were diluted to 1.0 mL with buffer. The degree of fluor incorporation was determined using a NanoDrop 1000 Spectrophotometer using each dye's respective absorbance maximum and molar extinction coefficient. Results are present in Table 5-B. Equivalents added were calculated by directly dissolving the dye in the vial from the vendor. The vials may have been overfilled therefore more dye than expected was added to the reaction.

TABLE 5-B

| Dy490 Equiv added | equiv incorp | Dy591 equiv added | Equi incorp | Dy649 equiv added | equiv incorp |
| --- | --- | --- | --- | --- | --- |
| 5.10 | 3.55 | 9.38 | 2.88 | 4.00 | 3.29 |
| 8.50 | 5.63 | 11.80 | 4.64 | 6.67 | 5.69 |
| 11.90 | 7.60 | 16.50 | 6.53 | 9.33 | 8.04 |

TABLE 5-B-continued

| Dy490 Equiv added | equiv incorp | Dy591 equiv added | Equi incorp | Dy649 equiv added | equiv incorp |
|---|---|---|---|---|---|
| 17.10 | 10.57 | 23.50 | 9.22 | 13.33 | 12.58 |
| 25.50 | 14.37 | 35.30 | 13.62 | 20.00 | 21.64 |

Figure 68:
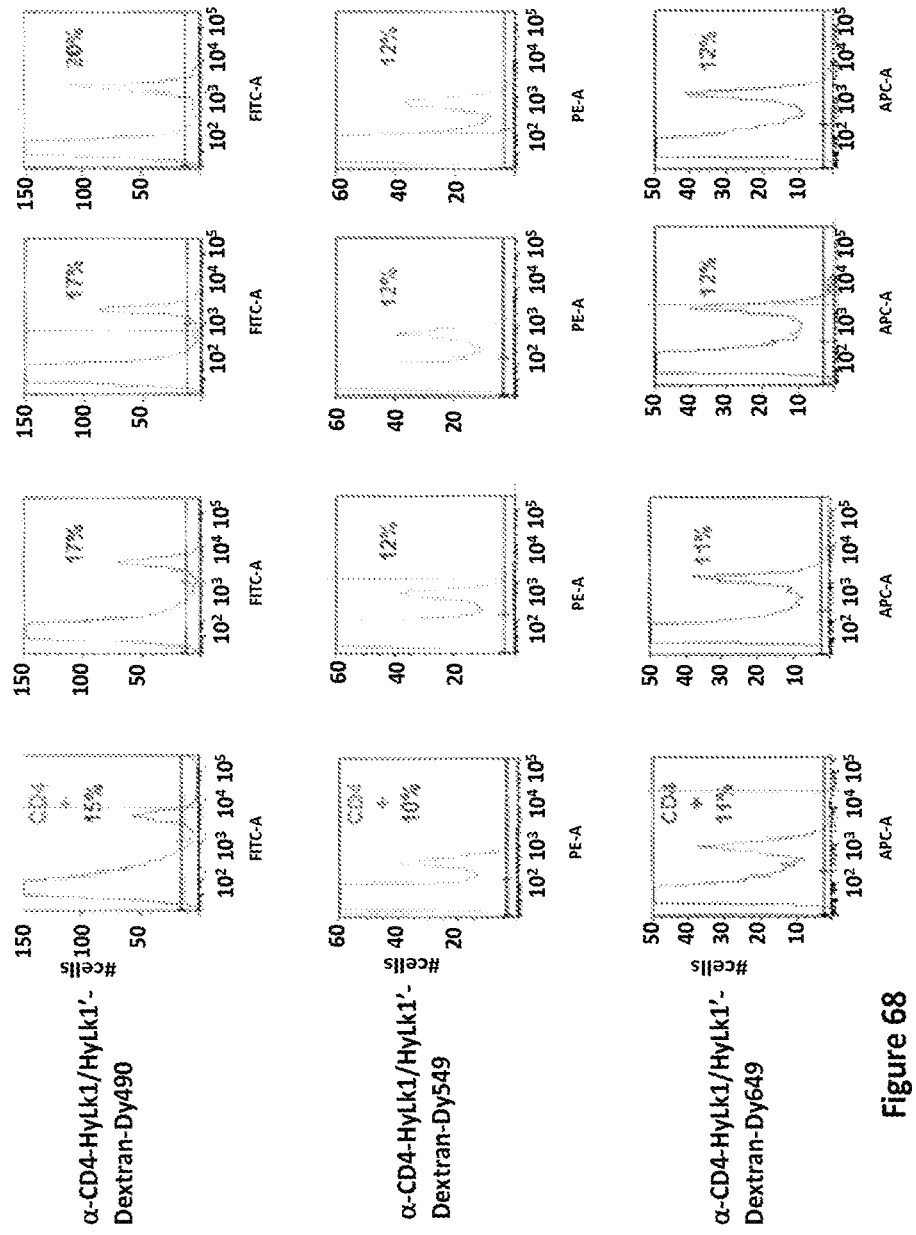
FIG. 68 illustrates the Flow cytometric results of the evaluation of complementary oligonucleotide-dextran-polyfluor conjugate detectors with increasing number of fluors/dextran scaffold, according to certain embodiments.

Flow Cytometer Procedure to test these conjugates: anti-CD4-HyLk1 conjugate (oligo/antibody ratio 4/1) on splenocytes from a C57BL/6 mouse were used to test these conjugates as described in Example 13. FIG. 68 presents the flow cytometric results of the testing of this panel of conjugates. FIG. 68 illustrates the evaluation of complementary oligonucleotide-dextran-polyfluor conjugate detectors with increasing number of fluors/dextran scaffold. The detectors were pre-assembled on α-CD4-HyLk1 antibodies, allowed to hybridize, added to cells, washed and fluorescence intensity of bound hybrid was detected by flow cytometry.

Example 13

Complementary-Oligonucleotide-HRP Conjugate Preparation:

Step 1) HyNic-modification of HRP: To a solution of HRP previously desalted into Modification Buffer (8.4 mg; 1.16 mL of a 7.27 mg/mL) was added sulfo-S-HyNic (Solulink Biosciences; 200 µL of a 11.25 mg/mL solution in Modification Buffer; 30 mol equivalents). The reaction mixture was gently vortexed then allowed to stand at room temperature for 2 h then at 4° C. for 16 h. The reaction mixture was desalted into Conjugation Buffer using a 2 mL Zeba column.

Step 2) HyNic-HRP/4FB-oligonucleotide conjugation: To a solution of HyNic-HRP (113 µL of a 6.45 mg/mL solution in Conjugation Buffer; 0.73 mg) was added 5'-4FB-HyLnk1' (73.5 µL of a 0.215 OD/µL solution in Conjugation Buffer) and aniline to a final concentration of 20 mM. The reaction was incubated overnight at 4° C. and the HRP-HyLnk1' conjugate was isolated by size exclusion chromatography on a SuperDex 200 column (GE HealthCare) eluting with PBS. EDTA to a final concentration of 1% was added to the conjugate to protect against nucleases. The final concentration of the conjugate was determined by measuring the absorbance at 403 nm and calculating the concentration using E1%, 403 nm=17.2.

Example 14

Flow Cytometry Procedure:

Antibodies used for conjugation to HyLk oligonucleotide sequences: α-CD4 (GK1.5), α-CD8 (2.43.1), and α-CD19 (1D3) were used to differentiate T and B cell populations. α-CD43 (S7) and α-CD62L (MEL-14), which recognize adhesion molecules, were used to define sub-populations of these cell types. These antibodies were conjugated to HyLk sequences as listed in Table 3.

Cell staining for flow cytometry analysis: Spleen from a C57BL/6 mouse was processed into a single cell suspension, and red blood cells were lysed by hypotonic solution. Splenocytes were used at a concentration of $0.3\times10^6$ cells/tube, and washed once in Facs buffer which consist of PBS with 0.2% BSA and 0.012% Sodium Azide. To block non-specific binding of antibodies to FcαR, cells were first incubated with 20 µL of a 2.4G2 hybridoma supernatant for 10 minutes at room temperature. Without washing the cells, 10 µL of primary Ab:HyLk oligonucleotide conjugates were added at their appropriate concentrations (Ab:HyLk pairs were titrated and used at 0.1-1.0 µg/sample). Cells were stained for 30 minutes at 4° C., and then washed two times with FACS buffer to remove free antibody. Complementary HyLkX':Dyomics-dye conjugates were then added, using 10 µL of the appropriate dilutions (the HyLkX'-Dy-dyes were titrated and used at 0.03-0.3 µg/sample). Cells were incubated for 15 minutes in the dark, at room temperature, and then washed two times with Facs buffer. Cells were resuspended in 350 µL of Facs buffer and run on an LSRII flow cytometer. For staining analysis, the lymphocyte population was selected by cell size on FSC vs. SSC dot plots. Analysis was performed using FlowJo software (Tree Star, Inc). Results are presented in FIG. 32.

Example 15

Western Blot Procedure: Chemiluminescent Detection of Tubulin by Western Blot Using HybriLink Antibody-Oligonucleotide Conjugates.

Methods:

Step 1) Cell culture and EGF-stimulation. A431 human epidermoid carcinoma cells (ATCC) were cultured in Dulbecco's Modified Essential Medium (High Glucose "DMEM-HI", from HyClone). DMEM was supplemented with 4 mM L-glutamine (Gemini BioProducts) and 10% fetal bovine serum (FBS, also from Gemini).

Cultures were grown to confluence (~$1.5\times10^7$ cells); supplemented media was removed from cultures by pipette, monolayers washed once with sterile D-PBS 1× (Sigma-Aldrich), and serum-free "starvation" DMEM was added to cultures for 24 hours to ensure complete metabolism of supplemental constituents.

Following treatment, cultures were harvested by manual dissociation (cell scraper) and transferred to conical tubes, in which they were pelleted by centrifugation for 5 minutes at 2000 RPM.

Step 2) Cell lysis and SDS-PAGE sample preparation: Lysis buffer ("Phospho-Safe", EMD) was supplemented with 1× each protease and phosphatase inhibitor cocktails, plus 5 mM EDTA (HALT™ by Pierce Protein Research Products.)

1 mL of ice-cold supplemented lysis buffer was added to each pellet, and cells were resuspended by vigorous pipetting for one minute. Suspensions were incubated on ice for 20 minutes with brief vortexing at 5-minute intervals. Lysates were clarified by high-speed centrifugation (16,500×g for 10 minutes at 4° C.).

Clarified supernatants were transferred to new sample tubes and an aliquot of the sample was analyzed for protein concentration by colorimetric analysis at 562 nm (BCA Assay Kit, Pierce).

To prepare samples for electrophoresis (SDS-PAGE), a concentrated Tris-glycerol buffer containing SDS as a denaturant, β-mercaptoethanol (BME) as a reducing agent, and Bromophenol Blue as a sample tracking dye, was diluted to 1× in clarified lysate. (All components obtained from Sigma-Aldrich.) Samples were heated at 95° C. for 5 minutes.

Step 3) SDS-PAGE and Electrotransfer: 20 µg of protein lysate was added in duplicate to lanes of a pre-cast polyacrylamide gel (7% Tris-Acetate, Novex™, Invitrogen) 20 µg of untreated lysate was loaded side-by-side as a control. Samples were electrophoresed for 60 minutes at 150 volts in the presence of tris-acetate electrophoresis buffer (Invitrogen).

Gels were immobilized on PVDF membrane (Immobilon-P™, Millipore) by electrotransfer at 30V for 2 hours. Successful transfer was confirmed by reversible protein stain (Memcode®, Pierce).

Step 4) Membrane Preparation: The membrane was immersed in 99% methanol (Ricca) for 15 seconds and dried on the benchtop for one hour to fix proteins. It was then rehydrated by brief methanol immersion followed by soaking in ultrapure water for 2 minutes.

A membrane blocking solution of 1% BSA in 1× Tris-Buffered Saline plus 0.05% Tween-20 detergent (TBS-T) was applied to the hydrated membrane for one hour at room temperature with gentle agitation. (BSA, United States Biological; TBS-T, prepared from components obtained from Sigma-Aldrich).

Excess blocking solution was subsequently washed away with 3×5 minute rinses of TBS-T. The sample membrane was cut into identical halves at this point to facilitate comparison of antibody detection strategies.

Step 5) Antibody Detection of Immobilized Tubulin: Purified rat IgG antibody against tubulin was obtained from a commercial source (Millipore).

α-tubulin:HyLk1 conjugate was prepared as described in Example 10. The conjugate was evaluated against unconjugated antibody control in a side-by-side Western blot comparison.

Blots were incubated in 2 µg/mL of either conjugated or unconjugated α-tubulin for 1 hour in 5 mL of blocking buffer, at room temperature with gentle agitation. Excess antibody was washed away by 3×5 minute rinses of TBS-T.

Step 6) Chemiluminescent Visualization of Anti-Tubulin: Complementary 'secondary' conjugates to the enzyme horseradish peroxidase (HRP) was added to each membrane for detection by a chemiluminescent substrate (SuperSignal West® Pico™ ECL assay kit, Pierce).

In the method of a standard western blot protocol, α-rat IgG:HRP (GE Healthcare) was added to the membrane strip previously incubated with the unconjugated rat α-tubulin. For the HybriLink™ western blot, oligonucleotide 1'-HRP conjugate was added to the membrane previously labeled with α-tubulin-HyLk1'.

HRP-conjugates were added at 100 ng/mL in 20 mL of blocking buffer and incubated with membranes at room temperature with rotation. The standard α-Rat IgG:HRP was incubated according to manufacturer's protocol for one hour, while the HybriLink secondary was incubated only briefly (for 15 minutes) in accordance with the goal of the project, which is to achieve comparable substrate detection in significantly less time than traditional methods.

Excess secondary conjugate was washed away with 3×5 minute rinses of TBS-T.

Chemiluminescent substrate was added to both membranes according to manufacturer's specifications, for 5 minutes at room temperature. Excess substrate was blotted away with filter paper (Whatman) and blots were visualized by exposure to autoradiography film (Phenix). Film was processed using a Konica developer and converted to digital image by a Canon document scanner. Results are presented in FIG. 36.

Example 16

Adaptor Design: The adapter design is shown in FIG. 37 wherein the Universal sequence is conjugated to the primary antibody at the 5'-end of the oligonucleotide. The Signal Generator (AG) is conjugated to the 5'-end of the complementary oligonucleotide. The adapter's sequence is constructed 5'- to 3'- to be complementary to the oligonucleotides on both the antibody and the signal generator. As demonstrated the alternate adapters as shown in FIG. 38 in which the signal generator is conjugated to the 5'-end of the oligonucleotide can be used. Table 6 below presents the adapters prepared and tested.

TABLE 6

| HyLk-Universal | Antibody-5'-cctgcgtcgttt aaggaagtac-3' |
|---|---|
| Ab-U/HyLk2'-SG | Antibody-5'-cctgcgtcgtttaag gaagtac-3'// SG-5'-cttatcgctttatgaccggacc-3' |
| Splint: U'-HyLk 2 | 5'-ggtccggtcataaagcgataatg TTAATTgtacttccttaaacgacgcag g-3' |
| Ab-U/HyLk3'-SG | Antibody-5'-cctgcgtcgtttaaggaagtac-3'// SG-5'-cttcacgattgccactttccac-3' |
| Splint: U'-HyLk 3 | 5'-gtggaaagtggcaatcgtgaagTT AATTgtacttccttaaacgacgcagg-3' |
| Ab-U/HyLk4'-SG | Antibody-5'-cctgcgtcgtttaaggaagtac-3'// SG-5'-gtatcgcactctatgtcagc-3' |
| Splint: U'/HyLk 4 | 5'-gctgacatagggtgcgatacTTAATT gtacttccttaaacgacgcagg-3' |
| Ab-U/HyLk5'-SG | Antibody-5'-cctgcgtcgtttaagga agtac-3'// SG-5'-agtatgcag agacgagcaca-3' |
| Splint: U'-HyLk 5 | 5'-tgtgctcgtctctgcatactTTAATT gtacttccttaaacgacgcagg-3' |
| Ab-U/HyLk6'-SG | Antibody-5'-cctgcgtcgtttaaggaa gtac-3'// SG-5'-ctgctgcatctcac gtacat-3' |
| Splint: U'-HyLk 6 | 5'-atgtacgtgatgcagcagTTAATT gtacttccttaaacgacgcagg-3' |

Table Notes:
CODE:
U = Universal;
Ab = antibody;
HyLk = oligonucleotide name;
SG = signal generator;
TTAATT = linker sequence

Example 17

Infrared Detection of Tubulin by Western Blot Using Antibody Oligonucleotide Conjugates, Adapter Oligonucleotides and Complementary Oligonucleotide-Poly-IR Dye Conjugates Methods:

A. Cell Culture and EGF-Stimulation.

A431 human epidermoid carcinoma cells (ATCC) were cultured in Dulbecco's Modified Essential Medium (High Glucose "DMEM-HI", from HyClone.) DMEM was supplemented with 4 mM L-glutamine (Gemini BioProducts) and 10% fetal bovine serum (FBS, also from Gemini).

Cultures were grown to confluence (~1.5×10$^7$ cells); supplemented media was removed from cultures by pipette, monolayers washed once with sterile D-PBS 1× (Sigma-Aldrich), and serum-free "starvation" DMEM was added to cultures for 24 hours to ensure complete metabolism of supplemental constituents.

Cultures were then treated with (or without) Epidermal Growth Factor (EGF, Invitrogen) to stimulate tyrosine phosphorylation throughout the proteome. EGF was added at 100 ng/mL in serum-free DMEM containing 1% bovine serum albumin (BSA, United States Biological) for 7.5 minutes. Mock cultures were incubated with serum-free media plus 1% BSA without EGF.

Following treatment, cultures were harvested by manual dissociation (cell scraper) and transferred to conical tubes, in which they were pelleted by centrifugation for 5 minutes at 2000 RPM.

B. Cell Lysis and SDS-PAGE Sample Preparation.

Lysis buffer ("Phospho-Safe", EMD) was supplemented with 1× each protease and phosphatase inhibitor cocktails, plus 5 mM EDTA (HALT™ by Pierce Protein Research Products.)

1 mL of ice-cold supplemented lysis buffer was added to each pellet, and cells were resuspended by vigorous pipetting for one minute. Suspensions were incubated on ice for 20 minutes with brief vortexing at 5-minute intervals. Lysates were clarified by high-speed centrifugation (16,500×g for 10 minutes at 4° C.).

Clarified supernatants were transferred to new sample tubes and an aliquot of each sample (EGF-treated vs. untreated) was analyzed for protein concentration by colorimetric analysis at 562 nm (BCA Assay Kit, Pierce).

To prepare samples for electrophoresis (SDS-PAGE), a concentrated Tris-glycerol buffer containing SDS as a denaturant, (3-mercaptoethanol (BME) as a reducing agent, and Bromophenol Blue as a sample tracking dye, was diluted to 1× in clarified lysate. (All components obtained from Sigma-Aldrich.) Samples were heated at 95° C. for 5 minutes.

C. SDS-PAGE and Electrotransfer.

20 μg of protein from EGF-treated lysate was added in duplicate to lanes of a pre-cast polyacrylamide gel (7% Tris-Acetate, Novex™, Invitrogen) 20 μg of untreated lysate was loaded side-by-side as a control. Samples were electrophoresed for 60 minutes at 150 volts in the presence of tris-acetate electrophoresis buffer (Invitrogen).

Gels were immobilized on PVDF membrane (Immobilon-P™, Millipore) by electrotransfer at 30V for 2 hours. Successful transfer was confirmed by reversible protein stain (Memcode®, Pierce).

D. Membrane Preparation.

The membrane was immersed in 99% methanol (Ricca) for 15 seconds and dried on the benchtop for one hour to fix proteins. It was then rehydrated by brief methanol immersion followed by soaking in ultrapure water for 2 minutes.

A membrane blocking solution of 1% BSA in 1× Tris-Buffered Saline plus 0.0.5% Tween-20 detergent (TBS-T) was applied to the hydrated membrane for one hour at room temperature with gentle agitation. (BSA, United States Biological; TBS-T, prepared from components obtained from Sigma-Aldrich.)

Excess blocking solution was subsequently washed away with 3×5 minute rinses of TBS-T. The sample membrane was cut into identical halves at this point to facilitate comparison of antibody detection strategies.

E. Antibody Detection of Immobilized Tubulin.

Purified tubulin antibody from rat (α-tubulin, clone YL1/2) was obtained from a commercial source (Millipore).

α-tubulin-HyLk1 conjugate was prepared as described in Example 10. The α-tubulin-HyLk1 conjugate was evaluated against unconjugated antibody control by side-by-side western blot comparison.

Blots were incubated in 2 μg/mL of either conjugated or unconjugated α-tubulin for 1 hour at room temperature in 5 mL of blocking buffer, with gentle agitation. Excess antibody was washed away by 3×5 minute rinses of TBS-T.

F. Visualization of Tubulin Using Infrared Dye-Conjugated Secondary Detectors.

Infrared detection of tubulin at 800 nm was conducted using either unconjugated control antibodies and anti-host infrared secondary detectors, or oligo-conjugated antibodies and oligo-infrared dye conjugate secondary probes.

Procedure was conducted as described in (A)-(E), except that the blotting membranes used for infrared detection were blocked in a proprietary buffer (Odyssey® Blocking Buffer, LI-COR Biosciences) rather than in 1% BSA-TBST. The membranes were blocked for one hour at room temperature, regardless of buffer.

Tubulin antibodies were applied as described in (E).

Infrared-dye conjugated host IgG antibodies (LI-COR Bioscience) were applied to control membranes labeled by unconjugated antibodies. IR800 dye (LI-COR Bioscience) conjugated to oligo sequence HyLk1' was applied to membranes labeled by α-tubulin-HyLk1.

Secondary conjugates were diluted at 1:10,000 in appropriate blocking buffer, supplemented with 0.2% Tween and 0.02% SDS, per manufacturer protocol. Blots were incubated for one hour at room temperature, and excess detector was removed by 3 washes of TBS-T.

Imaging was conducted using the Odyssey® Infrared Imaging System (LI-COR Bioscience).

G. Using Oligonucleotide Adapter Sequences to Visualize Tubulin Using Nonspecific Secondary Detectors.

Infrared detection of tubulin was conducted as described in Sections (A)-(G), except that the tubulin antibody used was conjugated to HyLk1 rather than HyLk2.

Oligonucleotide sequence adapter [HyLk1'-HyLk2] was applied after antibody labeling with α-tubulin-HyLk 1. Adapter was diluted at 100 ng/mL in blocking buffer and incubated on the membrane for 15 minutes at room temperature. Excess oligo adapter was removed by 3×5 minute washes of TBS-T.

Detector conjugate HyLk2'-poly-IR800CW was applied as described in (G). Labeled tubulin was imaged at 800 nm using the Odyssey® Infrared Imaging System. Results are presented in FIG. 39.

Example 18

Flow cytometry Using Oligonucleotide Adapters to Facilitate Staining of Antibody-Oligo Conjugates by Non-Complementary Oligo-Dye Detectors.

Methods:

A. Splenic Leukocyte Sample Preparation.

Spleen from a B6 mouse was processed into a single cell suspension. Erythrocytes were lysed by hypotonic solution. Leukocytes were counted and suspended overnight in a culture medium consisting of DMEM (HyClone) with 5% fetal bovine serum (Invitrogen), 1% HEPES (Sigma-Aldrich), 1% non-essential amino acids solution (Sigma-Aldrich), 1% penicillin/streptomycin antibiotic (Invitrogen), and 0.00033% (3-mercaptoethanol (GE Healthcare).

Samples were prepared the following day at a density of $6.0 \times 10^5$ cells/mL. Culture medium was removed by washing 2× in FACS buffer (D-PBS 1× with 0.2% BSA and 0.012% sodium azide). (Buffer components obtained from Sigma-Aldrich.)

Throughout this procedure, wash steps were conducted by centrifugation of samples for 5 minutes at 2000× g, followed by resuspension in 500 μL of FACS buffer.

B. Antibody Labeling.

Antibody against T-cell co-receptor CD4 (clone GK1.5) was purified from mouse hybridoma supernatant and supplied in a buffer of dialyzed PBS (University of Chicago, Fitch Monoclonal Antibody Facility).

α-CD4 antibody-HyLk1 conjugate was prepared as described in Example 12-A.

Prior to addition of α-CD4HyLk1 conjugate to leukocyte samples, non-specific binding of IgG to the Fcδ receptor was blocked by the addition of 20 μL supernatant from an α-Fcδ R producing hybridoma culture, clone 2.4G2 (University of Chicago, Fitch Monoclonal Antibody Facility.)

Antibody-oligonucleotide conjugate was then added at 1 μg/sample in 500 μL of FACS buffer and incubated for 30 minutes at 4° C.

Excess antibody conjugate was removed by 2 washes of FACS buffer.

C. Use of Oligonucleotide Adapters to Facilitate Cell Staining.

Samples to be stained by non-complementary HyLk4': Dy649 were first incubated with an oligonucleotide adapter of the structure [HyLkr:TTAATT: HyLk4].

Forward (5'->3') and reverse (3'->5') adapters were used in a 1:1 ratio to ensure a variety of structural orientations of the free HyLk4 sequence for detection by HyLk4':Dy649.

The adapter was applied at 2 μg/sample in 100 μL of FACS buffer for 15 minutes at room temperature.

Excess adapter was removed by 2 washes of FACS buffer.

D. Cell Staining with Oligonucleotide-Poly-Fluorochrome Detector Conjugates.

Following incubation with or without adapters, the samples were stained by oligonucleotide-poly-fluorochrome detector conjugates. Control samples were stained with complementary detector HyLk1':Dy490. Adapter-modified samples were stained with non-complementary detector HyLk4':Dy649.

Detectors were added at 30 ng/sample in 100 μL FACS buffer and incubated for 15 minutes at room temperature in the dark.

Excess detector was removed by 2 washes of FACS buffer. Samples were transferred to sterile, 12×75 mm tubes for flow cytometry (BD Falcon®) at a final suspension of approximately $3 \times 10^5$ cells in 500 μl. FACS buffer.

E. Analysis by Flow Cytometry.

Samples were analyzed using a FACScanto™ flow cytometer, raw data files were acquired with FACSDiva™ software (BD), and files were interpreted using FlowJo software (TreeStar). Results are presented in FIG. 40.

Example 19

Immunocytochemical Visualization of Microtubules Using HybriLink™ Oligonucleotide conjugates
Methods.
A. Cell Culture.

Human epidermoid carcinoma cell line A431 (American Type Culture Collection) is an adherent cell line exhibiting normal microtubule function throughout the cell cycle.

Cells were cultured in a medium consisting of DMEM (HyClone) with 10% fetal bovine serum (Invitrogen) supplemented with 4 mM stabilized L-glutamine (Gemini BioSciences).

After being grown to log phase, the culture monolayer was dissociated by 0.25% trypsin-53 mM EDTA (Invitrogen) in Hank's balanced salt solution (HBSS, Invitrogen). After recovery of cells by centrifugation, approximately 1.8×10μ cells in 100 μL culture medium were added to each well of an optical-glass based, culture treated, black 96-well plate (Corning CoStar®).

Plated cells were incubated overnight to allow complete adherence to the glass surface.

B. Sample Preparation for Labeling.

After one wash to remove culture medium in Dulbecco's Ca- and Mg-free PBS (DPBS, Sigma-Aldrich), cells were prepared for antibody labeling.

Microtubules were stabilized by a 30 second extraction in a buffer consisting of 80 mM PIPES, 5 mM EGTA, 1 mM $MgCl_2$, and 0.5% Triton-X-100 (components from Sigma-Aldrich). Cells were washed once in DPBS, and fixed by 5 minute incubation in ice-cold methanol (Ricca Chemical).

Fixed cells were rehydrated by 3×5 minute washes of Tris-buffered saline with 0.05% Tween®-20 (TBS-T, Sigma-Aldrich).

Non-specific binding of antibody was blocked by incubating for one hour in 1% BSA-DPBS at room temperature (BSA Fraction V, US Biological).

C. Target Labeling with Antibody.

To label microtubules, a rat IgG antibody against α- and β-tubulin (Millipore) was used. The antibody was conjugated to HyLk1 using the chemistry described in herein.

Cells were labeled by anti-tubulin-HyLk1 conjugate at a concentration of 10 μg/mL in 1% BSA-DPBS for two hours at room temperature.

Excess antibody conjugate was removed by 3×5 minute washes of DPBS.

D. Antibody Detection by Oligonucleotide:Dye Conjugate.

Detector HyLk1'-poly-Dy490 prepared as described in Example 12-A was applied to anti-tubulin-HyLk1 labeled cells at a concentration of 2 μg/mL in 1% BSA-DPBS for 30 minutes at room temperature in the dark.

After 3×5 minute washes of DPBS, cell nuclei were counterstained for 5 minutes in a solution of 0.5 μg/mL DAPI (Sigma-Aldrich) and post-fixed for 15 minutes in 10% neutral-buffered formalin (Sigma-Aldrich) to preserve dye stability for long-term sample viewing.

E. Observation.

Labeled microtubules were observed at 40× magnification with a FITC filter set on an AxioVert 40 CFL fluorescence-DIC microscope (Zeiss). Whole cells were viewed at 40× magnification by brightfield DIC microscopy. Images were acquired with AxioVision® software (Zeiss). Results are presented in FIGS. 52 and 53.

Example 20

Immunocytochemical Visualization of Microtubules Using HybriLink™ Oligonucleotide Conjugates.
Methods.

A. Cell culture. Human epidermoid carcinoma cell line A431 (American Type Culture Collection) is an adherent cell line exhibiting normal microtubule function throughout the cell cycle. Cells were cultured in a medium consisting of DMEM (HyClone) with 10% fetal bovine serum (Invitrogen) supplemented with 4 mM stabilized L-glutamine (Gemini BioSciences). After being grown to log phase, the culture monolayer was dissociated by 0.25% trypsin-53 mM EDTA (Invitrogen) in Hank's balanced salt solution (HBSS, Invitrogen). After recovery of cells by centrifugation, approximately $1.8 \times 10^4$ cells in 100 f·1 L culture medium were added to each well of an optical-glass based, culture treated, black 96-well plate (Corning CoStar®). Plated cells were incubated overnight to allow complete adherence to the glass surface.

B. Sample preparation for labeling. After one wash to remove culture medium in Dulbecco's Ca- and Mg-free PBS (DPBS, Sigma-Aldrich), cells were prepared for antibody labeling. Microtubules were stabilized by a 30 second extraction in a buffer consisting of 80 mM PIPES, 5 mM EGTA, 1 mM MgCh, and 0.5% Triton-X-100 (components from SigmaAldrich). Cells were washed once in DPBS, and fixed by 5 minute incubation in ice-cold methanol (Ricca Chemical). Fixed cells were rehydrated by 3×5 minute washes of Tris-buffered saline with 0.05% Tween®-20 (TBS-T, Sigma-Aldrich). Non-specific binding of antibody was blocked by incubating for one hour in I % BSADPBS at room temperature (BSA Fraction V, US Biological).

C. Target labeling with antibody. To label microtubules, a rat IgG antibody against α- and --tubulin (Millipore) was used. The antibody was conjugated to HyLk 1 using the chemistry described in herein. Cells were labeled by anti-tubulin-HyLk I conjugate at a concentration of 10 flg/mL in I % BSA-DPBS for two hours at room temperature. Excess antibody conjugate was removed by 3×5 minute washes of DPBS.

D. Antibody detection by oligonucleotide:dye conjugate. Detector HyLk1'-poly-Dy490 prepared as described in Example 12 was applied to anti-tubulin-HyLk1 labeled cells at a concentration of 2 flg/mL in 1% BSA-DPBS for 30 minutes at room temperature in the dark. After 3×5 minute washes of DPBS, cell nuclei were counterstained for 5 minutes in a solution of 0.5-tg/mL DAPI (Sigma-Aldrich) and post-fixed for 15 minutes in I 0% neutral buffered formalin (Sigma-Aldrich) to preserve dye stability for long-term sample viewing.

E. Observation. Labeled microtubules were observed at 40× magnification with a FITC filter set on an AxioVert 40 CFL fluorescence-Die microscope (Zeiss). Whole cells were viewed at 40× magnification by brightfield DIC microscopy. Images were acquired with AxioVision® software (Zeiss). Results are presented in FIGS. 52 and 53.

Example 21

Prophetic Example of Brightness Tuning.

In the development of a flow cytometry assay it is desired to detect and quantify two biological targets, Target A and Target B, employing two spectrally adjacent detection channels, Channel A and Channel B, respectively, where Target A is highly abundant in the sample and Target B is of significantly lower abundance, such that when employing two maximally labeled antibodies, anti-A and anti-B, spillover of the optical signal from anti-A into Channel B artifactually reduces the detectability of Target B. Since the intensity of the signal from anti-A is more than sufficient in this assay, reducing the degree of labeling (number of fluorophores per antibody molecule) of anti-A—and, optionally, increasing the degree of labeling of anti-B—can improve the detectability of Target B without significantly affecting the detectability of Target A.

A collection of separately contained reagents is provided to determine the degrees of labeling of anti-A and anti-B which best optimizes the detectability of Target B without unacceptably reducing the detectability of Target A. This collection comprises a tube of anti-A conjugated to an oligonucleotide, a tube of anti-B conjugated to the same oligonucleotide, three tubes each containing the complementary oligonucleotide conjugated to two, six, or ten Pacific Blue fluorophore moieties (PB-2, PB-6, and PB-10, respectively), and three tubes each containing the complementary oligonucleotide conjugated to two, six, or ten FITC fluorophore moieties (FITC-2, FITC-6, and FITC-10, respectively).

In separately contained reactions, three aliquots of anti-A are hybridized with aliquots of PB-2, PB-6, and PB-10, respectively, yielding the molecular probes anti-A:PB-2, anti-A:PB-6, and anti-A:PB-10 (hereinafter referred to for the sake of brevity as A:2, A:6, and A:10), and three aliquots of anti-B are hybridized with aliquots of FITC-2, FITC-6, and FITC-10, respectively, yielding the molecular probes anti-B:FITC-2, anti-B:FITC-6, and anti-B:FITC-10 (hereinafter referred to as B:2, B:6, and B:10).

Nine identical aliquots of a sample of the cells of interest are labeled with each of the nine possible two-way combinations of the molecular probes (A:2+B:2, A:2+B:6, . . . , A:10:B10), and the nine labeled cell aliquots are then separated evaluated via flow cytometry to determine the one two-way combination of molecular probes which optimally detects and quantifies the abundances of Target A and Target B in the sample.

Subsequent to this assay development study, the optimal two-way combination of the two molecular probes thus identified is employed in assays to determine the presence and abundance of Targets A and B in samples comprising this cell type.

Example 22

Prophetic Example of Labeled Antibody Catalog Simplification:

A vendor of primary-labeled antibodies whose catalog includes 800 antibodies and 30 fluorophores wishes to provide customers with the widest possible choice of antibody-fluorophore combinations without the necessity of manufacturing and marketing 800×30=24,000 different products. The vendor therefore manufactures and markets each of its 800 antibodies as conjugates with a first oligonucleotide, and each of its 30 fluorophores as conjugates with a second, complementary oligonucleotide, for a total of 830 products. A customer may purchase any antibody-oligo product in the vendor's catalog, any fluorophore-oligo product in the vendor's catalog, and assemble them via hybridization into any arbitrary fluorophore:antibody combination via a simple hybridization reaction.

Example 23

In standard solid phase oligonucleotide synthesis, the purity of the crude oligonucleotide, either deoxy, RNA or modified backbone-based oligonucleotides, may be approximately 80-90% depending in part on the length of the oligonucleotide as the yield of each step approximately 98-99%. The amount of failure sequences may increase as the length of the oligonucleotide increases. Chromatographic purification of the oligonucleotide, by either reverse phase (RP) or ion exchange (IEX), is used to increase the purity of the oligonucleotide however due to their poor resolution only marginally increase the purity at significant loss of yield. The yield of the oligonucleotide following chromatographic purification is typically 30-70% and methods are laborious and require expensive chromatographic equipment. There is a need to prepare oligonucleotides of high purity inexpensively and in high yields without the use of chromatographic equipment.

Figure 69:
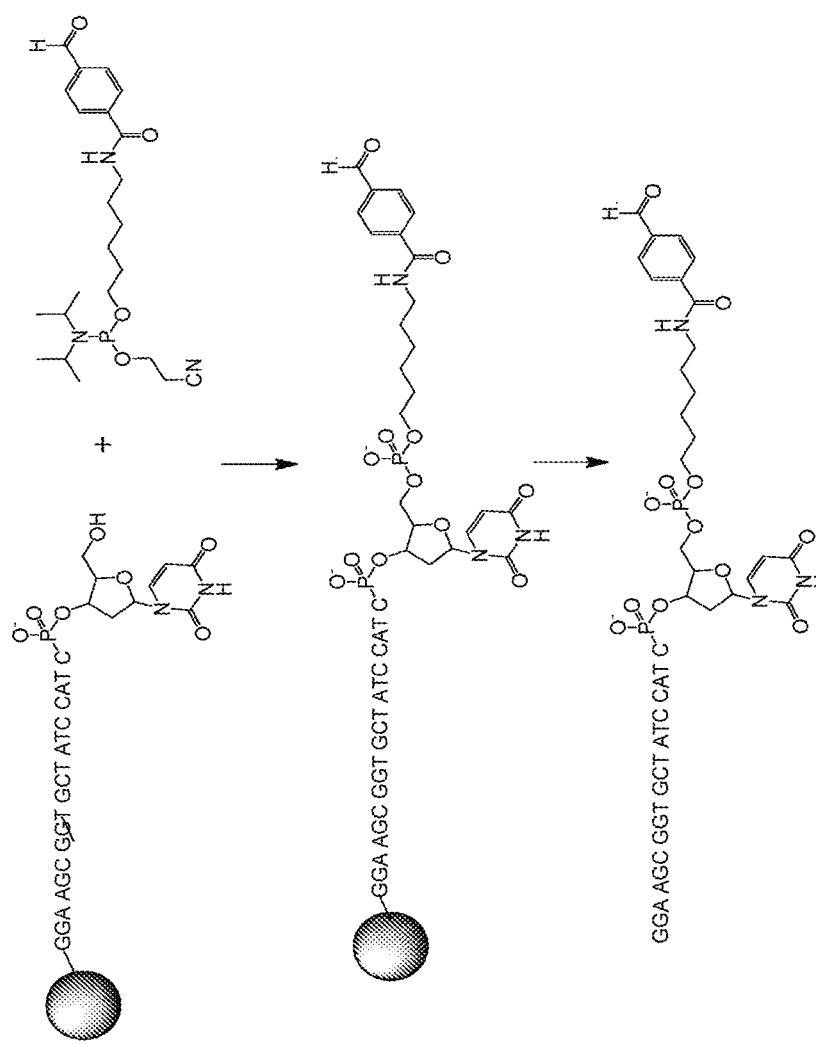
FIG. 69 illustrates an exemplary scheme for the incorporation of 4FB-moiety using a 4FB-phosphoamidite (X) on the 5'-end of an oligonucleotide during its solid phase synthesis, according to certain embodiments.

In most conjugation reaction it would be advantageous to have a linkable oligonucleotide that is of 90% or greater purity so that a higher proportion of oligonucleotide conjugates to the biomolecule or surface being modified resulting in a product that contains less unconjugated oligonucleotide. This would allow easier purification of the product or in some assays where unconjugated oligonucleotide does not substantially interfere with the assay a crude product can be used directly. Certain embodiments disclosed herein are directed to the situation where the linkable group incorporated on the oligonucleotide is an aromatic aldehyde derivative, 4-formylbenzaldehyde (4FB). FIG. 69 presents an exemplary synthetic scheme that may be used to prepare 4FB-modified oligonucleotides.

Figure 70:
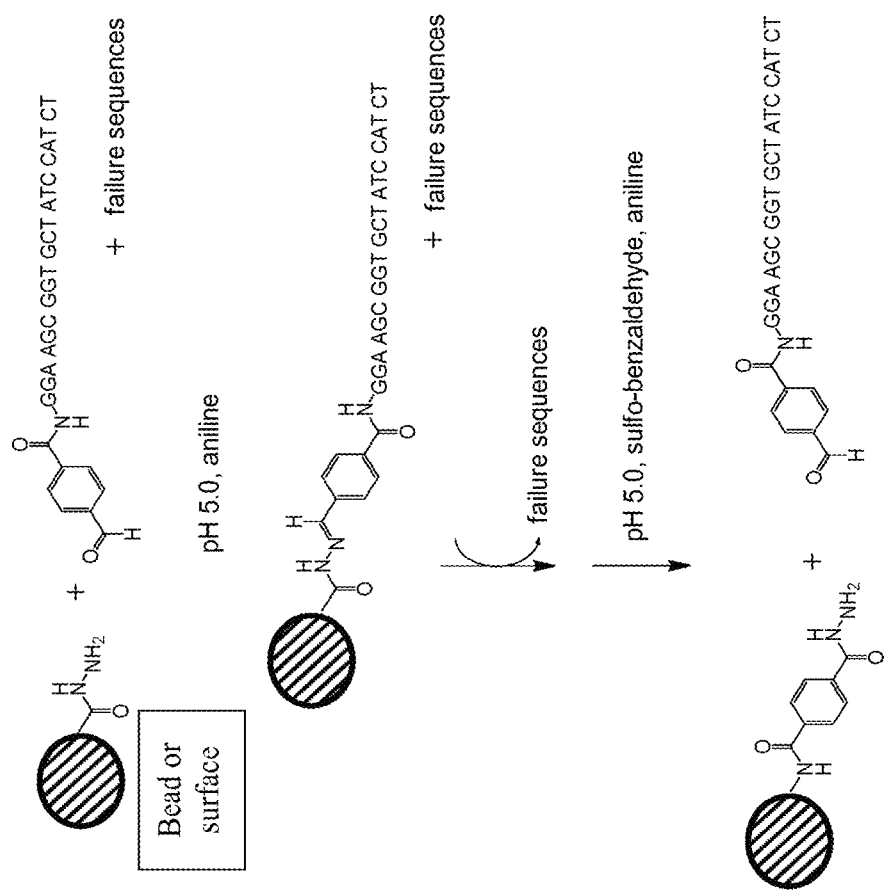
FIG. 70 illustrates an exemplary schematic representation of the process used to purify 4FB-oligonucleotides, according to certain embodiments.

In this example, we demonstrate methods in which 4FB-oligonucleotides can be purified by immobilization on hydrazide-beads, washing away the failure sequences and releasing the 4FB-oligonucleotide from the hydrazide-beads using acidic buffer containing, sulfo-benzaldehyde and aniline (see FIG. 70). The highly purified 5'-4FB oligonucleotide is prepared by (1) immobilizing the 5'-4FB-oligonucleotide on hydrazide beads using acidic buffer, pH 5-6, including 25 to 100 mM, for example 50 mM aniline, (2) wash the beads to remove failure sequences, (3) release the 5'-4-FB-oligonucleotide from the bead using a solution of sulfo-benzaldehyde and aniline in buffer, pH 6.0 and (4) exchanging the oligonucleotide into buffer of choice by diafiltration, dialysis or other methods known to those skilled in the art. In certain applications, the aniline may be replaced by other acceptable amino-benzene derivatives. The overall purity of the oligonucleotide isolated by this process is equal to or greater than 93% and the yield of highly purified oligonucleotide is approximately 70-80% based on total oligonucleotide loaded on the beads. This method is generally applicable to aromatic aldehydes-modified oligonucleotides or other aromatic aldehyde-modified biomolecules, surfaces, polymers, molecules or combinations thereof.

Figure 71A:
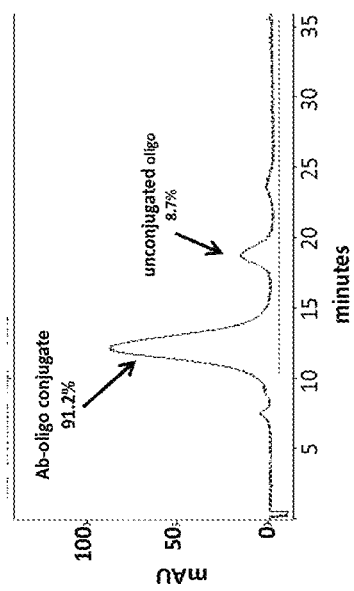
FIG. 71A shows results for conjugation of a 4FB-20mer oligonucleotide (4 mol equiv) to a HyNic-modified antibody, according to certain embodiments.
Figure 72:
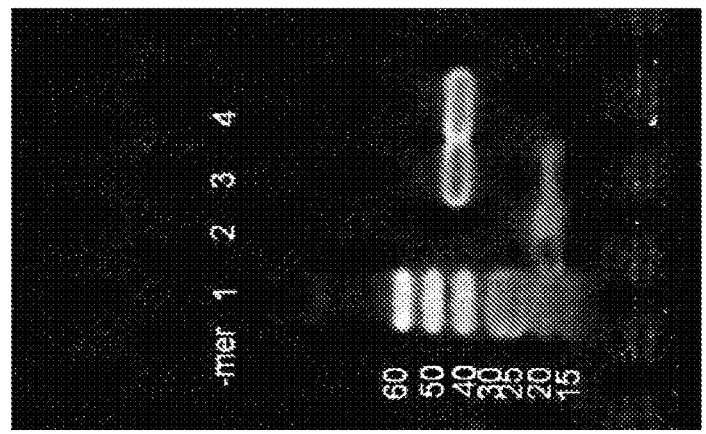
FIG. 72 shows a PAGE gel of the conjugation of a 20mer 4FB-oligonucleotide purified (Lane 2) to a HyNic-Peg2-9mer peptide (1.5 mol equiv (Lane 3) and 3.0 mol equiv (Lane 4)), according to certain embodiments.

Example 23 illustrates procedures using purified 4FB-oligonucleotides that result in 90% or greater conjugation of input oligonucleotide on HyNic-modified antibodies. FIG. 71A (purified 4FB-oligo) and 71B (crude 4FB-oligo) presents results demonstrating the efficiency of the conjugation of 4FB-oligonucleotides to a HyNic-modified antibody and FIG. 72 presents results of linking and a 4FB-oligonucleotide to a HyNic-modified peptide.

benzaldehyde and 120 mM aniline in Conjugation Buffer (× mL) and incubation at 40° C. for 2 h and a final incubation overnight at room temperature. The combined washings were concentrated using a 3K MWCO Vivaspin diafiltration device (Sartorius Stedim) and washed with water. Table 7 presents the yields for the recovered unbound and bound and released oligonucleotides.

TABLE 7

|  | ODs | 4FB-MSR | % recovered |
| --- | --- | --- | --- |
| Initial | 200.0 | 0.85 |  |
| Unbound recovered | 18.1 | 0.05 | 8.1 |
| Bound and released recovered | 157.8 | 1.03 | 79.0 |

Figure 71B:
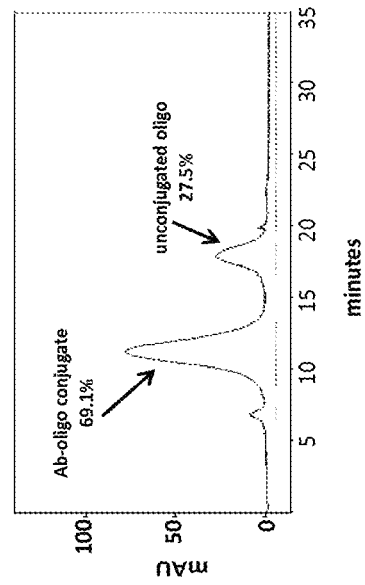
FIG. 71B shows results for a crude a 4FB-20mer oligonucleotide (5 mol equiv) to a HyNic-modified antibody, according to certain embodiments.

Conjugation of purified 4FB-oligonucleotide to HyNic-modified IgG: IgG (100 ug at 1 mg/mL) was buffered exchanged into Modification Buffer (100 mM phosphate; 150 mM NaCl, pH 8.0) using a 0.5 mL 40K MWCO Zeba Spin Desalting Column (ThermoPierce, Rockland, IL). The recovered protein concentration was confirmed by determining its A280 absorbance using a NanoDrop 1100 spectrophotometer. To the antibody solution was added S-HyNic (35 mol equivalents) in DMF (xx uL) and incubated at room temperature for 3 h. The HyNic-modified IgG was desalted into Conjugation Buffer (100 mM phosphate, 150 mM NaCl, pH 5.0) containing 25 mM aniline using a 0.5 mL 40K MWCO Zeba column pre-equilibrated with the Conjugation Buffer/aniline buffer. To the HyNic-IgG was added purified 4-FB-CLINK20-A oligonucleotide in × uL water and incubated at room temperature for 3 h. The product was desalted into PBS, pH 7.2 containing 1 mM EDTA and 0.05% azide using a 0.5 mL 40K MWCO Zeba column. Table 8 presents the results of three modifications with three different antibodies. The protein concentration was determined by Bradford protein assay. The MSR and the number of oligos/antibody were determined by AUC of analytical SEC chromatogram (see, for example, FIGS. 71A and 71B) using SuperDex200 column (GE Healthcare, Piscataway, NJ).

TABLE 8

| Antibody | Conc (mg/mL) | Amount (ug) | Free Oligo (%) | Conjugated (%) | MSR | Conc (mg/mL) | Yield (%) |
| --- | --- | --- | --- | --- | --- | --- | --- |
| Herceptin | 1.0 | 100 | 4.0 | 96.0 | 3.84 | 0.89 | 89 |
| CD4 | 1.0 | 100 | 6.9 | 91.2. | 3.65 | 0.80 | 80 |
| CD8 | 1.0 | 100 | 7.0 | 93.0 | 3.72 | 0.87 | 87 |

4FB-Oligonucleotide Purification:

Oligo 5'-4FB-CLINK20-A (61 mg; MW 6443; sequence 5'-4FB-GGAAGCGGTGCTATCCATCT) was dissolved in Conjugation Buffer (100 mM phosphate, 150 mM NaCl, pH 6.0; 3 mL; final concentration 0.491 OD/uL). Carbolink Beads (1 mL; ThermoPierce, Rockford, IL) were prewashed with Conjugation Buffer (3×5 mL). To the washed Carbolink beads was added 5'-4FB-CLINK20-A (200 ODs) and the mixture was placed in a 40° C. water bath for 2 h with shaking every 30 minutes then allowed to stand overnight at room temperature. The beads were washed with Conjugation Buffer (5×5 mL; the combined washes were retained) The immobilized oligonucleotide was dissociated from the bead by three treatments with a solution of 50 mM sulfo- FIG. 69 illustrates a scheme for the incorporation of 4FB-moiety using a 4FB-phosphoamidite (A) on the 5'-end of an oligonucleotide during its solid phase synthesis. FIG. 70 illustrates a schematic representation of the process used to purify 4FB-oligonucleotides as described in Example 23. Results are shown in FIG. 71A for conjugation of a 4FB-20mer oligonucleotide (4 mol equiv) to a HyNic-modified antibody (FIG. 71A) and in FIG. 71B for a crude 4FB-20mer oligonucleotide (5 mol equiv) to a HyNic-modified antibody using the method described herein.

Conjugation of purified 4FB-oligonucleotide to HyNic-Peptide: To two separate tubes containing 20 mer 5'-5-4FB-GGA AGC GGT GCT ATC CAT CT-3' (100 ug; 3.01 OD; 0.15 OD/uL) in Conjugation Buffer (20.04 uL; 100 mM phosphate, 150 mM NaCl, pH 6.0) was added HyNic-Peg2-c-Myc peptide (Solulink Biosciences, San Diego, CA) 1.5 and 3.0 mol equivalents at 4 mg/mL in water respectively followed by the addition of 1/10 volume of TurboLink Buffer (100 mM aniline, 100 mM phosphate, 150 mM NaCl, pH 6.0; Solulink Biosciences). The reactions were incubated at room temperature for 2 h then 48 h at 4° C. The reactions were analyzed by PAGE and the results are shown in FIG. 72. FIG. 72 shows a PAGE gel of the conjugation of a 20mer 4FB-oligonucleotide purified (Lane 2) to a HyNic-Peg2-9mer peptide (1.5 mol equiv (Lane 3) and 3.0 mol equiv (Lane 4)). This gel was developed using Sybr gold.

Example 24

Amino-Oligonucleotide-HyNic Modification:

FIG. 76 illustrates an exemplary step wise protocol that may be used to capture and detect an antigen from a biological sample, according to certain embodiments, wherein an antibody oligonucleotide conjugate is preassembled on a bead immobilized with its complementary oligo. The amino-oligonucleotide was desalted into SE Modification Buffer (100 mM Phosphate, 150 mM NaCl, 100 mM Sodium Sulfate, 10 mM EDTA, pH 7.4) using a 3 KD MWCO VivaSpin column (4×), the concentration was adjusted between 0.2-0.5 OD/ul. To the volume of amino-oligonucleotide was added a ½ volume of DMF followed by addition of S-HyNic (25 equivalents in DMF). The reaction was incubated at room temperature for 2 hours, diluted to 400 ul with SE Conjugation Buffer (100 mM Phosphate, 150 mM NaCl, 100 mM Sodium Sulfate, 10 mM EDTA, pH 6.0) and desalted using 3 KD MWCO VivaSpin column (4×). The MSR of HyNic-modified oligonucleotide was determined by mixing HyNic-oligonucleotide with 2-sulfo-benzaldehyde (SBA) reagent (0.5 mM 2-SBA in 0.1M IVIES buffer) and incubating at 40° C. for 1 hour, hydrazone formed between HyNic and 2-SBA forms a chromophoric hydrazone that absorbs at 350 nm with a molar extinction coefficient of 24500, and 260 nm (oligonucleotide) on a Spectrophotometer (NanoDrop, ND-1000) are measured and MSR calculated are shown in Table 1 (MSR of HyNic modified oligonucleotides). The OD/ul of the purified HyNic-oligonucleotide is measured and used directly in the following conjugation reaction.

TABLE 9

| Name | MS (Ml/M2) |
|---|---|
| HyNic-HyLkl' | 0.92 |
| HyNic-HyLk2' | 0.73 |
| HyNic-HyLk3' | 0.75 |

4FB-Compel beads preparation: Compel beads (Bangs Laboratories Inc., 6.3 um) (100 mg in 2.04 ml) were washed with 8 ml MES Activation Buffer (0.1 M MES, 0.5 M NaCl, pH 6.0) (2×) using a magnetic rack. 41.39 mg of EDC (Quanta Bio, Cat #10025, lot #BV34012) was weighed and dissolved in 300 ul HyClone H2O. 43.98 mg of Sulfo-NHS is dissolved into 1.5 ml of 1×MES Buffer (0.1 M IVIES, pH 5.0). To Compel beads was added EDC and Sulfo-NHS solutions prepared as above and reaction incubated at room temperature for about 20 minutes on a rotator followed by washing with 10 ml of MES Activation Buffer (4×). To the washed beads was added 9 ml of 0.5 M ethylenediamine in Borate Buffer (0.1 M Borate Buffer, pH 8.0) and the reaction was incubated at room temperature for about 2 hours on the rotator followed by washing with 10 ml of Modification Buffer (100 mM Phosphate, 150 mM NaCl, pH 7.4) containing 0.05% Tween-20 (3×), Hyclone $H_2O$ (3×), and Modification Buffer only (3×). To the washed beads was added Sulfo-4FB solution (53.37 mg in 944.3 ul Modification Buffer), the reaction was mixed by vortex and incubated at room temperature for about 2 hours on rotator followed by washing with 10 ml Conjugation Buffer (100 mM Phosphate, 150 mM NaCl, pH 6.0)/0.05% Tween-20 (3×), then Conjugation Buffer alone (6×), the concentration of the beads was subsequently determined. Serial dilutions were prepared from native Compel beads at the following concentrations: 1250, 625, 312, 156 and 78 ug/ml in Hyclone H2O, 200 ul of each solution was added to each well, standards in single well and sample in duplicate, OD at 600 nm was recorded and concentration of beads determined according to standards using SOFTmaxpro software (6.8 mg/ml). To measure the 4FB-binding capacity of modified beads, 44.1 uM 4-hydrazino-stibazole (SigmaAldrich) solution was prepared in 0.1 M IVIES Buffer/0.25 M NaCl and 100 ul was added to 100 ug of 4FB-Compel beads and native Compel beads, the reactions were incubated at room temperature for about one hour on a shaker and supernatant collected following centrifugation at 14,000 g for 4 minutes. 4-Hydrazino-stibazole binds to 4FB on beads to form a hydrazone (absorbance 350 nm, molar extinction coefficient 28500). Based on the reduction of 4-hydrazino-stibazole in the supernatant, 4FB-binding capacity of Compel beads was calculated to be 7.2 nmole/mg. These 4FB-Compel beads were used in the following experiments.

HyNic-oligonucleotide/4FB-compel beads conjugation: To the 3 mg 4FB-Compel beads was added HyNic-oligonucleotide (5.725 nmol/mg beads) in SE Conjugation Buffer followed by the addition of 1/10 of volume of TurboLink Buffer (100 mM aniline, 100 mm phosphate, 150 mM NaCl, pH 6.0). The reactions were incubated for 16 hours on a shaker. Unconjugated oligonucleotides were removed from Compel beads by washing with PBS-T (10 mM phosphate, 150 mM NaCl, pH 7.4)/0.05% Tween-20) (3×) and PBS (1×) and re-suspended into PBS at 3 mg/ml. The immobilized oligonucleotides on beads were quantified as following:

General procedure to quantify the amount of oligonucleotide immobilized on beads: The following example is representative of the protocol used.

Step 1) Complementary oligonucleotide/Dy490 modification: Amino-HyLk1 was desalted (4×) using a 3 KD MWCO VivaSpin column into Modification Buffer followed by adjusting the concentration to 0.5-0.6 OD/ul. To Amino-HyLk1 (10.5 OD in 18.6 ul; 0.56 OD/ul) was added a solution of Dy490 in anhydrous DMF (0.75 mg in 10 ul; 15 mol equiv) as shown in Table 10. The reaction mixture was incubated at room temperature for about 3 hours then desalted into PBS buffer using a 3 KD MWCO column (9×) until the flow through was clear of fluorescence. The % Dy490 incorporation on the oligonucleotides was determined by OD readings at 490 nm and 260 nm on a Spectrophotomemter (NanoDrop, ND-1000), as a peak is formed by modified Dy490 at 490 nm (OD 260 nm correction factor 0.235). The MSR of Dy490-modified oligonucleotides are listed in Table 10 (Oligonucleotides modified with Dy490). The OD/ul is determined and adjusted to 0.2 OD/ul and used in the following hybridization procedure.

TABLE 10

| Oligo | MSR |
| --- | --- |
| HyLk1 | 1.06 |
| HyLk2 | 1.03 |
| HyLk3 | 0.98 |

Step 2) Hybridization of Compel beads-HyLkX' with Dy490-HyLkX: 50 ug Compel-HyLkX' beads were washed with PBS-T (1×) then PBS (1×), centrifuged at 5000 g for 5 minutes to remove the supernatant. A 400 nM Dy490-HyLkX solution was prepared in PBS. To the Compel-HyLkX' beads the Dy490-HyLkX solution was added. The Dy490-HyLkX solution in the absence of beads or that received 4FB-compel beads without oligonucleotide conjugated were included as controls. The hybridization reaction was incubated at room temperature for 30-60 minutes on a shaker. Following centrifugation at 5000 g for 5 minutes, supernatant was collected for measuring fluorescence in solution and beads were washed with PBS/0.05% Tween-20 (2×) and PBS (1×) and subjected to FACS acquisition.

Step 3) Creation of a Dy490 standard curve using Dy490 NHS Ester: A 0.5 mg/ml solution of Dy490 in DMF was prepared. A 4000 nM Dy490 NHS Ester solution was prepared in PBS and 1:1 serial dilutions were prepared at the following concentrations: 4000, 2000, 1000, 500, 250, 125 and 62.5 nM. Each concentration was read on a fluorescence spectrophotometer (NanoDrop 3300) five times to create a linear standard curve for Dy490 fluorescence.

Step 4) The amount of HyLkX-Dy490 hybridized to the beads was determined using the following procedure: The fluorescence of the supernatant was measured and subtraction of concentration of each sample from the concentration of Dy490-HyLkX solution in the absence of beads to obtain the reduction of Dy490-HyLkX in each sample, yielded the amount of oligonucleotides being hybridized onto the beads, based on the fact that 50 ug beads in each sample are tested, immobilized oligonucleotides on beads in nmol/mg were calculated and listed in Table 11 (Oligonucleotides immobilized on Compel beads).

TABLE 11

| Name | Compels Beads (mg) | Immobilized oligonucleotides (nmol/mg) |
| --- | --- | --- |
| HyLk1' | 3 | 1.09 |
| HyLk2' | 3 | 1.02 |
| HyLk3' | 3 | 0.79 |

Step 5) Quantification of immobilized oligonucleotides on beads by FACS. Hybridized Compel beads were subjected to FACS acquisition after washing and 20,000 events collected under an appropriate setting. Results were analyzed as peak appeared on FL1 and "mean fluorescence intensity" (MFI) of each beads sample compared.

Protocol for preparation of a protein/oligonucleotide.

Step 1) BSA-HyNic modification: BSA (Jackson Immuno Research) solution was prepared at 10 mg/ml initial concentration and desalted to modification buffer using a 5 ml 7 KD MWCO Zeba column, the concentration was adjusted to 5 mg/ml after desalting. To the solution of BSA (3.6 ml of a 5 mg/ml solution) was added a solution of S-HyNic (71.4 ul of a 22.6 mg/ml solution in anhydrous DMF; 20 mol equiv). The reaction was gently vortexed and then incubated at room temperature for about 3 hours. The reaction mixture was desalted into conjugation buffer using a 10 ml 40 KD MWCO Zeba column and the concentration of BSA determined by BCA assay. The MSR of BSA-HyNic was 10.4.

Step 2) BSA-HyLkX conjugation using BSA-HyLk1 as the example: To HyNic-BSA (1.6 ml of 3.37 mg/ml in conjugation buffer) prepared in Step 1 was added 4FB-HyLk1 (Trilink, 4FB MSR 0.51) (158 ul of 0.642 OD/ul in conjugation buffer; 3 functional mole equivalent) and a 1/10 of volume of TurboLink Buffer (100 mM aniline, 100 mM phosphate, 150 mM NaCl, pH 6.0) was added. The reaction was mixed and incubated at room temperature for about 2 hours then 4° C. for about 16 hours. BSA-HyLk 1 conjugate was purified by size exclusion chromatography (Superdex200; GE HealthCare) using PBS as eluant at 0.5 ml/min (75 mM run) and the conjugate product collected between 15-26 min. The MSR of BSA-HyLk X were determined by area under the curve of the chromatograms and shown in Table 12 (MSR (oligos/BSA) of BSA-oligonucleotide conjugated).

TABLE 12

| Conjugate | MSR |
| --- | --- |
| BSA-HyLk1 | 2.96 |
| BSA-HyLk2 | 2.95 |
| BSA-HyLk3 | 3.00 |

Biotin/anti-rabbit IgG modification: Anti-rabbit IgG (Jackson ImmunoResearch) was desalted into Modification Buffer using a 2 ml 7KD MWCO Zeba Column and concentration determined (2.15 mg/me by NanoDrop (E1%=13.6). A solution of Sulfo-ChromaLink Biotin (Solulink)(18.4 mg/ml) in anhydrous DMF was prepared. To anti-rabbit IgG (0.84 mg; 391 ul of a 2.15 mg/ml solution) was added Sulfo-ChromaLink Biotin (4.2 ul; 15 mol equiv). The reaction mixture was incubated at room temperature for about 3 hours then desalted into PBS using a 2 ml 40 KDMWCO Zeba Column and the concentration determined to be 1.35 mg/ml by BCA assay and biotin incorporation of 5.34 biotins/antibody was determined spectrophotometrically using chromophoric bis-arylhydrazone linker of ChromaLink Biotin (A354, extinction coefficient 29,000).

Flow cytometric analysis of capturing antibody (anti-BSA) in solution by antigen (BSA) hybridized on beads through oligonucleotide and detected by biotin-$2^{nd}$ antibody followed by Streptavidin-RPE: HyLk1'-compel beads (50 ug/test; 17 ul of 3 mg/ml) were washed with PBS/T (PBS/0.05% Tween-20) followed by adding a 50 ul of PBS solution containing HyLk1-BSA conjugate (644 ng; 23 ul of 2.8 mg/ml). The hybridization reaction was incubated on a shaker at room temperature for about 45 minutes. The beads were washed with PBS/T (3×) by centrifugation at 5000 g for 5 minutes each time. Serial dilutions of anti-BSA (Fitzgerald) were prepared as the following: 366, 36.6, 3.66, 0.366, 0.0366 ng into 50 ul of PBS from 1 mg/ml solution and into which 50 ug beads re-suspended. The beads were incubated on the shaker at room temperature for about 1 hour followed by PBS/T wash (3×). To beads 50 ul of biotin modified anti-rabbit IgG (0.2 ug; 50 ul of 4 ug/ml) solution in PBS was added and incubated on the shaker at room temperature for about one hour followed by PBS/T wash (3×). To beads 50 ul of Streptavidin-R-Phycoerythrin (SAPE) (Invitrogen) (0.03 ug; 50 ul of 0.68 ug/ml) solution in PBS was prepared and added and the beads were incubated on the shaker at room temperature for around 30 minutes followed by PBS/T wash (3×). The beads were finally re-suspended into 300 ul PBS and subjected to acquisition on FACSCalibur, 20,000 events were collected per sample. Debris and clumps of beads were excluded by gating based on FSC vs. SSC dot plots. Analysis of PE+ beads population was performed using FlowJo software (Tree Star, Inc). Flow results are presented in FIG. 75.

Example 25

Preparation of Antibody-Oligonucleotides Conjugates of Increasing Oligonucleotide/Antibody Ratios Using Size Exclusion Chromatograph.

To α-CD4 antibody (3.42 mg at 4.94 mg/mL in Modification Buffer) was added S-HyNic (300 uL of 20 mg/mL solution in anhydrous DMF; 21 mol equiv). The reaction mixture was incubated at room temperature for 3 hours and desalted into Conjugation Buffer using 2×2 mL 7K MWCO Zeba columns. The protein concentration (BCA assay) was determined to be 3.83 mg/mL and the HyNic substitution ratio was 7.3 HyNic/α-CD4. The HyNic-modified α-CD4 antibody was divided into five tubes each containing 0.63 mg (165 uL). A solution of a 20mer 5'-4FB-oligonucleotide (MW 6312; 0.463 OD/uL) in nuclease free water was prepared. To the five aliquots of HyNic-α-CD4 were added 2.27, 3.98, 5.68, 7.95, 11.36 and 15.0 mol equiv of 5'-4FB-oligonucleotide followed by the addition of 1/10 volume of TurboLink Buffer (100 mL phosphate, 150 mM NaCl, 100 mM aniline, pH 6.0; Solulink Biosciences, San Diego, CA). The conjugates were purified by size exclusion chromatography using a Superdex200 column (GE Healthcare). Table 13 presents the data characterizing the α-CD4-oligonucleotide conjugate products.

TABLE 13

| Equiv 4FB-oligo added | Equiv 4FB-oligo incorporated | mg/mL |
| --- | --- | --- |
| 2.27 | 1.92 | 0.113 |
| 3.98 | 3.34 | 0.112 |
| 5.68 | 4.64 | 0.113 |
| 7.95 | 5.52 | 0.107 |
| 11.36 | 6.49 | 0.123 |
| 15.00 | 7.87 | 0.109 |

Figure 73:
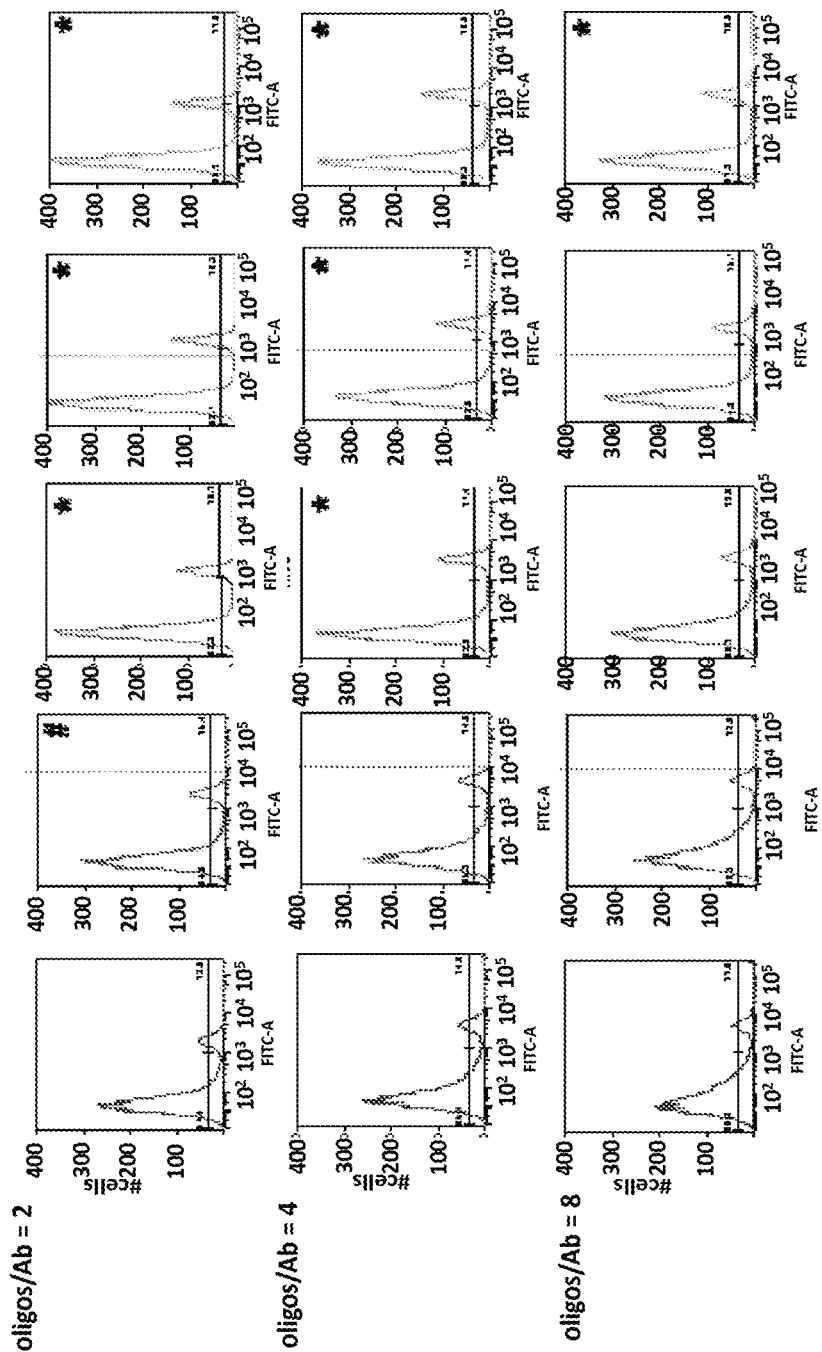
FIG. 73 shows the flow cytometric results analyzing antibody-oligonucleotide conjugates hybridized to its complementary oligonucleotide/dextran/poly-Dy490 detector with respect to the number of oligonucleotides conjugated to the antibody, according to certain embodiments.

Flow cytometric analyses of α-CD-oligonucleotide conjugates of increasing oligonucleotide/antibody ratios: The conjugates prepared as discussed herein were hybridized to their complementary oligonucleotide/dextran/Dy490 detector in 1/1 mole ratio based on incorporated oligonucleotides for 15 min at room temperature, added to cells for 30 min at 4° C., washed twice with PB. The conjugates were added to normal B6 mouse splenocytes as in Example 14 and analyzed on a FACS Canto using a 488 laser with a FITC filter. Results are presented in FIG. 73. FIG. 73 shows the flow cytometric results analyzing antibody-oligonucleotide conjugates hybridized to its complementary oligonucleotide/dextran/poly-Dy490 detector with respect to the number of oligonucleotides conjugated to the antibody. Here an α-CD4-antibody conjugated to increasing ratios of oligonucleotide/antibody hybridized to its detector complement were incubated with B6 mouse cells and analyzed by flow cytometry as described in Example 14.

Example 26

Prophetic Example Imaging:

A researcher wishing to determine the percentage of cells bearing a molecular target in a fixed, adherent cultured cell sample in a dish labels the sample first with a DNA-binding first fluorophore to label cell nuclei, then washes the sample to remove unbound DNA-binding dye, then labels the sample with a molecular probe comprising an antibody recognizing the target of interest conjugated to a first oligonucleotide hybridized to a second, complementary oligonucleotide conjugated to a second fluorophore using certain embodiments disclosed herein. After washing the sample to remove unbound molecular probe the sample is imaged in a fluorescence microscope and two fluorescent images are electronically recorded—one at the emission wavelength of the first fluorophore (labeling cellular nuclei), and one at the emission wavelength of the second fluorophore (labeling cells positive for the molecular target). Employing conventional image analysis algorithms, the total number of cells in the field is counted, the number of cells positive for the molecular target is counted, and the percentage of cells bearing the molecular target is calculated.

Example 27

Prophetic Example Imaging:

A histologist wishing to detect cells positive for a molecular target in a sectioned tissue specimen labels the tissue section with a molecular probe comprising an antibody recognizing the target of interest conjugated to a first oligonucleotide hybridized to a second, complementary oligonucleotide conjugated to either a fluorophore such as FITC or a chromophore-generating enzyme such as horseradish peroxidase using certain embodiments disclosed herein. The tissue section is next counter-stained with hematoxylin. The labeled tissue specimen is then observed microscopically (employing transmitted light microscopy in the case of a chromophore-labeled sample or fluorescence microscopy in the case of a fluorophore-labeled sample) and is manually and/or automatically scored for the presence/absence, abundance, distribution of label or combinations thereof.

Example 28

Prophetic Example Strip and Re-Probe:

A researcher desiring to identify a sub-population of cells in a chemically fixed adherent cell sample which contains six targets, Target A through Target F, uses a fluorescence microscope with only three available optical channels, Channels A, B, and C. It is therefore not possible for the researcher to measure the six targets simultaneously, or substantially simultaneously, using antibodies labeled with six different-colored fluorophores. The researcher therefore adopts the following 'strip-and-reprobe' experimental strategy.

The researcher first labels the cell sample with a cocktail comprising antibodies A, B, and C (Ab-A, Ab-B, and Ab-C, recognizing Targets A, B, and C, respectively) conjugated to oligonucleotides 1, 2 and 3, respectively, and hybridized with complementary oligonucleotides 1', 2', and 3' respectively, conjugated to fluorophores X, Y, and Z respectively using certain disclosed embodiments. The researcher then images the labeled adherent cell sample and records the locations on the dish of the cells positive for the Targets A, B, and C simultaneously or substantially simultaneously.

Next, the researcher strips the fluorescent signal moieties from the molecular probes bound to the cells by subjecting the sample to conditions of temperature and ionic conditions sufficient to dehybridize the molecular probes' oligonucleotide pairs, and washes away the dehybridized signal moieties using certain disclosed embodiments. After visually confirming the completeness of stripping (observing no residual fluorescent signals), the researcher next re-probes the cell sample (under temperature and ionic conditions sufficient to maintain oligonucleotide hybridization) by labeling it with a cocktail comprising antibodies D, E, and F, recognizing Targets D, E, and F, respectively, conjugated to oligonucleotides 1, 2 and 3, respectively, and hybridized with complementary oligonucleotides 1', 2', and 3' respectively, conjugated to fluorophores X, Y, and Z respectively using certain disclosed embodiments. The researcher then images the labeled adherent cell sample (observing the same fields observed in the first round of staining) and records the locations on the dish of the cells positive for the Targets D, E, and F simultaneously or substantially simultaneously. Cells marked in the first round of labeling as simultaneously, or substantially simultaneously, positive for Targets A, B, and C and marked in the second round of labeling as simultaneously, or substantially simultaneously, positive for Targets D, E, and F are therefore simultaneously, or substantially simultaneously, positive for Targets A, B, C, D, E and F. thereof.

Example 29

Prophetic Example Panel Optimization:

In the development of a flow cytometry assay it is desired to detect, distinguish, quantify or combinations thereof three separate sub-populations of cells in a sample, employing a reagent cocktail of three differently fluorescently labeled antibodies, Ab-A, Ab-B, and Ab-C, against three targets, Target A, Target B and Target C, respectively. After ruling out several possible fluorophores for practical considerations, the assay developer may, in principle, choose from among four remaining fluorophores (F1-1 through F1-4) to label the three antibodies, but faces a multitude of issues impacting the best choice of three from among these four, as well as the best choice of which fluor to place on which antibody, including at least one or more of the following considerations regarding spillover of signal between detection channels, different degrees of non-specific binding of the fluorophores to the cells, differential sensitivities of the fluorophores to photobleaching, and the differing intrinsic brightness's of the fluors due to their different quantum yields.

A collection of separately contained reagents is provided, comprising three tubes of Ab-A, Ab-B, and Ab-C, respectively, each conjugated to a first oligonucleotide, and four tubes of F1-1 through F1-4, respectively, each conjugated to a second oligonucleotide complementary to the first oligonucleotide using certain disclosed embodiments. In 12 separately contained reactions each antibody is hybridized to each fluorophore, respectively, yielding the molecular probes Ab-A:F1-1, Ab-A:F1-2, . . . , Ab-C:F1-4 using certain disclosed embodiments. Into separate tubes these molecular probes are next combined in the 24 possible 3-way combination cocktails (Ab-A:F1-1+Ab-B:F1-2+Ab-C:F1-3, Ab-A:F1-1+Ab-B:F1-2+Ab-C:F1-4, . . . , Ab-A:F1-4+Ab-B:F1-3+Ab-C:F1-2).

Twenty-four identical, or substantially identical, aliquots of a sample of the cells of interest are labeled with each of the 24 cocktails, respectively, and the 24 labeled cell aliquots are then separated evaluated via flow cytometry to identify the one cocktail composition which optimally detects, differentiates, and quantifies the sample's three sub-populations.

Subsequent to this assay development study, the optimal three-component cocktail thus identified is employed in assays to determine the presence and abundance of the three sub-populations of cells in samples using certain disclosed embodiments.

Example 30

Immunoturbidity:

4FB-OptiLink bead preparation: Carboxy-modified OptiLink beads as supplied (750 mg; 7.5 mL; Thermo Scientific Cat #83000550100290, 2.07 um in diameter) were dialyzed into 100 mM MES buffer pH 6.0 by injecting the suspension of beads into a Pierce Slide-A-Lyzer dialysis cassette (3.5 kD MWCO) and placing the cassette in 2 L 100 mM IVIES buffer pH 6.0 with gentle magnetic stirring for 6-16 hours (3×). The bead suspension was transferred to a 50 mL conical tube with a syringe. 819 mg of EDC (Quanta Bio, Cat #10025) was dissolved in 4 mL HyClone molecular biology grade water (cat #SH30538.03). 854 mg Sulfo-NHS (Solulink cat #S-4020) was dissolved in 15 mL MES buffer. Both of these solutions were added to the OptiLink beads, which were incubated at room temperature for 30 minutes on a rotator. The bead suspension was dialyzed again as described above and then transferred to 50 mL conical vials. A solution of ethylenediamine in Borate Buffer (0.5 M in 0.1 M borate, pH 8.0) was added to the beads and the reaction was incubated at room temperature for 12 hours on the rotator. The bead suspension was then dialyzed as described above into modification buffer (100 mM Phosphate, 150 mM NaCl, pH 7.4) and transferred into 50 mL conical vials. 1.453 g Sulfo-S-4FB was weighed and dissolved in 30 mL modification buffer. This solution was added to the beads, which were then incubated at RT for 16 hours on a rotator. The bead suspension was then dialyzed as described above in conjugation buffer (100 mM Phosphate, 150 mM NaCl, pH 6.0).

The concentration of the beads was subsequently determined. Serial dilutions were prepared from native OptiLink beads at the following concentrations: 197.6, 98.8, 49.4, 24.7 and 12.35 ug/ml in PBS (10 mM phosphate, 150 mM NaCl, pH 7.4). Similarly, a 2 uL aliquot of 4FB-OptiLlnk beads was diluted into 998 uL PBS (in duplicate). OD at 600 nm was recorded and concentration of beads determined (32.33 mg/mL) according to the standard curve generated from OD600 readings of the native beads. To measure the 4FB-binding capacity of the modified beads, a 246 uM S-Tag HyNic peptide solution was prepared in conjugation buffer. 100 uL of this solution was added to 0.5 mg 4FB-OptiLink beads (in duplicates) and 0.5 mg native OptiLink beads (in duplicates). The reactions were incubated at room temperature for 1 h on a shaker and supernatant collected following centrifugation at 10,000×g for 10 minutes. Based on the reduction of S-Tag HyNic peptide supernatant (as measured by OD 280), the 4FB-binding capacity of the OptiLink beads were calculated to be 28.0 nmol/mg. These 4FB-OptiLink beads are used in the following experiments.

Amino-oligonucleotide-HyNic Modification: The amino-oligonucleotides (HyLk-4' and HyLk-5') were desalted into Modification Buffer (100 mM Phosphate, 150 mM NaCl, pH 7.4) using a 3 kD MWCO VivaSpin column and centrifuging at 15,000×g for 10 minutes (4×). The concentration was adjusted between 0.3-0.5 OD/uL. To the volume of amino-oligonucleotide was added a ½ volume of DMF followed by addition of S-HyNic (20 mg/mL in DMF; 25 equivalents). The reaction was gently vortexed for 5 seconds and then incubated at room temperature for 2 hours. The solution was then diluted to 400 uL with Conjugation Buffer (100 mM Phosphate, 150 mM NaCl, pH 6.0) and desalted using 3 kD MWCO VivaSpin column by centrifuging at 15,000×g for 10 minutes (4×). A280 measurements of HyNic-HyLk-4' and -5' were measured to determine their final concentrations.

HyNic-oligonucleotide immobilization onto 4FB-OptiLink beads: To three aliquots of 4FB-OptiLink beads were added HyNic-oligonucleotide at 3 different equivalents for each oligo (14, 1.4, and 0.14 nmol/mg beads) in Conjugation Buffer followed by the addition of 1/10 of volume of Turbo-Link Buffer (100 mM aniline, 100 min phosphate, 150 mM NaCl, pH 6.0). The reactions were incubated for 16 hours on a shaker. Unconjugated oligonucleotides were removed from the beads by washing with PBS (10 mM phosphate, 150 mM NaCl, pH 7.4) after centrifuging the beads at 5,000×g for 10 minutes (4×). The beads were re-suspended in PBS at 10 mg/ml. Table 14 shows Oligonucleotides immobilized on OptiLink beads.

TABLE 14

| Oligo | OptiLink beads (mg) | Functional Equiv of oligonucleotide (nmol/mg) | Aniline con. (mM) | Total reaction volume (uL) |
|---|---|---|---|---|
| HyLk4' | 5 | 14, 1.4, 0.14 | 10 | 100 |
| HyLk5' | 5 | 14, 1.4, 0.14 | 10 | 100 |

α-bIgG-HyNic modification: Rabbit Anti-Bovine IgG (H+L) (α-bIgG) (Jackson Immuno Research, cat #301-005-003) solution was prepared at 2.4 mg/ml initial concentration and desalted to modification buffer using a 2 mL 7 kD MWCO zeba column. To the solution of α-bIgG (443.1 ug; 210 uL of a 2.11 mg/ml solution) was added a solution of S-HyNic (3.58 uL of a 4.8 mg/ml solution in anhydrous DMF; 20 mol equiv). The reaction was gently vortexed for 5 seconds and then incubated at room temperature for 3 hours. The reaction mixture was desalted into conjugation buffer using a 2 mL 40 kD MWCO zeba column and the concentration of α-bIgG determined by BCA assay.

α-bIgG-HyLkX conjugation (using IgG-HyLk4 as the example): To HyNic-α-bIgG (210 ug; 210 uL of 2.00 mg/mL in conjugation buffer) prepared in Step 4 was added 4FB-HyLk4 (IDT, 4FB-MSR=0.33) (2.789 uL of 0.91 OD/UL in conjugation buffer; 3 functional mole equivalents) and a 1/10 of volume of TurboLink Buffer (100 mM aniline, 100 mM phosphate, 150 mM NaCl, pH 6.0) was added. The reaction was mixed and incubated at room temperature for 4 hours and then 4° C. for 16 hours. α-bIgG-HyLk4 conjugate was purified by size exclusion chromatography (Superdex200; GE HealthCare) using PBS as eluent at 0.5 ml/min (45 min run) and the conjugate product collected between 11-17 mM. The MSR of the conjugate (number of oligos per α-bIgG) was determined by the area under the curve of the chromatograms from the HPLC trace. α-bIgG-HyLk conjugates were then concentrated to approximately 100 ug/mL with 10 kD MWCO Amicon filter units (Millipore cat #UFC801024). Concentrations of the conjugates were determined by BCA assay. Table 15 shows the MSR (oligos/α-bIgG) of α-bIgG-oligo conjugate.

TABLE 15

| Conjugate | Functional 4-FB oligo added (equiv) | MSR |
|---|---|---|
| α-bIgG-HyLk4 | 3 | 2.98 |
| α-bIgG-HyLk5 | 3 | 2.95 |

Preparation of control α-bIgG-OptiLink beads via EDC coupling: 9 mg (1 mL of a 9 mg/mL suspension) of OptiLink amino beads was washed with 1 mL 100 mM IVIES buffer, pH 5.0 (3×). Beads were vortexed for 20 seconds and sonicated for 20 seconds during each wash; beads were centrifuged at 10,000×g for 10 minutes to form a pellet from which the supernatant could be decanted. The beads were then suspended in 0.5 mL 100 mM IVIES buffer pH 5.0. To this suspension, a freshly prepared solution of 10.73 mg of EDC dissolved in 0.5 mL 100 mM IVIES buffer, pH 6.0 was added. Beads were then spun on a rotator at RT for 20 minutes. Beads were then washed as described above 3 times, and resuspended in 0.5 mL 100 mM MES buffer, pH 6.0. 309 ug of α-bIgG (140 uL of a 2.21 mg/mL solution of α-bIgG desalted into 100 mM MES buffer pH 5.0 with a 2 mL 7K MWCO zeba column) was then added to the beads. The beads were then spun on a rotator for 4 hours at RT. Beads were then washed 3 times as previously described, and were finally resuspended in 0.5 mL PBS (10 mM phosphate, 150 mM NaCl, pH 7.4).

Figure 74:
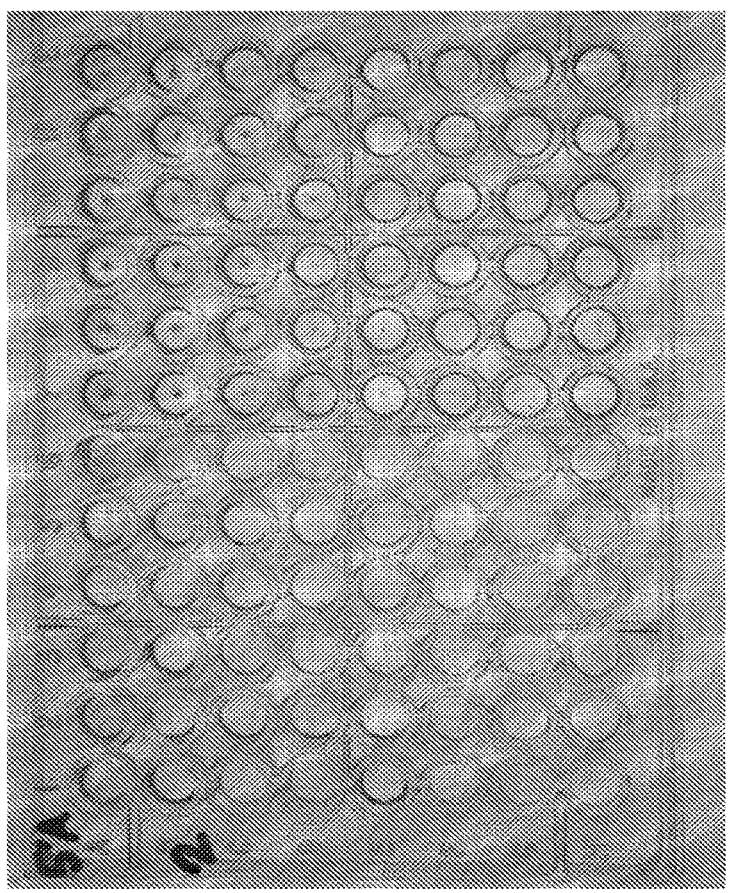
FIG. 74 shows Immunoturbidity assay results per certain embodiments.

Bovine IgG preparation: Bovine IgG (Sigma Aldrich γ-Globulins from bovine blood cat #G7516) (BIgG) was desalted using a 7 kD MWCO zeba column into modification buffer. This solution was concentrated to 1 mg/mL as determined by BCA assay. Dilutions were made into modification buffer to the following levels: 1 mg/mL, 100 ug/mL, 10 ug/mL, 1 ug/mL, 100 ng/mL, 50 ng/mL, 10 ng/mL, and 5 ng/mL. Agglutination: Samples of PBS, HyLkX'-modified beads/HyLkX-α-BIgG conjugate or EDC-coupled OptiLink-anti Bovine IgG beads were prepared and added to a 96-well plate. Serial dilutions by half were made starting with 109.68 ug beads per well down to 0.86 ug beads per well. The plate was then placed on a shaker at RT for 45 minutes to allow for hybridization and therefore immobilization of the αBIgG to the HyLk-OptiLink beads. A volume of the appropriate solution of α-bIgG solution was then added to the appropriate wells. Amounts of 100 ng, 10 ng, and 1 ng of α-bIgG were added to each amount of beads. The degree of agglutination was monitored both visually and by OD600. Results of the test are summarized in table 16 and are shown in FIG. 74. Table 16 provides the results of agglutination test with HyLk5'-OptiLink beads and the results shown in Table 16 indicate that the same level of antigen can be detected with 16 times fewer HybriLink-coupled beads when compared to the traditional EDC-coupled beads.

TABLE 16

| | EDC Beads | | | | HybriLink Beads | | | |
|---|---|---|---|---|---|---|---|---|
| | 0 ng Ag | 10 ng Ag | 1 ng Ag | | 0 ng Ag | 100 ng Ag | 10 ng Ag | 1 ng Ag |
| | 1 | 2 | 3 | 4 | 5 | 6 | 7 | 8 | 9 | 10 | 11 | 12 |
| A | − | + | + | + | + | − | + | + | + | + | + | + |
| B | − | + | + | + | + | − | + | + | + | + | + | + |

TABLE 16-continued

| | EDC Beads | | | HybriLink Beads | | | |
|---|---|---|---|---|---|---|---|
| | 0 ng Ag | 10 ng Ag | 1 ng Ag | 0 ng Ag | 100 ng Ag | 10 ng Ag | 1 ng Ag |
| | 1 | 2 | 3 | 4 | 5 | 6 | 7 | 8 | 9 | 10 | 11 | 12 |
| C | − | − | − | − | − | − | + | + | + | + | + | + |
| D | − | − | − | − | − | − | + | + | + | + | + | + |
| E | | | | | | | + | + | + | + | + | + |
| F | − | − | − | − | − | − | + | + | + | + | + | + |
| G | − | − | − | − | − | − | − | − | − | − | − | − |
| H | − | − | − | − | − | − | − | − | − | − | − | − |

Example 31

This example is directed to a method for detecting one or more biological targets of a complex sample in a detection assay using complementary detectors to which the fluor or signal generation moiety are directly conjugated. A-CD4 and α-CD8a were conjugated to the 20, 30 and 40mer amino-oligonucleotides listed in the Table 17 using the protocol described in Example 1. Table 17 also lists the MSR (oligonucleotides/antibody).

TABLE 17

| Antibody | Sequences | MSR |
|---|---|---|
| α-CD4 (Clone GK1.5) | (20 mer) 5'-C6-amino-GGA AGC GGT GCT ATC CAT CT | 3.0 |
| | (30 mer) 5'-C6-amino-CAC CCA GCC GAT GAC CTC TTA GTT TCA CGC-3 | 2.9 |
| | (40 mer) 5'-C6-amino-CAC CCA GCC GAT GAC CTC TTA GTT TCA CGC AAA GCA CAC G-3' | 3.1 |
| α-CD8a (Clone 53-6.7) | (20 mer) 5'-C6-amino-GGA AGC GGT GCT ATC CAT CT | 2.8 |
| | (30 mer) 5'-C6-amino-CAC CCA GCC GAT GAC CTC TTA GTT TCA CGC-3 | 3.0 |
| | (40 mer) 5'-C6-amino-CAC CCA GC CGAT GAC CTC TTA GTT TCA CGC AAA GCA CAC G-3' | 3.0 |

Fluorophore labeling of complementary amino-modified oligonucleotides: The complementary 20, 30 and 40mer multi-amino-modified oligonucleotides (Table 18) were conjugated to Dy490 and Dy649 dyes using protocols described in Example 12-A; Stop 3B. The amino-modified thymidines in the sequences are denoted by (T*) in the Table 18. The MSR (dyes/oligonucleotide) are also listed in the Table 18.

TABLE 14

| Complementary Multi-fluor Sequences | Fluor(s) | SR |
|---|---|---|
| (20 mer) 5'-C6-amino-AGA TGG A(T*)A GCA CCG CTT CC-C3-amino-3' | Dy490 | .1 |
| (30 mer) 5'-C6-amino-GCGTGAAAC(T*)AAGAGGTCA(T*)CGGCTGGGTG-C6-amino-3' | Dy490 Dy649 | .6 .6 |
| (40 mer) 5'-(C6-NH2)-CGTGTGCTT(T*)GCGTGAAAC(T*)AAGAGGTCA(T*)CGGCTGGGTG-C6-amino)-3' | Dy490 Dy649 | .5 .4 |

Figure 79:
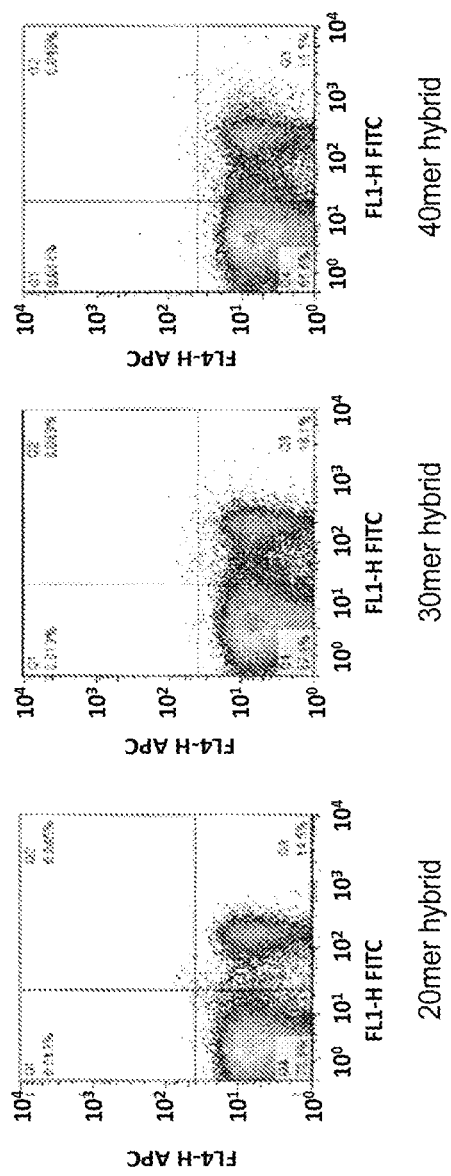
FIG. 79 presents the flow cytometry results of the binding of α-CD8 20, 30 and 40mer hybrids to CD8+ splenocytes, according to certain embodiments.

Bovine Flow cytometry results: The antibody-oligonucleotide/multi-fluor complementary oligonucleotide conjugate hybrids were prepared by incubating the antibody-oligonucleotide (1 mol equiv) with multi-fluor complementary oligonucleotide conjugate (4 mol equiv) for about 1 h at room temperature. The hybrids (500 ng) were added to splenocytes (1,000,000) and incubated at 4° C. for about 30 min, washed and analyzed by flow cytometry. FIG. 79 presents the flow cytometry results of the binding of α-CD8 20, 30 and 40mer hybrids to CD8+ splenocytes.

Example 32

Immunomagnetic Depletion Procedure:
Step 1) Preparation of Oligonucleotide and Antibody Conjugates. Biotinylated HyLk1' oligonucleotides were commercially synthesized (IDT, Coralville, Iowa). Oligonucleotides were biotinylated at the 5' end, with either no "spacer" sequence between the biotin group and the HybriLink sequence (5'-BIO:GTACTTCCTTAAACGACGCAGG-3'), or having a 44-base repeating TTAA spacer inserted between the biotin modified end and the HyLk1' sequence (5'-BIO:TTAATTAATTAATTAATTAATTTTAATTAATTAATTAATTAATTGTACTTCCTTAACGACGCAGG-3'. Her2 antibody (Herceptin®, Genentech, California) was either conjugated to oligo HyLk1 as previously described (Herceptin:HyLk1), or biotinylated (Herceptin:Biotin) and affinity purified by SoluLink Biosciences.

Step 2) Preparation of HyLk1' oligo- or Herceptin IgG-conjugated magnetic nanoparticles. Streptavidin (STV)-coated magnetic nanoparticles (0.8 µm, NanoLink™, SoluLink Biosciences) were transferred at 1 mg/mL into wash buffer (50 mM Tris-HCl, 150 mM NaCl, with 0.05% Tween-20, pH 8.0.) Washed nanospheres were separated from solution using a magnetic stand. To prepare antibody labeled beads, nanospheres were blocked at 1ing/mL for 30 m at 24° C. in a blocking buffer of sterile-filtered casein-TBS (Blocker™, Pierce Protein Research Products.) Blocked nanospheres were washed 3× in TBS-T prior to the addition of antibody. Nanospheres to which oligonucleotides were conjugated were left unblocked per manufacturer protocol. Conjugation of biotinylated oligonucleotide was conducted as follows: Oligonucleotides were solubilized in sterile H₂O to 1 nmol/µL and combined in equal portions of (BIO:H1'):(BIO:44:H1'). The mixed oligo solution was diluted to 10.4 nmol/mL into wash buffer and immediately applied to washed nanospheres at 250 µL/mg beads (=2.6 nmol/mg). Conjugation was allowed to proceed for 30 m at 24° C. with rotation. Conjugation of biotinylated antibody (αHer2:BIO) was conducted as follows: Protein content of Herceptin-biotin was confirmed by BCA assay (Pierce Protein Research Products). Antibody was applied at 40 µg/mL in 2504, TBS-T/mg nanospheres. Conjugation was allowed to proceed for 30 m at 24° C. with rotation. Following conjugation, supernatants from both sets of nanospheres (oligo- or antibody-labeled) were analyzed for remaining conjugate, either by A260 assay (oligo supernatant) or BCA assay (Herceptin supernatant). Oligo-conjugated nanospheres were determined to have 290 pmol HyLk1'/mg solids. Antibody-conjugated nanospheres were determined to have 30 µg IgG/mg solids. Conjugated nanospheres were stored overnight in TBS-T at 4° C. and used for immunomagnetic depletion the following day.

Step 3) Cell culture and tumor cell "spiking". SKBR-3 human adenocarcinoma cells (ATCC) were cultured in McCoy's 5A growth medium supplemented with 10% fetal bovine serum (FBS, Gemini BioSciences), 4 mM L-glutamine (Gemini), and 1KU/1KU penicillin/streptomycin solution ('pen/strep', Invitrogen). CCRF-CEM human T-cell lymphocytes were cultured in RPMI-1640 culture medium supplemented with 10% FBS and 1KU/1KU pen/strep. All cultures were grown in sterile, culture treated flasks in a humidified, 37° C. incubator maintained at 5% CO2. Just prior to immunodepletion, adherent SKBR-3 cells were harvested by trypsinization of the monolayer, followed by transfer to conical tubes. Non-adherent CCRF-CEM cells were transferred to conical tubes without trypsinization. Both cultures were pelleted by centrifugation for 5 min at 800×g, and resuspended in a buffer of 0.2% bovine serum albumin in phosphate buffered saline (BSA-PBS). After counting cells per mL, 10% tumor cells were added ("spiked") into CCRF-CEM lymphocytes. Samples for immunodepletion were aliquoted at $1 \times 10^6$ cells/mL prior to downstream handling.

Step 4) Herceptin labeling of spiked cell preparations. Prior to Herceptin labeling, $1 \times 10^6$ 'spiked' cells were blocked for 30 m at 24° C. in 1004, of 0.2% BSA-PBS buffer containing 10 µL, human Fc receptor antibodies (αFcX "TruStain", BioLegend, San Diego, California) Without washing, 15 µg of Herceptin:HyLk1 or 15 µg of Herceptin:Biotin was added to blocked cells. Labeling was allowed to proceed for 60 m at 4° C. with rotation. Cells were washed 2× in 0.2% BSA-PBS prior to magnetic depletion.

Step 5) Immunomagnetic depletion. Conjugated magnetic nanospheres were washed 3× in 1 mL PBS/mg solids to remove traces of Tween-20 detergent. 500 m nanospheres were added to washed, labeled or unlabeled cells. For HyLk1' conjugated nanospheres, 500 µg solids at 290 nmol oligo/mg solids presented 145 nmol HyLk1' per sample. According to current literature reporting $2 \times 10^6$ Her2 molecules per SKBR-3 tumor cell $\times 0.1 \times 10^6$ tumor cells per sample=$2 \times 10^{11}$ Her2 molecules=333 fmol Her2 per sample. Assuming 100% antibody binding, and a molar substitution ratio of 4.0 oligos per TgG molecule, this translates to 1.3 pmol oligo per labeled cell sample. 145 nmol HyLk1' immobilized on beads thus represents >100× excess of available complementary oligo to hybridize to labeled cells. For Herceptin:biotin conjugated nanospheres, 500 µg presents 15 µg IgG per sample, the same amount of Herceptin used to label cells in the HybriLink test group. Following addition of 500 µg nanospheres per sample, immunomagnetic capture (depletion) of Her2+ cells was allowed to proceed for 60 m at 4° C. with rotation. The microspheres were then isolated from cell suspension by magnetic separation. Cellular supernatants were placed on ice. Spheres were washed in 2×500 µL of 0.2% BSA-PBS and sample washes were combined with sample supernatants for analysis by flow cytometry of depleted cellular preparations.

Description of sample groups. Samples included the following preparations: (A) Unlabeled cells without nanospheres (undepleted sample). (B) Herceptin-HyLk1 labeled cells plus unlabeled nanospheres (mock control 1). (C) Unlabeled cells plus unlabeled nanospheres (mock control 2). (D) Unlabeled cells plus Herceptin:Biotin conjugated nanospheres (conventional, state-of-the-art method). (E) Herceptin:Biotin-labeled cells, plus streptavidin nanospheres (modification of conventional method). (F) Herceptin:HyLk cells plus HyLk1' labeled nanospheres (HybriLink novel method). See FIG. 81.

Step 6) Fluorescent staining of depleted cell samples. Fluorescent-conjugated, monoclonal antibodies against Her2 (αHer2:PE, BioLegend) and tumor cell antigen EpCAM (αEpCAM:APC, BioLegend) were applied to cells in a staining cocktail of 125 ng αHer2:PE plus 30 ng αEpCAM:APC in 1004, of 0.2% BSA-PBS for 60 m at 4° C. with rotation. Samples were pelleted by centrifugation for 5 m at 800×g, resuspended in 2504, 0.2% BSA-PBS, and immediately analyzed by cytometer. Undepleted, spiked cell samples were also stained with fluorescent host isotype controls (mouse IgG1:PE and mouse IgG2b:APC) to determine background levels of cellular staining, known to be high in most lymphocytes. Undepleted, unstained spiked cells were also prepared as an additional background control.

Figure 81:
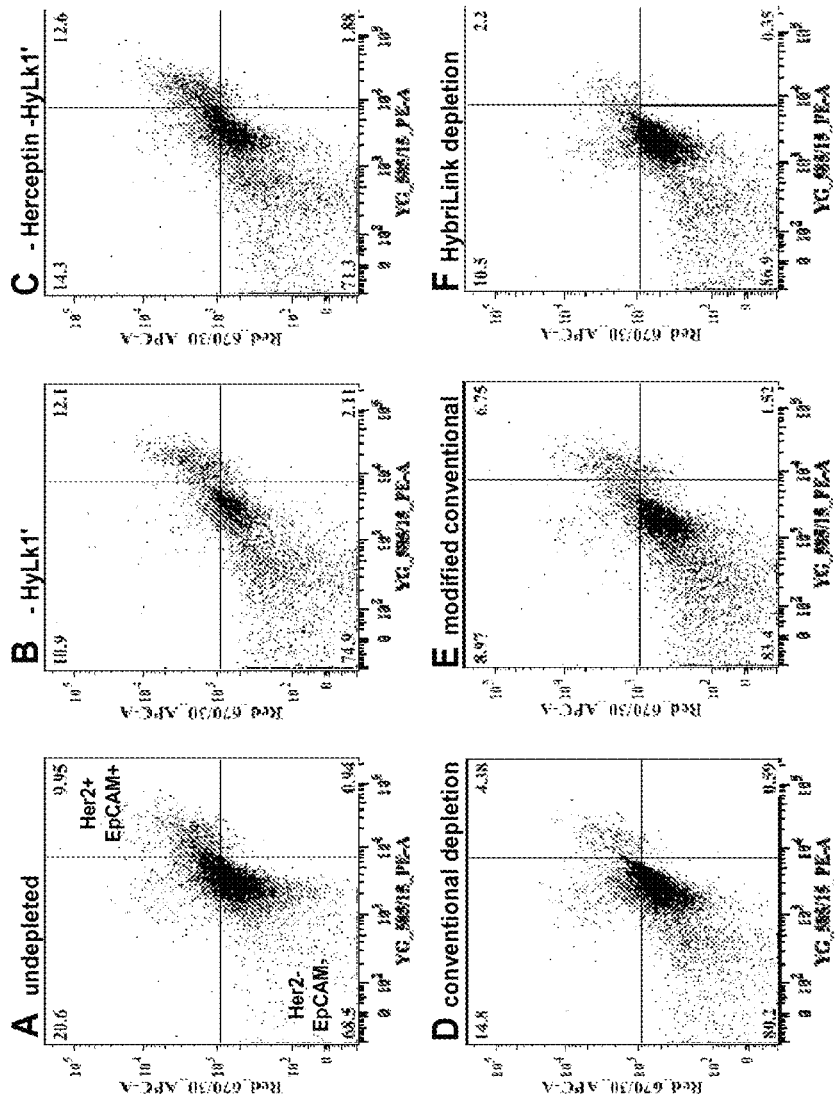
FIG. 81 is the flow cytometric results of the isolation of Her2+ cells from a complex mixture of cells using Herceptin directly immobilized on magnetic beads to a herceptin-oligonucleotide conjugate followed by addition of magnetic beads immobilized with the complementary oligonucleotide, according to certain embodiments.

Step 7) Flow cytometric analysis. Samples were analyzed using an LSRTT cytometer equipped with appropriate lasers and fluorescent emission detectors. 10,000 events were recorded per sample. Raw data files (.fcs) were exported to FlowJo software (TreeStar, Ashland, Oregon). 2D 'dot plots' were visualized as PE signal vs. APC signal. Quadrants were gated based on isotype-control background levels (data not shown). Her2+ cells were defined as those having relative fluorescence intensity (RFI)>8000 PE units. EpCAM+ cells were defined as those having RFI>1000 APC units. Her2+/EpCAM+ cells were defined as "tumor cells" meeting both fluorescence intensity criteria. Her2−/EpCAM− cells were defined as "leukocytes" meeting neither positive criteria. Experimental results are shown in FIG. 81 and Table 19.

TABLE 19

| Panel | depletion conditions | Her2+ EpCAM+ | % D | Her2− EpCAM− | % D | leukocytes: tumor cells | depletion ratio |
|---|---|---|---|---|---|---|---|
| A | undepleted | 9.95 | n/a | 68.5 | n/a | 6.9 | n/a |
| B | -HyLk1' | 12.6 | 26.6 | 71.3 | 4.1 | 5.7 | 0.8 |
| C | -Herceptin -HyLk1' | 12.1 | 21.6 | 74.9 | 9.3 | 6.2 | 0.9 |
| D | conventional method | 4.4 | −56.0 | 80.2 | 17.1 | 18.3 | 2.7 |
| E | modified conventional | 6.8 | −32.2 | 82.8 | 20.9 | 12.3 | 1.8 |
| F | HybriLink method | 2.2 | −77.9 | 85.9 | 25.4 | 39.0 | 5.7 |

In the following, further embodiments are explained with the help of subsequent examples starting at Example 20A.

Example 20A

A method for detecting one or more biological targets of a sample in a detection assay, comprising: i) providing a molecular probe, comprising a binding moiety and an oligonucleotide sequence, to a sample comprising one or more biological targets; ii) binding the one or more biological targets with the binding moiety; iii) providing a detectable component to the sample, wherein the detectable component comprises a signal generating moiety conjugated to an oligonucleotide sequence complementary to the oligonucleotide sequence of the molecular probe; v) hybridizing the oligonucleotide sequence of the target-bound molecular probe to the detectable component; and v) detecting a signal generated from the hybridized detectable component; wherein: a) the conjugation between the oligonucleotide sequence and the binding moiety and conjugation between the complementary oligonucleotide sequence and the signal generating moiety, comprise a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets.

Example 21A

The method of Example 20A, wherein sample is a complex sample.

Example 22A

The method of one or more of Examples 20A-21A, wherein the hydridization efficiency of the oligonucleotide sequence to the complementary oligonucleotide sequence is at least 50%.

Example 23A

The method of one or more of Examples 20A-22A, wherein the molecular probe has substantially the same solubility as the binding moiety.

Example 24A

The method of any one of Examples 20A-23A, wherein the molecular probe comprises a molecular weight of between about 15,000 Daltons to about 450,000 Daltons.

Example 25A

The method of one or more of Examples 20A-24A, wherein the method of detection generates less false positives than secondary antibody detection methods.

Example 26A

The method of one or more of Examples 20A-25A, wherein the method further comprises: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; wherein the prepared molecular probe and prepared detectable component have at least 90% purity.

Example 27A

The method of one or more of Examples 20A-26A, wherein the solubility of the molecular probe minimizes non-specific binding to the one or more biological targets.

Example 28A

The method of one or more of Examples 20A-27A, wherein the sample is homogeneous or heterogenous mixture;

Example 29A

The method of one or more of Examples 20A-28A, wherein the sample comprises biological fluids or fluidized biological tissue.

Example 30A

The method of one or more of Examples 20A-29A, wherein the sample comprises cells, membranes, biological molecules, metabolites, or disease biomarkers.

Example 31A

The method of one or more of Examples 20A-30A, wherein the sample comprises a range of analytes having a wide range of binding specificities.

Example 32A

The method of one or more of Examples 20A-31A, wherein the time of conducting the method, from the start of preparation to the end of detection is between about 2-3 hours.

Example 33A

The method of one or more of Examples 20A-32A, wherein the molecular probe is neutral in charge.

Example 34A

The method of one or more of Examples 20A-33A, wherein the method further comprises preparing and isolating a molecular probe, comprising a binding moiety conjugated to an oligonucleotide sequence, comprising: i) introducing a modified binding moiety into a buffered solution; ii) conjugating the modified binding moieties with at least one modified oligonucleotide at greater than 90% efficiency to form binding moiety-oligonucleotide conjugates; and iii) isolating the binding moiety-oligonucleotide conjugates from the conjugation solution by binding the conjugates to an immobilized binder, removing the unconjugated oligonucleotide in a wash step followed by release of the bound conjugate from the solid support.

Example 35A

The method of one or more of Examples 20A-34A, wherein the method further comprises preparing and isolating a detectable component, comprising a signal generating moiety conjugated to an oligonucleotide sequence complementary to the oligonucleotide sequence of the molecular probe, comprising: i) introducing a modified signal generating moiety into a buffered solution; ii) conjugating the modified signal generating moieties with at least one modified complementary oligonucleotide at greater than 90% efficiency to form signal generating moiety-complementary oligonucleotide conjugates; and iii) isolating the signal generating moiety-complementary oligonucleotide conjugates from the conjugation solution by binding the conjugates to an immobilized binder, removing the unconjugated oligonucleotide in a wash step followed by release of the bound conjugate from the solid support.

Example 36A

The method of one or more of Examples 20A-35A, wherein the method further comprises preparing and isolating a detectable component, comprising a scaffold, comprising one or more signal generating moieties, conjugated to an oligonucleotide sequence complementary to the oligonucleotide sequence of the molecular probe, comprising: i) introducing a modified scaffold, comprising the one or more signal generating moieties, into a buffered solution; ii) conjugating the modified scaffold with at least one modified complementary oligonucleotide at greater than 90% efficiency to form scaffold-complementary oligonucleotide conjugates; and iii) isolating the scaffold-complementary oligonucleotide conjugates from the conjugation solution by binding the conjugates to an immobilized binder, removing the unconjugated oligonucleotide in a wash step followed by release of the bound conjugate from the solid support.

Example 37A

The method of one or more of Examples 20A-36A, wherein the scaffold comprises a dendrimer, polysaccharide, or a dextran.

Example 38A

The method of one or more of Examples 20A-37A, wherein the one or more molecular probes comprise a range of specificities for the one or more biological targets.

Example 39A

The method of one or more of Examples 20A-38A, wherein the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof.

Example 40A

The method of one or more of Examples 20A-39A, wherein the binding moiety comprises an antibody, a protein, a peptide, a carbohydrate, a nuclear receptor, a small molecule, or combinations or derivatives thereof.

Example 41A

The method of one or more of Examples 20A-40A, wherein the one or more biological target comprises an antigen, a pathogen, a protein, a peptide, an epitope, a carbohydrate-containing molecule, a small molecule, or combinations or derivatives thereof.

Example 42A

The method of one or more of Examples 20A-41A, wherein the one or more signal generating moieties, comprise one or more fluorophors, biofluorescent proteins, quantum dots, Raman particles, or combinations or derivatives thereof.

Example 43A

The method of one or more of Examples 20A-42A, wherein the one or more signal generating moieties provides an enhanced signal that minimizes detection errors from background noise.

Example 44A

The method of one or more of Examples 20A-43A, wherein the one or more molecular probes and/or the one or more detectable components further comprise a spacer group, comprising a polymerized ethylene oxide, a PEG, or a PEO.

Example 45A

The method of one or more of Examples 20A-44A, wherein the modified binding moiety, the modified scaffold, the oligonucleotide sequence, and/or the complementary oligonucleotide sequence comprise HyNic or 4-FB.

Example 46A

The method of one or more of Examples 20A-45A, wherein the one or more molecular probes comprise unique, distinguishable, and/or specifically designed oligonucleotide sequences.

Example 47A

The method of one or more of Examples 20A-46A, wherein the one or more detectable components comprise unique, distinguishable, and/or specifically designed complementary oligonucleotide sequences.

Example 48A

The method of one or more of Examples 20A-47A, wherein the oligonucleotide sequences of the one or more molecular probes are uniquely and specifically designed to hybridize to the complementary oligonucleotide sequence of the one or more detectable components.

Example 49A

The method of one or more of Examples 20A-48A, wherein the oligonucleotide sequences and/or complementary oligonucleotide sequences, comprise 3'-oligonucleotides, 5'-oligonucleotides, LNAs, PNAs, or combinations or derivatives thereof.

Example 50A

The method of one or more of Examples 20A-49A, wherein the method further comprises: i) provides a universal adapter to the complex sample, wherein the universal adapter comprised an oligonucleotide sequence having a first sequence segment complementary to the oligonucleotide sequence of the molecular probe and a second sequence segment complementary to the oligonucleotide sequence of the detectable component; ii) hydridizing the oligonucleotide sequences of the one or more target-bound molecular probes to the first oligonucleotide sequence segment of the universal adapter; iii) providing the one or more detectable components to the complex sample; iv) hydridizing the oligonucleotide sequences of the one or more detectable components to the second oligonucleotide sequence segment of the universal adapter; and v) detecting one or more signals generated from the hydridized one or more detectable components.

Example 51A

The method of one or more of Examples 20A-50A, wherein the method further comprises: i) providing at least a first molecular probe and a second molecular probe, comprising a first binding moiety conjugated to a first oligonucleotide sequence and a second binding moiety conjugated to a second oligonucleotide sequence, respectively, to the complex sample comprising the one or more biological targets; ii) specifically binding the one or more biological targets with the binding moiety of the first molecular probe and the binding moiety of the second molecular probe; iii) providing the one or more detectable components to the complex sample; iv) hydridizing the first oligonucleotide sequence of the first target-bound molecular probe to a complementary oligonucleotide sequence conjugated to a bead; v) hydridizing the second oligonucleotide sequence of the second target-bound molecular probe to the complementary oligonucleotide sequences of the one or more detectable components; and vi) detecting one or more signals generated from the one or more hydridized detectable components.

Example 52A

The method of one or more of Examples 20A-51A, wherein the method further comprises: i) providing at least a first molecular probe and a second molecular probe, comprising a first binding moiety conjugated to a first oligonucleotide sequence and a second binding moiety conjugated to a second oligonucleotide sequence, respectively, to the complex sample comprising the one or more biological targets; ii) specifically binding the one or more biological targets with the binding moiety of the first molecular probe and the binding moiety of the second molecular probe; iii) providing a universal adapter to the complex sample, wherein the universal adapter comprised an oligonucleotide sequence having a first sequence segment complementary to the oligonucleotide sequence of the molecular probe and a second sequence segment complementary to the oligonucleotide sequence of the detectable component; iv) hydridizing the first oligonucleotide sequence of the first target-bound molecular probe to a first portion of the first oligonucleotide sequence segment of the universal adapter; v) hydridizing the second oligonucleotide sequence of the second target-bound molecular probe to a second portion of the first oligonucleotide sequence segment of the universal adapter; vi) providing the one or more detectable components to the complex sample; vii) hydridizing the oligonucleotide sequences of the one or more detectable components to the first and second portions of the second oligonucleotide sequence segment of the universal adapter; and viii) detecting one or more signals generated from the hydridized one or more detectable components.

Example 53A

A method for detecting one or more biological targets in a detection assay, comprising: i) providing at least a first and a second molecular probe, each comprising a binding moiety conjugated to an oligonucleotide sequence, to a sample comprising the one or more biological targets; ii) binding the one or more biological targets with the binding moiety of the first molecular probe and the binding moiety of the second molecular probe; iii) optionally hydridizing the oligonucleotide sequence of the first target-bound molecular probe to a complementary oligonucleotide sequence conjugated to a bead; iv) hydridizing the oligonucleotide sequence of the second target-bound molecular probe to a complementary oligonucleotide sequence conjugated to a detectable component; and v) detecting a signal generated from the hydridized detectable component; wherein: a) each binding moiety has a binding affinity for the one or more biological targets; and b) the conjugation between the respective oligonucleotide or complementary oligonucleotide sequences and the binding moiety of the first molecular probe, the binding moiety of the second molecular probe, the bead, or the detectable component, comprises a covalent bond linkage, comprising a hydrazone, oxime, triazine, or other bond, wherein the formation of the conjugate is at least 90% efficient.

Example 54A

A method for detecting one or more biological targets in a detection assay, comprising: i) providing a first molecular probe, comprising a first binding moiety conjugated to a first oligonucleotide sequence, to a sample comprising the one or more biological targets; ii) binding the one or more biological targets via the first binding moiety of the first molecular probe; iii) providing a second molecular probe, comprising a second binding moiety conjugated to a second oligonucleotide sequence, to the sample comprising the one or more biological targets; iv) binding the one or more biological targets via the second binding moiety of the second molecular probe; v) optionally hydridizing the first oligonucleotide sequence of the first target-bound molecular probe to a complementary oligonucleotide sequence conjugated to a bead; vi) hydridizing the second oligonucleotide sequence of the second target-bound molecular probe to a complementary oligonucleotide sequence conjugated to a detectable component; and vii) detecting a signal generated from the hydridized detectable component; wherein: a) each binding moiety has a binding affinity for the one or more biological targets; b) the conjugation between the respective oligonucleotide or complementary oligonucleotide sequences and the first binding moiety, the second binding moiety, the bead, or the detectable component, comprises a covalent bond linkage, comprising a hydrazone, oxime, triazine, or other bond, wherein the formation of the conjugate is at least 90% efficient.

Example 55A

A method for detecting one or more biological targets of a sample in a detection assay, comprising: i) providing a molecular probe, comprising a binding moiety and an oligonucleotide sequence, to a sample comprising one or more biological targets; ii) binding the one or more biological targets with the binding moiety; iii) providing a detectable component to the sample, wherein the detectable component comprises a signal generating moiety conjugated to an oligonucleotide sequence complementary to the oligonucleotide sequence of the molecular probe; iv) hydridizing the oligonucleotide sequence of the target-bound molecular probe to the detectable component; and v) detecting a signal generated from the hydridized detectable component; wherein: a) the conjugation between the oligonucleotide sequence and the binding moiety and conjugation between the complementary oligonucleotide sequence and the signal generating moiety, comprise a covalent bond linkage, comprising a hydrazone, oxime, triazine, or other bond, wherein the formation of the conjugates are at least 90% efficient; b) the binding moiety comprises a binding affinity of less than $10^{-4}$M for the one or more biological targets.

Example 56A

A method for detecting one or more biological targets of a complex sample in a detection assay, comprising: i) providing a molecular probe, comprising a binding moiety conjugated to an oligonucleotide sequence, to the complex sample comprising the one or more biological targets; ii) specifically binding the one or more biological targets with the binding moiety; iii) providing a detectable component to the complex sample, wherein the detectable component comprising a signal generating moiety conjugated to an oligonucleotide sequence complementary to the oligonucleotide sequence of the molecular probe; iv) hydridizing the oligonucleotide sequence of the target-bound molecular probe to the complementary oligonucleotide sequence of the detectable component; and v) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; and c) the hydridization efficiency of the oligonucleotide sequence to the complementary oligonucleotide sequence is at least 50%.

Example 57A

A method for detecting one or more biological targets of a complex sample in a detection assay, comprising: i) providing a molecular probe, comprising a binding moiety conjugated to an oligonucleotide sequence, to the complex sample comprising the one or more biological targets; ii) specifically binding the one or more biological targets with the binding moiety; iii) providing a detectable component to the complex sample, wherein the detectable component comprising a signal generating moiety conjugated to an oligonucleotide sequence complementary to the oligonucleotide sequence of the molecular probe; iv) hydridizing the oligonucleotide sequence of the target-bound molecular probe to the complementary oligonucleotide sequence of the detectable component; and v) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; and d) the molecular probe has substantially the same solubility as the binding moiety.

Example 58A

A method for detecting one or more biological targets of a complex sample in a detection assay, comprising: i) providing a molecular probe, comprising a binding moiety conjugated to an oligonucleotide sequence, to the complex sample comprising the one or more biological targets; ii) specifically binding the one or more biological targets with the binding moiety; iii) providing a detectable component to the complex sample, wherein the detectable component comprising a signal generating moiety conjugated to an oligonucleotide sequence complementary to the oligonucleotide sequence of the molecular probe; iv) hydridizing the oligonucleotide sequence of the target-bound molecular probe to the complementary oligonucleotide sequence of the detectable component; and v) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; and e) the molecular probe comprises a molecular weight of between about 15,000 Daltons to about 450,000 Daltons.

Example 59A

In certain embodiments, the method for detecting one or more biological targets of a complex sample in a detection assay, comprising: i) providing a molecular probe, comprising a binding moiety conjugated to an oligonucleotide sequence, to the complex sample comprising the one or more biological targets; ii) specifically binding the one or more biological targets with the binding moiety; iii) providing a detectable component to the complex sample, wherein the detectable component comprising a signal generating moiety conjugated to an oligonucleotide sequence complementary to the oligonucleotide sequence of the molecular probe; iv) hydridizing the oligonucleotide sequence of the target-bound molecular probe to the complementary oligonucleotide sequence of the detectable component; and v) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; and f) the method of detection generates less false positives than secondary antibody detection methods.

Example 60A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hybridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; and g) the prepared molecular probe and prepared detectable component have at least 90% purity.

Example 61A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hybridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets.

Example 62A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hybridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets; and i) the sample is homogeneous or heterogenous mixture.

Example 63A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hybridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets; i) the sample is homogeneous or heterogenous mixture; and j) the sample comprises biological fluids or fluidized biological tissue.

Example 64A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets; i) the sample is homogeneous or heterogenous mixture; j) the sample comprises biological fluids or fluidized biological tissue; and k) the sample comprises cells, membranes, biological molecules, metabolites, or disease biomarkers.

Example 65A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; and l) the sample comprises a range of analytes having a wide range of binding specificities.

Example 66A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; and m) the time of conducting the method, from the start of preparation to the end of detection is between about 2-3 hours.

Example 67A

A method for detecting one or more biological targets of a complex sample in a detection assay, comprising: i) preparing: a) a molecular probe, comprising a binding moiety conjugated to an oligonucleotide sequence; and b) a detectable component, comprising a signal generating moiety conjugated to an oligonucleotide sequence complementary to the oligonucleotide sequence of the molecular probe; ii) providing the molecular probe to the complex sample comprising the one or more biological targets; iii) specifically binding the one or more biological targets with the binding moiety; iv) providing the detectable component to the complex sample; v) hydridizing the oligonucleotide sequence of the target-bound molecular probe to the complementary oligonucleotide sequence of the detectable component; and vi) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared molecular probe and prepared detectable component have at least 90% purity; h) the solubility of the molecular probe minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; and n) the molecular probe is neutral in charge.

Example 68A

A method for detecting one or more biological targets of a complex sample in a detection assay, comprising: i) preparing and isolating a molecular probe, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating a detectable component, comprising a signal generating moiety conjugated to an oligonucleotide sequence complementary to the oligonucleotide sequence of the molecular probe, comprising: a) introducing a modified signal generating moiety into a buffered solution; b) conjugating the modified signal generating moieties with at least one modified complementary oligonucleotide at greater than 90% efficiency to form signal generating moiety-complementary oligonucleotide conjugates; and c) isolating the signal generating moiety-complementary oligonucleotide conjugates from the conjugation solution by binding the conjugates to an immobilized binder, removing the unconjugated oligonucleotide in a wash step followed by release of the bound conjugate from the solid support; and iii) providing the molecular probe to the complex sample comprising the one or more biological targets; iv) specifically binding the one or more biological targets with the binding moiety; v) providing the detectable component to the complex sample; vi) hydridizing the oligonucleotide sequence of the target-bound molecular probe to the complementary oligonucleotide sequence of the detectable component; and vii) detecting a signal generated from the hydridized detectable component; wherein: a) the conjugation between the oligonucleotide sequence and the binding moiety and conjugation between the complementary oligonucleotide sequence and the signal generating moiety, comprises a covalent bond linkage, comprising a hydrazone, oxime, triazine, or other bond, wherein the formation of the conjugates are at least 90% efficient; b) the binding moiety comprises a binding affinity of loss than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared and isolated molecular probe and prepared and isolated detectable component have at least 90% purity; h) the solubility of the molecular probe minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; and n) the molecular probe is neutral in charge.

Example 69A

A method for detecting one or more biological targets of a complex sample in a detection assay, comprising: i) preparing and isolating a molecular probe, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating a detectable component, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the molecular probe to the complex sample comprising the one or more biological targets; iv) specifically binding the one or more biological targets with the binding moiety; v) providing the detectable component to the complex sample; vi) hydridizing the oligonucleotide sequence of the target-bound molecular probe to the complementary oligonucleotide sequence of the detectable component; and vii) detecting a signal generated from the hydridized detectable component; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the molecular probe has substantially the same solubility as the binding moiety; e) the molecular probe comprises a molecular weight of between about 15,000 Daltons to about 450,000 Daltons; f) the method of detection generates less false positives than secondary antibody detection methods; g) the prepared and isolated molecular probe and prepared and isolated detectable component have at least 90% purity; h) the solubility of the molecular probe minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the molecular probe is neutral in charge; and o) the scaffold comprises a dendrimer, polysaccharide, or a dextran.

Example 70A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; and p) the one or more molecular probes comprise a range of specificities for the one or more biological targets.

Example 71A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; and q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof.

Example 72A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to for in scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof r) the binding moiety comprises an antibody, a protein, a peptide, a carbohydrate, a nuclear receptor, a small molecule, or combinations or derivatives thereof.

Example 73A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the ono or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; and s) the one or more biological target comprises an antigen, a pathogen, a protein, a peptide, an epitope, a carbohydrate-containing molecule, a small molecule, or combinations or derivatives thereof.

Example 74A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; and t) the one or more signal generating moieties, comprise one or more fluorophors, biofluorescent proteins, quantum dots, Raman particles, or combinations or derivatives thereof.

Example 75A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hybridizing the oligonucleotide sequences of the one or more target-bound molecular probes to the complementary oligonucleotide sequences of the one or more detectable components; and vii) detecting one or more signals generated from the one or more hybridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; and u) the one or more signal generating moieties provides an enhanced signal that minimizes detection errors from background noise.

Example 76A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; and v) the one or more molecular probes and/or the one or more detectable components further comprise a spacer group, comprising a polymerized ethylene oxide, a PEG, or a PEO.

Example 77A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hybridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; and w) the modified binding moiety, the modified scaffold, the oligonucleotide sequence, and/or the complementary oligonucleotide sequence comprise HyNic or 4-FB.

Example 78A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hybridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; and x) the one or more molecular probes comprise unique, distinguishable, and/or specifically designed oligonucleotide sequences.

Example 79A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; x) the one or more molecular probes comprise unique, distinguishable, and/or specifically designed oligonucleotide sequences; and y) the one or more detectable components comprise unique, distinguishable, and/or specifically designed complementary oligonucleotide sequences.

Example 80A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; x) the one or more molecular probes comprise unique, distinguishable, and/or specifically designed oligonucleotide sequences; y) the one or more detectable components comprise unique, distinguishable, and/or specifically designed complementary oligonucleotide sequences; and z) the oligonucleotide sequences of the one or more molecular probes are uniquely and specifically designed to hybridize to the complementary oligonucleotide sequence of the one or more detectable components.

Example 81A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing the one or more detectable components to the complex sample; vi) hydridizing the oligonucleotide sequences of the one or more target-bound molecular probes to the complementary oligonucleotide sequences of the one or more detectable components; and vii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; x) the one or more molecular probes comprise unique, distinguishable, and/or specifically designed oligonucleotide sequences; y) the one or more detectable components comprise unique, distinguishable, and/or specifically designed complementary oligonucleotide sequences; z) the oligonucleotide sequences of the one or more molecular probes are uniquely and specifically designed to hybridize to the complementary oligonucleotide sequence of the one or more detectable components; and a2) the oligonucleotide sequences and/or complementary oligonucleotide sequences, comprise 3'-oligonucleotides, 5'-oligonucleotides, LNAs, PNAs, or combinations or derivatives thereof.

Example 82A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence, comprising: a) introducing a modified scaffold, comprising the one or more signal generating moieties, into a buffered solution; b) conjugating the modified scaffold with at least one modified oligonucleotide at greater than 90% efficiency to form scaffold-oligonucleotide conjugates; and c) isolating the scaffold-oligonucleotide conjugates from the conjugation solution by binding the conjugates to an immobilized binder, removing the unconjugated oligonucleotide in a wash step followed by release of the bound conjugate from the solid support; and iii) providing the one or more molecular probes to the complex sample comprising the one or more biological targets; iv) specifically binding the one or more biological targets with the binding moieties of the one or more molecular probes; v) providing a universal adapter to the complex sample, wherein the universal adapter comprised an oligonucleotide sequence having a first sequence segment complementary to the oligonucleotide sequence of the molecular probe and a second sequence segment complementary to the oligonucleotide sequence of the detectable component; vi) hydridizing the oligonucleotide sequences of the one or more target-bound molecular probes to the first oligonucleotide sequence segment of the universal adapter; vii) providing the one or more detectable components to the complex sample; viii) hydridizing the oligonucleotide sequences of the one or more detectable components to the second oligonucleotide sequence segment of the universal adapter; and ix) detecting one or more signals generated from the hydridized one or more detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof r) the binding moiety comprises an antibody, a protein, a peptide, a carbohydrate, a nuclear receptor, a small molecule, or combinations or derivatives thereof, s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; x) the one or more molecular probes comprise unique, distinguishable, and/or specifically designed oligonucleotide sequences; y) the one or more detectable components comprise unique, distinguishable, and/or specifically designed complementary oligonucleotide sequences; z) the oligonucleotide sequences of the one or more molecular probes are uniquely and specifically designed to hybridize to the complementary oligonucleotide sequence of the one or more detectable components; and a2) the oligonucleotide sequences and/or complementary oligonucleotide sequences, comprise 3'-oligonucleotides, 5'-oligonucleotides, LNAs, PNAs, or combinations or derivatives thereof.

Example 83A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence complementary to the oligonucleotide sequence of the molecular probe, comprising: a) introducing a modified scaffold, comprising the one or more signal generating moieties, into a buffered solution; b) conjugating the modified scaffold with at least one modified complementary oligonucleotide at greater than 90% efficiency to form scaffold-complementary oligonucleotide conjugates; and c) isolating the scaffold-complementary oligonucleotide conjugates from the conjugation solution by binding the conjugates to an immobilized binder, removing the unconjugated oligonucleotide in a wash step followed by release of the bound conjugate from the solid support; and iii) providing at least a first molecular probe and a second molecular probe, comprising a first binding moiety conjugated to a first oligonucleotide sequence and a second binding moiety conjugated to a second oligonucleotide sequence, respectively, to the complex sample comprising the one or more biological targets; iv) specifically binding the one or more biological targets with the binding moiety of the first molecular probe and the binding moiety of the second molecular probe; v) providing the one or more detectable components to the complex sample; vi) hybridizing the first oligonucleotide sequence of the first target-bound molecular probe to a complementary oligonucleotide sequence conjugated to a bead; vii) hydridizing the second oligonucleotide sequence of the second target-bound molecular probe to the complementary oligonucleotide sequences of the one or more detectable components; and viii) detecting one or more signals generated from the one or more hydridized detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogenous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; x) the one or more molecular probes comprise unique, distinguishable, and/or specifically designed oligonucleotide sequences; y) the one or more detectable components comprise unique, distinguishable, and/or specifically designed complementary oligonucleotide sequences; z) the oligonucleotide sequences of the one or more molecular probes are uniquely and specifically designed to hybridize to the complementary oligonucleotide sequence of the one or more detectable components; a2) the oligonucleotide sequences and/or complementary oligonucleotide sequences, comprise 3'-oligonucleotides, 5'-oligonucleotides, LNAs, PNAs, or combinations or derivatives thereof.

Example 84A

A method for detecting one or more biological targets of a complex sample in a detection assay, comprising: i) preparing and isolating one or more molecular probes, comprising a binding moiety conjugated to an oligonucleotide sequence, comprising: a) introducing a modified binding moiety into a buffered solution; b) conjugating the modified binding moieties with at least one modified oligonucleotide at greater than 90% efficiency to form binding moiety-oligonucleotide conjugates; and c) isolating the binding moiety-oligonucleotide conjugates from the conjugation solution by binding the conjugates to an immobilized binder, removing the unconjugated oligonucleotide in a wash step followed by release of the bound conjugate from the solid support; and ii) preparing and isolating one or more detectable components, comprising a scaffold, comprising one or more signal generating moieties, conjugated to an oligonucleotide sequence, comprising: a) introducing a modified scaffold, comprising the one or more signal generating moieties, into a buffered solution; b) conjugating the modified scaffold with at least one modified oligonucleotide at greater than 90% efficiency to form scaffold-oligonucleotide conjugates; and c) isolating the scaffold-oligonucleotide conjugates from the conjugation solution by binding the conjugates to an immobilized binder, removing the unconjugated oligonucleotide in a wash step followed by release of the bound conjugate from the solid support; and iii) providing at least a first molecular probe and a second molecular probe, comprising a first binding moiety conjugated to a first oligonucleotide sequence and a second binding moiety conjugated to a second oligonucleotide sequence, respectively, to the complex sample comprising the one or more biological targets; iv) specifically binding the one or more biological targets with the binding moiety of the first molecular probe and the binding moiety of the second molecular probe; v) providing a universal adapter to the complex sample, wherein the universal adapter comprised an oligonucleotide sequence having a first sequence segment complementary to the oligonucleotide sequence of the molecular probe and a second sequence segment complementary to the oligonucleotide sequence of the detectable component; vi) hydridizing the first oligonucleotide sequence of the first target-bound molecular probe to a first portion of the first oligonucleotide sequence segment of the universal adapter; vii) hydridizing the second oligonucleotide sequence of the second target-bound molecular probe to a second portion of the first oligonucleotide sequence segment of the universal adapter; viii) providing the one or more detectable components to the complex sample; ix) hydridizing the oligonucleotide sequences of the one or more detectable components to the first and second portions of the second oligonucleotide sequence segment of the universal adapter; and x) detecting one or more signals generated from the hydridized one or more detectable components; wherein: a) the conjugation between the oligonucleotide sequence and the binding moiety and conjugation between the complementary oligonucleotide sequence and the scaffold, comprises a covalent bond linkage, comprising a hydrazone, oxime, triazine, or other bond, wherein the formation of the conjugates are at least 90% efficient; b) the binding moiety comprises a binding affinity of less than $10^{-4}$ M for the one or more biological targets; c) the hydridization efficiency of the oligonucleotide sequence to the complementary oligonucleotide sequence is at least 50%; d) the one or more molecular probes have substantially the same solubility as the one or more binding moieties, respectively; e) the one or more molecular probes comprise molecular weights of between about 15,000 Daltons to about 450,000 Daltons; f) the method of detection generates less false positives than secondary antibody detection methods; g) the prepared and isolated one or more molecular probes and one or more detectable components have at least 90% purity; h) the solubility of the one or more molecular probes minimizes non-specific binding to the one or more biological targets; i) the sample is homogeneous or heterogenous mixture; j) the sample comprises biological fluids or fluidized biological tissue; k) the sample comprises cells, membranes, biological molecules, metabolites, or disease biomarkers; l) the sample comprises a range of analytes having a wide range of binding specificities; m) the time of conducting the method, from the start of preparation to the end of detection is between about 2-3 hours; n) the one or more molecular probes are neutral in charge; o) the scaffold comprises a dendrimer, polysaccharide, or a dextran; p) the one or more molecular probes comprise a range of specificities for the one or more biological targets; q) the detection assay comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof; r) the binding moiety comprises an antibody, a protein, a peptide, a carbohydrate, a nuclear receptor, a small molecule, or combinations or derivatives thereof; s) the one or more biological target comprises an antigen, a pathogen, a protein, a peptide, an epitope, a carbohydrate-containing molecule, a small molecule, or combinations or derivatives thereof; t) the one or more signal generating moieties, comprise one or more fluorophors, biofluorescent proteins, quantum dots, Raman particles, or combinations or derivatives thereof; u) the one or more signal generating moieties provides an enhanced signal that minimizes detection errors from background noise; v) the one or more molecular probes and/or the one or more detectable components further comprise a spacer group, comprising a polymerized ethylene oxide, a PEG, or a PEO; w) the modified binding moiety, the modified scaffold, the oligonucleotide sequence, and/or the complementary oligonucleotide sequence comprise HyNic or 4-FB; x) the one or more molecular probes comprise unique, distinguishable, and/or specifically designed oligonucleotide sequences; y) the one or more detectable components comprise unique, distinguishable, and/or specifically designed complementary oligonucleotide sequences; z) the oligonucleotide sequences of the one or more molecular probes are uniquely and specifically designed to hybridize to the complementary oligonucleotide sequence of the one or more detectable components; and a2) the oligonucleotide sequences and/or complementary oligonucleotide sequences, comprise 3'-oligonucleotides, 5'-oligonucleotides, LNAs, PNAs, or combinations or derivatives thereof.

Example 85A

A method for detecting one or more biological targets in a detection assay, comprising: i) providing at least a first and a second molecular probe, each comprising a binding moiety conjugated to an oligonucleotide sequence, to a sample comprising the one or more biological targets; ii) binding the one or more biological targets with the binding moiety of the first molecular probe and the binding moiety of the second molecular probe; iii) optionally hydridizing the oligonucleotide sequence of the first target-bound molecular probe to a complementary oligonucleotide sequence conjugated to a bead; iv) hydridizing the oligonucleotide sequence of the second target-bound molecular probe to a complementary oligonucleotide sequence conjugated to a detectable component; and v) detecting a signal generated from the hydridized detectable component; wherein: a) each binding moiety has a binding affinity for the one or more biological targets; and b) the conjugation between the respective oligonucleotide or complementary oligonucleotide sequences and the binding moiety of the first molecular probe, the binding moiety of the second molecular probe, the bead, or the detectable component, comprises a covalent bond linkage, comprising a hydrazone, oxime, triazine, or other bond, wherein the formation of the conjugate is at least 90% efficient.

Example 86A

A method for detecting one or more biological targets in a detection assay, comprising: i) providing a first molecular probe, comprising a first binding moiety conjugated to a first oligonucleotide sequence, to a sample comprising the one or more biological targets; ii) binding the one or more biological targets via the first binding moiety of the first molecular probe; iii) providing a second molecular probe, comprising a second binding moiety conjugated to a second oligonucleotide sequence, to the sample comprising the one or more biological targets; iv) binding the one or more biological targets via the second binding moiety of the second molecular probe; v) optionally hydridizing the first oligonucleotide sequence of the first target-bound molecular probe to a complementary oligonucleotide sequence conjugated to a bead; vi) hydridizing the second oligonucleotide sequence of the second target-bound molecular probe to a complementary oligonucleotide sequence conjugated to a detectable component; and vii) detecting a signal generated from the hydridized detectable component; wherein: a) each binding moiety has a binding affinity for the one or more biological targets; b) the conjugation between the respective oligonucleotide or complementary oligonucleotide sequences and the first binding moiety, the second binding moiety, the bead, or the detectable component, comprises a covalent bond linkage, comprising a hydrazone, oxime, triazine, or other bond, wherein the formation of the conjugate is at least 90% efficient.

Example 87A

A method for crosslinking, comprising: i) introducing to a sample comprising one or more targets: a) one or more first antibody-oligonucleotide conjugates, comprising a first antibody conjugated to a first oligonucleotide sequence; and b) one or more second antibody-oligonucleotide conjugates, comprising a second antibody conjugated to a second oligonucleotide sequence; ii) binding the one or more targets with the first antibody of the one or more first antibody-oligonucleotide conjugates and with the second antibody of the one or more second antibody-oligonucleotide conjugates to form one or more sandwich-complexes; iii) contacting the one or more sandwich-complexes with: a) one or more first bead-oligonucleotide conjugate, comprising a first bead conjugated to a complementary first oligonucleotide sequence; and b) one or more second bead-oligonucleotide conjugate, comprising a second bead conjugated to a complementary second oligonucleotide sequence; iv) crosslinking the one or more sandwich-complexes by: a) hybridizing the first oligonucleotide sequences of the one or more sandwich-complexes with the complementary first oligonucleotide sequences of the one or more first bead-oligonucleotide conjugates; and b) hybridizing the second oligonucleotide sequences of the one or more sandwich-complexes with the complementary second oligonucleotide sequences of the one or more second bead-oligonucleotide conjugates.

Example 88A

The crosslinking method of Example 87A, wherein the formation of the crosslinked one or more sandwich-complexes forms an agglutination.

Example 89A

The crosslinking method of one or more of Examples 87A-88A, wherein the method further comprises detecting and/or measuring the degree of the formed agglutination to determine the amount of the one or more targets in the sample.

Example 90A

The crosslinking method of one or more of Examples 87A-89A, wherein the first antibody or the second antibody comprise a monoclonal antibody or a polyclonal antibody.

Example 91A

The crosslinking method of one or more of Examples 87A-90A, wherein the first antibody comprises a first monoclonal antibody and the second antibody comprises a second monoclonal antibody.

Example 92A

The crosslinking method of Example 91A, wherein the first monoclonal antibody is raised against a first epitope of the target and the second monoclonal antibody is raised against a second epitope of the target.

Example 93A

The crosslinking method of one or more of Examples 87A-92A, wherein the first antibody comprises a first polyclonal antibody and the second antibody comprises a second polyclonal antibody.

Example 94A

The crosslinking method of Example 93A, wherein a first portion of the first polyclonal antibody binds to a first epitope of the target and a second portion of the second polyclonal antibody binds to a second epitope of the target.

Example 95A

The crosslinking method of one or more of Examples 89A-94A, wherein the detection comprises a singleplex or multiplex detection, comprising: immunodetection, flow cytometry, immunohistochemistry, microscopy, imaging, high content screening (HCS), ELISA, ELISpot, arrays, bead arrays, or combinations or derivatives thereof.

Example 96A

A method of preparing a detectable component having one or more signal-generating moieties, comprising: i) modifying a scaffold with S-HyNic to form a HyNic-modified scaffold; ii) conjugating a 4FB-modified oligonucleotide to the HyNic-modified scaffold, wherein the conjugation is at least 90% efficient; and iii) modifying the scaffold of the oligonucleotide-scaffold conjugate with one or more signal-generating moieties to form the detectable component.

Example 97A

A method of preparing one or more components, comprising: i) modifying one or more scaffolds; ii) conjugating one or more modified oligonucleotides to the one or more modified scaffolds, wherein the conjugation is at least 90% efficient; and iii) modifying the scaffold of the one or more oligonucleotide-scaffold conjugates with one or more signal-generating moieties to form one or more components; wherein the conjugation between the one or more modified-oligonucleotides and the one or more modified scaffolds comprises a covalent bond linkage, comprising a hydrazone, oxime, triazine, or other bond.

Example 98A

The preparation method of Example 97A, wherein the one or more scaffolds comprises: a hydrophilic polymer, a dendrimer, a bead, or combinations thereof.

Example 99A

The preparation method of one or more of Examples 97A-98A, wherein the hydrophilic polymer comprises a polysaccharide molecule.

Example 100A

The preparation method of Example 99A wherein the polysaccharide molecule comprises a dextran or an amino-dextran.

Example 101A

The preparation method of one or more of Examples 97A-100A, wherein the one or more signal-generating moieties comprises a directly detectable signal-generating moiety or an indirectly detectable signal-generating moiety.

Example 102A

The preparation method of Example 101A, wherein the directly detectable signal-generating moiety comprises: a fluorescent dye; a luminescent species; a phosphorescent species; a radioactive substance; a nanoparticle; a diffracting particle; a raman particle; a metal particle; a magnetic particle; a bead; an RFID tag; a microbarcode particle; or combinations thereof.

Example 103A

The preparation method of one or more of Examples 101A-102A, wherein the indirectly detectable signal-generating moiety comprises: an enzyme; an antibody; an antigen; a nucleic acid; a nucleic acid analog; a ligand; a substrate; a hapten; or combinations thereof.

Example 104A

The preparation method of one or more of Examples 97A-103A, wherein the one or more scaffolds signal-generating moieties comprise: a fluorophore; a chromophore; a biofluorescent protein; a fluorophore labeled DNA dendrimer; a Quantum Dot; a chemiluminescent compound; a electrochemiluminescent label; a bioluminescent label; a polymer; a polymer particle; a bead; a Raman particle; a heavy metal chelate; gold or other metal particles or heavy atoms; a spin label; a radioactive isotope; a secondary reporter; a hapten; a nucleic acid or nucleic acid analog; a protein; a peptide ligand or substrate; a receptor; an enzyme; an enzyme substrate; an antibody; an antibody fragment; an antigen; or combinations or derivatives thereof. In addition, the preparation methods of one or more of Examples 97A-103A, wherein the one or more scaffolds signal-generating moieties may also comprise: polymer-based heavy metal chelates conjugated to antibodies and other binders may also be used to multiplex protein analysis using a technique named CyTOF (CYtometry Time Of Flight). Heavy metal isotopes of Ru, Rh, Pd, Ag, In, La, Hf, Re, Ir, Pt, Au, Ce, Pr, Nd, Sm, Eu, Gd, Tb, Dy, Ho, Er, Tm, Yb and Lu can be used.

Example 105A

A method for binding, comprising: i) providing at least a first molecular probe and a second molecular probe to a sample comprising a plurality of cells, wherein the first binding moiety is conjugated to a first oligonucleotide sequence and a second binding moiety is conjugated to a second oligonucleotide sequence; ii) specifically binding a first target of a first cell and a second target of a second cell of the plurality of cells, comprising: a) binding the first target with the first binding moiety of the first molecular probe; and b) binding the second target with the second binding moiety of the second molecular probe; iii) providing to the sample one or more detectable components, comprising: a) a first detectable component, comprising one or more signal generating moieties conjugated to a first oligonucleotide complementary to the first oligonucleotide sequence of the first molecular probe; and b) a second detectable component, comprising one or more signal generating moieties conjugated to a second oligonucleotide complementary to the second oligonucleotide sequence of the second molecular probe; iv) hybridizing the first oligonucleotide sequence of the first bound molecular probe to the complementary first oligonucleotide sequence of the first detectable component; v) hybridizing the second oligonucleotide sequence of the second bound molecular probe to the complementary second oligonucleotide sequence of the second detectable component; and vi) detecting by flow cytometry the one or more signals generated from the first hybridized detectable component and the second hybridized detectable component; wherein: a) the conjugation of the first molecular probe and the second molecular probe and the conjugation of the first detectable component and the second detectable component comprise a covalent bond linkage, comprising a hydrazone, oxime, triazine, or other bond; b) the formation of the conjugates are at least 90% efficient; and c) the first binding moiety has a binding affinity for the first target of less than $10^{-4}$ M and the second binding moiety has a binding affinity for the second target of less than $10^{-4}$ M.

Example 106A

The binding method of Example 105A, wherein the first target comprises a first biomarker of the first cell and the second target comprises a second biomarker of the second cell.

Example 107A

The binding method of one or more of Examples 105A-106A, wherein the first biomarker comprises a protein biomarker and the second biomarker comprises a protein biomarker.

Example 108A

The binding method of one or more of Examples 106A-107A, wherein the first biomarker comprises an adhesion molecule and the second biomarker comprises an adhesion molecule.

Example 109A

The binding method of one or more of Examples 105A-108A, wherein the plurality of cells comprises splenocytes.

Example 110A

The binding method of one or more of Examples 105-109, wherein the first cell is a T-cell and the second cell is a B-cell.

Example 111A

A method for binding, comprising: i) electrophoresing material derived from lysing a plurality of cells; ii) transferring the electrophoresed material to a membrane; iii) incubating the membrane with at least one molecular probe, comprising a binding moiety conjugated to an oligonucleotide sequence; iv) specifically binding at least one target of the electrophoresed material with the binding moiety of the at least one molecular probe; v) further incubating the membrane with at least one detectable component, comprising one or more signal generating moieties conjugated to an oligonucleotide complementary to the oligonucleotide sequence of the at least one molecular probe; and vi) hybridizing the oligonucleotide sequence of the at least one bound molecular probe to the complementary oligonucleotide sequence of the at least one detectable component; wherein: a) the conjugation of the at least one molecular probe and the conjugation of the at least one detectable component comprise a covalent bond linkage, comprising a hydrazone, oxime, triazine, or other bond; b) the formation of the conjugates are at least 90% efficient; and c) the binding moiety of the at least one molecular probe has a binding affinity for the at least one target of less than $10^{-4}$ M.

Example 112A

The binding method of Example 111, wherein the membrane comprises a PVDF membrane.

Example 113A

The binding method of one or more of Examples 111A-112A, wherein the one or more signal generating moieties of the at least one detectable component comprises horseradish peroxidase.

Example 114A

The binding method of one or more of Examples 111A-113A, wherein the electrophoresing of the lysate comprises a Western Blot.

Example 115A

The binding method of one or more of Examples 111A-114A, wherein the method comprises detecting the at least one signal generated from the one or more signal generating moieties on the at least one hybridized detectable component.

Example 116A

The binding method of one or more of Examples 111A-115A, wherein the detection comprises a singleplex or multiplex detection, comprising: immunodetection, flow cytometry, chemiluminescence detection, infrared detection, immunohistochemistry, ELISA, ELISpot, arrays, bead arrays, or combinations or derivatives thereof.

Example 117A

A method of binding one or more targets, comprising: i) preparing a plurality molecular probes, comprising at least: a) conjugating a universal oligonucleotide sequence to a first binding moiety to form a first molecular probe; and b) conjugating a universal oligonucleotide sequence to a second binding moiety to form a second molecular probe; ii) hybridizing the plurality of formed molecular probes with a plurality of universal adapters, comprising: a) introducing a first universal adapter to the first molecular probe, wherein the first universal adapter comprises an oligonucleotide sequence comprising: i) a complementary universal sequence segment; and ii) a first sequence segment; b) hybridizing the universal oligonucleotide sequence of the first molecular probe to the complementary universal sequence segment of the first universal adapter; c) introducing a second universal adapter to the second molecular probe, wherein the second universal adapter comprises an oligonucleotide sequence comprising: i) a complementary universal sequence segment; and ii) a second sequence segment; d) hybridizing the universal oligonucleotide sequence of the second molecular probe to the complementary universal sequence segment of the second universal adapter; and iii) introducing the plurality of hybridized molecular probes to a sample comprising one or more targets; iv) binding the one or more targets with the plurality of hybridized molecular probes, comprising: a) binding a first target of the one or more targets with the first binding moiety of the first hybridized molecular probe; b) binding a second target of the one or more targets with the second binding moiety of the second hybridized molecular probe; v) introducing to the sample a plurality of detectable components, comprising: a) a first detectable component comprising one or more signal generating moieties conjugated to a first oligonucleotide sequence complementary to the first sequence segment of the first universal adapter; and b) a second detectable component comprising one or more signal generating moieties conjugated to a second oligonucleotide sequence complementary to the second sequence segment of the second universal adapter; and vi) hybridizing the plurality of bound molecular probes with the plurality of detectable components, comprising: a) hybridizing the first sequence segment of the first bound molecular probe to the complementary first oligonucleotide sequence of the first detectable component; and b) hybridizing the second sequence segment of the second bound molecular probe to the complementary second oligonucleotide sequence of the second detectable component; wherein: a) the conjugation of the plurality of molecular probes and the conjugation of the plurality of the detectable components comprise a covalent bond linkage, comprising a hydrazone, oxime, triazine, or other bond; b) the formation of the conjugates are at least 90% efficient; and c) the first binding moiety has a binding affinity for the first target of less than $10^{-4}$ M and the second binding moiety has a binding affinity for the second target of less than $10^{-4}$ M.

Example 118A

The binding method of Example 117A, wherein the method further comprises detecting a signal generated from the hybridized detectable component.

Example 119A

The binding method of one or more of Examples 117A-118A, wherein the detectable component comprises a scaffold comprising one or more signal generating moieties.

Example 120A

The binding method of Example 119A, wherein the scaffold is conjugated to the oligonucleotide sequence.

Example 121A

The binding method of one or more of Examples 117A-120A, wherein the method comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof.

Example 122A

The binding method of Example 121A, wherein the target comprises cells and/or cellular components.

Example 123A

The binding method of Example 122A, wherein the cells are attached to a bead or a plate.

Example 124A

A method for binding one or more targets, comprising: i) forming at least one molecular probe by conjugating a universal oligonucleotide sequence to one or more binding moieties; ii) hybridizing the formed at least one molecular probe with at least one universal adapter, comprising: a) introducing the at least one universal adapter to the formed at least one molecular probe, wherein the at least one universal adapter comprises an oligonucleotide sequence comprising: i) a complementary universal sequence segment; and ii) a first sequence segment; and b) hybridizing the universal oligonucleotide sequence of the formed at least one molecular probe to the complementary universal sequence segment of the at least one universal adapter; iii) introducing the hybridized at least one molecular probe to a sample comprising the one or more targets; iv) binding at least one of the one or more targets with the binding moiety of the hybridized at least one molecular probe; v) introducing to the sample at least one detectable component comprising one or more signal generating moieties conjugated to an oligonucleotide sequence complementary to the first sequence segment of the at least one universal adapter; and vi) hybridizing the first sequence segment of the bound at least one molecular probe to the complementary oligonucleotide sequence of the at least one detectable component; wherein: a) the conjugation of the at least one molecular probe and the conjugation of the at least one detectable component comprise a covalent bond linkage, comprising a hydrazone, oxime, triazine, or other bond; b) the formation of the conjugates are at least 90% efficient; and c) the binding moiety has a binding affinity for the target of less than $10^{-4}$ M.

Example 125A

The binding method of Example 124A, wherein the one or more targets comprises cells, cellular components, biomarkers, biological components, or combinations thereof.

Example 126A

The binding method of Example 125A, wherein the cells are attached to a bead or a plate.

Example 127A

The binding method of one or more of Examples 125A-126A, wherein the cellular components comprises tubulin.

Example 128A

The binding method of one or more of Examples 124A-127A, wherein the at least one detectable component comprises a scaffold comprising one or more signal generating moieties.

Example 129A

The binding method of one or more of Examples 124A-128A, wherein the hybridized at least one detectable component generates a signal.

Example 130A

The binding method of Example 129A, wherein signal generated by the hybridized at least one detectable component is detected.

Example 131A

The binding method of Example 130A, wherein the method comprises a singleplex or multiplex detection assay, comprising immunodetection, flow cytometry, immunohistochemistry, microscopy, imaging, high content screening (HCS), ELISA, ELISpot, arrays, bead arrays, or combinations or derivatives thereof.

Example 132A

A method for detecting a target, comprising: i) conjugating a binding moiety to an oligonucleotide sequence to form a molecular probe; ii) introducing the molecular probe to a universal adapter, wherein the universal adapter comprises an oligonucleotide sequence having: a) a first sequence segment complementary to the oligonucleotide sequence of the molecular probe; and b) a second sequence segment; iii) hybridizing the oligonucleotide sequence of the molecular probe to the complementary first sequence segment of the universal adapter; iv) introducing the hybridized molecular probe to a sample comprising the target; v) binding the target with the binding moiety of the hybridized molecular probe; vi) introducing to the sample comprising the bound molecular probe a detectable component, wherein the detectable component comprises a complementary oligonucleotide sequence to the second sequence segment conjugated to one or more signal generating moieties; vii) hybridizing the second sequence segment of the molecular probe to the complementary oligonucleotide sequence of the detectable component; and viii) detecting signal generated from the hybridized detectable component; wherein: a) the conjugation of the molecular probe and the detectable component independently comprise a covalent bond linkage, comprising a hydrazone, oxime, triazine, or other bond; b) the formation of the conjugates are at least 90% efficient; and c) the binding moiety has a binding affinity for the biological target of less than $10^{-4}$ M.

Example 133A

A method for detecting one or more targets, comprising: i) providing at least a first molecular probe and a second molecular probe to a sample comprising the one or more targets, wherein the first binding moiety is conjugated to a first oligonucleotide sequence and a second binding moiety is conjugated to a second oligonucleotide sequence; ii) specifically binding a first target and a second target of the one or more targets, comprising: a) binding the first target with the first binding moiety of the first molecular probe; and b) binding the second target with the second binding moiety of the second molecular probe; iii) providing to the sample one or more detectable components, comprising: a) a first detectable component, comprising a first bead, having one or more signal generating moieties, conjugated to a first oligonucleotide complementary to the first oligonucleotide sequence of the first molecular probe; and b) a second detectable component, comprising a second bead, having one or more signal generating moieties conjugated to a second oligonucleotide complementary to the second oligonucleotide sequence of the second molecular probe; iv) hybridizing the first oligonucleotide sequence of the first bound molecular probe to the complementary first oligonucleotide sequence of the first detectable component; v) hybridizing the second oligonucleotide sequence of the second bound molecular probe to the complementary second oligonucleotide sequence of the second detectable component; and vi) detecting the one or more signals generated from at least the first hybridized detectable component and the second hybridized detectable component; wherein: a) the conjugation of the plurality of molecular probes and the conjugation of the plurality of the detectable components comprise a covalent bond linkage, comprising a hydrazone, oxime, triazine, or other bond; b) the formation of the conjugates are at least 90% efficient; and c) the first binding moiety has a binding affinity for the first target of less than $10^{-4}$ M and the second binding moiety has a binding affinity for the second target of less than $10^{-4}$ M.

Example 134A

A method for detecting one or more targets, comprising: i) providing at least a first molecular probe and a second molecular probe to a sample comprising the one or more targets, wherein the first binding moiety is conjugated to a first oligonucleotide sequence and a second binding moiety is conjugated to a second oligonucleotide sequence; ii) specifically binding a first target and a second target of the one or more targets, comprising: a) binding the first target with the first binding moiety of the first molecular probe; and b) binding the second target with the second binding moiety of the second molecular probe; iii) providing to the sample one or more detectable components, comprising: a) a first detectable component, comprising a first bead, having one or more signal generating moieties, conjugated to a first oligonucleotide complementary to the first oligonucleotide sequence of the first molecular probe; and b) a second detectable component, comprising one or more signal generating moieties conjugated to a second oligonucleotide complementary to the second oligonucleotide sequence of the second molecular probe; iv) hybridizing the first oligonucleotide sequence of the first bound molecular probe to the complementary first oligonucleotide sequence of the first detectable component; v) hybridizing the second oligonucleotide sequence of the second bound molecular probe to the complementary second oligonucleotide sequence of the second detectable component; and vi) detecting the one or more signals generated from at least the first hybridized detectable component and the second hybridized detectable component; wherein: a) the conjugation of the plurality of molecular probes and the conjugation of the plurality of the detectable components comprise a covalent bond linkage, comprising a hydrazone, oxime, triazine, or other bond; b) the formation of the conjugates are at least 90% efficient; and c) the first binding moiety has a binding affinity for the first target of less than $10^{-4}$ M and the second binding moiety has a binding affinity for the second target of less than $10^{-4}$ M.

Example 135A

The binding method of Example 134A, wherein the second detectable component comprises a scaffold comprising the one or more signal generating moieties.

Example 136A

The binding method of Example 135A, wherein the scaffold is conjugated to the complementary second oligonucleotide sequence.

Example 137A

The method of one or more of Examples 87A-136A, wherein the oligonucleotide sequences and/or complementary oligonucleotide sequences, comprise 3'-oligonucleotides, 5'-oligonucleotides, LNAs, PNAs, or combinations or derivatives thereof.

Example 1B

A purification method, comprising: i) providing a sample comprising at least one of the following: a) a carbonyl modified-molecule; and b) a carbonyl modified-biomolecule; ii) contacting the sample with a solid support comprising an acyl hydrazide group; iii) binding the carbonyl modified-molecule or the carbonyl modified-biomolecule to the acyl hydrazide group of the solid support; and iv) recovering a purified carbonyl modified-molecule or carbonyl modified-biomolecule by contacting the bound-carbonyl modified-molecule or the bound-carbonyl modified-biomolecule with a mixture comprising an aromatic or aliphatic carbonyl molecule and an aniline-containing compound.

Example 2B

The purification method of Example 1B, wherein the binding step comprises chemoselectively binding the carbonyl modified-molecule or the carbonyl modified-biomolecule to the acyl hydrazide group of the solid support.

Example 3B

The purification method of Examples 1B or 2B, wherein the method further comprises removing unmodified-molecule or unmodified-biomolecule from the bound-carbonyl modified-molecule or the bound-carbonyl modified-biomolecule by washing the solid support.

Example 4B

The purification method of any one of Examples 1B-3B, wherein the recovering step comprises releasing the chemoselectively bound-carbonyl modified-molecule or the chemoselectively bound-carbonyl modified-biomolecule from the solid support.

Example 5B

The purification method of any one of Examples 1B-4B, wherein the contacting with a mixture comprising an aromatic or aliphatic carbonyl molecule and an aniline-containing compound comprises incubating.

Example 6B

The purification method of any one of Examples 1B-5B, wherein the carbonyl modified-molecule is an aromatic carbonyl modified-molecule.

Example 7B

The purification method of any one of Examples 1B-6B, wherein the carbonyl modified-biomolecule is an aromatic carbonyl modified-biomolecule.

Example 8B

The purification method of any one of Examples 1B-7B, wherein the carbonyl moiety is an aromatic aldehyde.

Example 9B

The purification method of any one of Examples 1B-8B, wherein the carbonyl modified-molecule or the carbonyl modified-biomolecule is a 4FB-oligonucleotide.

Example 10B

The purification method of any one of Examples 1B-9B, wherein the aromatic aldehyde is 4-formylbenzamide.

Example 11B

The purification method of any one of Examples 1B-10B, wherein the acyl hydrazide group is immobilized or bound to the solid support.

Example 12B

The purification method of any one of Examples 1B-11B, wherein the immobilized hydrazide moiety of the acyl hydrazide group is an aliphatic hydrazide.

Example 13B

The purification method of any one of Examples 1B-12B, wherein the immobilized hydrazide moiety of the acyl hydrazide group is an aromatic hydrazide.

Example 14B

The purification method of any one of Examples 1B-13B, wherein the releasing aromatic carbonyl molecule is 2-sulfobenzaldehyde.

Example 15B

The purification method of any one of Examples 1B-14B, wherein the mixture utilized to conduct the releasing step comprises an aqueous buffer.

Example 16B

The purification method of any one of Examples 1B-15B, wherein the mixture utilized to conduct the releasing step comprises an aqueous buffer having an approximate pH 2.0-8.0.

Example 17B

The purification method of any one of Examples 1B-16B, wherein the method further comprises exchanging the release buffer for a suitable buffer or water.

Example 18B

The purification method of any one of Examples 1B-17B, wherein the mixture utilized to conduct the releasing step comprises the aromatic carbonyl molecule in a solution of 1-300 mM aniline.

Example 19B

The purification method of any one of Examples 1B-18B, wherein the mixture utilized to conduct the releasing step comprises the aromatic carbonyl molecule in a solution of 1-300 mM aniline in an aqueous buffer.

Example 20B

The purification method of any one of Examples 1B-19B, wherein the mixture utilized to conduct the releasing step comprises the aromatic carbonyl molecule in a solution of 1-300 mM aniline in an aqueous buffer having an approximate pH 2.0-8.0.

Example 21B

The purification method of any one of Examples 1B-20B, wherein the release buffer comprises 100 mM phosphate.

Example 22B

The purification method of any one of Examples 1B-21B, wherein the release buffer comprises 150 mM NaCl.

Example 23B

The purification method of any one of Examples 1B-22B, wherein the release buffer comprises a pH of about 5.0.

Example 24B

The purification method of any one of Examples 1B-23B, wherein the release buffer comprises 25 mM aniline.

Example 25B

The purification method of any one of Examples 1B-24B, wherein the carbonyl modified-molecule comprises a detectable component.

Example 26B

The purification method of any one of Examples 1B-25B, wherein the carbonyl modified-molecule comprises a detectable component comprising an oligonucleotide conjugated to one or more signal generating moieties.

Example 27B

The purification method of any one of Examples 1B-26B, wherein the carbonyl modified-molecule comprises a detectable component comprising an oligonucleotide conjugated to at least one scaffold comprising one or more signal generating moieties.

Example 28B

The purification method of any one of Examples 1B-27B, wherein the scaffold comprises a dendrimer, a polysaccharide, a dextran, a protein, a peptide, a further oligonucleotide sequence, a polymer, a hydrophilic polymer, a bead, a nanoparticle, or combinations or derivatives thereof.

Example 29B

The purification method of any one of Examples 1B-28B, wherein one or more signal generating moieties comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, a bead, an RFTD tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations thereof.

Example 30B

The purification method of any one of Examples 1B-29B, wherein the carbonyl modified-biomolecule comprises molecular probe.

Example 31B

The purification method of any one of Examples 1B-30B, wherein the carbonyl modified-biomolecule comprises molecular probe comprising a binding moiety conjugated to at least one oligonucleotide.

Example 32B

The purification method of any one of Examples 1B-31B, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 33B

The purification method of any one of Examples 1B-32B, wherein the molecular probe and/or the detectable component further comprises a spacer group, comprising a polymerized ethylene oxide, a PEG, a PEO, a protein, a peptide, a DNA, an RNA, an oligonucleotide sequence, or a dextran.

Example 34B

The purification method of any one of Examples 1B-33B, wherein the purification method purifies a genetically engineered protein.

Example 35B

The purification method of any one of Examples 1B-34B, wherein the genetically engineered protein comprises an incorporated an aliphatic or aromatic carbonyl group.

Example 36B

The purification method of any one of Examples 1B-35B, wherein the genetically engineered protein has been produced to incorporate an aliphatic or aromatic carbonyl group.

Example 1C

An assay method, comprising: i) providing to a sample comprising a plurality of targets: a) at least a first molecular probe comprising a first oligonucleotide sequence conjugated to a first binding moiety having an affinity for at least a first target of the plurality of targets; and b) at least a first particle, bead, or other surface, comprising a complementary second oligonucleotide sequence conjugated to said at least particle, bead, or other surface; wherein the amount of the second complementary oligonucleotide sequence is greater that the amount of the first oligonucleotide sequence; and iii) mixing or maintaining contact between said at least first molecular probe and said at least first particle, bead, or other surface, to hybridize all or substantially all of the first oligonucleotide sequence of the at least first molecular probe with the second complementary oligonucleotide sequence conjugated to said at least first particle, bead, or other surface.

Example 2C

The method of Example 1C, wherein the mode of addition comprises: i) the at least first molecular probe and the at least first particle, bead, or other surface, are combined together and hybridized prior to contacting the sample; ii) the at least first molecular probe is combined with the sample prior to the addition of the at least first particle, bead, or other surface; or iii) the at least first particle, bead, or other surface, is combined with the sample prior to the addition of the at least first molecular probe.

Example 3C

The method of Examples 1C or 2C, wherein the method comprises: i) the at least first molecular probe binding the target prior to hybridizing with the at least first particle, bead, or other surface; or ii) the at least first molecular probe hybridizing with the at least first particle, bead, or other surface, prior to binding the target.

Example 4C

An assay method, comprising: i) providing to a sample comprising a plurality of targets: a) at least a first molecular probe comprising a first oligonucleotide sequence conjugated to a first binding moiety having an affinity for at least a first target of the plurality of targets; b) at least a first particle, bead, or other surface, comprising a second oligonucleotide sequence conjugated to said at least particle, bead, or other surface; wherein the amount of the second oligonucleotide sequence is greater that the amount of the first oligonucleotide sequence; and c) at least a first universal adapter, comprising an oligonucleotide sequence having a first sequence segment complementary to the first oligonucleotide sequence of the at least first molecular probe and a second sequence segment complementary to the second oligonucleotide sequence of the at least first particle, bead, or other surface; and iii) mixing or maintaining contact between said at least first molecular probe, said at least first particle, bead, or other surface, and said at least first universal adapter, to hybridize all or substantially all of: a) the first oligognucleotide sequence of the at least first molecular probe with the first complementary oligognucleotide sequence segment of the at least first universal adapter; and b) the second oligognucleotide sequence of the at least first particle, bead, or other surface, with the second complementary oligognucleotide sequence segment of the at least first universal adapter.

Example 5C

The method of Example 4C, wherein the mode of addition comprises: i) the at least first molecular probe, the at least first universal adapter, and the at least first particle, bead, or other surface, are combined together and hybridized prior to contacting the sample; ii) the at least first molecular probe and the at least first universal adapter are combined together and hybridized prior to contacting the sample; iii) the at least first particle, bead, or other surface, and the at least first universal adapter are combined together and hybridized prior to contacting the sample; iv) the at least first molecular probe, alone or in combination with the at least first particle, bead, or other surface, is combined with the sample prior to the addition of the at least first universal adapter; or v) the at least first universal adapter is combined with the sample prior to the addition of the at least first molecular probe and/or the at least first particle, bead, or other surface.

Example 6C

The method of Examples 4C or 5C, wherein the method comprises: i) the at least first molecular probe hybridizing with the at least first universal adapter prior to said at least first molecular probe binding the target; ii) the at least first molecular probe hybridizing with the at least first universal adapter after said at least first molecular probe binds the target; iii) the at least first particle, bead, or other surface, hybridizing with the at least first universal adapter prior to the at least first molecular probe binding the target; iv) the at least first particle, bead, or other surface, hybridizing with the at least first universal adapter after the at least first molecular probe binds the target; v) the at least first universal adapter hybridizing with the at least first molecular probe and hybridizing with the at least first particle, bead, or other surface, prior to said at least first molecular probe binding the target; or vi) the at least first universal adapter hybridizing with the at least first molecular probe and hybridizing with the at least first particle, bead, or other surface, after said at least first molecular probe binds the target.

Example 7C

The method of any one of Examples 1C-6C, wherein the sample further comprises a plurality of non-target materials comprising at least a first non-target material.

Example 8C

The method of any one of Examples 1C-7C, wherein the at least first non-target material comprises one or more of the following: non-target antigens, non-target cells, or non-target cellular components.

Example 9C

The method of any one of Examples 1C-8C, wherein the at least first molecular probe is added in an excess amount as compared to the amount of the at least first target present in the sample.

Example 10C

The method of any one of Examples 1C-9C, wherein the at least first molecular probe recognizes the at least first target of the plurality of targets in the presence of the at least first non-target material.

Example 11C

The method of any one of Examples 1C-10C, wherein the at least first recognized-target is an antigen, an antigen on a cell surface, a cellular component, or a cell; wherein in said recognition is in the presence of one or more non-target materials.

Example 12C

The method of any one of Examples 1C-11C, wherein the at least first molecular probe binds the at least first target of the plurality of targets in the presence of the at least first non-target material.

Example 13C

The method of any one of Examples 1C-12C, wherein the at least first bound-target is an antigen, an antigen on a cell surface, a cellular component, or a cell; wherein in said binding is in the presence of one or more non-target materials.

Example 14C

The method of any one of Examples 1C-13C, wherein the at least first target is a biological target.

Example 15C

The method of any one of Examples 1C-14C, wherein the at least first target is a biological target comprising an antigen, a pathogen, a protein, a peptide, an epitope, a carbohydrate-containing molecule, a small molecule, or combinations or derivatives thereof.

Example 16C

The method of any one of Examples 1C-15C, wherein the at least first target is an antigen.

Example 17C

The method of any one of Examples 1C-16C, wherein the first binding moiety comprises an antibody, a monoclonal antibody, a polyclonal antibody, an enzyme, a protein, a peptide, a nuclear receptor, or an aptamer.

Example 18C

The method of any one of Examples 1C-17C, wherein the method is a cell depletion method.

Example 19C

The method of any one of Examples 1C-18C, wherein the method is an immunoprecipitation method.

Example 20C

The method of any one of Examples 1C-19C, wherein the complementary second oligonucleotide sequence is tethered to the at least first particle, bead, or other surface.

Example 21C

The method of any one of Examples 1C-20C, wherein said at least first particle, bead, or other surface, comprises at least one of the following: i) a magnetic bead, a paramagnetic bead, or a superparamagnetic bead; ii) a dense object, a buoyant object, or a stationary object; iii) a gel particle or a matrix, said gel particle or matrix comprising an agarose bead or a sepharose bead; and iv) a filter or a mesh.

Example 22C

The method of any one of Examples 1C-21C, wherein said at least first particle, bead, or other surface enables at least one of the following: i) magnetic separation; ii) mechanical separation; iii) chromatographic separation; and iv) filtration separation.

Example 23C

The method of any one of Examples 1C-22C, wherein the magnetic bead, a paramagnetic bead, or a superparamagnetic bead enables magnetic separation.

Example 24C

The method of any one of Examples 1C-23C, wherein the dense object, a buoyant object, or a stationary object enables mechanical separation.

Example 25C

The method of any one of Examples 1C-24C, wherein the gel particle or the matrix enables chromatographic separation.

Example 26C

The method of any one of Examples 1C-25C, wherein the filter or mesh enables filtration separation.

Example 27C

The method of any one of Examples 1C-26C, wherein the at least first bound-target is captured by separating said at least first particle, bead, or other surface from the mixture containing the non-target materials.

Example 28C

The method of any one of Examples 1C-27C, wherein the separation removes or excludes the mixture containing the non-target materials.

Example 29C

The method of any one of Examples 1C-28C, wherein the separation removes or excludes the at least first bound-target from the mixture containing the non-target materials.

Example 30C

The method of any one of Examples 1C-29C, wherein the separated at least first bound-target is further washed to remove residual non-target materials.

Example 31C

The method of any one of Examples 1C-30C, wherein the non-target materials are further washed to collect residual at least first bound-target.

Example 32C

The method of any one of Examples 1C-31C, wherein the method comprises a series of sequential or parallel steps to capture or exclude one or more targets in a sample comprising the plurality of targets.

Example 33C

The method of any one of Examples 1C-32C, wherein: i) the assay comprises a singleplex or multiplex assay; and ii) the assay further comprises detecting, measuring, or quantifying the level of binding and/or amount of the target present in the sample with one or more of the following: flow cytometry, immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunohistochemistry (IHC), immunocytochemistry (ICC), in situ hybridization (ISH), enzyme immuno-assay (EIA), enzyme linked immuno-assay (ELISA), ELISpot, immunoturbidity, latex agglutination, gold particle agglutination, visual inspection, a change in light transmittance through said sample, increased light transmittance through said sample, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 34C

The method of any one of Examples 1C-33C, wherein: i) the assay comprises a singleplex or multiplex assay; and ii) the assay further comprises detecting, measuring, or quantifying the level of binding and/or amount of the target present in the sample with one or more of the following: flow cytometry, microscopy, imaging, high content screening (HCS), multiplex bead array, microarray, antibody array, cellular array, immunohistochemistry (IHC), immunocytochemistry (ICC), in situ hybridization (ISH), enzyme immuno-assay (EIA), enzyme linked immuno-assay (ELISA), ELISpot, or a blotting method.

Example 35C

The method of any one of Examples 1C-34C, wherein: i) the assay comprises a singleplex or multiplex assay; and ii) the assay further comprises detecting, measuring, or quantifying the level of binding and/or amount of the target present in the sample with one or more of the following: flow cytometry, mass cytometry, lateral flow immunoassay, immunohistochemistry (IHC), immunocytochemistry (ICC), immunoprecipitation, pretargeting imaging, therapeutic agent, or combinations thereof.

Example 36C

The method of any one of Examples 1C-35C, wherein the sample is characterized as at least one or more of the following: i) a complex sample; and ii) a homogeneous or a heterogeneous mixture; wherein said sample comprises at least one or more of the following: a) one or more analytes having substantially the same or substantially different binding specificities; b) one or more of the following biologic components, comprising: cells, membranes, biological molecules, metabolites, or disease biomarkers; and c) a biological fluid or a fluidized biological tissue.

Example 37C

The method of any one of Examples 1C-36C, wherein the method comprises one or more of the following: i) the hybridization efficiency of the first oligonucleotide sequence to the second oligonucleotide sequence is at least 50% with respect to the at least first particle, bead, or other surface, under the hybridization conditions employed; ii) the hybridization efficiency of the first oligonucleotide sequence to the complementary first oligonucleotide sequence segment is at least 50% with respect to the at least first molecular probe, under the hybridization conditions employed; or iii) the hybridization efficiency of the second oligonucleotide sequence to the complementary second oligonucleotide sequence segment is at least 50% with respect to the at least first particle, bead, or other surface, under the hybridization conditions employed.

Example 38C

The method of any one of Examples 1C-37C, wherein the at least first molecular probe, the at least first particle, bead, or other surface, and/or at least first universal adapter further comprises a spacer group, comprising a polymerized ethylene oxide, a PEG, a PEO, a protein, a peptide, a DNA, an RNA, an oligonucleotide sequence, or a dextran.

Example 39C

The method of any one of Examples 1C-38C, wherein the conjugation of the first binding moiety to the first oligonucleotide sequence comprises a HyNic or a 4-FB residue; and wherein the conjugation of the at least first particle, bead, or other surface, to the second oligonucleotide sequence comprises a HyNic or a 4-FB residue.

Example 40C

The method of any one of Examples 1C-39C, wherein the first oligonucleotide sequence, second oligonucleotide sequence, and/or oligonucleotide sequence segment comprising an oligonucleotide sequence conjugated at the 3'-position, an oligonucleotide sequence conjugated at the 5'-position, linear oligonucleotide sequences, branched oligonucleotide sequences, LNAs, PNAs, oligonucleotide sequences optionally covalently attached to other moieties, or combinations or derivatives thereof.

Example 41C

The method of any one of Examples 1C-40C, wherein a plurality of molecular probes and a plurality of particles, beads, or other surfaces, are provided to the sample.

Example 42C

The method of any one of Examples 1C-41C, wherein a plurality of universal adapters are provided to the sample.

Example 43C

The method of any one of Examples 1C-42C, wherein the binding affinity for the at least first target is $10^{-4}$M or less.

Example 44C

The method of any one of Examples 1C-43C, wherein the method comprises an automated system or robotic system.

Example 45C

The method of any one of Examples 1C-44C, wherein the other surface comprises a scaffold, a plate, or solid array.

Example 46C

The method of any one of Examples 1C-44C, wherein the scaffold comprises a dendrimer, a polysaccharide, a dextran, a protein, a peptide, a further oligonucleotide sequence, a portion of the second oligonucleotide sequence that is not complementary to the first oligonucleotide sequence of the molecular probe, a polymer, a hydrophilic polymer, a bead, a nanoparticle, or combinations or derivatives thereof.

Example 1D

A method for assaying a target of a sample, comprising: i) providing to the sample: 1) a first molecular probe, comprising a first binding moiety conjugated to a first oligonucleotide sequence; and 2) a first bead conjugate, comprising a first bead conjugated to a second oligonucleotide sequence that is complementary to the first oligonucleotide sequence of the first molecular probe, wherein the first bead comprises or is encoded with one or more signal generating moieties; ii) binding the target in the sample with the first binding moiety of the first molecular probe; iii) hybridizing the first oligonucleotide sequence of the first molecular probe with the second oligonucleotide sequence of the first bead conjugate; and iv) providing to the sample a second binding moiety comprising one or more signal generating moieties; v) further binding the target of the first binding moiety-bound target with the second binding moiety to form a sandwich-complex; vi) detecting a signal generated from the sandwich complex; wherein the method is characterized by one or more of the following: a) the conjugation between the first oligonucleotide sequence and the first binding moiety and conjugation between the complementary second oligonucleotide sequence and the first bead conjugate, comprises one or more covalent bond linkages, comprising a hydrazone, oxime, triazine, or other covalent bond, wherein the formation of the conjugates are at least 90% efficient; and b) the first binding moiety and the second binding moiety comprise strong binding affinities for the target.

Example 2D

The method of Example 1D, wherein the mode of addition comprises: i) the first molecular probe and the first bead conjugate are combined together and hybridized prior to contacting the sample; ii) the first molecular probe is combined with the sample prior to the addition of the first bead conjugate; or iii) the first bead conjugate is combined with the sample prior to the addition of the first molecular probe.

Example 3D

The method of any one of Examples 1D-2D, wherein the method comprises: i) the first molecular probe binding the target prior to hybridizing with the first bead conjugate; or ii) the first molecular probe hybridizing with the first bead conjugate prior to binding the target.

Example 4D

A method for assaying a target of a sample, comprising: i) providing to the sample: 1) a first molecular probe, comprising a first binding moiety conjugated to a first oligonucleotide sequence; 2) a first bead conjugate, comprising a first bead conjugated to a second oligonucleotide sequence, wherein the first bead comprises or is encoded with one or more signal generating moieties; and 3) a first universal adapter, comprising an oligonucleotide sequence having a first sequence segment complementary to the first oligonucleotide sequence of the first molecular probe and a second sequence segment complementary to the second oligonucleotide sequence of the first bead conjugate; ii) binding the target in the sample with the first binding moiety of the first molecular probe; iii) hybridizing the first oligonucleotide sequence of the first molecular probe to the first oligonucleotide sequence segment of the first universal adapter; iv) hybridizing the second oligonucleotide sequence of the first bead conjugate to the complementary second oligonucleotide sequence segment of the first universal adaptor; and v) providing to the sample a second binding moiety comprising one or more signal generating moieties; iv) further binding the target of the first binding moiety-bound target with the second binding moiety to form a sandwich-complex; vi) detecting a signal generated from the sandwich complex; wherein the method is characterized by one or more of the following: a) the conjugation between the first oligonucleotide sequence and the first binding moiety and conjugation between the complementary second oligonucleotide sequence and the first bead conjugate, comprises one or more covalent bond linkages, comprising a hydrazone, oxime, triazine, or other covalent bond, wherein the formation of the conjugates are at least 90% efficient; and b) the first binding moiety and the second binding moiety comprise strong binding affinities for the target.

Example 5D

The method of Example 4D, wherein the mode of addition comprises: i) the first molecular probe, the first universal adapter, and the first bead conjugate are combined together and hybridized prior to contacting the sample; ii) the first molecular probe and the first universal adapter are combined together and hybridized prior to contacting the sample; iii) the first bead conjugate and the first universal adapter are combined together and hybridized prior to contacting the sample; iv) the first molecular probe, alone or in combination with the first bead conjugate, is combined with the sample prior to the addition of the first universal adapter; or v) the first universal adapter is combined with the sample prior to the addition of the first molecular probe and/or the first bead conjugate.

Example 6D

The method of Example 4D or 5D, wherein the method comprises: i) the first molecular probe hybridizing with the first universal adapter prior to said first molecular probe binding the target; ii) the first molecular probe hybridizing with the first universal adapter after said first molecular probe binds the target; iii) the first bead conjugate hybridizing with the first universal adapter prior to the first molecular probe binding the target; iv) the first bead conjugate hybridizing with the first universal adapter after the first molecular probe binds the target; v) the first universal adapter hybridizing with the first molecular probe and hybridizing with the first bead conjugate prior to said first molecular probe binding the target; or vi) the first universal adapter hybridizing with the first molecular probe and hybridizing with the first bead conjugate after said first molecular probe binds the target.

Example 7D

A method for crosslinking, comprising: i) introducing to a sample comprising one or more targets: a) one or more first antibody-oligonucleotide conjugates, comprising a first antibody conjugated to a first oligonucleotide sequence; and b) one or more second antibody-oligonucleotide conjugates, comprising a second antibody conjugated to a second oligonucleotide sequence; ii) binding at least a first target of the one or more targets with the first antibody of the one or more first antibody-oligonucleotide conjugates and with the second antibody of the one or more second antibody-oligonucleotide conjugates to form one or more sandwich-complexes; iii) contacting the one or more sandwich-complexes with: a) one or more first bead-oligonucleotide conjugate, comprising a first bead conjugated to a complementary first oligonucleotide sequence; and b) one or more second bead-oligonucleotide conjugate, comprising a second bead conjugated to a complementary second oligonucleotide sequence; iv) crosslinking the one or more sandwich-complexes by: a) hybridizing the first oligonucleotide sequences of the one or more sandwich-complexes with the complementary first oligonucleotide sequences of the one or more first bead-oligonucleotide conjugates; and b) hybridizing the second oligonucleotide sequences of the one or more sandwich-complexes with the complementary second oligonucleotide sequences of the one or more bead-oligonucleotide conjugates.

Example 8D

The crosslinking method of Example 7D, wherein the formation of the cross linked one or more sandwich-complexes forms an agglutination.

Example 9D

The crosslinking method of Examples 7D or 8D, wherein the method further comprises detecting, measuring, and/or quantifying the degree of the formed agglutination to determine the amount of the one or more targets in the sample.

Example 10D

The crosslinking method of any one of Examples 7D-9D, wherein the first antibody or the second antibody comprise a monoclonal antibody or a polyclonal antibody.

Example 11D

The crosslinking method of any one of Examples 7D-10, wherein: i) the first antibody comprises a first polyclonal antibody and the second antibody comprises a second polyclonal antibody; ii) the first antibody comprises a first monoclonal antibody and the second antibody comprises a second monoclonal antibody; iii) the first antibody comprises a first monoclonal antibody and the second antibody comprises a first polyclonal antibody; or iv) the first antibody comprises a first polyclonal antibody and the second antibody comprises a first monoclonal antibody.

Example 12D

The crosslinking method of Example 11D, wherein the first monoclonal antibody is raised against a first epitope of the target and the second monoclonal antibody is raised against a second epitope of the target.

Example 13D

The crosslinking method of any one of Examples 7D-12D, wherein the first antibody comprises a first polyclonal antibody and the second antibody comprises a second polyclonal antibody.

Example 14D

The crosslinking method of Example 13D, wherein a first portion of the first polyclonal antibody binds to a first epitope of the target and a second portion of the second polyclonal antibody binds to a second epitope of the target.

Example 15D

The crosslinking method of any one of Examples 7D-12D, wherein the first antibody comprises a first monoclonal antibody and the second antibody comprises a second monoclonal antibody.

Example 16D

The crosslinking method of any one of Examples 7D-12D, wherein the first antibody comprises a first monoclonal antibody and the second antibody comprises a first polyclonal antibody.

Example 17D

The method of any one of Examples 1D-16D, wherein: i) the assay comprises a singleplex or multiplex assay; and ii)

the assay detects, measures, or quantifies the level of binding and/or amount of the target present in the sample.

Example 18D

The method of any one of Examples 1D-17D, wherein method detects, measures, or quantifies the level of binding and/or amount of the target present in the sample with one or more of the following: immunoturbidity, latex agglutination, gold particle agglutination, visual inspection, a change in light transmittance through said sample, increased light transmittance through said sample, flow cytometry, immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunohistochemistry (IHC), immunocytochemistry (ICC), in situ hybridization (ISH), enzyme immuno-assay (EIA), enzyme linked immuno-assay (ELISA), ELISpot, a blotting method, a Western blot, a Southern blot, a South-western blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 19D

The method of any one of Examples 1D-18D, wherein: i) the assay comprises a singleplex or multiplex assay; and ii) the assay detects, measures, or quantifies the level of binding and/or amount of the target present in the sample with one or more of the following: immunoturbidity, latex agglutination, gold particle agglutination, visual inspection, a change in light transmittance through said sample, increased light transmittance through said sample, lateral flow immunoassay, immunodetection, flow cytometry, microscopy, imaging, high content screening (HCS), multiplex bead array, microarray, antibody array, cellular array, immunohistochemistry (IHC), immunocytochemistry (ICC), in situ hybridization (ISH), enzyme immuno-assay (EIA), enzyme linked immuno-assay (ELISA), ELISpot, or a blotting method.

Example 20D

The method of any one of Examples 1D-19D, wherein: i) the assay comprises a singleplex or multiplex assay; and ii) the assay detects, measures, or quantifies the level of binding and/or amount of the target present in the sample with one or more of the following: immunoturbidity, latex agglutination, gold particle agglutination, visual inspection, a change in light transmittance through said sample, increased light transmittance through said sample, lateral flow immunoassay, immunodetection, flow cytometry, microscopy, imaging, high content screening (HCS), mass cytometry, lateral flow immunoassay, immunohistochemistry (IHC), immunocytochemistry (ICC), immunoprecipitation, pretargeting imaging, therapeutic agent, or combinations thereof.

Example 21D

The method of any one of Examples 1D-20D, wherein the sample is characterized as at least one or more of the following: i) a complex sample; and ii) a homogeneous or a heterogeneous mixture; wherein said sample comprises at least one or more of the following: a) one or more analytes having substantially the same or substantially different binding specificities; b) one or more of the following biologic components, comprising: cells, membranes, biological molecules, metabolites, or disease biomarkers; and c) a biological fluid or a fluidized biological tissue.

Example 22D

The method of any one of Examples 1D-21D, wherein the hybridization efficiency of the first oligonucleotide sequence to the second oligonucleotide sequence is at least 50% with respect to the first bead, under the hybridization conditions employed.

Example 23D

The method of any one of Examples 1D-22D, wherein the first molecular probe comprises one or more of the following properties: i) a molecular weight of between about 15,000 Daltons to about 450,000 Daltons; ii) a solubility that is substantially the same as that of the unconjugated first binding moiety; iii) a solubility that minimizes non-specific binding to the target; iv) the first oligonucleotide sequence of the first molecular probe does not adversely affect the solubility of the first binding moiety; v) interacts and binds to the target via interactions other than exclusively electrostatic; vi) a unique, distinguishable, and/or specifically designed first oligonucleotide sequence; and vii) the first oligonucleotide sequence of the first molecular probe is uniquely and specifically designed to hybridize to the second oligonucleotide sequence of the first bead.

Example 24D

The method of any one of Examples 1D-23D, wherein the method of detection generates less false positives than secondary antibody detection methods.

Example 25D

The method of any one of Examples 1D-24D, wherein the method further comprises: i) preparing the first molecular probe; ii) preparing the first bead conjugate; and iii) optionally preparing the first universal adapter; wherein the prepared first molecular probe, prepared first bead conjugate, and optionally prepared first universal adapter, have at least 90% purity.

Example 26D

The method of any one of Examples 1D-25D, wherein the method further comprises preparing and isolating the first molecular probe, comprising: i) providing the first binding moiety; ii) conjugating the first binding moiety with at least one first oligonucleotide sequence at greater than 90% efficiency to form first binding moiety-oligonucleotide conjugates; and iii) isolating the first binding moiety-oligonucleotide conjugates from the conjugation mixture by binding, retaining, and/or retarding a substantial portion of: a) the conjugates, removing a substantial portion of the unconjugated first oligonucleotide sequence in a wash step followed by release of the bound, retained, and/or retarded conjugates; or b) the unconjugated first oligonucleotide sequences, followed by collecting a substantial portion of the non-bound, non-retained, and/or non-retarded conjugates in a wash step.

Example 27D

The method of any one of Examples 1D-26D, wherein the method further comprises preparing and isolating the first bead conjugate, comprising: i) providing the first bead; ii) conjugating the second oligonucleotide sequence with the first bead at greater than 90% efficiency to form first bead-second oligonucleotide conjugates; and iii) isolating the first bead-second oligonucleotide conjugates from the conjugation mixture by binding, retaining, and/or retarded a substantial portion of: a) the conjugates, removing a substantial portion of the unconjugated second oligonucleotide sequences in a wash step followed by release of the bound, retained, and/or retarded conjugates; orb) the unconjugated second oligonucleotide sequences, followed by collecting a substantial portion of the non-bound, non-retained, and/or non-retarded conjugates in a wash step.

Example 28D

The method of any one of Examples 1D-27D, wherein the first bead conjugate further comprises a scaffold conjugated to the second oligonucleotide sequence, and wherein said scaffold comprises one or more signal generating moieties.

Example 29D

The method of Example 28D, wherein the scaffold comprises a dendrimer, a polysaccharide, a dextran, a protein, a peptide, a further oligonucleotide sequence, a portion of the second oligonucleotide sequence that is not complementary to the first oligonucleotide sequence of the molecular probe, a polymer, a hydrophilic polymer, a bead, a nanoparticle, or combinations or derivatives thereof.

Example 30D

The method of any one of Examples 1D-29D, wherein the method further comprises preparing and isolating the first bead conjugate further comprising a scaffold conjugated to the second oligonucleotide sequence, wherein the scaffold comprises one or more signal generating moieties, said method comprising: i) providing a plurality of the scaffolds comprising the one or more signal generating moieties; ii) conjugating the second oligonucleotide sequence with at least one of the plurality of scaffolds at greater than 90% efficiency to form scaffold-second oligonucleotide conjugates; and iii) isolating the scaffold-second oligonucleotide conjugates from the conjugation mixture by binding, retaining, and/or retarding a substantial portion of: a) the conjugates, removing a substantial portion of the unconjugated second oligonucleotide sequences in a wash step followed by release of the bound, retained, and/or retarded conjugates; or b) the unconjugated second oligonucleotide sequences, followed by collecting a substantial portion of the non-bound, non-retained, and/or non-retarded conjugates in a wash step.

Example 31D

The method of any one of Examples 26D-30D, wherein the isolation step utilizes an immobilized binder, chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

Example 32D

The method of any one of Examples 26D-30D, wherein the isolation step utilizes an immobilized binder, affinity chromatography, size exclusion chromatography, electrophoresis, differential centrifugation, immunoprecipitation, hybridization, solvent extraction, dialysis, filtration, diafiltration, ion exchange chromatography, hydrophobic interaction chromatography, or combinations thereof.

Example 33D

The method of any one of Examples 26D-30D, wherein the isolation step utilizes an immobilized binder, affinity chromatography, size exclusion chromatography, differential centrifugation, dialysis, filtration, hydrophobic interaction chromatography, or combinations thereof.

Example 34D

The method of any one of Examples 1D-33D, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 35D

The method of any one of Examples 1D-34D, wherein the sample comprises one or more targets.

Example 36D

The method of any one of Examples 1D-35D, wherein the target is a biological target.

Example 37D

The method of Example 36D, wherein the biological target comprises an antigen, a pathogen, a protein, a peptide, an epitope, a carbohydrate-containing molecule, a small molecule, or combinations or derivatives thereof.

Example 38D

The method of any one of Examples 1D-37D, wherein the signal generating moiety or the one or more signal generating moieties of the first bead conjugate, the hybridized first bead conjugate, the second binding moiety, or of the scaffold, comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations or derivatives thereof.

Example 39D

The method of any one of Examples 1D-38D, wherein the one or more signal generating moieties provides an enhanced signal that minimizes detection errors from background noise, relative to conventionally labeled binding moieties.

Example 40D

The method of any one of Examples 1D-39D, wherein the molecular probe, the first bead conjugate, and/or universal adapter further comprises a spacer group, comprising a polymerized ethylene oxide, a PEG, a PEO, a protein, a peptide, a DNA, an RNA, an oligonucleotide sequence, or a dextran.

Example 41D

The method of any one of Examples 1D-40D, wherein the binding moiety, the first bead, the scaffold, the first oligonucleotide sequence, and/or the second oligonucleotide sequence comprise HyNic or 4-FB.

Example 42D

The method of any one of Examples 1D-41D, wherein the first bead conjugate comprises a unique, distinguishable, and/or specifically designed second oligonucleotide sequence.

Example 43D

The method of any one of Examples 1D-42D, wherein the first oligonucleotide sequence, second oligonucleotide sequence, and/or oligonucleotide sequence segment comprising an oligonucleotide sequence conjugated at the 3'-position, an oligonucleotide sequence conjugated at the 5'-position, linear oligonucleotide sequences, branched oligonucleotide sequences, LNAs, PNAs, oligonucleotide sequences optionally covalently attached to other moieties, or combinations or derivatives thereof.

Example 44D

The method of any one of Examples 1D-43D, wherein the sample comprises one or more targets.

Example 45D

The method of any one of Examples 1D-44D, wherein a plurality of molecular probes and a plurality of bead conjugates are provided to the sample.

Example 46D

The method of any one of Examples 1D-45D, wherein a plurality of universal adapters are provided to the sample.

Example 47D

The method of any one of Examples 1D-46D, wherein the binding affinity of the first binding moiety and/or of the second binding moiety for the target is $10^{-4}$ M or less.

Example 48D

The method of any one of Examples 1D-47D, wherein the binding affinity of the first binding moiety and/or of the second binding moiety for the at least first target is $10^{-4}$ M or less.

Example 49D

The method of any one of Examples 1D-48D, wherein the binding affinity of the first binding moiety and/or of the second binding moiety for the at least second target is $10^{-4}$ M or less.

Example 50D

The method of any one of Examples 1D-49D, wherein the method comprises an automated system or robotic system.

Example 51D

The method of any one of Examples 1D-50D, wherein the first bead conjugate comprises or is encoded with one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations or derivatives thereof.

Example 52D

The method of any one of Examples 1D-50D, wherein the first bead conjugate comprises or is encoded with one or more of the following: a fluorescent dye, a fluorophore, a fluorochrome, a fluorescent protein, a biofluorescent protein, a luminescent species, a chemiluminescent compound, a electrochemiluminescent label, a fluorophore labeled DNA dendrimer, Quantum Dot, a secondary reporter, a hapten, an enzyme, an antibody, a nanoparticle, a light scattering nanoparticle or microsphere, a bioluminescent label, a tandem dye, a FRET dye, a diffracting particle, a polymer particle, a bead, a solid surface, a metal particle, a molecule specifically recognized by another substance carrying a label or reacts with a substance carrying a label, a nucleic acid, a nucleic acid analog, oligonucleotide, oligonucleotide analog, complementary oligonucleotide, complementary oligonucleotide analog.

Example 53D

A method for assaying one or more targets of a sample, comprising: i) providing to the sample: 1) a plurality of molecular probes, comprising: A) at least a first molecular probe having a first binding moiety conjugated to a first oligonucleotide sequence; and B) at least a second molecular probe having a second binding moiety conjugated to a second oligonucleotide sequence; and 2) a plurality of detectable components, comprising: A) at least a first detectable component, comprising a first bead conjugated to a complementary first oligonucleotide sequence, wherein the first bead comprises one or more signal generating moieties; B) at least a second detectable component, comprising a second bead conjugated to a complementary second oligonucleotide sequence, wherein the second bead comprises one or more signal generating moieties; ii) binding the one or more targets, comprising at least one of the following: 1) binding at least a first target of the one or more targets in the sample with the first binding moiety of the at least first molecular probe; and 2) binding at least a second target of the one or more targets in the sample with the second binding moiety of the at least second molecular probe; iii) hybridizing the plurality of molecular probes and the plurality of detectable components, comprising at least one of the following: 1) hybridizing the first oligonucleotide sequence of at least first molecular probe to the first complementary oligonucleotide sequence segment of the at least first detectable component; and 2) hybridizing the second oligonucleotide sequence of at least second molecular probe to the second complementary oligonucleotide sequence segment of the at least second detectable component; and iv) detecting one or more signals generated from at least one of the following: 1) the at least first hybridized detectable component; and 2) the at least second hybridized detectable component; wherein the method is characterized by one or more of the following: a) the conjugation between the first oligonucleotide sequence and the first binding moiety, between the second oligonucleotide sequence and the second binding moiety, between the first complementary oligonucleotide sequence and the first bead, and between the second complementary oligonucleotide sequence and the second bead, comprises one or more covalent bond linkages, comprising a hydrazone, oxime, triazine, or other covalent bond, wherein the formation of the conjugates are at least 90% efficient; and b) the first binding moiety comprises a strong binding affinity for the at least first target of the one or more targets and the second binding moiety comprises a strong binding affinity for the at least second target of the one or more targets.

Example 54D

A method for assaying one or more targets of a sample, comprising: i) providing to the sample: a) a plurality of molecular probes, comprising: a first oligonucleotide sequence independently paired, via conjugation, to a plurality of binding moieties comprising at least a first binding moiety and at least a second binding moiety; b) a plurality of detectable components, comprising: a plurality of second oligonucleotide sequences independently paired, via conjugation, to a plurality of beads having one or more signal generating moieties comprising at least a first bead and at least a second bead; and c) a plurality of universal adapters, comprising: a first oligonucleotide sequence segment, complementary to the first oligonucleotide sequence of said plurality of molecular probes, independently paired with a plurality of second oligonucleotide sequence segments complementary to the plurality of second oligonucleotide sequences of said plurality of detectable components; ii) binding the one or more targets, comprising at least one of the following: a) binding at least a first target of the one or more targets in the sample with the first binding moiety of the at least first molecular probe; and b) binding at least a second target of the one or more targets in the sample with the second binding moiety of the at least second molecular probe; iii) hybridizing the plurality of molecular probes and the plurality of detectable components with the plurality of universal adapters; and iv) detecting one or more signals generated from at least one of the following: a) the at least first hybridized detectable component; and b) the at least second hybridized detectable component; wherein the method is characterized by one or more of the following: A) the conjugation between the first oligonucleotide sequence and the first binding moiety, between the second oligonucleotide sequence and the second binding moiety, between the first complementary oligonucleotide sequence and the first bead, and between the second complementary oligonucleotide sequence and the second bead, comprises one or more covalent bond linkages, comprising a hydrazone, oxime, triazine, or other covalent bond, wherein the formation of the conjugates are at least 90% efficient; and B) the first binding moiety comprises a strong binding affinity for the at least first target of the one or more targets and the second binding moiety comprises a strong binding affinity for the at least second target of the one or more targets.

Example 1E

A tunable detection system, comprising: i) a molecular probe prepared by conjugating a first oligonucleotide sequence to a binding moiety; and ii) a series of detectable components, comprising a range of signal generating moieties conjugated to a second oligonucleotide sequence, wherein the range of signal generating moieties generates a range of signal intensities, and wherein the second oligonucleotide sequence is complementary to the first oligonucleotide sequence; wherein the range of signal intensities generated can be tuned over a range from the limit of self-quenching to the intensity of a single signal generating moiety.

Example 2E

A tunable detection system, comprising: i) a molecular probe prepared by conjugating a first oligonucleotide sequence to a binding moiety; and ii) a series of detectable components, comprising a range of signal generating moieties conjugated to a second oligonucleotide sequence, wherein the range of signal generating moieties generates a range of signal intensities; and iii) a universal adapter, comprising a first oligonucleotide sequence segment complementary to the first oligonucleotide sequence and a second oligonucleotide sequence segment complementary to the second oligonucleotide sequence; wherein the range of signal intensities generated can be tuned over a range from the limit of self-quenching to intensity of a single signal generating moiety.

Example 3E

The tunable detection system of Examples 1E or 2E, wherein the signal generated is from a target in a sample bound by the molecular probe that is hybridized to the detectable component.

Example 4E

The tunable detection system of any one of Examples 1E-3E, wherein the detectable component or the hybridized detectable component comprises one or more signal generating moieties, comprising one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations thereof.

Example 5E

The tunable detection system of any one of Examples 1E-4E, wherein the detectable component comprises a scaffold conjugated to the second oligonucleotide sequence, and wherein said scaffold comprises the one or more signal generating moieties.

Example 6E

The tunable detection system of any one of Examples 1E-5E, wherein the scaffold comprises a dendrimer, a polysaccharide molecule, a dextran, a protein, a peptide, a second oligonucleotide sequence, a portion of the oligonucleotide sequence that is not complementary to the oligonucleotide sequence of the molecular probe, a polymer, a hydrophilic polymer, a bead, a nanoparticle, or combinations or derivatives thereof.

Example 7E

The tunable detection system of any one of Examples 1E-6E, wherein the tuning of the signal intensities generated is determined by selecting the identity of the detectable component or by having a greater or lesser number of signal generating moieties.

Example 8E

The tunable detection system of any one of Examples 1E-7E, wherein: i) the tunable detection system comprises a singleplex or multiplex tunable detection system; and ii) the tunable detection system detects, measures, or quantifies the level of binding and/or amount of one or more targets present in a sample from the generated signal by one or more of the following: flow cytometry, immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunohistochemistry (IHC), immunocytochemistry (ICC), in situ hybridization (ISH), enzyme immuno-assay (EIA), enzyme linked immuno-assay (ELISA), ELISpot, immunoturbidity, latex agglutination, gold particle agglutination, visual inspection, a change in light transmittance through said sample, increased light transmittance through said sample, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pre-targeting imaging, therapeutic agent, or combinations thereof.

Example 9E

The tunable detection system of any one of Examples 1E-8E, wherein the tunable detection system minimizes signal spillover.

Example 10E

A tunable detection system, comprising: i) a plurality of molecular probes comprising: 1) at least a first molecular probe prepared by conjugating a first oligonucleotide sequence to a first binding moiety; and 2) at least a second molecular probe prepared by conjugating a second oligonucleotide sequence to a second binding moiety; and ii) a plurality of detectable components comprising: 1) at least a first detectable component comprising a range of first signal generating moieties conjugated to a oligonucleotide sequence complementary to said first oligonucleotide sequence, wherein the range of first signal generating moieties generates a range of signal intensities; and 2) at least a second detectable component comprising a range of second signal generating moieties conjugated to a oligonucleotide sequence complementary to said second oligonucleotide sequence, wherein the range of second signal generating moieties generates a range of signal intensities; wherein the range of signal intensities generated from the at least first detectable component and the at least second detectable component can be individually tuned over a range from the limit of self-quenching to intensity of the single first signal generating moiety or the second signal generating moiety, respectively.

Example 11E

A tunable detection system, comprising: i) a plurality of molecular probes comprising a plurality of binding moieties independently conjugated to a universal oligonucleotide sequence, comprising: 1) at least a first molecular probe comprising a first binding moiety conjugated to a universal oligonucleotide sequence; and 2) at least a second molecular probe comprising a second binding moiety conjugated to a universal oligonucleotide sequence; and ii) a plurality of detectable components comprising a range of first signal generating moieties independently conjugated to a plurality of oligonucleotide sequences, comprising: 1) at least a first detectable component comprising a range of first signal generating moieties conjugated to first oligonucleotide sequence, wherein the range of first signal generating moieties generates a range of signal intensities; and 2) at least a second detectable component comprising a range of second signal generating moieties conjugated to a second oligonucleotide sequence, wherein the range of second signal generating moieties generates a range of signal intensities; and iii) a plurality of universal adapters, comprising a first oligonucleotide sequence segment complementary to the universal oligonucleotide sequence independently paired with a plurality of oligonucleotide sequence segments complementary to the plurality of oligonucleotide sequence of the plurality of detectable components; wherein the range of signal intensities generated from the at least first detectable component and the at least second detectable component can be individually tuned over a range from the limit of self-quenching to intensity of the single first signal generating moiety or the second signal generating moiety, respectively.

Example 12E

The tunable detection system of Examples 10E or 11E, wherein: i) the first signal generated is from at least a first target in a sample bound by the at least first molecular probe that is hybridized to the at least first detectable component; and ii) the second signal generated is from at least a second target in the sample bound by the at least second molecular probe that is hybridized to the at least second detectable component.

Example 13E

The tunable detection system of any one of Examples 10E-12E, wherein the plurality of detectable components, the at least first hybridized detectable component, and/or the at least second hybridized detectable component comprise one or more signal generating moieties, wherein said one or more signal generating moieties comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations thereof.

Example 14E

The tunable detection system of any one of Examples 10E-13E, wherein the at least first hybridized detectable component comprises a first scaffold conjugated to the first oligonucleotide sequence and/or the at least second hybridized detectable component comprises a second scaffold conjugated to the second oligonucleotide sequence.

Example 15E

The tunable detection system of any one of Examples 10E-14E, wherein the first scaffold and/or the second scaffold comprises a dendrimer, a polysaccharide molecule, a dextran, a protein, a peptide, an additional oligonucleotide sequence, a portion of the first or second oligonucleotide sequence that is not complementary to the first or second oligonucleotide sequence of the at least first or second molecular probe, a polymer, a hydrophilic polymer, a bead, a nanoparticle, or combinations or derivatives thereof.

Example 16E

The tunable detection system of any one of Examples 10E-15E, wherein the first scaffold and/or the second scaffold has one or more signal generating moieties.

Example 17E

The tunable detection system of any one of Examples 10E-16E, wherein: i) the tunable detection system comprises a singleplex or multiplex tunable detection system; and ii) the tunable detection system detects, measures, or quantifies the level of binding and/or amount of one or more targets present in a sample from the signal generated from the at least first detectable component and/or the signal generated from the at least second detectable component by one or more of the following: flow cytometry, immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunohistochemistry (IHC), immunocytochemistry (ICC), in situ hybridization (ISH), enzyme immuno-assay (EIA), enzyme linked immuno-assay (ELISA), ELISpot, immunoturbidity, latex agglutination, gold particle agglutination, visual inspection, a change in light transmittance through said sample, increased light transmittance through said sample, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 18E

The tunable detection system of any one of Examples 10E-17E, wherein the tunable detection system detects, measures, or quantifies the level of binding and/or amount of one or more targets present in a sample from the generated signal by one or more of the following: flow cytometry, microscopy, imaging, high content screening (HCS), multiplex bead array, microarray, antibody array, cellular array, immunohistochemistry (IHC), immunocytochemistry (ICC), in situ hybridization (ISH), enzyme immuno-assay (EIA), enzyme linked immuno-assay (ELISA), ELISpot, or blotting method

Example 19E

The tunable detection system of any one of Examples 10E-18E, wherein the tunable detection system minimizes signal spillover by varying one or more of the following: the identity of the first signal generating moiety, the number of the first signal generating moieties on the at least first detectable component, the identity of the second signal generating moiety, the number of the second signal generating moieties on the at least second detectable component.

Example 20E

The tunable detection system of any one of Examples 1E-19E, wherein the sample comprises a plurality of targets.

Example 21E

The tunable detection system of any one of Examples 1E-20E, wherein the tunable detection system comprises one or more of the following: i) the plurality of molecular probes comprises the plurality of binding moieties independently conjugated to a plurality of oligonucleotide sequences, comprising: 1) at least a first molecular probe comprising the first binding moiety conjugated to a first oligonucleotide sequence; and 2) at least a second molecular probe comprising the second binding moiety conjugated to a second oligonucleotide sequence; and ii) the plurality of detectable components comprising the range of first signal generating moieties independently conjugated to the universal oligonucleotide sequence, comprising: 1) at least a first detectable component comprising the range of first signal generating moieties conjugated to the universal oligonucleotide sequence, wherein the range of first signal generating moieties generates a range of signal intensities; and 2) at least a second detectable component comprising the range of second signal generating moieties conjugated to the universal oligonucleotide sequence, wherein the range of second signal generating moieties generates a range of signal intensities; and iii) a plurality of universal adapters, comprising a plurality of oligonucleotide sequence segments complementary to the plurality of oligonucleotide sequence of the plurality of molecular probes independently paired with a second oligonucleotide sequence segment complementary to the universal oligonucleotide sequence.

Example 22E

The tunable detection system of any one of Examples 1E-21E, wherein the plurality of targets comprises substantially similar or substantially different targets.

Example 23E

The tunable detection system of any one of Examples 1E-22E, wherein at least a first target of the plurality of targets is different among the plurality of targets.

Example 24E

The tunable detection system of any one of Examples 1E-23E, wherein the tunable detection system comprises an automated system or robotic system.

Example 25E

The tunable detection system of any one of Examples 1E-24E, wherein the tunable detection system further comprises removing the hybridized detectable component or plurality of detectable components from the bound target or plurality of targets, respectively, wherein said removal is by a washing or stripping process.

Example 26E

The tunable detection system of Example 25E, wherein the removal comprises de-hybridizing the detectable component or the plurality of detectable components, respectively.

Example 27E

The tunable detection system of Examples 25E or 26E, wherein the tunable detection system further comprises re-probing with a second detectable component or second plurality of detectable components, respectively, wherein said second detectable component comprises at least one second signal generating moieties conjugated to a second oligonucleotide sequence or a complementary second oligonucleotide sequence, or said second plurality of detectable components are prepared by independently pairing, via conjugation, a second plurality of signal generating moieties and a second plurality of second oligonucleotide sequences or a second plurality of complementary second oligonucleotide sequences.

Example 28E

The tunable detection system of any one of Examples 1E-27E, wherein the range of different signals generated from the signal generating moieties or plurality of signal generating moieties comprises between 2-20.

Example 29E

The tunable detection system of any one of Examples 1E-28E, wherein the range of different signals generated from the signal generating moieties or plurality of signal generating moieties comprises between 2-10.

Example 30E

The tunable detection system of any one of Examples 1E-29E, wherein the intensity of the signal generated can be tuned over a range 1.25 to 2×.

Example 31E

The tunable detection system of any one of Examples 1E-30E, wherein the intensity of the signal generated can be tuned over a range 1.5 to 3×.

Example 32E

The tunable detection system of any one of Examples 1E-31E, wherein the intensity of the signal generated can be tuned over a range 2 to 4×.

Example 33E

The tunable detection system of any one of Examples 1E-32E, wherein the intensity of the signal generated can be tuned over a range 1.25 to 1.75×.

Example 34E

The tunable detection system of any one of Examples 1E-33E, wherein the intensity of the signal generated can be tuned over a range 2 to 6×.

Example 35E

The tunable detection system of any one of Examples 1E-34E, wherein the intensity of the signal generated can be tuned over a range 3 to 5×.

Example 36E

The tunable detection system of any one of Examples 1E-35E, wherein the intensity of the signal generated can be tuned over a range 2 to 10×.

Example 37E

The tunable detection system of any one of Examples 1E-36E, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 1F

A manufacturing system, comprising: i) a first series, comprising a plurality of molecular probes, said first series prepared by independently pairing, via conjugation, a plurality of first oligonucleotide sequences to a plurality of binding moieties; and ii) a second series, comprising a plurality of detectable components, said second series prepared by independently pairing, via conjugation, a plurality of second oligonucleotide sequences to a plurality of signal generating moieties or to a plurality of scaffolds having one or more of the plurality of signal generating moieties, wherein the plurality of second oligonucleotide sequences are complementary to the plurality of first oligonucleotide sequences; wherein the manufacturing system is characterized by one or more of the following: a) the first series and the second series are made available for one or more users to combine the first series and the second series to produce one or more hybridized molecular probes; b) at least a portion of preassembled combinations of the first series and the second series are produced and made available for one or more users; c) the first series and the second series are made available for one or more users to combine the first series, the second series, and a sample potentially having one or more targets, to produce one or more hybridized target-bound molecular probes; d) the time in which to produce the possible combinations of said first series and said second series is less than that of conventional preparations; and e) the time in which to hybridize and detect of the target-bound hybrids formed from said first series and said second series is less than conventional conjugation and detection.

Example 2F

The manufacturing system of Example 1F, wherein the manufacturing system is further characterized by one or more of the following: i) the first series and/or second series is provided to one or more end users as a customized matrix or semi-matrix of the first series and the second series as independently selected and paired by said one or more end users, wherein the customized matrix or semi-matrix comprises an assay useful amount of said first series and said second series which are capable of producing a plurality of hybridized molecular probe-detectable components; ii) the manufacturing system reduces to manageable proportions the number of catalog products a vendor of labeled molecular probes must manufacture, stock, market, and distribute; and iii) at least 90% of the possible hybridized combinations of said first series and second series can be produced in 10 hours or less.

Example 3F

A manufacturing system, comprising: i) a first series, comprising a plurality of molecular probes, said first series prepared by independently pairing, via conjugation, a plurality of first oligonucleotide sequences to a plurality of binding moieties; ii) a second series, comprising a plurality of detectable components, said second series prepared by independently pairing, via conjugation, a plurality of second oligonucleotide sequences to a plurality of signal generating moieties or to a plurality of scaffolds having one or more of the plurality of signal generating moieties; and iii) a third series, comprising a plurality of universal adapters comprising a plurality of complementary first oligonucleotide sequence segments independently paired with a plurality of complementary second oligonucleotide sequence segments; wherein the manufacturing system is characterized by one or more of the following: a) the first series, the second series, and the third series, are made available for one or more users to combine the first series, the second series, and the third series, to produce one or more hybridized molecular probes; b) at least a portion of preassembled combinations of the first series, the second series, and the third series, are produced and made available for one or more users; c) the first series, the second series, and the third series, are made available for one or more users to combine the first series, the second series, the third series, and a sample potentially having one or more targets, to produce one or more hybridized target-bound molecular probes; d) the time in which to produce the possible combinations of said first series, said second series, and said third series, is less than that of conventional preparations; and e) the time in which to hybridize and detect of the target-bound hybrids formed from said first series, said second series, and said third series, is less than conventional conjugation and detection.

Example 4F

The manufacturing system of Example 3F, wherein the manufacturing system is further characterized by one or more of the following: i) the first series, second series, and/or third series is provided to one or more end users as a customized matrix or semi-matrix of the first series, the second series, and the third series, as independently selected and paired by said one or more end users, wherein the customized matrix or semi-matrix comprises an assay useful amount of said first series, said second series, and said third series which are capable of producing a plurality of hybridized molecular probe-detectable components; ii) the manufacturing system reduces to manageable proportions the number of catalog products a vendor of labeled molecular probes must manufacture, stock, market, and distribute; and iii) at least 90% of the possible hybridized combinations of said first series, second series, and third series can be produced in 10 hours or less.

Example 5F

The manufacturing system of any one of Examples 1F-4F, wherein the first series comprises a plurality of between 2-50 different molecular probes.

Example 6F

The manufacturing system of any one of Examples 1F-5F, wherein the first series comprises a plurality of between 2-25 different molecular probes.

Example 7F

The manufacturing system of any one of Examples 1F-6F, wherein the first series comprises: i) a plurality of different first oligonucleotide sequences; or ii) a plurality of identical first oligonucleotide sequences.

Example 8F

The manufacturing system of any one of Examples 1F-7F, wherein the second series comprises a plurality of between 2-50 different detectable components.

Example 9F

The manufacturing system of any one of Examples 1F-8F, wherein the second series comprises a plurality of between 2-25 different detectable components.

Example 10F

The manufacturing system of any one of Examples 1F-9F, wherein the second series comprises a plurality of scaffolds independently paired, via conjugation, with the plurality of second oligonucleotide sequences, wherein said plurality of scaffolds comprise one or more signal generating moieties.

Example 11F

The manufacturing system of any one of Examples 1F-10F, wherein the second series comprises: i) a plurality of different second oligonucleotide sequences; or ii) a plurality of identical second oligonucleotide sequences.

Example 12F

The manufacturing system of any one of Examples 3F-11F, wherein the third series comprises a plurality of between 2-50 different universal adapters.

Example 13F

The manufacturing system of any one of Examples 3F-12F, wherein the third series comprises a plurality of between 2-25 different universal adapters.

Example 14F

The manufacturing system of any one of Examples 3F-13F, wherein the third series comprises: i) a plurality of different complementary first oligonucleotide sequence segments; and ii) a plurality of identical complementary second oligonucleotide sequence segments.

Example 15F

The manufacturing system of any one of Examples 3F-14F, wherein the third series comprises: i) a plurality of identical complementary first oligonucleotide sequence segments; and ii) a plurality of different complementary second oligonucleotide sequence segments.

Example 16F

The manufacturing system of any one of Examples 1F-15F, wherein the manufacturing system produces at least one or more of the following: i) a customized first series; and ii) a customized second series; wherein the manufacturing system reduces to manageable proportions the number of catalog products a vendor of labeled molecular probes and/or detectable components to manufacture, stock, market, and/or distribute.

Example 17F

The manufacturing system of Example 16F, wherein the manufacturing system further produces a customized third series.

Example 18F

The manufacturing system of any one of Examples 1F-17F, wherein the manufacturing system enables a manufacturer to provide at least one or more of the following: i) a plurality of customizable molecular probes, comprising a plurality of first oligonucleotide sequences conjugated to a plurality of binding moieties; and ii) a plurality of customizable detectable components, comprising a plurality of second oligonucleotide sequences conjugated to a plurality of signal generating moieties.

Example 19F

The manufacturing system of Example 18F, wherein the manufacturing system further enables a manufacturer to provide a plurality of customizable universal adapters, comprising a plurality of first complementary oligonucleotide sequence segments independently paired with a plurality of second complementary oligonucleotide sequence segments.

Example 20F

The manufacturing system of any one of Examples 1F-19F, wherein the manufacturing system enables either the manufacturer or the end user to produce the plurality of customizable molecular probes and/or the plurality of customizable detectable components in a time at least 10% less, 20%, 30%, 40%, 50%, 75%, 100%, 200%, 300%, or 500% less than as required by conventional conjugations to prepare the directly labeled binding moieties.

Example 21F

The manufacturing system of Example 20F, wherein the manufacturing system further enables either the manufacturer or the end user to produce the plurality of customizable molecular probes, the plurality of customizable detectable components, and/or the plurality of customizable universal adapters in a time at least 10% less, 20%, 30%, 40%, 50%, 75%, 100%, 200%, 300%, or 500% less than as required by conventional conjugations to prepare the directly labeled binding moieties.

Example 22F

The manufacturing system of any one of Examples 1F-21F, wherein the manufacturing system enables either the manufacturer or the end user to hybridize the plurality of customizable molecular probes and the plurality of customizable detectable components to form a plurality of hybridized combinations in a time at least 10% less, 20%, 30%, 40%, 50%, 75%, 100%, 200%, 300%, or 500% less than as required by conventional conjugations to prepare the directly labeled binding moieties.

Example 23F

The manufacturing system of Example 22F, wherein the manufacturing system further enables either the manufacturer or the end user to hybridize the plurality of customizable molecular probes, the plurality of customizable detectable components, and the plurality of customizable universal adapters to form a plurality of hybridized combinations in a time at least 10% less, 20%, 30%, 40%, 50%, 75%, 100%, 200%, 300%, or 500% less than as required by conventional conjugations to prepare the directly labeled binding moieties.

Example 24F

The manufacturing system of any one of Examples 1F-23F, wherein, prior to contacting a sample comprising one or more targets, the manufacturing system enables the end user to hybridize the plurality of customizable molecular probes and the plurality of customizable detectable components, to form a plurality of hybridized combinations a time at least 10% less, 20%, 30%, 40%, 50%, 75%, 100%, 200%, 300%, or 500% less than as required by conventional conjugations to prepare the directly labeled binding moieties.

Example 25F

The manufacturing system of Example 24F, wherein, prior to contacting a sample comprising one or more targets, the manufacturing system further enables the end user to hybridize the plurality of customizable molecular probes, the plurality of customizable detectable components, and the plurality of customizable universal adapters to form a plurality of hybridized combinations in a time at least 10% less, 20%, 30%, 40%, 50%, 75%, 100%, 200%, 300%, or 500% less than as required by conventional conjugations to prepare the directly labeled binding moieties.

Example 26F

The manufacturing system of any one of Examples 1F-23F, wherein the manufacturing system enables the end user, after contacting a sample comprising one or more targets with either: i) the plurality of customizable molecular probes; or ii) the plurality of customizable detectable components; to hybridize the plurality of customizable molecular probes, either bound or non-bound to at least one of the one or more targets, and the plurality of customizable detectable components in the presence of the sample to form a plurality of hybridized combinations and/or a plurality of target-bound hybridized combinations in a time at least 10% less, 20%, 30%, 40%, 50%, 75%, 100%, 200%, 300%, or 500% less than as required by conventional conjugations to prepare the directly labeled binding moieties.

Example 27F

The manufacturing system of Example 26F, wherein the manufacturing system further enables the end user, after contacting a sample comprising one or more targets with either: i) the plurality of customizable molecular probes; ii) the plurality of customizable detectable components; or iii) the plurality of customizable universal adapters; to hybridize the plurality of customizable molecular probes, either bound or non-bound to at least one of the one or more targets, and the plurality of customizable detectable components and the plurality of customizable universal adapters in the presence of the sample to form a plurality of hybridized combinations and/or a plurality of target-bound hybridized combinations a time at least 10% less, 20%, 30%, 40%, 50%, 75%, 100%, 200%, 300%, or 500% less than as required by conventional conjugations to prepare the directly labeled binding moieties.

Example 28F

The manufacturing system of any one of Examples 1F-27F, wherein the manufacturing system enables the end user to choose the mode of addition of the first series and the second series to the sample comprising one or more targets.

Example 29F

The manufacturing system of any one of Examples 3F-28F, wherein the manufacturing system enables the end user to choose the mode of addition of the first series, the second series, and the third series to the sample comprising one or more targets.

Example 30F

The manufacturing system of any one of Examples 1F-29F, wherein the manufacturing system enables the end user to pre-assemble, via hybridization, prior to contacting the sample, in a time at least 10% less, 20%, 30%, 40%, 50%, 75%, 100%, 200%, 300%, or 500% less than as required by conventional conjugations to prepare the directly labeled binding moieties.

Example 31F

The manufacturing system of any one of Examples 1F-30F, wherein the manufacturing system enables either the manufacturer or the end user to produce a complete or semi-complete matrix of combination of said first series and said second series, in a time at least 10% less, 20%, 30%, 40%, 50%, 75%, 100%, 200%, 300%, or 500% less than as required by conventional conjugations to prepare the directly labeled binding moieties.

Example 32F

The manufacturing system of Example 31F, wherein the manufacturing system further enables either the manufacturer or the end user to produce a complete or semi-complete matrix of combination of said first series, said second series, and said third series, in a time at least 10% less, 20%, 30%, 40%, 50%, 7.5%, 100%, 200%, 300%, or 500% less than as required by conventional conjugations to prepare the directly labeled binding moieties Example 33F The manufacturing system of any one of Examples 1F-32F, wherein the manufacturing system enables a vendor or manufacturer to reduce to manageable proportions the number of products the vendor or the manufacturer of molecular probes, detectable components, and/or universal detectors, must produce, stock, market, and/or distribute, than vendors or manufacturers using conventional conjugations systems to prepare the directly labeled binding moieties.

Example 34F

The manufacturing system of any one of Examples 1F-33F, wherein the manufacturing system enables a vendor or manufacturer to offer a greater variety of molecular probes, detectable components, and/or universal detectors, than vendors or manufacturers using conventional conjugations systems to prepare the directly labeled binding moieties.

Example 35F

The manufacturing system of any one of Examples 3F-34F, wherein the manufacturing system enables a vendor or manufacturer to prepare a larger number and/or a more diverse set of molecular probes, detectable components, and/or universal detectors, than vendors or manufacturers using conventional conjugations systems to prepare the directly labeled binding moieties.

Example 36F

The manufacturing system of any one of Examples 1F-35F, wherein the manufacturing system enables a vendor or manufacturer to produce a customizable catalog of molecular probes, detectable components, and universal detectors, as compared to vendors or manufacturers using conventional conjugations systems to prepare the directly labeled binding moieties.

Example 37F

The manufacturing system of any one of Examples 1F-36F, wherein the manufacturing system enables a vendor or manufacturer to rapidly, reproducibly, and on demand, produce molecular probes having, on average, between about 1-4 oligonucleotide sequences conjugated onto a binding moiety.

Example 38F

The manufacturing system of any one of Examples 1F-37F, wherein the manufacturing system enables a vendor or manufacturer to rapidly, reproducibly, and on demand, produce detectable components having a predetermined number of signal generating moieties conjugated to the complementary second oligonucleotide sequences or the second oligonucleotide sequences.

Example 39F

The manufacturing system of any one of Examples 1F-38F, wherein the manufacturing system enables a vendor or manufacturer to rapidly, reproducibly, and on demand, produce detectable components having a predetermined number of scaffolds conjugated to the complementary second oligonucleotide sequences or the second oligonucleotide sequences, wherein the scaffolds comprise a plurality of signal generating moieties.

Example 40F

The manufacturing system of any one of Examples 1F-39F, wherein the manufacturing system enables a vendor or manufacturer to rapidly, reproducibly, and on demand, produce universal adapters having either: i) a complementary first oligonucleotide sequence segment independently paired with a plurality of different complementary second oligonucleotide sequence segments; or ii) a plurality of different complementary first oligonucleotide sequence segments independently paired with a complementary second oligonucleotide sequence segment.

Example 41F

The manufacturing system of any one of Examples 1F-40F, wherein the conjugation of least one of the following: i) between the first oligonucleotide sequence and the binding moiety of the first series; ii) between the second complementary oligonucleotide sequence and the signal generating moiety or the scaffold comprising the signal generating moieties of the second series; and ii) between the second oligonucleotide sequence and the signal generating moiety or the scaffold comprising the signal generating moieties of the second series when the third series is employed; comprises one or more covalent bond linkages, comprising a hydrazone, oxime, triazine, or other covalent bond, wherein the formation of the conjugates are at least 90% efficient.

Example 42F

The manufacturing system of any one of Examples 1F-41F, wherein manufacturing system enables the end user to prepare and utilize an assay comprising: i) a singleplex or multiplex assay; and ii) the assay detects, measures, or quantifies the level of binding and/or amount of the target present in the sample with one or more of the following: flow cytometry, immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunoturbidity, latex agglutination, gold particle agglutination, visual inspection, a change in light transmittance through said sample, increased light Example 43F The manufacturing system of any one of Examples 1F-42F, wherein manufacturing system enables the end user to prepare and utilize an assay comprising: i) a singleplex or multiplex assay; and ii) the assay detects, measures, or quantifies the level of binding and/or amount of the target present in the sample with one or more of the following: flow cytometry, microscopy, imaging, high content screening (HCS), multiplex bead array, microarray, antibody array, cellular array, immunohistochemistry (IHC), immunocytochemistry (ICC), in situ hybridization (ISH), enzyme immuno-assay (EIA), enzyme linked immuno-assay (ELISA), ELI Spot, or a blotting method.

Example 44F

The manufacturing system of any one of Examples 1F-43F, wherein manufacturing system enables the end user to prepare and utilize an assay comprising: i) a singleplex or multiplex assay; and ii) the assay detects, measures, or quantifies the level of binding and/or amount of the target present in the sample with one or more of the following: flow cytometry, mass cytometry, lateral flow immunoassay, immunohistochemistry (IHC), immunocytochemistry (ICC), immunoprecipitation, pretargeting imaging, therapeutic agent, or combinations thereof.

Example 45F

The manufacturing system of any one of Examples 1F-44F, wherein manufacturing system enables the end user to analyze a sample characterized as at least one or more of the following: i) a complex sample; and ii) a homogeneous or a heterogeneous mixture; wherein said sample comprises at least one or more of the following: a) one or more analytes having substantially the same or substantially different binding specificities; b) one or more of the following biologic components, comprising: cells, membranes, biological molecules, metabolites, or disease biomarkers; and c) a biological fluid or a fluidized biological tissue.

Example 46F

The manufacturing system of any one of Examples 1F-45F, wherein at least one of the molecular probes produced by the manufacturing system comprises one or more of the following properties: i) a molecular weight of between about 15,000 Daltons to about 450,000 Daltons; ii) a solubility that is substantially the same as that of the unconjugated binding moiety; iii) a solubility that minimizes non-specific binding to the target; iv) the first oligonucleotide sequence of the molecular probe does not adversely affect the solubility of the binding moiety; v) interacts and binds to the target via interactions other than exclusively electrostatic; vi) a unique, distinguishable, and/or specifically designed oligonucleotide sequence; and vii) the first oligonucleotide sequence of the molecular probe is uniquely and specifically designed to hybridize to the second oligonucleotide sequence of the detectable component.

Example 47F

The manufacturing system of any one of Examples 1F-46F, wherein the manufacturing system wherein the prepared molecular probes and prepared detectable components have at least 90% purity.

Example 48F

The manufacturing system of any one of Examples 3F-47F, wherein the manufacturing system wherein the prepared universal adapters have at least 90% purity.

Example 49F

The manufacturing system of any one of Examples 1F-48F, wherein the preparation further comprises an isolation step utilizing an immobilized binder, chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

Example 50F

The manufacturing system of Example 49F, wherein the isolation step utilizes an immobilized binder, affinity chromatography, size exclusion chromatography, electrophoresis, differential centrifugation, immunoprecipitation, hybridization, solvent extraction, dialysis, filtration, diafiltration, ion exchange chromatography, hydrophobic interaction chromatography, or combinations thereof.

Example 51F

The manufacturing system of Example 49F, wherein the isolation step utilizes an immobilized binder, affinity chromatography, size exclusion chromatography, differential centrifugation, dialysis, filtration, hydrophobic interaction chromatography, or combinations thereof.

Example 52F

The manufacturing system of any one of Examples 1F-51F, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 53F

The manufacturing system of any one of Examples 1F-52F, wherein the scaffold comprises a dendrimer, a polysaccharide, a dextran, a protein, a peptide, a further oligonucleotide sequence, a portion of the second oligonucleotide sequence that is not complementary to the first oligonucleotide sequence of the molecular probe, a polymer, a hydrophilic polymer, a bead, a nanoparticle, or combinations or derivatives thereof.

Example 54F

The manufacturing system of any one of Examples 1F-53F, wherein the signal generating moiety or the one or more signal generating moieties of the detectable component or the hybridized detectable component, comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations or derivatives thereof.

Example 55F

The manufacturing system of any one of Examples 1F-54F, wherein the one or more signal generating moieties provides an enhanced signal that minimizes detection errors from background noise, relative to conventionally labeled binding moieties.

Example 56F

The manufacturing system of any one of Examples 1F-66F, wherein the molecular probe, the detectable component, and/or universal adapter further comprises a spacer group, comprising a polymerized ethylene oxide, a PEG, a PEO, a protein, a peptide, a DNA, an RNA, an oligonucleotide sequence, or a dextran.

Example 57F

The manufacturing system of any one of Examples 1F-56F, wherein the binding moiety, the scaffold, the first oligonucleotide sequence, and/or the second oligonucleotide sequence comprise HyNic or 4-FB.

Example 58F

The manufacturing system of any one of Examples 1F-57F, wherein the detectable component comprises a unique, distinguishable, and/or specifically designed second oligonucleotide sequence.

Example 59F

The manufacturing system of any one of Examples 1F-58F, wherein the first oligonucleotide sequence, second oligonucleotide sequence, and/or oligonucleotide sequence segment comprising an oligonucleotide sequence conjugated at the 3'-position, an oligonucleotide sequence conjugated at the 5'-position, linear oligonucleotide sequences, branched oligonucleotide sequences, LNAs, PNAs, oligonucleotide sequences optionally covalently attached to other moieties, or combinations or derivatives thereof.

Example 60F

The manufacturing system of any one of Examples 1F-58F, wherein the manufacturing system enables the end user to analyze a sample comprising one or more targets.

Example 61F

The manufacturing system of Example 59F, wherein at least one target of the one or more targets is a biological target.

Example 62F

The manufacturing system of Example 61F, wherein the biological target comprises an antigen, a pathogen, a protein, a peptide, an epitope, a carbohydrate-containing molecule, a small molecule, or combinations or derivatives thereof.

Example 63F

The manufacturing system of any one of Examples 1F-62F, wherein the manufacturing system comprises an automated system or robotic system to prepare at least one of the following: the first series, the second series, and the third series.

Example 64F

The manufacturing system of any one of Examples 1F-62F, wherein the manufacturing system enables an end user to utilize an automated system or robotic system to prepare hybridized combinations of at least one of the following: i) the first series and the second series; ii) the first series and the third series; iii) the second series and the third series; and iv) the first series, the second series, and the third series.

Example 65F

The manufacturing system of Example 64F, wherein the hybridized combinations are prepared prior to contacting the sample or prepared while in contact with the sample.

Example 66F

The manufacturing system of any one of Examples 1F-65F, wherein the manufacturing system further enables the end user to remove the hybridized detectable component or plurality of detectable components from the bound target or plurality of targets, respectively, wherein said removal is by a washing or stripping process.

Example 67F

The manufacturing system of Example 66F, wherein the removal comprises de-hybridizing the detectable component or the plurality of detectable components, respectively.

Example 68F

The manufacturing system of Examples 66F or 67F, wherein the manufacturing system further enables re-probing with a second detectable component or second plurality of detectable components, respectively, wherein said second detectable component comprises at least one second signal generating moieties conjugated to a second oligonucleotide sequence or a complementary second oligonucleotide sequence, or said second plurality of detectable components are prepared by independently pairing, via conjugation, a second plurality of signal generating moieties and a second plurality of second oligonucleotide sequences or a second plurality of complementary second oligonucleotide sequences.

Example 69F

A manufacturing method, comprising: i) a first series, comprising a plurality of molecular probes, said first series prepared by independently pairing, via conjugation, a plurality of first oligonucleotide sequences to a plurality of binding moieties; and ii) a second series, comprising a plurality of detectable components, said second series prepared by independently pairing, via conjugation, a plurality of second oligonucleotide sequences to a plurality of signal generating moieties or to a plurality of scaffolds having one or more of the plurality of signal generating moieties, wherein the plurality of second oligonucleotide sequences are complementary to the plurality of first oligonucleotide sequences; wherein the manufacturing system is characterized by one or more of the following: a) the first series and the second series are made available for one or more users to combine the first series and the second series to produce one or more hybridized molecular probes; b) at least a portion of preassembled combinations of the first series and the second series are produced and made available for one or more users; c) the first series and the second series are made available for one or more users to combine the first series, the second series, and a sample potentially having one or more targets, to produce one or more hybridized target-bound molecular probes; d) the time in which to produce the possible combinations of said first series and said second series is less than that of conventional preparations; and e) the time in which to hybridize and detect of the target-bound hybrids formed from said first series and said second series is less than conventional conjugation and detection.

Example 70F

The manufacturing method of Example 69F, wherein the method further comprises providing to one or more end users a customized matrix or semi-matrix of the first series and the second series as independently selected and paired by said one or more end users, wherein the customized matrix or semi-matrix comprises an assay useful amount of said first series and said second series which are capable of producing a plurality of hybridized molecular probe-detectable components; wherein: a) the manufacturing method reduces to manageable proportions the number of catalog products a vendor of labeled molecular probes must manufacture, stock, market, and distribute; and b) at least 90% of the possible hybridized combinations of said first series and second series can be produced in 10 hours or less.

Example 71F

A manufacturing method, comprising: i) preparing a first series, comprising a plurality of molecular probes, said first series prepared by independently pairing, via conjugation, a plurality of first oligonucleotide sequences to a plurality of binding moieties; ii) preparing a second series, comprising a plurality of detectable components, said second series prepared by independently pairing, via conjugation, a plurality of second oligonucleotide sequences to a plurality of signal generating moieties or to a plurality of scaffolds having one or more of the plurality of signal generating moieties; and iii) preparing a third series, comprising a plurality of universal adapters comprising a plurality of complementary first oligonucleotide sequence segments independently paired with a plurality of complementary second oligonucleotide sequence segments; wherein the method is characterized by one or more of the following: a) the prepared first series, the prepared second series, and the prepared third series, are made available for one or more users to combine the prepared first series, the prepared second series, and the prepared third series, to produce one or more hybridized molecular probes; b) at least a portion of preassembled combinations of the prepared first series, the prepared second series, and the prepared third series, are produced and made available for one or more users; c) the prepared first series, the prepared second series, and the prepared third series, are made available for one or more users to combine the prepared first series, the prepared second series, the prepared third series, and a sample potentially having one or more targets, to produce one or more hybridized target-bound molecular probes; d) the lime in which to produce the possible combinations of said prepared first series, said prepared second series, and said prepared third series, is less than that of conventional preparations; and e) the time in which to hybridize and detect of the target-bound hybrids formed from said prepared first series, said prepared second series, and said prepared third series, is less than conventional conjugation and detection.

Example 72F

The manufacturing method of Example 71F, wherein the method further comprises providing to one or more end users a customized matrix or semi-matrix of the first series, the second series, and the third series, as independently selected and paired by said one or more end users, wherein the customized matrix or semi-matrix comprises an assay useful amount of said first series, said second series, and said third series which are capable of producing a plurality of hybridized molecular probe-detectable components; wherein: a) the manufacturing method reduces to manageable proportions the number of catalog products a vendor of labeled molecular probes must manufacture, stock, market, and distribute; and b) at least 90% of the possible hybridized combinations of said first series, second series, and third series can be produced in 10 hours or less.

Example 73F

A method of offering detectable molecular probes, comprising: i) offering to one or more users a first series, comprising a plurality of molecular probes, said first series prepared by independently pairing, via conjugation, a plurality of first oligonucleotide sequences to a plurality of binding moieties; ii) offering to one or more users a second series, comprising a plurality of detectable components, said second series prepared by independently pairing, via conjugation, a plurality of second oligonucleotide sequences to a plurality of signal generating moieties or to a plurality of scaffolds having one or more of the plurality of signal generating moieties, wherein the plurality of second oligonucleotide sequences are complementary to the plurality of first oligonucleotide sequences; and iii) providing the first series and the second series to the one or more users, to combine the first series, the second series, and a sample having one or more targets, at an appropriate time, and in an appropriate amount, to produce one or more hybridized target-bound molecular probes; wherein the method is characterized by one or more of the following: a) the first series and the second series are made available for one or more users to combine the first series and the second series to produce one or more hybridized molecular probes; b) at least a portion of preassembled combinations of the first series and the second series are produced and made available for one or more users; c) the first series and the second series are made available for one or more users to combine the first series, the second series, and a sample potentially having one or more targets, to produce one or more hybridized target-bound molecular probes; d) the time in which to produce the possible combinations of said first series and said second series is less than that of conventional preparations; and e) the time in which to hybridize and detect of the target-bound hybrids formed from said first series and said second series is less than conventional conjugation and detection.

Example 74F

The method of Example 73F, wherein: i) the first series and/or second series is provided to the one or more end users

219 as a customized matrix or semi-matrix of the first series and the second series, independently selected and paired by said one or more end users, wherein the customized matrix or semi-matrix comprises an assay useful amount of said first series and said second series which are capable of producing a plurality of hybridized molecular probe-detectable components; ii) the method reduces to manageable proportions the number of catalog products a vendor of labeled molecular probes must manufacture, stock, market, and distribute; and iii) at least 90% of the possible hybridized combinations of said first series and second series can be produced in 10 hours or less.

Example 75F

A method of offering detectable molecular probes, comprising: i) offering to one or more users a first series, comprising a plurality of molecular probes, said first series prepared by independently pairing, via conjugation, a plurality of first oligonucleotide sequences to a plurality of binding moieties; ii) offering to one or more users a second series, comprising a plurality of detectable components, said second series prepared by independently pairing, via conjugation, a plurality of second oligonucleotide sequences to a plurality of signal generating moieties or to a plurality of scaffolds having one or more of the plurality of signal generating moieties; and iii) offering to one or more users a third series, comprising a plurality of universal adapters comprising a plurality of complementary first oligonucleotide sequence segments independently paired with a plurality of complementary second oligonucleotide sequence segments; iii) providing the first series, the second series, and the third series to the one or more users, to combine the first series, the second series, the third series and a sample having one or more targets, at an appropriate time, and in an appropriate amount, to produce one or more hybridized target-bound molecular probes; wherein the method is characterized by one or more of the following: a) the first series and the second series are made available for one or more users to combine the first series and the second series to produce one or more hybridized molecular probes; b) at least a portion of preassembled combinations of the first series and the second series are produced and made available for one or more users; c) the first series and the second series are made available for one or more users to combine the first series, the second series, and a sample potentially having one or more targets, to produce one or more hybridized target-bound molecular probes; d) the time in which to produce the possible combinations of said first series and said second series is less than that of conventional preparations; and e) the time in which to hybridize and detect of the target-bound hybrids formed from said first series and said second series is less than conventional conjugation and detection.

Example 76F

The method of Example 75F, wherein: i) the first series, the second series, and/or the third series is provided to the one or more end users as a customized matrix or semi-matrix of the first series, the second series, and the third series, as independently selected and paired by said one or more end users, wherein the customized matrix or semi-matrix comprises an assay useful amount of said first series, said second series, and said third series which are capable of producing a plurality of hybridized molecular probe-detectable components; ii) the method reduces to manageable proportions

220 the number of catalog products a vendor of labeled molecular probes must manufacture, stock, market, and distribute; and iii) at least 90% of the possible hybridized combinations of said first series, said second series, and said third series can be produced in 10 hours or less.

Example 1G

A flow cytometry method for assaying a target of a sample, comprising: i) providing to the sample: 1) a molecular probe, comprising a binding moiety conjugated to a first oligonucleotide sequence; and 2) a detectable component, comprising a signal generating moiety conjugated to a second oligonucleotide sequence that is complementary to the first oligonucleotide sequence of the molecular probe; ii) binding the target in the sample with the binding moiety of the molecular probe; iii) hybridizing the first oligonucleotide sequence of the molecular probe with the second oligonucleotide sequence of the detectable component; and iv) detecting a signal generated from the hybridized detectable component using flow cytometry; wherein the method is characterized by one or more of the following: a) the conjugation between the first oligonucleotide sequence and the binding moiety and conjugation between the second oligonucleotide sequence and the signal generating moiety, comprises one or more covalent bond linkages, comprising a hydrazone, oxime, triazine, or other covalent bond, wherein the formation of the conjugates are at least 90% efficient; and b) the binding moiety comprises a strong binding affinity for the target.

Example 2G

The method of Example 1G, wherein the mode of addition comprises: i) the molecular probe and the detectable component are combined together and hybridized prior to contacting the sample; ii) the molecular probe is combined with the sample prior to the addition of the detectable component; or iii) the detectable component is combined with the sample prior to the addition of the molecular probe.

Example 3G

The method of any one of Examples 1G-2G, wherein the method comprises: i) the molecular probe binding the target prior to hybridizing with the detectable component; or ii) the molecular probe hybridizing with the detectable component prior to binding the target.

Example 4G

A flow cytometry method for assaying a target of a sample, comprising: i) providing to the sample: 1) a molecular probe, comprising a binding moiety conjugated to a first oligonucleotide sequence; 2) a detectable component, comprising a signal generating moiety conjugated to a second oligonucleotide sequence; and 3) a universal adapter, comprising an oligonucleotide sequence having a first sequence segment complementary to the first oligonucleotide sequence of the molecular probe and a second sequence segment complementary to the second oligonucleotide sequence of the detectable component; ii) binding the target in the sample with the binding moiety of the molecular probe; iii) hybridizing the first oligonucleotide sequence of the molecular probe to the first oligonucleotide sequence segment of the universal adapter; iv) hybridizing the second oligonucleotide sequence of the detectable component to the second oligonucleotide sequence segment of the universal adapter; and v) detecting a signal generated from the hybridized detectable component using flow cytometry; wherein the method is characterized by one or more of the following: a) the conjugation between the first oligonucleotide sequence and the binding moiety and conjugation between the second complementary oligonucleotide sequence and the signal generating moiety, comprises one or more covalent bond linkages, comprising a hydrazone, oxime, triazine, or other covalent bond, wherein the formation of the conjugates are at least 90% efficient; and b) the binding moiety comprises a strong binding affinity for the target.

Example 5G

The method of Example 4G, wherein the mode of addition comprises: i) the molecular probe, the universal adapter, and the detectable component are combined together and hybridized prior to contacting the sample; ii) the molecular probe and the universal adapter are combined together and hybridized prior to contacting the sample; iii) the detectable component and the universal adapter are combined together and hybridized prior to contacting the sample; iv) the molecular probe, alone or in combination with the detectable component, is combined with the sample prior to the addition of the universal adapter; or v) the universal adapter is combined with the sample prior to the addition of the molecular probe and/or the detectable component.

Example 6G

The method of Example 4G or 5G, wherein the method comprises: i) the molecular probe hybridizing with the universal adapter prior to said molecular probe binding the target; ii) the molecular probe hybridizing with the universal adapter after said molecular probe binds the target; iii) the detectable component hybridizing with the universal adapter prior to the molecular probe binding the target; iv) the detectable component hybridizing with the universal adapter after the molecular probe binds the target; v) the universal adapter hybridizing with the molecular probe and hybridizing with the detectable component prior to said molecular probe binding the target; or vi) the universal adapter hybridizing with the molecular probe and hybridizing with the detectable component after said molecular probe binds the target.

Example 7G

The method of any one of Examples 1G-6G, wherein: i) the assay comprises a singleplex or multiplex assay; and ii) the assay detects, measures, or quantifies the level of binding and/or amount of the target present in the sample with flow cytometry.

Example 8G

The method of any one of Examples 1G-7G, wherein method further comprises detecting, measuring, or quantifying the level of binding and/or amount of the target present in the sample with one or more of the following: immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunoturbidity, latex agglutination, gold particle agglutination, visual inspection, a change in light transmittance through said sample, increased light transmittance through said sample, immunohistochemistry (IHC), immunocytochemistry (ICC), in situ hybridization (ISH), enzyme immunoassay (EIA), enzyme linked immuno-assay (ELISA), ELISpot, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 9G

The method of any one of Examples 1G-8G, wherein: i) the assay comprises a singleplex or multiplex assay; and ii) the assay detects, measures, or quantifies the level of binding and/or amount of the target present in the sample with one or more of the following: flow cytometry, microscopy, imaging, high content screening (HCS), multiplex bead array, microarray, antibody array, cellular array, immunohistochemistry (INC), immunocytochemistry (ICC), in situ hybridization (TSH), enzyme immuno-assay (EIA), enzyme linked immuno-assay (ELISA), ELISpot, or a blotting method.

Example 10G

The method of any one of Examples 1G-9G, wherein: i) the assay comprises a singleplex or multiplex assay; and ii) the assay detects, measures, or quantifies the level of binding and/or amount of the target present in the sample with one or more of the following: flow cytometry, mass cytometry, lateral flow immunoassay, immunohistochemistry immunocytochemistry (ICC), immunoprecipitation, pretargeting imaging, therapeutic agent, or combinations thereof.

Example 11G

The method of any one of Examples 1G-10G, wherein the sample is characterized as at least one or more of the following: i) a complex sample; and ii) a homogeneous or a heterogeneous mixture; wherein said sample comprises at least one or more of the following: a) one or more analytes having substantially the same or substantially different binding specificities; b) one or more of the following biologic components, comprising: cells, membranes, biological molecules, metabolites, or disease biomarkers; and c) a biological fluid or a fluidized biological tissue.

Example 12G

The method of any one of Examples 1G-11G, wherein the hybridization efficiency of the first oligonucleotide sequence to the second oligonucleotide sequence is at least 50% with respect to the first detectable component, under the hybridization conditions employed.

Example 13G

The method of any one of Examples 1G-12G, wherein the molecular probe comprises one or more of the following properties: i) a molecular weight of between about 15,000 Daltons to about 450,000 Daltons; ii) a solubility that is substantially the same as that of the unconjugated binding moiety; iii) a solubility that minimizes non-specific binding to the target; iv) the first oligonucleotide sequence of the molecular probe does not adversely affect the solubility of the binding moiety; v) interacts and binds to the target via interactions other than exclusively electrostatic; vi) a unique, distinguishable, and/or specifically designed oligonucleotide sequence; and vii) the first oligonucleotide sequence of the molecular probe is uniquely and specifically designed to hybridize to the second oligonucleotide sequence of the detectable component.

Example 14G

The method of any one of Examples 1G-13G, wherein the method of detection generates less false positives than secondary antibody detection methods.

Example 15G

The method of any one of Examples 1G-14G, wherein the method further comprises: i) preparing the molecular probe; and ii) preparing the detectable component; wherein the prepared molecular probe and prepared detectable component have at least 90% purity.

Example 16G

The method of any one of Examples 1G-15G, wherein the method further comprises preparing and isolating the molecular probe, comprising: i) providing the binding moiety; ii) conjugating the binding moiety with at least one first oligonucleotide sequence at greater than 90% efficiency to form binding moiety-oligonucleotide conjugates; and iii) isolating the binding moiety-oligonucleotide conjugates from the conjugation mixture by binding, retaining, and/or retarding a substantial portion of: a) the conjugates, removing a substantial portion of the unconjugated first oligonucleotide sequence in a wash step followed by release of the bound, retained, and/or retarded conjugates; or b) the unconjugated first oligonucleotide sequences, followed by collecting a substantial portion of the non-bound, non-retained, and/or non-retarded conjugates in a wash step.

Example 17G

The method of any one of Examples 1G-16G, wherein the method further comprises preparing and isolating the detectable component, comprising: i) providing a plurality of the signal generating moiety; ii) conjugating the second oligonucleotide sequence with at least one of the plurality of the signal generating moiety at greater than 90% efficiency to form signal generating moiety-second oligonucleotide conjugates; and iii) isolating the signal generating moiety-second oligonucleotide conjugates from the conjugation mixture by binding, retaining, and/or retarded a substantial portion of: a) the conjugates, removing a substantial portion of the unconjugated second oligonucleotide sequences in a wash step followed by release of the bound, retained, and/or retarded conjugates; or b) the unconjugated second oligonucleotide sequences, followed by collecting a substantial portion of the non-bound, non-retained, and/or non-retarded conjugates in a wash step.

Example 18G

The method of any one of Examples 1G-17G, wherein the detectable component comprises a scaffold conjugated to the second oligonucleotide sequence, and wherein said scaffold comprises one or more signal generating moieties.

Example 19G

The method of Example 18G, wherein the scaffold comprises a dendrimer, a polysaccharide, a dextran, a protein, a peptide, a further oligonucleotide sequence, a portion of the second oligonucleotide sequence that is not complementary to the first oligonucleotide sequence of the molecular probe, a polymer, a hydrophilic polymer, a bead, a nanoparticle, or combinations or derivatives thereof.

Example 20G

The method of any one of Examples 1G-19G, wherein the method further comprises preparing and isolating a detectable component comprising a scaffold conjugated to the second oligonucleotide sequence, wherein the scaffold comprises one or more signal generating moieties, said method comprising: i) providing a plurality of the scaffolds comprising the one or more signal generating moieties; ii) conjugating the second oligonucleotide sequence with at least one of the plurality of scaffolds at greater than 90% efficiency to form scaffold-second oligonucleotide conjugates; and iii) isolating the scaffold-second oligonucleotide conjugates from the conjugation mixture by binding, retaining, and/or retarding a substantial portion of: a) the conjugates, removing a substantial portion of the unconjugated second oligonucleotide sequences in a wash step followed by release of the bound, retained, and/or retarded conjugates; orb) the unconjugated second oligonucleotide sequences, followed by collecting a substantial portion of the non-bound, non-retained, and/or non-retarded conjugates in a wash step.

Example 21G

The method of any one of Examples 16G-20G, wherein the isolation step utilizes an immobilized binder, chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

Example 22G

The method of any one of Examples 16G-20G, wherein the isolation step utilizes an immobilized binder, affinity chromatography, size exclusion chromatography, electrophoresis, differential centrifugation, immunoprecipitation, hybridization, solvent extraction, dialysis, filtration, diafiltration, ion exchange chromatography, hydrophobic interaction chromatography, or combinations thereof.

Example 23G

The method of any one of Examples 16G-20G, wherein the isolation step utilizes an immobilized binder, affinity chromatography, size exclusion chromatography, differential centrifugation, dialysis, filtration, hydrophobic interaction chromatography, or combinations thereof.

Example 24G

The method of any one of Examples 1G-23G, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 25G

The method of any one of Examples 1G-24G, wherein the sample comprises one or more targets.

Example 26G

The method of any one of Examples 1G-25G, wherein the target is a biological target.

Example 27G

The method of Example 26G, wherein the biological target comprises an antigen, a pathogen, a protein, a peptide, an epitope, a carbohydrate-containing molecule, a small molecule, or combinations or derivatives thereof.

Example 28G

The method of any one of Examples 1G-27G, wherein the signal generating moiety or the one or more signal generating moieties of the detectable component or the hybridized detectable component, comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations or derivatives thereof.

Example 29G

The method of any one of Examples 1G-28G, wherein the one or more signal generating moieties provides an enhanced signal that minimizes detection errors from background noise, relative to conventionally labeled binding moieties.

Example 30G

The method of any one of Examples 1G-29G, wherein the molecular probe, the detectable component, and/or universal adapter further comprises a spacer group, comprising a polymerized ethylene oxide, a PEG, a PEO, a protein, a peptide, a DNA, an RNA, an oligonucleotide sequence, or a dextran.

Example 31G

The method of any one of Examples 1G-30G, wherein the binding moiety, the scaffold, the first oligonucleotide sequence, and/or the second oligonucleotide sequence comprise HyNic or 4-FB.

Example 32G

The method of any one of Examples 1G-31G, wherein the detectable component comprises a unique, distinguishable, and/or specifically designed second oligonucleotide sequence.

Example 33G

The method of any one of Examples 1G-32G, wherein the first oligonucleotide sequence, second oligonucleotide sequence, and/or oligonucleotide sequence segment comprising an oligonucleotide sequence conjugated at the 3'-position, an oligonucleotide sequence conjugated at the 5'-position, linear oligonucleotide sequences, branched oligonucleotide sequences, LNAs, PNAs, oligonucleotide sequences optionally covalently attached to other moieties, or combinations or derivatives thereof.

Example 34G

The method of any one of Examples 1G-33G, wherein the sample comprises one or more targets comprising at least a first target and at least a second target.

Example 35G

The method of any one of Examples 1G-34G, wherein a plurality of molecular probes and a plurality of detectable components are provided to the sample.

Example 36G

The method of any one of Examples 1G-35G, wherein a plurality of universal adapters are provided to the sample.

Example 37G

The method of any one of Examples 1G-36G, wherein the binding affinity for the target is $10^{-4}$ M or less.

Example 38G

The method of any one of Examples 1G-37G, wherein the binding affinity for the at least first target is $10^{-4}$ M or less.

Example 39G

The method of any one of Examples 1G-38G, wherein the binding affinity for the at least second target is $10^{-4}$ M or less.

Example 40G

The method of any one of Examples 1G-39G, wherein the method comprises an automated system or robotic system.

Example 41G

The method of any one of Examples 1G-41G, wherein the method further comprises removing the hybridized detectable component or plurality of detectable components from the bound target or plurality of targets, respectively, wherein said removal is by a washing or stripping process.

Example 41G

The method of Example 41G, wherein the removal comprises de-hybridizing the detectable component or the plurality of detectable components, respectively.

Example 42G

The method of Examples 40G or 41G, wherein the method further comprises re-probing with a second detectable component or second plurality of detectable components, respectively, wherein said second detectable component comprises at least one second signal generating moieties conjugated to a second oligonucleotide sequence or a complementary second oligonucleotide sequence, or said second plurality of detectable components are prepared by independently pairing, via conjugation, a second plurality of signal generating moieties and a second plurality of second oligonucleotide sequences or a second plurality of complementary second oligonucleotide sequences.

Example 43G

A flow cytometry method for assaying one or more targets of a sample, comprising: i) providing to the sample: 1) a plurality of molecular probes, comprising: A) at least a first molecular probe having a first binding moiety conjugated to a first oligonucleotide sequence; and B) at least a second molecular probe having a second binding moiety conjugated to a second oligonucleotide sequence; and 2) a plurality of detectable components, comprising: A) at least a first detectable component having a first signal generating moiety conjugated to a first complementary oligonucleotide sequence; and B) at least a second detectable component having a second signal generating moiety conjugated to a second complementary oligonucleotide sequence; ii) binding the one or more targets, comprising at least one of the following: 1) binding at least a first target of the one or more targets in the sample with the first binding moiety of the at least first molecular probe; and 2) binding at least a second target of the one or more targets in the sample with the second binding moiety of the at least second molecular probe; iii) hybridizing the plurality of molecular probes and the plurality of detectable components, comprising at least one of the following: 1) hybridizing the first oligonucleotide sequence of at least first molecular probe to the first complementary oligonucleotide sequence segment of the at least first detectable component; and 2) hybridizing the second oligonucleotide sequence of at least second molecular probe to the second complementary oligonucleotide sequence segment of the at least second detectable component; and iv) detecting, using flow cytometry, one or more signals generated from at least one of the following: 1) the at least first hybridized detectable component; and 2) the at least second hybridized detectable component; wherein the method is characterized by one or more of the following: a) the conjugation between the first oligonucleotide sequence and the first binding moiety, between the second oligonucleotide sequence and the second binding moiety, between the first complementary oligonucleotide sequence and the first signal generating moiety, and between the second complementary oligonucleotide sequence and the second signal generating moiety, comprises one or more covalent bond linkages, comprising a hydrazone, oxime, triazine, or other covalent bond, wherein the formation of the conjugates are at least 90% efficient; and b) the first binding moiety comprises a strong binding affinity for the at least first target of the one or more targets and the second binding moiety comprises a strong binding affinity for the at least second target of the one or more targets.

Example 44G

A flow cytometry method for assaying one or more targets of a sample, comprising: i) providing to the sample: a) a plurality of molecular probes, comprising: a first oligonucleotide sequence independently paired, via conjugation, to a plurality of binding moieties comprising at least a first binding moiety and at least a second binding moiety; b) a plurality of detectable components, comprising: a plurality of second oligonucleotide sequences independently paired, via conjugation, to a plurality of one or more signal generating moieties comprising at least a first signal generating moiety and at least a second signal generating moiety; and c) a plurality of universal adapters, comprising: a first oligonucleotide sequence segment, complementary to the first oligonucleotide sequence of said plurality of molecular probes, independently paired with a plurality of second oligonucleotide sequence segments complementary to the plurality of second oligonucleotide sequences of said plurality of detectable components; ii) binding the one or more targets, comprising at least one of the following: a) binding at least a first target of the one or more targets in the sample with the first binding moiety of the at least first molecular probe; and b) binding at least a second target of the one or more targets in the sample with the second binding moiety of the at least second molecular probe; iii) hybridizing the plurality of molecular probes and the plurality of detectable components with the plurality of universal adapters; and iv) detecting, using flow cytometry, one or more signals generated from at least one of the following: a) the at least first hybridized detectable component; and b) the at least second hybridized detectable component; wherein the method is characterized by one or more of the following: A) the conjugation between the first oligonucleotide sequence and the first binding moiety, between the second oligonucleotide sequence and the second binding moiety, between the first complementary oligonucleotide sequence and the first signal generating moiety, and between the second complementary oligonucleotide sequence and the second signal generating moiety, comprises one or more covalent bond linkages, comprising a hydrazone, oxime, triazine, or other covalent bond, wherein the formation of the conjugates are at least 90% efficient; and B) the first binding moiety comprises a strong binding affinity for the at least first target of the one or more targets and the second binding moiety comprises a strong binding affinity for the at least second target of the one or more targets.

Example 1H

A method for assaying a target of a sample, comprising: i) providing to the sample: 1) a molecular probe, comprising a binding moiety conjugated to a first oligonucleotide sequence; and 2) a detectable component, comprising a signal generating moiety conjugated to a second oligonucleotide sequence that is complementary to the first oligonucleotide sequence of the molecular probe; ii) binding the target in the sample with the binding moiety of the molecular probe; iii) hybridizing the oligonucleotide sequence of the molecular probe with the second oligonucleotide sequence of the detectable component; and iv) detecting a signal generated from the hybridized detectable component using one or more of the following systems: microscopy, imaging, high content screening (HCS), mass cytometry, lateral flow immunoassay, immunodetection, immunohistochemistry (IHC), immunocytochemistry (ICC), or combinations thereof; wherein the method is characterized by one or more of the following: a) the conjugation between the first oligonucleotide sequence and the binding moiety and conjugation between the second oligonucleotide sequence and the signal generating moiety, comprises one or more covalent bond linkages, comprising a hydrazone, oxime, triazine, or other covalent bond, wherein the formation of the conjugates are at least 90% efficient; and b) the binding moiety comprises a strong binding affinity for the target.

Example 2H

The method of Example 1H, wherein the mode of addition comprises: i) the molecular probe and the detectable component are combined together and hybridized prior to contacting the sample; ii) the molecular probe is combined with the sample prior to the addition of the detectable component; or iii) the detectable component is combined with the sample prior to the addition of the molecular probe.

Example 3H

The method of any one of Examples 1H-2H, wherein the method comprises: i) the molecular probe binding the target prior to hybridizing with the detectable component; or ii) the molecular probe hybridizing with the detectable component prior to binding the target.

Example 4H

The method of any one of Examples 1H-3H, wherein: i) the assay comprises a singleplex or multiplex assay; and ii) the assay detects, measures, or quantifies the level of binding and/or amount of the target present in the sample with the one or more of following systems: microscopy, imaging, high content screening (HCS), mass cytometry, lateral flow immunoassay, immunodetection, immunohistochemistry (IHC), immunocytochemistry (ICC), or combinations thereof.

Example 5H

A method for assaying a target of a sample, comprising: i) providing to the sample: 1) a molecular probe, comprising a binding moiety conjugated to a first oligonucleotide sequence; 2) a detectable component, comprising a signal generating moiety conjugated to a second oligonucleotide sequence; and 3) a universal adapter, comprising an oligonucleotide sequence having a first sequence segment complementary to the first oligonucleotide sequence of the molecular probe and a second sequence segment complementary to the second oligonucleotide sequence of the detectable component; ii) binding the target in the sample with the binding moiety of the molecular probe; iii) hybridizing the first oligonucleotide sequence of the molecular probe to the first oligonucleotide sequence segment of the universal adapter; iv) hybridizing the second oligonucleotide sequence of the detectable component to the second oligonucleotide sequence segment of the universal adapter; and v) detecting a signal generated from the hybridized detectable component using one or more of the following systems: microscopy, imaging, high content screening (HCS), mass cytometry, lateral flow immunoassay, immunodetection, immunohistochemistry (IHC), immunocytochemistry (ICC), or combinations thereof; wherein the method is characterized by one or more of the following: a) the conjugation between the first oligonucleotide sequence and the binding moiety and conjugation between the second complementary oligonucleotide sequence and the signal generating moiety, comprises one or more covalent bond linkages, comprising a hydrazone, oxime, triazine, or other covalent bond, wherein the formation of the conjugates are at least 90% efficient; and b) the binding moiety comprises a strong binding affinity for the target.

Example 6H

The method of Example 5H, wherein the mode of addition comprises: i) the molecular probe, the universal adapter, and the detectable component are combined together and hybridized prior to contacting the sample; ii) the molecular probe and the universal adapter are combined together and hybridized prior to contacting the sample; iii) the detectable component and the universal adapter are combined together and hybridized prior to contacting the sample; iv) the molecular probe, alone or in combination with the detectable component, is combined with the sample prior to the addition of the universal adapter; or v) the universal adapter is combined with the sample prior to the addition of the molecular probe and/or the detectable component.

Example 7H

The method of Examples 5H or 6H, wherein the method comprises: i) the molecular probe hybridizing with the universal adapter prior to said molecular probe binding the target; ii) the molecular probe hybridizing with the universal adapter after said molecular probe binds the target; iii) the detectable component hybridizing with the universal adapter prior to the molecular probe binding the target; iv) the detectable component hybridizing with the universal adapter after the molecular probe binds the target; v) the universal adapter hybridizing with the molecular probe and hybridizing with the detectable component prior to said molecular probe binding the target; or vi) the universal adapter hybridizing with the molecular probe and hybridizing with the detectable component after said molecular probe binds the target.

Example 8H

The method of any one of Examples 1H-7H, wherein method further comprises detecting, measuring, or quantifying the level of binding and/or amount of the target present in the sample with one or more of the following: flow cytometry, immunomagnetic cellular depletion, immunomagnetic cell capture, array, bead array, multiplex bead array, microarray, antibody array, cellular array, chemiluminescence, infrared, immunoturbidity, latex agglutination, gold particle agglutination, visual inspection, a change in light transmittance through said sample, increased light transmittance through said sample, in situ hybridization (ISH), enzyme immuno-assay (EIA), enzyme linked immuno-assay (ELISA), ELISpot, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 9H

The method of any one of Examples 1H-8H, wherein the method carries out the detecting, measuring, or quantifying via microscopy, imaging, high content screening (HCS), or combinations thereof.

Example 10H

The method of any one of Examples 1H-9H, wherein the method carries out the detecting, measuring, or quantifying via mass cytometry, lateral flow immunoassay, Immunodetection, immunohistochemistry (IHC), immunocytochemistry (ICC), or combinations thereof.

Example 11H

The method of any one of Examples 1H-10H, wherein the sample is characterized as at least one or more of the following: i) a complex sample; and ii) a homogeneous or a heterogeneous mixture; wherein said sample comprises at least one or more of the following: a) one or more analytes having substantially the same or substantially different binding specificities; b) one or more of the following biologic components, comprising: cells, membranes, biological molecules, metabolites, or disease biomarkers; and c) a biological fluid or a fluidized biological tissue.

Example 12H

The method of any one of Examples 1H-11H, wherein the hybridization efficiency of the oligonucleotide sequence to the second oligonucleotide sequence is at least 50% with respect to the detectable component, under the hybridization conditions employed.

Example 13H

The method of any one of Examples 1H-12H, wherein the molecular probe comprises one or more of the following properties: i) a molecular weight of between about 15,000 Daltons to about 450,000 Daltons; ii) a solubility that is substantially the same as that of the unconjugated binding moiety; iii) a solubility that minimizes non-specific binding to the target; iv) the oligonucleotide sequence of the molecular probe does not adversely affect the solubility of the binding moiety; v) interacts and binds to the target via interactions other than exclusively electrostatic; vi) a unique, distinguishable, and/or specifically designed oligonucleotide sequence; and vii) the first oligonucleotide sequence of the molecular probe is uniquely and specifically designed to hybridize to the second oligonucleotide sequence of the detectable component or to the complementary first oligonucleotide sequence segment of the universal adapter.

Example 14H

The method of any one of Examples 1H-13H, wherein the method of detection generates less false positives than secondary antibody detection methods.

Example 15H

The method of any one of Examples 1H-14H, wherein the method further comprises: i) preparing the molecular probe; and ii) preparing the detectable component; wherein the prepared molecular probe and prepared detectable component have at least 90% purity.

Example 16H

The method of any one of Examples 1H-15H, wherein the method further comprises preparing and isolating the molecular probe, comprising: i) providing the binding moiety; ii) conjugating the binding moiety with at least one first oligonucleotide sequence at greater than 90% efficiency to form binding moiety-oligonucleotide conjugates; and iii) isolating the binding moiety-oligonucleotide conjugates from the conjugation mixture by binding, retaining, and/or retarding a substantial portion of: a) the conjugates, removing a substantial portion of the unconjugated first oligonucleotide sequence in a wash step followed by release of the bound, retained, and/or retarded conjugates; or b) the unconjugated first oligonucleotide sequences, followed by collecting a substantial portion of the non-bound, non-retained, and/or non-retarded conjugates in a wash step.

Example 17H

The method of any one of Examples 1H-16H, wherein the method further comprises preparing and isolating the detectable component, comprising: i) providing a plurality of the signal generating moiety; ii) conjugating the second oligonucleotide sequence with at least one of the plurality of the signal generating moiety at greater than 90% efficiency to form signal generating moiety-second oligonucleotide conjugates; and iii) isolating the signal generating moiety-second oligonucleotide conjugates from the conjugation mixture by binding, retaining, and/or retarding a substantial portion of: a) the conjugates, removing a substantial portion of the unconjugated second oligonucleotide sequences in a wash step followed by release of the bound, retained, and/or retarded conjugates; or b) the unconjugated second oligonucleotide sequences, followed by collecting a substantial portion of the non-bound, non-retained, and/or non-retarded conjugates in a wash step.

Example 18H

The method of any one of Examples 1H-17H, wherein the detectable component comprises a scaffold conjugated to the second oligonucleotide sequence, and wherein said scaffold comprises one or more signal generating moieties.

Example 19H

The method of Example 18H, wherein the scaffold comprises a dendrimer, a polysaccharide, a dextran, a protein, a peptide, a further oligonucleotide sequence, a portion of the second oligonucleotide sequence that is not complementary to the first oligonucleotide sequence of the molecular probe,

Example 20H

The method of any one of Examples 1H-19H, wherein the method further comprises preparing and isolating a detectable component comprising a scaffold conjugated to the second oligonucleotide sequence, wherein the scaffold comprises one or more signal generating moieties, said method comprising: i) providing a plurality of the scaffolds comprising the one or more signal generating moieties; ii) conjugating the second oligonucleotide sequence with at least one of the plurality of scaffolds at greater than 90% efficiency to form scaffold-second oligonucleotide conjugates; and iii) isolating the scaffold-second oligonucleotide conjugates from the conjugation mixture by binding, retaining, and/or retarding a substantial portion of: a) the conjugates, removing a substantial portion of the unconjugated second oligonucleotide sequences in a wash step followed by release of the bound, retained, and/or retarded conjugates; or b) the unconjugated second oligonucleotide sequences, followed by collecting a substantial portion of the non-bound, non-retained, and/or non-retarded conjugates in a wash step.

Example 21H

The method of any one of Examples 16-20H, wherein the isolation step utilizes an immobilized binder, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

Example 22H

The method of any one of Examples 16H-20H, wherein the isolation step utilizes an immobilized binder, affinity chromatography, size exclusion chromatography, electrophoresis, differential centrifugation, immunoprecipitation, hybridization, solvent extraction, dialysis, filtration, diafiltration, ion exchange chromatography, hydrophobic interaction chromatography, or combinations thereof.

Example 23H

The method of any one of Examples 16H-20H, wherein the isolation step utilizes an immobilized binder, affinity chromatography, size exclusion chromatography, differential centrifugation, dialysis, filtration, hydrophobic interaction chromatography, or combinations thereof.

Example 24H

The method of any one of Examples 1H-23H, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 25H

The method of any one of Examples 1H-24H, wherein the sample comprises one or more targets.

Example 26H

The method of any one of Examples 1H-25H, wherein the target is a biological target.

Example 27H

The method of Example 26H, wherein the biological target comprises an antigen, a pathogen, a protein, a peptide, an epitope, a carbohydrate-containing molecule, a small molecule, or combinations or derivatives thereof.

Example 28H

The method of any one of Examples 1H-27H, wherein the signal generating moiety or the one or more signal generating moieties of the detectable component or the hybridized detectable component, comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations or derivatives thereof.

Example 29H

The method of any one of Examples 1H-28H, wherein the one or more signal generating moieties provides an enhanced signal that minimizes detection errors from background noise, relative to conventionally labeled binding moieties.

Example 30H

The method of any one of Examples 1H-29H, wherein the molecular probe, the detectable component, and/or universal adapter further comprises a spacer group, comprising a polymerized ethylene oxide, a PEG, a PEO, a protein, a peptide, a DNA, an RNA, an oligonucleotide sequence, or a dextran.

Example 31H

The method of any one of Examples 1H-30H, wherein the binding moiety, the scaffold, the oligonucleotide sequence, and/or the complementary oligonucleotide sequence comprise HyNic or 4-FB.

Example 32H

The method of any one of Examples 1H-31H, wherein the detectable component comprises a unique, distinguishable, and/or specifically designed complementary oligonucleotide sequence.

Example 33H

The method of any one of Examples 1H-32H, wherein the oligonucleotide sequence, complementary oligonucleotide sequence, and/or oligonucleotide sequence segment comprises an oligonucleotide sequence conjugated at the 3'-position, an oligonucleotide sequence conjugated at the 5'-position, linear oligonucleotide sequences, branched oligonucleotide sequences, LNAs, PNAs, oligonucleotide sequences optionally covalently attached to other moieties, or combinations or derivatives thereof.

Example 34H

The method of any one of Examples 1H-33H, wherein the sample comprises one or more targets.

Example 35H

The method of any one of Examples 1H-34H, wherein a plurality of molecular probes and a plurality of detectable components are provided to the sample.

Example 36H

The method of any one of Examples 1H-35H, wherein a plurality of universal adapters are provided to the sample.

Example 37H

The method of any one of Examples 1H-36H, wherein the binding affinity for the target is $10^{-4}$ M or less.

Example 38H

The method of any one of Examples 1H-37H, wherein the binding affinity for the at least first target is $10^{-4}$ M or less.

Example 39H

The method of any one of Examples 1H-38H, wherein the binding affinity for the at least second target is $10^{-4}$ M or less.

Example 40H

The method of any one of Examples 1H-39H, wherein the method comprises an automated system or robotic system.

Example 41H

The method of any one of Examples 1H-41H, wherein the method further comprises removing the hybridized detectable component or plurality of detectable components from the bound target or plurality of targets, respectively, wherein said removal is by a washing or stripping process.

Example 41H

The method of Example 41H, wherein the removal comprises de-hybridizing the detectable component or the plurality of detectable components, respectively.

Example 42H

The method of Examples 40H or 41H, wherein the method further comprises re-probing with a second detectable component or second plurality of detectable components, respectively, wherein said second detectable component comprises at least one second signal generating moieties conjugated to a second oligonucleotide sequence or a complementary second oligonucleotide sequence, or said second plurality of detectable components are prepared by independently pairing, via conjugation, a second plurality of signal generating moieties and a second plurality of second oligonucleotide sequences or a second plurality of complementary second oligonucleotide sequences.

Example 43H

A method for assaying one or more targets of a sample, comprising: i) providing to the sample: 1) a plurality of molecular probes, comprising: A) at least a first molecular probe having a first binding moiety conjugated to a first oligonucleotide sequence; and B) at least a second molecular probe having a second binding moiety conjugated to a second oligonucleotide sequence; and 2) a plurality of detectable components, comprising: A) at least a first detectable component having a first signal generating moiety conjugated to a first complementary oligonucleotide sequence; and B) at least a second detectable component having a second signal generating moiety conjugated to a second complementary oligonucleotide sequence; ii) binding the one or more targets, comprising at least one of the following: 1) binding at least a first target of the one or more targets in the sample with the first binding moiety of the at least first molecular probe; and 2) binding at least a second target of the one or more targets in the sample with the second binding moiety of the at least second molecular probe; iii) hybridizing the plurality of molecular probes and the plurality of detectable components, comprising at least one of the following: 1) hybridizing the first oligonucleotide sequence of at least first molecular probe to the first complementary oligonucleotide sequence segment of the at least first detectable component; and 2) hybridizing the second oligonucleotide sequence of at least second molecular probe to the second complementary oligonucleotide sequence segment of the at least second detectable component; and iv) detecting one or more signals generated from the at least first hybridized detectable component and/or the at least second hybridized detectable component using one or more of the following systems: microscopy, imaging, high content screening (HCS), mass cytometry, lateral flow immunoassay, immunodetection, immunohistochemistry (IHC), immunocytochemistry (ICC), or combinations thereof; wherein the method is characterized by one or more of the following: a) the conjugation between the first oligonucleotide sequence and the first binding moiety, between the second oligonucleotide sequence and the second binding moiety, between the first complementary oligonucleotide sequence and the first signal generating moiety, and between the second complementary oligonucleotide sequence and the second signal generating moiety, comprises one or more covalent bond linkages, comprising a hydrazone, oxime, triazine, or other covalent bond, wherein the formation of the conjugates are at least 90% efficient; and b) the first binding moiety comprises a strong binding affinity for the at least first target of the one or more targets and the second binding moiety comprises a strong binding affinity for the at least second target of the one or more targets.

Example 44H

A method for assaying one or more targets of a sample, comprising: i) providing to the sample: a) a plurality of molecular probes, comprising: a first oligonucleotide sequence independently paired, via conjugation, to a plurality of binding moieties comprising at least a first binding moiety and at least a second binding moiety; b) a plurality of detectable components, comprising: a plurality of second oligonucleotide sequences independently paired, via conjugation, to a plurality of one or more signal generating moieties comprising at least a first signal generating moiety and at least a second signal generating moiety; and c) a plurality of universal adapters, comprising: a first oligonucleotide sequence segment, complementary to the first oligonucleotide sequence of said plurality of molecular probes, independently paired with a plurality of second oligonucleotide sequence segments complementary to the plurality of second oligonucleotide sequences of said plurality of detectable components; ii) binding the one or more targets, comprising at least one of the following: a) binding at least a first target of the one or more targets in the sample with the first binding moiety of the at least first molecular probe; and b) binding at least a second target of the one or more targets in the sample with the second binding moiety of the at least second molecular probe; iii) hybridizing the plurality of molecular probes and the plurality of detectable components with the plurality of universal adapters; and iv) detecting one or more signals generated from the at least first hybridized detectable component and/or the at least second hybridized detectable component using one or more of the following systems: microscopy, imaging, high content screening (HCS), mass cytometry, lateral flow immunoassay, immunodetection, immunohistochemistry (IHC), immunocytochemistry (ICC), or combinations thereof; wherein the method is characterized by one or more of the following: A) the conjugation between the first oligonucleotide sequence and the first binding moiety, between the second oligonucleotide sequence and the second binding moiety, between the first complementary oligonucleotide sequence and the first signal generating moiety, and between the second complementary oligonucleotide sequence and the second signal generating moiety, comprises one or more covalent bond linkages, comprising a hydrazone, oxime, triazine, or other covalent bond, wherein the formation of the conjugates are at least 90% efficient; and B) the first binding moiety comprises a strong binding affinity for the at least first target of the one or more targets and the second binding moiety comprises a strong binding affinity for the at least second target of the one or more targets.

Example 1I

A panel development system, comprising: i) a first panel comprising a plurality of molecular probes, said plurality of molecular probes prepared by independently pairing, via conjugation, a plurality of binding moieties and a plurality of oligonucleotide sequences; ii) a second panel comprising a plurality of detectable components, said plurality of detectable components prepared by independently pairing, via conjugation, a plurality of signal generating moieties and a plurality of complementary oligonucleotide sequences; iii) contacting a sample comprising a plurality of targets with the first panel and the second panel, wherein: a) at least a first target having one or more distinct bindings sites is bound by one or more molecular probes from the first panel; and b) one or more detectable components from the second panel independently hybridize with the one or more molecular probes bound to the at least first target; iv) detecting the presence of the at least first hybridized-target in said sample; v) determining a characteristic panel of molecular probes and detectable components from said first and second panels that identifies the at least first target among the plurality of targets in said sample.

Example 2I

The panel development system of Example 1I, wherein the plurality of oligonucleotide sequences in said first panel comprises between 2-40 different oligonucleotide sequences among the plurality of oligonucleotide sequences.

Example 3I

The panel development system of Example 1I or 2I, wherein the plurality of complementary oligonucleotide sequences in said second panel comprises between 2-40 different complementary oligonucleotide sequences among the plurality of complementary oligonucleotide sequences.

Example 4I

The panel development system of any one of Examples 1I-3I, wherein the panel development system further comprises a re-probe panel comprising a second plurality of detectable components, said second plurality of detectable components prepared by independently pairing, via conjugation, a second plurality of signal generating moieties and a second plurality of complementary oligonucleotide sequences.

Example 5I

A panel development system, comprising: i) a first panel comprising a plurality of molecular probes, said plurality of molecular probes prepared by independently pairing, via conjugation, a plurality of binding moieties and a plurality of first oligonucleotide sequences; ii) a second panel comprising a plurality of detectable components, said plurality of detectable components prepared by independently pairing, via conjugation, a plurality of signal generating moieties and a plurality of second oligonucleotide sequences; iii) a third panel comprising a plurality of universal adapters, said plurality of universal adapters comprising oligonucleotide sequences having independently paired a plurality of oligonucleotide sequence segments complementary to the plurality of first oligonucleotide sequences and a plurality of oligonucleotide sequence segments complementary to the plurality of second oligonucleotide sequences; iii) contacting a sample comprising a plurality of targets with the first panel and the second panel, wherein: a) at least a first target having one or more distinct bindings sites is bound by one or more molecular probes from the first panel; and b) one or more detectable components from the second panel independently hybridize with the one or more molecular probes bound to the at least first target; iv) detecting the presence of the at least first hybridized-target in said sample; v) determining a characteristic panel of molecular probes and detectable components from said first and second panels that identifies the at least first target among the plurality of targets in said sample.

Example 6I

The panel development system of Example 5I, wherein the panel development system is characterized by one or more of the following: i) the plurality of first oligonucleotide sequences are identical oligonucleotide sequences; ii) the plurality of first oligonucleotide sequence segments are identical oligonucleotide sequence segments; iii) the plurality of second oligonucleotide sequences comprises different oligonucleotide sequences; and iv) the plurality of second oligonucleotide sequence segments comprises oligonucleotide sequence segments complementary to the plurality of different second oligonucleotide sequences.

Example 7I

The panel development system of Example 5I or 6I, wherein the panel development system is characterized by one or more of the following: i) the plurality of first oligonucleotide sequences comprises different oligonucleotide sequences; ii) the plurality of first oligonucleotide sequence segments comprises oligonucleotide sequence segments complementary to the plurality of different first oligonucleotide sequences; iii) the plurality of second oligonucleotide sequences are identical oligonucleotide sequences; and iv) the plurality of second oligonucleotide sequence segments are identical oligonucleotide sequence segments.

Example 8I

The panel development system of any one of Examples 5I-7I, wherein the plurality of first oligonucleotide sequences in said first panel comprises between 2-40 different oligonucleotide sequences among the plurality of first oligonucleotide sequences.

Example 9I

The panel development system of any one of Examples 5I-8I, wherein the plurality of second oligonucleotide sequences in said second panel comprises between 2-40 different second oligonucleotide sequences among the plurality of second oligonucleotide sequences.

Example 10I

The panel development system of any one of Examples 5I-9I, wherein the panel development system further comprises a re-probe panel comprising a second plurality of detectable components, said second plurality of detectable components prepared by independently pairing, via conjugation, a second plurality of signal generating moieties and a second plurality of second oligonucleotide sequences.

Example 11I

The panel development system of any one of Examples 1I-10I, wherein the panel development system further comprises removing the hybridized plurality of detectable components from the bound plurality of targets, wherein said removal is by a washing or stripping process.

Example 12I

The panel development system of any one of Examples 1I-11I, wherein the panel development system further comprises a re-probing step comprising the contacting of the washed plurality of bound targets with said re-probe panel, followed by an additional detection step and determination of a characteristic panel of molecular probes and detectable components from said first, second, and re-probe panels that identifies the at least first target among the plurality of targets in said sample.

Example 13I

The panel development system of any one of Examples 1I-12I, wherein the plurality of binding moieties in said first panel comprises between 2-40 different binding moieties among the plurality of binding moieties.

Example 14I

The panel development system of any one of Examples 1I-13I, wherein the plurality of signal generating moieties in said second panel comprises between 2-40 different signal generating moieties among the plurality of signal generating moieties.

Example 15I

The panel development system of any one of Examples 1I-14I, wherein: i) the panel development system develops a singleplex or multiplex assay; and ii) the panel development system and the assay developed by the panel development system detects, measures, or quantifies the level of binding and/or amount of the target present in the sample with one or more of the following systems: flow cytometry, immunomagnetic cellular depletion, iimmunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunohistochemistry (IHC), immunocytochemistry (ICC), in situ hybridization (ISH), enzyme immuno-assay (EIA), enzyme linked immuno-assay (ELISA), ELISpot, immunoturbidity, latex agglutination, gold particle agglutination, visual inspection, a change in light transmittance through said sample, increased light transmittance through said sample, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 16I

The panel development system of any one of Examples 1I-15I, wherein the panel development system is a multiplexed panel development.

Example 17I

The panel development system of any one of Examples 1I-16I, wherein the sample comprises a plurality of cells or cell types, comprising tissue cells, cells cultured in vitro, recombinant cells, infected cells, cells from laboratory animals, cells from mammal patients, cells from human patients, mesenchemal stem cells, stem cells, immunocompetent cells, adipose cells, fibroblasts, natural-killer cells (NK-cells), monocytes, lymphocytes, lymph node cells, T-cells, B-cells, exudate cells, effusion cells, cancer cells, blood cells, red blood cells, leukocytes, white blood cells, organ cells, skin cells, liver cells, splenocytes, kidney cells, intestinal cells, lung cells, heart cells, or neuronal cells.

Example 18I

The panel development system of any one of Examples 1I-17I, wherein the sample comprises a plurality of cells having 2 or more different cell types.

Example 19I

The panel development system of any one of Examples 1I-18I, wherein the sample comprises a plurality of cells having 2-50 different cell types.

Example 20I

The panel development system of any one of Examples 1I-17I, wherein the system identifies a sub-population by assigning an immunophenotype resulting from signal pattern generated.

Example 21I

The panel development system of any one of Examples 1I-20I, wherein the system further analyzes a sub-population of the plurality of cells.

Example 22I

The panel development system of any one of Examples 1I-21I, wherein the sample comprises a plurality of different targets or different target types.

Example 23I

The panel development system of any one of Examples 1I-22I, wherein the sample comprises a plurality of similar targets or similar target types.

Example 24I

The panel development system of any one of Examples 1I-23I, wherein among a plurality of different targets in the sample at least a first target having one or more distinct bindings sites is bound by one or more molecular probes from the first panel.

Example 25I

The panel development system of any one of Examples 1I-24I, wherein the targets or target types comprises cells and/or cell types.

Example 26I

The panel development system of any one of Examples 1I-25I, wherein the one or more distinct binding sites are distinct markers.

Example 27I

The panel development system of any one of Examples 1I-26I, wherein the one or more distinct binding sites are biomarkers.

Example 28I

The panel development system of any one of Examples 1I-27I, wherein the system identifies a sub-population of targets within the sample.

Example 29I

The panel development system of any one of Examples 1I-28I, wherein the system further comprises at least one of the following: a) measuring the amount of the at least first target in said sample; b) quantifying the level of the at least first target in said sample; and c) identifying the type of the at least first target in said sample.

Example 30I

The panel development system of any one of Examples 1I-29I, wherein one or more of the plurality of signal generating moieties comprises one or more of the following: a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a Raman particle, a metal particle, a stable isotope, a heavy metal chelate, a magnetic particle, a bead, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations thereof.

Example 31I

The panel development system of any one of Examples 1I-30I, wherein the second panel comprises a plurality of detectable components, said plurality of detectable components prepared by independently pairing, via conjugation, a plurality of scaffolds and a plurality of complementary oligonucleotide sequences, wherein said plurality of scaffolds comprises a plurality of signal generating moieties.

Example 32I

The panel development system of any one of Examples 1I-31I, wherein the scaffold comprises a dendrimer, a polysaccharide molecule, a dextran, a protein, a peptide, a second oligonucleotide sequence, a portion of the oligonucleotide sequence that is not complementary to the oligonucleotide sequence of the molecular probe, a bead, a

243 polymer, a hydrophilic polymer, a bead, a nanoparticle, or combinations or derivatives thereof.

Example 33I

The panel development system of any one of Examples 1I-32I, wherein the first panel comprises at least two different molecular probes.

Example 34I

The panel development system of any one of Examples 1I-33I, wherein the first panel comprises at least 2-10 different molecular probes.

Example 35I

The panel development system of any one of Examples 1I-34I, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 36I

The panel development system of any one of Examples 1I-35I, wherein the second panel comprises at least two different detectable components.

Example 37I

The panel development system of any one of Examples 1I-36I, wherein the second panel comprises at least 2-10 different detectable components.

Example 38I

The panel development system of any one of Examples 1I-37I, wherein the sample comprises at least two different targets.

Example 39I

The panel development system of any one of Examples 1I-38I, wherein the sample comprises at least 2-50 different targets.

Example 40I

The panel development system of any one of Examples 1I-39I, wherein the panel development system comprises an automated system or robotic system.

Example 41I

A multiplexed flow cytometry assay method, comprising: i) contacting a sample comprising a plurality of cells with a first series of molecular probes and a second series of detectable components, wherein the plurality of cells comprises at least 5 different cell types; ii) binding protein markers on the plurality of cells with said first series; iii) hybridizing the first series or the protein marker-bound first series with the second series; and iv) optionally, identifying the cell types in the sample by assigning of immunophenotypes resulting from the hybridization of said protein marker-bound first series and said second series.

244

Example 42I

The method of Example 41I, further comprising: i) preparing said first series, wherein said first series comprises at least 4 different molecular probes, by independently pairing, via conjugation, at least 4 different binding moieties and at least 4 different oligonucleotide sequences; and ii) preparing said second series, wherein said second series comprises at least 4 different detectable components, by independently pairing, via conjugation, at least 4 different signal generating moieties and at least 4 different oligonucleotide sequences complementary to the sequences conjugated the binding moieties.

Example 43I

A panel development system, comprising: i) a plurality of molecular probes comprising: a) at least a first molecular probe comprising a first binding moiety conjugated to a first oligonucleotide sequence; and b) at least a second molecular probe comprising a second binding moiety conjugated to a second oligonucleotide sequence; ii) a plurality of detectable components, comprising: a) at least a first detectable component comprising a first signal generating moiety conjugated to a first complementary oligonucleotide sequence; and b) at least a second detectable component comprising a second signal generating moiety conjugated to a second complementary oligonucleotide sequence; and iii) providing a sample comprising a plurality of targets having at least a first target and at least a second target; iv) binding the at least a first target and the at least a second target of the plurality of targets with the first binding moiety of the at least first molecular probe and the second binding moiety of the at least second molecular probe, respectively; v) hybridizing the at least first molecular probe with the at least first detectable component and the at second molecular probe with the at least second detectable component, respectively; vi) detecting the at least first bound-target and the at least second bound-target in said sample, said detection comprising at least one of the following: a) detecting the presence of the at least first target and/or the at least second target in said sample; b) measuring the amount of the at least first target and/or the at least second target in said sample; c) quantifying the level of the at least first target and/or the at least second target in said sample; and d) identifying the type of the at least first target and/or the at least second target in said sample; and vii) assigning the phenotypes of the at least first target and the at least second target in said sample.

Example 44I

A panel development system, comprising: i) a panel of molecular probes comprising a plurality of molecular probes, said plurality of molecular probes comprising: a) a plurality of binding moieties comprising at least a first binding moiety and at least a second binding moiety; b) a plurality of oligonucleotide sequences comprising at least a first oligonucleotide sequence and at least a second oligonucleotide sequence; and c) preparing the panel of plurality of molecular probes, by independently pairing, via conjugation, the plurality of binding moieties and the plurality of oligonucleotide sequences; ii) a panel of detectable components comprising a plurality of detectable components, comprising: a) a plurality of signal generating moieties comprising at least a first signal generating moiety and at least a second signal generating moiety; b) a plurality of complementary oligonucleotide sequences comprising at least a first oligonucleotide sequence complementary to the at least first oligonucleotide sequence of the plurality of molecular probes and at least a second oligonucleotide sequence complementary to the at least second oligonucleotide sequence of the plurality of molecular probes; and c) preparing the panel of plurality of detectable components, by independently pairing, via conjugation, the plurality of signal generating moieties and the plurality of complementary oligonucleotide sequences; iii) providing a sample comprising a plurality of targets having at least a first target and at least a second target; iv) binding the at least a first target and the at least a second target of the plurality of targets with the at least first binding moiety and the at least second binding moiety of the panel of plurality of molecular probes, respectively; v) hybridizing the target-bound plurality of molecular probes with the panel of plurality of detectable components; vi) detecting the presence of the at least first bound-target and/or the at least second bound-target in said sample, said detection optionally further comprising at least one of the following: a) measuring the amount of the at least first target and/or the at least second target in said sample; b) quantifying the level of the at least first target and/or the at least second target in said sample; and c) identifying the type of the at least first target and/or the at least second target in said sample; vii) assigning the phenotype of the at least first target and the at least second target, respectively, in said sample; and viii) from the assigned phenotypes, selecting at least one of the following: a) the series of molecular probes from the plurality of molecular probes and the series of detectable components from the plurality of detectable components that distinguish the at least first target from the at least second target in said plurality of targets; and b) the series of molecular probes from the plurality of molecular probes and the series of detectable components from the plurality of detectable components that distinguish the at least second target the at least first target in said plurality of targets.

Example 45I

A panel development system, comprising: i) a first panel comprising a plurality of molecular probes, said plurality of molecular probes prepared by independently pairing, via conjugation, a plurality of binding moieties and a plurality of oligonucleotide sequences; ii) a second panel comprising a plurality of detectable components, said plurality of detectable components prepared by independently pairing, via conjugation, a plurality of signal generating moieties and a plurality of complementary oligonucleotide sequences; iii) providing a sample comprising a plurality of targets having at least a first target; iv) binding the at least a first target of the plurality of targets with at least a first binding moiety from the first panel; v) hybridizing the at least first target-bound molecular probe with the second panel; vi) detecting the presence of the at least first hybridized-target in said sample, said detection optionally further comprising at least one of the following: a) measuring the amount of the at least first target in said sample; b) quantifying the level of the at least first target in said sample; and c) identifying the type of the at least first target in said sample; vii) assigning the phenotype of the at least first target in said sample; and viii) from the assigned phenotype, selecting the series of molecular probes from the first panel and the series of detectable components from the second panel that distinguish the at least first target from the plurality of targets.

Example 46I

A panel development system, comprising: i) a first panel comprising a plurality of molecular probes, said plurality of molecular probes prepared by independently pairing, via conjugation, a plurality of binding moieties and a plurality of oligonucleotide sequences; ii) a second panel comprising a plurality of detectable components, said plurality of detectable components prepared by independently pairing, via conjugation, a plurality of signal generating moieties and a plurality of complementary oligonucleotide sequences; iii) providing a sample comprising a plurality of targets having at least a first target and at least a second target; iv) binding the at least a first target and the at least a second target of the plurality of targets with at least a first binding moiety and at least a second binding moiety, respectively, of the first panel; v) hybridizing the at least first target-bound molecular probe and the at least second target-bound molecular probe of the plurality of target-bound molecular probes with the second panel; vi) detecting the presence of the at least first hybridized-target and/or the at least second hybridized-target in said sample, said detection optionally further comprising at least one of the following: a) measuring the amount of the at least first target and/or the at least second target in said sample; b) quantifying the level of the at least first target and/or the at least second target in said sample; and c) identifying the type of the at least first target and/or the at least second target in said sample; vii) assigning the phenotype of the at least first target and/or the at least second target, respectively, in said sample; and viii) from the assigned phenotypes, selecting at least one of the following: a) the series of molecular probes from the first panel and the series of detectable components from the second panel that distinguish the at least first target from the at least second target in said plurality of targets; and b) the series of molecular probes from the first panel and the series of detectable components from the second panel that distinguish the at least second target the at least first target in said plurality of targets.

Example 1J

A method for assaying a target of a sample, comprising: i) providing to the sample: 1) a molecular probe, comprising a binding moiety conjugated to an oligonucleotide sequence; and 2) a detectable component, comprising a signal generating moiety conjugated to an oligonucleotide sequence complementary to the oligonucleotide sequence of the molecular probe; ii) binding the target in the sample with the binding moiety of the molecular probe; iii) hybridizing the oligonucleotide sequence of the molecular probe with the complementary oligonucleotide sequence of the detectable component; and iv) detecting a signal generated from the hybridized detectable component; wherein the method is characterized by one or more of the following: a) the conjugation between the oligonucleotide sequence and the binding moiety and conjugation between the complementary oligonucleotide sequence and the signal generating moiety, comprises one or more covalent bond linkages, comprising a hydrazone, oxime, triazine, or other covalent bond, wherein the formation of the conjugates are at least 90% efficient; and b) the binding moiety comprises a binding affinity of less than $10^{-4}$ M for the target.

Example 2J

The method of Example 1J, wherein the mode of addition comprises: i) the molecular probe and the detectable component are combined together and hybridized prior to contacting the sample; ii) the molecular probe is combined with the sample prior to the addition of the detectable component;

or iii) the detectable component is combined with the sample prior to the addition of the molecular probe.

Example 3J

The method of any one of Examples 1J-2J, wherein the method comprises: i) the molecular probe binding the target prior to hybridizing with the detectable component; or ii) the molecular probe hybridizing with the detectable component prior to binding the target.

Example 4J

A method for assaying a target of a sample, comprising: i) providing to the sample: 1) a molecular probe, comprising a binding moiety conjugated to a first oligonucleotide sequence; 2) a detectable component, comprising a signal generating moiety conjugated to a second oligonucleotide sequence; and 3) a universal adapter, comprising an oligonucleotide sequence having a first sequence segment complementary to the first oligonucleotide sequence of the molecular probe and a second sequence segment complementary to the second oligonucleotide sequence of the detectable component; ii) binding the target in the sample with the binding moiety of the molecular probe; iii) hybridizing the first oligonucleotide sequence of the molecular probe to the first oligonucleotide sequence segment of the universal adapter; iv) hybridizing the second oligonucleotide sequence of the detectable component to the second oligonucleotide sequence segment of the universal adapter; and v) detecting a signal generated from the hybridized detectable component; wherein the method is characterized by one or more of the following: a) the conjugation between the first oligonucleotide sequence and the binding moiety and conjugation between the second complementary oligonucleotide sequence and the signal generating moiety, comprises one or more covalent bond linkages, comprising a hydrazone, oxime, triazine, or other covalent bond, wherein the formation of the conjugates are at least 90% efficient; and b) the binding moiety comprises a binding affinity of less than $10^{-4}$ M for the target.

Example 5J

The method of Example 4J, wherein the mode of addition comprises: i) the molecular probe, the universal adapter, and the detectable component are combined together and hybridized prior to contacting the sample; ii) the molecular probe and the universal adapter are combined together and hybridized prior to contacting the sample; iii) the detectable component and the universal adapter are combined together and hybridized prior to contacting the sample; iv) the molecular probe, alone or in combination with the detectable component, is combined with the sample prior to the addition of the universal adapter; or v) the universal adapter is combined with the sample prior to the addition of the molecular probe and/or the detectable component.

Example 6J

The method of Examples 4J or 5J, wherein the method comprises: i) the molecular probe hybridizing with the universal adapter prior to said molecular probe binding the target; ii) the molecular probe hybridizing with the universal adapter after said molecular probe binds the target; iii) the detectable component hybridizing with the universal adapter prior to the molecular probe binding the target; iv) the detectable component hybridizing with the universal adapter after the molecular probe binds the target; v) the universal adapter hybridizing with the molecular probe and hybridizing with the detectable component prior to said molecular probe binding the target; or vi) the universal adapter hybridizing with the molecular probe and hybridizing with the detectable component after said molecular probe binds the target.

Example 7J

The method of any one of Examples 1J-6J, wherein: i) the assay comprises a singleplex or multiplex assay; and ii) the assay detects, measures, or quantifies the level of binding and/or amount of the target present in the sample with one or more of the following: flow cytometry, immunomagnetic cellular depletion, immunomagnetic cell capture, array, bead array, multiplex bead array, microarray, antibody array, cellular array, chemiluminescence, infrared, microscopy, imaging, high content screening (HCS), mass cytometry, lateral flow immunoassay, immunodetection, immunohistochemistry (IHC), immunocytochemistry (ICC), in situ hybridization (ISH), enzyme immuno-assay (EIA), enzyme linked immuno-assay (ELISA), ELISpot, immunoturbidity, latex agglutination, gold particle agglutination, visual inspection, a change in light transmittance through said sample, increased light transmittance through said sample, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, or combinations thereof.

Example 8J

The method of any one of Examples 1J-7J, wherein: i) the assay comprises a singleplex or multiplex assay; and ii) the assay detects, measures, or quantifies the level of binding and/or amount of the target present in the sample with one or more of the following: flow cytometry, microscopy, imaging, high content screening (HCS), multiplex bead array, microarray, antibody array, cellular array, immunohistochemistry (IHC), immunocytochemistry (ICC), in situ hybridization (ISH), enzyme immuno-assay (EIA), enzyme linked immuno-assay (ELISA), ELISpot, or a blotting method.

Example 9J

The method of any one of Examples 1J-8J, wherein: i) the assay comprises a singleplex or multiplex assay; and ii) the assay detects, measures, or quantifies the level of binding and/or amount of the target present in the sample with flow cytometry.

Example 10J

The method of any one of Examples 1J-9J, wherein the sample is characterized as at least one or more of the following: i) a complex sample; and ii) a homogeneous or a heterogeneous mixture; and wherein said sample comprises at least one or more of the following: a) a range of analytes having a wide range of binding specificities; b) a cell, a

Example 11J

The method of any one of Examples 1J-10J, wherein the hybridization efficiency of the oligonucleotide sequence to the complementary oligonucleotide sequence is at least 50% with respect to the detectable component, under the hybridization conditions employed.

Example 12J

The method of any one of Examples 1J-11J, wherein the molecular probe comprises one or more of the following properties: i) a molecular weight of between about 15,000 Daltons to about 450,000 Daltons; ii) a solubility that is substantially the same as that of the unconjugated binding moiety; iii) a solubility that minimizes non-specific binding to the target; iv) the oligonucleotide sequence of the molecular probe does not adversely affect the solubility of the binding moiety; v) interacts and binds to the target via interactions other than exclusively electrostatic; vi) a unique, distinguishable, and/or specifically designed oligonucleotide sequence; and vii) the oligonucleotide sequence of the molecular probe is uniquely and specifically designed to hybridize to the complementary oligonucleotide sequence of the detectable component.

Example 13J

The method of any one of Examples 1J-12J, wherein the method of detection generates less false positives than secondary antibody detection methods.

Example 14J

The method of any one of Examples 1J-13J, wherein the method further comprises: i) preparing the molecular probe; and ii) preparing the detectable component; wherein the prepared molecular probe and prepared detectable component have at least 90% purity.

Example 15J

The method of any one of Examples 1J-14J, wherein the method further comprises preparing and isolating the molecular probe, comprising: i) providing the binding moiety; ii) conjugating the binding moiety with at least one oligonucleotide at greater than 90% efficiency to form binding moiety-oligonucleotide conjugates; and iii) isolating the binding moiety-oligonucleotide conjugates from the conjugation mixture by binding, retaining, and/or retarding a substantial portion of: a) the conjugates, removing a substantial portion of the unconjugated oligonucleotide in a wash step followed by release of the bound, retained, and/or retarded conjugates; or b) the unconjugated oligonucleotides, followed by collecting a substantial portion of the non-bound, non-retained, and/or non-retarded conjugates in a wash step.

Example 16J

The method of any one of Examples 1J-15J, wherein the method further comprises preparing and isolating the detectable component, comprising: i) providing a plurality of the signal generating moiety; ii) conjugating the complementary oligonucleotide with at least one of the plurality of the signal generating moiety at greater than 90% efficiency to form signal generating moiety-complementary oligonucleotide conjugates; and iii) isolating the signal generating moiety-complementary oligonucleotide conjugates from the conjugation mixture by binding, retaining, and/or retarding a substantial portion of: a) the conjugates, removing a substantial portion of the unconjugated oligonucleotide in a wash step followed by release of the bound, retained, and/or retarded conjugates; or b) the unconjugated oligonucleotides, followed by collecting a substantial portion of the non-bound, non-retained, and/or non-retarded conjugates in a wash step.

Example 17J

The method of any one of Examples 1J-16J, wherein the detectable component comprises a scaffold conjugated to the complementary oligonucleotide sequence, and wherein said scaffold has one or more signal generating moieties.

Example 18J

The method of Example 17J, wherein the scaffold comprises a dendrimer, a polysaccharide, a dextran, a protein, a peptide, a second oligonucleotide sequence, a portion of the oligonucleotide sequence that is not complementary to the oligonucleotide sequence of the molecular probe, a polymer, a hydrophilic polymer, a bead, a nanoparticle, or combinations or derivatives thereof.

Example 19J

The method of any one of Examples 1J-18J, wherein the method further comprises preparing and isolating a detectable component comprising a scaffold conjugated to the oligonucleotide sequence complementary to the oligonucleotide sequence of the molecular probe, wherein the scaffold comprises one or more signal generating moieties, said method comprising: i) providing a plurality of the scaffold comprising the one or more signal generating moieties; ii) conjugating the complementary oligonucleotide with at least one of the plurality of scaffolds at greater than 90% efficiency to form scaffold-complementary oligonucleotide conjugates; and iii) isolating the scaffold-complementary oligonucleotide conjugates from the conjugation mixture by binding, retaining, and/or retarding a substantial portion of: a) the conjugates, removing a substantial portion of the unconjugated oligonucleotide in a wash step followed by release of the bound, retained, and/or retarded conjugates; or b) the unconjugated oligonucleotides, followed by collecting a substantial portion of the non-bound, non-retained, and/or non-retarded conjugates in a wash step.

Example 20J

The method of any one of Examples 15J-19J, wherein the isolation step utilizes an immobilized binder, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, or combinations thereof.

Example 21J

The method of any one of Examples 15J-19J, wherein the isolation step utilizes an immobilized binder, chromatography, or size exclusion chromatography.

Example 22J

The method of any one of Examples 1J-21J, wherein the binding moiety comprises an antibody, a monoclonal antibody, a polyclonal antibody, an enzyme, a protein, a peptide, a carbohydrate, a nuclear receptor, a small molecule, an aptamer, a chelator, or combinations or derivatives thereof.

Example 23J

The method of any one of Examples 1J-22J, wherein the sample comprises one or more targets.

Example 24J

The method of any one of Examples 1J-23J, wherein the target is a biological target.

Example 25J

The method of Example 24J, wherein the biological target comprises an antigen, a pathogen, a protein, a peptide, an epitope, a carbohydrate-containing molecule, a small molecule, or combinations or derivatives thereof.

Example 26J

The method of any one of Examples 1J-25J, wherein the one or more signal generating moieties, comprise one or more of the following: a directly detectable signal generating moiety, an indirectly detectable signal generating moiety, a fluorescent dye, a fluorophore, a fluorochrome, a chromophore, a fluorescent protein, a biofluorescent protein, a luminescent species, a chemiluminescent compound, a electrochemiluminescent label, a bioluminescent label, a phosphorescent species, a fluorophore labeled DNA dendrimer, Quantum Dot, a Raman particle, a tandem dye, a FRET dye, a heavy atom, a spin label, a radioactive isotope, a nanoparticle, a light scattering nanoparticle or microsphere, a diffracting particle, a polymer, a polymer particle, a bead, a solid surface, a metal particle, a stable isotope, a heavy metal chelate, a magnetic particle, an RFID tag, a microbarcode particle, an enzyme, an enzyme substrate, a molecule specifically recognized by another substance carrying a label or reacts with a substance carrying a label, an antibody, an antibody fragment, an antigen, a nucleic acid, a nucleic acid analog, oligonucleotide, oligonucleotide analog, complementary oligonucleotide, complementary oligonucleotide analog, a ligand, a protein, a peptide ligand, a protein substrate, a receptor; a substrate, a secondary reporter, a hapten, or combinations or derivatives thereof.

Example 27J

The method of any one of Examples 1J-26J, wherein the one or more signal generating moieties provides an enhanced signal that minimizes detection errors from background noise, relative to conventionally labeled binding moieties.

Example 28J

The method of any one of Examples 1J-27J, wherein the molecular probe, the detectable component, and/or universal adapter further comprises a spacer group, comprising a polymerized ethylene oxide, a PEG, a PEO, a protein, a peptide, a DNA, an RNA, an oligonucleotide sequence, or a dextran.

Example 29J

The method of any one of Examples 1J-28J, wherein the binding moiety, the scaffold, the oligonucleotide sequence, and/or the complementary oligonucleotide sequence comprise HyNic or 4-FB.

Example 30J

The method of any one of Examples 1J-29J, wherein the detectable component comprises a unique, distinguishable, and/or specifically designed complementary oligonucleotide sequence.

Example 31J

The method of any one of Examples 1J-30J, wherein the oligonucleotide sequence, complementary oligonucleotide sequence, and/or oligonucleotide sequence segment comprises an oligonucleotide sequence conjugated at the 3'-position, an oligonucleotide sequence conjugated at the 5'-position, linear oligonucleotide sequences, branched oligonucleotide sequences, LNAs, PNAs, oligonucleotide sequences optionally covalently attached to other moieties, or combinations or derivatives thereof.

Example 32J

The method of any one of Examples 1J-31J, wherein the sample comprises one or more targets, and to sample is provided: i) a plurality of molecular probes, comprising at least a first molecular probe and at least a second molecular probe; and ii) a plurality of detectable components, comprising at least a first detectable component and at least a second detectable component.

Example 33J

The method of any one of Examples 1J-32J, wherein the method further comprises binding the one or more targets, comprising at least one of the following: i) binding at least a first target of the one or more targets in the sample with the first binding moiety of the at least first molecular probe; and ii) binding at least a second target of the one or more targets in the sample with the second binding moiety of the at least second molecular probe.

Example 34J

The method of any one of Examples 1J-33J, wherein the method further comprises hybridizing the plurality of molecular probes and the plurality of detectable components, comprising at least one of the following: i) hybridizing the first oligonucleotide sequence of at least first molecular probe to the first complementary oligonucleotide sequence segment of the at least first detectable component; and ii) hybridizing the second oligonucleotide sequence of at least second molecular probe to the second complementary oligonucleotide sequence segment of the at least second detectable component.

Example 35J

The method of any one of Examples 1J-34J, wherein the method further comprises detecting one or more signals generated from at least one of the following: i) the at least first hybridized detectable component; and ii) the at least second hybridized detectable component.

Example 36J

The method of any one of Examples 1J-35J, wherein the conjugation between the first oligonucleotide sequence and the first binding moiety, between the second oligonucleotide sequence and the second binding moiety, between the first complementary oligonucleotide sequence and the first signal generating moiety, and between the second complementary oligonucleotide sequence and the second signal generating moiety, comprises one or more covalent bond linkages, comprising a hydrazone, oxime, triazine, or other covalent bond, wherein the formation of the conjugates are at least 90% efficient.

Example 37J

The method of any one of Examples 1J-36J, wherein the first binding moiety comprises a binding affinity of less than $10^{-4}$ M for the at least first target of the one or more targets and the second binding moiety comprises a binding affinity of less than $10^{-4}$ M for the at least second target of the one or more targets.

Example 38J

The method of any one of Examples 1J-37J, wherein the detectable component comprises a bead conjugated to the second oligonucleotide sequence or the complementary second oligonucleotide sequence, and wherein said bead comprises one or more signal generating moieties.

Example 39J

The method of any one of Examples 1J-38J, wherein: i) the at least first detectable component comprises a first bead; and/or ii) the at least second detectable component comprises a second bead; wherein said first bead and second bead comprise one or more signal generating moieties.

Example 40J

A method for crosslinking, comprising: i) introducing to a sample comprising one or more targets: a) one or more first antibody-oligonucleotide conjugates, comprising a first antibody conjugated to a first oligonucleotide sequence; and b) one or more second antibody-oligonucleotide conjugates, comprising a second antibody conjugated to a second oligonucleotide sequence; ii) binding the one or more targets with the first antibody of the one or more first antibody-oligonucleotide conjugates and with the second antibody of the one or more second antibody-oligonucleotide conjugates to form one or more sandwich-complexes; iii) contacting the one or more sandwich-complexes with: a) one or more first bead-oligonucleotide conjugate, comprising a first bead conjugated to a complementary first oligonucleotide sequence; and b) one or more second bead-oligonucleotide conjugate, comprising a second bead conjugated to a complementary second oligonucleotide sequence; iv) crosslinking the one or more sandwich-complexes by: a) hybridizing the first oligonucleotide sequences of the one or more sandwich-complexes with the complementary first oligonucleotide sequences of the one or more first bead-oligonucleotide conjugates; and b) hybridizing the second oligonucleotide sequences of the one or more sandwich-complexes with the complementary second oligonucleotide sequences of the one or more second bead-oligonucleotide conjugates.

Example 41J

The crosslinking method of Example 40J, wherein the formation of the crosslinked one or more sandwich-complexes forms an agglutination.

Example 42J

The crosslinking method of Examples 40J or 41J, wherein the method further comprises detecting, measuring, and/or quantifying the degree of the formed agglutination to determine the amount of the one or more targets in the sample.

Example 43J

The crosslinking method of any one of Examples 40J-42J, wherein the first antibody or the second antibody comprise a monoclonal antibody or a polyclonal antibody.

Example 44J

The crosslinking method of any one of Examples 40J-43J, wherein: i) the first antibody comprises a first polyclonal antibody and the second antibody comprises a second polyclonal antibody; ii) the first antibody comprises a first monoclonal antibody and the second antibody comprises a second monoclonal antibody; iii) the first antibody comprises a first monoclonal antibody and the second antibody comprises a first polyclonal antibody; or iv) the first antibody comprises a first polyclonal antibody and the second antibody comprises a first monoclonal antibody.

Example 45J

The crosslinking method of any one of Examples 40J-44J, wherein the first antibody comprises a first monoclonal antibody and the second antibody comprises a second monoclonal antibody.

Example 46J

The crosslinking method of any one of Examples 40J-44J, wherein the first antibody comprises a first polyclonal antibody and the second antibody comprises a second polyclonal antibody.

Example 47J

The crosslinking method of any one of Examples 40J-44J, wherein the first antibody comprises a first monoclonal antibody and the second antibody comprises a first polyclonal antibody.

Example 48J

The crosslinking method of any one of Examples 40J-47J, wherein the detection comprises a singleplex or multiplex detection, comprising: immunodetection, immunoturbidity, latex agglutination, gold particle agglutination, visual inspection, a change in light transmittance through said sample, increased light transmittance through said sample, flow cytometry, microscopy, imaging, high content screening (HCS), immunohistochemistry, ELISA, ELISpot, arrays, bead arrays, or combinations or derivatives thereof.

Example 49J

A method of preparing a detectable component having one or more signal-generating moieties, comprising: i) modifying a scaffold with S-HyNic to form a HyNic-modified scaffold; ii) conjugating a 4FB-modified oligonucleotide to the HyNic-modified scaffold, wherein the conjugation is at least 90% efficient; and iii) modifying the scaffold of the oligonucleotide-scaffold conjugate with one or more signal-generating moieties to form the detectable component.

Example 50J

A method of preparing one or more detectable components, comprising: i) modifying one or more scaffolds; ii) conjugating one or more modified oligonucleotides to the one or more modified scaffolds, wherein the conjugation is at least 90% efficient; and iii) modifying the scaffold of the one or more oligonucleotide-scaffold conjugates with one or more signal-generating moieties to form one or more components; wherein the conjugation between the one or more modified-oligonucleotides and the one or more modified scaffolds comprises one or more covalent bond linkages, comprising a hydrazone, oxime, triazine, or other covalent bond.

Example 51J

The preparation method of Examples 49J or 50J, wherein the one or more scaffolds comprises: a hydrophilic polymer, a dendrimer, a polysaccharide, a dextran, a protein, a peptide, a second oligonucleotide sequence, a portion of the oligonucleotide sequence that is not complementary to the oligonucleotide sequence of the molecular probe, a bead, a nanoparticle, or combinations thereof.

Example 52J

The preparation method of any one of Examples 49J-51J, wherein the hydrophilic polymer comprises a polysaccharide molecule.

Example 53J

The preparation method of Example 52J, wherein the polysaccharide molecule comprises a dextran or an aminodextran.

Example 54J

The preparation method of any one of Examples 49J-53J, wherein the one or more signal-generating moieties comprises a directly detectable signal-generating moiety or an indirectly detectable signal-generating moiety.

Example 55J

The preparation method of Example 54J, wherein the directly detectable signal-generating moiety comprises: a fluorescent dye; a luminescent species; a phosphorescent species; a radioactive substance; a nanoparticle; a diffracting particle; a raman particle; a metal particle; a magnetic particle; a bead; an RFID tag; a microbarcode particle; or combinations thereof.

Example 56J

The preparation method of any one of Examples 49J-55J, wherein the indirectly detectable signal-generating moiety comprises: an enzyme; an antibody; an antigen; a nucleic acid; a nucleic acid analog; oligonucleotide; oligonucleotide analog; complementary oligonucleotide; complementary oligonucleotide analog; a ligand; a substrate; a hapten; or combinations thereof.

Example 57J

The preparation method of any one of Examples 49J-56J, wherein the one or more scaffolds signal-generating moieties comprise: a fluorophore; a chromophore; a biofluorescent protein; a fluorophore labeled DNA dendrimer; a Quantum Dot; a chemiluminescent compound; a electrochemiluminescent label; a bioluminescent label; a polymer; a polymer particle; a bead; a Raman particle; a heavy metal chelate; gold or other metal particles or heavy atoms; a spin label; a radioactive isotope; a secondary reporter; a hapten; a nucleic acid or nucleic acid analog; oligonucleotide; oligonucleotide analog; complementary oligonucleotide; complementary oligonucleotide analog; a protein; a peptide ligand or substrate; a receptor; an enzyme; an enzyme substrate; an antibody; an antibody fragment; an antigen; or combinations or derivatives thereof.

Example 58J

The method of any one of Examples 1J-57J, wherein the plurality of targets comprises a plurality of cells, said plurality of cells comprising at least a first cell and at least a second cell.

Example 59J

The method of any one of Examples 1J-58J, wherein at least a first target comprises a first biomarker of the at least first cell and at least a second target comprises a second biomarker of the at least second cell.

Example 60J

The method of any one of Examples 1J-59J, wherein the first biomarker comprises a protein biomarker and the second biomarker comprises a protein biomarker.

Example 61J

The method of any one of Examples 1J-60J, wherein the first biomarker comprises an adhesion molecule and the second biomarker comprises an adhesion molecule.

Example 62J

The method of any one of Examples 1J-61J, wherein the plurality of cells comprises immuno-competent cells.

Example 63J

The method of any one of Examples 1J-62J, wherein the plurality of cells comprises at least one of the following: tissue cells, cells cultured in vitro, recombinant cells, infected cells, cells from laboratory animals, cells from mammal patients, cells from human patients, mesenchemal stem cells, stem cells, immuno-competent cells, adipose cells, fibroblasts, natural-killer cells (NK-cells), monocytes, lymphocytes, lymph node cells, T-cells, B-cells, exudate cells, effusion cells, cancer cells, blood cells, red blood cells, leukocytes, white blood cells, organ cells, skin cells, liver cells, splenocytes, kidney cells, intestinal cells, lung cells, heart cells, or neuronal cells.

Example 64J

The method of any one of Examples 1J-63J, wherein the first cell is a T-cell and the second cell is a B-cell.

Example 65J

A method for binding, comprising: i) incubating a plurality of cells or material derived from the plurality of cells with: a) at least one molecular probe, comprising a binding moiety conjugated to an oligonucleotide sequence; and b) at least one detectable component, comprising one or more signal generating moieties conjugated to a complementary oligonucleotide sequence; iii) binding at least one target from the plurality of cells with the binding moiety of the at least one molecular probe; and iv) hybridizing the oligonucleotide sequence of the at least one bound molecular probe to the complementary oligonucleotide sequence of the at least one detectable component; wherein the method is characterized by one or more of the following: a) the conjugation of the at least one molecular probe and the conjugation of the at least one detectable component comprises one or more covalent bond linkages, comprising a hydrazone, oxime, triazine, or other covalent bond; b) the formation of the conjugates are at least 90% efficient; and c) the binding moiety of the at least one molecular probe has a binding affinity for the at least one target of less than $10^{-4}$ M.

Example 66J

The method of Examples 65J, wherein the method further comprises the addition of at least one universal adapter comprising a first oligonucleotide sequence segment complementary to the first oligonucleotide sequence of the at least first molecular probe and a second oligonucleotide sequence segment complementary to the second oligonucleotide sequence of the at least first detectable component; wherein the first oligonucleotide sequence of the at least first molecular probe and the second oligonucleotide sequence of the at least first detectable component are non-complementary.

Example 67J

The method of Examples 65J or 66J, wherein the at least one target from the plurality of cells is derived by lysing the plurality of cells.

Example 68J

The method of any one of Examples 65J-67J, wherein the at least one target from the plurality of cells or from the material derived from the plurality of cells is derived by at least one of the following: electrophoresing material derived from lysing the plurality of cells, secretion by the plurality of cells, biological fluids, extracellular matrix proteins, cell culture media, genetically engineered proteins or nucleic acids produced by the plurality of cells, or food stuffs.

Example 69J

The method of any one of Examples 65J-68J, wherein the at least one molecular probe and the at least one detectable component are hybridized prior to incubating.

Example 70J

The method of any one of Examples 65J-69J, wherein the at least one molecular probe and the at least one detectable component are hybridized prior to incubating with the electrophoresed material.

Example 71J

The method of any one of Examples 65J-70J, wherein the method further comprises transferring the electrophoresed material to a membrane.

Example 72J

The method of any one of Examples 65J-71J, wherein the electrophoresing of the lysate comprises a Western Blot.

Example 73J

The method of any one of Examples 65J-72J, wherein the membrane comprises a PVDF membrane, a nitrocellulose membrane, or a nylon membrane.

Example 74J

The method of any one of Examples 1J-73J, wherein the one or more signal generating moieties of the at least one detectable component comprises horseradish peroxidase.

Example 75J

The method of any one of Examples 1J-74J, wherein the method comprises detecting the at least one signal generated from the one or more signal generating moieties on the at least one hybridized detectable component.

Example 76J

The method of any one of Examples 1J-75J, wherein the detection comprises a singleplex or multiplex detection, comprising: immunodetection, flow cytometry, chemiluminescence detection, colormetric detection, fluorescence detection, light-scattering detection, line-scanning, infrared detection, microscopy, imaging, high content screening (HCS), immunohistochemistry, ELISA, ELISpot, arrays, bead arrays, immunoturbidity, latex agglutination, gold particle agglutination, visual inspection, a change in light transmittance through said sample, increased light transmittance through said sample, or combinations or derivatives thereof.

Example 77J

The method of any one of Examples 1J-76J, wherein the target or the one or more targets comprises cells, cellular components, biomarkers, biological components, or combinations thereof.

Example 78J

The method of any one of Examples 1J-77J, wherein the cells are attached to a bead or a plate.

Example 79J

The method of any one of Examples 1J-78J, wherein the cellular components comprises tubulin.

Example 80J

A method of bead crosslinking or agglutination, comprising: i) hybridizing a plurality of antibody-oligonucleotide conjugates with a plurality of bead-complementary oligonucleotide conjugates to form a plurality of hybridized antibody-bead conjugates; ii) introducing the plurality of hybridized antibody-bead conjugates to a sample comprising one or more targets; iii) binding at least one target of the one or more targets with at least one hybridized antibody-bead conjugate of the plurality of hybridized antibody-bead conjugates; iv) forming a crosslinking or agglutination of the at least one target-bound hybridized antibody-bead conjugate; and v) analyzing the the agglutination to detect, measure, and/or quantify the presence or amount of the at least one target by at least one of the following: a) visual inspection; and b) decreased absorption.

Example 81J

The method of Example 80J, wherein the sample is a biological sample.

Example 82J

The method of Example 81J, wherein the least one target of the plurality of targets comprises a biological target.

Example 83J

The method of Example 82J, wherein the biological target comprises an antigen, a pathogen, a protein, a peptide, an epitope, a carbohydrate-containing molecule, a small molecule, or combinations or derivatives thereof.

The foregoing description of certain exemplary embodiments has been presented for purposes of illustration and description. It is not intended to be exhaustive of, or to limit, the disclosure to the precise form disclosed, and modification and variations are possible in light of the teachings herein or may be acquired from practice of the disclosed embodiments. The embodiments shown and described in order to explain the principles of the inventions and its practical application to enable one skilled in the art to utilize various embodiments and with various modifications as are suited to the particular application contemplated. Accordingly, such modifications and embodiments are intended to be included within the scope of the disclosure. Other substitutions, modifications, changes and omissions may be made in the design, operating conditions, and arrangement of the exemplary embodiment without departing from the spirit of the present disclosure.

What is claimed is:

1. A live cell flow cytometry method for detecting a target of a sample comprising living cells, comprising:
   i) mixing the sample comprising living cells with a molecular probe and a detectable component, wherein:
      1) the molecular probe comprises a binding moiety conjugated to a first oligonucleotide sequence, wherein
         a. the binding moiety comprises an antibody, an antibody-fragment, an enzyme, a protein, a peptide, a carbohydrate, a nuclear receptor, a chelator, or combinations or derivatives thereof; and
         b. the conjugation between the binding moiety and the first oligonucleotides comprises one or more covalent bond linkages selected from the group consisting of a hydrazine, an oxime, and a triazine; and
      2) the detectable component is not immobilized on a solid support and comprises a signal generator conjugated to a second oligonucleotide having a sequence complementary to the sequence of the first oligonucleotide, wherein
         a. the signal generator comprises a scaffold molecule further conjugated to more than one signal generating moieties, the scaffold molecule comprising a dendrimer, a polysaccharide, or combinations or derivatives thereof; and
         b. the second oligonucleotide is directly conjugated to the scaffold molecule of the signal generator via one or more covalent bond linkages selected from the group consisting of a hydrazine, an oxime, and a triazine;

ii) binding the target in the sample with the binding moiety of the molecular probe;
iii) hybridizing the first oligonucleotide with the second oligonucleotide;
iv) reducing the potential for cross-talk by adding to the molecular probe and the detectable component an oligonucleotide comprising at least one of:
   1) an unconjugated oligonucleotide having a sequence complementary to the sequence of the first oligonucleotide; and
   2) an unconjugated oligonucleotide having a sequence complementary to the sequence of the second oligonucleotide; then
v) detecting a signal generated from the detectable component hybridized to the target-bound molecular probe using flow cytometry, wherein the hybridized detectable component is not immobilized on a solid support; and
vi) removing the hybridized detectable component from the bound target, wherein the removal is by a stripping and washing process.

2. The method of claim 1, wherein:
the molecular probe and the detectable component are combined prior to adding the detectable component to the combined molecular probe and sample; or
the molecular probe and the sample are combined prior to adding the detectable component to the combined molecular probe and sample; or
the detectable component and the sample are combined prior to adding the molecular probe to the combined detectable component and sample.

3. The method of claim 1, wherein:
the molecular probe is bound to the target in the sample prior to hybridizing the first oligonucleotide with the second oligonucleotide; or
the first oligonucleotide is hybridized with the second oligonucleotide prior to binding the target in the sample.

4. The method of claim 1, wherein:
the detecting comprises a singleplex assay or multiplex assay; and
the detecting further detects, measures, or quantifies the level of binding or amount of the target present in the sample by employing one or more techniques selected from the group consisting of:
chemiluminescence, infrared, microscopy, imaging, high content screening, mass cytometry, lateral flow immunoassay, immunodetection, immunoturbidity, latex agglutination, gold particle agglutination, visual inspection, a change in light transmittance through the sample, increased light transmittance through the sample, immunohistochemistry, immunocytochemistry, in situ hybridization, enzyme immuno-assay, enzyme linked immuno-assay, ELISpot, a blotting method, a Western blot, a Southern blot, a Southwestern blot, labeling inside an electrophoresis system, labeling on a surface, labeling on an array, PCR amplification, elongation followed by PCR amplification, immunoprecipitation, co-immunoprecipitation, chromatin immunoprecipitation, pretargeting imaging, therapeutic agent, and combinations thereof.

5. The method of claim 1, wherein the prepared molecular probe and prepared detectable component have at least 90% purity.

6. The method of claim 1, further comprising preparing and isolating the molecular probe, wherein the preparing and isolating comprise:
   i) providing the binding moiety;
   ii) conjugating the binding moiety with the first oligonucleotide at greater than 90% efficiency to form a conjugation mixture comprising a binding moiety-oligonucleotide conjugate; and
   iii) isolating the binding moiety-oligonucleotide conjugate from the conjugation mixture by at least one of binding, retaining, or retarding a substantial portion of:
      1) the binding moiety-oligonucleotide conjugate, then removing by washing a substantial portion of unconjugated first oligonucleotide, followed by releasing bound, retained, or retarded conjugate; or
      2) the unconjugated first oligonucleotide, followed by collecting a substantial portion of at least one of non-bound, non-retained, or non-retarded conjugate by washing.

7. The method of claim 6, wherein the isolating utilizes a step selected from the group consisting of chromatography, affinity chromatography, size exclusion chromatography, HPLC, reverse-phase chromatography, electrophoresis, capillary electrophoresis, polyacrylamide gel electrophoresis, agarose gel electrophoresis, free flow electrophoresis, differential centrifugation, thin layer chromatography, immunoprecipitation, hybridization, solvent extraction, dialysis, filtration, diafiltration, tangential flow filtration, ion exchange chromatography, hydrophobic interaction chromatography, and combinations thereof.

8. The method of claim 1, further comprising preparing and isolating the detectable component, wherein the preparing and isolating comprises:
   i) providing a plurality of the signal generators;
   ii) conjugating the second oligonucleotide with at least one of the plurality of the signal generator at greater than 90% efficiency to form a conjugation mixture comprising a signal generator-second oligonucleotide conjugate; and
   iii) isolating the signal generator-second oligonucleotide conjugates from the conjugation mixture by at least one of binding, retaining, or retarded a substantial portion of:
      1) the signal generator-second oligonucleotide conjugate, then removing a substantial portion of the unconjugated second oligonucleotide by washing, followed by releasing the bound, retained, or retarded conjugate; or
      2) unconjugated second oligonucleotide, followed by collecting a substantial portion of at least one of the non-bound, non-retained, or non-retarded conjugate by washing.

9. The method of claim 8, wherein the plurality of signal generators of the detectable component or a hybridized detectable component comprises one or more components selected from the group consisting of:
a directly detectable signal generating moiety, an indirectly detectable signal generating moiety, a fluorescent dye, a fluorophore, a fluorochrome, a chromophore, a biofluorescent protein, a luminescent species, a chemiluminescent compound, a electrochemiluminescent label, a bioluminescent label, a phosphorescent species, a fluorophore labeled DNA dendrimer, Quantum Dot, a tandem dye, a FRET dye, a spin label, a radioactive isotope, a stable isotope, a heavy metal chelate, an enzyme, an enzyme substrate, a molecule specifically recognized by another substance carrying a label or reacts with a substance carrying a label, an antibody, an antibody fragment, an antigen, a nucleic acid, a nucleic acid analog, an oligonucleotide, an oligonucleotide analog, complementary oligonucleotide, a complementary oligonucleotide analog, a ligand, a protein, a peptide ligand, a protein substrate, a receptor, a substrate, a secondary reporter, a hapten, and-combinations or derivatives thereof.

10. The method of claim 1, wherein the scaffold molecule further comprises a component selected from the group consisting of a dextran, a protein, a peptide, a further oligonucleotide sequence, a portion of the second oligonucleotide that is not complementary to the first oligonucleotide, a polymer, a hydrophilic polymer, and combinations or derivatives thereof.

11. The method of claim 1, wherein the antibody comprises a monoclonal antibody or a polyclonal antibody.

12. The method of claim 1, wherein the target is a biological target.

13. The method of claim 12, wherein the biological target comprises a component selected from the group consisting of an antigen, a pathogen, a protein, a peptide, an epitope, a carbohydrate-containing molecule, a small molecule, and a combination or derivative thereof.

14. The method of claim 12, wherein the binding moiety is a monoclonal antibody or a polyclonal antibody.

15. The method of claim 12, wherein the biological target is a protein or a peptide.

16. The method of claim 1, wherein the method comprises an automated system or robotic system that performs one or more steps of the claimed method.

17. The method of claim 1, wherein
the first oligonucleotide is a 10-mer to 60-mer oligonucleotide; and
the second oligonucleotide is a 10-mer to 60-mer oligonucleotide.

18. The method of claim 1, wherein the molecular probe and the detectable component are combined prior to mixing the sample with the molecular probe and the detectable component.

19. The method of claim 18, wherein the first oligonucleotide is hybridized with the second oligonucleotide prior to mixing the sample with the molecular probe and the detectable component.

20. The method of claim 1, wherein reducing cross-talk according to step (iv) comprises adding the non-conjugated oligonucleotide(s) to a mixture of the molecular probe and the detectable component before mixing the sample with the molecular probe and the detectable component.

21. The method of claim 20, wherein the first oligonucleotide is hybridized with the second oligonucleotide before adding the non-conjugated oligonucleotide(s).

22. The method of claim 1, wherein a plurality of targets in the sample are simultaneously detected using a plurality of molecular probe and detectable components, wherein each molecular probe and detectable component pair is hybridized in accord with step (iii) and treated to reduce cross-talk in accord with step (iv) prior to mixing with the sample.

23. The method of claim 1, wherein the scaffold molecule comprises dextran.

24. The method of claim 1, wherein the scaffold molecule consists essentially of dextran.

25. The method of claim 1, wherein the detectable component consists essentially of the second oligonucleotide and a dextran conjugated to multiple fluorophores and wherein the second oligonucleotide is directly conjugated to the dextran via a hydrazone, triazine or oxime linkage.

* * * * *

UNITED STATES PATENT AND TRADEMARK OFFICE
CERTIFICATE OF CORRECTION

PATENT NO. : 12,291,738 B2
APPLICATION NO. : 17/369771
DATED : May 6, 2025
INVENTOR(S) : David A. Schwartz et al.

Page 1 of 1

It is certified that error appears in the above-identified patent and that said Letters Patent is hereby corrected as shown below:

In the Specification

In Column 1, Lines 35-38, delete "This invention was made with Government support under Grant number 5R43A1091340-02 awarded by National Institutes of Health. The government has certain rights in the invention." and insert --This invention was made with Government support under Grant number 5R43AI091340-02 awarded by National Institutes of Health. The government has certain rights in the invention.-- therefor.

Signed and Sealed this
First Day of July, 2025

Coke Morgan Stewart
*Acting Director of the United States Patent and Trademark Office*